(12) United States Patent
Marty et al.

(10) Patent No.: US 9,879,234 B2
(45) Date of Patent: Jan. 30, 2018

(54) ENZYMES, ENZYME COMPONENTS AND USES THEREOF

(71) Applicant: BASF PLANT SCIENCE COMPANY GMBH, Ludwigshafen (DE)

(72) Inventors: Laurent Marty, Bad Duerkheim (DE); Toralf Senger, Heidelberg (DE)

(73) Assignee: BASF PLANT SCIENCE COMPANY GMBH, Ludwigshafen (DE)

( * ) Notice: Subject to any disclaimer, the term of this patent is extended or adjusted under 35 U.S.C. 154(b) by 300 days.

(21) Appl. No.: 14/416,981

(22) PCT Filed: Jul. 30, 2013

(86) PCT No.: PCT/IB2013/056243
§ 371 (c)(1),
(2) Date: Jan. 23, 2015

(87) PCT Pub. No.: WO2014/020533
PCT Pub. Date: Feb. 6, 2014

(65) Prior Publication Data
US 2015/0203826 A1 Jul. 23, 2015

Related U.S. Application Data

(60) Provisional application No. 61/679,100, filed on Aug. 3, 2012.

(30) Foreign Application Priority Data

Aug. 3, 2012 (EP) .................................... 12179241

(51) Int. Cl.
*C12N 9/00* (2006.01)
*C12P 7/64* (2006.01)
*C12N 9/02* (2006.01)

(52) U.S. Cl.
CPC ........... *C12N 9/0071* (2013.01); *C12N 9/001* (2013.01); *C12P 7/6427* (2013.01); *C12Y 114/19* (2013.01)

(58) Field of Classification Search
None
See application file for complete search history.

(56) References Cited

U.S. PATENT DOCUMENTS

| 8,119,784 B2 | 2/2012 | Zhu et al. |
| 2008/0155705 A1 | 6/2008 | Zank et al. |
| 2013/0291228 A1 | 10/2013 | Senger et al. |
| 2015/0203826 A1 | 7/2015 | Marty et al. |

FOREIGN PATENT DOCUMENTS

| CN | 1860211 A | 11/2006 |
| CN | 101980595 A | 2/2011 |
| WO | WO-2008/022963 A2 | 2/2008 |

OTHER PUBLICATIONS

GenBank: Accession No. AY332747.1, Retrieved from the Internet <https://www.ncbi.nlm.nih.gov/nuccore/AY332747.1?from=60&to=1397&sat=4&sat_key=3>, [Retrieved on Mar. 8, 2017].*
Arondel et al, Map-based cloning of a gene controlling omega-3 fatty acid desaturation in Arabidopsis, Science, 258(5086) : 1353-5 (1992) (Prior Art).
Balvo, et al, Genetic connection between fatty acid metabolism and sporulation in Aspergillus nidulans, J.Biol. Chem, 276(28):25766-74 (2001) (Prior Art).
Broadwater et al., Desaturation and hydroxylation. Residues 148 and 324 of *Arabidopsis* FAD2, in addition to substrate chain length, exert a major influence in partitioning of catalytic specificity, J. Biol. Chem., 277(18):15613-20 (2002).
Broun et al., Catalytic plasticity of fatty acid modification enzymes underlying chemical diversity of plant lipids, Science, 282(5392):1315-7 (1998).
Cases et al., Identification of a gene encoding an acyl CoA:diacylglycerol acyltransferase, a key enzyme in triacylglycerol synthesis, Proc. Natl. Acad. Sci. USA, 95(22): 13018-23 (1998).
Frentzen, Acyltransferases from basic science to modified seed oils, Fett/Lipid, pp. 161-166, vol. 100 (1998) (Prior Art).
Genbank AAQ98793, delta-4 fatty acid desaturase [Pavlova lutheri] (Nov. 7, 2003).
Genbank AY926606.1, Pavlova salina delta-4 desaturase (D4Des) mRNA, complete cds (Dec. 1, 2006).
International Preliminary Report on Patentability, International Application No. PCT/IB2013/056243, dated Feb. 3, 2015.
International Search Report, International Application No. PCT/IB2013/056243, dated Feb. 6, 2014.
Knutzon et al., Identification of Delta5-desaturase from Mortierella alpina by heterologous expression in Bakers' yeast and canola, J. Biol. Chem., 273(45):29360-6 (1998).
Lu et al., An enzyme regulating triacylglycerol composition is encoded by the ROD1 gene of *Arabidopsis*, Proc. Natl. Acad. Sci. USA, 106(44): 18837-42 (2009).
Mantle et al., Differentiation of Claviceps purpurea in axenic culture, J. Gen. Microbiol., 93(2):321-34 (1976).
Mey et al., The biotrophic, non-appressorium-forming grass pathogen Claviceps purpurea needs a Fus3/Pmk1 homologous mitogen-activated protein kinase for colonization of rye ovarian tissue, Mol. Plant Microbe Interact. 15(4):303-12 (2002).
Okuley et al., *Arabidopsis* FAD2 gene encodes the enzyme that is essential for polyunsaturated lipid synthesis, Plant Cell, 6(1):147-58 (1994).
Qi et al, Production of very long chain polyunsaturated omega-3 and omega-6 fatty acids in plants, Nat. Biotechnol., 22:739-45, vo. 22 (2004).

(Continued)

*Primary Examiner* — Suzanne M Noakes
*Assistant Examiner* — Jae W Lee
(74) *Attorney, Agent, or Firm* — Marshall, Gerstein & Borun LLP

(57) ABSTRACT

The invention provides nucleic acid molecules which encodes a novel fatty acid desaturase, KCS, KCR and/or LACS from *Thraustochytrium aureum* and *Sphaeroforma arctica*. The invention also provides recombinant expression vectors containing the nucleic acid molecules, host cells into which the expression vectors have been introduced, and methods for large-scale production of long chain polyunsaturated fatty acids (LCPUFAs), e.g., ARA, EPA and DHA and for screening for delta-4 desaturases.

4 Claims, 24 Drawing Sheets

(56) References Cited

OTHER PUBLICATIONS

Qui et al., Identification of a delta4 fatty acid desaturase from *Thraustochystrium* sp. involved in the biosynthesis of docosahexanoic acid by heterologous expression in *Saccharomyces cerevisiae* adn *Brassica juncea*, J. Biol. Chem., 276(34):31561-6 (2001).

Shanklin et al, Desaturation and related modifications of fatty acids, Plant Physiol. Plant Mol. Biol., 49:611-41 (1998).

Slabas, Acyltransferases and their role in the biosynthesis of lipids—opportunities for new oils, J.Plant Physiology, 158:505-13 (2001).

Tonon et al., Identification of a very long chain polyunsaturated fatty acid delta4-desaturase from the microalga *Pavlova lutheri*, FEBS Lett., 553:440-4 (2003).

Tudzinski et al, Biotechnology and genetics of ergot alkaloids, App. Microbiol. Biotechnol., 57:593-605 (2001).

UniProt No. D6NST0, Delta-4 fatty acid desaturase [Pavlova viridis].

Vrinten et al., Biosynthesis of long chain polyunsaturated fatty acids in the marine ichtyosporean *Sphaeroforma aractica*, Lipids, 48:263-74 (2013).

Xu et al., Heterologous overexpression of a novel delta-4 desaturase gene from the marine microalga Pavlova viridis in *Escherichia coli* as a Mistic fusion, World J. Microbiol. Biotechnol., 27:2931-7 (2011).

Zank, Cloning and functional expression of the first plant fatty acid elongase specific for delta6-polyunsaturated fatty acids, Biochemical Society Transactions, 28:654-8 (2000).

\* cited by examiner

Figure 2

```
Q6VPV2_PAVLU                                        ------------------------------------------MPPSAASE-GG--VAE--------
D6NST0_9EUKA                                        ------------------------------------------MPPSAAKDAGG--AAE--------
A0PJ29_9EUKA                                        ------------------------------------------MPPSAAKQMG--ASTG-------
d4Des(Sa)                                           ------------------------------------------MPPHSRTKVVSDSDPE-------
d4Des(Tc)                                           ------------------------------------------MTVG-------------------
Q8S3C0_9STRA-Thraustochytrium_sp_ATCC21685           ------------------------------------------MTVG-------------------
Q45G27_9STRA-Thraustochytrium_sp_FJN-10              ------------------------------------------MTVG-------------------
Q8GZS4_9STRA-Thraustochytrium_aureum                 ------------------------------------------MTVG-------------------
Q8GZS5_9STRA-Thraustochytrium_aureum                 ------------------------------------------MTVG-------------------
Q8GZS6_9STRA-Thraustochytrium_aureum                 ------------------------------------------MTVG-------------------
Q8GZS3_9STRA-Thraustochytrium_aureum                 ------------------------------------------MTVG-------------------
B8LEI2_THAPS-Thalassiosira_pseudonana                ------------------------------------MCNGNLPASTAQLK---------------
Q4G2T0_THAPS-Thalassiosira_pseudonana                ------------------------------------MGNGNLPASTAQLK---------------
Q6WNG7_EUGGR-Euglena_gracilis                       MLVLFGNFYVKQYSQKNGKPENGATPENGAKPQPCENGTVEKRENDTANVRPTRPAGPPP------
F2U823_SALS5-Salpingoeca                            ------------------------------------------------------------------
Q4QFK0_LEIMA-Leishmania_major                       ------------------------------------------------------------------

Q6VPV2_PAVLU                                        ------------LRA--AEVASYTRKAVDERPDLTIVGDA-------------------VYDAK
D6NST0_9EUKA                                        ------------LRA--AELASYTRKAVTERSDLTIVGDA-------------------VYDAK
A0PJ29_9EUKA                                        ------------VHAGVTDSSAFTRKDVADRPDLTIVGDS-------------------VYDAK
d4Des(Sa)                                           ------------LSDLKMKHFTREEILNHTNDKYCILEDG-------------------VYDLI
d4Des(Tc)                                           ------------YDEIPFEQVRAHNKPDDAWCAIHGH----------------------VYDVT
Q8S3C0_9STRA-Thraustochytrium_sp_ATCC21685           ------------YDEIPFEQVRAHNKPDDAWCAIHGH----------------------VYDVT
Q45G27_9STRA-Thraustochytrium_sp_FJN-10              ------------YDGEIPFEQVRAHNKPDDAWCAIHGH---------------------VYDVT
Q8GZS4_9STRA-Thraustochytrium_aureum                 ------------FDETVIMDTVRNHNMPDDAWCAIHGT---------------------VYDIT
Q8GZS5_9STRA-Thraustochytrium_aureum                 ------------FDETVIMDTVRNHNMPDDAWCAIHGT---------------------VYDIT
Q8GZS6_9STRA-Thraustochytrium_aureum                 ------------FDETVIMDTVRNHNMPDDAWCAIHGT---------------------VYDIT
Q8GZS3_9STRA-Thraustochytrium_aureum                 ------------FDETVIMDTVRNHNMPDDAWCAIHGT---------------------VYDIT
B8LEI2_THAPS-Thalassiosira_pseudonana                ------STSKPQQQHEHRTISKSELAQHNTPKSAWCAVHSTPATDPSHSNNKQHAHLVLDIT
Q4G2T0_THAPS-Thalassiosira_pseudonana                ------STSKPQQQHEHRTISKSELAQHNTPKSAWCAVHSTPATDPSHSNNKQHAHLVLDIT
Q6WNG7_EUGGR-Euglena_gracilis                       ATYYDSLAVSGQGKERLFTTDEVRRHILPTDGWLTCHEG--------------------VYDVT
F2U823_SALS5-Salpingoeca                            -------------MTTVVVDGR-------------------------------------AYDGE
Q4QFK0_LEIMA-Leishmania_major                       ------------MNQCCHSHLSTLEPMPDLKKDVLSIDGI-------------------YYDTE
```

```
Q6VPV2_PAVLU                                    AFRDEHPGGAHFVSLFGGRDATEAFMEYHRRAWPKARMSKFFV---------------------
D6NST0_9EUKA                                    AFREEHPGGAHFVSLFGGRDATEAFMEYHRRAWPKARMSKFFV---------------------
A0PJ29_9EUKA                                    AFRSEHPGGAHFVSLFGGRDATEAFMEYHRRAWPKSRMSRFHV---------------------
d4Des(Sa)                                       NFRDKHPGG-DVLDFFPGQDATPHFYMLHQYESLPSVLAEYKV---------------------
d4Des(Tc)                                       KFASVHPGG-DILLLAAGKEATVLYETYHVRGVSDAVLRKYRIGKLPDGQGGANEKEKRT
Q8S3C0_9STRA-Thraustochytrium_sp_ATCC21685       KFASVHPGG-DILLLAAGKEATVLYETYHVRGVSDAVLRKYRIGKLPDGQGGANEKEKRT
Q45G27_9STRA-Thraustochytrium_sp_FJN-10          KFASVHPGG-DILLLAAGKDATVLYETYHVRGVSDAVLRKYRIGKLPDGQGGANEKEKRT
Q8GZS4_9STRA-Thraustochytrium_aureum             KFSKVHPGG-DIIMLAAGKEATILFETYHIKGVPDAVLRKYKVGKLPQGKKGETS----HM
Q8GZS5_9STRA-Thraustochytrium_aureum             KFSKVHPGG-DIIMLAAGKEATILFETYHIKGVPDAVLRKYKVGKLPQGKKGETS----HM
Q8GZS6_9STRA-Thraustochytrium_aureum             KFSKVHPGG-DIIMLAAGKEATILFETYHIKGVPDAVLRKYKVGKLPQGKKGETS----HM
Q8GZS3_9STRA-Thraustochytrium_aureum             KFSKVHPGG-DIIMLAAGKEATILFETYHIKGVPDAVLRKYKVGKLPQGKKGETS----HM
B8LEI2_THAPS-Thalassiosira_pseudonana            DFASRHPGG-DLILLASGKDASVLFETYHPRGVPTSLIQKLQIGVMEEEA--------------
Q4G2T0_THAPS-Thalassiosira_pseudonana            DFASRHPGG-DLILLASGKDASVLFETYHPRGVPTSLIQKLQIGVMEEEA--------------
Q6WNG7_EUGGR-Euglena_gracilis                    DFLAKHPGGG-VITLGLGRDCTILIESYHPAGRPDKVMEKYRIGTLQDPK--------------
F2U823_SALS5-Salpingoeca                         RFARVHPGGHTFVALYGGRDASDAFATYHRRRFPHEKMAQYRIEEKQQASTCALCVAEKE
Q4QFK0_LEIMA-Leishmania_major                    KLALMHPGGAMVVRLCNGRECTAIFLSYHRRRFPHALYEKYQVPKDQ-------V Q6VPV2_PAVLU                                    -GSLDASEKPTQADSAYLRLCAEVNALLPKGSG---GFAPPSYWLKAAALVVAAVSIEGYM
D6NST0_9EUKA                                    -GSLAPSEKPTQVDEGYLRLCAEVNGLLPKGSG---GFAPASYWLKAAALIVAALTLEGYM
A0PJ29_9EUKA                                    -GSLASTEEPVAADEGYLQLCARIAKMVPSVSS---GFAPASYWVKAGLILGSAIALEAYM
d4Des(Sa)                                       -GSVARDDSYVYHTPLMKQIKSAVRKVMPMQEW---WAPPSWYIKACAILAATLYTDYLW
d4Des(Tc)                                       LSGLSSASYYTW-NSDFYRVMRERVVARLKERGKARRGGYELWIKAFLLLVGFWSSLYWM
Q8S3C0_9STRA-Thraustochytrium_sp_ATCC21685       LSGLSSASYYTW-NSDFYRVMRERVVARLKERGKARRGGYELWIKAFLLLVGFWSSLYWM
Q45G27_9STRA-Thraustochytrium_sp_FJN-10          LSGLSSASYYTW-NSDFYRVMRERVVARLKERGKARRGGYELWIKALLLLVGFWSSLCWM
Q8GZS4_9STRA-Thraustochytrium_aureum             PTGLDSAFYYSW-DSEFYRVLRERVAKKLAEPGLMQRARMELWAKAIFLLAGFWGSLYAM
Q8GZS5_9STRA-Thraustochytrium_aureum             PTGLDSASYYSW-DSEFYRVLRERVAKKLAEPGLMQRARMELWAKAIFLLAGFWGSLYAM
Q8GZS6_9STRA-Thraustochytrium_aureum             PTGLDSASYYSW-DSEFYRVLRERVAKKLAEPGLMQRARMELWAKAIFLLAGFWGSLYAM
Q8GZS3_9STRA-Thraustochytrium_aureum             PTGLDSASYYSW-DSEFYRVLRERVAKKLAEPGLMQRARMELWAKAIFLLAGFWGSLYAM
B8LEI2_THAPS-Thalassiosira_pseudonana            ----FRDSFYSWTDSDFYTVLKRVRVVERLEERGLDRRGSKEIWIKALFLLVGFWYCLYKM
Q4G2T0_THAPS-Thalassiosira_pseudonana            ----FRDSFYSWTDSDFYTVLKRVRVVERLEERGLDRRGSKEIWIKALFLLVGFWYCLYKM
Q6WNG7_EUGGR-Euglena_gracilis                    ---------TFYAWGESDFYPELKRRALARLKEAGQARRGG--LGVKALLVLTLFFVSWYMW
F2U823_SALS5-Salpingoeca                         AGMTASTSSTCQQDEDFFELCKEVNSFLYKTHRNKGFAPTRYFAKAILLMALEMFFE-YQ
Q4QFK0_LEIMA-Leishmania_major                    HPDSLIEQRQQPSYDSYLQLCKRIQPIIAPTKG---FAPWYFYLKAATWLAVMLGLDLYS
```

Figure 2 (continued)

```
Q6VPV2_PAVLU              LLR------GKTLLLSVFLGLVFAWIGLNIQHDANHGALSRHSVINYCLGYAQDWIGGNM
D6NST0_9EUKA              LLR------GKTLFLSVLLGLVFAWIGLNIQHDANHGALSRYPAVNYCLGYMQDWIGGNM
A0PJ29_9EUKA              LYA------GKRLLPSIVLGWLFALIGLNIQHDANHGALSKSASVNLALGLCQDWIGGSM
d4Des(Sa)                 IAS------GPTIPLAIVSGLLYAAIGLNIQHDANHGSVSRNPMVNRLFGYSQDWIGGSR
d4Des(Tc)                 CT----LDPSFGAILAAMSLGVFAAFVGTCIQHDGNHGAFAQSRWVNKVAGWTLDMIGASG
Q8S3C0_9STRA-Thraustochytrium_sp_ATCC21685  CT----LDPSFGAILAAMSLGVFAAFVGTCIQHDGNHGAFAQSRWVNKVAGWTLDMIGASG
Q45G27_9STRA-Thraustochytrium_sp_FJN-10     CT----LDPSFGAILAAMSLGVFAAFVGTCIQHDGNHGAFAQSRWVNKVAGWTLDMIGASG
Q8GZS4_9STRA-Thraustochytrium_aureum        CV----LDPHGGAMVAAVTLGVFAAFVGTCIQHDGSHGAFSKSRFMNKAAGWTLDMIGASA
Q8GZS5_9STRA-Thraustochytrium_aureum        CV----LDPHGGAMVAAVTLGVFAAFVGTCIQHDGSHGAFSKSRFMNKAAGWTLDMIGASA
Q8GZS6_9STRA-Thraustochytrium_aureum        CV----LDPHGGAMVAAVTLGVFAAFVGTCIQHDGSHGAFSKSRFMNKAAGWTLDMIGASA
Q8GZS3_9STRA-Thraustochytrium_aureum        CV----LDPHGGAMVAAVTLGVFAAFVGTCIQHDGSHGAFSKSRFMNKAAGWTLDMIGASA
B8LEI2_THAPS-Thalassiosira_pseudonana       YTTSDIDQYGIAIAYSIGMGTFAAFIGTCIQHDGNHGAFAQNKLLNKLAGWTLDMIGASA
Q4G2T0_THAPS-Thalassiosira_pseudonana       YTTSDIDQYGIAIAYSIGMGTFAAFIGTCIQHDGNHGAFAQNKLLNKLAGWTLDMIGASA
Q6WNG7_EUGGR-Euglena_gracilis               VA-------HKSFLWAAVWGFAGSHVGLSIQHDGNHGAFSRNTLVNRLAGWGMDLIGASS
F2U823_SALS5-Salpingoeca                    LIT------APTLLKGFVVGLLVALIGLNIQHDANHGSLSPKPWVNTLFGFAQDWIGGNS
Q4QFK0_LEIMA-Leishmania_major               LFY------RRAYFLTVIQSLSMAMVGLNVQHDANHGALSCDWRVNRILGLSQDLLGGSS Q6VPV2_PAVLU              VLWLQEHVVMHHLHT-----------NDVDADPDQ-KAHGVLRLKPTDGW
D6NST0_9EUKA              VLWLQEHVVMHHLHT-----------NDVDHDPDQ-KAHGALRLKPTDSW
A0PJ29_9EUKA              ILWLQEHVVMHHLHT-----------NDVDKDPDQ-KAHGALRLKPTDAW
d4Des(Sa)                 MLWIRQHVVGHHTHC-----------NRHQHDPDV-KGGSVITLSRYSLP
d4Des(Tc)                 MTWEFQHVLGHHPYTNLIEEENGLQKVSGKKMDTKLADQESDPDVFSTYPMRLHPWHQK
Q8S3C0_9STRA-Thraustochytrium_sp_ATCC21685  MTWEFQHVLGHHPYTNLIEEENGLQKVSGKKMDTKLADQESDPDVFSTYPMRLHPWHQK
Q45G27_9STRA-Thraustochytrium_sp_FJN-10     MTWEFQHALGHHPYTNLIEEENGLQKVSGKKMDTKLADQESDPDVFSTYPMRLHPWHQK
Q8GZS4_9STRA-Thraustochytrium_aureum        MTWEMQHVLGHHPYTNLIEMENGLAKVKGADVDPKKVDQESDPDVFSTYPMLRLHPWHRQ
Q8GZS5_9STRA-Thraustochytrium_aureum        MTWEMQHVLGHHPYTNLIEMENGLAKVKGADVDPKKVDQESDPDVFSTYPMLRLHPWHRQ
Q8GZS6_9STRA-Thraustochytrium_aureum        MTWEMQHVLGHHPYTNLIEMENGLAKVKGADVDPKKVDQESDPDVFSTYPMLRLHPWHRQ
Q8GZS3_9STRA-Thraustochytrium_aureum        MTWEMQHVLGHHPYTNLIEMENGLAKVKGADVDPKKVDQESDPDVFSTYPMLRLHPWHRQ
B8LEI2_THAPS-Thalassiosira_pseudonana       FTWELQHMLGHHPYTNVLDGVEEERKERGEDVALEEKDQESDPDVFSSFPLMRMHPHHTI
Q4G2T0_THAPS-Thalassiosira_pseudonana       FTWELQHMLGHHPYTNVLDGVEEERKERGEDVALEEKDQESDPDVFSSFPLMRMHPHHTI
Q6WNG7_EUGGR-Euglena_gracilis               TVWEYQHVIGHHQYTNLVS-------DTLFSLPENDPDVFSSYPLMRMHPDTAW
F2U823_SALS5-Salpingoeca                    LLWLQQHVAIHHVEC-----------NDLDHDKDM-LETPLLRFSPLHGK
Q4QFK0_LEIMA-Leishmania_major               ISWIVNHDYVHHVYT-----------NEPGRDADL-EIP-LLRLHSGIPV
```

Figure 2 (continued)

```
Q6VPV2_PAVLU                              MPWHALQQLYILPGEAMYAFKLLFLDALELLAWRWEG--EKISPLARAL-FAPAVACKLG
D6NST0_9EUKA                              LPWHSLQQVYILPGEAMYAFKLLSLDALELLAWRWEG--EPISQLAAPL-YAPAVVCKLA
A0PJ29_9EUKA                              SPMHWLQHLYLLPGETMYAFKLLFLDISELVMWRWEG--EPISKLAGYL-FMPSLLLKLT
d4Des(Sa)                                 KEFHHIQQYFLPLIQLLGFQWVFLGLHDLIEMKYKG--EKLPESYRKE-RNIAIGLRVF
d4Des(Tc)                                 RWYHRFQHIYGPFIFGFMTINKVVTQDVGVVLRKRLFQIDAECRYASPMYVARFWIMKAL
Q8S3C0_9STRA-Thraustochytrium_sp_ATCC21685 RWYHRFQHIYGPFIFGFMTINKVVTQDVGVVLRKRLFQIDAECRYASPMYVARFWIMKAL
Q45G27_9STRA-Thraustochytrium_sp_FJN-10   RWYHRFQHIYGPFIFGFMTINKVVTQDVGVVFRKRLFQIDAECRYASPMYVARFWIMKAL
Q8GZS4_9STRA-Thraustochytrium_aureum      RFYHKFQHLYAPFIFGFMTINKVISQDVGVVLRKRLFQIDANCRYGSPWYVARFWIMKLL
Q8GZS5_9STRA-Thraustochytrium_aureum      RFYHKFQHLYAPFIFGFMTINKVISQDVGVVLRKRLFQIDANCRYGSPWYVARFWIMKLL
Q8GZS6_9STRA-Thraustochytrium_aureum      RFYHKFQHLYAPLIFGFMTINKVISQDVGVVLRKRLFQIDANCRYGSPWNVARFWIMKLL
Q8GZS3_9STRA-Thraustochytrium_aureum      RFYHKFQHLYAPFIFGSMTINKVISQDVGVVLRKRLFQIDANCRYGSPWYVARFWIMKLL
B8LEI2_THAPS-Thalassiosira_pseudonana     SWYHKYQHLYAPPLFALMTLAKVFQQDFEVATSGRLYHIDANVRYGSVWNVMRFWAMKVI
Q4G2T0_THAPS-Thalassiosira_pseudonana     SWYHKYQHLYAPPLFALMTLAKVFQQDFEVATSGRLYHIDANVRYGSVWNVMRFWAMKVI
Q6WNG7_EUGGR-Euglena_gracilis             QPHHRFQHLFAFPLFALMTISKVLTSDFAVCLSMKKGSIDCSSRLVPLEGQLLFWGAKLA
F2U823_SALS5-Salpingoeca                  YAWQALQHVYFVLLEAGYATKVLLADWYNLLMNMYEG--VPISPLVRPWRWASVAARVV
Q4QFK0_LEIMA-Leishmania_major             RLAHCLQQFYIFFLEAVFGPVHVLFN------IIFLAKG--PSEKQRLIKTQWVSLCMLSI Q6VPV2_PAVLU                              FWARFVALPLWLQPTVHTALCICATVCTGSFYLAFFFISHNFDGVGSVGPKG--------
D6NST0_9EUKA                              FWARFVALPLWLQPSLHTAACICATVCTGSFYLAFFFISHNFDGVASVGPQG--------
A0PJ29_9EUKA                              FWARFVALPLYLAPSVHTAVCIAATVMTGSFYLAFFFISHNFEGVASVGPDGS-------
d4Des(Sa)                                 FFIRKFVVPFALHFSWYTLLCTYLWMAIAALYLGFFFLSHIFVGAKSLPEDAK-------
d4Des(Tc)                                 TVLYMVALPCYMQGPWHGLKLFAIAHFTCGEVLATMFIVNHIIEGVSYASKDAVKGT---
Q8S3C0_9STRA-Thraustochytrium_sp_ATCC21685 TVLYMVALPCYMQGPWHGLKLFAIAHFTCGEVLATMFIVNHIIEGVSYASKDAVKGT---
Q45G27_9STRA-Thraustochytrium_sp_FJN-10   TVLYMVALPCYMQGPWHGLKLFAIAHFTCGEVLATMFIVNHVIEGVSYASKDAVKGT---
Q8GZS4_9STRA-Thraustochytrium_aureum      TTLYMVALPCYMQGPWHGLKLFFMAHFTCGEVLATMFIVNHIIEGVSYASKDAVKGV---
Q8GZS5_9STRA-Thraustochytrium_aureum      TTLYTVALPMYMQGPAQGLKLFFMAHFTCGEVLATMFIVNHIIEGVSYASKDAVKGV---
Q8GZS6_9STRA-Thraustochytrium_aureum      TTLYMVALPMYMQGPAQGLKLFFMAHFTCGEVLATMFIVNHIIEGVSYASKDAVKGV---
Q8GZS3_9STRA-Thraustochytrium_aureum      TTLYMVALPMYMQGPAQGLKLFFMAHFTCGEVLATMFIVNHIIEGVSYASKDAVKGV---
B8LEI2_THAPS-Thalassiosira_pseudonana     TMGYMMGLPIYFHGVLRGVGLFVIGHLACGELLATMFIVNHVIEGVSYGTKDLVGGASHG
Q4G2T0_THAPS-Thalassiosira_pseudonana     TMGYMMGLPIYFHGVLRGVGLFVIGHLACGELLATMFIVNHVIEGVSYGTKDLVGGASHG
Q6WNG7_EUGGR-Euglena_gracilis             NFLLQIVLPCYLHGTAMGLALFSVAHLVSGEYLAICFIINHISESCEFMN----------
F2U823_SALS5-Salpingoeca                  WTLRLIVIPLYLHSWQVYLPCLAVMAMVGGFYLAFFFLLSHNFEGVYHVLVPSSDPV---
Q4QFK0_LEIMA-Leishmania_major             IPYRLLCNFLHATSFCDGLMSCVLQYAFGGFYLAYFFLLSHNFDGAKKVGTSD-------
```

```
Q6VPV2_PAVLU                                         SMLQHMGKMGTRPG--AEKGGKAE-----------------------------
D6NST0_9EUKA                                         AMMSHLGKMAARPTS-ADKLARPSEKSSVECRLRLGAACARGSQASDAASLISWLG
A0PJ29_9EUKA                                         STLRHMYALGRRPRSKAE--------------------------------------
d4Des(Sa)                                            STFRQVKALGSVAVYN-EFMEGL---------------------------------
d4Des(Tc)                                            KMLEHLRQLGNEETHESWQRAA----------------------------------
Q8S3C0_9STRA-Thraustochytrium_sp_ATCC21685            KMLEHLRQLGNEETHESWQRAA----------------------------------
Q45G27_9STRA-Thraustochytrium_sp_FJN-10               KMLEHLRRLGNEETHESWQRAA----------------------------------
Q8GZS4_9STRA-Thraustochytrium_aureum                  KMLSHLRTLGNED-LTAWST------------------------------------
Q8GZS5_9STRA-Thraustochytrium_aureum                  KMLSHLRTLGNED-LTARST------------------------------------
Q8GZS6_9STRA-Thraustochytrium_aureum                  KMLSHLRTLGNED-LTAWST------------------------------------
Q8GZS3_9STRA-Thraustochytrium_aureum                  KMLSHLRTLGNED-LTAWST------------------------------------
B8LEI2_THAPS-Thalassiosira_pseudonana                 KMISHLKFLGKAKCE-----------------------------------------
Q4G2T0_THAPS-Thalassiosira_pseudonana                 KMISHLKFLGKAKCE-----------------------------------------
Q6WNG7_EUGGR-Euglena_gracilis                         GMVQHLRLMGAPPVPTNGDKKS----------------------------------
F2U823_SALS5-Salpingoeca                              STSNFLRAQGISSL----------------------------------MKRKV---
Q4QFK0_LEIMA-Leishmania_major                         STFRHMEQYGRGRE----------------------------------KRKSA---
```

>SEQ-87 - 92.6% sequence identity to SEQ ID NO 79
MPPHSRTKVGDPELSDLMKHFTREEILNHTNDDYCILEDGVYDLVNFRDKHPGGDVVDFFPGQDATPHFYMYHQYESPPSVLAEYKVGSIARDDSYVYHTPLMKQICSEVRKV
MPMQEGWAPPSWYIKACAILAATLYTDYLWIASGPTIPLAIVSGLLYAAIGLNIQHDANHGSVSRNPMVNRLFGYSQDWIGGSRMLWIQQHVGHHTCNRIQHDPDVKGGSV
IRLSRYSLPKPFHHIQQYFLPLEQLLGFQMVFLGAHDLIEMRYKGEKLPESYRKERNIAIGLRVFFVRKFAVPLALHFSWYTLLCTYLWMCIAALYLGFFILSHIFVGAK
SLPEDANIDWARHQIESSSNVCGEKLGISNGLNFQIEHHLFPRMSHAHYSKIQPVVQKVCEENGVNYKKFGTIGSNLGSLFRQLKALGSVAIYEFMEGL >SEQ-88 - 91.9% sequence identity to SEQ ID NO 79
MPPHSRTKGSDPELSDMKHFTREEILNHTRDKYCILEDGVYDLTNFRDKHPGGDFLDLFPGQDATPHFYMLHQKESPPSVLAEYKVGSLARDDSYTHHTALMKQIKSAVRKVM
PMQEWWAPPSWYIKACAILAATLYTDYLWIASGPTIFLAIVSGLLYAAIGLNIQHDANHGSVSRNPVVNRLFGYSQDWIGGSRMLWIRQHVVGHHTCNRHQHDPDVKGGSVI
TLSRYSLPKPWHHIQQYFLPLIQLLGFQWVFLGLHDLIEMKYKGEKIPESYRKERNIAIGCRVFFVRKFAVPFALHPSWYTLLCTYLWMAIGAFYLGFFILSHNFVGIKS
LPEDANIEWARHQIESSSNVCGEKLGISNGGLNYQIEHHLFPRMSHAHYSKIQPVVQKVCEENGVNYKHFGTILSNLDSTFRQVGALGAVAIYEFMAGL >SEQ-89 - 91.7% sequence identity to SEQ ID NO 79
MPPHSRTKVSDPELSDMKHFTREEILDHTNDKYCILEDGVYDLTNFRDKHPGGDVLDFFPGQDATPHFYELHRYESLPSVLAEYKVGSVARDDSYVYATPLMKQIKSAVRKVI
PMQEWWAPPSWWIKACAILAAALYTDYLWIASGPTIPLAIVIGLLYAAIGLNIQHDANHGSISRNPMVNRLFGYSQDWIGGSRMLWIRQHVVGHHTCNRHDHDPDVKGGSVI
TLSPYSLPKEFHHIQQLYFLPLPLEQLLGFWVFLGLHDLIEWKYKGEKLPELYRKERNIAIGCRIEFFARKFVIPFALHFSWYTLLCVYLWMATASLYLGFFILSHIFIGAKS
LPEDANIDWARHQIESSSNVGGEKLGILNGGLNYQIEHHLFPRMSHAHYSKIQPVVQKVCEENGVNYKKFGTILSNLDSMFRHVKALGSVAVEFMAGL >SEQ-90 - 91.7% sequence identity to SEQ ID NO 79
MPPHSRTKVSDAELSDMKHFTRERILNHTNDKICILGDGVYDLSNFRDKHPGGDVLDFFPGQDATPHFYMFHKYASLPSVLAEYKVGSLARDDSYVQHTELMKQIKSAVRAVM
PMQEWWAPPSWYIKACALIAATLYTDYLWIARGPTIFLGIVSGLLYAAIGLNIQHDANHGSVSRNPVVNRLFGYSQDWIGGSRVLWIRQHVVGHHTNDHQHDPDVKGGGVI
KLSPVSLPLEFHHIQQYFLPLDQLLGFWVFLGLHDLIEMKWKGEKLPELYRKEYNIAIGLRVFFIRKEYNIAIGLRVFFIRKFVVPFALHFSWYTLICTYLWMATAALYLAFFILSHIFVGAKS
LPEDAKNIDWARHQIESSSNVCGEKLGISNGGLNYQIEHHLFPRMNHAHYSKIEPVVQKVCEENGVNYKKFGTILSNLDSTFRQVKALGSVPVYEFMEGL >SEQ-91 - 91.7% sequence identity to SEQ ID NO 79
MPPSSRKVSDPELSDMKHFTRERILNHTNDKYCIVEDGVYDLPNFRDKHPGGDVLDFFGGQDATPHFFMFHQYESLPSVLAEYKVGSLARDDSYVYHTELMKQIKSAVRKVI
PMQEWWAPPSWYIKACAILAATLYTDYLWIAKGPTIPLAIVLGLLYAAIGLNIQHDANHGSVSRNPMVNRLFGYSQDWIGGSRVLWIRQHVVGHHTCNRIQHDPDVKGGSVI
TLSRYSLPMEFHHIQQYFLPLDQLLGFWVFLGLHELIEMKWKGEKLPESYRKERNIAVGCRVFFARKFVVPFALEFSWYTLLCTYLWMAIAAFYLGFFILSHIFVGAKS
LGEDAKNIDWARHQIESSSNVCGEWLGILNGGLNYQIEHHLFPRMNHAHYSKIEPVVQKVCEENGVNYKKFGTILSNLDSMFRQVKALGSVAVEFMEGL >SEQ-92 - 91.7% sequence identity to SEQ ID NO 79
MPPYSRTEVVSDPELKDMEHFSREEILNHTDKYCILGDGVYDLTNFRDKHPGGEFLSFFPGQDATPHFWMLHQRESLPGVLAEYKVGSVARDDSYVYHDPLMKRICSAVRGV
MPMQEWWAPPSWYIKACAILAATLYTDYLWIASGPTIPLAIVSGLLYAAIGLNIQHDANHGSLSRNPMVNRLFGYSQDWIGGSRMWLRQHVVGHHTCNRHQHDPDVKGGSV
ITLSPYSLPKEFHHIQQLYFLPLIQLLGFQMVFLGLHLIEMKYKGEKLPEIYRKERNPAIGLRLFFFIRKFVVPLALHFSWYTLLCTYLWMAIAALYLGFFILSHIFLGGL
SLPEDANIDWARHQIESSSNVCGEKLGIMNGGLNYQIEHHLFPRMSHAHYSKIQPVVQKVCEENGVNYKHFGTILSNLDSTFRQVKALGSVPTYEFLGGL >SEQ-93 - 91.7% sequence identity to SEQ ID NO 79
MPPHSRTKVSDDPELSDLMKHFAREEILNDNDDYCILEDGVYDLTNFRDKHPGGDVLDFFPGQDATPHFYMFHQYESLPSVLAKYKVGSVARDDSYVYHTPLMLQIKSEVRA
VLPMQEWWAPPSWYIKACAILAATLYTDYLWIASGPTIFLAIVSGLLYAAIGLNIQHDANHGSVSRNPMVNRLFGYSQDWIGGSRMLWIRQHVVGHHTHCNDHQHDPDVKGGS
AITLSPTSLPKEFHHIQQYFLPLDQLYGFQWVFLGLHDLIEMKYEGEKLPEIYRKERNIAIGLRVFFVRKFAIPFALHFSWYTLLCTYLMWAIAALYLGFFFILSHIFVGV
KSLGEDGKNIDWARHQIESSSNVCGEKLGISNGGLNYQIEHHLFPRMNHAHYSTIQPIVQRVCEENGVNYKKFGTILSNLDSTFSQIKALGSVAVYEFMEKI >SEQ-94 - 91.5% sequence identity to SEQ ID NO 79
MPPHSRTKVSDDPELSDMKHFARERIANHTNDRKYCILEDGVYDLTNFRDKHPGGDVLDIFPGQDATPHFYMYHQKEMPPSVLAEYKVGSVARDDSYVYHTPLQKQLKSAVRKVM
PKGSWWAPPSWYIKACAILAATLYLDYLWILSGPTIPLAIVIGLLYAAIGLNIQHDANHGSVSRNPMVNRLFGYGQDWIGGSRMLWIRQHVVGHHTHCNRVQHDPDIKGGSVI
TLSRYSLPLEFHHIQQYFLPLEQLLGFQWVFLGAHDLIEMKYKGEKLPESYRKEYNIAIGLRVFFWIRKFVVPFALHFSWYTLLCTYLMATAALYLGFFILSHIFIGAKS
LPEDANIDWARHQIESSSNVCGDKLGISNGGLNYQIEHHLFPRMSHAHYSKIQPVVQKVCEEMGVNYKKFGTIGSNLDSTFRYVKALGSVAVEFMEGL >SEQ-95 - 91.5% sequence identity to SEQ ID NO 79
MPPHSRTKVSDPELSDMKHFTREKILNHTNDRKYCILGDGVYDCTNFRDKHPGDGFLDFFGGQDATPHFYQLHQYESLPSVLAKYKVGSVARDDSYVYHHTELMKQIKSAVRAVM
PMGEWWAPPSWYIKACAILAATLYTDYLWIASGPTILLAIVIGLLYAAIGLNIQHDANHGAVSRNPMVNRLFGYSQDWIGGSRMLWIRQHVVGHHLHCNRIQHDPDVKGGSVI
TLSRYSLPMEFHHIQQYFLPLIQLYGFQWVFLGLNDLIEMKYKGEKLPESYRKERNIAIGCRVFFIRKFAVPFALHFSWYTLLCTCLWMAIAALYLGFFFILSHIFVGAKS
LPEDANIDWARHQIESSSNVGGEWLGIMNGGLNYQIEHHLFPRMSHAHYSKIQPIVQRVCEENGVNYKHFPTILSNLGSTFRYIGALGSVPVYEFMEGL >SEQ-96 - 91.5% sequence identity to SEQ ID NO 79
MPPHSRTKVSDPELSDMKHFTYEEILNHTNDRKYCILEDGVYDLTNFRDKHPGGDVLDFFPGQDATPHFYQLHQREWPPSIMAEYKVGSVDRDDSYVYHTSLMKQICCAVRKVM
PRQSWWAPPSWYIKACALLAATLYLDYLWIASGPTILLAIVSGLLYAAIGLNIQHDANHGSLSRNPMVNRLFGYSQDWIGGSRMLWIRQHVVGHHTHCNRHQHDPDVKGGSAI
TLSPYSLPKEFHHIQQYFLPLIQLYGFQWVFLGLHDLIEMKYKGEPLSEIYRKERNPAIGLRIFFFIRKFVVPFALHFSWYTLLCTYLMAIAALYLGFFFILSHIFVGAKS
LPEDANIDWARHQIESSSNVCGEKLGIMNGGLNYQIEHHLFPRMSHAHYSKIQPVVQKICEDNGVNYKKFGTILSNLDSTFRYVKALGSVAVEFMEKL >SEQ-97 - 91.2% sequence identity to SEQ ID NO 79
MPPHSRTKGSDPELSDMKHFTREEKLNHTRDKICILGDGVYDLVCFRDEHPGGDVVDFFPGQDATPHFYMLHQYEWMLPSVLAEYKVGSVARDDSYVYHTPLMKSAVRAVM
PMQEGWAPPSWYIKACALIVATLYTDYLWIASGPTIPLAIVSGLLYAAIGLNIQHDANHGSVSRNPMVNRLFGYSQDWIGGSRMLWIRQHVVGHHTHCNDHQHDPDIKGGSVI
TLKRYDLWLPFHHIQQYFLPGIQLLGFQWVFLGLHDLIEMKYKGEKLPPSYRKLRNIAIGLRVFFIRKFVVPFALHFSWYTLLCIYLMAIAALYLAFFFILSHIFVGVKS
LPEDANIDWARHQIESSSNVCGEKLGISNGGLNYQIEHHLFPRMSHAHYSKIQPVVQKVCEENGINYKKFGTIASNLDSTFRQVKALGSVPVEFMEGL >SEQ-98 - 91.2% sequence identity to SEQ ID NO 79
MPPHARTKVSDPELSDMKHFTREEILNHTNDDYCILGDGVYDSTNFRDKHPGDGVLDFFPGQDATPHFYMLHQYESLPSVLARYKVGSVARDDSFTYHTPLMKQIKSEVRKIL
PMGEWWAPPSWYIKACALLAATLYLDYLWIASGPTIPLAIVSGLLYAAIGLNIQHDANHGSLSRNPVVNRLFGYSQDWIGGSRVLWIQHVVGHHTHCNRHQHDPDVKGGSVI
TLSRYSLPKEFHHIQQYFLPLEQLLGFQWVFLGLNDLIEWKYKGEKLPESYRKDRAIAIGLRVFFIRKFVIPFALHFSWYTLLCVYLMAIAALYLCFFFILSNLDATFRQVKALGSVAVEFMEKL
LPEDANIDWARHQIESSSNVCGEKLGILNGGLNYQIEHHLFPRMSHAHYSKIAPVVQKVCEENGVNYKKFGTILSNLDATFRQVKALGSVAVEFMEKL

Figure 3 (continued)

>SEQ-99 - 91% sequence identity to SEQ ID NO 79
MPPHSATKGSDVPELSDAKHFAREEILNHTRDKYCILGDGVYDSTAFRDKHPGGDYLDFFPGQDATPHFYQFHQYASLPSVLAEYKVGSVARDDSYVQHTELMKQICSAVRKV
MPMQEWWAPPSWYIKACALLAATLYTDYLMIASGPTIPLAIVSGLLYAWIGLNIQHDANHGSVSRNPMVNRLFGYSQDWIGGSRMLWIRKHVVGHHTHCNRVQHDPDVKGGSV
ITLSRYSLPLEWHHIQQIYFLPLIQLYGFQWVFLGLHDLLEMKYGEKLPPIYRKERNIAIGCRVFFFIRKFVVPFALHFTWYTLLCTYLWMAIAALYLGFFILSHIFVGAK
SLPPDANIDWARHQIESSSNVCGEKLGIINGGLNYQIEHHLFPRMSHSHYSKIQPVVQKVCEENGVNYKKFGTILSNLDSTFKQVKALGSVAVYEFMEGL >SEQ-100 - 91% sequence identity to SEQ ID NO 79
MPPHSRTEVSDPELSDLMKHFTREEILNHNNDKYCILEDGVYDLTCFRDKHPGGDVLDFFPGQDATPGFYMLHQYASPPSVLAEYKVGSVERDDSYVQHTSGMKQIKSAVRAV
MPMQEWWAPPSWWIKACAILAATLYTDYLMIASGPTIPLAIVIGLLYAAIGLNIQHDANHGSISRNPMVNRLFGYSQDWIGGSRMLWIRQHVGHHTHCNRHQHDPDIKGGSV
ITLSPYSLPKEFHHIQQYYFLPLDQLYGFQWVFLGLHDLIDWKYKGEKLPESYRPDFNIAIGLRVFFFARFFAVPFALHFSWYTLLCTYLWVAIAALYLGFFILSHIFIGIK
SLPEDAKNIDWARHQIESSSNVCGEKLGHSNGGLNYQIEHHLFPRMSHAHYSKIQPVVQKVCEENGVNYKKFPTILSNLDSLFRQVKGLGSVATEFMEGL >SEQ-101 - 91% sequence identity to SEQ ID NO 79
MPPHSRTKGSDPELSDLMKHFTREEILGHTNPDYCILGDGVYDLTNFRDEHPGGDVLDFFPGQDATPHFFQFHQREWLPSVLAEYFVGSVARDDSYVQHTSLMKQIKSAVRKV
MPMGEWWAPPSWYIKACAILVATLYTDYLMIASGPTIPLAIVIGLLYAAIGLNIQHDANHGSVSRNPMVNRLFGYSQDWIGGSRMLWIRQHVGHHTHCNRIQHDPDVKGGSV
LTLSRYSLPKEFHHIQQYFFLPLIQLLGFQWVFLGLHDLIEMKYKGEKLPESYRKEYNIAIGLRVFFARKVVVPFALHFSWYTLLCIYAWMASASLYLGFFILSHLFVGAK
SLPEDANIDWARHQIESSSNVCGEKLGHSNGGLNYQIEHHLFPRMSHAHYSKIQPVVQKICEENGVNYKHFGTILSNLDSTFRQVKALGSVAVYEFMEKP >SEQ-102 - 91% sequence identity to SEQ ID NO 79
MPPHSRRKVSDPELSDLMKHFTRERILNHTRDKYCILEDGVYDLTNFRDKHPGGDVLDFFPGQDATPHFYQYHQESLPSVLARYKVGSVERDDSYVYHDPLMLQIKSAVRKV
IPMQEWWAPPSWYIKACALIVATLFTDYLMIASGPTILLAIVSGLLYAWIGLNIQHDANHGSVSRNPMVNRLFGYSQDWIGGNRMLWIRQHVGHHTHCNRVQHDPDVKGGSV
ITLSPYSLMKEFHHLQQYFLPLEQLLGFQWIFLGLHDLIEWKGEKLPESYRKERGIAIGLKVGFWIRFFVVPFALQFSWYTLLCTYLWMATAALYLGFFFILSHLFIGVK
SIPEDANIDWARHQIESSSNVCGEKLGIMNGGLNYQIEHHLFPRMSHAHYSKIQPVVQKVCEEDGVNYKKFGTILSNLGSTFKQVGALGSVAVEFMEGL >SEQ-103 - 91% sequence identity to SEQ ID NO 79
MPPHSRTKVSDPELSAMKHFTREEILNHTNDKYCILEDGVYDLTNFRDKHPGGDVLDFFPGQDATPHFYMLHQKESLPAVLAEYKVGSVARDDSYVYHDALHKQIKSAVRKVM
PMQEWWAPPSWYIKACALIVATIVATLYTDYLMIASGPTILLAIVSGLLFAWIGLNIQHDANHGSVSRNPMVNRLFGYSQDWIGGSRMLWIRQHVGHHTHCNRHQHDPDVKGGSVI
TLSGRYSLPKEFHHLQQYFLPLEQLGFQWVFLGLIEWKYKGEKLSESYRKEGKLPESYRKERGIAIGLKVGFWIRFFVVPFALHFTWYTLLCTYLWVCIAALYLGFFILSHIFVGVKS
LGEDANIDWARHQIESSSNVCGEKLGIINGGLNYQIEHHLFPRMSHAHYSKIQPVVQKVCEENGVNYKHFGTILSNLDSTFKQVGGLGSVPVYEFMEGL >SEQ-104 - 91% sequence identity to SEQ ID NO 79
MPPHSRTKVSDDPELSDLMKHFTYEEILNDTRDKYCILGDVYDSTNFRDKHPGGDSTNFRDKHPGGDVLDFFPGQDSTNFRDKHPGGDVLDFFPGQDATPHFYMYHQREWLPSVLSEFKVGSLARDDSYVYHTPLMKQIKSAVRK
VMPMQEWWAPPSWYIKACAILVATLYTDYLWIARGPTIPLAIVSGLLYAAIGLNIQHDANHGSISRNPMVNRLFGYSQDWIGGSRMLWIRQHVGHHTHNRHQHDPDVKGGS
VITLSPTSLPMEFHHIQQIYFLPLEALLGFQWVFLDDLLEMKYKGEKLPESYRKERNIAIGLRVFFIRKVVLPFALHFSWYTLLCTCLWMAIAAFYLGFFILSHNFVGA
KSLPEDANVDWARHQIESSSNVCGEKLGISNGGLNYQIEHHLFPRMSHAHYSKIQPVVQKVCEENGVKYKKFGTILSNLDSTFRHVGALGSVAVYEFMEKL

Figure 3 (continued)

>SEQ-105 - 91% sequence identity to SEQ ID NO 79
MPPHARRKVSDPELSAAKHFTRERILNHTRDKYCILEDGVYDLTNFRDEHPGGDVLDIFPGQDATPHFYMLHRYESPPSVLAEYKVGSVARDDSFTYHTPLMKRIKSAVRAVM
PMQEWWAPPSWYIKACAILVATLYLPLIQLLGFQWVFLGLHDLIEMKYKGEKLPPSYRKERNIAIGCRVFFFIRKFVVPFALHFSWYTLLCTCLWMAIAALYLAFFFILSHIFVGAKS
TLSRYSGPKEFHHIQQIYFLPLIQLLGFQWVFLGLHDLIEMKYKGEKLPPSYRKERNIAIGCRVFFFIRKFVVPFALHFSWYTLLCTCLWMAIAALYLAFFFILSHIFVGAKS
LPEDAKNIEWARHQIESSSNVCGEKLGHSNGGLNYQIEHHLFPRLSHSHYSKIQPVVQKVCEENGVNYKKFPTIGSNLDSTFRHVKALGSVAVYEFMEGL >SEQ-106 - 90.8% sequence identity to SEQ ID NO 79
MPPHSRTKVSAPELSDMKHFTREEIANHTNDKLCILEDGVYDLTNFRDKHPGGDFLDFFPGQDATPHFYMLHQREWLPSVLAEYKVGSVARDDSYVQHDPLMKRIKSAVRKVI
PMQEWWAPPSWYIKACAILIATLYTDYLWIASGPTIPLAIVSGLLFAAIGLNIQHDANHGSVSRNPMVNYLFGYGQDWIGGSRMLWIRQHVGHHTCNRVQHDPVKGGSVI
RLSRYSLPMEFHHIQQYFLPLPEQLLGFQWVFLGLHDLIEMKYKGEKLPESYRKEFNIAIGLRVGFFARKFVVPFALHPSWYTLLCTCLWMAIAAFYLAFFILSHIFVGAKS
LPPDANIDWARHQIETSSNVCGDWLGHSNGGLNYQIEHHLFPMSHAHYSKIQPIVQKVCEENGVNYKHFGTILSNLDSIFRQVKALGSVATYEFMEGL >SEQ-107 - 90.8% sequence identity to SEQ ID NO 79
MPPHSRTKVSDPELSALMKHFTREEILGDNNDKYCILEDGVYDLTNFRDKHPGGEVLDFFPGQDATPGFYMLHQYASLPAVLAEYGVGSVARDDSYVHHTPLMKQICSDVRKV
MPMGEGWAPPSWYIKACAILAATLYTDYLWIARGPTIPLAIVIGLLFAAIGLNIQHDANHGSVSRMLWIRQHVGGSRMLWIRQHVGHHLHCNRHQHDPVKGGSV
ITLSRYSLWLEFHHIQQYFLPLIQLLGFQWVFLPLDQLLGFQWVFLGLHDLIEWKKGEKLPESARPERNIAIGLRVFFARKIIVPFALHFSWYTLLCTCLWMATAALYLGFFFILSHIFVGAK
SLPEDANIDWARHQIESSSNVGGEKLGILNGGLNYQIEHHLFPRMSHAHYSKIQPVVQKVCEENGVNYKHFGTIASNLDSTFSQVGALGSVAVEFMEGL >SEQ-108 - 90.8% sequence identity to SEQ ID NO 79
MPPHSRKVSDPELKDLMKHFTREEKLNHTNDKYCILEDGVYDLTNFRDKHPGGDVLDLFPGQDATPGFYMLHRYEMLPSVLAEYKVGSVARDDSYVYHTPGYKQIKSAVNKV
MPMQEWWAPPSWYIKACAILAATLYTDYLWIARGPTIPLAIVLGLLYAAIGLNIQHDANHGSVSRNPMVNRLFGYSQDWIGGSRMLWRQHVGHHTHCNDIQHDPVKGGGA
ITLSRVSIPKEFHHIQQYFLPLDQLLGFQWVFLGLHDLIEWKWGEKLPPSYRKERNPAIGCRVFFFIRKFVVPLALHFSWYTLLCTYLWATGALYLGFFFILSHIFVGAG
SLPEDANIDWGRHQIESSSNVCGEKLGISNGGLNYQIEHHLFPRMSHAHYSKIQPVVQKICEENGVNYKKFGTILSNLDSTFSQVKALGSVPVEFMEGL >SEQ-109 - 90.8% sequence identity to SEQ ID NO 79
MPPHSRTKVSVPELSDLAKHFTREEILNHTNDKYCILEDGVYDLTNFRDKHPGGDVLDFFPGQDATPHFYMLHRYEWPPSVLAEYKVGSVARDDSYVYHTPLMKQIKSAVRKV
IPMGEGWAPPSWYIKACAILAATLYTDYYIWIAKGPTIPLAIVSGLLYAAIGLNIQHDANHGSISRNPMVNYLFGYSQDWIGGSRMLWIQQHVGHHTHCNEIDHDPVKGGSV
ITLKRSSLPKEWHHIQQYFLPLEQLLGFQWVFLPLEQLLGFQWVFLGLHDLIEWKYKGEKLPEIYRKEFNIAIGCRVFFEARKFAVPFALHFSWYTLLCTYLWMAIGALYLGFFFILSHIFVGAK
SLGPEANIEWARHQIESSSNVCGEKLGILNGGLNYQIEHHLFPRMSHAHYSKIAPVVQRVCEENGVNYKKFGTILSNLDSTFRQVKALGSVAVEFMEGL >SEQ-110 - 90.8% sequence identity to SEQ ID NO 79
MPPHSRTKVSDPELSDLMKHFTREKILNHTNDKYCILEDGVYDLTNFRDKHPGGDFLDFFPGQDATPHFYMLHQYEWLPSVLAEYKVGSQDWIGGSRMLWIRQHVGHHTSNRHQHDPVKGGSV
MPMQEWWAPPSWWIKACAILIATLYTDYLWIASGPTIPLAIISGLLYAAIGLNIQHDANHGSVSRNPMVNLFGYSQDWIGGSRMLWIRQHVGHHTSNRHQHDPVKGGSV
ITLSRYSLPMEFHHIQQYFLPLDALYGFQWVFLGLHDLIEMKWKGEPLPELYRKERNIAIGLKVFFIRKFVVPFALHFSWYTLLCTCAWMAIAALYLAFFFILSHNFVGIK
SLPEDASIDWARHQIESSSNVGEKLGILNGGLNYQIEHHLFPRMSHAHYSKIEPVVQKVCEENGVNYKKFGTIGSNLGATFRYVKALGSVPTYNEFMEGL

Figure 3 (continued)

>SEQ-111 - 90.8% sequence identity to SEQ ID NO 79
MPPHSRTKGSDDPELSDMKHFTYEEILNHTNPKYCILEDGVYDLNNFRDKHPGGDFLDFFPGQDATPHFYMFHQHVSLPSVLAEYKVGSIARDDSYVYHDPLMKQIKSAVRGV
MPMQEWWAPPSWYIKACAILAATLYTDYYWLASGPTIPLGIVSGLLYAAIGLNIQHDANHGSLSRNPMVNRLFGYSQDWIGGNRMLWIRQHVVGHHTHCNRIDHDPDVKGGGV
ITLSRSSLPKEFHHIQQYYFLPLEQLYGFQWVFLGLHDLLEMKYKGEKLPESARKERNIAIGLRVFFFIRKFVVPFWLHFSWYTLLCTYLWMATAAFYLCFFFILSHIFVGVK
SLPEDAKNIDWARHQIESSSNVCGEKLGISNGGLNYQIEHHLFPRMHHAHYSKIAPVVQKVCEEMGVNYKKFGTILSNLDSTFRQIKALGSVAVYEYMEGL >SEQ-112 - 90.8% sequence identity to SEQ ID NO 79
MPPHSRTKVSDDPELSDMKHFSREEILDHTRDKYCILEDGVYDLNNFRDKHPGGDVLDFFPGQDATPGFYMLHQRESLPGVLAEYFVGSIARDDSFVHHEPLMKQICSAVRGV
LPMQEWWAPPSWYIKACAILAATLYTDYLWIASGPTIPLSIVIGLLYAAIGLNIQHDANHGSVSRNPMVNRLFGYSQDWIGGSRVLWIQKHVVGHHTHCNRVDHDPDVKGGSV
ITLSPSSLPKEFHHIQQYYFLPLDQLLGFQWVFLGLHDLIEMRYKGEKLPESYRKEFNIAIGLRVFFFIRKFVVPFALHFSWYTLLCTYLWMAIAALYLGFFFILSHIFVGVK
SLPEDAKNIDWARHQIESSSNVCGEWLGHSNGGLNYQIEHHLFPRMNHAHYSKIQPVVQKVCEENGVNYKKFPTIGSNLDSIFRQVKALGAVAVYEFMEGP >SEQ-113 - 90.8% sequence identity to SEQ ID NO 79
MPPHSRRKVSDSDPELRDLMKHFTREEILNHTNDKYCILEDGVYDLTNFRDKHPGGDYLDFFPGQDATPHFYMYHQYVSLPSLLAEYKVGSVARDDSYVYHTPLMKQIKADVR
KVMPMGEWWAPPSWYIKACALIVATLHTDYLWIASGPTIPLAIVLGLLYAAIGLNIQHDANHGSVSRNPMVNRLFGYSQDWIGGSRMLWIRQHVVGHHTHCNRHQHDPDVKGG
SVIQLSPTSLPLEFHAIQQYYFLPGIQLLGFKWVFLGLHDLIEMKYKGEKLSESYRKDRNIAIGLRVFFWVRFFVVPFALHFSWYTILCIYLWMAIGALYLGFFFILSHIFVG
AKSLPPDAKNIDWARHQIESSSNVCGDKLGISNGGLNYQIEHHLFPRLSHAHYAPIQPVVRKVCEENGVNYKKFGTIGSNLDSTFQYVKALGSVAVYEFMEGL >SEQ-114 - 90.6% sequence identity to SEQ ID NO 79
MPPHSRTKVSDPELSDMEHFARERILNHTNDKYCILEDGVYDLTNFRDKHPGGDYLDIFPGQDATPHFYMLHQYEWPPSVLARYKVGSLARDDSYVQHTPLMKQICSAVRKVM
PMQEWWAPPSWYIKACAILAATLYTDYYWIASGPTIPLGIVSGLLYAAIGLNIQHDANHGSVSRNPMVNRLFGYSQDWIGGSRLLWIRQHVVGHHTHCNDHQHDPDVKGGSVL
TLSRVSLPKEFHHIQQYYFLPLIVLYGFQWVFLDLHDLIEMRYKGEKLPESYRPERNIAIGCRIFFFARKFAVPFALHFSWYTLLCTYLWVAIASLYLGFFFILSHNFVGAKS
LPEDANIDWARHQIENSSNVCGEKLGILNGGLNYQIEHHLFPRMHHAHYSKIQPVVQKVCEENGVNYKHFGTILSNLDSIFRQVKALGSVAVEFMEGL >SEQ-115 - 90.6% sequence identity to SEQ ID NO 79
MPPHSRTKVGDPELKDMKHFTYERILNHTRDKYCILEDGVYDSTNFRDKHPGGDVLDFFPGQDATPHFYMLHKYEWPPSILAEYKVGSVARDDSYVQATPLMLQIKSAVRKVM
PMQEWWAPPSWYIKACAILAATLYTDYLWIARGPTILLAIVSGLLYAWIGLNIQHDANHGAVSRNPMVNRLFGYSQDWIGGSRMLWIRQHVVGHHTHTNRHQHDPDVKGGSVI
TLSRYDLPKEFHHIQQYYFLPGEQLLGFQWVFLGLHELIEMKWKGEKLPESYRPERNPAIGLKVGFWIRKVVIPFALHFSWYTLLCTYLWMAIAALYLGFFFILSHIFVGVKS
LPEDANIDWARHQIESSSNVCGEKLGIMNGGLNYQIEHHLFPRMSHAHYSKIQPVVQKVCEENGVNYKKFGTILSNLDATFRQIKALGSVAVYEYMEGL >SEQ-116 - 90.6% sequence identity to SEQ ID NO 79
MPPHSRKKVVSDPELSDLMKHFSYERILNHTNDDYCILGDGVYDLTNFRDKHPGGDYLDFFPGQDATPHFWMLHQKESPPSVLAEYKVGSVARDDSYVYYDPLMKQIKSAVRK
VMPMQEGWAPPSWYIKACAILAATLYTDYLWLASGPTIPLSIVSGLLYAWIGLNIQHDANHGSLSRNPMVNRLFGYGQDWIGGSRMLWIRQHVVGHHTHSNRHQHDPDLKGGS
VIRLSRTSLPLEFHHIQQYYFLPLDQLLGFQWVFLGLNDLIEMRYKGEPLPESYRKERNIAIGLKIFFFVRKFVVPFALHFSWYTLLCTCAWMAIAALYLGFFFILSHIFVGA
KSLPEDANIDWARHQIESSSNVCGEKLGHSNGGLNYQIEHHLFPRMSHAHYSKIQPVVQRVCEENGVNYKKFGTILSNLDSTFSQVKALGAVAVYEFMGGL

Figure 3 (continued)

>SEQ-117 - 90.6% sequence identity to SEQ ID NO 79
MPPHSRTKVSDDPELSDAKHFTREEILGHTNDKYCILEDGVYDCTNFRDKHPGGDVLDIFGGQDATPHFYMLHQYESPPSVLAKYKVGSVERDDSYVYHEPLMKQIKSAVRKV
IPMQEGWAPPSWIKACALLAATLYTDYLWIARGPTIPLAIVSGLLYAAIGLNIQHDANHGSVSRNPMVNRLFGYSQDWIGGSMLWIRQHVVNHHTCNRIDHDPDVKGGSV
ITLSRYSLPKEFHAIQQYYFLPLEQLLGFKWIFLGAHDLIEMKYKGEKIPESYRKERNIAIGLRVFFFIRKIVVPFALHPSWYTLLCTYLWMCIAALYLAFFFILSHIFVGAK
SLPPDANIDWARHQIENSSNVCGEWLGYLNGGLNYQIEHHLFPRMSHAHYSKIQPVVQKVCEENGVNYKKFGTILSNLDSTFRQVKALGAVPVEFMEGL >SEQ-118 - 90.6% sequence identity to SEQ ID NO 79
MPPHSRRKVSDDPELRDLKAKHFTYTEILNHTNDDLCILEDGVYDLTNFRDKHPGGDVIDIFPGQDATPGFYMLHKYESLPSVLAEFKVGSVARDDSYVYHTPLMLQIKSAVRK
VLPMGEWWAPPSWYIKACAILAATLYLDYWIARGPTILLAIVLGLLYAAIGLNIQHDANHGSVRNPMVNRLFGYAQDWIGGSRMLWIQQHVGHHTHCNDHQHDPVKGGS
VITLSRYSLPLEFHHIQQYFLPLEQLLGFQWVFLGAHDLIEMKYEGEKLPESYRKERNIAIGCRVFFIRKFVVPFALHFSWYTLLCTYAWVAIAAFYLGFFFILSHIFIGA
KSLPEDAKNIDWVRHQIESSNVCGEKLGHSNGGLNYQIEHHLFPRMSHAHYSKIQPVVQKCEEMGINYKKFGTIGSNLDSTLRQVKALGSVAVYEFMEGL >SEQ-119 - 90.3% sequence identity to SEQ ID NO 79
MPPHSRTEVSDPELKAMKHFTREEILNHTNDDICILEDGVYDLTNFRDKHPGGDYLDFFPGRDATPHFYMLHQYESLPSVLAEYKVGSIARDDSYVYHTPGMKQICAEVRKVM
PMGEWWAPPSWYIKACAIIAATLYTDYLWIASGPTIPLAIVSGLLYAAIGLNIQHDANHGSVSRNPMVNRLFGYSQDWIGGSRMLWIRQHVVGHHTNRHQHDPDVKGGSVI
TLSRYSLWKEFHHIQQYFLPLDQLLGFQWVFLGLHDLIEMKYKGEKIPESARPEYNPAIGLRVFFIRKFVVPFWLHFSWYTLICTYAWMAIAAFYLGFFFILSHNFVGAKS
LPPDANIDWARHQIETSSNVCGEKLGISNGGLNYQIEHHLFPRMHAHYSKIQPVVQKICEENGVNYKHFGTIGSNLDSTLQQVKALGSVPVYEFMEGL >SEQ-120 - 90.3% sequence identity to SEQ ID NO 79
MPPHSRTKVSDDPELRDMKHFTREEILNHTNDDYCILGDGVYDLTNFRDKHPGGDVLSFFPGQDATPHFYMLHQYESLPSVLAEYKVGSIARDDSYVYAEPLQKQIKSAVRKV
LPMGEWWAPPSWYIKACAILAATLFLDYLWIASGPTIFLAIVSGLLYAAIGLNIQHDANHGSVRNPMVNRLFGYSQDWIIGGSRMLWIRQHVVGHHTHCNEHDHDPDVKGGSV
IQLSPYDLWMPFHHIQQIYFLPLIVLLGFQWVFLGLHDLIEMKYKGEKLPPSYRKEYNPAIGLRVFFIRKFVVPFWLHFSWYTLLCTCLWMAIAAFYLGFFFILSHLFVGAKS
SLPEDASIDWARHQIESSNVGGEKLGHSNGGLNYQIEHHLFPRMSHAHYSKIQPVVQKVCEENGVNYKKFPTIGSNLDSIFRQVKALASVAVEFMEGL >SEQ-121 - 90.3% sequence identity to SEQ ID NO 79
MPPHSRTKVSDDPELKDMKHFTREEILNHTNDKYCILEDGVYDLTNFRDEHPGGDVLDFFPGQDATPHFYQLHRYEWPPSVLSEYKVGSVARDDSYVHHTPLHKQLKSAVRKVL
PMGEWWAPPSWYIKACALIIATLYTDYLWIASGPTIELAIVSGLLFAWIGLNIQHDANHGSVRNPMVNRLFGYSQDWIGGSRMLWIRQHVVGHHTCNRHDHDPDVKGGGVI
RLSRYSLPMPFHHIQQIYFLPLIQLYGFQWVFLGLHDLIEMKYKGEKIPESYRKLYNIAVGLKVFFFIRKFVVPFALHFSWYTLLCTYLWMAIAALYLGFFFILSHLFVGAKS
LPEDANIEWARHQIESSSNVCGEKIGISNGGLNYQIEHHLFPRMSHAHYAKIQPVVQKVCEENGINYKKFGTILSNLGSTFQQVKAIGSVAVEFMEGI >SEQ-122 - 90.3% sequence identity to SEQ ID NO 79
MPPHSRTKVSDPELSDLMKHFSRTRILNHTNDKYCILEDGVYDLTNFRDKHPGGDVLDLFPGQDATPHFYELHQYEWLPAVLAEYGVGSIARDDSYVYHDPLMLRLKCEVNGV
MPRGEGWAPPSWYIKACAILAATLYTDYLWIASGPTIFLAIVSGLLYAAIGLNIQHDANHGSVSRNPMVNRLFGYSQDWIGGSRMLWIRQHVVGHHISNRHDHDPDVKGGGV
IRLSRYSLPKEFHHIQQIYFLPLIQLYGFQWVFLGLHDLIEMKYKGEKLPESYRKERNIAIGLRVFFIRKFILPFALHFSWYTLLCTCLWVAIAALYLGFFFILSHIFVGAK
SLPEDAKNIDWARHQIEHHLFPRMHAHYAKIQPVVQKVCEENGINYKKFGTILSNLGSTFQQVKAIGSVAVYEFMEGP

Figure 3 (continued)

>SEQ-123 - 90.1% sequence identity to SEQ ID NO 79
MPPHSRTKVSAPELSDLMKHFTREKILNHTNDKICILEDGVYDATNFRDKHPGGDYLDFFPGQDATPHFYMYHQYESPPSVLAEFKVGSVARDDSYTYHDPLYKRIKSDVRKV
LPMQEWWAPPSWYIKACAILAAALYLDYLMIASGPTIPLAIVSGLLNIQHDANHGSVSRNPMVNRLFGYSQDWIGGSRLLWIRQHVVGHHTHCNRVQHDPDVKGGSV
ITLSRYSLWKEFHHIQQYFLPLIQLYGFQWVFLGLHDLIDWKYKGEKLPESCRKERAIAIGLRVGFFARKFVLPLMLHFSWYTLLCTCLWMAVAALYLGFFFILSHIFVGAK
SLPEDANIDWARHQIESSSNVGGEKLGISNGGLNYQIEHHLFPRMSHSHYSPIAPVVQKVCEENGVNYKHFGTILSNLDSTFRQIKALGSVAVEFMEGL >SEQ-124 - 90.1% sequence identity to SEQ ID NO 79
MPPHSATKVSVPELSDLAKHFTREEILNHTNDKYCILEDGVYDLTNFRDKHPGGDVIDFFPGQDATPHFWMFHQKESPPSVLSEYKVGSVARDDSYTHHDPLMKQIKSAVRKV
IPRQEWWAPPSWWIKACAILAATLHTDYLWIASGPTIPLAIVSGLLYAWIGLNIQHDANHGSVSRNPMVNRLFGYSQDWIGGSRMLWIRQHVVGHHTHCNDHQHDPDVKGGSV
ITLSPYSLPKEFHAIQQYFLPLDQLYGFQWVFLGAHDLIEMKYKGEPLPESYRKEYNIAIGLRVFFIRKFVLPFALHPTWYTLLCIYLWMAIAAFYLGFFILSHIFVGAK
SLPPDAKNIDWARHQIESSSNVCGEWLGISNGGLNYQIEHHLFPRMNHAHYSKIEPVVQKVCEENGVNYKHFGTIGSNLDSTFRQVKALGAVPVEFMEGL >SEQ-125 - 90.1% sequence identity to SEQ ID NO 79
MPPHSRTEVSDDPELSDMKHFTREEILNHTNDKLCILEDGVYDFRDKHPGGDFLDFFPGQDATPHFYMYHQYESPPSVLAKYKVGSVDRDDSYVYHTPLMKQIKSAVRKI
MPRQEWWAPPSWWIKACAILVATLYTDYLWIASGPTILLGIVSGLLYAIGLNIQHDANHGSVSRNPVVNRLFGYSQDWIGGSRMLWIRQHVVGHHTHTNDIQHDPDVKGGSV
IRLSRYSIWKPFHHIQQYFLPLDQLYGFQWVFLGLHDLIEMKYKGEKLPESYRPLRNIAIGLRVFFVRKFVLPFALHFSWYTLLCIYLWMAIAALYLGFFFILSHIFVGAK
SLPEDGNIDWVRHQIESSSNVGGEKLGISNGGLNYQIEHHLFPRMSHAHYSKIQPVVQKVCEEDGVKYKKFGTIASNLDSTLSQVKALGSVAVEFMEGL >SEQ-126 - 90.1% sequence identity to SEQ ID NO 79
MPPHSRTKGGDPELSDMKHFTREKILNHTNDKYCIVEDGVYDLTNFRDKHPGGDVLDFFGGQDATPHFFMLHQRESPPSLLAEYKVGSVARDDSYVYHTPLMKQICSAVNGVM
PMGEGWAPPSWYIKACAILAATLYLDWLWIASGPTIPLAIVSGLLYAIGLNIQHDANGAVSRNPAVNRLFGYSQDWIGGSRMLWIRQHVVGHHTHCNDHQHDPDVKGGSAI
TLSRTDLPKEFHHIQQYFLPLEQLLGFQWVFLGLHDLIEMKYKGEPLPESYRKLRNIAVGCRIFFFARKFAVPFALHFSWYTLLCTCLWMAIAALYLGFFILSHIFVGAKS
LPPDANIDWARHQIESSSNVCGEKLGISNGGLNYQIEHHLFPRMSHAHYSKIQPVVRKVCEENGINYKKFGTILSNLDSTFRQLKAIGSVPVYEFMEGL >SEQ-127 - 90.1% sequence identity to SEQ ID NO 79
MPPHSAKKGSDVPELRDLMKHFTRTEILNHTNDKLCILGDGVYDLTNFRDKHPGGDVLDFFPGQDATPHFYMLHQYESLPSVLAEYGVGSVRDDSYVYHTPLHKQIKSAVRK
VMPMQEWWAPPSWYIKACAILAATLYLDYLMIASGPTIPLAIVSGLLYAAIGLNIQHDANHGVSRNPAVNRLFGYSQDWIGGSRMLWIRQHVVGHHTHCNRHQHDPDVKGGG
VITLSPYSLPKEFHHIQQYFLPLEQLLGFKWVFLGLHDLIEMKYKGEKLPESYRKERNIAVGLRVFFIRKFVIPFALHFSWHTLLCIYLWMAIGALYLGFFFVLSHIFVGV
GSLGEDANVDWARHQIETSSNVCGEKLGIMNGGLNYQIEHHLFPRMSHAHYSPIQPVVQKVCEENGVKYKKFGTILSNLDSTFSQVKALGSVATEFMGKI >SEQ-128 - 89.9% sequence identity to SEQ ID NO 79
MPPHSRTKVGDPELSDMKHFTREEILDHTNDKLCILEDGVYDATAFRDKHPGGDVLDFFPGQDATPHFYMYHQHESPPSVLAEYKVGSLARDDSYVYHTAGMKQIKSAVRGII
PMQEWWAPPSWYIKACAILAATLYTDYLWIASGPTIPLAIVSGLLYAIGLNIQHDANHGVSRNPAVNRLFGYSQDWIGGSMMLWIRQHVVGHHTHNRIDHDPDVKGGSVI
QLSPSSLPKPWHHIQQYFLPLIQLLGFQWLHFGEKLIEWKYKGEKLPESCRKERNIAIGCRIFFFARKFAVPFWLHFSWYTLLCTYLWMAIAALYLGFFFILSHIFIGAGS
LPEDANIDWARHQIESSSNVCGEKLGIINGGLNYQIEHHLFPRMSHAHYSKIQPVVQKVCEENGVNYKHFGTILSNLDSTFRQVKALGSVPVEFMEGP

Figure 3 (continued)

>SEQ-129 - 89.9% sequence identity to SEQ ID NO 79
MPPHSRTKVSDVPELSDLMKHFTREEILNHNNDKICILGDGVYDLTNFRDKHPGGDVLDFFPGQDATPHFYMYHQYESPPSVLAEYKVGSVARDDKYVQHTPLMKQIKADVRK
VMPMGEWWAPPSWYIKACAILIATLYTDYLMIARGPTIPLAIVSGLLYAAIGLNIQHDANHGSLSRNPMVNRLFGYAQDWIGGSRMLWIRQHVVGHHLHCNRIDHDPDVKGGS
VIKLSPYDGPKEWHHIQQIYFLPLIQLYGFQWFLGLHDLIEWRYKGEKLPESYRKEFNIAIGLRVFFIRFFVLPFALHFSWHTLLCTYLMAIGALYLAFFILSHIFVGA
KSLPPDANIDWARHQIESSSNVCGEWLGISNGGLNYQIEHHLFPRMHHAHYSPIQPVVQRVCEENGVNYKKFGTIASNLDSTFRQVKALGSVAVEFMEGL >SEQ-130 - 89.7% sequence identity to SEQ ID NO 79
MPPHSRTKVSDDAELSDMKHFTREEILDHTNDKYCILEDGVYDCTNFRDKHPGGDVIDEFFPGQDATPHFYMLHQKAWPPSVLAEYFVGSVARDDSYVQHEPLHKQICSAVRKV
MPMQEWWAPPSWYIKACAILAATLYTDYLMIASGPTIPLSIVSGLLYAAIGLNIQHDANHGSVSRNPMVNYLFGYGQDWIGGSRVLWIRQHVVGHHTHTNDHDPDVKGGSV
ITLSRSSGPKEWHHIQQYFLPGIQLYGFKWVFLGLHDLIEWKYKGEKLPEIYRKERNIAIGLRVFFIRKFVSWYTLLCTYAWMATGAFYLGFFILSHIFIGAK
SLPEDANIDWARHQIESSSNVCGEKLGYSNGGLNYQIEHHLFPRMSHAHYSKIQPVVRKVCEDNGVNYKHFGTILSNLGSTFRQVKALGSVAVEFMEGP >SEQ-131 - 89.7% sequence identity to SEQ ID NO 79
MPPHARTKGSDPELKDMKHFTREEILNHNNDKYCILGDGVYDLTNFRDKHPGGDYLDFFGGQDATPHFYEYHQHESPPSVLAEYKVGSVARDDSYVQHTELMKQIKSAVRGVL
PMQEWWAPPSWYIKACALIVATLYLDYLMIASGPTIFLAIVSGLLYAAIGLNIQHDANHGSVSRNPVVNRLFGYSQDWIGGSRMLWIQKHVVGHHLHCNRHQHDPDVKGGSVI
TLSPYSGWKEFHHLQQIYFLPLIQLLGFQWVFLGLHDLIEMKYKGEKLPEIYRKLRNIAIGCRVFFIRKFVVPFWLHFSWYTLLCTYLWMASAALYLGFFILSHIFGAKS
LPEDANIDWARRQIESSSNVCGEKLGHSNGGLNYQIEHHLFPRMSHAHYAKIQPVVQKVCEENGVNYKHFGTILSNLDSTFRQVKALGSVAVYEFLEGL >SEQ-132 - 89.7% sequence identity to SEQ ID NO 79
MPPHGRTEGSDPELRDMKHFTRERILDHTNDKLCILEDGVYDLNNFRDKHPGGDFLDFFPGQDATPHFFQLHQYESLPSVLAEYKVGSVARDDSYVVHDPLMKQLKSAVRAVM
PKQEGWAPPSWYIKACAILAATLYLDYLMIASGPTIPLAIVSGLLYAAIGLNIQHDANHGSISRNPMVNYLFGYSQDWIGGSRMLWIRQHVVGHHTHCNRHQHDPDVKGGSVI
TLSPYSLPKEWHHIQQYFLPLDQLLGFQWVFLGHINGGLNYQIEHHLFPRMSHAHYSKIEPVVQKVCEENGVNYKKFGTILSNLDSTFRQVKALGSVPVEFMEGL
LPEDAKNIDWARHQIESSSNVCGDKLGYSNGGLNYQIEHHLFPRMSHAHYSKIQPVVQKVCEENGVNYKKFGTILSNLDSTFRQVKALGSVPVEFMEGL >SEQ-133 - 89.7% sequence identity to SEQ ID NO 79
MPPHSRTKVSDPELRDLMKHFTREEILNHTNDDYCILGDGVYDLTNFRDKHPGGDFLDFFPGQDATPHFYMLHQRESLPSVLAEYFVGSVRDDSYVQHEPLMKQIKSAVRKI
MPKQEWWAPPSWWIKACAILAAALYTDYLMILSGPTIPLAIVSGLLYAWIGLNIQHDANHGSISRNPMVNRLFGYSQDWIGGSRMLWIRQHVVGHHICNRHDHDPDLKGGSA
IQLSRVSLPKEFHHIQQYFLPLEQLYGFQWVFLGLHDLIDMKWKGEKLPESYRKEFNIAIGLRVGFFIRKEVPPLALHFSWYTLLCTYLWMAIAALYLCFFILSHIFVGIK
SLPEDAKNIDWARHQIESSSNVGGEKLGHINGGLNYQIEHHLFPRMSHAHYAKIQPVVQKVCEENGVNYKHFGTIASNLDALFRQVKALGSVPVYEFMEGL >SEQ-134 - 89.7% sequence identity to SEQ ID NO 79
MPPHSRTKVGDPELRAMEHFTRERILNHTNDKYCILEDGVYDLTNFRDKHPGGDVIDFFPGRDATPHFYMLHQRESLPSVLAEYFVGSVARDDSYVYTPLHKQIKSAVRGVM
PMQSWWAPPSWYIKACAILAATLHTDYLMIASGPTIPLAIVGLLYAAIGLNIQHDANHGSVSRNPMVNRLFGYSQDWIGGSRMLWIRQHVVGHHIHTNRHQHDPDVKGGSVI
RLSRYSLMKEFHHIQQYFLPLEQYGFQWIFLGLHDLIEMKYKGEKLPELYRKEFNIAIGLRVFFFARKFVVPFALHFSWYTLLCTYLWMAIGAFYLCFFILSHIFVGVKS
IPEDANIDWARHQIESSSNVCGEWLGISNGGLNYQIEHHLFPRMSHAHYSKIEPVVQKVCEENGVNYKKFPTILSNLDSTFRQIGALGSVAVEYMEKL

Figure 3 (continued)

```
>SEQ-135 - 89.7% sequence identity to SEQ ID NO 79
MPPHGRTKVSDDPELSDMKHFTREEILNHTNDKYCILEDGVYDLTNFRDEHPGGDVLDFFPGQDATPHFWMYHRYASPPSVLAEYKVGSVDRDDSYVYHEPLMKQLKADVRKV
MPMQEGWAPPSWWIKACAILAATLHLDYLMIAKGPTIPLAIVSGLLYAAIGLNIQHDANHGSVSRNPMVNRLFGYSQDWIGGSRMLWIREHVVGHHTCNRHQHDPDVKGGSV
ITLSPYSLPLPFHHIQQYYFLPLEQLYGFQWVFLGLHDLIEMKYKGEPLPESYRKERNIAIGLRVFFVRKIVVPFALHFSWYTLLCTYLWMASAAFYLAFFFILSHIFVGVK
SLGEDANIDWARRQIESSSNVCGEKLGISNGGLNYQIEHHLFPRMSHAHYSKIQPVVQKVCEEDGVNYKKFPTILSNLDATFRHVGALGSVAVEFMEKL >SEQ-136 - 89.7% sequence identity to SEQ ID NO 79
MPPHSRRKVSDPELSDAKHFTYTEKLNHTNPKYCILEDGVYDLSNFRDKHPGGDVLDFFPGQDATPHFYMYHQYESPPSVMAEYKVGSVARDDSYVYATELMLQIKSAVRKVM
PMQEWWAPPSWYIKACAIIAATLYTDYLMIASGPTIPLAIVLGLLYAWIGLNIQHDANHGSVSRNPMVNRLFGYSQDWIGGSRMLWIRQHVVGHHTCNRIQHDPDVKGGGVI
TLSRTSLPKEFHHIQQLYFLPLIQLYGFQWVFLDLHDLIEMKYKGEPLPPLYRKEFAIAIGLRVGFWIRKFVVPFALHFSWYTLLCIYLWMASAAFYLGFFFILSHIFVGAKS
LPEDAKNIDWARHQIESSSNVCGEKLGHSNGGLNYQIEHHLFPRMSHAHYAPIQPVVQKICEENGINYKKFGTILSNLDSTFRQVKALGSRATEFMEGL >SEQ-137 - 89.7% sequence identity to SEQ ID NO 79
MPPHARSEVSDPELSDLMKHFTRERILNHHNDKYCILGDGVYDCVNFRDKHPGGDFVDFFPGQDATPHFFMLHRHESLPSVLAEYKVGSVARDDSYVYHDPLMKQICSAVRKV
MPMQSWWAPPSWWIKACAILAATLYTDYLWIASGPTIPLAIVLGLLYAAIGLNIQHDANHGSVSRNPMVNYLFGYSQDWIGGSRMLWIRQHVVGHHTHTNDHDHDPDVKGGSV
ITLSRYSLPKEFHHIQQIYFLPLIQLYGFQWVFLDAHDLIEMKYKGEKIPESYRKERAIAIGCRVFFFIRKFVFFIRKEVLPFALHFSWHTLLCTCLWMAIAALYLGFFFILSHIFVGAK
SIGEDANIDWGRRQIESSSNVCGEKLGIINGGLNYQIEHHLFPRMSHAHYSKIQPVVQKVCEENGVNYKKFGTIGSNLDSTFRHLKALGSVAVYEFMEGP >SEQ-138 - 89.7% sequence identity to SEQ ID NO 79
MPPHARTKVGDPELSDLMEHFTREEILGHENDKYCILEDGVYDLNNFRDKHPGGDVLDIFPGQDATPHFWMLHQRVSPPSVLAEYKVGSVARDDSYVYHTPLYKQIKSAVRKV
IPMGEWWAPPSWWIKACAILAATLYTDYYWIASGPTIPLAIVIGLLYAAIGLNIQHDANHGSVSRNPMVNRLFGYSQDWIGGSRMLWIRQHVVGHHTCNRHQHDPDVKGGSV
ITLSRTSLMMPFHHIQQIYFLPGEQLLGFQWVFLGHDLIEMKYKGEKLPESARKERNIAIGLRIEFFIRKFVVPFALHFSWHTLLCTYLWMASAALYLGFFFILSHIFVGAG
SLPPEAKNIDWGRHQIESSSNVGGEKLGILNGGLNFQIEHHLFPRMSHAHYSKIQPVVQKVCEENGVNYKKFPTILSNLDSTFKQIGALGSVAVEFLEGL >SEQ-139 - 89.7% sequence identity to SEQ ID NO 79
MPPHSRTKVSDPELSALMKHFTREKKLNHTNDDYCILGDGVYDLTAFRDKHPGGDVLTAFRDKHPGGDYIDFFPGQDATPHFFMLHQYESLPAVLAEYKVGSIARDDSYVYYTALMKQIKSAVRAV
MPMGEWWAPPSWYIKACAILAATLYTDYLWIASGPTILLAIVSGLLFAAIGLNIQHDANHGSVSRNPMVNRLFGYSQDWIGGSRMLWIREHVVNHHLHTNRHQHDPDLKGGSV
ITLSRTDLPKPFHHIQQYYFLPLEQLYGFQWVFLGLHDLIEMKYKGEPLPESYRKERNIAVGLRVFFFIRFFIIPFWLEFSWYTLLCTYLWMAIAALYLGFFFILSHIFVGAK
SLPEDANIDWARRQIESSSNVCGEKLGHSNGGLNFQIEHHLFPRMSHAHYSKIQPVVQKVCEENGINYKKFGTIGSNLDSTFRHVKALGSVAVEFMEGP >SEQ-140 - 89.4% sequence identity to SEQ ID NO 79
MPPHSRIKVSDPELSMKHFTREEILNHTRDKYCILEDGVYDATAFRDKHPGGDYIDFFPGQDYIDFFPGQDATPHFYMLHRYESLPSVLAEYKVGSVARDDSYVQHDELMLQLKAAVRAVM
PQEWWAPPSWYIKACAILAATLYDYLMIASGPTIPLGIVLGLLYAAIGLNIQHDANHGSVSRNPVVNRLFGYSQDWIGGSRMLRQHVVGHHLHSNEHQHDPDIKGGSAI
RLSPYSLPKEWHHIQQLYFLPGIQLLGFQWVFLGLHDLIEMKYKGEKLPPSYRKERNIAIGCRVFWIRKFVVPFALHFSWYTLLCTYLWMAIGALYLGFFVLSHIFVGAKS
LPEDAKNVDWARHQIESSSNVCGEKLGISNGGLNYQIEHHLFPRMSHAHYSKIQPVVRKVCEENGINYKHFPTILSNLDSTFRQVKALGSVPTEFMEGL
```

Figure 3 (continued)

>SEQ-141 - 89.4% sequence identity to SEQ ID NO 79
MPPHSRTKVSDAELSDLMKHFTREEILNDTNDKYCILEDGVYDLTNFRDKHPGGDVLDFFPGQDATPGFWMFHQYAWLPSVLAEYKVGSIARDDSYVQYTPLMLQIKCAVRKV
LPMQSWWAPPSWYIKACAILIATLYTLPLEQLLGFQWIFLGLHDLIEWKYEGEKIPESYRKLRNIAIGCRVFFFIRKFAIPFALHFSWYTLLCTYLWMATAALYLGFFILSHIFVGAK
ITLSPSSLMLEWHHIQQYFLPLDQLLGFQWIFLGLHDLIEWKYEGEKIPESYRKLRNIAIGCRVFFFIRKFAIPFALHFSWYTLLCTYLWMATAALYLGFFILSHIFVGAK
SLPEDANIDWARRQIESSSNVCGEWLGISNGGLNYQIEHHLFPRMSHAHYSKIQPVVQKVCEENGVNYKKFPTILSNLGSTFQHVKALGSVAVEFMEGL >SEQ-142 - 89.4% sequence identity to SEQ ID NO 79
MPPHSRTKVGSDPELRDLMKHFTREEILNHTRDKYCILEDGVYDLTNFRDKHPGGDVVDFFPGQDATPGFYMLHQYESLPSVLAKYFVGSVARDDSYVYHDPLQKQIKSAVRK
IMPRQEWWAPPSWWIKACAILAATLYDYLWIAKGPTIFLAIISGLLYAAIGLNIQHDANHGSVSRNPMVNRLFGYSQDWIGGSRMLWIRQHVGHHTHCNRHQHDPDVKGGS
VIKLKPTSLWLEFHHIQQYFLPLDQLLGFQWIFLGLHDLIEMRYKGEKLPPSYRKERNPAIGCRVFFSWYTLLCTYLMVAIGALYLGFFILSHIFVGA
KSLPEDANIDWARHQIESSSNVGGDKLGYSNGGLNYQIEHHLFPRMSHAHYSKIQPVVQRVCEENGINYKKFGTILSNLDSIFQQVKALASVPVEYMEGL >SEQ-143 - 89.4% sequence identity to SEQ ID NO 79
MPPHARTKVSDPELSDAKHFTREEILNHTNDKLCILEDGVYDAPNFRDKHPGGDVLDFFPGQDATPHFYMLHQYEWPPSVLAEYKVGSVARDDSYTQATPLMKQIKSAVRKVM
PMGEWWAPPSWYIKACALLAATLHTDYLWIASGPTIPLAIVSGLLYAAIGLNIQHDANHGSVSRNPMVNRLFGYSQDWIGGSMMLWIRQHVGHHTSNRHQHDPDVKGGSVI
KLSRYSLPLEFHHIQQIYFLPGDQLYGFQWVFLGLHDLIEMKYKGEKISESYRKERNPAIGCKVFFFIRKFVPFWLHFSWYTLLCVCLWMATAAFYLGFFILSHNFVGVKS
LGPDAKNVDWARHQIESSSNVCGEWLGISNGGLNYQIEHHLFPRMNHAHYSKIQPVVQKVCEENGVNYKKFGTILSNLGSTFRQVKALGSVAVYNEFLAGL >SEQ-144 - 89.4% sequence identity to SEQ ID NO 79
MPPHSATKVSDPELSDMKHFTREKILDHTNDKYCILEDGVYDCPNFRDKHPGGDVLDFFPGQDATPHFEEYHQHEWLPSVLAEYFVGSVDRDDSYVYHTSLMKQIKAAVRGIM
PRQEWWAPPSWYIKACALLAATLYTDYLWIASGPTIPLAIVSGLLYAAIGLNIQHDANHGSISRNPMVNRLFGYSQDWIGGSRMLWIRQHVGHHTCNRHDHDPLKGGSVI
KLSRYDLPKEFHHIQQYYFLPLAGLLGFQWVFLDLHDLIEMKYKGEKLPESCRPLRNIAIGLRIFEWIRKFVPFALHFSWYTLLCTLWMATAALYLCFFILSHIFVGIKS
LPEDAKNIDWARKNIQIENSSSNVCGEKLGISNGGLNYQIEHHLFPRMSHAHYSKIQPVVQKVCEENGVNYKKFGTILSNLDSTFKQLGALGSRATEFMAGL >SEQ-145 - 89.4% sequence identity to SEQ ID NO 79
MPPHSRTKVSDDPELKDLMKHFSYEEILNDTNDKYCILGDGVYDATNFRDKHPGGDVLDIFGGRDATPHFYELHQYESLPSVLAEYKVGSVDRDDSYVYHDPLMLQIKSAVRK
VMPMQEWWAPPSWYIKACAILVATLYTDYLMIASGPTIPLAIVLGLLYAAIGLNIQHDANHGSISRNPMVNRLFGYSQDWIGGSRMLWIREHVGHHTHCNDHQHDPDIKGGS
AITLSRYSLPKEWHHIQQYYFLPLIALLGFQWVFLGHSNGGLNYQIEHHLFPRMSHAHYSKIQPVVRKVCEDNGVNYKKFPTILSNLDSMFRQVKALGSRATEFMEGL
KSLPEDANVDWARHQIESSSNVCGEKLGHSNGGLNYQIEHHLFPRMSHAHYSKIQPVVRKVCEDNGVNYKKFPTILSNLDSMFRQVKALGSRATEFMEGL >SEQ-146 - 89.4% sequence identity to SEQ ID NO 79
MPPHSGTKVSDDPELMKHFTYEEIANHTNDDYCILEDGVYDLVNFRDEHPGGDVLDFFPGQDATPGFYMLHRYESLPAVLAEYKVGSVERDDSYVHHDPLMKQICSEVRK
IMPMQEWWAPPSWYIKACAILVGLIFAAIGLNIQHDANHGSVSRNPMVNRLFGYSQDWIGGSRVIWIRQHVGHHTCNEVQHDPDVKGGG
VITLSRTSLPKEFHHIQYYFLPLDQLLGFQWVFLDLHDLLEMKKWKGEKLPESARPERNIAIGLKVFFFIRKVVPFWLQFSWHTLLCTYLMWATAALYLAFFILSHIFVGA
KSIPPDANIDWARHQIESSSNVCGEKLGISNGGLNYQIEHHLFPRMSHAHYSPIQPVVQKVCEENGVNYKKFPTILSNLDSTFRQIKALGSVATEFMEGL

Figure 3 (continued)

>SEQ-147 - 89.2% sequence identity to SEQ ID NO 79
MPPHSRTKGSAPELSDMKHFSRERILNHTNDDYCILEDGVYDLTNFRDKHPGGDFLDFFPGQDATPHFYMFHQYEWLPSVLAEYGVGSVARDDSYVQHTPLMKQLKSAVRKVM
PMQEWWAPPSWYIKACAILAATLYTDYLWIAKGPTIPLAIVSGLLFAAIGLNIQHDANHGSISRNPMVNRLFGYSQDWIGGGRMLWIREHVVGHHTHCNEIQHDPDVKGGSVI
TLSPYDLWKEFHHIQQYYFLPLIQLYGFKWVFLGLHDLIEMKYKGEKLPESARKERNIAVGLRVFFFIRKVVVPFALHFTWYTILCTYLWMAIAALYLGFFFILSHIFVGAKS
LGPDANVDWARHQIESSSNVGGEKLGHSNGGLNFQIEHHLFPRMHHAHYAKIQPVVQKICEENGVNYKKFGTILSNLDSMFSQVKALGAVAVEFMEGL >SEQ-148 - 89.2% sequence identity to SEQ ID NO 79
MPPYSRTKVSVPELSDMKHFTREEILNHTNDKLCIVEDGVYDCTNFRDKHPGGDVLDLFPGQDATPHFYMFHQYEWLPSVLARYKVGSVARDDSYVYHTPLMKQIKSDVRKIL
PMQEWWAPPSWYIKACAILVAALYLDYLWIASGPTIFLAIVSGLLYAAIGLNIQHDANHGSVSRNPMVNRLFGYSQDWIGGGMMLWIRQHVVGHHTHCNDIQHDPDVKGGSVI
KLSRTSIPLEWHHLQQYYFLPLIQLLGFQWVFLDLHDLIEMKYKGEKLPESYRKERNIAIGLRVFFFIRKFVVPFALHFSWYTLLCTYLWMAIAALYLGFFFILSHLFVGAKS
LPPDGSIDWARHQIESSSNVGGEKLGISNGGLNYQIEHHLFPRLSHAHYAKIQPVVQKVCEENGVNYKKFPTILSNLGSMFRQVKALGSVPVEFMAKL >SEQ-149 - 89.2% sequence identity to SEQ ID NO 79
MPPHSRTEVGDPELSDMKHFTREEIANHTNDDYCILEDGVYDLTCFRDKHPGGDVLDFFPGQDATPHFFMFHQYESLPSVLAEYGVGSVARDDSYVQHDPLMKQIKSAVRKIM
PMGSWWAPPSWWIKACAILAATLYTDYLWIARGPTIPLAIILGLLYAAIGLNIQHDANHGSVSRNPMVNRLFGYSQDWIGGNRMLWIRQHVVGHHTHCNRHDHDPDVKGGSVI
RLSRYSLPKPWHHIQQIYFLPLIQLLGFQWVFLGLHDLIEMRYEGEKLPESYRKERGIAVGLRVGFFIRKFVVPFWLHFSWYTLLCTCLWMAIGAFYLGFFFILSHIFVGAKS
LPEDGNIDWARHQIESSSNVGGEKLGYSNGGLNFQIEHHLFPRMSHAHYAKIEPVVQKVCEENGVNYKKFPTILSNLDSTFRQVKALGSVPVEFMEGL >SEQ-150 - 89.2% sequence identity to SEQ ID NO 79
MPPHSGTKVSDPELSAMKHFAREEILNHTNDKICILEDGVYDLVNFRDKHPGGDYLDFFPGQDATPHFYMLHRYESPPSVLAEYKVGSVARDDSYVYHTPLMKQIKSAVRKVM
PMQEWWAPPSWYIKACAILAATLHTDYLMIASGPTIPLAIVSGLLFAAIGLNIQHDANHGSVSRNPMVNRLFGYAQDWIGGSRMLWIQQHVVGHHTHCNRIDHDPDVKGGSVI
TLSRTSLPLEFHHIQQLYFLPLIQLYGFQWVFLDLHDLIEMKYKGEKLPELYRPEYGIAIGLRVFFWIRKFIVPFALHFSWYTLLCTYLWMAIGAFYLGFFFILSHIFVGAKS
LGEDGNIDWARHQIESSSNVCGEKLGYMNGGLNYQIEHHLFPRLSHAHYSKIQPVVRKVCEENGVNYKKFGTIASNLDSLFRYLGGLGSVPVYEFMEGL >SEQ-151 - 89.2% sequence identity to SEQ ID NO 79
MPPHSRTKVSDPELSDMKHFTREEKLNDTNDDYCILEDGVYDLSNFRDKHPGGDYVDFFGGQDATPHFYMLHQRESPPSVMSKFKVGSVARDDSYVYHTPLMKQIKSAVRKVM
PKQEWWAPPSWYIKACAILIATLFTDYLMIASGPTIPLAIVSGLLYAWIGLNIQHDANHGSVSRNPMVNRLFGYSQDWIGGSRMLWIQQHVVGHHTHCNRHQHDPDVKGGSAI
TLSPYSLWKEWHHIQQYYFLPLIQLLGFQWVFLGLHDLIEMKYKGEPLPPSYRKERNIAIGLRVFFWIRKVVVPFWLQFSWYTLLCTYLWMAIGALYLGFFFILSHIFVGAKS
LPEDANIDWARHQIESSSNVCGEKLGYLNGGLNFQIEHHLFPRMSHAHYSTIQPVVQKVCEENGVNYKKFGTILSNLDSMLRQVGALGSVPTEFLEGL >SEQ-152 - 89.2% sequence identity to SEQ ID NO 79
MPPYSRTKVVSDPELSDAKHFTREEILNHTRDKYCILEDGVYDCTNFRDKHPGGDVLDFFPGQDATPHFYMLHRYVWLPSLLSEFKVGSVARDDSYVYHTELHKQICSAVRKV
IPMQEWWAPPSWYIKACAILVATLYTDYLWIASGPTIFLGIIIGLLYAAIGLNIQHDANHGSISRNPMVNRLFGYSQDWIGGSRMLWIRQHVVGHHTHCNRHQHDPDIKGGSV
ITLSRVDLPKEFHHIQQLYFLPLIQLYGFQWVFLGLHDLIEMKWKGEKLSESARKEYAIAIGLRVFFFIRKVVVPFALHFSWYTLLCTYLWVAIGALYLGFFFILSHIFIGAK
SLPEDAKNIDWARHQIETSSNVCGEWLGIMNGGLNYQIEHHLFPRMSHAHYAKIQPVVQKVCEENGVNYKHFGTILSNLDSLFRHVKALGSVAVEFMAGL

Figure 3 (continued)

```
>SEQ-153 - 89.2% sequence identity to SEQ ID NO 79
MPPHSATKVSVPELSDMKHFTREEILNHTNDDYCILEDGVYDLTNFRDKHPGGDFLDLFGGQDATPHFYMLHQRASPPSVLAEYKVGSVDRDDSYVQHTPLMQIKSAVRKII
PKQEWWAPPSWYIKACALLIATLYTDYWIASGPTIPLAIVLGLLYAAIGLNIQHDANHGAVSRNPVVNRLFGYSQDWIGGSMMLWIRQHVVNHHTHCNRHQHDPDVKGGSVI
TLSPYSLPKEWHHIQQYFLPGEQLLGFQWVFLGLNELIEMKYKGEKLPEIYRKERAIAVGLRVFFARKFVIPFALHFSWYTLLCTCLWMASAALYLGFFFILSHIFVGAKS
LGPDAKNIEWARHQIESSSNVCGEKLGISNGGLNYQIEHHLFPRMSHAHYSPIQPVVQKVCEKNGVNYKKFGTIGSNLDSTFRQVKALGSRAVYEFMEGL >SEQ-154 - 89.2% sequence identity to SEQ ID NO 79
MPPHSRTKVSAPELSDLMKHFTREEILNHTRDKYCIVGDGVYDLTNFRDKHPGGEFLDFFGGQDATPHFYMLHQYEWPPSILAEYKVGSLDRDDSYVHHESLMKQIKSDVRKI
MPMQEWWAPPSWYIKACALIVATLYTDYWIASGPTIPLAIVSGLLYAAIGLNIQHDANHGAVSRNPMVNRLFGYSQDWIGGSRLLWIRQHVVGHHTHCNDHQHDPDVKGGSV
LTLSRYSLWMEFHHLQQYYFLPLEQLLGFQWIFLGLHDLIEMRYKGEPLPPSYRKERGIAIGCRVFFIRKFVVPFALHFSWYTLLCTYLMMAIAALYLGFFFILSHIFIGAK
SLPPDANIDWARHQIESSSNVCGDWLGISNGGLNYQIEHHLFPRMNHAHYSKIQPIVQKVCEENGVNYKKFGTILSNLDSMFRQVKALGSVAVYEFMEGL >SEQ-155 - 89.2% sequence identity to SEQ ID NO 79
MPPHARTKVVGDDPELSALMKHFTREEILNHTNDDYCILEDGVYDCSAFRDKHPGGDVLSFFPGQDATPHFYMFHQRESPPAVLAEYKVGSVARDDSYVYHTPLMLQIKSAVR
KVMPMGEWWAPPSWWIKACAIIAATLYLDYLMIARGPTIPLAIVSGLLFAAIGLNIQHDANHGSISRNPMVNRLFGYSQDWIGGSRMLWIRQHVVNHHTHCNRHQHDPDVKGG
SVIRLSPYSLWKEFHHIQQYYFLPLDQLYGFQWVFLDLHDLIEMKYKGEKLSELYRKERNPAIGLRVFFWARKVVVPFALHPTWYTLLCTYLMMAIAALYLGFFFILSHLFVG
VKSLPEDANIDWARHQIESSSNVCGEKLGISNGGLNYQIEHHLFPRMSHSHYSPIQPVVQKVCEENGVNYKKFPTILSNLDSTFRQVKGLGSRAVEFMGGL >SEQ-156 - 89.2% sequence identity to SEQ ID NO 79
MPPHSRTKVSDPELSDMKHFTREKILNHTRDDYCILEDGVYDLTCFRDKHPGGDVLDFFPGQDATPHFYMLHQRASLPSVLSEYKVGSVARDDSYVHHDALMKQIKSAVRGIM
PMQEWWAPPSWYIKACAILIATLHTDYYWIASGPTIPLAIVSGLLYAAIGLNIQHDANHGSVSRNPMVNRLFGYSQDWIGGSRVLWIRQHVVGHHTHCNRVQHDPDVKGGSVI
RLGRYDLPKEFHHLQQIYFLPGEQLLGFKWVFLGLHNGGLNYQIEHHLFPRLHHAHYSKIQPVVRKVCEENGVNYKKFGTILSNLDAMFRQVKALGSVAVYNEFMEGL
LPEEGNIEWARHQIESSSNVCGEWLGISNGGLNYQIEHHLFPRLHHAHYSKIQPVVRKVCEENGVNYKKFGTILSNLDAMFRQVKALGSVAVYNEFMEGL >SEQ-157 - 89.2% sequence identity to SEQ ID NO 79
MPPHSGTKVSDPELSDLMKHFTREEILNHTNDKYCILEDGVYDSTCFRDEHPGGEVLDFFPGQDATPGFYELHQYEWLPSVLAEYKVGSVARDDSYVYHTPGMKQIKSAVNKV
MPKQEWWAPPSWYIKACAIIAAALYTDYLMIASGPTIPLAIVGLLYAAIGLNIQHDANHGSVSRNPMVNRLFGYGQDWIGGGRMIWLQQHVVGHHTHCNRVQHDPDVKGGSV
LQLSRYDLWKEFHHIQQYFLPMDALLIGFQWVFLGLHDLIEMKYKGEKLPEIYRKDRNIAIGLKVFFIRKFIIPFALQFSWYTLLCTYLMVCVAAFYLGFFFILSHIFIGAK
SLPEDAKNIDWARHQIESSSNVCGEWLGISNGGLNYQIEHHLFPRMSHAHYSKIAPVVQKVCEENGVNYKKFPTIASNLDSLFRQVKALGSVAVEFMEGL >SEQ-158 - 89% sequence identity to SEQ ID NO 79
MPPHSRTKGSDDPELSDLAKHFTRTKKLNHENDKYCILGDGVYDSTCFRDKHPGGDVLDFFPGQDATPHFYMYHQYESLPSVLAEYKVGSIDRDDSYVQHTPLMKQIKADVRK
VMPMQEGWAPPSWYIKEFHHIQQYFLPLEQLYGFQWVFLGLNDLLEMKYKGEKLPPSCRKERNIAIGLRVFFWIRKFVVPFALHFSWYTLLCIYLMWATAALYLGFFFILSHIFVGA
AIRLSRYSLPKEFHHIQQYYFLPLEQLYGFQWVFLGLNDLLEMKYKGEKLPPSCRKERNIAIGLRVFFWIRKFVVPFALHFSWYTLLCIYLMWATAALYLGFFFILSHIFVGA
KSLPPDANIDWARRQIESSSNVCGEKLGISNGGLNYQIEHHLFPRMSHAHYSKIQPVVRKVCEENGVNYKKFPTIGSNLDSTFRQVKALGSVPVEFMEGL
```

Figure 3 (continued)

>SEQ-159 - 89% sequence identity to SEQ ID NO 79
MPPHAGTEVSDPELSDMKHFTREEILNHTNDKICILEDGVYDCTAFRDKHPGGDVLDFFPGQDATPHFWMFHQRESPPSVLAEYKVGSVARDSYVYHTEGMLQIKSAVRKVM
PKQEWWAPPSWYIKACAILAATLYTDYLWILSGPTIFLAIVSGLLYAAIGLNIQHDANHGSVSRNPMVNRLFGYSQDWIGGNMMLWIRKHVVGHHTHCNDHQHDPDVKGGSVI
TLSPYSGWMEFHHIQQYYFLPLDQLYGFQWVFLGLHELIEMKYKGEKLPEICRKERGIAIGLRVFFWIRKFVVPFALHFSWYTLLCTYLWMAIAALYLAFFVLSHIFVGAKS
LPPDANIDWARHQIESSSNVCGEKLGILNGGLNYQIEHHLFPRMSHSHYSTIQPVVQKVCEENGVNYKHFGTILSNLDSTFRQVKALGSVPIEFMEGL >SEQ-160 - 89% sequence identity to SEQ ID NO 79
MPPHSRTKVGDPELSDMKHFTREEILNHTNDDYCILEDGVYDCNNFRDKHPGGDFLDFFPGQDATPHFYMLHQRESLPSVLAEFKVGSVARDDSYVYHDPGHKQIKCAVRGVM
PRQEWWAPPSWYIKACAILAATLYTDYLWIASGPTIPLAIVIGLLYAAIGLNIQHDANHGAVSRNPMVNRLFGYSQDWIGGSRVLWIRQHVVGHHLHCNDVQHDPDIKGGSVI
TLSPYSGWKEFHHIQQLYFLPLEQLYGFQWVFLGLHDLIEMKYKGEPLPESYRPEYNIAIGLRIFFFARKFVVPFALEFSWYTLLCTYLWMAIAALYLGFFFILSHIFGVKS
LPPDANVDWARHQIENSSNVCGEKLGISNGGLNYQIEHHLFPRMSHAHYSKIQPVVQKVCEENGVNYKKFPTILSNLDSLFKQIKALGAVAVEFMEGL >SEQ-161 - 89% sequence identity to SEQ ID NO 79
MPPHSRTKGSDPELSDAKHFTRERILNDTNDKLCILGDGVYDLTAFRDKHPGGDFLDFFPGQDATPHFYMLHQYEWLPSVLAKYKVGSIARDDSYVHHDPLMKQIKSAVRAVL
PRQEWWAPPSWYIKACAILAATLYTDYLWIASGPTIPLAIISGLLYAAIGLNIQHDANHGSVSRNPMVNRLFGYSQDWIGGSRMLWIRQHVVGHHLHTNRHDHDPDVKGGSVL
TLSRYSIWKEFHHIQQLYFLPLDQLLGFQWVFLGLHDLIEMRYKGEKLPPSYRPLRNIAIGLRVGFFIRFFVVPFALHFSWYTLLCTYAWMCIGALYLGFFFILSHIFVGAGS
LPEDAKNIDWARHQIETSSNVCGEKLGISNGGLNYQIEHHLFPRMSHSHYSPIQPVVQKVCEENGVNYKKFGTILSNLDSLFSQIKALGSVPTYEFMEGL >SEQ-162 - 89% sequence identity to SEQ ID NO 79
MPPHGRTKVSDPELSDMEHFSRTEILNHTNDKLCILEDGVYDLTNFRDKHPGGDYLDFFPGQDATPHFYEFHQYESPPSVMAEYFVGSVARDDSYVYHTPLMKQIKSAVNKVL
PMGSWWAPPSWYIKACAILAATLYTDYLMIASGPTIPLAIVSGLLYAAIGLNIQHDANHGGVSRNPMVNRLFGYSQDWIGGSRMLWIRQHVVGHHTHCNRVQHDPDVKGGGVI
TLSPYSLWMEFHHIQQYYFLPLEVLYGFQWVFLGLHDLIEWKYKGEKLSESYRKDRNPAIGLRVFFFARFFVLPFALEFSWYTLLCTYLWMAIGAFYLGFFFILSHIFIGAKS
IPEDAKNIDWVRHQIESSSNVCGEKLGISNGGLNYQIEHHLFPRMSHAHYSKIQPVVQKVCEENGVNYKKFGTIGSNLDSIFKQVKALGSVATYEFMEGP >SEQ-163 - 89% sequence identity to SEQ ID NO 79
MPPHSATKVSDVPELSDLMKHFSREEILNHTNDKICILGDGVYDLTNFRDKHPGGDVIDFFPGQDATPHFYMLHQYESPPSVLAEYKVGSVARDDSYVYHDPLMKRICSAVRK
VMPMQEWWAPPSWWIKACALLAATLYTDYLWLASGPTIPLAIVLGLLYAAIGLNIQHDANHGSVSRNPMVNRLFGYSQDWIGGSRMLWIRQHVVGHHITNRHQHDPDVKGGS
AIRLSPTSLPKEFHHIQQYFLPLPIQLLGFQWVFLGANDLIEMKYEGEKLPESYRPERNIAIGCRVFFFIRKEIVPFALEFTWYTLLCTYLWMATAALYLGFFFILSHIFGA
KSLGPDGNIDWARHQIENSSNVGGEKLGISNGGLNYQIEHHLFPRMHHAHYSTIQPVVQKVCEEMGVNYKKFGTIGSNLDSTLRQVKGLGSVPTEFMEGL >SEQ-164 - 89% sequence identity to SEQ ID NO 79
MPPHSRRKVGSDPELRDMKHFTREEILNHNNDKYCILEDGVYDLTNFRDKHPGGDVLDFFPGQDATPHFYMLHQRESLPSILAEYKVGSVARDDSYVVATSLMKRIKSEVRGV
MPMGSWWAPPSWYIKACAILAATLYLDYLWIASGPTIPLAIVLFAAIGLNIQHDANHGSVSRNPAVNRLFGYSQDWIGGNRMLWIREHVVGHHLHTNRHQHDPDIKGGSV
LQLSRVSIPKEFHHIQQYYFLPLIQLYGFQWVFLGLHDLIEMKYKGEPLPPSYRKERNIAIGCRLFFFIRKFVVPFALHFSWYTLLCVCLWMAIGALYLGFFFVLSHIFIGAK
SLPEDGNIDWARHQIESSSNVCGEKLGIMNGGLNYQIEHHLFPRMSHAHYAKIAPVVQKVCEENGVNYKKFGTIGSNLDSTFRQIGALGSVAVEFMEGL

Figure 3 (continued)

>SEQ-165 - 88.8% sequence identity to SEQ ID NO 79
MPPHSRTKVSDPELSDLMKHFTREEILGDTNDDYCILGDGVYDLTNFRDKHPGGDYLDFFPGQDATPHFYQLHQYEWPPSVLAEFGVGSVARDDSYVHHTPLMKRIKSAVNKV
MPRQEWWAPPSWWIKACAILAATLYTDYLWIASGPTILLAIVIGLLYAAIGLNIQHDANHGSVSRNPMVNRLFGYSQDWIGGSMMLWLRQHVGHHTCNDHQHDPDVKGGSV
LTLSRYSLPMEFHHIQQIYFLPLEQLLGFQWVFLDLHDLIEMKYGEKLPESYRKERNIAIGCRIFFVRKFVVPFALHPSWYTLLCTYLWMATAALYLGFFILSHIFVGIK
SLPEDANIDWARHQIESSSNVCGDKLGYINGGLNYQIEHHLFPRLSHAYSKIQPVVQKVCEKNGVNYKHFPTIASNLGSTFRQLGALGAVAVYEFMGGL >SEQ-166 - 88.8% sequence identity to SEQ ID NO 79
MPPHSRTKVSDPELSDMEHFTREEILNHTNDKLCILEDGVYDLTNFRDKHPGGDVLDFFPGQDATPHFYMFHRYESLPSVLAEYKVGSIARDDSYVYATELMKQIKSAVRKVI
PMQEGWAPPSWYIKACAILIATLYLDYLWLLSGPTIPLAIVSGLLYAAIGLNIQHDANHGSVSRNPMVNRLFGYGQDWIGGSRLLWIRQHVGHHTCNRHQHDPDVKGGSVI
QLSRYDGWMEFHAIQQYFLPLEQLYGFKWVFLGAHDLIEMKWEGEKLPELYRKERNIAIGLRVFFARKFVIPFALHFSWYTLLCVYLWAIAALYLGFFILSHIFVGAKS
LPEDGSVEWARHQIESSSNVCGEKLGISNGGLNYQIEHHLFPRMSHAHYSKIQPVVQKVCEEMGVNYKKFGTIGSNLGSTFQQVGALGAVAVEFMEGL >SEQ-167 - 88.8% sequence identity to SEQ ID NO 79
MPPHSATKVVSAPELSDMKHFSREKILNHENDKICILEDGVYDLTNFRDKHPGGDVLDFFPGQDATPHFYMLHQYESLPSVMAEYKVGSVARDDKYVHHTPLMKQIKSEVRKV
MPMQEWWAPPSWYIKACAILAATLYTDYLWIASGPTIPLAIVSGLLFAAIGLNIQHDANHGSVSRNPMVNRLFGYSQDWIGGNRMLWIRQHVGHHLHSNRHDHDPDLKGGSV
IQLSRYSLPKEFHHLQQYFLPLIQLYGFQWVFLGAHDLIEWRKGEKLPPSYRPEFNIAIGCRIFFFIRKFVVPFALHPSWYTLLCTYLWMATAALYLGFFILSHIFVGVK
SLPEDANIEWARRQIESSSNVGGEKLGILNGGLNYQIEHHLFPRMSHAHYSPIQPVVQKVCEENGVNYKKFGTIGSNLGSTFRQVKALGSRATEFLEGL >SEQ-168 - 88.8% sequence identity to SEQ ID NO 79
MPPHSRRKVSDAPELRDMKHFSREEILDHNNDKYCILEDGVYDLTAFRDKHPGGEVLDFFPGQDATPHFYMYHQYESPPSVLAEYKVGSVARDDSFVYHTELMKQICAAVNKV
MPMQSWWAPPSWYIKACALLAATLYTDYLWIASGPTILLAIVIGLLYAAIGLNIQHDANHGALSRNPMVNRLFGYSQDWIGGSRMLWIRQHVNHHTCNRHDHDPDVKGGSV
IQLKRYSLPLPFHHIQQYFLPLIQLLGFQWVFLGLHELIEMKYGLIENGLNYQIEHHLFPRMSHAHYSKIQPVVQKVCEEMGVNYKKFGTILSNLDSTLRQVKALGSVPVEYMAGL
SLGEEANIDWARHQIESSSNVCGEKLGISNGGLNFQIEHHLFPRMSHAHYSKIQPVVQKVCEENGINYKHFGTILSNLGSTFRQVKALGSVPVEFMAKL >SEQ-169 - 88.5% sequence identity to SEQ ID NO 79
MPPHSRSEVSDPELSDLMKHFTREEILNHTNDDLCILGDGVYDLTNFRDKHPGGEVLDFFPGRDATPHFFMLHQREWLPSVLAEYKVGSVARDDSYVYHEPGMKQIKSAVRK
VMPQEGWAPPSWYIKACAILVATLYTLPDYLWIASGPTIFLAIVSGLLYAAIGLNIQHDANHGSVSRNPMVNRLFGYSQDWIGGSRMLWIRQHVGHHTCNRIQHDPDVKGGS
AIQLSRYSLMWEHHHIQQYFLPLPDQLLGFWIFLGLHLDLIEWKYEGEPLPESYRKERNPAIGLRVFFIRKFVIPFALHPSWYTLLCTCLWMATASLYLGFFILSHIFVGA
KSLPEDASVEWARHQIETSSSNVGGEKLGISNGGLNFQIEHHLFPRMSHAHYSKIQPVVQKVCEENGINYKHFGTILSNLGSTFRQVKALGSVPVEFMAKL >SEQ-170 - 88.3% sequence identity to SEQ ID NO 79
MPPHGRTKVGPELSDMKHFTREEILNHTNDKYCILEDGVYDASAFRDKHPGGDFLDFFPGQDATPGFYMFHQHEWPPSVLAEFYKVGSVARDDSYVYHTPLMKQICSAVRKVM
PKGEWWAPPSWYIKACAILAATLYTDYLWIASGPTIPLAIVIGLLYAAIGLNIQHDANHGAVSRNPMVNRLFGYSQDWIGGSRLLWIRQHVGHHTCNDVQHDPDLKGGSVI
TLSRTSLPKEFHHIQQYFLPLEALYGFQWVFLPLEAHDLIEMKYKGEKLSPSYRKLRNIAIGLRIFFARKFVIPFALHFSWYTLLCTCAWMATATLYLGFFILSHIFVGAKS
LPEDGNVDWARHQIESSSNVCGEKLGHLNGGLNYQIEHHLFPRMSHAHYSTIEPVVQKVCEENGVKYKKFGTILSNLDSTFKQVKALGSVAVEFMEGL

Figure 3 (continued)

>SEQ-171 - 88.3% sequence identity to SEQ ID NO 79
MPPHSRKKGSDPELSDLAKHFTRERILNHTRDKYCILEDGVYDLTNFRDKHPGGDVLDFFPGQDATPHFYMLHQYEWPPSVLARYGVGSVARDDSYVYADPLMLQICSAVNKV
IPMQEWWAPPSWWIKACAILVATLFTDYLWLAKGPTIPLAIVSGLLFAAIGLNIQHDANHGSVSRNPMVNRLFGYSQDWIGGSRMLWLRQHVVGHHTHCNRIDHDPDVKGGSV
IRLSRYSLPKEFHHIQQIYFLPLIQLLGFQWVFLGLHDLIEMRYKGEKLPESYRKERNPAVGLRIFFFARKFVIPFALHFSWYTLLCTCAWMAIAALYLGFFFILSHIFVGIK
SLGPDANVDWARHQIESSSNVCGEWLGILNGGLNYQIEHHLFPRMNHAHYSKIQPIVQKVCEENGVNYKHFGTILSNLDSTFRQIKALGSRAVEFMEGL >SEQ-172 - 88.3% sequence identity to SEQ ID NO 79
MPPHSRTKGSDVAELSDLMKHFTRTEIANHTRDKYCILEDGVYDANNFRDKHPGGDVIDIFPGQDATPHFFELHQYASPPSVLSEYKVGSVARDDSYVYHTPLMKQIKSAVRK
VMPKGEGWAPPSWYIKACAILAATLYLDYYWIARGPTIPLAIVSGLLYAAIGLNIQHDANHGSVSRNPMVNRLFGYSQDWIGGSRMLWIRQHVVGHHTHCNRHDHDPDVKGGS
VITLSRYSIPKEWHHIQQLYFLPLIQLYGFQWVFLDLHDLIEMKWEGEPLPESYRKERNPAIGLRLFFFVRKIVVPFALHFSWYTLLCTYLWMAIGALYLCFFFILSHNFVGI
KSIPEDASIDWARHQIESSSNVGGEWLGYLNGGLNYQIEHHLFPRMSHAHYSKIQPVVQKVCEENGVNYKKFGTILSNLDSTFRHVKALGAVAVYEFMEGL >SEQ-173 - 88.3% sequence identity to SEQ ID NO 79
MPPHGRTKVSDVPELSDLAKHFSREEILNHTNDKYCILEDGVYDATNFRDKHPGGDVIDFFPGRDATPHFWMLHRYEWPPSVLAEYGVGSVARDDKFVHHTALMKQIKSAVRA
VLPMQEWWAPPSWYIKACAILAATLFTDYLWIASGPTIPLAIVLGLLYAWIGLNIQHDANHGSVSRNPVVNRLFGYSQDWIGGGRMLWIRQHVVGHHTHCNRHDHDPDVKGGS
VITLKRVSLPLEWHHIQQYYFLPLIQLLGFQWVFLGLNDLIEWKYKGEKLSEICRKERNIAIGLRVFFFVRKFVVPFALHFSWHTLLCTYLWMAIAALYLGFFFILSHIFVGA
KSLGEDANIDWARHQIETSSNVGGDKLGYSNGGLNYQIEHHLFPRMNHAHYAKIQPVVQKVCEENGVKYKHFGTILSNLDSTFKQVKALGSVAVYEFLAGL >SEQ-174 - 88.3% sequence identity to SEQ ID NO 79
MPPHAGTKVSDDPELRDLMKHFTREEILNHTNPKYCILGDGVYDATNFRDKHPGGDVLDFFPGQDATPGFYMFHQYESLPGLLARYKVGSVARDDSYTHHDPLMKQLCSAVRK
VMPMQEWWAPPSWYIKACAILIATLYLDYLMIASGPTIPLAIVLGLLFAAIGLNIQHDANHGSVSRNPMVNRLFGYAQDWIGGSRMLWIRQHVVGHHTHCNDVQHDPDVKGGS
VIQLSRYSLPKPFHHLQQYYFLPLEQLYGFQWVFLGLHDLIEMKYKGEKLPESYRKEFNPAIGLRVGFFIRFFVVPFALQFSWYTLLCTCLWMAVAAFYLGFFFILSHIFVGV
KSLPEDANIDWARHQIESSSNVCGEKLGISNGGLNYQIEHHLFPRLSHAHYAPIQPVVQKVCEDNGINYKKFGTILSNLDSTFRQVKALGAVATYEFLAGL >SEQ-175 - 88.3% sequence identity to SEQ ID NO 79
MPPHSRTKVSDPELSDLMKHFTREEILNHNNDKYCILEDGVYDLTNFRDKHPGGDVLDLFPGQDATPGFYMLHQHVSLPSVLAEYKVGSVDRDDSYVYHTPLQKQLCSAVRKV
IPMQEWWAPPSWYIKACAILAATLYTDYLWIASGPTIPLAIVSGLLYAAIGLNIQHDANHGGVSRNPAVNYLFGYAQDWIGGGRMLWIQKHVVNHHIHTNDVQHDPDVKGGSA
IKLKRYSLWKEFHHIQQYYFLPLIQLLGFQWVFLGLHDLIEMKYKGEPLPPSARPERGIAIGLRVFFFIRKFVLPFALHFSWYTLLCIYLWMAIAALYLGFFFVLSHIFVGAK
SLPPDANIDWARHQIESSSNVCGEKLGISNGGLNYQIEHHLFPRMNHAHYSKIQPIVQRICEDNGVNYKKFPTIGSNLDSLFSQVKALGSVAIYEFMGGL >SEQ-176 - 88.1% sequence identity to SEQ ID NO 79
MPPHSRKKVGSDPELSDMKHFTREEKLNHTNDKYCILGDGVYDLTNFRDKHPGGDVLSFFPGQDATPHFFMLHRKESPPSVLAEYKVGSVERDDKYTYHTPLMKQIKAAVRKV
MPRGEWWAPPSWYIKACAILAATLYTDWLWLASGPTIPLAIVSGLLYAAIGLNIQHDANHGSISRNPVVNRLFGYSQDWIGGSMMLWIREHVVGHHTHCNRHQHDPDVKGGSV
ITLSPTDLWLPFHHIQQYYFLPLDQLYGFQWVFLGLHELIEMKYKGEPLPESYRKERNPAIGCKVFFFIRKFAVPFWLQPSWYTLLCVYLWMAIAAFYLGFFFILSHIFVGAK
SIPEDAKSIDWARHQIESSSNVCGEKLGISNGGLNYQIEHHLFPRMSHAHYSKIQPVVQRVCEENGINYKKFGTIGSNLDSLLRQVKALGSVAVEFMEGL

Figure 3 (continued)

>SEQ-177 - 88.1% sequence identity to SEQ ID NO 79
MPPHSRTKVSDPELSDLMKHFTREEILNHTNDKICILEDGVYDATNFRDKHPGGDVLDIFPGQDATPHFYMLHQRESPPGLLAKYKVGSVARDDSYVYHEPLMKQIKCEVNKV
LPKQEWWAPPSWYIKACAILVATLYLDYWIARGPTIPLAIVSGLLYAAIGLNIQHDANHGSVSRNPAVNRLFGYSQDWIGGSRMLWIRKHVVGHHLHCNRHQHDPDVKGGSV
LTLSPYSLPKEFHHIQQLYFLPLIVLYGFKWVFLGLHDLIEMRYKGEKLPELYRKEFNIAIGLRLFFFIRKFVVPFALHPSWHTLLCTCLWVASAALYLGFFILSHIFVGAG
SLPEDASIDWARHQIESSSNVGGEKLGISNGGLNYQIEHHLFPRMSHAHYSKIQPVVQKVCEENGINYKKFGTILSNLDSLFRHLGAIGSRATYEFMEGL >SEQ-178 - 87.9% sequence identity to SEQ ID NO 79
MPPHGRTEGGDPELSDMKHFTYEEILNHTRDKICIVEDGVYDLTNFRDKHPGGDVVDLFGGQDATPHFYMLHQYESPPSILAEYKVGSIARDDSYVYHTPGMKRIKAEVRKVM
PKGEWWAPPSWYIKACAILAAALYTDYLWIASGPTIPLAIVSGLLYAWIGLNIQHDANHGSVSRNPMVNRLFGYSQDWIGGSRMLWIQQHVVGHHIHCNRVQHDPDVKGGSVI
KLSPYSLPMEFHHIQQYYFLPLEQLYGFQWVFLGLLLEMKYKGEKIPEIARKERGIAIGLRVFFFVRKFVVPLALEFTWHTLLCTYLWMCVAAFYLGFFILSHIFVGIGS
LPEDAKNIDWARHQIESSSNVCGEKLGYSNGGLNYQIEHHLFPRMSHAHYSKIQPVVQKVCEENGVNYKKFGTILSNLDSMFRQVKALGSVAVYEFMEGL >SEQ-179 - 87.9% sequence identity to SEQ ID NO 79
MPPHSRTKVSDPELRDMKHFTRTEILNHTRDKYCILGDGVYDLTCFRDKHPGGDVLDFFPGQDATPHFYMLHQYEWPPAVLAEYKVGSVARDDSYVHHTPLMKQIKSEVRKVM
PMQEWWAPPSWYIKACALLVAALYTDYLMIASGPTIPLAIVSGLLYAAIGLNIQHDANHGAVSRNPMVNRLFGYSQDWIGGSRMLWIREHVVGHHLHCNRIQHDPDVKGGSAI
RLSRYSLMKPWHHLQQIYFLPLIQLLGFKWVFLDLHDLIEMKYKGEKLPELYRPLRNIAIGCRIFFFIRKFALPFWLHFTWYTLLCTCLWMAIASLYLAFFFILSHIFVGIKS
LGEDANIDWARHQIESSSNVGGDKLGYSNGGLNYQIEHHLFPRMSHAHYSKIEPVVQKVCEENGVNYKKFPTILSNLDSTFRQVKALGSVAVEFMEGL >SEQ-180 - 87.9% sequence identity to SEQ ID NO 79
MPPHSRTKVSDPELKDMKHFAREEILNHTNDKYCILEDGVYDLTNFRDKHPGGDVLDFFPGQDATPHFYMLHRYAWPPSVLAEYKVGSVDRDDSYVYHTSLYLQIKSAVRKVI
PMQEWWAPPSWWIKACALLAATLYTDYLMIASGPTIPLGIVSGLLYAAIGLNIQHDANHGSVSRNPMVNRLFGYSQDWIGGSRMLWIREHVVGHHTHCNRHQHDPDVKGGGVL
KLSRYDIWMEFHHIQQLYFLPLEQLLGFQWVFLGLHDLIDMKWKGEKLSESARPERGIAIGLRVFFWIRKFSWYTLLCTYAWVASAAFYLGFFILSHIFVGAKS
LPPDASVDWARHQIETSSNVGGEKLGISNGGLNYQIEHHLFPRMSHAHYSKIQPVVQKVCEENGVNYKKFPTIASNLDSTFSQVKALGSVAVEFMGGI >SEQ-181 - 87.4% sequence identity to SEQ ID NO 79
MPPHARSKVSDPELSDMKHFTRERILNDENDKICILEDGVYDLTNFRDKHPGGDYVDFFGGQDATPHFYMFHQYESPPSVLAEYKVGSVARDDSFVYHEPLMKQIKSAVRKVM
PRGEWWAPPSWYIKACAILAATLYTDYLWIARGPTIPLAIVIGLLFAAIGLNIQHDANHGSLSRNPMVNRLFGYSQDWIGGSRLLWLREHVVGHHTNCNRHDHDPDVKGGGVL
KLSRSSLPMEFHHIQQIYFLPLEQLLGFQWVFLGLHDLIEMKYKGEPLPELYRKERNIAVGLRVFFFIRKEVVPFALHPSWHTLLCICLWMAIGALYLGFFILSHIFVGIKS
LPEDAKNIDWARHQIESSSNVCGEKLGHSNGGLNYQIEHHLFPRMSHSHYSKIEPVVQKVCEDNGINYKKFGTILSNLDSTLRQLGALGSRPVEFMEGL >SEQ-182 - 87.4% sequence identity to SEQ ID NO 79
MPPHSRTKVVSDPELSDMEHFTRTEILNHENDKYCILEDGVYDLSNFRDKHPGGEYLDFFPGQDATPGFFQLHQYASLPGVLARYKVGSIDRDDSYVQHTSLMKQICSAVRKV
MPRGEWWAPPSWWIKACAIIATLYDLMIASGPTIPLAIVSGLLFAAIGLNIQHDANHGALSRNPMVNRLFGYAQDWIGGSMMLWIQQHVVGHHTHCNRVQHDPDVKGGGGV
ITLSPTSLPLEFHHIQQYFLPLIQLLGFQWVFLHSWYTLLCIYLWMAIGALYLAFFFILSHIFVGAK
SLPEDGKNIDWARHQIESSSNVCGEKLGISNGGLNYQIEHHLFPRMSHSHYSKIQPVVQKVCEENGINYKKFGTILSNLDSIFRQVGALGSVAVEFLEGL

Figure 3 (continued)

>SEQ-183 - 87.2% sequence identity to SEQ ID NO 79
MPPHSRTKGSDDPELSDLMKHFTREKILNDNDKYCIVGDGVYDATNFRDKHPGGEFLDFFPGQDATPHFYMFHQYESLPSILAEYKVGSLERDDSYTYHDSLMKQIKSAVRK
VIPMQEWWAPPSWYIKACAILIATLYLDYLMIASGPTIFLAIVLGLLYAMIGLNIQHDANHGSVSRNPMVNRLFGYSQDWIGGSRVLMIRQHVVGHHIHSNRHQHDPDVKGGG
VITLSRVSLPKEFHHIQQYYFLPLEQLLGFKWVFLGLHDLIDMKYKGEKLPESYRKERGIAIGCRVGFFARKIVPFALQFSWHTLLCVYLWVAIATLYLAFFILSHIFIGA
KSLPPDANIDWARHQIESSSNVCGEKLGIMNGLNYQIEHHLFPRMSHAHYSTIQPVVQRVCEENGVNYKHFGTIGSNLDSTFRQVKALGSVAVEFLEGL >SEQ-184 - 87% sequence identity to SEQ ID NO 79
MPPHAATEVSVPELSDLMKHFSRTEILNDTRDKYCILEDGVYDLPNFRDKHPGGDYVDFFPGQDATPHFYMLHQYEWPPSVLAEYGVGSVARDDSFVHHDPLMLQLCSDVRKV
MPMGEWWAPPSWWIKACAILAATLYLDYLMLASGPTIPLAIISGLLYAAAIGLNIQHDANHGSVSRNPMVNRLFGYSQDWIGGSRMLWIRQHVGHHIHCNRHQHDPDVKGGGV
ITLSRYDLPMEFHHLQQLYFLPLIALLGFQWVFLGLHDLIEWKYKGEKLPEIYRKERGIAIGLRVFFWARFFVVPFALEFSWYTLLCTYLMAIAALYLGFFILSHIFVGAK
SLPEDASIDWARRQIETSSNVGGEWLGIINGGLNFQIEHHLFPRMSHAHYSTIQPVVQKVCEENGVNYKKFGTIGSNLDSTFKQVKALGSVPYEFMAGL >SEQ-185 - 87% sequence identity to SEQ ID NO 79
MPPHSRTKVSVPELSDMKHFTREEILNDTNDDYCILEDGVYDLTNFRDKHPGGDFIDIFPGRDATPHFYMYHQRESPPSVLSEYKVGSLERDDSFVHYTALMKQLKSEVNKIM
PMGEGWAPPSWYIKACALLVATLYTDYLMIAKGPTIPLSIVIGLLYAWIGLNIQHDANHGSVSRMLWIQQHVVGHHIHCNRIQHDPDVKGGSVI
RLSRYSLMKEFHHIQQYYFLPLEQLLGFQWVFLGLNDLIDMKWKGEKLPESARKERNIAIGLKVFFEIRKFVVPFALQFSWYTLLCTYAWMAIAALYLGFFFILSHIFVGAKS
LPEEANIDWARHQIESSSNVCGEWLGHLNGGLNYQIEHHLFPRMSHAHYSKIQPVVQKVCEENGVKYKKFGTILSNLDSTFRQVKALGSVPIEFMEGL >SEQ-186 - 85.4% sequence identity to SEQ ID NO 79
MPPHSRTKVSDDAELKDLMKHFAREEKLNHTNDKLCILEDGVYDLPNFRDEHPGGDVLSFFPGRDATPHFYQLHQKESPPALLAEYKVGSVARDDSYVQYTPLHLQICADVNK
VMPRQEWWAPPSWWIKACALLAATLYTDYLMIASGPTIPLSIVLGLLFAWIGLNIQHDANHGGVSRNPMVNRLFGYGQDWIGGSRMLWIQQHVVGHHITHCNRHQHDPDVKGGS
VLKLSRYDLWLEWHHIQQYYFLPGEQLYGFQWVFLGLHELIEMKYKGEKLPESCRKERNPAIGLRVGFWIRKIVVPFALHFSWYTLLCTCLWMAIGSLYLGFFVLSHIFVGA
KSLPEDASIDWARRQIESSSNVCGDKLGISNGGLNYQIEHHLFPRMSHAHYSKIQPVVQKVCEDDGVNYKKFGTILSNLDSTFRQLKALGSVPVEFLEGL

Figure 3 (continued)

ENZYMES, ENZYME COMPONENTS AND USES THEREOF

This application is a National Stage application of International Application No. PCT/IB2013/056243, filed Jul. 30, 2013, which claims the benefit of U.S. Provisional Application No. 61/679,100, filed Aug. 3, 2012, the entire contents of which are hereby incorporated herein by reference. This application also claims priority under 35 U.S.C. § 119 to European Patent Application No. 12179241.0, filed Aug. 3, 2012, all of which are hereby incorporated herein by reference in their entirety.

REFERENCE TO SEQUENCE LISTING SUBMITTED VIA EFS-WEB

This application was filed electronically via EFS-Web and includes an electronically submitted sequence listing in .txt format. The .txt file contains a sequence listing entitled "Seq_List.txt" created on Jul. 30, 2013, and is 540,672 bytes in size. The sequence listing contained in this .txt file is part of the specification and is hereby incorporated by reference herein in its entirety.

The invention in principle pertains to the field of recombinant manufacture of fatty acids. It provides nucleic acid molecules which encode lysophospholipid-coenzyme A synthase (LACS), desaturases, elongases and elongase components. The invention also provides recombinant expression vectors containing desaturase, KCS, KCR and/or LACS nucleic acid molecules, host cells into which the expression vectors have been introduced, and methods for large-scale production of long chain polyunsaturated fatty acids (LCPUFAs), e.g. arachidonic acid (ARA, omega-6 unsaturated fatty acid), eicosapentaenoic acid (EPA, omega-3 unsaturated fatty acid) and/or docosapentaenoic acid (DHA, omega-3 unsaturated fatty acid).

Fatty acids are carboxylic acids with long-chain hydrocarbon side groups that play a fundamental role in many biological processes. Fatty acids are rarely found free in nature but, rather, occur in esterified form as the major component of lipids. As such, lipids/fatty acids are sources of energy (e.g., b-oxidation). In addition, lipids/fatty acids are an integral part of cell membranes and, therefore, are indispensable for processing biological or biochemical information.

Fatty acids can be divided into two groups: saturated fatty acids formed of single carbon bonds and the unsaturated fatty acids which contain one or more carbon double bonds in cis-configuration. Unsaturated fatty acids are produced by terminal desaturases that belong to the class of nonheme-iron enzymes. Each of these enzymes are part of an electron-transport system that contains two other proteins, namely cytochrome $b_5$ and NADH-cytochrome $b_5$ reductase. Specifically, such enzymes catalyze the formation of double bonds between the carbon atoms of a fatty acid molecule, for example, by catalyzing the oxygen-dependent dehydrogenation of fatty acids (Sperling et al., 2003). Human and other mammals have a limited spectrum of desaturases that are required for the formation of particular double bonds in unsaturated fatty acids and thus, have a limited capacity for synthesizing essential fatty acids, e.g., long chain polyunsaturated fatty acids (LCPUFAs). Thus, humans have to take up some fatty acids through their diet. Such essential fatty acids include, for example, linoleic acid (C18:2) and linolenic acid (C18:3). In contrast, insects, microorganisms and plants are able to synthesize a much larger variety of unsaturated fatty acids and their derivatives. Indeed, the biosynthesis of fatty acids is a major activity of plants and microorganisms.

Long chain polyunsaturated fatty acids (LCPUFAs) such as docosahexaenoic acid (DHA, 22:6 (4,7,10,13,16,19)) are essential components of cell membranes of various tissues and organelles in mammals (nerve, retina, brain and immune cells). For example, over 30% of fatty acids in brain phospholipid are 22:6 (n-3) and 20:4 (n-6) (Crawford, M. A., et al., (1997) Am. J. Clin. Nutr. 66:1032S-1041S). In retina, DHA accounts for more than 60% of the total fatty acids in the rod outer segment, the photosensitive part of the photoreceptor cell (Giusto, N. M., et al. (2000) Prog. Lipid Res. 39:315-391). Clinical studies have shown that DHA is essential for the growth and development of the brain in infants, and for maintenance of normal brain function in adults (Martinetz, M. (1992) J. Pediatr. 120:S129-S138). DHA also has significant effects on photoreceptor function involved in the signal transduction process, rhodopsin activation, and rod and cone development (Giusto, N. M., et al. (2000) Prog. Lipid Res. 39:315-391). In addition, some positive effects of DHA were also found on diseases such as hypertension, arthritis, atherosclerosis, depression, thrombosis and cancers (Horrocks, L. A. and Yeo, Y. K. (1999) Pharmacol. Res. 40:211-215). Therefore, appropriate dietary supply of the fatty acid is important for human health. Because such fatty acids cannot be efficiently synthesized by infants, young children and senior citizens, it is particularly important for these individuals to adequately intake these fatty acids from the diet (Spector, A. A. (1999) Lipids 34:S1-S3).

Currently the major sources of DHA are oils from fish and algae. Fish oil is a major and traditional source for this fatty acid, however, it is usually oxidized by the time it is sold. In addition, the supply of fish oil is highly variable, particularly in view of the shrinking fish populations. Moreover, the algal source of oil is expensive due to low yield and the high costs of extraction.

The biosynthesis of LCPUFA and the incorporation of LCPUFA into membrane lipids or triacylglycerides proceeds via various metabolic pathways (Abbadi 2001, European Journal of Lipid Science & Technology 103:106-113). In bacteria such as Vibrio, and microalgae, such as *Schizochytrium*, malonyl-CoA is converted into LCPUFA via an LCPUFA-producing polyketide synthase (Metz 2001, Science 293: 290-293; WO 00/42195; WO 98/27203; WO 98/55625). In microalgae, such as *Phaeodactylum*, and mosses, such as *Physcomitrella*, unsaturated fatty acids such as linoleic acid or linolenic acid are converted in a plurality of desaturation and elongation steps to give LCPUFA (Zank 2000, Biochemical Society Transactions 28: 654-658). Desaturation takes place either on acyl groups bound to Coenzyme A (acyl-CoA) or on acyl groups of membrane lipids, whereas elongation is biochemically restricted to acyl chains bound to CoA. In mammals, the biosynthesis of DHA comprises a chain shortening via beta-oxidation, in addition to desaturation and elongation steps. In microorganisms and lower plants, LCPUFA are present either exclusively in the form of membrane lipids, as is the case in *Physcomitrella* and *Phaeodactylum*, or in membrane lipids and triacylglycerides, as is the case in *Schizochytrium* and *Mortierella*. Incorporation of LCPUFA into lipids and oils, as well as the transfer of the fatty acid moiety (acyl group) between lipids and other molecular species such as acyl-CoA, is catalyzed by various transferases, such as acyltransferases and transacylases. These enzymes are known to carry out the incorporation or interexchange of saturated and unsaturated fatty acids (Slabas 2001, J. Plant Physiology 158: 505-513, Frentzen 1998, Fett/Lipid 100: 161-166, Cases 1998, Proc. Nat. Acad. Sci. USA 95: 13018-13023, Lu et al 2009, Proc. Nat. Acad. Sci. USA vol 106: no. 44: 18837-18842). One group of acyltransferases having three distinct enzymatic activities are enzymes of the "Kennedy pathway", which are located on the cytoplasmic side of the membrane system of the endoplasmic reticulum (ER). The ER-bound acyltransferases in the microsomal fraction use acyl-CoA as the activated form of fatty acids. Glycerol-3-phosphate acyltransferase (GPAT) catalyzes the incorporation of acyl groups at the sn-1 position of glycerol-3-phosphate. 1-Acylglycerol-3-phosphate acyltransferase, also known as lysophosphatidic acid acyltransferase (LPAAT), catalyze the incorporation of acyl groups at the sn-2 position of lysophosphatidic acid (LPA). After dephosphorylation of phosphatidic acid by phosphatidic acid phosphatase (PAP), diacylglycerol acyltransferase (DGAT) catalyzes the incorporation of acyl groups at the sn-3 position of diacylglycerols. Further enzymes directly involved in TAG biosynthesis—apart from the said Kennedy pathway enzymes—are the phospholipid diacylglycerol acyltransferase (PDAT), an enzyme that transfers acyl groups from the sn-2 position of membrane lipids to the sn-3 position of diacylglycerols; diacylglyceroldiacylglycerol transacylase (DDAT), an enzyme that transfers acylgroups from the sn-2 position of one diacylglycerol-molecule to the sn-3 position of another diacylglycerol-molecule and phosphatidylcholine:diacylglycerol cholinephosphotransferase (PDCT), an enzyme transfers the polar phosphatodyclcholine headgroup from the sn-3 position of an poly unsaturated phospholipid (e.g. containing 18:2n-6 or 18:3n-3), to the sn-3 position of a saturated (e.g. containing 18:0) or mono unsaturased (e.g. containing 18:1n-9) diacylgcylerole Lysophospholipid acyltransferase (LPLAT) represents a class of acyltransferases that are capable of incorporating activated acyl groups from acyl-CoA to membrane lipids, and possibly catalyze also the reverse reaction. More specifically, LPLATs can have activity as lysophosphophatidylethanolamine acyltransferase (LPEAT) and lysophosphatidylcholine acyltransferase (LPCAT). Further enzymes, such as lecithin cholesterol acyltransferase (LCAT) can be involved in the transfer of acyl groups from membrane lipids into triacylglycerides, as well. Generally, fatty acids in a cell are bound as thioesters. Formation of these thiosesers from free fatty acids occurs by the action of a Lysophospholipid-Coenzyme A Synthase (LACS).

EPA and ARA are both delta (d) 5 essential fatty acids. They form a unique class of food and feed constituents for humans and animals. EPA belongs to the n-3 series with five double bonds in the acyl chain. EPA is found in marine food and is abundant in oily fish from North Atlantic. ARA belongs to the n-6 series with four double bonds. The lack of a double bond in the ω-3 position confers on ARA different properties than those found in EPA. The eicosanoids produced from AA have strong inflammatory and platelet aggregating properties, whereas those derived from EPA have anti-inflammatory and anti-platelet aggregating properties. ARA can be obtained from some foods such as meat, fish and eggs, but the concentration is low.

Gamma-linolenic acid (GLA) is another essential fatty acid found in mammals. GLA is the metabolic intermediate for very long chain n-6 fatty acids and for various active molecules. In mammals, formation of long chain polyunsaturated fatty acids is rate-limited by Δ6 desaturation. Many physiological and pathological conditions such as aging, stress, diabetes, eczema, and some infections have been shown to depress the Δ6 desaturation step. In addition, GLA is readily catabolized from the oxidation and rapid cell division associated with certain disorders, e.g., cancer or inflammation. Therefore, dietary supplementation with GLA can reduce the risks of these disorders. Clinical studies have shown that dietary supplementation with GLA is effective in treating some pathological conditions such as atopic eczema, premenstrual syndrome, diabetes, hypercholesterolemia, and inflammatory and cardiovascular disorders.

Although biotechnology offers an attractive route for the production of specialty fatty acids, current techniques fail to provide an efficient means for the large scale production of unsaturated fatty acids. Accordingly, there exists a need for an improved and efficient method of producing unsaturated fatty acids, such as DHA, EPA and ARA.

As DHA is a particularly important polyunsaturated fatty acids, there is a high need for efficient production of this fatty acid. A particularly critical step in the production of DHA is the delta-4 desaturation step. This step is performed by delta-4 desaturases. These enzymes utilize docosapentaenoic acid (DPA, 22:5 delta7,10,13,16,19) bound to ACP, to CoA or in phospholipids as substrate to produce the respective DHA bound to ACP, to CoA or in phospholipids. DPA, in turn, is produced by a delta-5 elongase. Generally, these elongases elongate acyl-CoA fatty acids. It has been observed that desaturation efficiency can be greatly increased if a desaturase is employed which use, as substrates, fatty acids bound to the same backbone as those used during elongation. Specifically, desaturation efficiency has been shown to be increased by providing an acyl-coA desaturase (Domergue et al, Biochem. J. 2005, 483-490).

There is thus a need for delta-4 desaturases having high desaturation efficiency when paired with a delta-5 elongase. So far, such desaturases were only known from *Pavlova/Rebecca* species (Uniprot identifiers Q6VPV2_PAVLU and A0PJ29_9EUKA, putatively also D6NST0_9EUKA). This has made it difficult to screen for further desaturases having high desaturation efficiency when paired with a delta-5 elongase, because due to the similarity of the delta-4 desaturases of *Pavlova/Rebecca*, it is not possible to ascertain whether amino acids conserved in these desaturases are required for their function, or if they are retained only because not enough time has passed to create further mutations.

The inventors now provide a delta-4 desaturase having high desaturation efficiency when paired with a heterologous delta-5 elongase. The delta-4 desaturase has a very low sequence identity to the *Pavlova/Rebecca* desaturases mentioned above. The invention thus also provides a list of allowable mutations to the delta-4 desaturase, such that only few of these mutations would abolish the delta-4 desaturase activity as such or the high desaturation efficiency when paired with a delta-5 desaturase. Accordingly, the invention provides a method for screening for further delta-4 desaturases having high desaturation efficiency when paired with a heterologous delta-5 elongase.

DETAILED DESCRIPTION OF THE INVENTION

Specifically, the invention provides a delta-4 desaturase having at least 60%, preferably at least 69%, even more preferably at least 74% and even more preferably at least 81% sequence identity to the amino acid sequence according to any of SEQ ID NO. 79, 86 or 85, wherein the sequence preferably also comprises a motif selected from "KHPGG", "QHPGG" or "RHPGG", preferably a motif selected from "KHPGGD", "QHPGGD" or "RHPGGD", and a motif selected from "GLNIQHDANHG" or "HVVGHH", preferably a motif selected from "AAIGLNIQHDANHG" or "QHVVGHH".

It was particularly surprising that a delta-4 desaturase having high desaturation efficiency when paired with a heterologous delta-5 desaturase could be provided which has such low sequence identity to the above mentioned delta-4 desaturases of Pavlov/Rebecca. It was also particularly surprising that in the motiv "EHPGG" conserved in Pavlova/Rebecca the first amino acid G, which is an acidic amino acid, could be replaced by K, which is a basic amino acid, without abolishing the high desaturation efficiency. It can thus be extrapolated that surprisingly also "QHPGG" and "RHPGG" are valid motifs in place of "EHPGG". Also, it was surprising that the motif "HVVMHH" conserved in Pavlova/Rebecca delta-4 desaturases could be replaced by "HVVGHH", replacing hydrophobic methionine M by the inconspicuous glycine G. And it was surprising that the first amino acid E of the conserved Pavlova/Rebecca motif "EHVVMHH" could be replaced by Q, again exchanging an acidic amino acid for a non-acidic amino acid. It was unexpected that such significant changes in amino acid properties in conserved motifs would be possible without abolishing the desaturation efficiency when compared with a heterologous delta-5 elongase.

The delta-4 desaturase of the present invention at least comprises the following conserved sequence motifs, wherein "X" denotes any amino acid: "HPGG", "QDWIGG", "NGGLN", "QIEHHLFPR" and "IGLNIQH-DXNHG". As shown in the alignment of FIG. 2, these sequences are required for delta-4 desaturase activity.

Preferably, the delta-4 desaturase of the present invention comprises at least 5, more preferably at least 6, even more preferably at least 7 and most preferably all the following conserved sequence motifs, wherein "X" denotes any amino acid: "DPDXK", "HPGG", "NGGLNXQIEHHLFPR", "GYXQDWIGG", "IGLNIQHDANHG", "YLXFFF", "HVVXHHXH" and "FXGXDAT". These longer conserved sequence motifs are also found in delta-4 desaturases of genus Sphaeroforma, Pavlova or Rebecca as shown in FIG. 2.

More preferably, the delta-4 desaturase of the present invention comprises at least 5, more preferably at least 6, even more preferably at least 7, even more preferably at least 8, even more preferably at least 9, even more preferably at least 10, even more preferably at least 11, even more preferably at least 12, even more preferably at least 13, even more preferably at least 14 and most preferably all of the following conserved sequence motifs: "DPD[VILMATQ]K", "HPGG", "NGGLN[FWY]QIEHHLFPR", "GY[ASGM]QDWIGG", "Y[FI]LP", "IGLNIQHDANHG", "YL[AG]FFF", "HVV[GNASKDWM]HH[LIFT]H", "AP[PA]S", "F[WF][AVCGSPI]R", "F[GP]G[RQ]DAT", "T[LIMVFCA][LIVCA]C", "P[LF][WA]L", "KA[CA]A" and "I[VL][GADE]D[GA]". In this list, "X" again denotes any amino acid. A list of amino acids in brackets indicates that one member chosen among the members of list is present at the corresponding position of the motif, wherein each individual list is ordered in decreasing preference. For example, a motiv "PLWL" is preferred over a motiv "PLAL" or "PFWL" or "PFAL", and one of these four motifs must be present in the more preferred delta-4 desaturases of the present invention. Some of the amino acids in the lists are not found in delta-4 desaturases of genus Sphaeroforma, Pavlova or Rebecca as shown in FIG. 2.

However, according to the invention these new amino acids are similar enough to those amino acids found at corresponding positions in the delta-4 desaturases of genus Sphaeroforma, Pavlova or Rebecca, such that the new amino acids will generally not abolish or severely reduce the delta-4 desaturase efficiency, particularly the high efficiency of desaturation when combined with a delta-5 elongase for producing polyunsaturated fatty acids from the substrate or substrates of said delta-5 elongase.

Most preferably the delta-4 desaturase of the present invention comprises at least 5, more preferably at least 6, even more preferably at least 7, even more preferably at least 8, even more preferably at least 9, even more preferably at least 10, even more preferably at least 11, even more preferably at least 12, even more preferably at least 13, even more preferably at least 14 and most preferably all of the following conserved sequence motifs: "DPD[VQ]K", "HPGG", "NGGLN[YF]QIEHHLFPR", "GY[SAM]QD-WIGG", "Y[FI]LP", "IGLNIQHDANHG", "YL[AG]FFF", "HVV[GM]HH[LT]H", "AP[PA]S", "F[FW][AI]R", "F[GP]G[RQ]DAT", "T[LA][LA]C", "P[LF][AW]L", "KA[AC]A" and "I[VL][GE]D[GA]". As described above, a list of amino acids in brackets indicates that one member chosen among the members of list is present at the corresponding position of the motif, wherein each individual list is ordered in decreasing preference.

According to the invention, there is further provided a delta-4 desaturase having the amino acid sequence SEQ ID NO. 85 and optionally one or more of the following mutations: H4S, H4Y, H4Q, H4E, H4N, A5S, A5G, A5C, A5P, A5T, A5V, A6R, A6G, A6K, A6S, A6N, T7K, T7S, T7R, T7N, T7A, T7G, K8E, K8D, K8R, K8Q, V9-, V9I, V9L, V9A, G10V, G10I, G10A, G10M, G10C, G11S, G11N, G11D, G11A, G11K, D12-, S13-, D14A, D14V, D14I, D14E, D14G, D14P, P15A, P15G, P15S, P15V, P15T, R18K, R18S, R18T, R18A, R18Q, D19A, D19G, D19P, D19S, L20-, K21-, M22A, M22L, M22I, M22V, E23K, E23R, E23Q, H24Y, H24F, H24I, H24M, H24L, H24Q, H24R, H24V, F25Y, F25W, F25I, F25A, S26T, S26A, S26C, S26G, S26N, Y27R, Y27F, E28T, E28D, E28N, E28S, R29K, R29E, R29Q, R29D, I30K, I30L, I30V, L31A, L31I, N32D, N32G, N32H, N32S, N32T, N32R, N32K, N32E, N32Q, N32A, N32V, D33H, D33N, D33T, E34T, E34N, E34D, E34Q, E34R, R35N, R35K, R35H, D36P, D36E, D36N, D36S, D37E, D37K, L38I, L38V, L38M, L38F, L38Y, C39T, C39A, C39S, C39V, V41L, V41I, V41M, V41T, G42A, G42D, G42E, G44A, A48S, A48C, A48L, A48R, A48K, T49S, T49V, T49N, T49P, T49K, T49A, A50C, A50N, A50G, D53E, D53N, K54Q, K54R, A59-, D60E, D60N, D60H, F61Y, F61W, F61V, F61I, V62L, V62I, V62M, V62A, V62T, D63S, D63N, D63E, L64I, L64F, L64M, G66P, R68Q, R68H, R68D, R68N, P72E, P72D, P72Q, H73G, H73A, H73N, H73S, F75W, F75M, F75Y, E76Q, E76M, E76H, Y77F, Y77W, Y77H, Y77L, R79K, R79Q, R79H, R80H, R80K, R80Q, R80Y, R80N, E81A, E81V, E81Q, E81L, E81P, W82G, W82S, P83D, P83V, P83K, P83A, P83T, P83E, P83Q, P83M, P83L, P84K, P84R, A85S, A85G, A85C, A85T, A85P, A85V, V86I, V86L, V86M, V86R, V86A, V86T, L87M, L87I, L87V, L87F, A88S, A88C, A88G, K89R, K89E, K89Q, K89P, K89N, Y90F, Y90W, K91F, K91G, K91Y, K91L, K91W, L95I, L95V, L95M, D96A, D96E, D96G, D96P, R97K, R97P, R97Q, R97H, R97E, R97A, D98E, D98N, D98S, D99E, D99Q, S100K, S100G, S100N, S100P, Y101F, Y101W, Y101H, Y101P, V102T, V102I, V102L, Q103H, Q103E, Q103R, Q103N, Q103K, Q103D, Q103Y, H104A, H104Y, H104V, H104I, H104F, H104R, D105E, D105P, D105T, S106P, S106E, S106A, S106D, S106N, S106T, G107L, G107I, G107M, G107A, Y108H, Y108Q, Y108W, Y108M, Y108V, Y109K, L109M, L109I, L109V, R110Q, R110K, R110H, R110E, L111I, L111F, C112G, C112A, C112N, C112S, C112K, A113C, A113S, A113G, E114D, E114Q, E114P, E114S, E114K, E114A, N116R, N116D, N116H, G117A, G117K, G117R, G117S, G118L, I118V, L119I, L119M, K121R, K121M, K121Q, K121L, G122W, G122Q, G122N, S123E, S123D, S123N, S123G, G124W, G124A, G124N, G125-, W126F, P129A, P129G, W131Y, W132Y, I133L, I133V, C136A, C136G, C136S, L138I, L138V, L138M, L139I, L139V, L139M, V140A, V140I, V140L, V140C, V140M, A142T, A142P, A142S, A142G, L143I, L143V, Y144F, Y144H, Y144W, Y144S, Y144T, L145I, L145V, L145M, L145F, L145T, D146E, D146N, D146Q, Y147W, Y147F, Y147H, Y147G, Y148F, Y148H, Y148L, M149W, M149L, M149I, M149F, L150I, L150V, A151L, A151C, A151G, A151S, R152K, R152S, R152N, R152Q, R152D, P154K, P154E, P154R, I156L, I156V, L157F, L157I, L157M, L157Y, L157W, L157P, A159S, A159G, A159C, A159T, A159P, A159V, I160V, I160L, I161V, I161L, I161F, L162I, L162V, L162M, L162F, L162C, L162A, L162T, L162S, L165I, L165V, F166Y, W168G, W168A, W168C, A181G, A181C, A181T, A181P, A181V, L182I, L182V, L182M, N185H, N185Y, P186S, V187M, V187A, V187I, V187P, V188I, V188L, V188A, V188T, Y190R, Y190H, Y190W, L191C, L191I, F192L, F192I, A195S, A195G, A195M, A195Q, A195K, S202N, S202G, S202D, S202T, S202A, S202K, M203R, M203L, M203Q, M203I, M204L, M204V, M204I, M204Q, M204C, L207I, L207V, Q208R, Q208E, Q208K, Q209E, Q209K, Q209R, Q209D, Q209H, G213N, G213A, G213S, G213K, G213D, G213W, G213M, L216I, L216F, L216T, T218C, T218S, T218V, T218A, T218N, T218P, D220E, D220N, D220R, D220G, I221V, I221F, I221Y, I221H, D222N, D222Q, D222P, H223Y, H223F, H223Q, H223W, H223R, H223E, H223N, H223M, H223V, H223P, H223I, H223L, H223D, H223A, V227I, V227L, V227M, V227A, V227T, V227Q, G229A, G230H, G230N, G230D, G231S, G231N, G231A, A232V, A232T, A232I, A232G, L233I, L233V, R234K, R234Q, R234N, R234E, R234H, R234T, K236S, K236G, K236A, K236T, P237K, P237D, P237E, P237Y, T238V, T238S, T238P, T238N, T238A, T238I, T238Y, D239S, D239I, D239E, G240I, G240L, G240F, G240C, G240M, G240S, W241F, W241Y, W241P, L242M, L242I, L242V, L242F, L242K, P243E, P243D, W244F, H246A, H246S, H246Y, H246G, H246N, L247I, L247V, L250I, L250V, L250M, L250F, L250Y, F252I, F252Y, L255G, L255M, L255A, L255K, L255C, L255F, E256D, E256Q, E256K, E256P, E256R, E256N, E256S, E256V, E256A, E256T, E256G, E256H, E256I, A257V, A257Q, A257L, A257C, A257P, A257E, L258M, L258I, Y259F, Y259W, Y259H, Y259L, G260A, G260C, K262Q, K262R, W263L, W263F, V264I, V264L, V264M, V264F, F265Y, F265W, F265H, F265S, D267G, L268A, L268I, L268V, H269N, H269Q, H269R, H269L, E270D, E270Q, E270K, L272I, L272F, E273D, E273A, E273G, E273P, W274F, W274Y, W274M, K275R, K275E, K275Q, W276Y, E277K, E277D, E277R, P280K, P280R, I281L, I281V, P282S, P282D, P282N, P282G, P283E, P283D, P283Q, L284I, L284M, L284V, L284C, L284A, L284T, L284S, A285Y, A285C, A285F, A285V, A285S, A285L, R286K, R286Q, R286H, R286E, R286L, R286M, R286V, R286A, P287K, P287D, P287E, P287G, P287Q, P287S, P287R, E288D, E288L, E288K, E288V, E288Q, F289Y, F289R, F289H, A290G, A290S, A290N, A290C, P291I, V293I, V293L, G294A, G294S, G294P, G294N, G294K, G294R, G294E, G294D, G294Q, G294T, G294H, G294C, G294W, G294M, G294Y, G294V, C295L, C295I, K296R, K296E, K296Q, K296N, K296P, L297I, L297V, G298F, G298A, G298W, G298S, W300F, A301V, A301C, A301G, A301S, A301P, A301I, F303Y, F303W, F303K, V304I, V304F, V304L, V304Y, A305V, A305I, A305L, A305T, A305C, L306I, L306V, L306M, L308F, L308I, W309A, W309G, H311Q, H311E, H311R, H311Y, H311N, P312F, P312Y, S313T, S313N, S313G, S313A, W314F, W314L, W314Y, W314I, W314M, W314V, H315Y, L317I, L317M, L317V, L317F, L317C, L317A, L318I, L318V, L318C, L318A, V320I, V320T, V320P, V320L, C321Y, A322L, A322C, A322S, A322G, W323T, V324I, V324L, V324M, C325A, C325G, C325S, T326S, T326V, T326N, T326I, T326P, T326L, G327A, G327N, G327K, S328A, S328T, S328L, S328C, S328V, F329L, F329Y, A332G, A332C, A332S, A332V, A332P, A332T, I336V, I336F, I336L, L337I, L337F, L337M, I340N, I340L, I340V, I340M, I340F, I340T, I342V, I342D, I342L, I342C, V344I, V344L, V344A, V344M, K345G, K345R, K345A, I347V, I347L, G348P, P349D, P349E, D350E, D350N, D350Q, D350G, D350R, D350K, G351A, G351C, G351S, G351P, G351V, K352-, S353-, L354-, P355-, P355D, P355S, R356-, N357S, N357D, N357G, N357E, I358V, I358A, I358L, D359E, D359N, D359P, D359T, W360F, A361G, A361V, A361C, A361S, A361T, R362Q, R362K, R362H, R363H, R363K, R363N, I365V, I365L, T367S, T367N, T367P, T367V, T367A, T367D, G372C, G372A, G372N, G372S, E374D, E374K, E374R, E374N, E374Q, E374H, E374S, E374P, E374A, E374T, E374V, E374G, E374M, E374Y, W375K, W375G, G377A, G377W, H378Y, H378N, H378F, H378Q, H378R, H378M, H378I, H378E, H378W, H378D, H378V, L379I, L379M, L379S, L379V, L379A, L379T, F385W, F385Y, L395M, L395I, L395F, H396S, H396N, H396Y, H396Q, H396E, A398S, A398C, A398G, H399Y, A401S, A401G, A401N, K402T, K402P, K402S, K402R, K402E, K402Q, Q404E, Q404A, Q404R, Q404K, Q404H, Q404V, V406I, V406L, V406M, V406A, V406T, Q408R, Q408H, Q408E, Q408N, Q408M, K409R, K409Q, K409T, K409M, V410I, V410H, V410R, C411I, C411A, C411V, E413D, E413K, E413Q, E413R, E413P, E413I, E413S, E413H, E413A, N414K, N414D, N414L, N414G, N414S, V416I, V416F, V416L, V416Y, N417K, N417R, N417G, K419R, K419G, K419S, H420Y, H420Q, H420R, H420N, H420E, H420K, P422G, P422D, I424V, I424C, G425A, G425L, G425N, G425P, G425D, G429D, G429N, G429S, S430A, S430T, S430C, S430N, M431L, M431I, M431V, M431T, M431F, M431C, L432F, L432I, L432M, S433R, S433K, S433Q, S433A, S433T, S433N, H434Y, H434Q, H434N, H434R, L435I, L435M, L435V, L435F, G436K, G436S, G436P, A437G, A437K, A437P, A437S, L438I, L438M, L438V, G439A, G439N, G439S, G439D, A440S, A440C, A440T, A440V, R441V, R441I, R441L, P442A, P442V, T443V, T443I, T443A, T443G, T443L, W444-, W444Y, W444F, W444S, N445-, A446-, E447D, E447Q, E447K, F448Y, F448W, F448K, M449L, M449I, M449G, A450G, A450E, A450S, A450P, A450D, A450C, G451K, G451R, G451N, G451D, L452P, L452I, L452V, L452A, L452M, E453-, E453D, E453S, E454-, K455-, S456-, S457-, V458-, E459-, C460-, R461-, L462-, R463-, L464-, G465-, A466-, A467-, C468-, A469-, R470-, G471-, C472-, C472S, W473-, W473Q, C474-, C474A, S475-, D476-, A477-, A478-, S479-, L480-, I481-, S482-, W483-, L484-, G485-. Preferably, the amino acid sequence also comprises a motif selected from "KHPGG", "QHPGG" or "RHPGG", preferably a motif selected from "KHPGGD", "QHPGGD" or "RHPGGD", and a motif selected from "GLNIQHDANHG" or "HVVGHH", preferably a motif selected from "AAIGLNIQHDANHG" or "QHVVGHH".

According to the invention, there is also provided a delta-4 desaturase having the amino acid sequence SEQ ID NO. 86, i.e. matching the sequence in an alignment and not considering mismatches due to the mutations mentioned hereafter, and optionally one or more of the following mutations: H4S, H4Y, H4Q, H4E, H4N, A5S, A5G, A5C, A5P, A5T, A5V, A6R, A6G, A6K, A6S, A6N, T7K, T7S, T7R, T7N, T7A, T7G, K8E, K8D, K8R, K8Q, G9V, G9I, G9A, G9M, G9C, G10S, G10N, G10D, G10A, G10K, D11A, D11V, D11I, D11E, D11G, D11P, P12A, P12G, P12S, P12V, P12T, R15K, R15S, R15T, R15A, R15Q, D16A, D16G, D16P, D16S, M17A, M17L, M17I, M17V, E18K, E18R, E18Q, H19Y, H19F, H19I, H19M, H19L, H19Q, H19R, H19V, F20Y, F20W, F20I, F20A, S21T, S21A, S21C, S21G, S21N, Y22R, Y22F, E23T, E23D, E23N, E23S, R24K, R24E, R24Q, R24D, I25K, I25L, I25V, L26A, L26I, N27D, N27G, N27H, N27S, N27T, N27R, N27K, N27E, N27Q, N27A, N27V, D28H, D28N, D28T, E29T, E29N, E29D, E29Q, E29R, R30N, R30K, R30H, D31P, D31E, D31N, D31S, D32E, D32K, L33I, L33V, L33M, L33F, L33Y, C34T, C34A, C34S, C34V, V36L, V36I, V36M, V36T, G37A, G37D, G37E, G39A, A43S, A43C, A43L, A43R, A43K, T44S, T44V, T44N, T44P, T44K, T44A, A45C, A45N, A45G, D48E, D48N, K49Q, K49R, D54E, D54N, D54H, F55Y, F55W, F55V, F55I, V56L, V56I, V56M, V56A, V56T, D57S, D57N, D57E, L58I, L58F, L58M, G60P, R62Q, R62H, R62D, R62N, P66E, P66D, P66Q, H67Q, H67A, H67N, H67S, F69W, F69M, F69Y, E70Q, E70M, E70H, Y71F, Y71W, Y71H, Y71L, R73K, R73Q, R73H, R74H, R74K, R74Q, R74Y, R74N, E75A, E75V, E75Q, E75L, E75P, W76G, W76S, P77D, P77V, P77K, P77A, P77T, P77E, P77Q, P77M, P77L, P78K, P78R, A79S, A79G, A79C, A79T, A79P, A79V, V80I, V80L, V80M, V80R, V80A, V80T, L81M, L81I, L81V, L81F, A82S, A82C, A82G, K83R, K83E, K83Q, K83P, K83N, Y84F, Y84W, K85F, K85G, K85Y, K85L, K85W, L89I, L89V, L89M, D90A, D90E, D90G, D90P, R91K, R91P, R91Q, R91H, R91E, R91A, D92E, D92N, D92S, D93E, D93Q, S94K, S94G, S94N, S94P, Y95F, Y95W, Y95H, Y95P, V96T, V96I, V96L, Q97H, Q97E, Q97R, Q97N, Q97K, Q97D, Q97Y, H98A, H98Y, H98V, H98I, H98F, H98R, D99E, D99P, D99T, S100P, S100E, S100A, S100D, S100N, S100T, G101L, G101I, G101M, G101A, Y102H, Y102Q, Y102W, Y102M, Y102V, L103K, L103M, L103I, L103V, R104Q, R104K, R104H, R104E, L105I, L105F, C106G, C106A, C106N, C106S, C106K, A107C, A107S, A107G, E108D, E108Q, E108P, E108S, E108K, E108A, N110R, N110D, N110H, G111A, G111K, G111R, G111S, I112L, I112V, L113I, L113M, K115R, K115M, K115Q, K115L, G116W, G116Q, G116N, S117E, S117D, S117N, S117G, G118W, G118A, G118N, W119F, P122A, P122G, W124Y, W125Y, I126L, I126V, C129A, C129G, C129S, L131I, L131V, L131M, L132I, L132V, L132M, V133A, V133I, V133L, V133C, V133M, A135T, A135P, A135S, A135G, L136I, L136V, Y137F, Y137H, Y137W, Y137S, Y137T, L138I, L138V, L138M, L138F, L138T, D139E, D139N, D139Q, Y140W, Y140F, Y140H, Y140G, Y141F, Y141H, Y141L, M142W, M142L, M142I, M142F, L143I, L143V, A144L, A144C, A144G, A144S, R145K, R145S, R145N, R145Q, R145D, P147K, P147E, P147R, I149L, I149V, L150F, L150I, L150M, L150Y, L150W, L150P, A152S, A152G, A152C, A152T, A152P, A152V, I153V, I153L, I154V, I154L, I154F, L155I, L155V, L155M, L155F, L155C, L155A, L155T, L155S, L158I, L158V, F159Y, W161G, W161A, W161C, A174S, A174G, A174C, A174T, A174P, A174V, L175I, L175V, L175M, N178H, N178Y, P179S, V180M, V180A, V180I, V180P, V181I, V181L, V181A, V181T, Y183R, Y183H, Y183W, L184C, L184I, F185L, F185I, A188S, A188G, A188M, A188Q, A188K, S195N, S195G, S195D, S195T, S195A, S195K, M196R, M196L, M196Q, M196I, M197L, M197V, M197I, M197Q, M197C, L200I, L200V, Q201R, Q201E, Q201K, Q202E, Q202K, Q202R, Q202D, Q202H, G206N, G206A, G206S, G206K, G206D, G206W, G206M, L209I, L209F, L209T, T211C, T211S, T211V, T211A, T211N, T211P, D213E, D213N, D213R, D213G, I214V, I214F, I214Y, I214H, D215N, D215Q, D215P, H216Y, H216F, H216Q, H216W, H216R, H216E, H216N, H216M, H216V, H216P, H216I, H216L, H216D, H216A, V220I, V220L, V220M, V220A, V220T, V220Q, G222A, G223H, G223N, G223D, G224S, G224N, G224A, A225V, A225T, A225I, A225G, L226I, L226V, R227K, R227Q, R227N, R227E, R227H, R227T, K229S, K229G, K229A, K229T, P230K, P230D, P230E, P230R, T231V, T231S, T231P, T231N, T231A, T231I, T231Y, D232S, D232G, D232E, G233I, G233L, G233F, G233C, G233M, G233S, W234F, W234Y, W234P, L235M, L235I, L235V, L235F, L235K, P236E, P236D, W237F, H239A, H239S, H239Y, H239G, H239N, L240I, L240V, L243I, L243V, L243M, L243F, L243Y, F245I, F245Y, L248G, L248M, L248A, L248K, L248C, L248F, E249D, E249Q, E249K, E249P, E249R, E249N, E249S, E249V, E249A, E249T, E249G, E249H, E249I, A250V, A250Q, A250L, A250C, A250P, A250E, L251M, L251I, Y252F, Y252W, Y252H, Y252L, G253A, G253C, K255Q, K255R, W256L, W256F, V257I, V257L, V257M, V257F, F258Y, F258W, F258H, F258S, D260G, L261A, L261I, L261V, H262N, H262Q, H262R, H262L, E263D, E263Q, E263K, L265I, L265F, E266D, E266A, E266G, E266P, W267F, W267Y, W267M, K268R, K268E, K268Q, W269Y, E270K, E270D, E270R, P273K, P273R, I274L, I274V, P275S, P275D, P275N, P275G, P276E, P276D, P276Q, L277I, L277M, L277V, L277C, L277A, L277T, L277S, A278Y, A278C, A278F, A278V, A278S, A278L, R279K, R279Q, R279H, R279E, R279I, R279M, R279V, R279A, P280K, P280D, P280E, P280G, P280Q, P280S, P280R, P280A, E281D, E281L, E281K, E281V, E281Q, F282Y, F282R, F282H, A283G, A283S, A283N, A283C, P284I, V286I, V286L, G287A, G287S, G287P, G287N, G287K, G287R, G287E, G287D, G287Q, G287T, G287H, G287C, G287W, G287M, G287Y, G287V, C288L, C288I, K289R, K289E, K289Q, K289N, K289P, L290I, L290V, G291F, G291A, G291W, G291S, W293F, A294Y, A294C, A294G, A294S, A294P, A294I, F296Y, F296W, F296K, V297I, V297F, V297L, V297Y, A298V, A298I, A298L, A298T, A298C, L299I, L299V, L299M, L301F, L301I, W302A, W302G, H304Q, H304E, H304R, H304Y, H304N, P305F, P305Y, S306T, S306N, S306G, S306A, W307F, W307L, W307Y, W307I, W307M, W307V, H308Y, L310I, L310M, L310V, L310F, L310C, L310A, L311I, L311V, L311C, L311A, V313I, V313T, V313P, V313L, C314Y, A315L, A315C, A315S, A315G, W316T, V317I, V317L, V317M, C318A, C318G, C318S, T319S, T319V, T319N, T319I, T319P, T319L, G320A, G320N, G320K, S321A, S321T, S321L, S321C, S321V, F322L, F322Y, A325G, A325C, A325S, A325V, A325P, A325T, I329V, I329F, I329L, I330I, I330F, L330M, I333N, I333L, I333V, I333M, I333F, I333T, I335V, I335D, I335L, I335C, I335I, V337I, V337L, V337A, V337M, K338G, K338R, K338A, I340V, I340L, G341P, P342D, P342E, D343E, D343N, D343Q, D343G, D343R, D343K, G344A, G344C, G344S, G344P, G344V, N345S, N345D, N345G, N345E, I346A, I346L, D347E, D347N, D347D, D347T, W348F, A349G, A349V, A349C, A349S, A349T, R350Q, R350K, R350H, R351H, R351K, R351N, I353V, I353L, T355S, T355N, T355P, T355V, T355A, T355D, G360C, G360A, G360N, G360S, E362D, E362K, E362R, E362N, E362Q, E362H, E362S, E362P, E362A, E362T, E362V, E362G, E362M, E362Y, W363K, W363G, G365A, G365W, H366Y, H366N, H366F, H366Q, H366R, H366M, H366I, H366E, H366W, H366D, H366V, L367I, L367M, L367S, L367V, L367A, L367T, F373W, F373Y, L383M, L383I, L383F, H384S, H384N, H384Y, H384Q, H384E, A386S, A386C, A386G, H387Y, A389S, A389G, A389N, K390T, K390P, K390S, K390R, K390E, K390Q, Q392E, Q392A, Q392R, Q392K, Q392H, Q392P, V394I, V394L, V394M, V394A, V394T, Q396R, Q396H, Q396E, Q396N, Q396M, K397R, K397Q, K397T, K397M, V398I, V398H, V398R, C399I, C399A, C399V, E401D, E401K, E401Q, E401R, E401P, E401N, E401S, E401H, E401A, N402M, N402D, N402L, N402G, N402S, V404I, V404F, V404L, V404Y, N405K, N405R, N405G, K407R, K407G, K407S, H408Y, H408Q, H408R, H408N, H408E, H408K, P410G, I412V, I412C, G413A, G413L, G413N, G413P, G413D, G417D, G417N, G417S, S418A, S418T, S418C, S418N, M419L, M419I, M419V, M419T, M419F, M419C, L420F, L420I, L420M, S421R, S421K, S421Q, S421A, S421T, S421N, H422Y, H422Q, H422N, H422R, L423I, L423M, L423V, L423F, G424K, G424S, G424P, A425G, A425K, A425P, A425S, L426I, L426M, L426V, G427A, G427N, G427S, G427D, A428S, A428C, A428T, A428V, R429V, R429I, R429L, P430A, P430V, T431V, T431I, T431A, T431G, T431L, E432D, E432Q, E432K, F433Y, F433W, F433K, M434L, M434I, M434G, A435G, A435E, A435S, A435P, A435D, A435C, G436K, G436R, G436N, G436D, L437P, L437I, L437V, L437A, L437M. Preferably, the amino acid sequence also comprises a motif selected from "KHPGG", "QHPGG" or "RHPGG", preferably a motif selected from "KHPGGD", "QHPGGD" or "RHPGGD", and a motif selected from "GLNIQHDANHG" or "HVVGHH", preferably a motif selected from "AAIGLNIQHDANHG" or "QHVVGHH".

Particularly preferred is a delta-4 desaturase having the backbone of SEQ ID NO. 86 with optionally one or more of the following mutations: H4S, H4Y, H4Q, H4E, H4N, A5S, A5G, A5C, A5P, A5T, A5V, A6R, A6G, A6K, A6S, A6N, T7K, T7S, T7R, T7N, T7A, T7G, K8E, K8D, K8R, K8Q, G9V, G9I, G9A, G9M, G9C, G10S, G10N, G10D, G10A, G10K, D11A, D11V, D11I, D11E, D11G, D11P, P12A, P12G, P12S, P12V, P12T, R15K, R15S, R15T, R15A, R15Q, D16A, D16G, D16P, D16S, M17A, M17L, M17I, M17V, E18K, E18R, E18Q, H19Y, H19F, H19I, F20Y, F20W, S21T, S21A, S21C, S21G, S21N, Y22R, Y22F, E23T, E23D, E23N, E23S, R24K, R24E, R24Q, R24D, I25K, I25L, I25V, L26A, L26I, N27D, N27G, N27H, N27S, N27T, N27R, D28H, D28N, D28T, E29T, E29N, E29D, E29Q, E29R, R30N, R30K, R30H, D31P, D31E, D31N, D31S, D32E, D32K, L33I, L33V, L33M, L33F, C34T, C34A, C34S, C34V, V36L, V36I, V36M, V36T, G37A, G37D, G37E, G39A, A43S, A43C, A43L, A43R, A43K, T44S, T44V, T44N, T44P, T44K, T44A, A45C, A45N, A45G, D48E, D48N, K49Q, K49R, D54E, D54N, D54H, F55Y, F55W, F55V, F55I, V56L, V56I, V56M, V56A, V56T, D57S, D57N, D57E, L58I, L58F, L58M, G60P, R62Q, R62H, R62D, R62N, P66E, P66D, P66Q, H67G, H67A, H67N, H67S, F69W, F69M, F69Y, E70Q, E70M, E70H, Y71F, Y71W, Y71H, Y71L, R73K, R73Q, R73H, R74H, R74K, R74Q, R74Y, R74N, E75A, E75V, E75Q, E75L, E75P, W76G, P77D, P77V, P77K, P78K, P78R, A79S, A79G, A79C, A79T, A79P, A79V, V80I, V80L, V80M, V80R, V80A, V80T, L81M, L81I, L81V, L81F, A82S, A82C, A82G, K83R, K83E, K83Q, K83P, K83N, Y84F, Y84W, K85F, K85G, K85Y, K85L, K85W, L89I, L89V, L89M, D90A, D90E, D90G, D90P, R91K, R91P, D92E, D92N, D92S, D93E, D93Q, S94K, S94G, S94N, S94P, Y95F, Y95W, Y95H, V96T, V96I, V96L, Q97H, Q97E, Q97R, Q97N, H98A, H98Y, H98V, H98I, H98F, H98R, D99E, D99P, D99T, S100P, S100E, S100A, S100D, S100N, S100T, G101L, G101I, G101M, G101A, Y102H, Y102Q, Y102W, Y102M, Y102V, L103K, L103M, L103I, L103V, R104Q, R104K, R104H, R104E, L105I, L105F, C106G, C106A, A107C, A107S, A107G, E108D, E108Q, E108P, E108S, N110R, N110D, N110H, G111A, G111K, G111R, G111S, I112L, I112V, L113I, L113M, K115R, K115M, K115Q, K115L, G116W, G116G, G116N, S117E, S117D, S117N, S117G, G118W, G118A, G118N, W119F, P122A, P122G, W124Y, W125Y, I126L, I126V, C129A, C129G, C129S, L131I, L131V, L131M, L132I, L132V, L132M, V133A, V133I, V133L, V133C, V133M, A135T, A135P, A135S, A135G, L136I, L136V, Y137F, Y137H, Y137W, Y137S, Y137T, L138I, L138V, D139E, D139N, D139Q, Y140W, Y140F, Y140H, Y141F, Y141H, M142W, M142L, M142I, M142F, L143I, L143V, A144L, A144C, A144G, A144S, R145K, R145S, R145N, R145Q, R145D, P147K, P147E, P147R, I149L, I149V, L150F, L150I, L150M, L150Y, A152S, A152G, A152C, A152T, A152P, A152V, I153V, I153L, I154V, I154L, L155I, L155V, L155M, L155F, L158I, L158V, F159Y, W161G, W161A, W161C, A174S, A174G, A174C, A174T, A174P, A174V, L175I, L175V, L175M, N178H, N178Y, V180M, V180A, V180I, V180P, V181I, V181L, V181A, V181T, Y183R, Y183H, Y183W, L184C, L184I, F185L, F185I, A188S, A188G, A188M, A188Q, A188K, S195N, S195G, S195D, S195T, S195A, S195K, M196R, M196L, M196Q, M196I, M197L, M197V, M197I, M197Q, M197C, L200I, L200V, Q201R, Q201E, Q201K, Q202E, Q202K, Q202R, Q202D, Q202H, G206N, G206A, G206S, G206K, L209I, L209F, L209T, T211C, T211S, T211V, T211A, T211N, T211P, D213E, D213N, D213R, D213G, I214V, I214F, I214Y, D215N, D215Q, D215P, H216Y, V220I, V220L, V220M, V220A, V220T, G223H, G223N, G223D, G224S, G224N, G224A, A225V, A225T, A225I, A225G, L226I, L226V, R227K, R227Q, R227N, R227E, R227H, K229S, K229G, K229A, K229T, P230K, P230D, P230E, P230R, T231V, T231S, T231P, T231N, T231A, D232S, D232G, D232E, G233I, G233L, G233F, W234F, L235M, L235I, P236E, P236D, H239A, H239S, H239Y, H239G, H239N, L240I, L240V, L243I, L243V, L243M, L243F, F245I, F245Y, L248G, L248M, L248A, L248K, L248C, L248F, E249D, E249Q, E249K, A250V, A250Q, A250L, A250C, A250P, A250E, L251M, L251I, Y252F, G253A, G253C, K255Q, K255R, W256L, W256F, V257I, V257L, V257M, V257F, F258Y, D260G, L261A, L261I, L261V, H262N, H262Q, H262R, E263D, E263Q, E263K, L265I, L265F, E266D, E266A, E266G, E266P, W267F, W267Y, K268R, K268E, K268Q, W269Y, E270K, E270D, E270R, P273K, P273R, I274L, I274V, P275S, P275D, P275N, P275G, P276E, P276D, L277I, L277M, L277V, L277C, A278Y, A278C, A278F, A278V, A278S, A278L, R279K, R279Q, P280K, P280D, P280E, E281D, E281K, E281V, E281G, F282Y, F282R, F282H, A283G, A283S, A283N, A283C, P284I, V286I, V286L, G287A, G287S, G287P, C288L, C288I, K289R, K289E, K289Q, K289N, K289P, L290I, L290V, G291F, G291A, G291W, G291S, A294V, A294C, A294G, A294S, F296Y, F296W, F296K, V297I, V297F, V297L, V297Y, V297V, A298I, A298L, A298T, A298C, L299I, L299V, L299M, L301F, L301I, W302A, W302G, H304Q, H304E, H304R, H304Y, H304N, P305F, P305Y, S306T, S306N, S306G, S306A, W307F, W307L, H308Y, L310I, L310M, L310V, L310F, L311I, L311V, L311C, V313I, V313T, V313P, V313L, C314Y, A315L, A315C, A315S, A315G, W316T, V317I, V317L, C318A, C318G, C318S, T319S, T319V, T319N, T319I, T319P, T319L, G320A, G320N, G320K, S321A, S321T, S321L, S321C, S321V, F322L, F322Y, A325G, A325C, A325S, A325V, A325P, A325T, I329V, I329F, I329L, L330I, L330F, L330M, I333N, I333L, I333V, I333M, I333F, I333T, I335V, I335D, I335L, I335C, V337I, V337L, V337A, V337M, K338G, K338R, K338A, I340V, I340L, P342D, D343E, D343N, D343Q, D343G, G344A, G344C, G344S, G344P, G344V, N345S, N345D, N345G, N345E, I346V, I346A, I346L, D347E, D347N, D347P, D347T, W348F, A349G, A349V, A349C, A349S, A349T, R350Q, R350K, R350H, R351H, R351K, R351N, I353V, I353L, T355S, T355N, T355P, T355V, T355A, T355D, G360C, G360A, G360N, G360S, E362D, E362K, E362R, W363K, W363G, G365A, G365W, H366Y, H366N, H366F, H366Q, H366R, L367I, L367M, L367S, L367V, L367A, L367T, F373W, F373Y, L383M, L383I, L383F, H384S, H384N, H384Y, H384Q, H384E, A386S, A386C, A386G, H387Y, A389S, A389G, A389N, K390T, K390P, K390S, K390R, K390E, Q392E, Q392A, Q392R, Q392K, Q392H, Q392P, V394I, V394L, V394M, V394A, V394T, Q396R, Q396H, Q396E, Q396N, Q396M, K397R, K397Q, K397T, K397M, V398I, V398H, V398R, C399I, C399A, C399V, E401D, E401K, E401Q, E401R, E401P, N402M, N402D, N402L, N402G, N402S, V404I, V404F, V404L, V404Y, N405K, N405R, N405G, K407R, K407G, K407S, H408Y, H408Q, H408R, P410G, P410D, I412V, I412C, G413A, G413L, G413N, G413P, G413D, G417D, G417N, G417S, S418A, S418T, S418C, S418N, M419L, M419I, M419V, M419T, M419F, M419C, L420F, L420I, L420M, S421R, S421K, S421Q, S421A, S421T, S421N, H422Y, H422Q, H422N, H422R, L423I, L423M, L423V, L423F, G424K, G424S, G424P, A425G, A425K, A425P, A425S, L426I, L426M, L426V, G427A, G427N, G427S, G427D, A428S, A428C, A428T, A428V, R429V, R429I, R429L, P430A, P430V, T431V, T431I, T431A, T431Q, T431L, E432D, E432Q, E432K, F433Y, F433W, F433K, M434I, M434I, M434G, A435G, A435E, A435S, A435P, A435D, A435C, G436K, G436R, G436N, G436D, L437P, L437I, L437V, L437A, L437M. Preferably, the amino acid sequence also comprises a motif selected from "KHPGG", "QHPGG" or "RHPGG", preferably a motif selected from "KHPGGD", "QHPGGD" or "RHPGGD", and a motif selected from "GLNIQHDANHG" or "HVVGHH", preferably a motif selected from "AAIGLNIQHDANHG" or "QHVVGHH".

Also preferred according to the present invention is a delta-4 desaturase having the backbone of SEQ ID NO. 86 with optionally one or more of the following mutations: H4S, H4Y, A5S, A5G, A6R, A6G, T7K, T7S, T7R, K8E, G9V, G10S, D11A, D11V, P12A, R15K, R15S, D16A, M17A, E18K, S21T, S21A, E23T, R24K, I25K, L26A, N27D, N27G, D28H, E29T, E29N, R30N, D31P, L33I, V36L, A43S, A43C, T44S, T44V, T44N, T44P, A45C, D54E, F55Y, V56L, V56I, D57S, L58I, R62Q, H67G, F69W, E70Q, Y71F, R73K, R74H, R74K, E75A, E75V, A79S, A79G, V80I, V80L, L81M, A82S, K83R, K83E, Y84F, K85F, K85G, L89I, D90A, D90E, S94K, Y95F, V96T, Q97H, H98A, H98Y, D99E, S100P, S100E, S100A, G101L, Y102H, Y102Q, L103K, R104Q, A107C, E108D, N110R, G111A, L113I, K115R, S117E, L131I, L132I, V133A, V133I, A135T, Y137F, Y137H, Y140W, M142W, A144L, R145K, R145S, L150F, A152S, A152G, L155I, A174S, A174G, L175I, V180M, V180A, Y183R, A188S, A188G, S195N, S195G, M196R, M197L, M197V, Q201R, Q202E, Q202K, G206N, L209I, T211C, T211S, D213E, I214V, V220I, V220L, A225V, R227K, R227Q, K229S, K229G, T231V, T231S, G233I, L235M, H239A, L243I, L248G, L248M, E249D, A250V, A250Q, K255Q, V257I, L261A, H262N, E266D, K268R, E270K, P275S, L277I, A278Y, A278C, E281D, E281I, F282Y, A283G, K289R, L290I, G291F, A294V, V297I, A298V, A298I, L299I, H304Q, H304E, S306T, L310I, L311I, V313I, A315L, T319S, T319V, S321A, S321T, A325G, A325C, I329V, I333N, I333L, I335V, V337I, K338G, D343E, G344A, N345S, I346V, D347E, A349G, A349V, T355S, T355N, G360C, E362D, H366Y, L367I, L367M, H384S, H384N, A386S, A389S, K390T, K390P, Q392E, Q392A, V394I, Q396R, K397R, V398I, E401D, E401K, N402M, N402D, V404I, N405K, G413A, S418A, M419L, M419I, L420F, S421R, S421K, S421Q, H422Y, L423I, A425G, L426I, G427A, A428S, R429V, T431V, T431I, F433Y, M434L, A435G, A435E, G436K, L437P, L437I.

Preferably, the amino acid sequence also comprises a motif selected from "KHPGG", "QHPGG" or "RHPGG", preferably a motif selected from "KHPGGD", "QHPGGD" or "RHPGGD", and a motif selected from "GLNIQHDANHG" or "HVVGHH", preferably a motif selected from "AAIGLNIQHDANHG" or "QHVVGHH".

Even more preferably the delta-4 desaturase of the present invention has the backbone of SEQ ID NO. 86 with optionally one or more of the following mutations: H4S, A5S, A6R, T7K, T7S, K8E, K8D, G9V, G10S, D11A, D11V, P12A, R15S, D16A, M17A, E18K, S21T, Y22R, E23T, R24E, I25K, L26A, D28H, D28T, E29T, R30N, D31P, D31S, D32K, C34T, V36L, G37E, G39A, A43L, T44K, A45N, D48E, D54H, F55V, V56L, D57S, L58F, G60P, R62Q, P66E, H67A, E70M, Y71L, R73Q, R74Y, E75A, P78K, A79S, V80R, L81M, A82S, K83E, Y84F, K85F, L89V, D90A, R91P, D92S, D93E, S94K, V96T, H98A, H98V, D99T, S100P, S100E, G101L, G101A, Y102M, L103K, R104Q, L105I, A107S, N110R, G111A, G111R, L113M, K115M, G116Q, S117E, G118W, W119F, P122A, W124Y, W125Y, I126L, C129A, L131I, L132I, L132V, V133A, A135T, L136V, Y137S, Y137T, L138I, D139E, M142W, L143I, A144L, R145S, P147K, I149L, L150F, A152S, I153V, L158V, F159Y, W161A, A174S, L175V, N178H, N178Y, V180M, V180A, V181I, Y183R, L184C, F185L, A188S, A188M, S195N, M196R, M197V, L200I, Q201R, Q202E, L209T, T211C, D213R, D215Q, G223H, G224S, A225V, L226I, K229S, P230R, D232S, G233L, L235M, P236E, H239A, H239S, L240I, L243V, F245I, L248G, A250Q, L251M, G253A, K255Q, W256L, V257L, D260G, L261A, E263D, L265I, E266A, K268R, W269Y, E270K, P273K, I274L, P275S, P276E, A278Y, P280K, E281L, F282Y, F282R, A283N, P284I, V286I, G287A, C288L, K289R, L290V, G291F, G291A, F296K, V297F, A298V, L299V, L301F, W302A, H304P, P305F, S306T, W307L, H308Y, C314Y, A315L, W316T, C318A, T319I, G320A, S321A, F322L, A325G, I329F, L330I, I333N, V337A, A338G, D343Q, G344A, N345S, I346A, D347T, W348F, A349G, A349T, R350Q, R351H, I353V, T355S, G360C, E362K, W363K, G365A, L367S, F373Y, L383M, H384S, A386S, H387Y, A389S, K390T, Q392A, V394L, Q396R, K397Q, K397T, V398H, V398R, C399I, E401K, N402M, N402L, V404F, V404Y, N405K, K407R, K407S, P410G, I412V, G413L, G417D, G417S, S418A, M419T, L420F, L420M, S421R, S421Q, H422Q, L423M, L423V, G424K, A425K, L426M, G427A, A428S, A428T, R429V, P430A, T431V, T431G, E432D, F433K, M434L, M434G, A435G, A435E, G436K, G436R, L437P, L437A. Preferably, the amino acid sequence also comprises
  a motif selected from "KHPGG", "QHPGG" or "RHPGG", preferably a motif selected from "KHPGGD", "QHPGGD" or "RHPGGD", and
  a motif selected from "GLNIQHDANHG" or "HVVGHH", preferably a motif selected from "AAIGLNIQHDANHG" or "QHVVGHH".

And even more preferably the delta-4 desaturase of the present invention has the backbone of SEQ ID NO. 86 with one or more of the following mutations: H4S, A5S, A6R, T7K, T7S, K8E, G9V, G10S, D11A, D11V, P12A, R15S, D16A, M17A, E18K, S21T, E23T, I25K, L26A, D28H, E29T, R30N, D31P, V36L, V56L, D57S, R62Q, E75A, A79S, L81M, A82S, K83E, Y84F, K85F, D90A, S94K, V96T, H98A, S100P, S100E, G101L, L103K, R104Q, N110R, G111A, S117E, L131I, L132I, V133A, A135T, M142W, A144L, R145S, L150F, A152S, A174S, V180M, V180A, Y183R, A188S, S195N, M196R, M197V, Q201R, Q202E, T211C, A225V, K229S, L235M, H239A, L248G, A250Q, K255Q, L261A, K268R, E270K, P275S, A278Y, E281L, F282Y, K289R, G291F, A298V, H304Q, S306T, A315L, S321A, A325G, I333N, K338G, G344A, N345S, A349V, T355S, G360C, H384S, A386S, A389S, K390T, Q392A, Q396R, E401K, N402M, N405K, S418A, L420F, S421R, S421Q, G427A, A428S, R429V, T431V, M434L, A435G, A435E, G436K, L437P. Preferably, the amino acid sequence also comprises
  a motif selected from "KHPGG", "QHPGG" or "RHPGG", preferably a motif selected from "KHPGGD", "QHPGGD" or "RHPGGD", and
  a motif selected from "GLNIQHDANHG" or "HVVGHH", preferably a motif selected from "AAIGLNIQHDANHG" or "QHVVGHH".

It is understood that mutations are preferably chosen to increase the sequence identity between the mutated sequence and the sequence of SEQ ID NO. 79. This way, the danger of exceptionally preparing a non-functional mutant is decreased.

Thus, it is also preferred that the delta-4 desaturase of the present invention has the backbone of SEQ ID NO. 79, preferably with one or more of the following mutations: V9-, V10G, S11G, D12-, S13-, L20-, K21-, E29R, K37D, E42G, F63L, F63I, L76Y, L76F, L76W, Q78R, Y79R, S81W, L82P, S84A, E88K, Y89F, V94L, V94I, T104D, Q109R, K111C, A113E, R115N, W123G, W124F, W129Y, Y130W, I136L, L137I, D144E, Y145W, Y145F, W147M, I158V, S160L, Y164F, S179A, I205L, C216T, R218D, S229G, T232R, R235P, P239W, E241P, F242W, V262I, V262L, D268E, M272W, Y274W, K278P, L279I, K285P, I289P, I291V, R294K, V295L, V295I, F298W, V304L, V304I, H309Q, F310P, Y313H, A323C, A325G, L327F, G330A, A342V, A342I, P346G, E347P, A349G, K350-, W354F, S361T, C366G, K369W, I372H, Y379F, K414H, G416P, D423G, T425M, F426L, Q428H, V429L, V429I, A436P, Y438-, N439-, E440D. Among these mutations, the following are more preferred: V9-, V10G, S11G, D12-, S13-, L20-, K21-, E29R, F63L, L76Y, L76f, S81W, L82P, Y89F, V94L, T104D, K111C, W123G, W124F, Y130W, I136L, Y164F, R218D, S229G, T232R, R235P, P239W, E241P, F242W, V262i, M272W, Y274W, K285P, F298W, V304L, A325G, L327F, E347P, K350-, C366G, K369W, I372H, K414H, G416P, Q428H, V429L, A436P, Y438-, N439-. Even more preferred are the following mutations: V9-, D12-, S13-, L20-, K21-, L82P, W123G, Y130W, R235P, P239W, E241P, M272W, Y274W, K285P, F298W, K350-, C366G, G416P, Y438-, N439-. The 10 most preferred mutations of SEQ ID NO. 79 individually or in combination still leading to a delta-4 desaturase of high efficiency when combined with a delta-5 elongase are V9-, D12-, S13-, L20-, K21-, Y130W, R235P, K350-, Y438-, N439-. In these lists, "-" denotes a deletion.

The invention also provides a method for screening for delta-4 desaturase genes, comprising the steps of
  a) extracting genetic material of an organism belonging to the taxonomic ranks of Ichthyosporea or Haptophyceae, preferably to the order of Ichthyophonida or Pavlovales, more preferably of genus *Anurofeca, Creolimax, Ichthyophonus, Pseudoperkinsus, Psorospermium* or *Sphaeroforma*,
  b) hybridizing to the genetic material a nucleic acid coding for at least 10, preferably at least 20 consecutive amino acids of the delta-4 desaturase of the present invention as defined above or below under stringent conditions, and
  c) detecting hybridization or lack of hybridization.

Hybridization indicates that the organism the genetic material of which is provided in step a) does comprise a gene for a delta-4 desaturase.

Particularly preferred is to detect hybridization or lack of hybridization by a nucleic acid amplification reaction. Such reaction will only provide significant products if a probe has hybridized to the genetic material serving as template for the amplification reaction. Thus, the invention also provides a method for screening for delta-4 desaturase genes, comprising the steps of
  a) extracting genetic material of an organism belonging to the taxonomic ranks of Ichthyosporea or Haptophyceae, preferably to the order of Ichthyophonida or Pavlovales, more preferably of genus *Anurofeca, Creolimax, Ichthyophonus, Pseudoperkinsus, Psorospermium* or *Sphaeroforma*,
  b) providing the reactants for a nucleic acid amplification reaction for amplifying a nucleic acid coding for at least 10, preferably at least 20 consecutive amino acids of the delta-4 desaturase of the present invention as defined above or below under stringent conditions, and
  c) detecting amplification or lack of amplification.

Amplification indicates that the organism the genetic material of which is provided in step a) does comprise a gene for a delta-4 desaturase.

The nucleic acid used for hybridization or the reactants used for nucleic acid amplification, particularly for a polymerase chain reaction, are preferably directed to a nucleic acid section coding for a conserved amino acid motif, wherein the motif preferably comprises
  a motif selected from "KHPGG", "QHPGG" or "RHPGG", preferably a motif selected from "KHPGGD", "QHPGGD" or "RHPGGD", and
  a motif selected from "GLNIQHDXNHG" or "HVVGHH", preferably a motif selected from "AAIGLNIQHDANHG" or "QHVVGHH".

Suitable primers for a polymerase chain reaction are described below.

Thus, the present invention also relates to a polynucleotide comprising a nucleic acid sequence elected from the group consisting of:

a) a nucleic acid sequence having a nucleotide sequence as shown in SEQ ID NOs: 1, 4, 7, 10, 13, 16, 19, 22, 25, 28, 31, 78 or 83 b) a nucleic acid sequence encoding a polypeptide having an amino acid sequence as shown in SEQ ID NOs: 2, 5, 8, 11, 14, 17, 20, 23, 26, 29, 32, 79, 84, 85 or 86, or a delta-4 desaturase as described above, c) a nucleic acid sequence being at least 70% identical to the nucleic acid sequence of a) or b), wherein said nucleic acid sequence encodes a polypeptide having desaturase, keto-acyl-CoA synthase (KCS) or keto-acyl-CoA reductase (KCR) or lysophospholipid-coenzyme A synthase (LACS) activity d) a nucleic acid sequence encoding a polypeptide having desaturase, keto-acyl-CoA synthase (KCS), keto-acyl-CoA reductase (KCR) or lysophospholipid-coenzyme A synthase (LACS) activity and having an amino acid sequence which is at least 60% identical to the amino acid sequence of any one of a) to c); and e) a nucleic acid sequence which is capable of hybridizing under stringent conditions to any one of a) to d), wherein said nucleic acid sequence encodes a polypeptide having desaturase, keto-acyl-CoA synthase (KCS), keto-acyl-CoA reductase (KCR) or lysophospholipid-coenzyme A synthase (LACS) activity.

The term "polynucleotide" as used in accordance with the present invention relates to a polynucleotide comprising a nucleic acid sequence which encodes a polypeptide having desaturase, keto-acyl-CoA-synthase, keto-acyl-CoA-reductase or lysophospholipid-coenzyme A synthase activity. Preferably, the polypeptide encoded by the polynucleotide of the present invention having desaturase, KCS, KCR or LACS activity, respectively, upon expression in a plant shall be capable of increasing the amount of PUFA and, in particular, LCPUFA in, e.g., seed oils or the entire plant or parts thereof. Such an increase is, preferably, statistically significant when compared to a LCPUFA producing transgenic control plant which expresses the minimal set of desaturases and elongases required for LCPUFA synthesis but does not express the polynucleotide of the present invention. Whether an increase is significant can be determined by statistical tests well known in the art including, e.g., Student's t-test. More preferably, the increase is an increase of the amount of triglycerides containing LCPUFA of at least 5%, at least 10%, at least 15%, at least 20% or at least 30% compared to said control. Preferably, the LCPUFA referred to before is a polyunsaturated fatty acid having a C-20, C-22 or C-24 fatty acid body, more preferably, ARA, EPA or DHA. Suitable assays for measuring the activities mentioned before are described in the accompanying Examples.

The term "acyltransferase activity" or "acyltransferase" as used herein encompasses all enymatic activities and enzymes which are capable of transferring or are involved in the transfer of PUFA and, in particular; LCPUFA from the acly-CoA pool or the membrane phospholipis to the triglycerides, from the acyl-CoA pool to membrane lipids and from membrane lipids to the acyl-CoA pool by a transesterification process. It will be understood that this acyltransferase activity will result in an increase of the LCPUFA esterified to triglycerides in, e.g., seed oils. In particular, it is envisaged that these acyl-transferases are capable of producing triglycerides having esterified EPA or even DHA, or that these acyltransferases are capable of enhancing synthesis of desired PUFA by increasing the flux for specific intermediates of the desired PUFA between the acyl-CoA pool (the site of elongation) and membrane lipids (the predominant site of desaturation). Specifically, acyltransferase activity as used herein relates to lysophospholipid acyltransferase (LPLAT) activity, preferably, lysophosphatidylcholine acyltransferase (LPCAT) or Lysophosphophatidylethanolamine acyltransferase (LPEAT) activity, lyso-phosphphatidic acid acyltransferase (LPAAT) activity, glycerol-3-phosphate acyl-transferase (GPAT) activity or diacylglycerol acyltransferase (DGAT), and, more preferably, to LPLAT, LPAAT, DGAT or GPAT activity.

The term "desaturase" encompasses all enymatic activities and enzymes catalyzing the desaturation of fatty acids with different lengths and numbers of unsaturated carbon atom double bonds. Specifically this includes delta 4 (d4)-desaturase, catalyzing the dehydrogenation of the $4^{th}$ and $5^{th}$ carbon atom. Delta 5 (d5)-desaturase catalyzing the dehydrogenation of the $5^{th}$ and $6^{th}$ carbon atom. Delta 6 (d6)-desaturase catalyzing the dehydrogenation of the $6^{th}$ and $7^{th}$ carbon atom. Delta 8 (d8)-desaturase catalyzing the dehydrogenation of the $8^{th}$ and $9^{th}$ carbon atom. Delta 9 (d9)-desaturase catalyzing the dehydrogenation of the $9^{th}$ and $10^{th}$ carbon atom. Delta 12 (d12)-desaturase catalyzing the dehydrogenation of the $12^{th}$ and $13^{th}$ carbon atom. Delta 15 (d15)-desaturase catalyzing the dehydrogenation of the $15^{th}$ and $16^{th}$ carbon atom. It is understood that fatty acids can be bound to the acyl-carrier protein (ACP), to coenzyme A (CoA) or in phospholipids, thereby forming different pools. Desaturases generally exhibit a preference for one of these pools.

The terms "elongase" and "d5Elo, d6Elo or d9Elo" are synonymous to KCS and refer to keto-acyl-CoA-synthase enzymatic activity, which allows to introduce two carbon atoms in a fatty acid whereby the fatty acid is elongated. Specifically, d5Elo, d6Elo or d9Elo catalyzes the introduction of two carbon atoms into fatty acids having 18 or 20 carbon atoms and double bonds in the positions 5, 6, or 9, respectively.

The term "KCR" as used herein refer to keto-acyl-CoA-reductase activity, which reduces the keto-group of keto-acyl-CoA to a hydroxyl-group, in the process of fatty acid elongation.

The term "DH" as used herein refers to dehydratase activity, removing the hydroxyl-group leading to the formation of a acyl-2-en-CoA ester (delta-2-enoyl-CoA) and $H_2O$ during fatty acid elongation.

The term "ECR" as used herein refers to enoyl-CoA reductase activity, reducing the double bond of delta-2-enoyl-CoA, in course of fatty acid elongation, generating the elongated acyl-CoA ester.

Fatty acid elongation is catalyzed in four steps, represented by four enzymes: KCS (keto-acyl-CoA-synthase), KCR (keto-acyl-CoA-reductase), DH (dehydratase) and ECR (enoyl-CoA-reductase). In the first step a fatty acid-CoA ester is condensed with malonyl-CoA producing a keto-acly-CoA intermediate, which is elongated by two carbon atoms, and $CO_2$. The keto-group of the intermediate is then reduced by the KCR to a hydroxyl-group. In the next step the DH cleaves of the hydroxyl-group ($H_2O$ is produced), forming a acyl-2-en-CoA ester (delta-2-enoyl-CoA). In the final step the double bound at position 2, 3 is reduced by the ECR forming the elongated acyl-CoA ester (Buchanan, Gruissem, Jones (2000) Biochemistry & Molecular biology of plants, American Society of Plant Physiologists).

In the studies underlying this invention, enzymes with superior desaturase, KCS KCR, DH, and ECR catalytic activities for the production of PUFA has been provided.

More preferably, polynucleotides having a nucleic acid sequence as shown in SEQ ID NOs: 1 encoding polypeptides having amino acid sequences as shown in SEQ ID NOs: 2 or variants thereof, preferably, exhibit d6-desaturase activity.

Polynucleotides having a nucleic acid sequence as shown in SEQ ID NOs: 4 encoding polypeptides having amino acid sequences as shown in SEQ ID NOs: 5 or variants thereof, preferably, exhibit d9-desaturase activity.

Polynucleotides having a nucleic acid sequence as shown in SEQ ID NOs: 7 and 10 encoding polypeptides having amino acid sequences as shown in SEQ ID NOs: 8 and 11 or variants thereof, preferably, exhibit o3-desaturase activity.

Polynucleotides having a nucleic acid sequence as shown in SEQ ID NOs: 13 encoding polypeptides having amino acid sequences as shown in SEQ ID NOs: 14 or variants thereof, preferably, exhibit d12-desaturase activity.

Polynucleotides having a nucleic acid sequence as shown in SEQ ID NOs: 78 encoding polypeptides having amino acid sequences as shown in SEQ ID NOs: 79 or variants thereof, preferably, exhibit d4-desaturase activity. Further preferred delta-4 desaturase polypeptide sequences have been described supra in detail.

Polynucleotides having a nucleic acid sequence as shown in SEQ ID NO. 83 encoding polypeptides having amino acid sequences as shown in SEQ ID NO. 84 or variants thereof, preferably, exhibit lysophospholipid-coenzyme A synthase activity.

Polynucleotides having a nucleic acid sequence as shown in SEQ ID NOs: 16, 19, 22, 25 or 28 encoding polypeptides having amino acid sequences as shown in SEQ ID NOs: 17, 20, 23, 26 or 29 or variants thereof, preferably, exhibit keto-acyl-CoA synthase activity. Specifically, SEQ ID NO. 16 encoding polypeptide SEQ ID NO 17 exhibits d5-elongase activity; SEQ ID NO. 19, 22 and 25 encoding polypeptide SEQ ID NO 20, 23 and 26, respectively, exhibits d6-elongase activity; SEQ ID NO. 28, encoding polypeptide SEQ ID NO 29 exhibits d9-elongase activity.

Polynucleotides having a nucleic acid sequence as shown in SEQ ID NOs: 31 encoding polypeptides having amino acid sequences as shown in SEQ ID NOs: 32 or variants thereof, preferably, exhibit keto-acyl-CoA reductase activity.

A polynucleotide encoding a polypeptide having a desaturase, KCS, KCR and LACS activity as specified above has been obtained in accordance with the present invention, preferably, from *Thraustochytrium aureum* and *Sphaeroforma arctica*. However, orthologs, paralogs or other homologs may be identified from other species. Preferably, they are obtained from plants such as algae, for example *Isochrysis, Mantoniella, Ostreococcus* or *Crypthecodinium*, algae/diatoms such as *Phaeodactylum, Thalassiosira* or *Thraustochytrium*, choanoflagellates such as *Monosiga*, mosses such as *Physcomitrella* or *Ceratodon*, or higher plants such as the Primulaceae such as *Aleuritia, Calendula stellata, Osteospermum spinescens* or *Osteospermum hyoseroides*, microorganisms such as fungi, such as *Aspergillus, Phytophthora, Entomophthora, Mucor* or *Mortierella*, bacteria such as *Shewanella*, yeasts or animals. Preferred animals are nematodes such as *Caenorhabditis*, insects or vertebrates. Among the vertebrates, the nucleic acid molecules may, preferably, be derived from Euteleostomi, Actinopterygii; Neopterygii; Teleostei; Euteleostei, Protacanthopterygii, Salmoniformes; Salmonidae or *Oncorhynchus*, more preferably, from the order of the Salmoniformes, most preferably, the family of the Salmonidae, such as the genus *Salmo*, for example from the genera and species *Oncorhynchus mykiss, Trutta trutta* or *Salmo trutta fario*. Moreover, the nucleic acid molecules may be obtained from the diatoms such as the genera *Thalassiosira* or *Phaeodactylum*.

Thus, the term "polynucleotide" as used in accordance with the present invention further encompasses variants of the aforementioned specific polynucleotides representing orthologs, paralogs or other homologs of the polynucleotide of the present invention. Moreover, variants of the polynucleotide of the present invention also include artificially generated muteins. Said muteins include, e.g., enzymes which are generated by mutagenesis techniques and which exhibit improved or altered substrate specificity, or codon optimized polynucleotides. The polynucleotide variants, preferably, comprise a nucleic acid sequence characterized in that the sequence can be derived from the aforementioned specific nucleic acid sequences shown in any one of SEQ ID NOs: 1, 4, 7, 10, 13, 16, 19, 22, 25, 28, 31, 78 or 83 by a polynucleotide encoding a polypeptide having an amino acid sequence as shown in any one of SEQ ID NOs: 2, 5, 8, 11, 14, 17, 20, 23, 26, 29, 32, 79, 84, 85 or 86 by at least one nucleotide substitution, addition and/or deletion, whereby the variant nucleic acid sequence shall still encode a polypeptide having a desaturase, KCS, KCR and LACS activity as specified above. Variants also encompass polynucleotides comprising a nucleic acid sequence which is capable of hybridizing to the aforementioned specific nucleic acid sequences, preferably, under stringent hybridization conditions. These stringent conditions are known to the skilled worker and can be found in Current Protocols in Molecular Biology, John Wiley & Sons, N.Y. (1989), 6.3.1-6.3.6. A preferred example for stringent hybridization conditions are hybridization conditions in 6× sodium chloride/sodium citrate (=SSC) at approximately 45° C., followed by one or more wash steps in 0.2×SSC, 0.1% SDS at 50 to 65° C. The skilled worker knows that these hybridization conditions differ depending on the type of nucleic acid and, for example when organic solvents are present, with regard to the temperature and concentration of the buffer. For example, under "standard hybridization conditions" the temperature differs depending on the type of nucleic acid between 42° C. and 58° C. in aqueous buffer with a concentration of 0.1 to 5×SSC (pH 7.2). If organic solvent is present in the abovementioned buffer, for example 50% formamide, the temperature under standard conditions is approximately 42° C. The hybridization conditions for DNA: DNA hybrids are, preferably, 0.1×SSC and 20° C. to 45° C., preferably between 30° C. and 45° C. The hybridization conditions for DNA:RNA hybrids are, preferably, 0.1×SSC and 30° C. to 55° C., preferably between 45° C. and 55° C. The abovementioned hybridization temperatures are determined for example for a nucleic acid with approximately 100 by (=base pairs) in length and a G+C content of 50% in the absence of formamide. The skilled worker knows how to determine the hybridization conditions required by referring to textbooks such as the textbook mentioned above, or the following textbooks: Sambrook et al., "Molecular Cloning", Cold Spring Harbor Laboratory, 1989; Hames and Higgins (Ed.) 1985, "Nucleic Acids Hybridization: A Practical Approach", IRL Press at Oxford University Press, Oxford; Brown (Ed.) 1991, "Essential Molecular Biology: A Practical Approach", IRL Press at Oxford University Press, Oxford. Alternatively, polynucleotide variants are obtainable by PCR-based techniques such as mixed oligonucleotide primer-based amplification of DNA, i.e. using degenerated primers against conserved domains of the polypeptides of the present invention. Conserved domains of the polypeptide of the present invention may be identified by a sequence comparison of the nucleic acid sequences of the polynucleotides or the amino acid sequences of the polypeptides of the present invention. Oligonucleotides suitable as PCR primers as well as suitable PCR conditions are described in the accompanying Examples. As a template, DNA or cDNA from bacteria, fungi, plants or animals may be used. Further, variants include polynucleotides comprising nucleic acid sequences which are at least 50%, at least 55%, at least 60%, at least 65%, at least 70%, at least 75%, at least 80%, at least 85%, at least 90%, at least 95%, at least 98% or at least 99% identical to the nucleic acid sequences shown in any one of SEQ ID NOs: 1, 4, 7, 10, 13, 16, 19, 22, 25, 28, 31, 78 or 83 preferably, encoding polypeptides retaining desaturase, KCS, KCR and LACS activity as specified above. Moreover, also encompassed are polynucleotides which comprise nucleic acid sequences encoding a polypeptide having an amino acid sequences which are at least 50%, at least 55%, at least 60%, at least 65%, at least 70%, at least 75%, at least 80%, at least 85%, at least 90%, at least 95%, at least 98% or at least 99% identical to the amino acid sequences shown in any one of SEQ ID NOs: 2, 5, 8, 11, 14, 17, 20, 23, 26, 29, 32, 79, 84, 85 or 86 wherein the polypeptide, preferably, retains desaturase, KCS, KCR and LACS as specified above. The percent identity values are, preferably, calculated over the entire amino acid or nucleic acid sequence region. A series of programs based on a variety of algorithms is available to the skilled worker for comparing different sequences. In a preferred embodiment, the percent identity between two amino acid sequences is determined using the Needleman and Wunsch algorithm (Needleman 1970, J. Mol. Biol. (48):444-453) which has been incorporated into the needle program in the EMBOSS software package (*EMBOSS: The European Molecular Biology Open Software Suite*, Rice, P., Longden, I., and Bleasby, A, Trends in Genetics 16(6), 276-277, 2000), using either a BLOSUM 45 or PAM250 scoring matrix for distantly related proteins, or either a BLOSUM 62 or PAM160 scoring matrix for closer related proteins, and a gap opening penalty of 16, 14, 12, 10, 8, 6, or 4 and a gap extension penalty of 0.5, 1, 2, 3, 4, 5, or 6. Guides for local installation of the EMBOSS package as well as links to WEB-Services can be found at http://emboss.sourceforge.net. A preferred, non-limiting example of parameters to be used for aligning two amino acid sequences using the needle program are the default parameters, including the EBLOSUM62 scoring matrix, a gap opening penalty of 10 and a gap extension penalty of 0.5. In yet another preferred embodiment, the percent identity between two nucleotide sequences is determined using the needle program in the EMBOSS software package (*EMBOSS: The European Molecular Biology Open Software Suite*, Rice, P., Longden, I., and Bleasby, A, Trends in Genetics 16(6), 276-277, 2000), using the EDNAFULL scoring matrix and a gap opening penalty of 16, 14, 12, 10, 8, 6, or 4 and a gap extension penalty of 0.5, 1, 2, 3, 4, 5, or 6. A preferred, non-limiting example of parameters to be used in conjunction for aligning two nucleic acid sequences using the needle program are the default parameters, including the EDNAFULL scoring matrix, a gap opening penalty of 10 and a gap extension penalty of 0.5. The nucleic acid and protein sequences of the present invention can further be used as a "query sequence" to perform a search against public databases to, for example, identify other family members or related sequences. Such searches can be performed using the BLAST series of programs (version 2.2) of Altschul et al. (Altschul 1990, J. Mol. Biol. 215:403-10). BLAST using desaturase, KCS, KCR and LACS nucleic acid sequences of the invention as query sequence can be performed with the BLASTn, BLASTx or the tBLASTx program using default parameters to obtain either nucleotide sequences (BLASTn, tBLASTx) or amino acid sequences (BLASTx) homologous to desaturase, KCS, KCR and LACS sequences of the invention. BLAST using desaturase, KCS, KCR and LACS protein sequences of the invention as query sequence can be performed with the BLASTp or the tBLASTn program using default parameters to obtain either amino acid sequences (BLASTp) or nucleic acid sequences (tBLASTn) homologous to desaturase, KCS, KCR and LACS sequences of the invention. To obtain gapped alignments for comparison purposes, Gapped BLAST using default parameters can be utilized as described in Altschul et al. (Altschul 1997, Nucleic Acids Res. 25(17): 3389-3402).

TABLE 1

Relation of sequence types: DNA or PRT (Protein) of query- and hit-sequences for various BLAST programs

| Input query sequence | Converted Query | Algorithm | Converted Hit | Actual Database |
|---|---|---|---|---|
| DNA | | BLASTn | | DNA |
| PRT | | BLASTp | | PRT |
| DNA | PRT | BLASTx | | PRT |
| PRT | | tBLASTn | PRT | DNA |
| DNA | PRT | tBLASTx | PRT | DNA |

A polynucleotide comprising a fragment of any of the aforementioned nucleic acid sequences is also encompassed as a polynucleotide of the present invention. The fragments shall encode polypeptides which still have desaturase, KCS, KCR or LACS activity as specified above. Accordingly, the polypeptide may comprise or consist of the domains of the polypeptide of the present invention conferring the said biological activity. A fragment as meant herein, preferably, comprises at least 50, at least 100, at least 250 or at least 500 consecutive nucleotides of any one of the aforementioned nucleic acid sequences or encodes an amino acid sequence comprising at least 20, at least 30, at least 50, at least 80, at least 100 or at least 150 consecutive amino acids of any one of the aforementioned amino acid sequences.

The variant polynucleotides or fragments referred to above, preferably, encode polypeptides retaining desaturase, KCS, KCR or LACS activity to a significant extent, preferably, at least 10%, at least 20%, at least 30%, at least 40%, at least 50%, at least 60%, at least 70%, at least 80% or at least 90% of the desaturase, KCS, KCR or LACS activity exhibited by any of the polypeptide shown in any one of SEQ ID NOs: 2, 5, 8, 11, 14, 17, 20, 23, 26, 29, 32, 79, 84, 85 or 86. The activity may be tested as described in the accompanying Examples.

The polynucleotides of the present invention either essentially consist of the aforementioned nucleic acid sequences or comprise the aforementioned nucleic acid sequences. Thus, they may contain further nucleic acid sequences as well. Preferably, the polynucleotide of the present invention may comprise in addition to an open reading frame further untranslated sequence at the 3' and at the 5' terminus of the coding gene region: at least 500, preferably 200, more preferably 100 nucleotides of the sequence upstream of the 5' terminus of the coding region and at least 100, preferably 50, more preferably 20 nucleotides of the sequence downstream of the 3' terminus of the coding gene region. Furthermore, the polynucleotides of the present invention may encode fusion proteins wherein one partner of the fusion protein is a polypeptide being encoded by a nucleic acid sequence recited above. Such fusion proteins may comprise as additional part other enzymes of the fatty acid or PUFA biosynthesis pathways, polypeptides for monitoring expression (e.g., green, yellow, blue or red fluorescent proteins, alkaline phosphatase and the like) or so called "tags" which may serve as a detectable marker or as an auxiliary measure for purification purposes. Tags for the different purposes are well known in the art and comprise FLAG-tags, 6-histidine-tags, MYC-tags and the like.

The polynucleotide of the present invention shall be provided, preferably, either as an isolated polynucleotide (i.e. purified or at least isolated from its natural context such as its natural gene locus) or in genetically modified or exogenously (i.e. artificially) manipulated form. An isolated polynucleotide can, for example, comprise less than approximately 5 kb, 4 kb, 3 kb, 2 kb, 1 kb, 0.5 kb or 0.1 kb of nucleotide sequences which naturally flank the nucleic acid molecule in the genomic DNA of the cell from which the nucleic acid is derived. The polynucleotide, preferably, is provided in the form of double or single stranded molecule. It will be understood that the present invention by referring to any of the aforementioned polynucleotides of the invention also refers to complementary or reverse complementary strands of the specific sequences or variants thereof referred to before. The polynucleotide encompasses DNA, including cDNA and genomic DNA, or RNA polynucleotides.

However, the present invention also pertains to polynucleotide variants which are derived from the polynucleotides of the present invention and are capable of interfering with the transcription or translation of the polynucleotides of the present invention. Such variant polynucleotides include antisense nucleic acids, ribozymes, siRNA molecules, morpholino nucleic acids (phosphorodiamidate morpholino oligos), triple-helix forming oligonucleotides, inhibitory oligonucleotides, or micro RNA molecules all of which shall specifically recognize the polynucleotide of the invention due to the presence of complementary or substantially complementary sequences. These techniques are well known to the skilled artisan. Suitable variant polynucleotides of the aforementioned kind can be readily designed based on the structure of the polynucleotides of this invention.

Moreover, comprised are also chemically modified polynucleotides including naturally occurring modified polynucleotides such as glycosylated or methylated polynucleotides or artificial modified ones such as biotinylated polynucleotides.

In the studies underlying the present invention, advantageously, polynucleotides where identified encoding desaturases, keto-acyl-CoA-synthases, keto-acyl-CoA-reductases and lysophospholipid-coenzyme A synthase from *Thraustochytrium aureum* and *Sphaeroforma arctica*. In particular, the *Thraustochytrium aureum* d6-desaturase (pd6Des(Ta)_c3318), d9-desaturase (pd9Des(Ta)_c4008), o3-desaturase (po3Des(Ta)_c959, po3Des(Ta)_c1830), d12-desaturase (pd12Des(Ta)_c1219) keto-acyl-CoA-synthase (pd5Elo (Ta)_ c1, pd6Elo(Ta)_c231, pd6Elo(Ta)_c752, pd6Elo(Ta)_c4696, pd9Elo(Ta)_c4589) keto-acyl-CoA-reductase (pKR (Ta)_c1703) and the *Sphaeroforma arctica* d4-desaturase d4Des(Sa) and lysophospholipid-coenzyme A synthase (LACS). The polynucleotides of the present invention are particularly suitable for the recombinant manufacture of LCPUFAs and, in particular, arachidonic acid (ARA), eicosapentaenoic acid (EPA) and/or docosapentaenoic acid (DHA).

In a preferred embodiment of the polynucleotide of the present invention, said polynucleotide further comprises an expression control sequence operatively linked to the said nucleic acid sequence.

The term "expression control sequence" as used herein refers to a nucleic acid sequence which is capable of governing, i.e. initiating and controlling, transcription of a nucleic acid sequence of interest, in the present case the nucleic sequences recited above. Such a sequence usually comprises or consists of a promoter or a combination of a promoter and enhancer sequences. Expression of a polynucleotide comprises transcription of the nucleic acid molecule, preferably, into a translatable mRNA. Additional regulatory elements may include transcriptional as well as translational enhancers. The following promoters and expression control sequences may be, preferably, used in an expression vector according to the present invention. The cos, tac, trp, tet, trp-tet, lpp, lac, lpp-lac, laclq, T7, T5, T3, gal, trc, ara, SP6, λ-PR or λ-PL promoters are, preferably, used in Gram-negative bacteria. For Gram-positive bacteria, promoters amy and SPO2 may be used. From yeast or fungal promoters ADC1, AOX1r, GAL1, MFα, AC, P-60, CYC1, GAPDH, TEF, rp28, ADH are, preferably, used. For animal cell or organism expression, the promoters CMV-, SV40-, RSV-promoter (*Rous sarcoma* virus), CMV-enhancer, SV40-enhancer are preferably used. From plants the promoters CaMV/35S (Franck 1980, Cell 21: 285-294], PRP1 (Ward 1993, Plant. Mol. Biol. 22), SSU, OCS, lib4, usp, STLS1, B33, nos or the ubiquitin or phaseolin promoter. Also preferred in this context are inducible promoters, such as the promoters described in EP 0 388 186 A1 (i.e. a benzylsulfonamide-inducible promoter), Getz 1992, Plant J. 2:397-404 (i.e. a tetracyclin-inducible promoter), EP 0 335 528 A1 (i.e. a abscisic-acid-inducible promoter) or WO 93/21334 (i.e. a ethanol- or cyclohexenol-inducible promoter). Further suitable plant promoters are the promoter of cytosolic FBPase or the ST-LSI promoter from potato (Stockhaus 1989, EMBO J. 8, 2445), the phosphoribosyl-pyrophosphate amidotransferase promoter from *Glycine max* (Genbank accession No. U87999) or the node-specific promoter described in EP 0 249 676 A1. Particularly preferred are promoters which enable the expression in tissues which are involved in the biosynthesis of fatty acids. Also particularly preferred are seed-specific promoters such as the USP promoter in accordance with the practice, but also other promoters such as the LeB4, DC3, phaseolin or napin promoters. Further especially preferred promoters are seed-specific promoters which can be used for monocotyledonous or dicotyledonous plants and which are described in U.S. Pat. No. 5,608,152 (napin promoter from oilseed rape), WO 98/45461 (oleosin promoter from *Arobidopsis*, U.S. Pat. No. 5,504,200 (phaseolin promoter from *Phaseolus vulgaris*), WO 91/13980 (Bce4 promoter from *Brassica*), by Baeumlein et al., Plant J., 2, 2, 1992:233-239 (LeB4 promoter from a legume), these promoters being suitable for dicots. The following promoters are suitable for monocots: Ipt-2 or Ipt-1 promoter from barley (WO 95/15389 and WO 95/23230), hordein promoter from barley and other promoters which are suitable and which are described in WO 99/16890. In principle, it is possible to use all natural promoters together with their regulatory sequences, such as those mentioned above, for the novel process. Likewise, it is possible and advantageous to use synthetic promoters, either additionally or alone, especially when they mediate a seed-specific expression, such as, for example, as described in WO 99/16890. In a particular embodiment, seed-specific promoters are utilized to enhance the production of the desired PUFA or LCPUFA.

The term "operatively linked" as used herein means that the expression control sequence and the nucleic acid of interest are linked so that the expression of the said nucleic acid of interest can be governed by the said expression control sequence, i.e. the expression control sequence shall be functionally linked to the said nucleic acid sequence to be expressed. Accordingly, the expression control sequence and, the nucleic acid sequence to be expressed may be physically linked to each other, e.g., by inserting the expression control sequence at the 5' end of the nucleic acid sequence to be expressed. Alternatively, the expression control sequence and the nucleic acid to be expressed may be merely in physical proximity so that the expression control sequence is capable of governing the expression of at least one nucleic acid sequence of interest. The expression control sequence and the nucleic acid to be expressed are, preferably, separated by not more than 500 bp, 300 bp, 100 bp, 80 bp, 60 bp, 40 bp, 20 bp, 10 by or 5 bp.

In a further preferred embodiment of the polynucleotide of the present invention, said polynucleotide further comprises a terminator sequence operatively linked to the nucleic acid sequence.

The term "terminator" as used herein refers to a nucleic acid sequence which is capable of terminating transcription. These sequences will cause dissociation of the transcription machinery from the nucleic acid sequence to be transcribed. Preferably, the terminator shall be active in plants and, in particular, in plant seeds. Suitable terminators are known in the art and, preferably, include polyadenylation signals such as the SV40-poly-A site or the tk-poly-A site or one of the plant specific signals indicated in Loke et al. (Loke 2005, Plant Physiol 138, pp. 1457-1468), downstream of the nucleic acid sequence to be expressed.

The present invention also relates to a vector comprising the polynucleotide of the present invention.

The term "vector" or "construct", preferably, encompasses phage, plasmid, viral vectors as well as artificial chromosomes, such as bacterial or yeast artificial chromosomes. Moreover, the term also relates to targeting constructs which allow for random or site-directed integration of the targeting construct into genomic DNA. Such target constructs, preferably, comprise DNA of sufficient length for either homologous or heterologous recombination as described in detail below. The vector encompassing the polynucleotide of the present invention, preferably, further comprises selectable markers for propagation and/or selection in a host. The vector may be incorporated into a host cell by various techniques well known in the art. If introduced into a host cell, the vector may reside in the cytoplasm or may be incorporated into the genome. In the latter case, it is to be understood that the vector may further comprise nucleic acid sequences which allow for homologous recombination or heterologous insertion. Vectors can be introduced into prokaryotic or eukaryotic cells via conventional transformation or transfection techniques. The terms "transformation" and "transfection", conjugation and transduction, as used in the present context, are intended to comprise a multiplicity of prior-art processes for introducing foreign nucleic acid (for example DNA) into a host cell, including calcium phosphate, rubidium chloride or calcium chloride co-precipitation, DEAE-dextran-mediated transfection, lipofection, natural competence, carbon-based clusters, chemically mediated transfer, electroporation or particle bombardment. Suitable methods for the transformation or transfection of host cells, including plant cells, can be found in Sambrook et al. (Molecular Cloning: A Laboratory Manual, 2$^{nd}$ ed., Cold Spring Harbor Laboratory, Cold Spring Harbor Laboratory Press, Cold Spring Harbor, N.Y., 1989) and other laboratory manuals, such as Methods in Molecular Biology, 1995, Vol. 44, *Agrobacterium* protocols, Ed.: Gartland and Davey, Humana Press, Totowa, N.J. Alternatively, a plasmid vector may be introduced by heat shock or electroporation techniques. Should the vector be a virus, it may be packaged in vitro using an appropriate packaging cell line prior to application to host cells.

Preferably, the vector referred to herein is suitable as a cloning vector, i.e. replicable in microbial systems. Such vectors ensure efficient cloning in bacteria and, preferably, yeasts or fungi and make possible the stable transformation of plants. Those which must be mentioned are, in particular, various binary and co-integrated vector systems which are suitable for the T-DNA-mediated transformation. Such vector systems are, as a rule, characterized in that they contain at least the vir genes, which are required for the *Agrobacterium*-mediated transformation, and the sequences which delimit the T-DNA (T-DNA border). These vector systems, preferably, also comprise further cis-regulatory regions such as promoters and terminators and/or selection markers with which suitable transformed host cells or organisms can be identified. While co-integrated vector systems have vir genes and T-DNA sequences arranged on the same vector, binary systems are based on at least two vectors, one of which bears vir genes, but no T-DNA, while a second one bears T-DNA, but no vir gene. As a consequence, the last-mentioned vectors are relatively small, easy to manipulate and can be replicated both in *E. coli* and in *Agrobacterium*. These binary vectors include vectors from the pBIB-HYG, pPZP, pBecks, pGreen series. Preferably used in accordance with the invention are Bin19, pBI101, pBinAR, pGPTV and pCAMBIA. An overview of binary vectors and their use can be found in Hellens et al, Trends in Plant Science (2000) 5, 446-451. Furthermore, by using appropriate cloning vectors, the polynucleotides can be introduced into host cells or organisms such as plants or animals and, thus, be used in the transformation of plants, such as those which are published, and cited, in: Plant Molecular Biology and Biotechnology (CRC Press, Boca Raton, Fla.), chapter 6/7, pp. 71-119 (1993); F. F. White, Vectors for Gene Transfer in Higher Plants; in: Transgenic Plants, vol. 1, Engineering and Utilization, Ed.: Kung and R. Wu, Academic Press, 1993, 15-38; B. Jenes et al., Techniques for Gene Transfer, in: Transgenic Plants, vol. 1, Engineering and Utilization, Ed.: Kung and R. Wu, Academic Press (1993), 128-143; Potrykus 1991, Annu. Rev. Plant Physiol. Plant Molec. Biol. 42, 205-225.

More preferably, the vector of the present invention is an expression vector. In such an expression vector, i.e. a vector which comprises the polynucleotide of the invention having the nucleic acid sequence operatively linked to an expression control sequence (also called "expression cassette") allowing expression in prokaryotic or eukaryotic cells or isolated fractions thereof. Suitable expression vectors are known in the art such as Okayama-Berg cDNA expression vector pcDV1 (Pharmacia), pCDM8, pRc/CMV, pcDNA1, pcDNA3 (Invitrogene) or pSPORT1 (GIBCO BRL). Further examples of typical fusion expression vectors are pGEX (Pharmacia Biotech Inc; Smith 1988, Gene 67:31-40), pMAL (New England Biolabs, Beverly, Mass.) and pRIT5 (Pharmacia, Piscataway, N.J.), where glutathione S-transferase (GST), maltose E-binding protein and protein A, respectively, are fused with the recombinant target protein.

Examples of suitable inducible nonfusion *E. coli* expression vectors are, inter alia, pTrc (Amann 1988, Gene 69:301-315) and pET 11d (Studier 1990, Methods in Enzymology 185, 60-89). The target gene expression of the pTrc vector is based on the transcription from a hybrid trp-lac fusion promoter by host RNA polymerase. The target gene expression from the pET 11d vector is based on the transcription of a T7-gn10-lac fusion promoter, which is mediated by a coexpressed viral RNA polymerase (T7 gn1). This viral polymerase is provided by the host strains BL21 (DE3) or HMS174 (DE3) from a resident λ-prophage which harbors a T7 gn1 gene under the transcriptional control of the lacUV 5 promoter. The skilled worker is familiar with other vectors which are suitable in prokaryotic organisms; these vectors are, for example, in *E. coli*, pLG338, pACYC184, the pBR series such as pBR322, the pUC series such as pUC18 or pUC19, the M113mp series, pKC30, pRep4, pHS1, pHS2, pPLc236, pMBL24, pLG200, pUR290, pIN-III113-B1, λgt11 or pBdCl, in *Streptomyces* pIJ101, pIJ364, pIJ702 or pIJ361, in *Bacillus* pUB110, pC194 or pBD214, in *Corynebacterium* pSA77 or pAJ667. Examples of vectors for expression in the yeast *S. cerevisiae* comprise pYep Sec1 (Baldari 1987, Embo J. 6:229-234), pMFa (Kurjan 1982, Cell 30:933-943), pJRY88 (Schultz 1987, Gene 54:113-123) and pYES2 (Invitrogen Corporation, San Diego, Calif.). Vectors and processes for the construction of vectors which are suitable for use in other fungi, such as the filamentous fungi, comprise those which are described in detail in: van den Hondel, C. A. M. J. J., & Punt, P. J. (1991) "Gene transfer systems and vector development for filamentous fungi, in: Applied Molecular Genetics of fungi, J. F. Peberdy et al., Ed., pp. 1-28, Cambridge University Press: Cambridge, or in: More Gene Manipulations in Fungi (J. W. Bennett & L. L. Lasure, Ed., pp. 396-428: Academic Press: San Diego). Further suitable yeast vectors are, for example, pAG-1, YEp6, YEp13 or pEMBLYe23. As an alternative, the polynucleotides of the present invention can be also expressed in insect cells using baculovirus expression vectors. Baculovirus vectors which are available for the expression of proteins in cultured insect cells (for example Sf9 cells) comprise the pAc series (Smith 1983, Mol. Cell Biol. 3:2156-2165) and the pVL series (Lucklow 1989, Virology 170:31-39).

The polynucleotide of the present invention can be expressed in single-cell plant cells (such as algae), see Falciatore 1999, Marine Biotechnology 1 (3):239-251 and the references cited therein, and plant cells from higher plants (for example Spermatophytes, such as arable crops) by using plant expression vectors. Examples of plant expression vectors comprise those which are described in detail in: Becker 1992, Plant Mol. Biol. 20:1195-1197; Bevan 1984, Nucl. Acids Res. 12:8711-8721; Vectors for Gene Transfer in Higher Plants; in: Transgenic Plants, Vol. 1, Engineering and Utilization, Ed.: Kung and R. Wu, Academic Press, 1993, p. 15-38. A plant expression cassette, preferably, comprises regulatory sequences which are capable of controlling the gene expression in plant cells and which are functionally linked so that each sequence can fulfill its function, such as transcriptional termination, for example polyadenylation signals. Preferred polyadenylation signals are those which are derived from *Agrobacterium tumefaciens* T-DNA, such as the gene 3 of the Ti plasmid pTiACH5, which is known as octopine synthase (Gielen 1984, EMBO J. 3, 835) or functional equivalents of these, but all other terminators which are functionally active in plants are also suitable. Since plant gene expression is very often not limited to transcriptional levels, a plant expression cassette preferably comprises other functionally linked sequences such as translation enhancers, for example the overdrive sequence, which comprises the 5'-untranslated tobacco mosaic virus leader sequence, which increases the protein/RNA ratio (Gallie 1987, Nucl. Acids Research 15:8693-8711). As described above, plant gene expression must be functionally linked to a suitable promoter which performs the expression of the gene in a timely, cell-specific or tissue-specific manner. Promoters which can be used are constitutive promoters (Benfey 1989, EMBO J. 8:2195-2202) such as those which are derived from plant viruses such as 35S CAMV (Franck 1980, Cell 21:285-294), 19S CaMV (see U.S. Pat. No. 5,352,605 and WO 84/02913) or plant promoters such as the promoter of the Rubisco small subunit, which is described in U.S. Pat. No. 4,962,028. Other preferred sequences for the use in functional linkage in plant gene expression cassettes are targeting sequences which are required for targeting the gene product into its relevant cell compartment (for a review, see Kermode 1996, Crit. Rev. Plant Sci. 15, 4: 285-423 and references cited therein), for example into the vacuole, the nucleus, all types of plastids, such as amyloplasts, chloroplasts, chromoplasts, the extracellular space, the mitochondria, the endoplasmic reticulum, oil bodies, peroxisomes and other compartments of plant cells. As described above, plant gene expression can also be facilitated via a chemically inducible promoter (for a review, see Gatz 1997, Annu. Rev. Plant Physiol. Plant Mol. Biol., 48:89-108). Chemically inducible promoters are particularly suitable if it is desired that genes are expressed in a time-specific manner. Examples of such promoters are a salicylic-acid-inducible promoter (WO 95/19443), a tetracyclin-inducible promoter (Gatz 1992, Plant J. 2, 397-404) and an ethanol-inducible promoter. Promoters which respond to biotic or abiotic stress conditions are also suitable promoters, for example the pathogen-induced PRP1-gene promoter (Ward 1993, Plant Mol. Biol. 22:361-366), the heat-inducible hsp80 promoter from tomato (U.S. Pat. No. 5,187,267), the cold-inducible alpha-amylase promoter from potato (WO 96/12814) or the wound-inducible pinII promoter (EP 0 375 091 A). The promoters which are especially preferred are those which bring about the expression of genes in tissues and organs in which fatty acid, lipid and oil biosynthesis takes place, in seed cells such as the cells of endosperm and of the developing embryo. Suitable promoters are the napin gene promoter from oilseed rape (U.S. Pat. No. 5,608,152), the USP promoter from *Vicia faba* (Baeumlein 1991, Mol. Gen. Genet. 225 (3):459-67), the oleosin promoter from *Arabidopsis* (WO 98/45461), the phaseolin promoter from *Phaseolus vulgaris* (U.S. Pat. No. 5,504, 200), the Bce4 promoter from *Brassica* (WO 91/13980) or the legumin B4 promoter (LeB4; Baeumlein 1992, Plant Journal, 2 (2):233-9), and promoters which bring about the seed-specific expression in monocotyledonous plants such as maize, barley, wheat, rye, rice and the like. Suitable promoters to be taken into consideration are the lpt2 or lpt1 gene promoter from barley (WO 95/15389 and WO 95/23230) or those which are described in WO 99/16890 (promoters from the barley hordein gene, the rice glutelin gene, the rice oryzin gene, the rice prolamin gene, the wheat gliadin gene, wheat glutelin gene, the maize zein gene, the oat glutelin gene, the *sorghum* kasirin gene, the rye secalin gene). Likewise, especially suitable are promoters which bring about the plastid-specific expression since plastids are the compartment in which the precursors and some end products of lipid biosynthesis are synthesized. Suitable promoters such as the viral RNA-polymerase promoter, are described in WO 95/16783 and WO 97/06250, and the clpP promoter from *Arabidopsis*, described in WO 99/46394. The abovementioned vectors are only a small overview of vectors to be used in accordance with the present invention. Further vectors are known to the skilled worker and are described, for example, in: Cloning Vectors (Ed., Pouwels, P. H., et al., Elsevier, Amsterdam-New York-Oxford, 1985, ISBN 0 444 904018). For further suitable expression systems for prokaryotic and eukaryotic cells see the chapters 16 and 17 of Sambrook, loc cit.

It follows from the above that, preferably, said vector is an expression vector. More preferably, the said polynucleotide of the present invention is under the control of a seed-specific promoter in the vector of the present invention. A preferred seed-specific promoter as meant herein is selected from the group consisting of Conlinin 1, Conlinin 2, napin, LuFad3, USP, LeB4, Arc, Fae, ACP, LuPXR, and SBP. For details, see, e.g., US 2003-0159174.

Moreover, the present invention relates to a host cell comprising the polynucleotide or the vector of the present invention.

Preferably, said host cell is a plant cell and, more preferably, a plant cell obtained from an oilseed crop. More preferably, said oilseed crop is selected from the group consisting of flax (*Linum* sp.), rapeseed (*Brassica* sp.), soybean (*Glycine* and *Soja* sp.), sunflower (*Helianthus* sp.), cotton (*Gossypium* sp.), corn (*Zea mays*), olive (*Olea* sp.), safflower (*Carthamus* sp.), cocoa (*Theobroma cacoa*), peanut (*Arachis* sp.), hemp, camelina, crambe, oil palm, coconuts, groundnuts, sesame seed, castor bean, lesquerella, tallow tree, sheanuts, tungnuts, kapok fruit, poppy seed, jojoba seeds and perilla.

Also preferably, said host cell is a microorganism. More preferably, said microorganism is a bacterium, a fungus or algae. More preferably, it is selected from the group consisting of *Candida, Cryptococcus, Lipomyces, Rhodosporidium, Yarrowia,* and *Schizochytrium*.

Moreover, a host cell according to the present invention may also be an animal cell. Preferably, said animal host cell is a host cell of a fish or a cell line obtained therefrom. More preferably, the fish host cell is from herring, salmon, sardine, redfish, eel, carp, trout, halibut, mackerel, zander or tuna.

Generally, the controlling steps in the production of LCPUFAs, i.e., the long chain unsaturated fatty acid biosynthetic pathway, are catalyzed by membrane-associated fatty acid elongase complexes. Plants and most other eukaryotic organisms have specialized elongase system for the extension of fatty acids beyond C18 atoms. These elongase reactions have several important features in common with the fatty acid synthase complex (FAS). However, the elongase complex is different from the FAS complex as the complex is localized in the cytosol and membrane bound, ACP is not involved and the elongase 3-keto-acyl-CoA-synthase catalyzes the condensation of malonyl-CoA with an acyl primer. The elongase complex consists of four components with different catalytic functions, the keto-acyl-CoA-synthase (KCS, condensation reaction of malonyl-CoA to acyl-CoA, creation of a 2 C atom longer keto-acyl-CoA fatty acid), the keto-acyl-CoA-reductase (KCR, reduction of the 3-keto group to a 3-hydroxy-group), the dehydratase (DH, dehydration results in a delta-2-enoyl-acyl-CoA fatty acid) and the enoly-CoA-reductase (ECR, reduction of the double bond at position 2, release from the complex). For the production of LCPUFAs including ARA, EPA and/or DHA the elongation and desaturation reactions could be essential. Higher plants do not have the necessary enzyme set to produce LCPUFAs (4 or more double bonds, 20 or more C atoms). Therefore the catalytic activities have to be conferred to the plants or plant cells. Critical steps in the process of LCPUFA biosynthesis are the elongation of fatty acids from 18 to 24 carbon atoms and desaturation of carbon atoms. Polynucleotides of the present invention surprisingly catalyze the keto-acyl-CoA-synthase, keto-acyl-CoA-reductase reactions and therefore catalyze the elongation of 18 carbon atoms fatty acids. Polynucleotides of the present invention surprisingly catalyze the desaturation of the $4^{th}$, $9^{th}$, $12^{th}$, $15^{th}$ and $17^{th}$ fatty acids carbon atom bonds. By delivering these enzymes increased levels of PUFAs and LCPUFAs are produced.

However, it will be understood that dependent on the host cell, further, enzymatic activities may be conferred to the host cells, e.g., by recombinant technologies. Accordingly, the present invention, preferably, envisages a host cell which in addition to the polynucleotide of the present invention comprises polynucleotides encoding such desaturases and/or elongases as required depending on the selected host cell. Preferred desaturases and/or elongases which shall be present in the host cell are at least one enzyme selected from the group consisting of: d4-desaturase, d5-desaturase, d5-elongase, d6-desaturase, d12-desaturase, d15-desaturase, ω3-desaturase d-6-elongase or d-9-elongase. Especially preferred are the bifunctional d12d15-desaturases d12d15Des(Ac) from *Acanthamoeba castellanii* (WO2007042510), d12d15Des(Cp) from *Claviceps purpurea* (WO2008006202) and d12d15Des(Lg)1 from *Lottia gigantea* (WO2009016202), the d12-desaturases d12Des (Co) from *Calendula officinalis* (WO200185968), d12Des (Lb) from *Laccaria bicolor* (WO2009016202), d12Des(Mb) from *Monosiga brevicollis* (WO2009016202), d12Des(Mg) from *Mycosphaerella graminicola* (WO2009016202), d12Des(Nh) from *Nectria haematococca* (WO2009016202), d12Des(Ol) from *Ostreococcus lucimarinus* (WO2008040787), d12Des(Pb) from *Phycomyces blakesleeanus* (WO2009016202), d12Des(Ps) from *Phytophthora sojae* (WO2006100241) and d12Des(Tp) from *Thalassiosira pseudonana* (WO2006069710), the d15-desaturases d15Des(Hr) from *Helobdella robusta* (WO2009016202), d15Des(Mc) from *Microcoleus chthonoplastes* (WO2009016202), d15Des(Mf) from *Mycosphaerella fijiensis* (WO2009016202), d15Des(Mg) from *Mycosphaerella graminicola* (WO2009016202) and d15Des (Nh)2 from *Nectria haematococca* (WO2009016202), the d4-desaturases d4Des(Eg) from *Euglena gracilis* (WO2004090123), d4Des(Tc) from *Thraustochytrium* sp. (WO2002026946) and d4Des(Tp) from *Thalassiosira pseudonana* (WO2006069710), the d5-desaturases d5Des (Ol)2 from *Ostreococcus lucimarinus* (WO2008040787), d5Des(Pp) from *Physcomitrella patens* (WO2004057001), d5Des(Pt) from *Phaeodactylum tricornutum* (WO2002057465), d5Des(Tc) from *Thraustochytrium* sp. (WO2002026946), d5Des(Tp) from *Thalassiosira pseudonana* (WO2006069710) and the d6-desaturases d6Des(Cp) from *Ceratodon purpureus* (WO2000075341), d6Des(Ol) from *Ostreococcus lucimarinus* (WO2008040787), d6Des (Ot) from *Ostreococcus tauri* (WO2006069710), d6Des(Pf) from *Primula farinosa* (WO2003072784), d6Des(Pir)_BO from *Pythium irregulare* (WO2002026946), d6Des(Pir) from *Pythium irregulare* (WO2002026946), d6Des(Plu) from *Primula luteola* (WO2003072784), d6Des(Pp) from *Physcomitrella patens* (WO200102591), d6Des(Pt) from *Phaeodactylum tricornutum* (WO2002057465), d6Des(Pv) from *Primula vialii* (WO2003072784) and d6Des(Tp) from *Thalassiosira pseudonana* (WO2006069710), the d8-desaturases d8Des(Ac) from *Acanthamoeba castellanii* (EP1790731), d8Des(Eg) from *Euglena gracilis*

(WO200034439) and d8Des(Pm) from *Perkinsus marinus* (WO2007093776), the o3-desaturases o3Des(Pi) from *Phytophthora infestans* (WO2005083053), o3Des(Pir) from *Pythium irregulare* (WO2008022963), o3Des(Pir)2 from *Pythium irregulare* (WO2008022963) and o3Des(Ps) from *Phytophthora sojae* (WO2006100241), the bifunctional d5d6-elongases d5d6Elo(Om)2 from *Oncorhynchus mykiss* (WO2005012316), d5d6Elo(Ta) from *Thraustochytrium aureum* (WO2005012316) and d5d6Elo(Tc) from *Thraustochytrium* sp. (WO2005012316), the d5-elongases d5Elo (At) from *Arabidopsis thaliana* (WO2005012316), d5Elo (At)2 from *Arabidopsis thaliana* (WO2005012316), d5Elo (Ci) from *Ciona intestinalis* (WO2005012316), d5Elo(Ol) from *Ostreococcus lucimarinus* (WO2008040787), d5Elo (Ot) from *Ostreococcus tauri* (WO2005012316), d5Elo(Tp) from *Thalassiosira pseudonana* (WO2005012316) and d5Elo(Xl) from *Xenopus laevis* (WO2005012316), the d6-elongases d6Elo(Ol) from *Ostreococcus lucimarinus* (WO2008040787), d6Elo(Ot) from *Ostreococcus tauri* (WO2005012316), d6Elo(Pi) from *Phytophthora infestans* (WO2003064638), d6Elo(Pir) from *Pythium irregulare* (WO2009016208), d6Elo(Pp) from *Physcomitrella patens* (WO2001059128), d6Elo(Ps) from *Phytophthora sojae* (WO2006100241), d6Elo(Ps)2 from *Phytophthora sojae* (WO2006100241), d6Elo(Ps)3 from *Phytophthora sojae* (WO2006100241), d6Elo(Pt) from *Phaeodactylum tricornutum* (WO2005012316), d6Elo(Tc) from *Thraustochytrium* sp. (WO2005012316) and d6Elo(Tp) from *Thalassiosira pseudonana* (WO2005012316), the d9-elongases d9Elo (Ig) from *Isochrysis galbana* (WO2002077213), d9Elo(Pm) from *Perkinsus marinus* (WO2007093776) and d9Elo(Ro) from *Rhizopus oryzae* (WO2009016208). Particularly, if the manufacture of ARA is envisaged in higher plants, the enzymes recited in table 5 or 6, below (i.e. additionally a d6-desaturase, d6-elongase, d5-desaturase, and d12-desaturase) or enzymes having essentially the same activity may be combined in a host cell. If the manufacture of EPA is envisaged in higher plants, the enzymes recited in table 7, below (i.e. additionally a d6-desaturase, d6-elongase, d5-desaturase, d12-desaturase, omega 3-desaturase and d15-desaturase), or enzymes having essentially the same activity may be combined in a host cell. If the manufacture of DHA is envisaged in higher plants, the enzymes recited in table 8, below (i.e. additionally a d6-desaturase, d6-elongase, d5-desaturase, d12-desaturase, omega 3-desaturase, d15-desaturase, d5-elongase, and d4-desaturase), or enzymes having essentially the same activity may be combined in a host cell.

The present invention also relates to a cell, preferably a host cell as specified above or a cell of a non-human organism specified elsewhere herein, said cell comprising a polynucleotide which is obtained from the polynucleotide of the present invention by a point mutation, a truncation, an inversion, a deletion, an addition, a substitution and homologous recombination. How to carry out such modifications to a polynucleotide is well known to the skilled artisan and has been described elsewhere in this specification in detail.

The present invention also provides a plant or part of a plant comprising the delta-4 desaturase, keto-acyl-CoA synthase (KCS), keto-acyl-CoA reductase (KCR) or lysophospholipid-coenzyme A synthase (LACS) activity and/or corresponding nucleic acids, and also provides a corresponding dead plant or part thereof, preferably harvest material, e.g. seeds or leaves, or refuse material, for example straw, dead leaves and press cake. Press cake is the substance obtained after pressing plant seeds or other plant material for oil extraction. Such press cakes generally still comprise high concentrations of polyunsaturated fatty acids and are suitable particularly as animal feed, e.g. fish feed. The invention also provides a container comprising plant material, preferably seeds, and/or refuse material as described above.

The present invention furthermore pertains to a method for the manufacture of a polypeptide encoded by a polynucleotide of any the present invention comprising
  a) cultivating the host cell of the invention under conditions which allow for the production of the said polypeptide; and
  b) obtaining the polypeptide from the host cell of step a).

Suitable conditions which allow for expression of the polynucleotide of the invention comprised by the host cell depend on the host cell as well as the expression control sequence used for governing expression of the said polynucleotide. These conditions and how to select them are very well known to those skilled in the art. The expressed polypeptide may be obtained, for example, by all conventional purification techniques including affinity chromatography, size exclusion chromatography, high pressure liquid chromatography (HPLC) and precipitation techniques including antibody precipitation. It is to be understood that the method may—although preferred—not necessarily yield an essentially pure preparation of the polypeptide. It is to be understood that depending on the host cell which is used for the aforementioned method, the polypeptides produced thereby may become posttranslationally modified or processed otherwise.

The present invention encompasses a polypeptide encoded by the polynucleotide of the present invention or which is obtainable by the aforementioned method.

The term "polypeptide" as used herein encompasses essentially purified polypeptides or polypeptide preparations comprising other proteins in addition. Further, the term also relates to the fusion proteins or polypeptide fragments being at least partially encoded by the polynucleotide of the present invention referred to above. Moreover, it includes chemically modified polypeptides. Such modifications may be artificial modifications or naturally occurring modifications such as phosphorylation, glycosylation, myristylation and the like (Review in Mann 2003, Nat. Biotechnol. 21, 255-261, review with focus on plants in Huber 2004, Curr. Opin. Plant Biol. 7, 318-322). Currently, more than 300 posttranslational modifications are known (see full ABFRC Delta mass list at www.abrf.org/index.cfm/dm.home). The polypeptide of the present invention shall exhibit the desaturase, keto-acyl-CoA-synthase and keto-acyl-CoA-reductase activity referred to above.

Encompassed by the present invention is, furthermore, an antibody which specifically recognizes the polypeptide of the invention.

Antibodies against the polypeptides of the invention can be prepared by well known methods using a purified polypeptide according to the invention or a suitable fragment derived therefrom as an antigen. A fragment which is suitable as an antigen may be identified by antigenicity determining algorithms well known in the art. Such fragments may be obtained either from the polypeptide of the invention by proteolytic digestion or may be a synthetic peptide. Preferably, the antibody of the present invention is a monoclonal antibody, a polyclonal antibody, a single chain antibody, a chimerized antibody or a fragment of any of these antibodies, such as Fab, Fv or scFv fragments etc. Also comprised as antibodies by the present invention are bispecific antibodies, synthetic antibodies or chemically modified derivatives of any of the aforementioned antibodies. The antibody of the present invention shall specifically bind (i.e. does significantly not cross react with other polypeptides or peptides) to the polypeptide of the invention. Specific binding can be tested by various well known techniques. Antibodies or fragments thereof can be obtained by using methods which are described, e.g., in Harlow and Lane "Antibodies, A Laboratory Manual", CSH Press, Cold Spring Harbor, 1988. Monoclonal antibodies can be prepared by the techniques originally described in Köhler 1975, Nature 256, 495, and Galfré 1981, Meth. Enzymol. 73, 3, which comprise the fusion of mouse myeloma cells to spleen cells derived from immunized mammals. The antibodies can be used, for example, for the immunoprecipitation, immunolocalization or purification (e.g., by affinity chromatography) of the polypeptides of the invention as well as for the monitoring of the presence of said variant polypeptides, for example, in recombinant organisms, and for the identification of proteins or compounds interacting with the proteins according to the invention.

Moreover, the antibody according to the present invention can be applied for identifying the presence or absence of the polypeptides of the present invention. Preferably, the antibody is used for identifying non-human transgenic organisms as specified elsewhere herein and, preferably, transgenic plants, which comprise the polypeptides of the present invention. To this end, the antibody may be provided in form of a kit which allows for identifying non-human transgenic organisms and, preferably, transgenic plants comprising the polypeptides of the present invention. The kit, in addition to the antibody of the present invention, may further comprise a detection agent for detecting a complex of the antibody of the invention and the polypeptide of the invention.

Moreover, the present invention contemplates a non-human transgenic organism comprising the polynucleotide or the vector of the present invention.

Preferably, the non-human transgenic organism is a plant, plant part, or plant seed. Preferred plants to be used for introducing the polynucleotide or the vector of the invention are plants which are capable of synthesizing fatty acids, such as all dicotyledonous or monocotyledonous plants, algae or mosses. It is to be understood that host cells derived from a plant may also be used for producing a plant according to the present invention. Preferred plants are selected from the group of the plant families Adelotheciaceae, Anacardiaceae, Asteraceae, Apiaceae, Betulaceae, Boraginaceae, Brassicaceae, Bromeliaceae, Caricaceae, Cannabaceae, Convolvulaceae, Chenopodiaceae, Crypthecodiniaceae, Cucurbitaceae, Ditrichaceae, Elaeagnaceae, Ericaceae, Euphorbiaceae, Fabaceae, Geraniaceae, Gramineae, Juglandaceae, Lauraceae, Leguminosae, Linaceae, Prasinophyceae or vegetable plants or ornamentals such as *Tagetes*. Examples which may be mentioned are the following plants selected from the group consisting of: Adelotheciaceae such as the genera *Physcomitrella*, such as the genus and species *Physcomitrella patens*, Anacardiaceae such as the genera *Pistacia, Mangifera, Anacardium*, for example the genus and species *Pistacia vera* [pistachio], *Mangifer indica* [mango] or *Anacardium occidentale* [cashew], Asteraceae, such as the genera *Calendula, Carthamus, Centaurea, Cichorium, Cynara, Helianthus, Lactuca, Locusta, Tagetes, Valeriana*, for example the genus and species *Calendula officinalis* [common marigold], *Carthamus tinctorius* [safflower], *Centaurea cyanus* [cornflower], *Cichorium intybus* [chicory], *Cynara scolymus* [artichoke], *Helianthus annus* [sunflower], *Lactuca sativa, Lactuca crispa, Lactuca esculenta, Lactuca scariola* L. ssp. *sativa, Lactuca scariola* L. var. *integrata, Lactuca scariola* L. var. *integrifolia, Lactuca sativa* subsp. *romana, Locusta communis, Valeriana locusta* [salad vegetables], *Tagetes lucida, Tagetes erecta* or *Tagetes tenuifolia* [african or french marigold], Apiaceae, such as the genus *Daucus*, for example the genus and species *Daucus carota* [carrot], Betulaceae, such as the genus *Corylus*, for example the genera and species *Corylus avellana* or *Corylus colurna* [hazelnut], Boraginaceae, such as the genus *Borago*, for example the genus and species *Borago officinalis* [borage], Brassicaceae, such as the genera *Brassica, Melanosinapis, Sinapis, Arabadopsis*, for example the genera and species *Brassica napus, Brassica rapa* ssp. [oilseed rape], *Sinapis arvensis Brassica juncea, Brassica juncea* var. *juncea, Brassica juncea* var. *crispifolia, Brassica juncea* var. *foliosa, Brassica nigra, Brassica sinapioides, Melanosinapis communis* [mustard], *Brassica oleracea* [fodder beet] or *Arabidopsis thaliana*, Bromeliaceae, such as the genera *Anana, Bromelia* (pineapple), for example the genera and species *Anana comosus, Ananas ananas* or *Bromelia comosa* [pineapple], Caricaceae, such as the genus *Carica*, such as the genus and species *Carica papaya* [pawpaw], Cannabaceae, such as the genus *Cannabis*, such as the genus and species *Cannabis sativa* [hemp], Convolvulaceae, such as the genera *Ipomea, Convolvulus*, for example the genera and species *Ipomoea batatus, Ipomoea pandurata, Convolvulus batatas, Convolvulus tiliaceus, Ipomoea fastigiata, Ipomoea tiliacea, Ipomoea triloba* or *Convolvulus panduratus* [sweet potato, batate], Chenopodiaceae, such as the genus *Beta*, such as the genera and species *Beta vulgaris, Beta vulgaris* var. *altissima, Beta vulgaris* var. *Vulgaris, Beta maritima, Beta vulgaris* var. *perennis, Beta vulgaris* var. *conditiva* or *Beta vulgaris* var. *esculenta* [sugarbeet], Crypthecodiniaceae, such as the genus *Crypthecodinium*, for example the genus and species *Cryptecodinium cohnii*, Cucurbitaceae, such as the genus *Cucurbita*, for example the genera and species *Cucurbita maxima, Cucurbita mixta, Cucurbita pepo* or *Cucurbita moschata* [pumpkin/squash], Cymbellaceae such as the genera *Amphora, Cymbella, Okedenia, Phaeodactylum, Reimeria*, for example the genus and species *Phaeodactylum tricornutum*, Ditrichaceae such as the genera *Ditrichaceae, Astomiopsis, Ceratodon, Chrysoblastella, Ditrichum, Distichium, Eccremidium, Lophidion, Philibertiella, Pleuridium, Saelania, Trichodon, Skottsbergia*, for example the genera and species *Ceratodon antarcticus, Ceratodon columbiae, Ceratodon heterophyllus, Ceratodon purpureus, Ceratodon purpureus, Ceratodon purpureus* ssp. *convolutus, Ceratodon, purpureus* spp. *stenocarpus, Ceratodon purpureus* var. *rotundifolius, Ceratodon ratodon, Ceratodon stenocarpus, Chrysoblastella chilensis, Ditrichum ambiguum, Ditrichum brevisetum, Ditrichum crispatissimum, Ditrichum difficile, Ditrichum falcifolium, Ditrichum flexicaule, Ditrichum giganteum, Ditrichum heteromallum, Ditrichum lineare, Ditrichum lineare, Ditrichum montanum, Ditrichum montanum, Ditrichum pallidum, Ditrichum punctulatum, Ditrichum pusillum, Ditrichum pusillum* var. *tortile, Ditrichum rhynchostegium, Ditrichum schimperi, Ditrichum tortile, Distichium capillaceum, Distichium hagenii, Distichium inclinatum, Distichium macounii, Eccremidium floridanum, Eccremidium whiteleggei, Lophidion strictus, Pleuridium acuminatum, Pleuridium alternifolium, Pleuridium holdridgei, Pleuridium mexicanum, Pleuridium ravenelli, Pleuridium subulatum, Saelania glaucescens, Trichodon borealis, Trichodon cylindricus* or *Trichodon cylindricus* var. *oblongus*, Elaeagnaceae such as the genus *Elaeagnus*, for example the genus and species *Olea europaea* [olive], Ericaceae such as the genus *Kalmia*, for example the genera and species *Kalmia latifolia, Kalmia angustifolia, Kalmia microphylla, Kalmia polifolia, Kalmia occidentalis, Cistus chamaerhodendros* or *Kalmia lucida* [mountain laurel], Euphorbiaceae such as the genera *Manihot, Janipha, Jatropha, Ricinus*, for example the genera and species *Manihot utilissima, Janipha manihot, Jatropha manihot, Manihot aipil, Manihot dulcis, Manihot manihot, Manihot melanobasis, Manihot esculenta* [manihot] or *Ricinus communis* [castor-oil plant], Fabaceae such as the genera *Pisum, Albizia, Cathormion, Feuillea, Inga, Pithecolobium, Acacia, Mimosa, Medicajo, Glycine, Dolichos, Phaseolus, Soja*, for example the genera and species *Pisum sativum, Pisum arvense, Pisum humile* [pea], *Albizia berteriana, Albizia julibrissin, Albizia lebbeck, Acacia berteriana, Acacia littoralis, Albizia berteriana, Albizzia berteriana, Cathormion berteriana, Feuillea berteriana, Inga fragrans, Pithecellobium berterianum, Pithecellobium fragrans, Pithecolobium berterianum, Pseudalbizzia berteriana, Acacia julibrissin, Acacia nemu, Albizia nemu, Feuilleea julibrissin, Mimosa julibrissin, Mimosa speciosa, Sericanrda julibrissin, Acacia lebbeck, Acacia macrophylla, Albizia lebbek, Feuilleea lebbeck, Mimosa lebbeck, Mimosa speciosa* [silk tree], *Medicago sativa, Medicago falcata, Medicago varia* [alfalfa], *Glycine max Dolichos soja, Glycine gracilis, Glycine hispida, Phaseolus max, Soja hispida* or *Soja max* [soybean], Funariaceae such as the genera *Aphanorrhegma, Entosthodon, Funaria, Physcomitrella, Physcomitrium*, for example the genera and species *Aphanorrhegma serratum, Entosthodon attenuatus, Entosthodon bolanderi, Entosthodon bonplandii, Entosthodon californicus, Entosthodon drummondii, Entosthodon jamesonii, Entosthodon leibergii, Entosthodon neoscoticus, Entosthodon rubrisetus, Entosthodon spathulifolius, Entosthodon tucsoni, Funaria americana, Funaria bolanderi, Funaria calcarea, Funaria californica, Funaria calvescens, Funaria convoluta, Funaria flavicans, Funaria groutiana, Funaria hygrometrica, Funaria hygrometrica* var. *arctica, Funaria hygrometrica* var. *calvescens, Funaria hygrometrica* var. *convoluta, Funaria hygrometrica* var. *muralis, Funaria hygrometrica* var. *utahensis, Funaria microstoma, Funaria microstoma* var. *obtusifolia, Funaria muhlenbergii, Funaria orcuttii, Funaria plano-convexa, Funaria polaris, Funaria ravenelii, Funaria rubriseta, Funaria serrata, Funaria sonorae, Funaria sublimbatus, Funaria tucsoni, Physcomitrella californica, Physcomitrella patens, Physcomitrella readeri, Physcomitrium australe, Physcomitrium californicum, Physcomitrium collenchymatum, Physcomitrium coloradense, Physcomitrium cupuliferum, Physcomitrium drummondii, Physcomitrium eurystomum, Physcomitrium flexifolium, Physcomitrium hookeri, Physcomitrium hookeri* var. *serratum, Physcomitrium immersum, Physcomitrium kellermanii, Physcomitrium megalocarpum, Physcomitrium pyriforme, Physcomitrium pyriforme* var. *serratum, Physcomitrium rufipes, Physcomitrium sandbergii, Physcomitrium subsphaericum, Physcomitrium washingtoniense*, Geraniaceae, such as the genera *Pelargonium, Cocos, Oleum*, for example the genera and species *Cocos nucifera, Pelargonium grossularioides* or *Oleum cocois* [coconut], Gramineae, such as the genus *Saccharum*, for example the genus and species *Saccharum officinarum*, Juglandaceae, such as the genera *Juglans, Wallia*, for example the genera and species *Juglans regia, Juglans ailanthifolia, Juglans sieboldiana, Juglans cinerea, Wallia cinerea, Juglans bixbyi, Juglans californica, Juglans hindsii, Juglans intermedia, Juglans jamaicensis, Juglans major, Juglans microcarpa, Juglans nigra* or *Wallia nigra* [walnut], Lauraceae, such as the genera *Persea, Laurus*, for example the genera and species *Laurus nobilis* [bay], *Persea americana, Persea gratissima* or *Persea persea* [avocado], Leguminosae, such as the genus *Arachis*, for example the genus and species *Arachis hypogaea* [peanut], Linaceae, such as the genera *Linum, Adenolinum*, for example the genera and species *Linum usitatissimum, Linum humile, Linum austriacum, Linum bienne, Linum angustifolium, Linum catharticum, Linum flavum, Linum grandiflorum, Adenolinum grandiflorum, Linum lewisii, Linum narbonense, Linum perenne, Linum perenne* var. *lewisii, Linum pratense* or *Linum trigynum* [linseed], Lythrarieae, such as the genus *Punica*, for example the genus and species *Punica granatum* [pomegranate], Malvaceae, such as the genus *Gossypium*, for example the genera and species *Gossypium hirsutum, Gossypium arboreum, Gossypium barbadense, Gossypium herbaceum* or *Gossypium thurberi* [cotton], Marchantiaceae, such as the genus *Marchantia*, for example the genera and species *Marchantia berteroana, Marchantia foliacea, Marchantia macropora*, Musaceae, such as the genus *Musa*, for example the genera and species *Musa nana, Musa acuminata, Musa paradisiaca, Musa* spp. [banana], Onagraceae, such as the genera *Camissonia, Oenothera*, for example the genera and species *Oenothera biennis* or *Camissonia brevipes* [evening primrose], Palmae, such as the genus *Elacis*, for example the genus and species *Elaeis guineensis* [oil palm], Papaveraceae, such as the genus *Papaver*, for example the genera and species *Papaver orientale, Papaver rhoeas, Papaver dubium* [poppy], Pedaliaceae, such as the genus *Sesamum*, for example the genus and species *Sesamum indicum* [sesame], Piperaceae, such as the genera *Piper, Artanthe, Peperomia, Steffensia*, for example the genera and species *Piper aduncum, Piper amalago, Piper angustifolium, Piper auritum, Piper betel, Piper cubeba, Piper longum, Piper nigrum, Piper retrofractum, Artanthe adunca, Artanthe elongata, Peperomia elongata, Piper elongatum, Steffensia elongata* [cayenne pepper], Poaceae, such as the genera *Hordeum, Secale, Avena, Sorghum, Andropogon, Holcus, Panicum, Oryza, Zea* (maize), *Triticum*, for example the genera and species *Hordeum vulgare, Hordeum jubatum, Hordeum murinum, Hordeum secalinum, Hordeum distichon, Hordeum aegiceras, Hordeum hexastichon, Hordeum hexastichum, Hordeum irregulare, Hordeum sativum, Hordeum secalinum* [barley], *Secale cereale* [rye], *Avena sativa, Avena fatua, Avena byzantina, Avena fatua* var. *sativa, Avena hybrida* [oats], *Sorghum bicolor, Sorghum halepense, Sorghum saccharatum, Sorghum vulgare, Andropogon drummondii, Holcus bicolor, Holcus sorghum, Sorghum aethiopicum, Sorghum arundinaceum, Sorghum caffrorum, Sorghum cernuum, Sorghum dochna, Sorghum drummondii, Sorghum durra, Sorghum guineense, Sorghum lanceolatum, Sorghum nervosum, Sorghum saccharatum, Sorghum subglabrescens, Sorghum verticilliflorum, Sorghum vulgare, Holcus halepensis, Sorghum miliaceum, Panicum militaceum* [millet], *Oryza sativa, Oryza latifolia* [rice], *Zea mays* [maize], *Triticum aestivum, Triticum durum, Triticum turgidum, Triticum hybernum, Triticum macha, Triticum sativum* or *Triticum vulgare* [wheat], Porphyridiaceae, such as the genera *Chroothece, Flintiella, Petrovanella, Porphyridium, Rhodella, Rhodosorus, Vanhoeffenia*, for example the genus and species *Porphyridium cruentum*, Proteaceae, such as the genus *Macadamia*, for example the genus and species *Macadamia intergrifolia* [macadamia], Prasinophyceae such as the genera *Nephroselmis, Prasinococcus, Scherffelia, Tetraselmis, Mantoniella, Ostreococcus*, for example the genera and species *Nephroselmis olivacea, Prasinococcus capsulatus, Scherffelia dubia, Tetraselmis chui, Tetraselmis suecica, Mantoniella squamata, Ostreococcus tauri*, Rubiaceae such as the genus *Cofea*, for example the genera and species *Cofea* spp., *Coffea arabica, Coffea canephora* or *Coffea liberica* [coffee], Scrophulariaceae such as the genus

*Verbascum*, for example the genera and species *Verbascum blattaria, Verbascum chaixii, Verbascum densiflorum, Verbascum lagurus, Verbascum longifolium, Verbascum lychnitis, Verbascum nigrum, Verbascum olympicum, Verbascum phlomoides, Verbascum phoenicum, Verbascum pulverulentum* or *Verbascum thapsus* [mullein], Solanaceae such as the genera *Capsicum, Nicotiana, Solanum, Lycopersicon*, for example the genera and species *Capsicum annuum, Capsicum annuum* var. *glabriusculum, Capsicum frutescens* [pepper], *Capsicum annuum* [paprika], *Nicotiana tabacum, Nicotiana alata, Nicotiana attenuata, Nicotiana glauca, Nicotiana langsdorffii, Nicotiana obtusifolia, Nicotiana quadrivalvis, Nicotiana repanda, Nicotiana rustica, Nicotiana sylvestris* [tobacco], *Solanum tuberosum* [potato], *Solanum melongena* [eggplant], *Lycopersicon esculentum, Lycopersicon lycopersicum, Lycopersicon pyriforme, Solanum integrifolium* or *Solanum lycopersicum* [tomato], Sterculiaceae, such as the genus *Theobroma*, for example the genus and species *Theobroma cacao* [cacao] or Theaceae, such as the genus *Camellia*, for example the genus and species *Camellia sinensis* [tea]. In particular preferred plants to be used as transgenic plants in accordance with the present invention are oil fruit crops which comprise large amounts of lipid compounds, such as peanut, oilseed rape, canola, sunflower, safflower, poppy, mustard, hemp, castor-oil plant, olive, sesame, *Calendula, Punica*, evening primrose, mullein, thistle, wild roses, hazelnut, almond, *macadamia*, avocado, bay, pumpkin/squash, linseed, soybean, pistachios, borage, trees (oil palm, coconut, walnut) or crops such as maize, wheat, rye, oats, triticale, rice, barley, cotton, cassava, pepper, *Tagetes*, Solanaceae plants such as potato, tobacco, eggplant and tomato, *Vicia* species, pea, alfalfa or bushy plants (coffee, cacao, tea), *Salix* species, and perennial grasses and fodder crops. Preferred plants according to the invention are oil crop plants such as peanut, oilseed rape, canola, sunflower, safflower, poppy, mustard, hemp, castor-oil plant, olive, *Calendula, Punica*, evening primrose, pumpkin/squash, linseed, soybean, borage, trees (oil palm, coconut). Especially preferred are sunflower, safflower, tobacco, mullein, sesame, cotton, pumpkin/squash, poppy, evening primrose, walnut, linseed, hemp, thistle or safflower. Very especially preferred plants are plants such as safflower, sunflower, poppy, evening primrose, walnut, linseed, or hemp.

Preferred mosses are *Physcomitrella* or *Ceratodon*. Preferred algae are *Isochrysis, Mantoniella, Ostreococcus* or *Crypthecodinium*, and algae/diatoms such as *Phaeodactylum* or *Thraustochytrium*. More preferably, said algae or mosses are selected from the group consisting of: *Shewanella, Physcomitrella, Thraustochytrium, Fusarium, Phytophthora, Ceratodon, Isochrysis, Aleurita, Muscarioides, Mortierella, Phaeodactylum, Cryphthecodinium*, specifically from the genera and species *Thalassiosira pseudonona, Euglena gracilis, Physcomitrella patens, Phytophthora infestans, Fusarium graminaeum, Cryptocodinium cohnii, Ceratodon purpureus, Isochrysis galbana, Aleurita farinosa, Thraustochytrium* sp., *Muscarioides viallii, Mortierella alpina, Phaeodactylum tricornutum* or *Caenorhabditis elegans* or especially advantageously *Phytophthora infestans, Thalassiosira pseudonona* and *Cryptocodinium cohnii*.

Transgenic plants may be obtained by transformation techniques as elsewhere in this specification. Preferably, transgenic plants can be obtained by T-DNA-mediated transformation. Such vector systems are, as a rule, characterized in that they contain at least the vir genes, which are required for the *Agrobacterium*-mediated transformation, and the sequences which delimit the T-DNA (T-DNA border). Suitable vectors are described elsewhere in the specification in detail.

Also encompassed are transgenic non-human animals comprising the vector or polynucleotide of the present invention. Preferred non-human transgenic animals envisaged by the present invention are fish, such as herring, salmon, sardine, redfish, eel, carp, trout, halibut, mackerel, zander or tuna.

However, it will be understood that dependent on the non-human transgenic organism specified above, further, enzymatic activities may be conferred to the said organism, e.g., by recombinant technologies. Accordingly, the present invention, preferably, envisages a non-human transgenic organism specified above which in addition to the polynucleotide of the present invention comprises polynucleotides encoding such desaturases and/or elongases as required depending on the selected host cell. Preferred desaturases and/or elongases which shall be present in the organism are at least one enzyme selected from the group of desaturases and/or elongases or the combinations specifically recited elsewhere in this specification (see above and tables 5, 6 and 7).

Furthermore, the present invention encompasses a method for the manufacture of polyunsaturated fatty acids comprising:
  a) cultivating the host cell of the invention under conditions which allow for the production of polyunsaturated fatty acids in said host cell; and
  b) obtaining said polyunsaturated fatty acids from the said host cell.

The term "polyunsaturated fatty acids (PUFA)" as used herein refers to fatty acids comprising at least two, preferably, three, four, five or six, double bonds. Moreover, it is to be understood that such fatty acids comprise, preferably, from 18 to 24 carbon atoms in the fatty acid chain. More preferably, the term relates to long chain PUFA (LCPUFA) having from 20 to 24 carbon atoms in the fatty acid chain. Preferred unsaturated fatty acids in the sense of the present invention are selected from the group consisting of DGLA 20:3 (8,11,14), ARA 20:4 (5,8,11,14), iARA 20:4 (8,11,14,17), EPA 20:5 (5,8,11,14,17), DPA 22:5 (4,7,10,13,16), DHA 22:6 (4,7,10,13,16,19), 20:4 (8,11,14,17), more preferably, arachidonic acid (ARA) 20:4 (5,8,11,14), eicosapentaenoic acid (EPA) 20:5 (5,8,11,14,17), and docosahexaenoic acid (DHA) 22:6 (4,7,10,13,16,19). Thus, it will be understood that most preferably, the methods provided by the present invention pertaining to the manufacture of ARA, EPA or DHA. Moreover, also encompassed are the intermediates of LCPUFA which occur during synthesis. Such intermediates are, preferably, formed from substrates by the desaturase, keto-acyl-CoA-synthase and keto-acyl-CoA-reductase activity of the polypeptide of the present invention. Preferably, substrates encompass LA 18:2 (9,12), GLA 18:3 (6,9,12), DGLA 20:3 (8,11,14), ARA 20:4 (5,8,11,14), eicosadienoic acid 20:2 (11,14), eicosatetraenoic acid 20:4 (8,11,14,17), eicosapentaenoic acid 20:5 (5,8,11,14,17).

The term "cultivating" as used herein refers maintaining and growing the host cells under culture conditions which allow the cells to produce the said polyunsaturated fatty acid, i.e. the PUFA and/or LCPUFA referred to above. This implies that the polynucleotide of the present invention is expressed in the host cell so that the desaturase, keto-acyl-CoA-synthase and keto-acyl-CoA-reductase activity is present. Suitable culture conditions for cultivating the host cell are described in more detail below.

The term "obtaining" as used herein encompasses the provision of the cell culture including the host cells and the culture medium as well as the provision of purified or partially purified preparations thereof comprising the polyunsaturated fatty acids, preferably, ARA, EPA, DHA, in free or in —CoA bound form, as membrane phospholipids or as triacylglyceride esters. More preferably, the PUFA and LCPUFA are to be obtained as triglyceride esters, e.g., in form of an oil. More details on purification techniques can be found elsewhere herein below.

The host cells to be used in the method of the invention are grown or cultured in the manner with which the skilled worker is familiar, depending on the host organism. Usually, host cells are grown in a liquid medium comprising a carbon source, usually in the form of sugars, a nitrogen source, usually in the form of organic nitrogen sources such as yeast extract or salts such as ammonium sulfate, trace elements such as salts of iron, manganese and magnesium and, if appropriate, vitamins, at temperatures of between 0° C. and 100° C., preferably between 10° C. and 60° C. under oxygen or anaerobic atmosphere dependent on the type of organism. The pH of the liquid medium can either be kept constant, that is to say regulated during the culturing period, or not. The cultures can be grown batchwise, semibatchwise or continuously. Nutrients can be provided at the beginning of the fermentation or administered semicontinuously or continuously: The produced PUFA or LCPUFA can be isolated from the host cells as described above by processes known to the skilled worker, e.g., by extraction, distillation, crystallization, if appropriate precipitation with salt, and/or chromatography. It might be required to disrupt the host cells prior to purification. To this end, the host cells can be disrupted beforehand. The culture medium to be used must suitably meet the requirements of the host cells in question. Descriptions of culture media for various microorganisms which can be used as host cells according to the present invention can be found in the textbook "Manual of Methods for General Bacteriology" of the American Society for Bacteriology (Washington D.C., USA, 1981). Culture media can also be obtained from various commercial suppliers. All media components are sterilized, either by heat or by filter sterilization. All media components may be present at the start of the cultivation or added continuously or batchwise, as desired. If the polynucleotide or vector of the invention which has been introduced in the host cell further comprises an expressible selection marker, such as an antibiotic resistance gene, it might be necessary to add a selection agent to the culture, such as a antibiotic in order to maintain the stability of the introduced polynucleotide. The culture is continued until formation of the desired product is at a maximum. This is normally achieved within 10 to 160 hours. The fermentation broths can be used directly or can be processed further. The biomass may, according to requirement, be removed completely or partially from the fermentation broth by separation methods such as, for example, centrifugation, filtration, decanting or a combination of these methods or be left completely in said broth. The fatty acid preparations obtained by the method of the invention, e.g., oils, comprising the desired PUFA or LCPUFA as triglyceride esters are also suitable as starting material for the chemical synthesis of further products of interest. For example, they can be used in combination with one another or alone for the preparation of pharmaceutical or cosmetic compositions, foodstuffs, or animal feeds. Chemically pure triglycerides comprising the desired PUFA or LCPUFA can also be manufactured by the methods described above. To this end, the fatty acid preparations are further purified by extraction, distillation, crystallization, chromatography or combinations of these methods. In order to release the fatty acid moieties from the triglycerides, hydrolysis may be also required. The said chemically pure triglycerides or free fatty acids are, in particular, suitable for applications in the food industry or for cosmetic and pharmacological compositions.

Moreover, the present invention relates to a method for the manufacture of poly-unsaturated fatty acids comprising:
 a) cultivating the non-human transgenic organism of the invention under conditions which allow for the production of poly-unsaturated fatty acids in said host cell; and
 b) obtaining said poly-unsaturated fatty acids from the said non-human transgenic organism.

Further, it follows from the above that a method for the manufacture of an oil, lipid or fatty acid composition is also envisaged by the present invention comprising the steps of any one of the aforementioned methods and the further step of formulating PUFA or LCPUFA as oil, lipid or fatty acid composition. Preferably, said oil, lipid or fatty acid composition is to be used for feed, foodstuffs, cosmetics or medicaments. Accordingly, the formulation of the PUFA or LCPUFA shall be carried out according to the GMP standards for the individual envisaged products. For example, an oil may be obtained from plant seeds by an oil mill. However, for product safety reasons, sterilization may be required under the applicable GMP standard. Similar standards will apply for lipid or fatty acid compositions to be applied in cosmetic or pharmaceutical compositions. All these measures for formulating oil, lipid or fatty acid compositions as products are comprised by the aforementioned manufacture.

For the production of ARA it is, preferably, envisaged to cultivate a host cell of the invention or a non-human transgenic organism which comprises a combination of polynucleotides of the present invention. Preferably, a combination of the polynucleotides of the invention is envisaged which encode a d12 desaturase, a d6 desaturase, a d6 elongase, a d5 desaturase and KCR (see also Table 5 in the accompanying Examples).

For the production of ARA it is, alternatively but also preferably, envisaged to cultivate a host cell of the invention or a non-human transgenic organism which comprises a combination of polynucleotides of the present invention. Preferably, a combination of the polynucleotides of the invention is envisaged which encode a d12 desaturase, a d9 elongase, a d8 desaturase, a d5 desaturase and KCR (see also Table 6 in the accompanying Examples).

For the production of EPA it is, preferably, envisaged to cultivate a host cell of the invention or a non-human transgenic organism which comprises a combination of polynucleotides of the present invention. Preferably, a combination of the polynucleotides which are preferably applied for the ARA production specified above is used together with a polynucleotide of the present invention encoding a d15 desaturase and a polynucleotide of the present invention encoding a omega-3 desaturase (i.e. a combination of the activities referred to either in Table 7 with those of Table 5 or Table 6).

For the production of DHA it is, preferably, envisaged to cultivate a host cell of the invention or a non-human transgenic organism which comprises a combination of polynucleotides of the present invention. Preferably, a combination of the polynucleotides which are preferably applied for the EPA production specified above is used together with a polynucleotide of the present invention encoding a d5 elongase and a polynucleotide of the present invention encoding a d4 desaturase (i.e. a combination of the activities referred to either in Table 5 and Table 7 with those of Table 8 or Table 6 and Table 7 with those of Table 8)

The present invention also relates to an oil comprising a polyunsaturated fatty acid obtainable by the aforementioned methods.

The term "oil" refers to a fatty acid mixture comprising unsaturated and/or saturated fatty acids which are esterified to triglycerides. Preferably, the triglycerides in the oil of the invention comprise PUFA or LCPUFA as referred to above. The amount of esterified PUFA and/or LCPUFA is, preferably, approximately 30%, a content of 50% is more preferred, a content of 60%, 70%, 80% or more is even more preferred. The oil may further comprise free fatty acids, preferably, the PUFA and LCPUFA referred to above. For the analysis, the fatty acid content can be, e.g., determined by GC analysis after converting the fatty acids into the methyl esters by transesterification. The content of the various fatty acids in the oil or fat can vary, in particular depending on the source. The oil, however, shall have a non-naturally occurring composition with respect to the PUFA and/or LCPUFA composition and content. It is known that most of the fatty acids in plant oil are esterified in triacylglycerides. Accordingly, in the oil of the invention, the PUFAs and LCPUFAs are, preferably, also occur in esterified form in the triacylglcerides. It will be understood that such a unique oil composition and the unique esterification pattern of PUFA and LCPUFA in the triglycerides of the oil shall only be obtainable by applying the methods of the present invention specified above. Moreover, the oil of the invention may comprise other molecular species as well. Specifically, it may comprise minor impurities of the polynucleotide or vector of the invention. Such impurities, however, can be detected only by highly sensitive techniques such as PCR.

All references cited in this specification are herewith incorporated by reference with respect to their entire disclosure content and the disclosure content specifically mentioned in this specification.

FIGURES

FIG. 1 shows the production of d5 elongated fatty acids in yeast transformed with pYes-pd5Elo(Ta)_c1. The fatty acid spectrum of transgenic yeast fed with different fatty acid are depicted. A: control pYes fed with 20:5n-3, B: pYes-pd5Elo(Ta)_c1 fed with 20:5n-3. The formation of 22:5n-3 demonstrates d5-Elongase activity of pd5Elo(Ta)_c1. The observed rate of conversion of 20:5n-3 to 22:5n-3 is listed in table 5.

Figure 2:
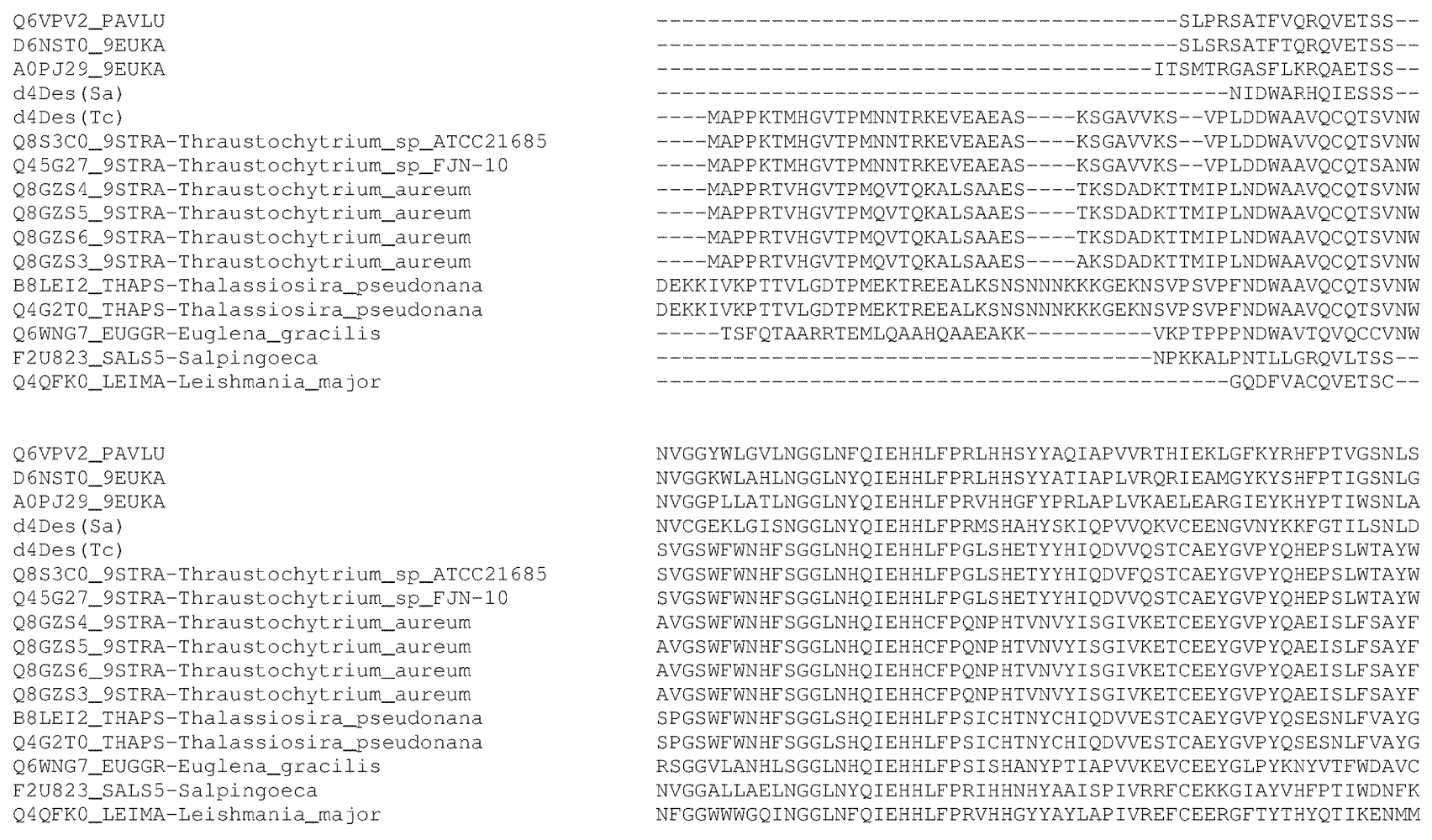

FIG. 2 shows an alignment of various delta-4 desaturase polypeptide sequences. "d4Des(Sa)" is the sequence SEQ ID NO. 79 according to the present invention; "d4des(Tc)" indicates the delta-4 desaturase of Thraustochytrium as described herein.

FIG. 3 shows a list of various delta-4 desaturase polypeptide sequences according to the invention, in decreasing order of sequence identity to SEQ ID NO. 79. The sequences are obtained by mutating the sequence of SEQ ID NO. 79 while maintaining preferred conserved sequence motifs as described above.

Figure 1:
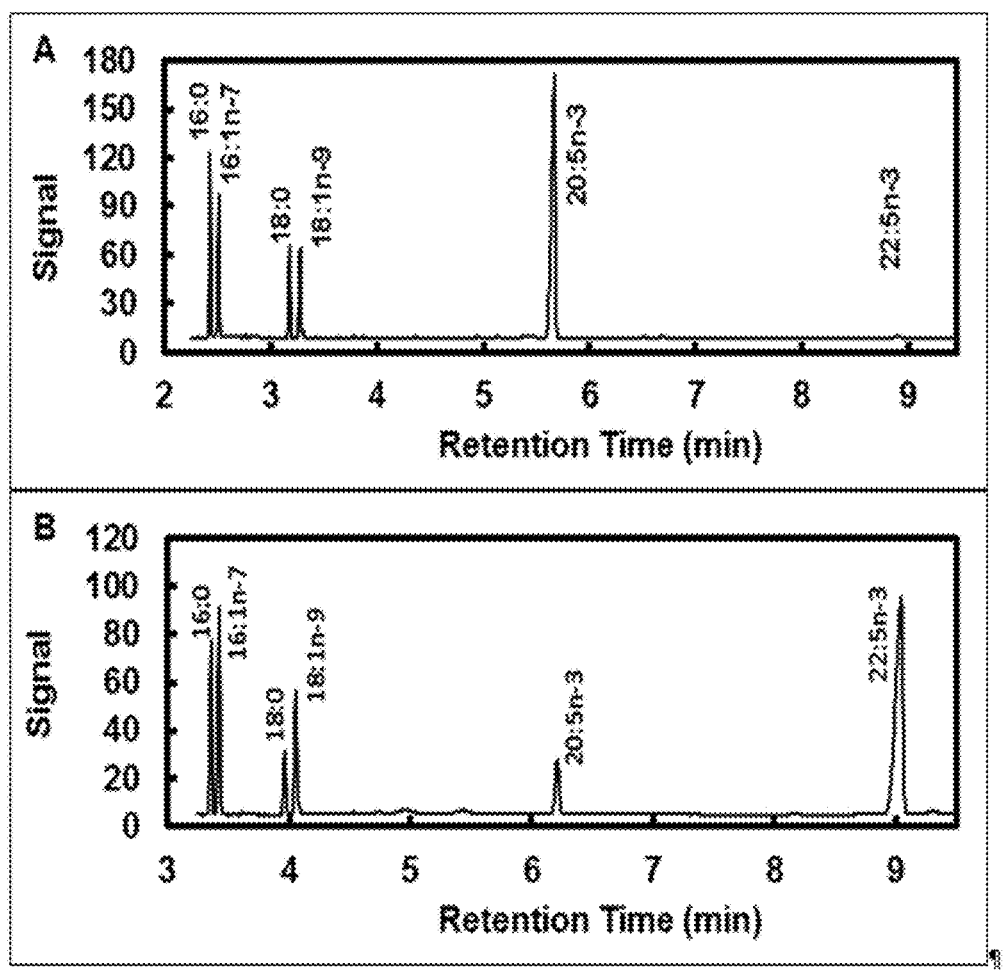

The invention will now be illustrated by the following Examples which, however, shall not be construed as limiting the scope of the claims or of the invention.

EXAMPLES

Example 1: General Cloning Methods

Cloning methods as e.g. use of restriction endonucleases to cut double stranded DNA at specific sites, agarose gel electrophoreses, purification of DNA fragments, transfer of nucleic acids onto nitrocellulose and nylon membranes, ligation of DNA fragments, transformation of E. coli cells and culture of bacteria were performed as described in Sambrook et al. (1989) (Cold Spring Harbor Laboratory Press: ISBN 0-87965-309-6).

Example 2: Sequence Analysis of Recombinant DNA

Sequencing of recombinant DNA molecules was performed using a laser-fluorescence DNA sequencer (Applied Biosystems Inc, USA) employing the sanger method (Sanger et al. (1977) Proc. Natl. Acad. Sci. USA 74, 5463-5467). Expression constructs harboring fragments obtained by polymerase chain reaction were subjected to sequencing to confirm the correctness of the expression cassettes consisting of promoter, nucleic acid molecule to be expressed and terminator to avoid mutations that might result from handling of the DNA during cloning, e.g. due to incorrect primers, mutations from exposure to UV-light or errors of polymerases.

Example 3: Cloning of Yeast Expression Construct Via Homologous Recombination The open reading frame listed in SEQ ID NOs: 1, 4, 7, 10, 13, 16, 19, 22, 25, 28, 31, 78 and 83 encoding polypeptides with the amino acid sequence SEQ ID NOs: 2, 5, 8, 11, 14, 17, 20, 23, 26, 29, 32,79, 84, 85 or 86 that have desaturase, elongase, KCR or LACS activity, respectively can be amplified using the primers listed in table 2 in a polymerase chain reaction. By doing so, the open reading frame is 5' fused to about 60 nucleotides of the 3' end of the GAL1 promoter sequence with simultaneous introduction of an Asc I and/or Nco I restriction site between the fusion site and 3' fused to about 60 nucleotides of the 5' end of the CYC1 terminator sequence with simultaneous introduction of an Pac I restriction site. To integrate these fragments into pYES2.1 TOPO downstream of the galactose inducible GAL1 Promoter via homologous recombination, the vector pYES2.1 (Invitrogen) can be digested using the restriction endonucleases Pvu II and Xba I, and Saccharomyces cerevisiae can be transformed with 5 to 20 ng of linearized pYES2.1 TOPO vector and 20 to 100 ng PCR product per 50 μl competent cells using the transformation method described by Schiestl et al. (Schiestl et al. (1989) Curr. Genet. 16(5-6), pp. 339-346), to obtain pYes-pd6Des(Ta)_c3318, pYes-pd9Des(Ta)_c4008, pYes-po3Des(Ta)_c959, pYes-po3Des(Ta)_c1830, pYes-pd12Des(Ta)_c1219, pYes-pd5Elo(Ta)_c1, pYes-pd6Elo(Ta)_c231, pYes-pd6Elo(Ta)_c752, pYes-pd6Elo(Ta)_c4696, pYes-pd9Elo(Ta)_c4589, pYes-pKCR(Ta)_c1703 and pYes-d4Des(Sa) in various wildtype yeasts. Positive transformants can be selected based on the complementation of the URA auxotrophy of the chosen S. cerevisiae strain. To validate the correctness of the expression construct harbored by a particular yeast clone, plasmids can be isolated as described in Current Protocols in Molecular Biology (Hoffmann, Curr. Protoc. Mol. Biol. 2001 May; Chapter 13:Unit13.11), transformed into E. coli for amplification and subjected to sequencing of the expression cassette as described in Example 2.

TABLE 2

Primer sequences for cloning polynucleotides of desaturase, keto-acyl-CoA-synthase, keto-acyl-CoA-reductase, dehydratase and enoyl-CoA-reductase of the invention for expression in yeast

| Gene-Name | Primer | SEQ-ID |
|---|---|---|
| pd6Des(Ta)_c3318 | Forward: ataaaagtatcaacaaaaaattgttaatatacctctatactttaacgtcaaggagaaaaaaccccggatcggcgcgccaccatgttcaaccaggcaagcgagct | 34 |
| | Reverse: aactataaaaaaataaatagggacctagacttcaggttgtctaactccttccttttcggttagagcggatttaattaactagccctgcgcgttaatggctt | 35 |
| pd9Des(Ta)_c4008 | Forward: ataaaagtatcaacaaaaaattgttaatatacctctatactttaacgtcaaggagaaaaaaccccggatcggcgcgccaccatggcggcaacatgtggggcca | 36 |
| | Reverse: aactataaaaaaataaatagggacctagacttcaggttgtctaactccttccttttcggttagagcggatttaattaatcacgccaccgtgcgctcgcgca | 37 |
| po3Des(Ta)_c959 | Forward: ataaaagtatcaacaaaaaattgttaatatacctctatactttaacgtcaaggagaaaaaaccccggatcggcgcgccaccatggcgccagcggttgcaaggc | 38 |
| | Reverse: aactataaaaaaataaatagggacctagacttcaggttgtctaactccttccttttcggttagagcggatttaattaattgggccttttggactcgcgct | 39 |
| po3Des(Ta)_c1830 | Forward: ataaaagtatcaacaaaaaattgttaatatacctctatactttaacgtcaaggagaaaaaaccccggatcggcgcgccaccatggcgcccccaaaggtcttctc | 40 |
| | Reverse: aactataaaaaaataaatagggacctagacttcaggttgtctaactccttccttttcggttagagcggatttaattaatcagagcttggcgtcgcgcgggt | 41 |
| pd12Des(Ta)_c1219 | Forward: ataaaagtatcaacaaaaaattgttaatatacctctatactttaacgtcaaggagaaaaaaccccggatcggcgcgccaccatgtgcaaggtcgatgggacaaa | 42 |
| | Reverse: aactataaaaaaataaatagggacctagacttcaggttgtctaactccttccttttcggttagagcggatttaattaatcagagcttttggccgcacgct | 43 |
| pd5Elo(Ta)_c1 | Forward: ataaaagtatcaacaaaaaattgttaatatacctctatactttaacgtcaaggagaaaaaaccccggatcggcgcgccaccatggcgacgcgcacctcgaagag | 44 |
| | Reverse: aactataaaaaaataaatagggacctagacttcaggttgtctaactccttccttttcggttagagcggatttaattaatcactcggacttggtgggggcgc | 45 |
| pd6Elo(Ta)_c231 | Forward: ataaaagtatcaacaaaaaattgttaatatacctctatactttaacgtcaaggagaaaaaaccccggatcggcgcgccaccatggccgcggccttcatggactt | 46 |
| | Reverse: aactataaaaaaataaatagggacctagacttcaggttgtctaactccttccttttcggttagagcggatttaattaatcactccaccttggccttgggcc | 47 |
| pd6Elo(Ta)_c752 | Forward: ataaaagtatcaacaaaaaattgttaatatacctctatactttaacgtcaaggagaaaaaaccccggatcggcgcgccaccatggaaaatacaatggagcacaa | 48 |
| | Reverse: aactataaaaaaataaatagggacctagacttcaggttgtctaactccttccttttcggttagagcggatttaattaatcaggtcgacttgagcttgtcgg | 49 |
| pd6Elo(Ta)_c4696 | Forward: ataaaagtatcaacaaaaaattgttaatatacctctatactttaacgtcaaggagaaaaaaccccggatcggcgcgccaccatgcgcaccgcgtacgaagcagc | 50 |
| | Reverse: aactataaaaaaataaatagggacctagacttcaggttgtctaactccttccttttcggttagagcggatttaattaactactgcttcttcttctgttgca | 51 |

TABLE 2-continued

Primer sequences for cloning polynucleotides of desaturase,
keto-acyl-CoA-synthase, keto-acyl-CoA-reductase, dehydratase and
enoyl-CoA-reductase of the invention for expression in yeast

| Gene-Name | Primer | SEQ-ID |
|---|---|---|
| pd9Elo(Ta)_c4589 | Forward: ataaaagtatcaacaaaaaattgttaatatacctctatactttaacgtcaaggagaaaaaacccggatcggcgcgccaccatggacgtctatgacgcacagcc | 52 |
| | Reverse: aactataaaaaaataaatagggacctagacttcaggttgtctaactccttccttttcggttagagcggatttaattaatcactgcgacttgagctggtccg | 53 |
| pKCR(Ta)_c1703 | Forward: ataaaagtatcaacaaaaaattgttaatatacctctatactttaacgtcaaggagaaaaaacccggatcggcgcgccaccatgaccgagactgtgctgtgggt | 54 |
| | Reverse: aactataaaaaaataaatagggacctagacttcaggttgtctaactccttccttttcggttagagcggatttaattaatcaagcgaccttcttcggcgacg | 55 |
| d4Des(Sa) | Forward: ataaaagtatcaacaaaaaattgttaatatacctctatactttaacgtcaaggagaaaaaacccggatcggcgcgccaccatgaccgagactgtgctgtgggt | 81 |
| | Reverse: aactataaaaaaataaatagggacctagacttcaggttgtctaactccttccttttcggttagagcggatttaattaatcaagcgaccttcttcggcgacg | 82 |

TABLE 3

Coding polynucleotide sequences, amino acid sequences encoded thereby
and expressed sequences (mRNA) of desaturases, elongases or elongase
component from Thraustochytrium aureum of the invention.

| Gene name | Activity | ORF in bp | SEQ-ID No. | Amino acids | SEQ-ID No. | mRNA in bp | SEQ-ID No. |
|---|---|---|---|---|---|---|---|
| pd6Des(Ta)_c3318 | d6-desaturase | 1641 | 1 | 547 | 2 | 1910 | 3 |
| pd9Des(Ta)_c4008 | d9-desaturase | 1176 | 4 | 354 | 5 | 1440 | 6 |
| po3Des(Ta)_c959 | o3-desaturase | 1119 | 7 | 373 | 8 | 1184 | 9 |
| po3Des(Ta)_c1830 | o3-desaturase | 1566 | 10 | 522 | 11 | 1845 | 12 |
| pd12Des(Ta)_c1219 | d12-desaturase | 1185 | 13 | 394 | 14 | 1463 | 15 |
| pd5Elo(Ta)_c1 | d5-elongase | 951 | 16 | 316 | 17 | 1253 | 18 |
| pd6Elo(Ta)_c231 | d6-elongase | 912 | 19 | 303 | 20 | 1189 | 21 |
| pd6Elo(Ta)_c752 | d6-elongase | 1176 | 22 | 392 | 23 | 1313 | 24 |
| pd6Elo(Ta)_c4696 | d6-elongase | 969 | 25 | 322 | 26 | 1207 | 27 |
| pd9Elo(Ta)_c4589 | d9-elongase | 789 | 28 | 263 | 29 | 1031 | 30 |
| pKCR(Ta)_c1703 | keto-acyl-CoA reductase | 1071 | 31 | 356 | 32 | 1304 | 33 |
| d4Des(Sa) | d4-desaturase | 942 | 78 | 445 | 79 | 1453 | 80 |
| SA-LACS1 | LACS | | 83 | | 84 | | |

Example 4: Activity Assay in Yeast

As an example the superior activity of identified polypeptides can be confirmed by heterologous expression in yeast. Table 4 and 5 show activity assays of yeasts transformed with pYes-pd6Des(Ta)_c3318 (comprising the Thraustrochytrium aureum delta-6-desaturase gene), pYes-pd9Des(Ta)_c4008 (comprising the Thraustrochytrium aureum delta-9-desaturase gene), pYes-po3Des(Ta)_c959 (comprising the Thraustrochytrium aureum omega-3-desaturase gene), pYes-po3Des(Ta)_c1830 (comprising the Thraustrochytrium aureum omega-3-desaturase gene), pYes-pd12Des(Ta)_c1219 (comprising the Thraustrochytrium aureum delta-12-desaturase gene), pYes-pd5Elo(Ta)_c1 (comprising the Thraustrochytrium aureum delta-5-elongase gene), pYes-pd6Elo(Ta)_c231 (comprising the Thraustrochytrium aureum delta-6-elongase gene), pYes-pd6Elo(Ta)_c752 (comprising the Thraustrochytrium aureum delta-6-elongase gene), pYes-pd6Elo(Ta)_c4696 (comprising the Thraustrochytrium aureum delta-6-elongase gene), pYes-pd9Elo(Ta)_c4589 (comprising the Thraustrochytrium aureum delta-9-elongase gene), pYes-pKCR(Ta)_c1703 (comprising the Thraustrochytrium aureum KCR gene) and pYes-d4Des(Sa) (comprising the Sphaeroforma erotica delta-4-desaturase gene) constructs. Yeast cells containing the respective plasmids were incubated 12 h in liquid drop out base medium lacking uracil (DOB-U medium) at 28° C., 200 rpm incubated, followed by an additional 12 h in induction medium (DOB-U+2% (w/v) galactose+2% (w/v) raffinose). To the induction medium 250 µM of the respective fatty acids were added to check for enzyme activity and specificity. In addition, the fed substrate, the expected product fatty acid are indicated in table 4 and table 5.

In the gas chromatograms of yeast extracts, transformed with pYes-pd5Elo(Ta)_c1 and fed with 20:5n-3 or 20:4n-6, the fatty acids 22:5n-3 and 22:4n-6 were detected (Table 5, FIG. 1). This result shows that pYes-pd5Elo(Ta)_c1 has d5-elongase activity and exhibits a surprisingly high conversion rate. In a direct comparison of the gene d4Des(Sa) of SEQ ID NO 78 against d4Des(Tc) of SEQ ID NO 76 in a parallel experiment, d4Des(Sa) expressed by construct pYes-d4Des(Sa) was found to have a surprisingly high convertion rate (conversion efficiency) of 22%, compared to convertion rate of only 10% for the gene d4Des(Tc). According to the invention it is believed that the delta-4 desaturases of Sphaeroforma arctica and Thraustochytrium sp. exhibit a preference for different fatty acid pools, i.e. for fatty acids bound to ACP, to CoA or in phospholipids.

TABLE 4

Yeast feeding experiment setup

| Gene | Vector | Substrate | Product |
|---|---|---|---|
| pd6Des(Ta)_c3318 | pYes-pd6Des(Ta)_c3318 | 18:2n-6 | 18:3n-6 |
| pd6Des(Ta)_c3318 | pYes-pd6Des(Ta)_c3318 | 18:3n-3 | 18:4n-3 |
| pd9Des(Ta)_c4008 | pYes-pd9Des(Ta)_c4008 | 18:0 | 18:1n-9 |
| po3Des(Ta)_c959 | pYes-po3Des(Ta)_c959 | 18:2n-6 | 18:3n-3 |
| po3Des(Ta)_c959 | pYes-po3Des(Ta)_c959 | 20:4n-6 | 20:5n-3 |
| po3Des(Ta)_c1830 | pYes-po3Des(Ta)_c1830 | 18:2n-6 | 18:3n-3 |
| po3Des(Ta)_c1830 | pYes-po3Des(Ta)_c1830 | 20:4n-6 | 20:5n-3 |
| pd12Des(Ta)_c1219 | pYes-pd12Des(Ta)_c1219 | 18:1n-9 | 18:2n-6 |
| pd5Elo(Ta)_c1 | pYes-pd5Elo(Ta)_c1 | 20:4n-6 | 22:4n-6 |
| pd5Elo(Ta)_c1 | pYes-pd5Elo(Ta)_c1 | 20:5n-3 | 20:5n-3 |
| pd6Elo(Ta)_c231 | pYes-pd6Elo(Ta)_c231 | 18:3n-6 | 20:3n-6 |
| pd6Elo(Ta)_c231 | pYes-pd6Elo(Ta)_c231 | 18:4n-3 | 20:4n-3 |
| pd6Elo(Ta)_c752 | pYes-pd6Elo(Ta)_c752 | 18:3n-6 | 20:3n-6 |
| pd6Elo(Ta)_c752 | pYes-pd6Elo(Ta)_c752 | 18:4n-3 | 20:4n-3 |
| pd6Elo(Ta)_c4696 | pYes-pd6Elo(Ta)_c4696 | 18:3n-6 | 20:3n-6 |
| pd6Elo(Ta)_c4696 | pYes-pd6Elo(Ta)_c4696 | 18:4n-3 | 20:4n-3 |
| pd9Elo(Ta)_c4589 | pYes-pd9Elo(Ta)_c4589 | 18:2n-6 | 20:2n-6 |
| pd9Elo(Ta)_c4589 | pYes-pd9Elo(Ta)_c4589 | 18:3n-3 | 20:3n-3 |
| d4Des(Sa) | pYes-d4Des(Sa) | 22:4n-6 | 22:5n-6 |
| d4Des(Sa) | pYes-d4Des(Sa) | 22:5n-3 | 22:6n-3 |

TABLE 5

Yeast feeding experiment result. The substrate and product fatty acid are given as percentage of the total fatty acid pool.

| Vector | Substrate | | Product | | Conversion (%) | Activity | Figure |
|---|---|---|---|---|---|---|---|
| pYes | 20:5n-3 | 54.3 | 20:5n-3 | 0.0 | 0.00 | — | 1A |
| pYes | 20:5n-3 | 63.0 | 20:5n-3 | 0.0 | 0.00 | — | |
| pYes-pd5Elo(Ta)_c1 | 20:5n-3 | 6.9 | 20:5n-3 | 49.6 | 87.74 | d5Elo | 1B |
| pYes-pd5Elo(Ta)_c1 | 20:5n-3 | 6.1 | 20:5n-3 | 46.4 | 88.35 | d5Elo | |
| pYes-pd5Elo(Ta)_c1 | 20:4n-6 | 3.3 | 20:4n-6 | 26.3 | 88.89 | d5Elo | |
| pYes-pd5Elo(Ta)_c1 | 20:4n-6 | 3.7 | 20:4n-6 | 29.3 | 88.69 | d5Elo | |
| pYes-d4Des(Sa) | 22:5n-5 | | 22:6n-3 | | 38.40 | d4Des | |
| pYes-d4Des(Sa) | 22:4n-6 | | 22:5n-6 | | 13.80 | d4Des | |

Example 5: Expression of Desaturase, KCS and KCR in Plants

The novel desaturases, KCS and KCR from Thraustochytrium aureum and Sphaeroforma arctica can be cloned into a plant transformation vector as described in WO2003/093482, WO2005/083093 or WO2007/093776.

Exemplary suitable combinations of genes for the superior production of ARA, EPA and/or DHA are described in tables 6, 7, 8 and 9.

TABLE 6

Gene combinations for the production of arachidonic acid (ARA). At least one enzyme with a d12-desaturase, d6-desaturase, d6-elongase and d5-desaturase activity are required for arachidonic acid biosynthesis. Various biosynthetic steps can be catalyzed by enzymes of Thraustochytrium aureum of the present invention.

| Activity | Gene | Source organism | SEQ ID NO: |
|---|---|---|---|
| d12-desaturase | d12Des(Ps) | Phytophthora soja | 56 |
| | pd12Des(Ta)_c1219 | Thraustochytrium aureum | 13 |
| d6-desaturase | d6Des(Ot) | Ostreococcus tauri | 58 |
| | pd6Des(Ta)_c3318 | Thraustochytrium aureum | 1 |

TABLE 6-continued

Gene combinations for the production of arachidonic acid (ARA). At least one enzyme with a d12-desaturase, d6-desaturase, d6-elongase and d5-desaturase activity are required for arachidonic acid biosynthesis. Various biosynthetic steps can be catalyzed by enzymes of Thraustochytrium aureum of the present invention.

| Activity | Gene | Source organism | SEQ ID NO: |
| --- | --- | --- | --- |
| d6-elongase | d6Elo(Tp) | Thalassiosira pseudonana | 60 |
|  | d6Elo(Pp) | Physcomitrella patens | 62 |
|  | pd6Elo(Ta)_c231 | Thraustochytrium aureum | 19 |
|  | pd6Elo(Ta)_c752 | Thraustochytrium aureum | 22 |
|  | pd6Elo(Ta)_c4696 | Thraustochytrium aureum | 25 |
| d5-desaturase | d5Des(Ta) | Thraustochytrium sp. | 64 |
| KCR | pKCR(Ta)_c1703 | Thraustochytrium aureum | 31 |

Arachidonic acid may be produced by an alterative pathway involving d9-elongase and d8-desaturase activity. Table 7 shows a combination of genes for this pathway.

TABLE 7

Gene combinations of the alternative pathway for the production of arachidonic acid. Several biosynthetic steps can be catalyzed by enzymes of Thraustochytrium aureum of the present invention.

| Activity | Gene | Source organism | SEQ ID NO: |
| --- | --- | --- | --- |
| d12-desaturase | d12Des(Ps) | Phytophthora soja | 56 |
|  | pd12Des(Ta)_c1219 | Thraustochytrium aureum | 13 |
| d9-elongase | d9Elo(Ig) | Isochrysis galbana | 66 |
|  | pd9Elo(Ta)_c4589 | Thraustochytrium aureum | 28 |
| d8-desaturase | d8Des(Pm) | Perkinsus marinus | 68 |
| d5-desaturase | d5Des(Ta) | Thraustochytrium sp. | 64 |
| KCR | pKCR(Ta)_c1703 | Thraustochytrium aureum | 31 |

For the production of EPA, the genes listed in table 8 are combined with the genes listed in table 6 or 7.

TABLE 8

For the production of EPA, in addition to combinations of genes listed in table 6 or 7, genes listed in this table can be used.

| Activity | Gene | Source organism | SEQ ID NO: |
| --- | --- | --- | --- |
| d15-desaturase | d15Des(Hr) | Helobdella robusta | 70 |
| omega-3 desaturase | o3Des(Pi) | Phytophthora infestans | 72 |
|  | po3Des(Ta)_c959 | Thraustochytrium aureum | 7 |
|  | po3Des(Ta)_c1830 | Thraustochytrium aureum | 10 |

In addition to the genes of table 6 or 7 the genes listed in table 8 and 9 can be used for the biosynthesis of DHA. These genes allow to elongate EPA by 2 carbon atom and dehydrogenation at the $4^{th}$ and $5^{th}$ carbon atom, resulting in the generation of DHA.

TABLE 9

For the production of DHA, in addition to the genes of table 6 or 7 and 8, the genes listed in this table can be used.

| Activity | Gene | Source organism | SEQ ID NO: |
| --- | --- | --- | --- |
| d5-elongase | d5Elo(Ot) | Ostreococcus tauri | 74 |
|  | pd5Elo(Ta)_c1 | Thraustochytrium aureum | 16 |
| d4-desaturase | d4Des(Tc) | Thraustochytrium sp. | 76 |
|  | d4Des(Sa) | Sphaeroforma erotica | 78 |

Transgenic rapeseed lines are generated as described in Deblaere et al. (1984), (Nucl. Acids. Res. 13, 4777-4788) and seeds of transgenic rapeseed plants are analyzed as described in Qiu et al. (2001)(J. Biol. Chem. 276, 31561-31566).

Example 6: Yeast Feeding with LACS

To investigate the role of this gene by including it in cultures that also carried an elongase and a desaturase gene pair, namely D6ELO(SA) (i.e. delta-6-elongase of Sphaeroforma arctica), and D5DES(SA) (i.e. delta-5-desaturase of Sphaeroforma erotica), both described in WO2011064181 and WO2011064183. When cultures were induced in the presence of GLA, the first elongation to DGLA in cultures carrying SA-LACS1 (Sphaeroforma arctica LACS, SEQ ID NO. 83/84) was lower than that in cultures carrying an empty pYES2.1/V5-His-TOPO vector, reflecting the higher, probably saturated level of substrate available due to the more efficient uptake of GLA in the presence of the acyl CoA-synthetase. However, although DGLA accumulated to similar levels in both samples, desaturation to ARA was approximately 1.6 times as high in the presence of the LACS gene. Similarly, further elongations of DGLA to 22:3n-6 and ARA to 22:4n-6 were more efficient in the presence of SA-LACS1, with elongation of the desaturated product ARA about 1.7 fold higher in the presence of SA-LACS1. Results from experiments where cultures were supplemented with SDA showed a similar trend, with approximately 40% more 20:4Δ, 8,11,14.17 desaturated to EPA, and 25% more EPA extended to DHA. The overall lower conversion ratios for this experiment compared to experiments using single genes reflected reduced efficiencies due to different vectors and multiple gene expression.

TABLE 10

Effect of S. arctica LACS on elongation and desaturation reactions, when co-expressed in yeast expressing.

| Genes | Reaction: | | | |
|---|---|---|---|---|
| | GLA to DGLA | DGLA to ARA | DGLA to 22:3n-6 | ARA to 22:4n-6 |
| Vector control/D6ELO(SA)/ D5DES(SA) | 30.3 ± 1.2 | 43.2 ± 5.1 | 41.7 ± 3.3 | 15.7 ± 1.9 |
| SA-LACS1/ D6ELO(SA)/ D5DES(SA) | 24.4 ± 1.3 | 68.7 ± 4.9 | 48.5 ± 2.3 | 25.5% ± 2.1% |

| Genes | Reaction: | | | |
|---|---|---|---|---|
| | SDA to 20:4n-3 | 20:4n-3 to EPA | 20:4n-3 to 22:4n-3 | EPA to DPA |
| Vector control/D6ELO(SA)/ D5DES(SA) | 32.7% ± 2.3% | 51.5% ± 3.8% | 50.9% ± 2.7% | 30.8% ± 3.1% |
| SA-LACS1/ D6ELO(SA)/ D5DES(SA) | 24.2% ± 1.4% | 71.6% ± 7.3% | 51.9% ± 1.3% | 40.2% ± 1.1% |

REFERENCE LIST

Arondel, V., Lemieux, B., Hwang, I., Gibson, S., Goodman, H. M., and Somerville, C. R. (1992). Map-based cloning of a gene controlling omega-3 fatty acid desaturation in Arabidopsis. Science 258, 1353-1355.

Broadwater, J. A., Whittle, E., and Shanklin, J. (2002). Desaturation and hydroxylation. Residues 148 and 324 of Arabidopsis FAD2, in addition to substrate chain length, exert a major influence in partitioning of catalytic specificity. J. Biol. Chem. 277, 15613-15620.

Broun, P., Shanklin, J., Whittle, E., and Somerville, C. (1998b). Catalytic plasticity of fatty acid modification enzymes underlying chemical diversity of plant lipids. Science 282, 1315-1317.

Calvo, A. M., Gardner, H. W., and Keller, N. P. (2001). Genetic connection between fatty acid metabolism and sporulation in Aspergillus nidulans. J. Biol. Chem. 276, 25766-25774.

Knutzon, D. S., Thurmond, J. M., Huang, Y. S., Chaudhary, S., Bobik, E. G., Jr., Chan, G. M., Kirchner, S. J., and Mukerji, P. (1998). Identification of Delta5-dehydratase from Mortierella alpina by heterologous expression in Bakers' yeast and canola. J. Biol. Chem. 273, 29360-29366.

Mantle, P. G. and Nisbet, L. J. (1976). Differentiation of Claviceps purpurea in axenic culture. J. Gen. Microbiol. 93, 321-334.

Mey, G., Oeser, B., Lebrun, M. H., and Tudzynski, P. (2002). The biotrophic, non-appressorium-forming grass pathogen Claviceps purpurea needs a Fus3/Pmk1 homologous mitogen-activated protein kinase for colonization of rye ovarian tissue. Mol. Plant Microbe Interact. 15, 303-312.

Okuley, J., Lightner, J., Feldmann, K., Yadav, N., Lark, E., and Browse, J. (1994). Arabidopsis FAD2 gene encodes the enzyme that is essential for polyunsaturated lipid synthesis. Plant Cell 6, 147-158.

Qi, B., Fraser, T., Mugford, S., Dobson, G., Sayanova, O., Butler, J., Napier, J. A., Stobart, A. K., and Lazarus, C. M. (2004). Production of very long chain polyunsaturated omega-3 and omega-6 fatty acids in plants. Nat. Biotechnol. 22, 739-745.

Shanklin, J. and Cahoon, E. B. (1998). DESATURATION AND RELATED MODIFICATIONS OF FATTY ACIDS1. Annu. Rev. Plant Physiol Plant Mol. Biol. 49, 611-641.

Tudzynski, P., Correia, T., and Keller, U. (2001). Biotechnology and genetics of ergot alkaloids. Appl. Microbiol. Biotechnol. 57, 593-605.

The invention claimed is:

1. A method for the manufacture of polyunsaturated fatty acids comprising:
  a) cultivating a host cell comprising a polynucleotide encoding a delta-4 desaturase comprising a nucleic acid sequence selected from the group consisting of:
    i) a nucleic acid sequence of SEQ ID NO: 78; and
    ii) a nucleic acid sequence encoding a polypeptide having at least 80% sequence identity to SEQ ID NO: 79 and having delta-4 desaturase activity,
  under conditions which allow for the production of polyunsaturated fatty acids in said host cell, wherein said polynucleotide further comprises a heterologous expression control sequence operatively linked to said nucleic acid sequence; and
  b) obtaining said polyunsaturated fatty acids from said host cell.

2. The method of claim 1, wherein said poly-unsaturated fatty acid is arachidonic acid (ARA), eicosapentaenoic acid (EPA) or docosahexaenoic acid (DHA).

3. A method for the manufacture of an oil, lipid or fatty acid composition comprising the steps of the method of claim 1 and the further step of formulating the polyunsaturated fatty acid as oil, lipid or fatty acid composition.

4. The method of claim 1, wherein the delta-4 desaturase is heterologous to the host cell.

* * * * *

SEQUENCE LISTING

<160> NUMBER OF SEQ ID NOS: 186

<210> SEQ ID NO 1
<211> LENGTH: 1497
<212> TYPE: DNA
<213> ORGANISM: Thraustochytrium aureum

<400> SEQUENCE: 1

```
atgttcaacc aggcaagcga gctcgagtac aagcgccgcc agcccgcggc gaggccggac     60
ggcacggtgt ggcgcgagaa gaaaggagaa gccgtcgcta gccccgtgga ggccaagtcg    120
atcgcggaga agcgcgccca aggcaaagcc agaaaagtga cctgggagga agtaggcaag    180
cacaactccc gggaggacct gtggctcgtc gtcgacggca aggctttcga cgtctcgagc    240
ttcgccgaca agcatcccgg cggctacaga ccctcgtcg ccatggccgg ccgcgactcg    300
accgaggtga tgaacgagtt ccaccggcg gccgtcttcg acaagtacct gccgccgtac    360
tacatcggag acgttgtcga ctacaaagtc cccgagctga tcgccgacta ccgccaagtg    420
cgccaagagc ttctcgcgcg tggcctgttc cgcacctcca cctcgtacta cttggccaag    480
ttcgtctggc tcgccagcat cctcgcgcca acgtctacg gggtcctggc ctgctccagc    540
accacggctc acatgatctc cgcagccggg ctggccctct tctggcagca gctggccttt    600
gtcggccacg acgtcggcca ctcggcggtc tcgcacgaac gcgcgatcga ctactactgg    660
ggtgggctct tcggcaacct tcttgggggg atcagcctgt cctggtggaa gcacagccac    720
gagacccacc acgtaacctg caactcgatc gagatggacc cggacattca gcacctgccc    780
ttcatcgcga ttacctccaa gattttcaag gggcgcttct ggagcaccta ccacctcaag    840
tggttcgaga ccgacgcctt tgcgcgcttc tttgtgatgc accagaaggc gctcttttac    900
ccgatcatga gcttggcgcg cttcaacctc tacgtgcaga gctggatcct cctcctcttc    960
cgcgaggacc gcgacaaggt ccccaacaag ttcatcgaaa tggcctcgct tctcggcttt   1020
tgggtctggc tcttcgcgct cgtgagctcc ttgccgagct ggggcgagcg gctcgcgttc   1080
ttgtacctca gccacgcctt cgcgggcatc ctgcacattc agatcactct gagccacttc   1140
atttctgaaa ccttccacgg ccggtcgacg gacaactgga tcaagcacca gatgctgaca   1200
accacggaca ttacttgccc aaagtacatg gactggttcc acggcggcct tcagttccag   1260
cttgagcatc accttttccc gcgcctgccg cggcacaacc tgcgcatcgc gcgggaccgc   1320
atcatcgcgc tcgctgcaaa gcacaacctt ccttacgcgg agatgacctt tctggaggcc   1380
aaccggaagc tggttggaat ccttggtgag acggcagccg acgcgcagaa cctcaagaaa   1440
ggcgacgggg gcttctacac cagcccgatt ttcgaagcca ttaacgcgca gggctag      1497
```

<210> SEQ ID NO 2
<211> LENGTH: 498
<212> TYPE: PRT
<213> ORGANISM: Thraustochytrium aureum

<400> SEQUENCE: 2

```
Met Phe Asn Gln Ala Ser Glu Leu Glu Tyr Lys Arg Arg Gln Pro Ala
1               5                   10                  15

Ala Arg Pro Asp Gly Thr Val Trp Arg Glu Lys Lys Gly Glu Ala Val
            20                  25                  30

Ala Ser Pro Val Glu Ala Lys Ser Ile Ala Glu Lys Arg Ala Gln Gly
        35                  40                  45

Lys Ala Arg Lys Val Thr Trp Glu Glu Val Gly Lys His Asn Ser Arg
    50                  55                  60
```

-continued

Glu Asp Leu Trp Leu Val Val Asp Gly Lys Ala Phe Asp Val Ser Ser
65                  70                  75                  80

Phe Ala Asp Lys His Pro Gly Gly Tyr Arg Pro Leu Val Ala Met Ala
            85                  90                  95

Gly Arg Asp Ser Thr Glu Val Met Asn Glu Phe His Pro Ala Ala Val
            100                 105                 110

Phe Asp Lys Tyr Leu Pro Pro Tyr Tyr Ile Gly Asp Val Val Asp Tyr
            115                 120                 125

Lys Val Pro Glu Leu Ile Ala Asp Tyr Arg Gln Val Arg Gln Glu Leu
130                 135                 140

Leu Ala Arg Gly Leu Phe Arg Thr Ser Thr Ser Tyr Tyr Leu Ala Lys
145                 150                 155                 160

Phe Val Trp Leu Ala Ser Ile Leu Ala Pro Thr Leu Tyr Gly Val Leu
            165                 170                 175

Ala Cys Ser Ser Thr Thr Ala His Met Ile Ser Ala Ala Gly Leu Ala
            180                 185                 190

Leu Phe Trp Gln Gln Leu Ala Phe Val Gly His Asp Val Gly His Ser
            195                 200                 205

Ala Val Ser His Glu Arg Ala Ile Asp Tyr Tyr Trp Gly Gly Leu Phe
210                 215                 220

Gly Asn Leu Leu Gly Gly Ile Ser Leu Ser Trp Trp Lys His Ser His
225                 230                 235                 240

Glu Thr His His Val Thr Cys Asn Ser Ile Glu Met Asp Pro Asp Ile
            245                 250                 255

Gln His Leu Pro Phe Ile Ala Ile Thr Ser Lys Ile Phe Lys Gly Arg
            260                 265                 270

Phe Trp Ser Thr Tyr His Leu Lys Trp Phe Glu Thr Asp Ala Phe Ala
            275                 280                 285

Arg Phe Phe Val Met His Gln Lys Ala Leu Phe Tyr Pro Ile Met Ser
290                 295                 300

Leu Ala Arg Phe Asn Leu Tyr Val Gln Ser Trp Ile Leu Leu Leu Phe
305                 310                 315                 320

Arg Glu Asp Arg Asp Lys Val Pro Asn Lys Phe Ile Glu Met Ala Ser
            325                 330                 335

Leu Leu Gly Phe Trp Val Trp Leu Phe Ala Leu Val Ser Ser Leu Pro
            340                 345                 350

Ser Trp Gly Glu Arg Leu Ala Phe Leu Tyr Leu Ser His Ala Phe Ala
            355                 360                 365

Gly Ile Leu His Ile Gln Ile Thr Leu Ser His Phe Ile Ser Glu Thr
            370                 375                 380

Phe His Gly Arg Ser Thr Asp Asn Trp Ile Lys His Gln Met Leu Thr
385                 390                 395                 400

Thr Thr Asp Ile Thr Cys Pro Lys Tyr Met Asp Trp Phe His Gly Gly
            405                 410                 415

Leu Gln Phe Gln Leu Glu His His Leu Phe Pro Arg Leu Pro Arg His
            420                 425                 430

Asn Leu Arg Ile Ala Arg Asp Arg Ile Ile Ala Leu Ala Ala Lys His
            435                 440                 445

Asn Leu Pro Tyr Ala Glu Met Thr Phe Leu Glu Ala Asn Arg Lys Leu
            450                 455                 460

Val Gly Ile Leu Gly Glu Thr Ala Ala Asp Ala Gln Asn Leu Lys Lys
465                 470                 475                 480

Gly Asp Gly Gly Phe Tyr Thr Ser Pro Ile Phe Glu Ala Ile Asn Ala
            485                 490                 495

Gln Gly

<210> SEQ ID NO 3
<211> LENGTH: 1910
<212> TYPE: RNA
<213> ORGANISM: Thraustochytrium aureum

<400> SEQUENCE: 3

| | | | | | |
|---|---|---|---|---|---|
| aaacaccaac | guaggcaggc | gacgacgcgc | gaccgucgcg | cagcccucgc | accaacgagc | 60 |
| gcagcuuuga | aggacgagcu | gcagcaccga | acgaacagag | cgccagccag | cgagggcuca | 120 |
| ggcagcgccc | ccgccaggug | cccgagcgag | ugacuccacu | ugcgcaaacc | gcgcuuugaa | 180 |
| ggcgucguga | agaugagcuc | caucaugcug | aacgcaaccg | cggguagcgc | cagcuuuacg | 240 |
| ccagccguug | cugcgcuguu | aggcguggag | gccagcaagg | cccugucgca | guccgugaug | 300 |
| gcggcggugu | uccugauuag | uuugcugggc | cagaugacca | uguucaacca | ggcaagcgag | 360 |
| cucgaguaca | agcgccgcca | gcccgcggcg | aggccggacg | gcacggugug | cgcgagaag | 420 |
| aaaggagaag | ccgucgcuag | ccccguggag | gccaagucga | ucgcggagaa | cgcgcccaa | 480 |
| ggcaaagcca | gaaaagugac | cugggaggaa | guaggcaagc | acaacucccg | ggaggaccug | 540 |
| uggcucgucg | ucgacggcaa | ggcuuucgac | gucucgagcu | ucgccgacaa | gcauccggc | 600 |
| ggcuacagac | cccucgucgc | cauggccggc | cgcgacucga | ccgaggugau | gaacgaguuc | 660 |
| caccccggcgg | ccgucuucga | caaguaccug | ccgccuacu | acaucggaga | cguugucgac | 720 |
| uacaaagucc | ccgagcugau | cgccgacuac | cgccaagugc | gccaagagcu | ucucgcgcgu | 780 |
| ggccuguucc | gcaccuccac | cucguacuac | uuggccaagu | cgucuggcu | cgccagcauc | 840 |
| cucgcgccaa | cgcucuacgg | gguccuggcc | ugcuccagca | ccacggcuca | caugaucucc | 900 |
| gcagccgggc | uggcccucuu | cuggcagcag | cuggccuuug | ucggccacga | cgucggccac | 960 |
| ucggcgggucu | cgcacgaacg | cgcgaucgac | uacuacuggg | gugggcucuu | cggcaaccuu | 1020 |
| cuuggggggga | ucagccuguc | cugguggaag | cacagccacg | agacccacca | cguaaccugc | 1080 |
| aacucgaucg | agauggaccc | ggacauucag | caccugcccu | ucaucgcgau | uaccuccaag | 1140 |
| auuuucaagg | ggcgcuucug | gagcaccuac | caccucaagu | gguucgagac | cgacgccuuu | 1200 |
| gcgcgcuucu | uugugaugca | ccagaaggcg | cucuuuuacc | cgaucaugag | cuggcgcgc | 1260 |
| uucaaccucu | acgugcagag | cuggauccuc | cuccucuucc | gcgaggaccg | cgacaagguc | 1320 |
| cccaacaagu | caucgaaaau | ggccucgcuu | ucggcuuuu | gggucuggcu | cuucgcgcuc | 1380 |
| gugagcuccu | ugccgagcug | gggcgagcgg | cucgcguucu | uguaccucag | ccacgccuuc | 1440 |
| gcgggcaucc | ugcacauuca | gaucacucug | agccacuuca | uuucugaaac | cuccacggc | 1500 |
| cggucgacgg | acaacuggau | caagcaccag | augcugacaa | ccacggacau | uacuugccca | 1560 |
| aaguacaugg | acugguucca | cggcggccuu | caguccagc | uugagcauca | ccuuuucccg | 1620 |
| cgccugccgc | ggcacaaccu | gcgcaucgcg | cgggaccgca | ucaucgcgcu | cgcugcaaag | 1680 |
| cacaaccuuc | cuuacgcgga | gaugaccuuu | cuggaggcca | accggaagcu | gguuggaauc | 1740 |
| cuuggugaga | cggcagccga | cgcgcagaac | cucaagaaag | cgacgggggg | cuucuacacc | 1800 |
| agccccgauuu | ucgaagccau | uaacgcgcag | ggcuagcagg | gcuaggacuu | ucccaccag | 1860 |
| cgcaauuucu | uucuuuuuua | gguacaaaaa | aaaaaaaaa | aaaaaauaaa | | 1910 |

<210> SEQ ID NO 4

```
<211> LENGTH: 1179
<212> TYPE: DNA
<213> ORGANISM: Thraustochytrium aureum

<400> SEQUENCE: 4
atggcggcca acatgtgggg ccagaacgct tcggcgagcg tggtcgaggc caaccccgaa      60
gtcgtggcga gtcgcatgat tggcctcgcg acggctctgg ccgtcggcgg cggcatggcg     120
tactacggaa cacgcgtgcc caaggacgac aaggtcctca aaatcgccga catgcccgag     180
ggctacaagg cgcgctccaa ggaagagcag gcggccatcg acaagtacga gcgcgaccaa     240
acgctttccc ttgtcccgtg gctcctcgcg aacacaagct gggtgatggc gacctacatc     300
ctcggcgtaa acgtcctcgc cgccttcgcc gtgccgcacc tgttcgactg caagtggcag     360
acgctcgccg gtatgttggc attctacatg attggcgggt ttggcgtcac aggcggcctg     420
cacaggctgt ggagccacaa gtcgtacaag ggcaacgtgg tgtaccgttt cttggtcatg     480
atctgctcct ccattgcaaa ccagggcaca atctaccact ggagccgcga ccaccgaacg     540
caccacaagt actccgagac gaaggcagac ccgcacaacg cgctgcgcga ttttttcttc     600
gcccacgtag gctggctgct cctgaaaaag gacccgcgcg tcaagtttgc tggaaaccaa     660
attcctatgg atgacctggc cgccatgccc gaggtgcagc tgcaaaagcg ctttgacccg     720
ctctggaacc tggcctggtc tttcgttgcc ccggccatcg ttggcaactt gctctggggc     780
gagaccgtgt acaagggctt tctgctcatg gcgttcttc gctatgtgct ctgcctgaac      840
gggacgtggc tcgtcaacag cgctgcgcac ctgtacggag ccatccgta tgacgagcac      900
attaacccag cggagaactc gatggtgtcc atcctctcga tgggcgaggg ctggcacaac     960
tggcaccacg cgttcccgca cgactatgcc gcttcggagc tcggtgtcag ctcgcagtac    1020
aaccctacca agctcttgat cgacatctgc gcgatcttcg gcttggtctc ggatcgccgc    1080
cgcgcgcacg accactggga ggcccggatg aagaagcggg gtatctccaa ggtcggcctc    1140
gagggccccgc ctctcctgcg cgagcgcacg gtggcgtga                          1179

<210> SEQ ID NO 5
<211> LENGTH: 354
<212> TYPE: PRT
<213> ORGANISM: Thraustochytrium aureum

<400> SEQUENCE: 5
```

Met Ala Tyr Tyr Gly Thr Arg Val Pro Lys Asp Asp Lys Val Leu Lys
1               5                   10                  15

Ile Ala Asp Met Pro Glu Gly Tyr Lys Ala Arg Ser Lys Glu Glu Gln
            20                  25                  30

Ala Ala Ile Asp Lys Tyr Glu Arg Asp Gln Thr Leu Ser Leu Val Pro
        35                  40                  45

Trp Leu Leu Arg Asn Thr Ser Trp Val Met Ala Thr Tyr Ile Leu Gly
    50                  55                  60

Val Asn Val Leu Ala Ala Phe Ala Val Pro His Leu Phe Asp Cys Lys
65                  70                  75                  80

Trp Gln Thr Leu Ala Gly Met Leu Ala Phe Tyr Met Ile Gly Gly Phe
                85                  90                  95

Gly Val Thr Gly Gly Leu His Arg Leu Trp Ser His Lys Ser Tyr Lys
            100                 105                 110

Gly Asn Val Val Tyr Arg Phe Leu Val Met Ile Cys Ser Ser Ile Ala
        115                 120                 125

Asn Gln Gly Thr Ile Tyr His Trp Ser Arg Asp His Arg Thr His His

```
                    130                 135                 140
Lys Tyr Ser Glu Thr Lys Ala Asp Pro His Asn Ala Leu Arg Glu Phe
145                 150                 155                 160

Phe Phe Ala His Val Gly Trp Leu Leu Leu Lys Lys Asp Pro Arg Val
                165                 170                 175

Lys Phe Ala Gly Asn Gln Ile Pro Met Asp Asp Leu Ala Ala Met Pro
                180                 185                 190

Glu Val Gln Leu Gln Lys Arg Phe Asp Pro Leu Trp Asn Leu Ala Trp
                195                 200                 205

Ser Phe Val Ala Pro Ala Ile Val Gly Asn Leu Leu Trp Gly Glu Thr
        210                 215                 220

Val Tyr Lys Gly Phe Leu Leu Met Gly Val Leu Arg Tyr Val Leu Cys
225                 230                 235                 240

Leu Asn Gly Thr Trp Leu Val Asn Ser Ala Ala His Leu Tyr Gly Gly
                245                 250                 255

His Pro Tyr Asp Glu His Ile Asn Pro Ala Glu Asn Ser Met Val Ser
                260                 265                 270

Ile Leu Ser Met Gly Glu Gly Trp His Asn Trp His Ala Phe Pro
        275                 280                 285

His Asp Tyr Ala Ala Ser Glu Leu Gly Val Ser Ser Gln Tyr Asn Pro
        290                 295                 300

Thr Lys Leu Leu Ile Asp Ile Cys Ala Ile Phe Gly Leu Val Ser Asp
305                 310                 315                 320

Arg Arg Arg Ala His Asp His Trp Glu Ala Arg Met Lys Lys Arg Gly
                325                 330                 335

Ile Ser Lys Val Gly Leu Glu Gly Pro Pro Leu Leu Arg Glu Arg Thr
                340                 345                 350

Val Ala

<210> SEQ ID NO 6
<211> LENGTH: 1440
<212> TYPE: RNA
<213> ORGANISM: Thraustochytrium aureum

<400> SEQUENCE: 6
aaccccaauc auucaacuug agacgcguca cgaacaagcc cugcaaccgc cugacuugau      60
uccucgcuga ccagcgcucg cgcacaagga cguagcucgu gcauggcgg ccaacaugug    120
gggccagaac gcuucggcga gcguggucga ggccaacccc gaagucgugg cgagucgcau   180
gauuggccuc gcgacggcuc uggccgucgg cggcggcaug cgcuacuacg aacacgcgu    240
gcccaaggac gacaaggucc ucaaaaucgc cgacaugccc gagggcuaca aggcgcgcuc   300
caaggaagag caggcggcca ucgacaagua cgagcgcgac caaacgcuuu ccuugcccc    360
guggcuccug cgcaacacaa gcuggugau ggcgaccuac auccucggcg uaaacguccu    420
cgccgccuuc gccgcugccg caccuguucg acugcaagug gcagacgcuc gccgguaugu   480
uggcauucua caugauuggc ggguuggcg ucacaggcgg ccugcacagg cuguggagcc    540
acaagucgua caaggcaac guggguacc guuucuuggu caugaucugc uccuccauug    600
caaaccaggg cacaaucuac cacuggagcc gcgaccaccg aacgcaccac aaguacuccg   660
agacgaaggc agacccgcac aacgcgcugc gcgaguuuuu cuucgcccac guaggcuggc   720
ugcuccugaa aaaggacccg cgcgucaagu ugcuggaaaa ccaaauuccu augaugaccc   780
uggccgccau gcccgagguu cagcugcaaa agcgcuuuga cccgcucugg aaccuggccu   840
```

```
ggucuuucgu ugccccggcc aucguuggca acuugcucug gggcgagacc guguacaagg    900
gcuuucugcu caugggcguu cuucgcuaug ugcucugccu gaacgggacg uggcucguca    960
acagcgcugc gcaccuguac ggaggccauc cguaugacga gcacauuaac ccagcggaga   1020
acucgauggu guccauccuc ucgauggggcg agggcuggca caacuggcac acgcguucc   1080 cgcacgacua ugccgcuucg gagcucggug ucagcucgca guacaacccu accaagcucu   1140
ugaucgacau cugcgcgauc uucgcuuggu ucucggaucg ccgccgcgcg cacgaccacu   1200
gggaggcccg gaugaagaag cggggguaucu ccaaggucgg ccucgagggc ccgccucucc   1260
ugcgcgagcg cacgguggcg uaggcgcucg cucgacugcg aaccgcuagg gcgguccccgu   1320 ccgcuguaac uuguagcugc cacaacaccc gagcccucga ggcuccacua guagucaugu   1380
ugauugaugu gaucaucuua aaguuuuuuu aaaaaaaaaa aaaaaaaaaa acaaaaaaaa   1440
```

```
<210> SEQ ID NO 7
<211> LENGTH: 1119
<212> TYPE: DNA
<213> ORGANISM: Thraustochytrium aureum

<400> SEQUENCE: 7
```

```
atggcgccag cggttggcaa ggcggcgagc ggcgcgacgc tcgcgagcag cgccaaagac     60
gtgcccaagg tggagaggaa cgggcacttg ttcaacaagg aggcgcccaa gccaaggcag    120
gacgccaagg agtatgacat cttcaccgga gaccacgggc tcaagcgcca ggaggacctc    180
caggacttta tctggacgct gagcgacgag ccgcacgcga tccggcgcaa gctgatgatg    240
aaggagatgg gcaaggagat ccaaaagctg accgggcccg agtggcgcac cgtgccgatc    300
gtcctggtca tgctggccat ccaaatcggc atcgggtact acctccgcgc ggaggcgggc    360
tcgctcaagt tttgggtctt cgcgtacgtc ttcggggggca cgctggcgca gatcctgttc    420
ctcgccaacc acgagatctc gcacaacctg gcgttccgct cgcaacgcgc caacaagctc    480
ttcgggatcc tgaccaacac gcccatgctg gtgccgtact ttatcgcgtt caaggactac    540
cacaacgagc accacaagtt ccagggcacg gacgggattg acaccgacct gcccaccgag    600
ctggaggcgc gcctcatgtc gtcggtgcct ggcaagctgt tctacatgtt caaccagacc    660
tggttttacg ccctccgccc ggtcttcatc aagccgcagc ccttcaccgc ctggcacgct    720
ctcaacctcg ccgtgcaggt cgcctttatc ggcgccgtgg tgaacgcctg gggcgtgggc    780
cccatctggt actttctggc ctctgcgcac tttgccggct cctggcaccc gctcgcgagc    840
cactttatcg ccgagcacta cacctttgcc ggcgaggccg agacggccag ctactacggc    900
ccgctcaact acttgacctg gaacgtgggc taccacgacc agcaccacga cttttccctac    960 gtgccgtgga ccgcctcccc ggagctgcgc aagatcggcg ccaagtacta cgaccacgtc   1020
ccctaccaca gagctgggt gcgggcgctc tggcacttcc tctggaaccc gcacatcacc   1080
atgtacaacc gcgtcaagcg cgagtccaaa aaggcccaa                          1119
```

```
<210> SEQ ID NO 8
<211> LENGTH: 373
<212> TYPE: PRT
<213> ORGANISM: Thraustochytrium aureum

<400> SEQUENCE: 8
```

```
Met Ala Pro Ala Val Gly Lys Ala Ala Ser Gly Ala Thr Leu Ala Ser
1               5                   10                  15

Ser Ala Lys Asp Val Pro Lys Val Glu Arg Asn Gly His Leu Phe Asn
            20                  25                  30
```

```
Lys Glu Ala Pro Lys Pro Arg Gln Asp Ala Lys Glu Tyr Asp Ile Phe
         35                  40                  45

Thr Gly Asp His Gly Leu Lys Arg Gln Glu Asp Leu Gln Asp Phe Ile
 50                  55                  60

Trp Thr Leu Ser Asp Glu Pro His Ala Ile Arg Arg Lys Leu Met Met
 65                  70                  75                  80

Lys Glu Met Gly Lys Glu Ile Gln Lys Leu Thr Gly Pro Glu Trp Arg
                 85                  90                  95

Thr Val Pro Ile Val Leu Val Met Leu Ala Ile Gln Ile Gly Ile Gly
             100                 105                 110

Tyr Tyr Leu Arg Ala Glu Ala Gly Ser Leu Lys Phe Trp Val Phe Ala
         115                 120                 125

Tyr Val Phe Gly Gly Thr Leu Ala Gln Ile Leu Phe Leu Ala Asn His
 130                 135                 140

Glu Ile Ser His Asn Leu Ala Phe Arg Ser Gln Arg Ala Asn Lys Leu
145                 150                 155                 160

Phe Gly Ile Leu Thr Asn Thr Pro Met Leu Val Pro Tyr Phe Ile Ala
                 165                 170                 175

Phe Lys Asp Tyr His Asn Glu His His Lys Phe Gln Gly Thr Asp Gly
             180                 185                 190

Ile Asp Thr Asp Leu Pro Thr Glu Leu Glu Ala Arg Leu Met Ser Ser
         195                 200                 205

Val Pro Gly Lys Leu Phe Tyr Met Phe Asn Gln Thr Trp Phe Tyr Ala
210                 215                 220

Leu Arg Pro Val Phe Ile Lys Pro Gln Pro Phe Thr Ala Trp His Ala
225                 230                 235                 240

Leu Asn Leu Ala Val Gln Val Ala Phe Ile Gly Ala Val Val Asn Ala
                 245                 250                 255

Trp Gly Val Gly Pro Ile Trp Tyr Phe Leu Ala Ser Ala His Phe Ala
             260                 265                 270

Gly Ser Trp His Pro Leu Ala Ser His Phe Ile Ala Glu His Tyr Thr
         275                 280                 285

Phe Ala Gly Glu Ala Glu Thr Ala Ser Tyr Tyr Gly Pro Leu Asn Tyr
 290                 295                 300

Leu Thr Trp Asn Val Gly Tyr His Asp Gln His His Asp Phe Pro Tyr
305                 310                 315                 320

Val Pro Trp Ser Arg Leu Pro Glu Leu Arg Lys Ile Gly Ala Lys Tyr
                 325                 330                 335

Tyr Asp His Val Pro Tyr His Lys Ser Trp Val Arg Ala Leu Trp His
             340                 345                 350

Phe Leu Trp Asn Pro His Ile Thr Met Tyr Asn Arg Val Lys Arg Glu
         355                 360                 365

Ser Lys Lys Ala Gln
    370

<210> SEQ ID NO 9
<211> LENGTH: 1184
<212> TYPE: RNA
<213> ORGANISM: Thraustochytrium aureum

<400> SEQUENCE: 9
agggauggcg ccagcgguug gcaaggcggc gagcggcgcg acgcucgcga gcagcgccaa    60
agacgugccc aagguggaga ggaacgggca cuuguucaac aaggaggcgc ccaagccaag   120
```

```
gcaggacgcc aaggaguaug acaucuucac cggagaccac gggcucaagc gccaggagga      180
ccuccaggac uuuaucugga cgcugagcga cgagccgcac gcgauccggc gcaagcugau      240
gaugaaggag augggcaagg agauccaaaa gcugaccggg cccgagugga gcaccgugcc      300
gaucguccug gucaugcugg ccauccaaau cggcaucggg uacuaccucc gcgcggaggc      360
gggcucgcuc aaguuuggg ucuucgcgua cgucuucggg ggcacgcugg cgcagauccu       420
guuccucgcc aaccacgaga ucucgcacaa ccuggcguuc cgcucgcaac gcgccaacaa      480
gcucuucggg auccugacca acacgcccau gcuggugccg uacuuuaucg cguucaagga      540
cuaccacaac gagcaccaca aguuccaggg cacggacggg auugacaccg accugcccac      600
cgagcuggag gcgcgcccuca ugucgucggu gccuggcaag cuguucuaca guucaaccaa    660
gaccugguuu uacgccccucc gcccggucuu caucaagccg cagcccuuca ccgccuggca    720
cgcucucaac cucgccgugc aggucgccuu uauccggcgcc guggugaacg ccuggggcgu    780
gggccccauc ugguacuuuc uggccucugc gcacuuugcc ggcuccuggc acccgcucgc     840
gagccacuuu aucgccgagc acuacaccuu ugccggcgag gccgagacgg ccagcuacua    900
cggcccgcuc aacuacuuga ccuggaacgu gggcuaccac gaccagcacc acgacuuucc    960
cuacgugccg uggagccgcc ucccggagcu gcgcaagauc ggcgccaagu acuacgacca   1020
cguccccuac cacaagagcu ggugcgggc gcucuggcac uuccucugga acccgcacau    1080
caccauguac aaccgcguca agcgcgaguc caaaaaggcc caauaaagaa gaccaacguc   1140
acaacagagu acaaaguaa aaaaaaaaaa aaaaaaaaaa aaaa                     1184

<210> SEQ ID NO 10
<211> LENGTH: 1569
<212> TYPE: DNA
<213> ORGANISM: Thraustochytrium aureum

<400> SEQUENCE: 10
atggcgcccc caaaggtctt ctcgcgcgca gaggtggcca agcacaacac cgaggaagac       60
tgctggatcg tgatcgaggg acgcgtctac gatgtgacca gttttgctgg catgcaccct     120
ggcggcgagg agatcttgct gtcgatcggc ggcaccgacg caaccgagga cttttacggc     180
ctgcacagac agagcgtgct cgacaagttt ggccccaagc tcatggtagg cgtgaccgag     240
gacgccgaca tggaggaggt ctccaagccc acgaacgggc tgaccaagtg gcggagatc      300 tcaaaggtgc cgtacgccga cgtttgcc tggcgcggct tcaagacgcc attccacgac       360
gagtctcacg tgcgcttccg caagtacatt cgcgagtttt atgaccgcga gttgcgccag     420
ctcgcgatcg agtgcgagga ctccaacgag cccgccacgc tcgagatcat gcaaaagatt    480
agccaagccg cctcctgca cacccgcctt ggccctgggc gcacctcaa gctgctgccg       540 atgccctgcg ggatcaagcc ggaagagttc acttacacgc acgagaagat tttgcaggag   600
gagacggcac gcctccaatg cccggtttc ctcgactcgc tgttcgcggg gttcaacatc      660
agcgccccgc cgctcgtcaa ctacggcacg gacaagatgc gcaaagaggt gctcccccgag  720 attctggccg gccgtaagcg ttcctgcctg ccatcacgg aagcttttgc tggctccgac     780
gtggccggcc tccgcaccac agccaagctc accccccgacg caagcacta cattgtcaac    840 ggtaccaaga agtggattac caacgccacc tttgccgact acttcgtcac ggccgtgcgc    900
acaggggggc ccggcgcggg cggcatttcg atgatgctca ttcccaaggg ggagggtgtc    960
cgcgtcaagc tgatcaagac ggcctacagc agcgcagcag gcacgggta cgtcatgttt   1020 gagaacgtca aggtccccgc cgagaacctc atgggcgcag agaacaaggg ctttggcctc   1080
```

-continued

```
gtcatgagca acttcaacca cgagcgctat gtgatcgccg ttgctgtcat cgcgggctgc    1140
cgcctcgctg tcgaggagtg cttcaagtgg gccatgcagc gcaaggtgtt tggcaagccg    1200
ctcatgagcc aagctgtcat tcgcgaaaag ctcggccgca tggtggccgc cgtcgaggcc    1260
gccgacgcgt acgccgatct catcacgcac cagatgaaca acatggacta caaggagcaa    1320
aacatgaaac tcggcggccc catttcgctt ctcaagtacc aggcgacgcg caccgcgcac    1380
ctcgtcgcgg acgatgcggt gcagatcttc ggaggccgcg cgtcacgaa cggcgccatg     1440 ggccgcgtgg tgcgcaactt tgccaagagc tacaagctcc ccagcgttta cggggctcc    1500 gaggagatca tggtggacct cggcgttcgt caagccctcc gcttttaccc gcgcgacgcc    1560
aagctctga                                                           1569
```

<210> SEQ ID NO 11
<211> LENGTH: 522
<212> TYPE: PRT
<213> ORGANISM: Thraustochytrium aureum

<400> SEQUENCE: 11

```
Met Ala Pro Pro Lys Val Phe Ser Arg Ala Glu Val Ala Lys His Asn
1               5                   10                  15

Thr Glu Glu Asp Cys Trp Ile Val Ile Glu Gly Arg Val Tyr Asp Val
            20                  25                  30

Thr Ser Phe Ala Gly Met His Pro Gly Gly Glu Ile Leu Leu Ser
        35                  40                  45

Ile Gly Gly Thr Asp Ala Thr Glu Asp Phe Tyr Gly Leu His Arg Gln
    50                  55                  60

Ser Val Leu Asp Lys Phe Gly Pro Lys Leu Met Val Gly Val Thr Glu
65                  70                  75                  80

Asp Ala Asp Met Glu Glu Val Ser Lys Pro Thr Asn Gly Leu Thr Lys
                85                  90                  95

Trp Ala Glu Ile Ser Lys Val Pro Tyr Ala Glu Thr Phe Ala Trp Arg
            100                 105                 110

Gly Phe Lys Thr Pro Phe His Asp Glu Ser His Val Arg Phe Arg Lys
        115                 120                 125

Tyr Ile Arg Glu Phe Tyr Asp Arg Glu Leu Arg Gln Leu Ala Ile Glu
    130                 135                 140

Cys Glu Asp Ser Asn Glu Pro Ala Thr Leu Glu Ile Met Gln Lys Ile
145                 150                 155                 160

Ser Gln Ala Gly Leu Leu His Thr Arg Leu Gly Pro Gly Pro His Leu
                165                 170                 175

Lys Leu Leu Pro Met Pro Cys Gly Ile Lys Pro Glu Glu Phe Thr Tyr
            180                 185                 190

Thr His Glu Lys Ile Leu Gln Glu Glu Thr Ala Arg Leu Gln Cys Pro
        195                 200                 205

Gly Phe Leu Asp Ser Leu Phe Ala Gly Phe Asn Ile Ser Ala Pro Pro
    210                 215                 220

Leu Val Asn Tyr Gly Thr Asp Lys Met Arg Lys Glu Val Leu Pro Glu
225                 230                 235                 240

Ile Leu Ala Gly Arg Lys Arg Ser Cys Leu Ala Ile Thr Glu Ala Phe
                245                 250                 255

Ala Gly Ser Asp Val Ala Gly Leu Arg Thr Thr Ala Lys Leu Thr Pro
            260                 265                 270

Asp Gly Lys His Tyr Ile Val Asn Gly Thr Lys Lys Trp Ile Thr Asn
```

```
                  275                 280                 285
Ala Thr Phe Ala Asp Tyr Phe Val Thr Ala Val Arg Thr Gly Gly Pro
    290                 295                 300
Gly Ala Gly Gly Ile Ser Met Met Leu Ile Pro Lys Gly Glu Gly Val
305                 310                 315                 320
Arg Val Lys Leu Ile Lys Thr Ala Tyr Ser Ala Ala Gly Thr Gly
                325                 330                 335
Tyr Val Met Phe Glu Asn Val Lys Val Pro Ala Glu Asn Leu Met Gly
            340                 345                 350
Ala Glu Asn Lys Gly Phe Gly Leu Val Met Ser Asn Phe Asn His Glu
        355                 360                 365
Arg Tyr Val Ile Ala Val Ala Val Ile Ala Gly Cys Arg Leu Ala Val
    370                 375                 380
Glu Glu Cys Phe Lys Trp Ala Met Gln Arg Lys Val Phe Gly Lys Pro
385                 390                 395                 400
Leu Met Ser Gln Ala Val Ile Arg Glu Lys Leu Gly Arg Met Val Ala
                405                 410                 415
Ala Val Glu Ala Ala Asp Ala Tyr Ala Asp Leu Ile Thr His Gln Met
            420                 425                 430
Asn Asn Met Asp Tyr Lys Glu Gln Asn Met Lys Leu Gly Gly Pro Ile
        435                 440                 445
Ser Leu Leu Lys Tyr Gln Ala Thr Arg Thr Ala His Leu Val Ala Asp
    450                 455                 460
Asp Ala Val Gln Ile Phe Gly Arg Gly Val Thr Asn Gly Ala Met
465                 470                 475                 480
Gly Arg Val Val Arg Asn Phe Ala Lys Ser Tyr Lys Leu Pro Ser Val
                485                 490                 495
Tyr Gly Gly Ser Glu Glu Ile Met Val Asp Leu Gly Val Arg Gln Ala
            500                 505                 510
Leu Arg Phe Tyr Pro Arg Asp Ala Lys Leu
        515                 520

<210> SEQ ID NO 12
<211> LENGTH: 1845
<212> TYPE: RNA
<213> ORGANISM: Thraustochytrium aureum

<400> SEQUENCE: 12 gcuaucccu gaacgaccaa cgaagcgcag gccgcgagcu acacgaggca cuuacggcug    60
cagaggcguc gagagccgag gcacacccgc gucgcgcaca ggcaagcacu gccugaaucg   120
cccgccacau ggcgccccca aaggucuucu cgcgcgcaga ggugccaag cacaacaccg   180 aggaagacug cuggaucgug aucgagggac gcgucuacga ugugaccagu uuugcuggca   240
ugcacccugg cggcgaggag aucuugcugu cgaucggcgg caccgacgca accgaggacu   300
uuuacggccu gcacagacag agcgugcucg acaaguuugg ccccaagcuc augguaggcg   360
ugaccgagga cgccgacaug gaggaggucu ccaagcccac gaacgggcug accaaguggg   420
cggagaucuc aaaggugccg uacgccgaga cguuugccug gcgcggcuuc aagacgccau   480
uccacgacga gucucacgug cgcuuccgca aguacauucg cgaguuuuau gaccgcgagu   540
ugcgccagcu cgcgaucgag ugcgaggacu ccaacgagcc cgccacgcuc gagaucaugc   600
aaaagauuag ccaagccggc cuccugcaca cccgccuugg cccugggccg caccucaagc   660
ugcugccgau gcccugcggg aucaagccgg aagaguucac uuacacgcac gagaagauuu   720
```

```
ugcaggagga cacggcacgc cuccaaugcc ccgguuuccu cgacucgcug uucgcggggu      780
ucaacaucag cgccccgccg cucgucaacu acggcacgga caagaugcgc aaagaggugc      840
uccccgagau ucuggccggc cguaagcguu ccugccuggc caucacggaa gcuuuugcug      900
gcuccgacgu ggccggccuc cgcaccacag ccaagcucac ccccgacggc aagcacuaca      960
uugucaacgg uaccaagaag uggauuacca acgccaccuu ugccgacuac uucgucacgg     1020
ccgugcgcac agggggggccc ggcgcgggcg gcauuucgau gaugcucauu cccaagggggg    1080 agggguuccg cgucaagcug aucaagacgg ccuacagcag cgcagcaggc acggggguacg    1140 ucauguuuga aacgucaag guccccgccg agaaccucau gggcgcagag aacaagggcu      1200
uuggccucgu caugagcaac uucaaccacg agcgcuaugu gaucgccguu gcugucaucg     1260
cgggcugccg ccucgcuguc gaggagugcu ucaaguggggc caugcagcgc aagguguuug    1320
gcaagccgcu caugagccaa gcugucauuc gcgaaaagcu cggccgcaug uggccgccg      1380 ucgaggccgc cgacgcguac gccgaucuca ucacgcacca gaugaacaac auggacuaca    1440
aggagcaaaa caugaaacuc ggcggccccca uuucgcuucu caaguaccag gcgacgcgca   1500
ccgcgcaccu cgucgcggac gaugcggugc agaucuucgg aggccgcggc gucacgaacg     1560
gcgccauggg ccgcguggug cgcaacuuug ccaagagcua caagcucccc agcguuuacg    1620 gggggcuccga ggagaucaug guggaccucg cguucgguca agcccuccgc uuuuacccgc   1680
gcgacgccaa gcucuagcua ggcugcgccg cucucgccu cccuccguccg cucgcacaac    1740 aaguagacgc caaccaguuu cggccgcgcc ucaaauaucg ucuaaagguca uuuauugcuu   1800 acccggaaaa aaaaaaaaa aaaaaaaaaa aaaaauaaa aaaaa                       1845
```

<210> SEQ ID NO 13
<211> LENGTH: 1185
<212> TYPE: DNA
<213> ORGANISM: Thraustochytrium aureum

<400> SEQUENCE: 13

```
atgtgcaagg tcgatgggac aaaccgggcg agctcggctc aagcccaggc agagcaggaa      60
aagctgccaa ccatcggcga gctgcgcaag gctgtgcccg cgcactgttt cgaaaagtcg     120
acgttgaaga gcctgttctt cgtggctcgt gacctggcgt tttgcagcgc catcgggtac    180
gcggcctggg agtacatccc cgtcgagtgg tcaatcaagg ccatcgccct gtggaccctg    240
tacgccatag tgcagggcac cgtggcgacc ggggtctggg ttctgggcca cgaaggcgga    300
cacggaggaa tctcgagcta ctctattgtc aacgatactg tcgggtacgt gctgcactcg    360
atcctgctcg tgccgtactt ttcctggcag acaagccac aggcgccacc acgcgcggtg    420
caacaacctc ctggacgggg agtcgcaaac ccggacctca agcgcaaggt ttacaagatg    480
tacgaaaaga tcctcgacac ggtgggcgag gaagcctttg tgatcatgca gatcgtcctt    540
caccttgtct tagggtggcc catgtacctg ctgatgcacg cgaccgggtc tcgccgcagc    600
cccgtgactg gcaaaagta caccaaaaag cccaatcact tcaactgggg tgcgagcaac    660
gagcagtacc cggccaagtt gcgcttcaag atttttctgt cctcgcttgg cgtgatcgcg    720
acgctcgcag ggatcgccgt gctggccaac aagctcggcg ccgccaaggt ctcgctcatg    780
tactttggcc cctacctcgt ggtgaatgcc tggctcgtgg atacacctg gctccagcac    840 accgaccagg acgccccgca ctatggcgag gacgagtgga cctggatcaa gggcgccatg    900
acgacgatcg accgccccta ccctggatt gtggacgagc tccaccacca catcggcacg    960
acgcacgttt gccaccacct gttttccgac atgccgcact acaaggccca ggaagccacc   1020
```

```
gaggcgctca agccggtgct cggcaagcac taccgcttcg acccgacccc gctggcgcag    1080
gccatgtgga acaccgctcg cgactgccac tacgtcgagg cctcgacgg agtgcagtac    1140 ccgcagtcaa tcatcgccga aagcgtgcg gccaaaaagc tctga                    1185
```

<210> SEQ ID NO 14
<211> LENGTH: 394
<212> TYPE: PRT
<213> ORGANISM: Thraustochytrium aureum

<400> SEQUENCE: 14

Met Cys Lys Val Asp Gly Thr Asn Arg Ala Ser Ser Ala Gln Ala Gln
1               5                   10                  15

Ala Glu Gln Glu Lys Leu Pro Thr Ile Gly Glu Leu Arg Lys Ala Val
            20                  25                  30

Pro Ala His Cys Phe Glu Lys Ser Thr Leu Lys Ser Leu Phe Phe Val
        35                  40                  45

Ala Arg Asp Leu Ala Phe Cys Ser Ala Ile Gly Tyr Ala Ala Trp Glu
    50                  55                  60

Tyr Ile Pro Val Glu Trp Ser Ile Lys Ala Ile Ala Leu Trp Thr Leu
65                  70                  75                  80

Tyr Ala Ile Val Gln Gly Thr Val Ala Thr Gly Val Trp Val Leu Gly
                85                  90                  95

His Glu Gly Gly His Gly Ile Ser Ser Tyr Ser Ile Val Asn Asp
            100                 105                 110

Thr Val Gly Tyr Val Leu His Ser Ile Leu Leu Val Pro Tyr Phe Ser
        115                 120                 125

Trp Gln Asp Lys Pro Gln Ala Pro Pro Arg Ala Val Gln Gln Pro Pro
    130                 135                 140

Gly Arg Gly Val Ala Asn Pro Asp Leu Lys Arg Lys Val Tyr Lys Met
145                 150                 155                 160

Tyr Glu Lys Ile Leu Asp Thr Val Gly Glu Ala Phe Val Ile Met
                165                 170                 175

Gln Ile Val Leu His Leu Val Leu Gly Trp Pro Met Tyr Leu Leu Met
            180                 185                 190

His Ala Thr Gly Ser Arg Arg Ser Pro Val Thr Gly Gln Lys Tyr Thr
        195                 200                 205

Lys Lys Pro Asn His Phe Asn Trp Gly Ala Ser Asn Glu Gln Tyr Pro
    210                 215                 220

Ala Lys Leu Arg Phe Lys Ile Phe Leu Ser Ser Leu Gly Val Ile Ala
225                 230                 235                 240

Thr Leu Ala Gly Ile Ala Val Leu Ala Asn Lys Leu Gly Ala Ala Lys
                245                 250                 255

Val Ser Leu Met Tyr Phe Gly Pro Tyr Leu Val Val Asn Ala Trp Leu
            260                 265                 270

Val Gly Tyr Thr Trp Leu Gln His Thr Asp Gln Asp Ala Pro His Tyr
        275                 280                 285

Gly Glu Asp Glu Trp Thr Trp Ile Lys Gly Ala Met Thr Thr Ile Asp
    290                 295                 300

Arg Pro Tyr Pro Trp Ile Val Asp Glu Leu His His Ile Gly Thr
305                 310                 315                 320

Thr His Val Cys His His Leu Phe Ser Asp Met Pro His Tyr Lys Ala
                325                 330                 335

Gln Glu Ala Thr Glu Ala Leu Lys Pro Val Leu Gly Lys His Tyr Arg

```
                340                 345                 350
    Phe Asp Pro Thr Pro Leu Ala Gln Ala Met Trp Asn Thr Ala Arg Asp
            355                 360                 365

Cys His Tyr Val Glu Gly Leu Asp Gly Val Gln Tyr Pro Gln Ser Ile
        370                 375                 380

Ile Ala Glu Lys Arg Ala Ala Lys Lys Leu
    385                 390

<210> SEQ ID NO 15
<211> LENGTH: 1463
<212> TYPE: RNA
<213> ORGANISM: Thraustochytrium aureum

<400> SEQUENCE: 15
aaccccaauc gacaccacga ccgcgcaacg agcgcgccgc aggcagcaga cucgaguccg        60
aaagggcuca gauugaaaag gagcacaaga ugugcaaggu cgaugggaca aaccgggcga       120
gcucggcuca agcccaggca gagcaggaaa agcugccaac caucggcgag cugcgcaagg       180
cugugcccgc gcacuguuuc gaaaagucga cguugaagag ccuguucuuc guggcucgug       240
accuggcguu uugcagcgcc aucggguacg cggccuggga guacaucccc gucgaguggu       300
caaucaaggc caucgcccug uggacccugu acgccauagu gcagggcacc guggcgaccg       360
gggucugggu ucugggccac gaaggcggac acggaggaau ucgagcuac ucuauuguca       420 acgauacugu cggguacgug cugcacucga uccugcucgu gccguacuuu uccuggcagg       480
acaagccaca ggcgccacca cgcgcggugc aacaaccucc uggacgggga gucgcaaacc       540
cggaccucaa gcgcaagguu uacaagaugu acgaaaagau ccucgacacg gugggcgagg       600
aagccuuugu gaucaugcag aucguccuuc accugucuu aggugggccc auguaccugc       660
ugaugcacgc gaccggggucu cgccgcagcc ccgugacugg gcaaaaguac accaaaaagc       720
ccaaucacuu caacuggggu gcgagcaacg agcaguaccc ggccaaguug cgcuucaaga       780
uuuuucuguc cucgcuuggc gugaucgcga cgcucgcagg gaucgccgug cuggccaaca       840
agcucggcgc cgccaagguc ucgcucaugu acuuuggccc cuaccucgug gugaaugccu       900 ggcucgugg auacaccugg cuccagcaca ccgaccagga cgccccgcac uauggcgagg       960 acgagugga cuggaucaag ggcgccauga cgacgaucga ccgccccuac cccuggauug      1020
uggacgagcu ccaccaccac aucggcacga cgcacguuug ccaccaccug uuuuccgaca      1080
ugccgcacua caaggcccag gaagccaccg aggcgcucaa gccggugcuc ggcaagcacu      1140
accgcuucga cccgaccccg cuggcgcagg ccauguggaa caccgcucgc gacugccacu      1200
acgucgaggg ccucgacgga gugcaguacc cgcagucaau caucgccgag aagcgugcgg      1260
ccaaaaagcu cuagagcucu ggcucaaggg acaccgugcc gaaggcugcg auguuuguga      1320
guuagcgggg uccugcgcug cggugcgccg gggcggggcg ggcauuucca ccucggccuc      1380
gucgcauucc aauuugcugg accucaaccu gaacguuuug ucaaucaaga uacaaaaaaa      1440
acccaucauc auuauuugac uaa                                            1463

<210> SEQ ID NO 16
<211> LENGTH: 951
<212> TYPE: DNA
<213> ORGANISM: Thraustochytrium aureum

<400> SEQUENCE: 16
atggcgacgc gcacctcgaa gagcgctccg gcggttttcca agtcggccaa ggttgccgcg        60
```

-continued

```
ccggcgaaga agcggtcggt cgacaggagc gacggtttct tccgcacgtt caacctgtgc      120
gccctgtacg ggtctgccct cgcctatgcg tacaagcacg gccaggtgga caatgacggc      180
cagggggctgt actttcacaa gtcgcccatg tacgcgttcg ccgtgtcgga cgtcatgacc    240
ttcggcgcgc cgctgatgta cgtgctcggt gtgatgctgc tcagcaggta catggcggac     300
aaaaagcccc tgactggctt catcaagacc tacatccagc ccgtctacaa cgtggtccaa     360
atcgcggtgt gcggctggat ggtgtgggc ctctggccgc aggtcgacct ggccaacggc       420
aacccttttcg gcctcaacaa gtcgcgcgac tcgaacatcg agttttttcgt gttcgtgcac   480
ctcctgacaa gtttctcga ctggagcgac acgttcatga tgatcctcaa gaaaaactac      540
gcccaggtta gctttctgca ggtgttccac cacgcaacga tcggcatggt gtggtcgttc     600
cttcttcagc gtggctgggg ctcgggcacc gccgcgtacg gtgctttcat caactcggtc    660
acgcacgtga tcatgtactc gcactacttt gccacctcgc tcaacatcaa caacccgttc     720
aagcggtaca tcacgagctt ccagctcgcc cagtttgcaa gctgcatcgt gcatgcccta     780
ctggtgcttg ccttcgagga ggtgtacccg ctcgagtacg cttacctgca gatcagctac    840
cacatcatca tgctctacct gttcggacgc cgcatgaact ggagccccga gtggtgcacc    900
ggtgagatcg acggcttga cgcccccaag cgccccccacca agtccgagtg a             951
```

<210> SEQ ID NO 17
<211> LENGTH: 316
<212> TYPE: PRT
<213> ORGANISM: Thraustochytrium aureum

<400> SEQUENCE: 17

```
Met Ala Thr Arg Thr Ser Lys Ser Ala Pro Ala Val Ser Lys Ser Ala
1               5                   10                  15

Lys Val Ala Ala Pro Ala Lys Lys Arg Ser Val Asp Arg Ser Asp Gly
            20                  25                  30

Phe Phe Arg Thr Phe Asn Leu Cys Ala Leu Tyr Gly Ser Ala Leu Ala
        35                  40                  45

Tyr Ala Tyr Lys His Gly Gln Val Asp Asn Asp Gly Gln Gly Leu Tyr
    50                  55                  60

Phe His Lys Ser Pro Met Tyr Ala Phe Ala Val Ser Asp Val Met Thr
65                  70                  75                  80

Phe Gly Ala Pro Leu Met Tyr Val Leu Gly Val Met Leu Leu Ser Arg
                85                  90                  95

Tyr Met Ala Asp Lys Lys Pro Leu Thr Gly Phe Ile Lys Thr Tyr Ile
            100                 105                 110

Gln Pro Val Tyr Asn Val Val Gln Ile Ala Val Cys Gly Trp Met Val
        115                 120                 125

Trp Gly Leu Trp Pro Gln Val Asp Leu Ala Asn Gly Asn Pro Phe Gly
    130                 135                 140

Leu Asn Lys Ser Arg Asp Ser Asn Ile Glu Phe Val Phe Val His
145                 150                 155                 160

Leu Leu Thr Lys Phe Leu Asp Trp Ser Asp Thr Phe Met Met Ile Leu
                165                 170                 175

Lys Lys Asn Tyr Ala Gln Val Ser Phe Leu Gln Val Phe His His Ala
            180                 185                 190

Thr Ile Gly Met Val Trp Ser Phe Leu Leu Gln Arg Gly Trp Gly Ser
        195                 200                 205

Gly Thr Ala Ala Tyr Gly Ala Phe Ile Asn Ser Val Thr His Val Ile
    210                 215                 220
```

```
Met Tyr Ser His Tyr Phe Ala Thr Ser Leu Asn Ile Asn Asn Pro Phe
225                 230                 235                 240

Lys Arg Tyr Ile Thr Ser Phe Gln Leu Ala Gln Phe Ala Ser Cys Ile
                245                 250                 255

Val His Ala Leu Leu Val Leu Ala Phe Glu Glu Val Tyr Pro Leu Glu
            260                 265                 270

Tyr Ala Tyr Leu Gln Ile Ser Tyr His Ile Ile Met Leu Tyr Leu Phe
        275                 280                 285

Gly Arg Arg Met Asn Trp Ser Pro Glu Trp Cys Thr Gly Glu Ile Asp
    290                 295                 300

Gly Leu Asp Ala Pro Ser Ala Pro Thr Lys Ser Glu
305                 310                 315

<210> SEQ ID NO 18
<211> LENGTH: 1253
<212> TYPE: RNA
<213> ORGANISM: Thraustochytrium aureum

<400> SEQUENCE: 18
gcucaaaccc cgaacguguu ucucccagga cgugccgcug ucgcucgcug auccacccga      60
agcgcggucg gcuggcacgg ucgcucggcu ggaaguugag uaguuugcuu ucuguugcug     120 cgcugccuuug uaaacgcgac cauggcgacg cgcaccucga agagcgcucc ggcguuucc     180 aagucggcca agguugccgc gccggcgaag aagcggucgg ucgacaggag cgacgguuuc     240
uuccgcacgu ucaaccugug cgcccuguac gggucugccc ucgccuaugc guacaagcac     300
ggccaggugg acaaugacgg ccaggggcug uacuuucaca agcgcccau guacgcguuc     360 gccgucgg acgucaugac cuucggcgcg ccgcugaugu acgugcucgg ugugaugcug     420
cucagcaggu acauggcgga caaaaagccc cugacuggcu ucaucaagac cuacauccag     480
cccgucuaca acguggucca aaucgcggug ugcggcugga ugugugggg ccucuggccg     540 caggucgacc uggccaacgg caacccuuuc ggccucaaca agcgcgcga cucgaacauc     600 gaguuuuucg uguucgugca ccuccugaca aaguuucucg acuggagcga cacguucaug     660
augauccuca agaaaaacua cgcccagguu agcuuucugc agguguucca ccacgcaacg     720
aucggcaugg uguggucguu ccuucuucag cguggcuggg gcucgggcac cgccgcguac     780
ggugcuuuca ucaacucggu cacgcacgug aucauguacu cgcacuacuu ugccaccucg     840
cucaacauca caaacccguu caagcgguac aucacgagcu uccagcucgc ccaguuugca     900
agcugcaucu gcaugcccu acuggugcuu gccuucgagg agguguaccc gcucgaguac     960
gcuuaccugc agaucagcua ccacaucauc augcucuacc uguucggacg ccgcaugaac    1020
uggagccccg agguggucac cggugagauc gacggccuug acgccccaag cgccccccac    1080
aaguccgagu aaaccuguuu ccggcuggcu cccgagccau gcuuaccaug aaugaaccug    1140
caaacagucu gagguccuug ugcaaaccgc ucagugggac gucgacgaag aaagaaacaa    1200
uguguacucg uacuuaagaa aaaaaaaaaa aaaaaaaaa aaaaaaaaa aaa             1253

<210> SEQ ID NO 19
<211> LENGTH: 912
<212> TYPE: DNA
<213> ORGANISM: Thraustochytrium aureum

<400> SEQUENCE: 19
atggccgcgg ccttcatgga cttgctgccg gtctttgagt gggagcgtat ggacctggac       60
```

```
gcaatcttgg ccgtctcaga cttcctcgcc ggaaacatgc acatcccctt catcctctcg      120
ggcatctacg tcgtggtcgt gtttgggatc cagtacctcc tcgaggacag caagccattc      180
gacctaaagc tcccctggc tctgtggagc ctcggcctgg ccctcttcag cgtgttcggc       240
tcgctccgaa ccgtgccgac gctcgccaaa ctggggtgga accgcggcct cttgcacgtg      300
gtgtgcggcg acacgcggta tgattggctc gtactcgagc cggcggggc ctggacagtg       360 ctcttcatct tctccaaagc gcccgagcta atcgacacac tgttcatcgt tctgcgcaag      420
cgcaaactca tcacgctcca ctggtaccac cacatcacgg tgcttctctt ctgctggcac     480
tcgttggcca cgctctgcat gaacggactc atcttctcgt ccatgaacct caccgtacac     540
gccttcatgt actttttcta cacgctggcc gcgctcgggt accggcccac tgccttcgcg     600
gtctacatca cgctgctgca gatcctgcag atgctcgtcg ggactgcggt tacggtctac     660
gtcaacttgc agcaagttgc cgccaaagcg gaggacccgt cggcgctcga ggcggcgtcc     720
aaggactggc tcaacgtcac gtgggacaag tttagctcgc gggagaaccc ggagaccatc     780
tcgacttgcg agaccgtgca ccctgcaagt gcgttcgcgg gcctcgccat gtacgcgagc     840
tacctgtggc tcttcagcgc gttcttctac tacgcctaca tggcgccgcg gcccaaggcc     900
aaggtggagt ga                                                          912
```

<210> SEQ ID NO 20
<211> LENGTH: 303
<212> TYPE: PRT
<213> ORGANISM: Thraustochytrium aureum

<400> SEQUENCE: 20

```
Met Ala Ala Ala Phe Met Asp Leu Leu Pro Val Phe Glu Trp Glu Arg
1               5                   10                  15

Met Asp Leu Asp Ala Ile Leu Ala Val Ser Asp Phe Leu Ala Gly Asn
            20                  25                  30

Met His Ile Pro Phe Ile Leu Ser Gly Ile Tyr Val Val Val Phe
        35                  40                  45

Gly Ile Gln Tyr Leu Leu Glu Asp Ser Lys Pro Phe Asp Leu Lys Leu
    50                  55                  60

Pro Leu Ala Leu Trp Ser Leu Gly Leu Ala Leu Phe Ser Val Phe Gly
65                  70                  75                  80

Ser Leu Arg Thr Val Pro Thr Leu Ala Lys Leu Gly Trp Asn Arg Gly
                85                  90                  95

Leu Leu His Val Val Cys Gly Asp Thr Arg Tyr Asp Trp Leu Val Leu
            100                 105                 110

Glu Pro Ala Gly Ala Trp Thr Val Leu Phe Ile Phe Ser Lys Ala Pro
        115                 120                 125

Glu Leu Ile Asp Thr Leu Phe Ile Val Leu Arg Lys Arg Lys Leu Ile
    130                 135                 140

Thr Leu His Trp Tyr His His Ile Thr Val Leu Leu Phe Cys Trp His
145                 150                 155                 160

Ser Leu Ala Thr Leu Cys Met Asn Gly Leu Ile Phe Ser Ser Met Asn
                165                 170                 175

Leu Thr Val His Ala Phe Met Tyr Phe Phe Tyr Thr Leu Ala Ala Leu
            180                 185                 190

Gly Tyr Arg Pro Thr Ala Phe Ala Val Tyr Ile Thr Leu Leu Gln Ile
        195                 200                 205

Leu Gln Met Leu Val Gly Thr Ala Val Thr Val Tyr Val Asn Leu Gln
    210                 215                 220
```

Gln Val Ala Ala Lys Ala Glu Asp Pro Ser Ala Leu Glu Ala Ser
225                 230                 235                 240

Lys Asp Trp Leu Asn Val Thr Trp Asp Lys Phe Ser Ser Arg Glu Asn
            245                 250                 255

Pro Glu Thr Ile Ser Thr Cys Glu Thr Val His Pro Ala Ser Ala Phe
        260                 265                 270

Ala Gly Leu Ala Met Tyr Ala Ser Tyr Leu Trp Leu Phe Ser Ala Phe
    275                 280                 285

Phe Tyr Tyr Ala Tyr Met Ala Pro Arg Pro Lys Ala Lys Val Glu
290                 295                 300

<210> SEQ ID NO 21
<211> LENGTH: 1189
<212> TYPE: RNA
<213> ORGANISM: Thraustochytrium aureum

<400> SEQUENCE: 21
aaugggcggc cgccuguaaa ccgcguucug ccucacguac gcggcgcuca uggccgcggc        60
cuucauggac uugcugccgg ucuuugagug ggagcguaug gaccuggacg caaucuuggc       120
cgucucagac uuccucgccg aaacaugca caucccuuc auccucucgg gcaucuacgu         180
cguggucgug uuugggaucc aguaccuccu cgaggacagc aagccauucg accuaaagcu       240
cccccuggcu cuguggagcc ucggccuggc ccucuucagc guguucggcu cgcuccgaac       300
cgugccgacg cucgccaaac uggggguggaa ccgcggccuc uugcacgugg ugugcggcga     360
cacgcgguau gauuggcucg uacucgagcc ggcgggggcc uggacaguge ucuucaucuu      420 cuccaaagcg cccgagcuaa ucgacacacu guucaucguu cugcgcaagc gcaaacucau     480
cacgcuccac ugguaccacc acaucacggu gcuucucuuc ugcuggcacu cguuggccac    540
gcucugcaug aacggacuca ucuucucguc caugaaccuc accguacacg ccuucaugua    600
cuuuuucuac acgcuggccg cgcucgggua ccggcccacu gccuucgcgg cuacaucac     660 gcugcugcag auccugcaga ugcucgucgg gacugcgguu acggucuacg ucaacuugca    720
gcaaguugcc gccaaagcgg aggacccguc ggcgcucgag gcggcgucca aggacuggcu    780
caacgucacg ugggacaagu uuagcucgcg ggagaacccg agaccaucu cgacuugcga     840 gaccgugcac ccugcaagug cguucgcggg ccucgcaug uacgcgagcu accguggcu      900 cuucagcgcg uucuucuacu acgccuacau ggcgccgcgg cccaaggcca agguggagua    960
agccugcgcu gcgcugccug gcagcugggc ccaggcccca gcguaggcu cgcagcuuua    1020 guaguaguag uaguuguugu cguuguuguu gggucgugcg aggcgucuu ggccuucgcc    1080 ggccgcgauu cgcccucaacg cgacgcguug ggaaagaaag gagaaaaaaa cagauuugcc  1140
acugcaauaa aaaaaaaaaa aaaaaaaaaa aaaaaaaaaa aaaaaaaa               1189

<210> SEQ ID NO 22
<211> LENGTH: 1179
<212> TYPE: DNA
<213> ORGANISM: Thraustochytrium aureum

<400> SEQUENCE: 22
atggaaaata caatggagca acagccgc gccatcgata agatgaacgc gggcgttgtg         60
cggcgcgtgg tcaagttcgg cacgcaggac gtgagccagg cctgcggcgt aatctcgatg     120
ggacacaacg agctactcgg cgagagcggg ccgcggcgcc gcggcgaatc cgtggagaag    180
cgcaaagagc gcaagcagcg ccagaatctc ggcgccaaac tgttcacggc gtactgcatc     240

```
gtgttcgcgg cgctgatgct gctctccttc atggacctgc ttcccgtgtt tgagtgggag    300
ctgatgaact tgggaccgc ggagaaggtc tcggtatggc tcggcgagca catgcacctg     360
ccgttcgtgt ttgcgctctt gtacgtgatc gtaatctttg gatccagtt tgcaatggac    420
ggcaagaccg agtttgacct gaggtaccca cttgcgatct ggtcgctcgc gctcgcgctg    480
ttcagcctgg gcggctccct gcgcaccgtg cccgtcctaa tcaagctcct ccacaccaag    540
ggcgtcatgc acgtcgtgtg cggggacacg cggcaggact gggtcatcga caacccggcc    600
ggggtgtgga cgatgctctt catcttttcc aaggtgcccg agctgatcga cacgctgttc    660
atcgtgctgc gcaagcgcaa actgatcacg ctgcactggt accaccacat acggtgatg    720
accttttgct ggcactcgtg ggccacttac tgcctgaacg gcctcgtgta ctcgtccatg    780
aacctcactg tgcacgcgtt catgtacttt ttttacacgc tcaccgcgct cgggtaccgg    840
cccacgcgat tcgcgatcta catcaccgtg atccagatcc tgcaaatgct cgtcggcacc    900
gcggtcaccg tctacgtcaa ctaccacatc aactttgtcg tcacgcagcc gctgagcctc    960
tcgctgcgca caaactggga cgcgctcgcg ccggagccaa acacggatcc cagctgcaag   1020
gtccacaccc tcaacgccct ggcgggcctc tgcatgtacg ggagctacct gtggctcttt   1080
tgcgtgttct tttatgtcag ctatatccag cccaagccgg ccaagagcaa gtctttggcc   1140
tctggggagg ctgctgccga caagctcaag tcgacctga                          1179
```

<210> SEQ ID NO 23
<211> LENGTH: 392
<212> TYPE: PRT
<213> ORGANISM: Thraustochytrium aureum

<400> SEQUENCE: 23

```
Met Glu Asn Thr Met Glu His Asn Ser Arg Ala Ile Asp Lys Met Asn
1               5                   10                  15

Ala Gly Val Val Arg Arg Val Val Lys Phe Gly Thr Gln Asp Val Ser
                20                  25                  30

Gln Ala Cys Gly Val Ile Ser Met Gly His Asn Glu Leu Leu Gly Glu
            35                  40                  45

Ser Gly Pro Arg Arg Gly Glu Ser Val Glu Lys Arg Lys Glu Arg
        50                  55                  60

Lys Gln Arg Gln Asn Leu Gly Ala Lys Leu Phe Thr Ala Tyr Cys Ile
65                  70                  75                  80

Val Phe Ala Ala Leu Met Leu Ser Phe Met Asp Leu Leu Pro Val
                85                  90                  95

Phe Glu Trp Glu Leu Met Asn Phe Gly Thr Ala Glu Lys Val Ser Val
            100                 105                 110

Trp Leu Gly Glu His Met His Leu Pro Phe Val Phe Ala Leu Leu Tyr
        115                 120                 125

Val Ile Val Ile Phe Gly Ile Gln Phe Ala Met Asp Gly Lys Thr Glu
    130                 135                 140

Phe Asp Leu Arg Tyr Pro Leu Ala Ile Trp Ser Leu Ala Leu Ala Leu
145                 150                 155                 160

Phe Ser Leu Gly Gly Ser Leu Arg Thr Val Pro Val Leu Ile Lys Leu
                165                 170                 175

Leu His Thr Lys Gly Val Met His Val Val Cys Gly Asp Thr Arg Gln
            180                 185                 190

Asp Trp Val Ile Asp Asn Pro Ala Gly Val Trp Thr Met Leu Phe Ile
        195                 200                 205
```

```
Phe Ser Lys Val Pro Glu Leu Ile Asp Thr Leu Phe Ile Val Leu Arg
            210                 215                 220

Lys Arg Lys Leu Ile Thr Leu His Trp Tyr His Ile Thr Val Met
225                 230                 235                 240

Thr Phe Cys Trp His Ser Trp Ala Thr Tyr Cys Leu Asn Gly Leu Val
                    245                 250                 255

Tyr Ser Ser Met Asn Leu Thr Val His Ala Phe Met Tyr Phe Phe Tyr
                260                 265                 270

Thr Leu Thr Ala Leu Gly Tyr Arg Pro Thr Arg Phe Ala Ile Tyr Ile
            275                 280                 285

Thr Val Ile Gln Ile Leu Gln Met Leu Val Gly Thr Ala Val Thr Val
        290                 295                 300

Tyr Val Asn Tyr His Ile Asn Phe Val Val Thr Gln Pro Leu Ser Leu
305                 310                 315                 320

Ser Leu Arg Thr Asn Trp Asp Ala Leu Ala Pro Glu Pro Asn Thr Asp
                325                 330                 335

Pro Ser Cys Lys Val His Thr Leu Asn Ala Leu Ala Gly Leu Cys Met
                340                 345                 350

Tyr Gly Ser Tyr Leu Trp Leu Phe Cys Val Phe Phe Tyr Val Ser Tyr
            355                 360                 365

Ile Gln Pro Lys Pro Ala Lys Ser Lys Ser Leu Ala Ser Gly Glu Ala
        370                 375                 380

Ala Ala Asp Lys Leu Lys Ser Thr
385                 390

<210> SEQ ID NO 24
<211> LENGTH: 1313
<212> TYPE: RNA
<213> ORGANISM: Thraustochytrium aureum

<400> SEQUENCE: 24
aauggaaaau acaauggagc acaacagccg cgccaucgau aagaugaacg cgggcguugu     60
gcggcgcgug gucaaguucg gcacgcagga cgugagccag gccugcggcg uaaucucgau    120
gggacacaac gagcuacucg gcgagagcgg gccgcggcgc cgcggcgaau ccguggagaa    180
gcgcaaagag cgcaagcagc gccagaaucu cggcgccaaa cuguucacgg cguacugcau    240
cguguucgcg gcgcugaugc ugcucucccu ucauggaccu guucccgugu uugagugggg    300
gcugaugaac uuugggaccg cggagaaggu ucgguaugg ucggcgagc acaugcaccu     360 gccguucgug uuugcgcucu uguacgugau cguaaucuuu gggauccagu uugcaaugga    420
cggcaagacc gaguuugacc ugagguaccc acuugcgauc uggucgcucg cgcucgcgcu    480
guucagcccu ggcggcuccc ugcgcaccgu gcccguccua aucaagcucc uccacaccaa    540
gggcgucaug cacgucgugu gcggggacac gcggcaggac uggucaucg acaacccggc     600 cggggugugg acgaugcucu ucaucuuuuc caaggcgccc gagcugaucg acacgcuguu    660
caucgugcug cgcaagcgca aacugaucac gcugcacugg uaccaccaca ucacggugau    720
gaccuuuugc uggcacucgu gggccacuua cugccugaac ggccucgugu acugguccau    780
gaaccucacu gugcacgcgu ucauguacuu uuuuuacacg cucaccgcgc ucggguaccg    840
gcccacgcga uucgcgaucu acaucaccgu gauccagauc cugcaaaugc ucgucggcac    900
cgcggucacc gucacguca acuaccacau caacuuuguc gucacgcagc cgcugagccu    960
cucgcugcgc acaaacuggg acgcgcucgc gccggagcca aacacggauc ccagcugcaa   1020
```

| | |
|---|---|
| gguccacacc cucaacgccc uggcgggccu cugcauguac gggagcuacc uguggcucuu | 1080 |
| uugcguguuc uuuuauguca gcuauauucca gcccaagccg gccaagagca agucuuuggc | 1140 |
| cucuggggag gcugcugccg acaagcucaa gucgaccuga gcgaccgugc cuccguuucc | 1200 |
| aaagccgccg uccuucggcg cggggauaaac cguuuucaga cgaaacgaaa gagaagaaag | 1260 |
| aagacaaaaa ggacuaaccu acgguaguag gguaacguaa aaaaaaaaa aaa | 1313 |

<210> SEQ ID NO 25
<211> LENGTH: 969
<212> TYPE: DNA
<213> ORGANISM: Thraustochytrium aureum

<400> SEQUENCE: 25

| | |
|---|---|
| atgcgcaccg cgtacgaagc agcgtggtcg ggcaccgtgc acaaggtcaa caacacccac | 60 |
| cacgtgttca agacgagggg cggcggcgag tgcttcttcc agagcacgta ccaacttttg | 120 |
| cccgagctgg agccaccccc gctttacccg ttccgcgaga cggaaggcgt tttcgatggg | 180 |
| agccccatgt cggcctacat gcgcgagtac tttcagatcc cgctcatcct cgtggccctg | 240 |
| tacgtcgtgg tcatcttctc ggggcgcgcg gtcatgtctt gcttgccggc cgcagacctc | 300 |
| acagtgccgc tcgcgctgtg gaacctggcg ctctcccttt tcagctgggt cggcgtcttc | 360 |
| cgcaccgtgc cgcaccttttt ggggacgatc gcgcaccgcg gggtctactt tagcatgtgc | 420 |
| gagccggttt cgccacgtt tggcgcctcc gaggtcggct tgtgggcctg ctcttcatc | 480 |
| atctccaaga tccccgagct catcgacacg gttttcatcg tcttgcggaa gaagccgctc | 540 |
| atttttcttgc actggtacca ccacgtcacg gtcctcctct actgctgggc cagctacaca | 600 |
| acgcagaaca gcgccgggct ctactttatc tgcatgaact acaccgtcca tgcaattatg | 660 |
| tacggctact actttctcaa ggcggtcaac atgtggccgc ggttcatccc gtcgtggacc | 720 |
| atcacgctgc tccagctcag ccagatggtc ggcggcatcg tggtctgcta cctcacgtac | 780 |
| aagtacgaga aggaggacgg gcttccgtgc tcgatctccg aggtcgcctt caacaccggc | 840 |
| gtcgtcatgt acgggagcta ttttctcctg ttcctgcaaa tcctgttctc gcttctctct | 900 |
| ggcggcaaga aaaagtcggc aggccgtccc aaggcggatg ccgggctgca acagaagaag | 960 |
| aagcagtag | 969 |

<210> SEQ ID NO 26
<211> LENGTH: 322
<212> TYPE: PRT
<213> ORGANISM: Thraustochytrium aureum

<400> SEQUENCE: 26

Met Arg Thr Ala Tyr Glu Ala Ala Trp Ser Gly Thr Val His Lys Val
1               5                   10                  15

Asn Asn Thr His His Val Phe Lys Thr Arg Gly Gly Gly Glu Cys Phe
            20                  25                  30

Phe Gln Ser Thr Tyr Gln Leu Leu Pro Glu Leu Glu Pro Thr Pro Leu
        35                  40                  45

Tyr Pro Phe Arg Glu Thr Glu Gly Val Phe Asp Gly Ser Pro Met Ser
    50                  55                  60

Ala Tyr Met Arg Glu Tyr Phe Gln Ile Pro Leu Ile Leu Val Ala Leu
65                  70                  75                  80

Tyr Val Val Val Ile Phe Ser Gly Arg Ala Val Met Ser Cys Leu Pro
            85                  90                  95

Ala Ala Asp Leu Thr Val Pro Leu Ala Leu Trp Asn Leu Ala Leu Ser

|  | 100 |  |  |  | 105 |  |  |  | 110 |  |  |
|---|---|---|---|---|---|---|---|---|---|---|---|

Leu Phe Ser Trp Val Gly Val Phe Arg Thr Val Pro His Leu Leu Gly
                115                 120                 125

Thr Ile Ala His Arg Gly Val Tyr Phe Ser Met Cys Glu Pro Val Cys
130                 135                 140

Ala Thr Phe Gly Ala Ser Glu Val Gly Leu Trp Ala Trp Leu Phe Ile
145                 150                 155                 160

Ile Ser Lys Ile Pro Glu Leu Ile Asp Thr Val Phe Ile Val Leu Arg
                165                 170                 175

Lys Lys Pro Leu Ile Phe Leu His Trp Tyr His His Val Thr Val Leu
                180                 185                 190

Leu Tyr Cys Trp Ala Ser Tyr Thr Thr Gln Asn Ser Ala Gly Leu Tyr
                195                 200                 205

Phe Ile Cys Met Asn Tyr Thr Val His Ala Ile Met Tyr Gly Tyr Tyr
                210                 215                 220

Phe Leu Lys Ala Val Asn Met Trp Pro Arg Phe Ile Pro Ser Trp Thr
225                 230                 235                 240

Ile Thr Leu Leu Gln Leu Ser Gln Met Val Gly Gly Ile Val Val Cys
                245                 250                 255

Tyr Leu Thr Tyr Lys Tyr Glu Lys Glu Asp Gly Leu Pro Cys Ser Ile
                260                 265                 270

Ser Glu Val Ala Phe Asn Thr Gly Val Val Met Tyr Gly Ser Tyr Phe
                275                 280                 285

Leu Leu Phe Leu Gln Ile Leu Phe Ser Leu Leu Ser Gly Gly Lys Lys
                290                 295                 300

Lys Ser Ala Gly Arg Pro Lys Ala Asp Ala Gly Leu Gln Gln Lys Lys
305                 310                 315                 320

Lys Gln

<210> SEQ ID NO 27
<211> LENGTH: 1207
<212> TYPE: RNA
<213> ORGANISM: Thraustochytrium aureum

<400> SEQUENCE: 27
gcucagguuu uguuuagca acccugaugc cgcagagccc cgggacugga aggcgacggg    60
ggacuggug gcggacaugc gcaccgcgua cgaagcagcg uggucgggca ccgugcacaa   120
ggucaacaac acccaccacg uguucaagac gaggggcggc ggcgagugcu ucuuccagag   180
cacguaccaa cuuuugcccg agcuggagcc caccccgcuu uacccguucc gcgagacgga   240
aggcguuuuc gaugggagcc ccaugucggc cuacaugcgc gaguacuuuc agaucccgcu   300
cauccucgug gccuguacg ucgggucau cuucucgggg cgcgcgguca ugucuugcuu   360
gccggccgca gaccucacag ugccgcucgc gcuguggaac cuggcgcucu cccuuuucag   420
cugggucggc gucuuccgca ccgugccgca ccuuuugggg acgaucgcgc accgcggggu   480
cuacuuuagc augugcgagc cgguuugcgc cacguuuggc gccuccgagg ucggcuugug   540
ggccuggcuc uucaucaucu ccaagauccc cgagcucauc gacacgguuu ucaucgucuu   600
gcggaagaag ccgcucauuu ucuugcacug guaccaccac gucacgguuc uccucuacug   660
cugggccagc uacacaacgc agaacagcgc cgggcucuac uuuaucugca ugaacuacac   720
cguccaugca auuaugguacg gcuacuacuu ucucaaggcg gucaacaugu ggccgcgguu   780
cauccccgucg uggaccauca cgcugcucca gcucagccaa auggucggcg gcaucguggu   840
cugcuaccuc acguacaagu acgagaagga ggacgggcuu ccgugcucga ucuccgaggu 900
cgccuucaac accggcgucg ucauguacgg gagcuauuuu cuccuguucc ugcaaauccu 960
guucucgcuu cucucuggcg gcaagaaaaa gucggcaggc cgucccaagg cggaugccgg 1020
gcugcaacag aagaagaagc aguaggcugc cgcgagcaug cguuccgcgg cgcuggaaag 1080
ccugaaacau gcaaugcaug cgccagucua uugcgaucug cguuggaaga aaauaaagaa 1140
gaaacggacu uuaucuagaa ccgaaaaaaa aaaaaaaaaa aaaaaaaaaa aauaaaaaaa 1200
aaaaaaa 1207

<210> SEQ ID NO 28
<211> LENGTH: 792
<212> TYPE: DNA
<213> ORGANISM: Thraustochytrium aureum

<400> SEQUENCE: 28
atggacgtct atgacgcaca gccgtggacc gccgaggcgc tcggcccccct ctgggatgac 60 ctgtacttgc ttgtgcctgt ctacatggtc tgcgtagcag cgctgcggcg agtgggcccg 120
tggcgagtga gcgagacgca gagcaagtcg tacaagttca acgccgcgtt ttggaagccc 180
atcatgatcg cctacaacgt tgcgatgacg ctgttctcgt tcgtgtgctt tgcaggcatg 240
gcctacgtcg tcctcgtcaa gcagcagggc gagttcgcgg ggccggactg tcaggcatac 300
gacaggcagc cgctgttccg aaacatcgtg tacgcgttct tcgtgagcaa gttcgtcgag 360
ttcgcggaca cgctgttcct catcgtcaag ggcaagcctg tgtcatggct gcacttttc 420 caccactgcg gcgcagcaat caacatgggc ctgttatcgc gtagcggcat ggaggcgacg 480
tggttgtttg tcttgctgaa cgggtttgtg catacggtca tgtacacata ctacggctgc 540
gccctggcgg gggtccgcct gcgcggcaag tcgctcatca cggtcatgca gatcgcgcaa 600
ttcctcctcg ggcttttccgt gttctggcag tacaagaacg tcacctgctt tagtcagagc 660
acgccgctca tgttcacctt tggtacact tacacgtacg tcggcatcgt gctgctcttc 720
ttcctcaact ttttcgcgca gagctacgtc atgccgcgca agacaaaagc ggaccagctc 780
aagtcgcagt ga 792

<210> SEQ ID NO 29
<211> LENGTH: 263
<212> TYPE: PRT
<213> ORGANISM: Thraustochytrium aureum

<400> SEQUENCE: 29

Met Asp Val Tyr Asp Ala Gln Pro Trp Thr Ala Glu Ala Leu Gly Pro
1               5                   10                  15

Leu Trp Asp Asp Leu Tyr Leu Leu Val Pro Val Tyr Met Val Cys Val
            20                  25                  30

Ala Ala Leu Arg Arg Val Gly Pro Trp Arg Val Ser Glu Thr Gln Ser
        35                  40                  45

Lys Ser Tyr Lys Phe Asn Ala Ala Phe Trp Lys Pro Ile Met Ile Ala
    50                  55                  60

Tyr Asn Val Ala Met Thr Leu Phe Ser Phe Val Cys Phe Ala Gly Met
65                  70                  75                  80

Ala Tyr Val Val Leu Val Lys Gln Gln Gly Glu Phe Ala Gly Pro Asp
                85                  90                  95

Cys Gln Ala Tyr Asp Arg Gln Pro Leu Phe Arg Asn Ile Val Tyr Ala
            100                 105                 110

```
Phe Phe Val Ser Lys Phe Val Glu Phe Ala Asp Thr Leu Phe Leu Ile
            115                 120                 125

Val Lys Gly Lys Pro Val Ser Trp Leu His Phe His His Cys Gly
130                 135                 140

Ala Ala Ile Asn Met Gly Leu Leu Ser Arg Ser Gly Met Glu Ala Thr
145                 150                 155                 160

Trp Leu Phe Val Leu Leu Asn Gly Phe Val His Thr Val Met Tyr Thr
                165                 170                 175

Tyr Tyr Gly Cys Ala Leu Ala Gly Val Arg Leu Arg Gly Lys Ser Leu
            180                 185                 190

Ile Thr Val Met Gln Ile Ala Gln Phe Leu Leu Gly Leu Ser Val Phe
            195                 200                 205

Trp Gln Tyr Lys Asn Val Thr Cys Phe Ser Gln Ser Thr Pro Leu Met
210                 215                 220

Phe Thr Phe Trp Tyr Thr Tyr Thr Tyr Val Gly Ile Val Leu Leu Phe
225                 230                 235                 240

Phe Leu Asn Phe Phe Ala Gln Ser Tyr Val Met Pro Arg Lys Thr Lys
                245                 250                 255

Ala Asp Gln Leu Lys Ser Gln
            260

<210> SEQ ID NO 30
<211> LENGTH: 1031
<212> TYPE: RNA
<213> ORGANISM: Thraustochytrium aureum

<400> SEQUENCE: 30 auccccauu gaccgauuug cagcggucgg cugcucgagc gacgcagagc caagucggcg      60
cgcggugacu uggaaaugga cgucuaugac gcacagccgu ggaccgccga ggcgcucggc     120
ccccucuggg augaccugua cuugcuugug ccugucuaca uggucugcgu agcagcgcug     180
cggcgagugg gcccguggcg agugagcgag acgcagagca agucuacaa guucaacgcc     240
gcguuuugga agcccaucau gaucgccuac aacguugcga ugacgcuguu cucguucgug     300
ugcuuugcag gcauggccua cgucguccuc gucaagcagc agggcgaguu cgcggggccg     360
gacugucagg cauacgacag gcagccgcug uuccgaaaca ucguguacgc guucuucgug     420
agcaaguucg ucgaguucgc ggacacgcug uccucaucg ucaagggcaa gccuguguca     480
uggcugcacu uuuccacca cugcggcgca gcaaucaaca ugggccuguu aucgcguagc     540
ggcauggagg cgacgugguu guuugucuug cugaacgggu uugugcauac ggucauguac     600
acauacuacg gcugcgcccu ggcggggguc cgccugcgcg gcaagucgcu caucacgguc     660
augcagaucg cgcaauuccu ccucgggcuu uccguguucu ggcaguacaa gaacgucacc     720
ugcuuuaguc agagcacgcc gcucauguuc accuuuuggu acacuuacac guacgucggc     780
aucgugcugc ucuucuuccu caacuuuuuc gcgcagagcu acgucaugcc gcgcaagaca     840
aaagcggacc agcucaaguc gcaguagugg ucuuucgcgc ccaccacggc cccggcgccc     900
acggcgaugc gccaggacug cgcucgagca guuugcau caggacaaca caaccgccuc     960
aauuguuuuu aaguuaaaaa aaaaaaaaaa aaaaaaaaaa aaaaaaaaaa aaaaaaaaaa    1020
aaaaaaaua a                                                           1031

<210> SEQ ID NO 31
<211> LENGTH: 942
<212> TYPE: DNA
<213> ORGANISM: Thraustochytrium aureum
```

<400> SEQUENCE: 31

```
atgaccgaga ctgtgctgtg ggtgctgggc atcgtgtggg tcgtgtcgtt cgcgtcgtac      60
ctcgtgccgc agctcctgct caagctgcgc agtgtgcaga atctgaagga caagtatggc     120
gcaaagtggg ctctggtcac cggcgggtct agcgggattg ccgtgcgat cgttgagacg      180
ctcgctggcc aaggcctcaa catcgtcgtc gttgccatgc aggacaaggt cctcgacact     240
tctgtggagg agtacaagaa ggcgttccca agtgtcgaat tcgcaaggt ggggtcgac       300
ctgtcctccg cggaccgaat gcagcccatg cgtgaggcga ccaaagatat cgatgtgcag     360
gtcatcgtga acaacgccgg ctatatcaag accggtttct ttgcggagac cccttcggc     420
gcgcagctgg cgaaccacaa cgtgaacgca accgccgcca tggaggttgc ccaccactac    480
atcagcgcga tgcgggctaa gggtctcaaa gggtgcgtca ccttcacctc gtccccggct    540
ggattcatgc cgtgcccttt cagcgtcatg tacgcgcga ccaaggcgta tttgactact     600
tttgcgcaga gcctggcgcc ggagcttcgg tgtgacggga tcgacgttg cgttgtgcac     660
ccctcgcccg tcgcctcgag cttttacgac aatacccacg ctcttgacgc cctgctgttc    720
ttcaaaagca ccgcgacggg gccgcagact atcgccaaca tcttgctcgc caacgtcggc    780
cgagcagtca ccatcgacca gggctactac ccaatctgcg tcaagctgct tcttaaagtg    840
ctcgacgtca actttctcgc cgagaccatc gcctccgtag cacactttat gcccgacttt    900
aaggccatga agtccacctc gtcgccgaag aaggtcgctt ga                       942
```

<210> SEQ ID NO 32
<211> LENGTH: 313
<212> TYPE: PRT
<213> ORGANISM: Thraustochytrium aureum

<400> SEQUENCE: 32

```
Met Thr Glu Thr Val Leu Trp Val Leu Gly Ile Val Trp Val Ser
1               5                   10                  15

Phe Ala Ser Tyr Leu Val Pro Gln Leu Leu Lys Leu Arg Ser Val
                20                  25                  30

Gln Asn Leu Lys Asp Lys Tyr Gly Ala Lys Trp Ala Leu Val Thr Gly
            35                  40                  45

Gly Ser Ser Gly Ile Gly Arg Ala Ile Val Glu Thr Leu Ala Gly Gln
        50                  55                  60

Gly Leu Asn Ile Val Val Ala Met Gln Asp Lys Val Leu Asp Thr
65                  70                  75                  80

Ser Val Glu Glu Tyr Lys Lys Ala Phe Pro Ser Val Glu Phe Arg Lys
                85                  90                  95

Val Gly Val Asp Leu Ser Ser Ala Asp Arg Met Gln Pro Met Arg Glu
            100                 105                 110

Ala Thr Lys Asp Ile Asp Val Gln Val Ile Val Asn Asn Ala Gly Tyr
        115                 120                 125

Ile Lys Thr Gly Phe Phe Ala Glu Thr Pro Phe Gly Ala Gln Leu Ala
    130                 135                 140

Asn His Asn Val Asn Ala Thr Ala Ala Met Glu Val Ala His His Tyr
145                 150                 155                 160

Ile Ser Ala Met Arg Ala Lys Gly Leu Lys Gly Cys Val Thr Phe Thr
                165                 170                 175

Ser Ser Pro Ala Gly Phe Met Pro Cys Pro Phe Ser Val Met Tyr Gly
            180                 185                 190
```

```
Ala Thr Lys Ala Tyr Leu Thr Thr Phe Ala Gln Ser Leu Ala Pro Glu
            195                 200                 205

Leu Arg Cys Asp Gly Ile Asp Val Cys Val Val His Pro Ser Pro Val
    210                 215                 220

Ala Ser Ser Phe Tyr Asp Asn Thr His Ala Leu Asp Ala Leu Leu Phe
225                 230                 235                 240

Phe Lys Ser Thr Ala Thr Gly Pro Gln Thr Ile Ala Asn Ile Leu Leu
                245                 250                 255

Ala Asn Val Gly Arg Ala Val Thr Ile Asp Gln Gly Tyr Tyr Pro Ile
            260                 265                 270

Cys Val Lys Leu Leu Leu Lys Val Leu Asp Val Asn Phe Leu Ala Glu
            275                 280                 285

Thr Ile Ala Ser Val Ala His Phe Met Pro Asp Phe Lys Ala Met Lys
            290                 295                 300

Ser Thr Ser Ser Pro Lys Lys Val Ala
305                 310
```

<210> SEQ ID NO 33
<211> LENGTH: 1246
<212> TYPE: RNA
<213> ORGANISM: Thraustochytrium aureum

<400> SEQUENCE: 33

```
aagcuugugu gagcugagcg aaggcgcguc aucgugcagg cacgaugacc gagacugugc    60
ugugggugcu gggcaucgug ugggucgugu cguucgcguc guaccucgug ccgcagcucc   120
ugcucaagcu gcgcagugug cagaaucuga aggacaagua uggcgcaaag ugggcucugg   180
ucaccggcgg gucuagcggg auuggccgug cgaucguuga gacgcucgcu ggccaaggcc   240
ucaacaucgu cgucguugcc augcaggaca aggccucga cacuucgug gaggaguaca    300
agaaggcguu cccaagugug gaauuucgca aggugggggu cgaccugucc uccgcggacc   360
gaaugcagcc caugcgugag gcgaccaaag auaucgaugu gcaggucauc gugaacaacg   420
ccggcuauau caagaccggu ucuuugcgg agaccccuuu cggcgcgcag cuggcgaacc   480
acaacgugaa cgcaaccgcc gccauggagu ugcccacca cuacaucagc gcgaugcggg   540
cuaagggucu caaaggguge gucaccuuca ccucgucccc ggcuggauuc augccgugcc   600
cuuucagcgu caugacggc gcgaccaagg cguauuugac uacuuuugcg cagagccugg   660
cgccggagcu ucggugugac gggaucgacg uuugcguugu gcaccccucg cccgucgccu   720
cgagcuuuua cgacaauacc cacgcucuug acgcccugcu guucuucaaa agcaccgcga   780
cggggccgca gacuaucgcc aacaucuugc ucgccaacgu cggccagca gucaccaucg   840
accagggcua cuacccaauc ugcgucaagc ugcuucuuaa agugcucgac gucaacuuuc   900
ucgccgagac caucgccucc guagcacacu uuaugcccga cuuuaaggcc augaaguccca   960
ccucgucgcc gaagaagguc gcuugagcgc ccgcacggac agaggcgcca ggaucaagca  1020
guuuccgacc ccccuuugcc uuuuccuaca cgcaccagcg agccgucucgu gcguuuggac  1080
gcgcagaguc ucgcaggcaa cgcuucacg guccggaacg auaaauagcu ucaucaccuu  1140
caacaugcgc ucaacaacga uucggcgcaa agcaaagcua accaguaagg accuacaaaa  1200
aaaaaaaaaa aaaaaaaaaa aaauaaaaa aaaaaaaaaa aaaaaa                   1246
```

<210> SEQ ID NO 34
<211> LENGTH: 104
<212> TYPE: DNA
<213> ORGANISM: Artificial

```
<220> FEATURE:
<223> OTHER INFORMATION: Primer

<400> SEQUENCE: 34
ataaaagtat caacaaaaaa ttgttaatat acctctatac tttaacgtca aggagaaaaa      60
accccggatc ggcgcgccac catgttcaac caggcaagcg agct                      104

<210> SEQ ID NO 35
<211> LENGTH: 101
<212> TYPE: DNA
<213> ORGANISM: Artificial
<220> FEATURE:
<223> OTHER INFORMATION: Primer

<400> SEQUENCE: 35
aactataaaa aaataaatag ggacctagac ttcaggttgt ctaactcctt cctttcggt       60 tagagcggat ttaattaact agccctgcgc gttaatggct t                         101

<210> SEQ ID NO 36
<211> LENGTH: 104
<212> TYPE: DNA
<213> ORGANISM: Artificial
<220> FEATURE:
<223> OTHER INFORMATION: Primer

<400> SEQUENCE: 36
ataaaagtat caacaaaaaa ttgttaatat acctctatac tttaacgtca aggagaaaaa      60
accccggatc ggcgcgccac catggcggcc aacatgtggg gcca                      104

<210> SEQ ID NO 37
<211> LENGTH: 101
<212> TYPE: DNA
<213> ORGANISM: Artificial
<220> FEATURE:
<223> OTHER INFORMATION: Primer

<400> SEQUENCE: 37
aactataaaa aaataaatag ggacctagac ttcaggttgt ctaactcctt cctttcggt       60 tagagcggat ttaattaatc acgccaccgt gcgctcgcgc a                         101

<210> SEQ ID NO 38
<211> LENGTH: 104
<212> TYPE: DNA
<213> ORGANISM: Artificial
<220> FEATURE:
<223> OTHER INFORMATION: Primer

<400> SEQUENCE: 38
ataaaagtat caacaaaaaa ttgttaatat acctctatac tttaacgtca aggagaaaaa      60
accccggatc ggcgcgccac catggcgcca gcggttggca aggc                      104

<210> SEQ ID NO 39
<211> LENGTH: 101
<212> TYPE: DNA
<213> ORGANISM: Artificial
<220> FEATURE:
<223> OTHER INFORMATION: Primer

<400> SEQUENCE: 39
aactataaaa aaataaatag ggacctagac ttcaggttgt ctaactcctt cctttcggt       60 tagagcggat ttaattaatt gggccttttt ggactcgcgc t                         101
```

<210> SEQ ID NO 40
<211> LENGTH: 104
<212> TYPE: DNA
<213> ORGANISM: Artificial
<220> FEATURE:
<223> OTHER INFORMATION: Primer

<400> SEQUENCE: 40
ataaaagtat caacaaaaaa ttgttaatat acctctatac tttaacgtca aggagaaaaa     60
accccggatc ggcgcgccac catggcgccc ccaaaggtct tctc                    104

<210> SEQ ID NO 41
<211> LENGTH: 101
<212> TYPE: DNA
<213> ORGANISM: Artificial
<220> FEATURE:
<223> OTHER INFORMATION: Primer

<400> SEQUENCE: 41
aactataaaa aaataaatag ggacctagac ttcaggttgt ctaactcctt cctttttcggt    60 tagagcggat ttaattaatc agagcttggc gtcgcgcggg t                       101

<210> SEQ ID NO 42
<211> LENGTH: 104
<212> TYPE: DNA
<213> ORGANISM: Artificial
<220> FEATURE:
<223> OTHER INFORMATION: Primer

<400> SEQUENCE: 42
ataaaagtat caacaaaaaa ttgttaatat acctctatac tttaacgtca aggagaaaaa     60
accccggatc ggcgcgccac catgtgcaag gtcgatggga caaa                    104

<210> SEQ ID NO 43
<211> LENGTH: 101
<212> TYPE: DNA
<213> ORGANISM: Artificial
<220> FEATURE:
<223> OTHER INFORMATION: Primer

<400> SEQUENCE: 43
aactataaaa aaataaatag ggacctagac ttcaggttgt ctaactcctt cctttttcggt    60 tagagcggat ttaattaatc agagcttttt ggccgcacgc t                       101

<210> SEQ ID NO 44
<211> LENGTH: 104
<212> TYPE: DNA
<213> ORGANISM: Artificial
<220> FEATURE:
<223> OTHER INFORMATION: Primer

<400> SEQUENCE: 44
ataaaagtat caacaaaaaa ttgttaatat acctctatac tttaacgtca aggagaaaaa     60
accccggatc ggcgcgccac catggcgacg cgcacctcga agag                    104

<210> SEQ ID NO 45
<211> LENGTH: 101
<212> TYPE: DNA
<213> ORGANISM: Artificial
<220> FEATURE:
<223> OTHER INFORMATION: Primer

<400> SEQUENCE: 45

```
aactataaaa aaataaatag ggacctagac ttcaggttgt ctaactcctt cctttcggt      60 tagagcggat ttaattaatc actcggactt ggtgggggcg c                         101
```

<210> SEQ ID NO 46
<211> LENGTH: 104
<212> TYPE: DNA
<213> ORGANISM: Artificial
<220> FEATURE:
<223> OTHER INFORMATION: Primer

<400> SEQUENCE: 46

```
ataaaagtat caacaaaaaa ttgttaatat acctctatac tttaacgtca aggagaaaaa      60
accccggatc ggcgcgccac catggccgcg gccttcatgg actt                      104
```

<210> SEQ ID NO 47
<211> LENGTH: 101
<212> TYPE: DNA
<213> ORGANISM: Artificial
<220> FEATURE:
<223> OTHER INFORMATION: Primer

<400> SEQUENCE: 47

```
aactataaaa aaataaatag ggacctagac ttcaggttgt ctaactcctt cctttcggt       60 tagagcggat ttaattaatc actccacctt ggccttgggc c                         101
```

<210> SEQ ID NO 48
<211> LENGTH: 104
<212> TYPE: DNA
<213> ORGANISM: Artificial
<220> FEATURE:
<223> OTHER INFORMATION: Primer

<400> SEQUENCE: 48

```
ataaaagtat caacaaaaaa ttgttaatat acctctatac tttaacgtca aggagaaaaa      60
accccggatc ggcgcgccac catggaaaat acaatggagc acaa                      104
```

<210> SEQ ID NO 49
<211> LENGTH: 101
<212> TYPE: DNA
<213> ORGANISM: Artificial
<220> FEATURE:
<223> OTHER INFORMATION: Primer

<400> SEQUENCE: 49

```
aactataaaa aaataaatag ggacctagac ttcaggttgt ctaactcctt cctttcggt       60 tagagcggat ttaattaatc aggtcgactt gagcttgtcg g                         101
```

<210> SEQ ID NO 50
<211> LENGTH: 104
<212> TYPE: DNA
<213> ORGANISM: Artificial
<220> FEATURE:
<223> OTHER INFORMATION: Primer

<400> SEQUENCE: 50

```
ataaaagtat caacaaaaaa ttgttaatat acctctatac tttaacgtca aggagaaaaa      60
accccggatc ggcgcgccac catgcgcacc gcgtacgaag cagc                      104
```

<210> SEQ ID NO 51
<211> LENGTH: 101
<212> TYPE: DNA

```
<213> ORGANISM: Artificial
<220> FEATURE:
<223> OTHER INFORMATION: Primer

<400> SEQUENCE: 51
aactataaaa aaataaatag ggacctagac ttcaggttgt ctaactcctt ccttttcggt      60
tagagcggat ttaattaact actgcttctt cttctgttgc a                        101

<210> SEQ ID NO 52
<211> LENGTH: 104
<212> TYPE: DNA
<213> ORGANISM: Artificial
<220> FEATURE:
<223> OTHER INFORMATION: Primer

<400> SEQUENCE: 52
ataaaagtat caacaaaaaa ttgttaatat acctctatac tttaacgtca aggagaaaaa      60
accccggatc ggcgcgccac catggacgtc tatgacgcac agcc                     104

<210> SEQ ID NO 53
<211> LENGTH: 101
<212> TYPE: DNA
<213> ORGANISM: Artificial
<220> FEATURE:
<223> OTHER INFORMATION: Primer

<400> SEQUENCE: 53
aactataaaa aaataaatag ggacctagac ttcaggttgt ctaactcctt ccttttcggt      60
tagagcggat ttaattaatc actgcgactt gagctggtcc g                        101

<210> SEQ ID NO 54
<211> LENGTH: 104
<212> TYPE: DNA
<213> ORGANISM: Artificial
<220> FEATURE:
<223> OTHER INFORMATION: Primer

<400> SEQUENCE: 54
ataaaagtat caacaaaaaa ttgttaatat acctctatac tttaacgtca aggagaaaaa      60
accccggatc ggcgcgccac catgaccgag actgtgctgt gggt                     104

<210> SEQ ID NO 55
<211> LENGTH: 101
<212> TYPE: DNA
<213> ORGANISM: Artificial
<220> FEATURE:
<223> OTHER INFORMATION: Primer

<400> SEQUENCE: 55
aactataaaa aaataaatag ggacctagac ttcaggttgt ctaactcctt ccttttcggt      60
tagagcggat ttaattaatc aagcgacctt cttcggcgac g                        101

<210> SEQ ID NO 56
<211> LENGTH: 1197
<212> TYPE: DNA
<213> ORGANISM: Phytophthora soja

<400> SEQUENCE: 56
atggcaattc tgaatccgga agcagatagc gcagcaaatc tggcaaccga ttcagaagca      60
aaacagcgtc agctggccga agcaggttat acccatgttg aaggtgcacc ggcaccgctg    120
ccgctggaac tgccgcattt ttcactgcgt gatctgcgtg cagcaattcc gaaacattgt    180
```

```
tttgaacgta gctttgttac cagcacctat tatatgatta aaaacgtgct gacctgcgca    240
gcactgtttt atgcagcaac ctttattgat cgtgctggtg cagcagccta tgttctgtgg    300
cctgtttatt ggtttttttca gggttcatat ctgaccggtg tttgggttat tgcacatgaa   360
tgtggtcatc aggcctattg tagctcagaa gttgtgaata atctgattgg tctggttctg    420
cattcagcac tgctggttcc gtatcattct tggcgtatta gccatcgtaa acatcattca    480
aataccggta gctgcgaaaa tgatgaagtt tttgttccgg ttacccgtag cgttctggca    540
agcagctgga atgaaaccct ggaagatagt ccgctgtatc agctgtatcg tattgtttat    600
atgctggttg ttggttggat gccgggttac ctgttttta atgcaaccgg tccgaccaaa     660
tattggggta aatcacgtag ccatttaat ccgtatagcg caattatgc cgatcgtgaa      720
cgttggatga ttgttctgtc agatattttt ctggttgcaa tgctggcagt tctggcagca    780
ctggttcata ccttttagctt taatacgatg gtgaagtttt atgtggtgcc gtattttatt   840
gtgaatgcct atctggtgct gattacctat ctgcagcaca ccgataccta tattccgcac   900
tttcgtgaag gtgaatggaa ttggctgcgt ggtgcactgt gtaccgttga tcgtagcttt    960
ggtccgtttc tggattcagt tgttcatcgt attgttgata cccatgtgtg ccatcatatt   1020
tttagcaaaa tgccgtttta tcattgcgaa gaagccacca acgcaattaa accgctgctg   1080
ggtaaatttt atctgaaaga taccacaccg gttccggttg cactgtggcg ttcatatacc   1140
cattgtaaat ttgtggaaga tgatggcaaa gtggtgtttt acaaaaacaa actgtaa      1197

<210> SEQ ID NO 57
<211> LENGTH: 398
<212> TYPE: PRT
<213> ORGANISM: Phytophthora soja

<400> SEQUENCE: 57

Met Ala Ile Leu Asn Pro Glu Ala Asp Ser Ala Ala Asn Leu Ala Thr
1               5                   10                  15

Asp Ser Glu Ala Lys Gln Arg Gln Leu Ala Glu Ala Gly Tyr Thr His
            20                  25                  30

Val Glu Gly Ala Pro Ala Pro Leu Pro Leu Glu Leu Pro His Phe Ser
        35                  40                  45

Leu Arg Asp Leu Arg Ala Ala Ile Pro Lys His Cys Phe Glu Arg Ser
    50                  55                  60

Phe Val Thr Ser Thr Tyr Tyr Met Ile Lys Asn Val Leu Thr Cys Ala
65                  70                  75                  80

Ala Leu Phe Tyr Ala Ala Thr Phe Ile Asp Arg Ala Gly Ala Ala Ala
                85                  90                  95

Tyr Val Leu Trp Pro Val Tyr Trp Phe Phe Gln Gly Ser Tyr Leu Thr
            100                 105                 110

Gly Val Trp Val Ile Ala His Glu Cys Gly His Gln Ala Tyr Cys Ser
        115                 120                 125

Ser Glu Val Val Asn Asn Leu Ile Gly Leu Val Leu His Ser Ala Leu
    130                 135                 140

Leu Val Pro Tyr His Ser Trp Arg Ile Ser His Arg Lys His His Ser
145                 150                 155                 160

Asn Thr Gly Ser Cys Glu Asn Asp Glu Val Phe Val Pro Val Thr Arg
                165                 170                 175

Ser Val Leu Ala Ser Ser Trp Asn Glu Thr Leu Glu Asp Ser Pro Leu
            180                 185                 190
```

Tyr Gln Leu Tyr Arg Ile Val Tyr Met Leu Val Val Gly Trp Met Pro
         195                 200                 205

Gly Tyr Leu Phe Phe Asn Ala Thr Gly Pro Thr Lys Tyr Trp Gly Lys
     210                 215                 220

Ser Arg Ser His Phe Asn Pro Tyr Ser Ala Ile Tyr Ala Asp Arg Glu
225                 230                 235                 240

Arg Trp Met Ile Val Leu Ser Asp Ile Phe Leu Val Ala Met Leu Ala
                 245                 250                 255

Val Leu Ala Ala Leu Val His Thr Phe Ser Phe Asn Thr Met Val Lys
             260                 265                 270

Phe Tyr Val Val Pro Tyr Phe Ile Val Asn Ala Tyr Leu Val Leu Ile
         275                 280                 285

Thr Tyr Leu Gln His Thr Asp Thr Tyr Ile Pro His Phe Arg Glu Gly
     290                 295                 300

Glu Trp Asn Trp Leu Arg Gly Ala Leu Cys Thr Val Asp Arg Ser Phe
305                 310                 315                 320

Gly Pro Phe Leu Asp Ser Val Val His Arg Ile Val Asp Thr His Val
                 325                 330                 335

Cys His His Ile Phe Ser Lys Met Pro Phe Tyr His Cys Glu Glu Ala
             340                 345                 350

Thr Asn Ala Ile Lys Pro Leu Leu Gly Lys Phe Tyr Leu Lys Asp Thr
         355                 360                 365

Thr Pro Val Pro Val Ala Leu Trp Arg Ser Tyr Thr His Cys Lys Phe
     370                 375                 380

Val Glu Asp Asp Gly Lys Val Val Phe Tyr Lys Asn Lys Leu
385                 390                 395

<210> SEQ ID NO 58
<211> LENGTH: 1371
<212> TYPE: DNA
<213> ORGANISM: Ostreococcus tauri

<400> SEQUENCE: 58
atgtgtgttg agaccgagaa caacgatgga atccctactg tggagatcgc tttcgatgga      60
gagagagaaa gagctgaggc taacgtgaag ttgtctgctg agaagatgga acctgctgct     120
ttggctaaga ccttcgctag aagatacgtg gttatcgagg agttgagta cgatgtgacc     180
gatttcaaac accctggagg aaccgtgatt ttctacgctc tctctaacac tggagctgat     240
gctactgagg ctttcaagga gttccaccac agatctagaa aggctaggaa ggctttggct     300
gctttgcctt ctagacctgc taagaccgct aaagtggatg atgctgagat gctccaggat     360
ttcgctaagt ggagaaagga gttggagagg gacggattct tcaagccttc tcctgctcac     420
gttgcttaca gattcgctga gttggctgct atgtacgctt gggaacctta cttgatgtac     480
gctagatacg ttgtgtcctc tgtgttggtt tacgcttgct cttcggagc tagatgtgga     540
tgggttcaac acgagggagg acactcttct tgaccggaa acatctggtg ggataagaga     600
atccaagctt tcactgctgg attcggattg gctggatctg agatatgtg aactccatg      660
cacaacaagc accacgctac tcctcaaaaa gtgaggcacg atatggattt ggataccact     720
cctgctgttg ctttcttcaa caccgctgtg aggataata gacctagggg attctctaag     780
tactggctca gattgcaagc ttggaccttc attcctgtga cttctggatt ggtgttgctc     840
ttctggatgt tcttcctcca cccttctaag gctttgaagg aggaaagta cgaggagctt     900
gtgtggatgt tggctgctca cgtgattaga acctggacca ttaaggctgt tactggattc     960

```
accgctatgc aatcctacgg actcttcttg gctacttctt gggtttccgg atgctacttg   1020
ttcgctcact tctctacttc tcacacccac ttggatgttg ttcctgctga tgagcacttg   1080
tcttgggtta ggtacgctgt ggatcacacc attgatatcg atccttctca gggatgggtt   1140
aactggttga tgggatactt gaactgccaa gtgattcacc acctcttccc ttctatgcct   1200
caattcagac aacctgaggt gtccagaaga ttcgttgctt tcgctaagaa gtggaacctc   1260
aactacaagg tgatgactta tgctggagct tggaaggcta ctttgggaaa cctcgataat   1320
gtgggaaagc actactacgt gcacggacaa cactctggaa agaccgcttg a            1371
```

<210> SEQ ID NO 59
<211> LENGTH: 456
<212> TYPE: PRT
<213> ORGANISM: Ostreococcus tauri

<400> SEQUENCE: 59

```
Met Cys Val Glu Thr Glu Asn Asp Gly Ile Pro Thr Val Glu Ile
1               5                   10                  15

Ala Phe Asp Gly Glu Arg Glu Arg Ala Glu Ala Asn Val Lys Leu Ser
            20                  25                  30

Ala Glu Lys Met Glu Pro Ala Ala Leu Ala Lys Thr Phe Ala Arg Arg
        35                  40                  45

Tyr Val Val Ile Glu Gly Val Glu Tyr Asp Val Thr Asp Phe Lys His
    50                  55                  60

Pro Gly Gly Thr Val Ile Phe Tyr Ala Leu Ser Asn Thr Gly Ala Asp
65                  70                  75                  80

Ala Thr Glu Ala Phe Lys Glu Phe His His Arg Ser Arg Lys Ala Arg
                85                  90                  95

Lys Ala Leu Ala Ala Leu Pro Ser Arg Pro Ala Lys Thr Ala Lys Val
            100                 105                 110

Asp Asp Ala Glu Met Leu Gln Asp Phe Ala Lys Trp Arg Lys Glu Leu
        115                 120                 125

Glu Arg Asp Gly Phe Phe Lys Pro Ser Pro Ala His Val Ala Tyr Arg
    130                 135                 140

Phe Ala Glu Leu Ala Ala Met Tyr Ala Leu Gly Thr Tyr Leu Met Tyr
145                 150                 155                 160

Ala Arg Tyr Val Val Ser Ser Val Leu Val Tyr Ala Cys Phe Phe Gly
                165                 170                 175

Ala Arg Cys Gly Trp Val Gln His Glu Gly Gly His Ser Ser Leu Thr
            180                 185                 190

Gly Asn Ile Trp Trp Asp Lys Arg Ile Gln Ala Phe Thr Ala Gly Phe
        195                 200                 205

Gly Leu Ala Gly Ser Gly Asp Met Trp Asn Ser Met His Asn Lys His
    210                 215                 220

His Ala Thr Pro Gln Lys Val Arg His Asp Met Asp Leu Asp Thr Thr
225                 230                 235                 240

Pro Ala Val Ala Phe Phe Asn Thr Ala Val Glu Asp Asn Arg Pro Arg
                245                 250                 255

Gly Phe Ser Lys Tyr Trp Leu Arg Leu Gln Ala Trp Thr Phe Ile Pro
            260                 265                 270

Val Thr Ser Gly Leu Val Leu Phe Trp Met Phe Phe Leu His Pro
        275                 280                 285

Ser Lys Ala Leu Lys Gly Gly Lys Tyr Glu Glu Leu Val Trp Met Leu
    290                 295                 300
```

Ala Ala His Val Ile Arg Thr Trp Thr Ile Lys Ala Val Thr Gly Phe
305                 310                 315                 320

Thr Ala Met Gln Ser Tyr Gly Leu Phe Leu Ala Thr Ser Trp Val Ser
            325                 330                 335

Gly Cys Tyr Leu Phe Ala His Phe Ser Thr Ser His Thr His Leu Asp
            340                 345                 350

Val Val Pro Ala Asp Glu His Leu Ser Trp Val Arg Tyr Ala Val Asp
            355                 360                 365

His Thr Ile Asp Ile Asp Pro Ser Gln Gly Trp Val Asn Trp Leu Met
    370                 375                 380

Gly Tyr Leu Asn Cys Gln Val Ile His His Leu Phe Pro Ser Met Pro
385                 390                 395                 400

Gln Phe Arg Gln Pro Glu Val Ser Arg Arg Phe Val Ala Phe Ala Lys
            405                 410                 415

Lys Trp Asn Leu Asn Tyr Lys Val Met Thr Tyr Ala Gly Ala Trp Lys
            420                 425                 430

Ala Thr Leu Gly Asn Leu Asp Asn Val Gly Lys His Tyr Tyr Val His
            435                 440                 445

Gly Gln His Ser Gly Lys Thr Ala
    450                 455

<210> SEQ ID NO 60
<211> LENGTH: 819
<212> TYPE: DNA
<213> ORGANISM: Thalassiosira pseudonana

<400> SEQUENCE: 60
atggatgctt ataacgctgc tatggataag attggagctg ctatcatcga ttggagtgat     60
ccagatggaa agttcagagc tgatagggag gattggtggt tgtgcgattt cagatccgct    120
atcaccattg ctctcatcta catcgctttc gtgatcttgg gatctgctgt gatgcaatct    180
ctcccagcta tggacccata ccctatcaag ttcctctaca acgtgtctca aatcttcctc    240
tgcgcttaca tgactgttga ggctggattc ctcgcttata ggaacggata caccgttatg    300
ccatgcaacc acttcaacgt gaacgatcca ccagttgcta acttgctctg gctcttctac    360
atctccaaag tgtgggattt ctgggatacc atcttcattg tgctcggaaa gaagtggaga    420
caactctctt tcttgcacgt gtaccaccac accaccatct tcctcttcta ctggttgaac    480
gctaacgtgc tctacgatgg agatatcttc ttgaccatcc tcctcaacgg attcattcac    540
accgtgatgt acacctacta cttcatctgc atgcacacca aggattctaa gaccggaaag    600
tctttgccaa tctggtggaa gtcatctttg accgctttcc aactcttgca attcaccatc    660
atgatgtccc aagctaccta cttggttttc cacggatgcg ataaggtttc cctcagaatc    720
accatcgtgt acttcgtgta cattctctcc cttttcttcc tcttcgctca gttcttcgtg    780
caatcctaca tggctccaaa gaagaagaag tccgcttga                           819

<210> SEQ ID NO 61
<211> LENGTH: 272
<212> TYPE: PRT
<213> ORGANISM: Thalassiosira pseudonana

<400> SEQUENCE: 61

Met Asp Ala Tyr Asn Ala Ala Met Asp Lys Ile Gly Ala Ala Ile Ile
1               5                   10                  15

Asp Trp Ser Asp Pro Asp Gly Lys Phe Arg Ala Asp Arg Glu Asp Trp
            20                  25                  30

```
Trp Leu Cys Asp Phe Arg Ser Ala Ile Thr Ile Ala Leu Ile Tyr Ile
         35                  40                  45

Ala Phe Val Ile Leu Gly Ser Ala Val Met Gln Ser Leu Pro Ala Met
 50                  55                  60

Asp Pro Tyr Pro Ile Lys Phe Leu Tyr Asn Val Ser Gln Ile Phe Leu
 65                  70                  75                  80

Cys Ala Tyr Met Thr Val Glu Ala Gly Phe Leu Ala Tyr Arg Asn Gly
                 85                  90                  95

Tyr Thr Val Met Pro Cys Asn His Phe Asn Val Asn Asp Pro Pro Val
                100                 105                 110

Ala Asn Leu Leu Trp Leu Phe Tyr Ile Ser Lys Val Trp Asp Phe Trp
            115                 120                 125

Asp Thr Ile Phe Ile Val Leu Gly Lys Lys Trp Arg Gln Leu Ser Phe
130                 135                 140

Leu His Val Tyr His His Thr Thr Ile Phe Leu Phe Tyr Trp Leu Asn
145                 150                 155                 160

Ala Asn Val Leu Tyr Asp Gly Asp Ile Phe Leu Thr Ile Leu Leu Asn
                165                 170                 175

Gly Phe Ile His Thr Val Met Tyr Thr Tyr Phe Ile Cys Met His
            180                 185                 190

Thr Lys Asp Ser Lys Thr Gly Lys Ser Leu Pro Ile Trp Trp Lys Ser
            195                 200                 205

Ser Leu Thr Ala Phe Gln Leu Gln Phe Thr Ile Met Met Ser Gln
210                 215                 220

Ala Thr Tyr Leu Val Phe His Gly Cys Asp Lys Val Ser Leu Arg Ile
225                 230                 235                 240

Thr Ile Val Tyr Phe Val Tyr Ile Leu Ser Leu Phe Phe Leu Phe Ala
                245                 250                 255

Gln Phe Phe Val Gln Ser Tyr Met Ala Pro Lys Lys Lys Ser Ala
            260                 265                 270

<210> SEQ ID NO 62
<211> LENGTH: 873
<212> TYPE: DNA
<213> ORGANISM: Physcomitrella patens

<400> SEQUENCE: 62
atggaagttg ttgagaggtt ctacggagag ttggatggaa aggtttccca aggagtgaac      60
gctttgttgg atctttcgg agttgagttg actgataccc aactactaa gggattgcca      120 ctcgttgatt ctccaactcc aattgtgttg ggagtgtctg tttacttgac catcgtgatc      180
ggaggattgc tttggatcaa ggctagagat ctcaagccaa gagcttctga gccattcttg      240
ttgcaagctt tggtgttggt gcacaacttg ttctgcttcg ctttgtctct ttacatgtgt      300
gtgggaatcg cttaccaagc tatcacctgg agatattcct tgtggggaaa cgcttataac      360
ccaaagcaca aggagatggc tatcctcgtt tacctcttct acatgtccaa gtacgtggag      420
ttcatggata ccgtgatcat gatcctcaag agatctacca gacagatttc tttcctccac      480
gtgtaccacc actcttctat ctcccttatc tggtgggcta ttgctcacca cgctccagga      540
ggagaggctt attggagcgc tgctctcaac tctggagtgc acgtgttgat gtacgcttac      600
tacttcttgg ctgcttgctt gagatcttcc ccaaagctca agaacaagta cctcttctgg      660
ggaagatacc tcacccaatt ccagatgttc cagtttatgc tcaacttggt gcaagcttac      720
tacgatatga agaccaacgc tccatatcca cagtggctca tcaagatcct cttctactac      780
```

```
atgatctccc tcttgttcct cttcggaaac ttctacgtgc aaaagtacat caagccatca      840
gatggaaagc aaaagggagc taagaccgag tga                                   873
```

<210> SEQ ID NO 63
<211> LENGTH: 290
<212> TYPE: PRT
<213> ORGANISM: Physcomitrella patens

<400> SEQUENCE: 63

```
Met Glu Val Val Glu Arg Phe Tyr Gly Glu Leu Asp Gly Lys Val Ser
1               5                   10                  15

Gln Gly Val Asn Ala Leu Leu Gly Ser Phe Gly Val Glu Leu Thr Asp
            20                  25                  30

Thr Pro Thr Thr Lys Gly Leu Pro Leu Val Asp Ser Pro Thr Pro Ile
        35                  40                  45

Val Leu Gly Val Ser Val Tyr Leu Thr Ile Val Ile Gly Gly Leu Leu
    50                  55                  60

Trp Ile Lys Ala Arg Asp Leu Lys Pro Arg Ala Ser Glu Pro Phe Leu
65                  70                  75                  80

Leu Gln Ala Leu Val Leu Val His Asn Leu Phe Cys Phe Ala Leu Ser
                85                  90                  95

Leu Tyr Met Cys Val Gly Ile Ala Tyr Gln Ala Ile Thr Trp Arg Tyr
            100                 105                 110

Ser Leu Trp Gly Asn Ala Tyr Asn Pro Lys His Lys Glu Met Ala Ile
        115                 120                 125

Leu Val Tyr Leu Phe Tyr Met Ser Lys Tyr Val Glu Phe Met Asp Thr
    130                 135                 140

Val Ile Met Ile Leu Lys Arg Ser Thr Arg Gln Ile Ser Phe Leu His
145                 150                 155                 160

Val Tyr His His Ser Ser Ile Ser Leu Ile Trp Trp Ala Ile Ala His
                165                 170                 175

His Ala Pro Gly Gly Glu Ala Tyr Trp Ser Ala Ala Leu Asn Ser Gly
            180                 185                 190

Val His Val Leu Met Tyr Ala Tyr Tyr Phe Leu Ala Ala Cys Leu Arg
        195                 200                 205

Ser Ser Pro Lys Leu Lys Asn Lys Tyr Leu Phe Trp Gly Arg Tyr Leu
    210                 215                 220

Thr Gln Phe Gln Met Phe Gln Phe Met Leu Asn Leu Val Gln Ala Tyr
225                 230                 235                 240

Tyr Asp Met Lys Thr Asn Ala Pro Tyr Pro Gln Trp Leu Ile Lys Ile
                245                 250                 255

Leu Phe Tyr Tyr Met Ile Ser Leu Leu Phe Leu Phe Gly Asn Phe Tyr
            260                 265                 270

Val Gln Lys Tyr Ile Lys Pro Ser Asp Gly Lys Gln Lys Gly Ala Lys
        275                 280                 285

Thr Glu
    290
```

<210> SEQ ID NO 64
<211> LENGTH: 1320
<212> TYPE: DNA
<213> ORGANISM: Thraustochytrium sp.

<400> SEQUENCE: 64

```
atgggaaaag gatctgaggg aagatctgct gctagagaga tgactgctga ggctaacgga      60
```

-continued

```
gataagagaa agaccatcct cattgaggga gtgttgtacg atgctaccaa cttcaaacac      120
ccaggaggtt ccattattaa cttcctcacc gagggagaag ctggagttga tgctacccaa      180
gcttacagag agttccatca gagatccgga aaggctgata agtacctcaa gtccctccca      240
aagttggatg cttctaaggt ggagtctagg ttctctgcta aggagcaggc tagaagggac      300
gctatgacca gggattacgc tgctttcaga gaggagttgg ttgctgaggg atacttcgat      360
ccatctatcc cacacatgat ctacagagtg gtggagattg tggctttgtt cgctttgtct      420
ttctggttga tgtctaaggc ttctccaacc tctttggttt tgggagtggt gatgaacgga      480
atcgctcaag aagatgcgg atgggttatg cacgagatgg gacacggatc tttcactgga       540
gttatctggc tcgatgatag gatgtgcgag ttcttctacg gagttggatg tggaatgtct      600
ggacactact ggaagaacca gcactctaag caccacgctg ctccaaacag attggagcac      660
gatgtggatt tgaacaccct tgccactcgt tgctttcaacg agagagttgt gaggaaggtt     720
aagccaggat ctttgttggc tttgtggctc agagttcagg cttatttgtt cgctccagtg      780
tcttgcttgt tgatcggatt gggatggacc ttgtacttgc acccaagata tatgctcagg      840
accaagagac acatggagtt tgtgtggatc ttcgctagat atatcggatg gttctccttg      900
atgggagctt gggatattc tcctggaact tctgtgggaa tgtacctctg ctcttcgga       960 cttggatgca tctacatctt cctccaattc gctgtgtctc acacccactt gccagttacc     1020
aacccagagg atcaattgca ctggcttgag tacgctgctg atcacaccgt gaacatctct      1080
accaagtctt ggttggttac ctggtggatg tctaacctca acttccaaat cgagcaccac      1140
ttgttcccaa ccgctccaca attcaggttc aaggagatct ctccaagagt tgaggctctc      1200
ttcaagagac acaacctccc ttactacgat ttgccataca cctctgctgt ttctactacc      1260
ttcgctaacc tctactctgt tggacactct gttggagctg ataccaagaa gcaggattga     1320
```

<210> SEQ ID NO 65
<211> LENGTH: 439
<212> TYPE: PRT
<213> ORGANISM: Thraustochytrium sp.

<400> SEQUENCE: 65

| Met | Gly | Lys | Gly | Ser | Glu | Gly | Arg | Ser | Ala | Ala | Arg | Glu | Met | Thr | Ala |
|---|---|---|---|---|---|---|---|---|---|---|---|---|---|---|---|
| 1 | | | | 5 | | | | | 10 | | | | | 15 | |

Glu Ala Asn Gly Asp Lys Arg Lys Thr Ile Leu Ile Glu Gly Val Leu
           20                  25                  30

Tyr Asp Ala Thr Asn Phe Lys His Pro Gly Gly Ser Ile Ile Asn Phe
        35                  40                  45

Leu Thr Glu Gly Glu Ala Gly Val Asp Ala Thr Gln Ala Tyr Arg Glu
    50                  55                  60

Phe His Gln Arg Ser Gly Lys Ala Asp Lys Tyr Leu Lys Ser Leu Pro
65                  70                  75                  80

Lys Leu Asp Ala Ser Lys Val Glu Ser Arg Phe Ser Ala Lys Glu Gln
                85                  90                  95

Ala Arg Arg Asp Ala Met Thr Arg Asp Tyr Ala Ala Phe Arg Glu Glu
            100                 105                 110

Leu Val Ala Glu Gly Tyr Phe Asp Pro Ser Ile Pro His Met Ile Tyr
        115                 120                 125

Arg Val Val Glu Ile Val Ala Leu Phe Ala Leu Ser Phe Trp Leu Met
    130                 135                 140

Ser Lys Ala Ser Pro Thr Ser Leu Val Leu Gly Val Val Met Asn Gly

```
            145                 150                 155                 160
Ile Ala Gln Gly Arg Cys Gly Trp Val Met His Glu Met Gly His Gly
                165                 170                 175

Ser Phe Thr Gly Val Ile Trp Leu Asp Asp Arg Met Cys Glu Phe Phe
            180                 185                 190

Tyr Gly Val Gly Cys Gly Met Ser Gly His Tyr Trp Lys Asn Gln His
        195                 200                 205

Ser Lys His His Ala Ala Pro Asn Arg Leu Glu His Asp Val Asp Leu
    210                 215                 220

Asn Thr Leu Pro Leu Val Ala Phe Asn Glu Arg Val Val Arg Lys Val
225                 230                 235                 240

Lys Pro Gly Ser Leu Leu Ala Leu Trp Leu Arg Val Gln Ala Tyr Leu
                245                 250                 255

Phe Ala Pro Val Ser Cys Leu Leu Ile Gly Leu Gly Trp Thr Leu Tyr
            260                 265                 270

Leu His Pro Arg Tyr Met Leu Arg Thr Lys Arg His Met Glu Phe Val
        275                 280                 285

Trp Ile Phe Ala Arg Tyr Ile Gly Trp Phe Ser Leu Met Gly Ala Leu
    290                 295                 300

Gly Tyr Ser Pro Gly Thr Ser Val Gly Met Tyr Leu Cys Ser Phe Gly
305                 310                 315                 320

Leu Gly Cys Ile Tyr Ile Phe Leu Gln Phe Ala Val Ser His Thr His
                325                 330                 335

Leu Pro Val Thr Asn Pro Glu Asp Gln Leu His Trp Leu Glu Tyr Ala
            340                 345                 350

Ala Asp His Thr Val Asn Ile Ser Thr Lys Ser Trp Leu Val Thr Trp
        355                 360                 365

Trp Met Ser Asn Leu Asn Phe Gln Ile Glu His Leu Phe Pro Thr
    370                 375                 380

Ala Pro Gln Phe Arg Phe Lys Glu Ile Ser Pro Arg Val Glu Ala Leu
385                 390                 395                 400

Phe Lys Arg His Asn Leu Pro Tyr Tyr Asp Leu Pro Tyr Thr Ser Ala
                405                 410                 415

Val Ser Thr Thr Phe Ala Asn Leu Tyr Ser Val Gly His Ser Val Gly
            420                 425                 430

Ala Asp Thr Lys Lys Gln Asp
        435

<210> SEQ ID NO 66
<211> LENGTH: 792
<212> TYPE: DNA
<213> ORGANISM: Isochrysis galbana

<400> SEQUENCE: 66
atggccctcg caaacgacgc gggagagcgc atctgggcgg ctgtgaccga cccggaaatc    60
ctcattggca ccttctcgta cttgctactc aaaccgctgc tccgcaattc cgggctggtg   120
gatgagaaga agggcgcata caggacgtcc atgatctggt acaacgttct gctggcgctc   180
ttctctgcgc tgagcttcta cgtgacggcg accgccctcg ctgggactac tggtacgggc   240
gcgtggctgc gcaggcaaac cggcgacaca ccgcagccgc tcttccagtg cccgtccccg   300
gtttgggact cgaagctctt cacatggacc gccaaggcat tctattactc aagtacgtg    360 gagtacctcg acacggcctg gctggtgctc aagggcaaga gggtctcctt ctctccaggcc   420 ttccaccact tggcgcgcc gtgggatgtg tacctcggca ttcggctgca caacgagggc   480
```

```
gtatggatct tcatgttttt caactcgttc attcacacca tcatgtacac ctactacggc    540
ctcaccgccg ccgggtataa gttcaaggcc aagccgctca tcaccgcgat gcagatctgc    600
cagttcgtgg gcggcttcct gttggtctgg gactacatca acgtcccctg cttcaactcg    660
gacaaaggga gttgttcag ctgggctttc aactatgcat acgtcggctc ggtcttcttg    720
ctcttctgcc acttttcta ccaggacaac ttggcaacga gaaatcggc caaggcgggc      780 aagcagctct ag                                                        792
```

<210> SEQ ID NO 67
<211> LENGTH: 263
<212> TYPE: PRT
<213> ORGANISM: Isochrysis galbana

<400> SEQUENCE: 67

```
Met Ala Leu Ala Asn Asp Ala Gly Glu Arg Ile Trp Ala Ala Val Thr
1               5                   10                  15

Asp Pro Glu Ile Leu Ile Gly Thr Phe Ser Tyr Leu Leu Leu Lys Pro
            20                  25                  30

Leu Leu Arg Asn Ser Gly Leu Val Asp Glu Lys Lys Gly Ala Tyr Arg
        35                  40                  45

Thr Ser Met Ile Trp Tyr Asn Val Leu Leu Ala Leu Phe Ser Ala Leu
    50                  55                  60

Ser Phe Tyr Val Thr Ala Thr Ala Leu Gly Trp Asp Tyr Gly Thr Gly
65                  70                  75                  80

Ala Trp Leu Arg Arg Gln Thr Gly Asp Thr Pro Gln Pro Leu Phe Gln
                85                  90                  95

Cys Pro Ser Pro Val Trp Asp Ser Lys Leu Phe Thr Trp Thr Ala Lys
            100                 105                 110

Ala Phe Tyr Tyr Ser Lys Tyr Val Glu Tyr Leu Asp Thr Ala Trp Leu
        115                 120                 125

Val Leu Lys Gly Lys Arg Val Ser Phe Leu Gln Ala Phe His His Phe
    130                 135                 140

Gly Ala Pro Trp Asp Val Tyr Leu Gly Ile Arg Leu His Asn Glu Gly
145                 150                 155                 160

Val Trp Ile Phe Met Phe Phe Asn Ser Phe Ile His Thr Ile Met Tyr
                165                 170                 175

Thr Tyr Tyr Gly Leu Thr Ala Ala Gly Tyr Lys Phe Lys Ala Lys Pro
            180                 185                 190

Leu Ile Thr Ala Met Gln Ile Cys Gln Phe Val Gly Gly Phe Leu Leu
        195                 200                 205

Val Trp Asp Tyr Ile Asn Val Pro Cys Phe Asn Ser Asp Lys Gly Lys
    210                 215                 220

Leu Phe Ser Trp Ala Phe Asn Tyr Ala Tyr Val Gly Ser Val Phe Leu
225                 230                 235                 240

Leu Phe Cys His Phe Phe Tyr Gln Asp Asn Leu Ala Thr Lys Lys Ser
                245                 250                 255

Ala Lys Ala Gly Lys Gln Leu
            260
```

<210> SEQ ID NO 68
<211> LENGTH: 1236
<212> TYPE: DNA
<213> ORGANISM: Perkinsus marinus

<400> SEQUENCE: 68

```
atgtcttctc ttaccctcta cagaggcccc ttttcccgaa tggtgctccc tcgtcaggaa    60
atctgcatcg atggtcgcat atacgatgtc actgagttca tcaatcgtca tccaggtggt   120
aagattatcc tcttccaagt tggtgctgat gccactgatg cttttcgtga gtttcatgct   180
ggcagtgaga aggcagagaa gatcctcaaa accctaccat cccgtgatga tgacggtact   240
ttccttcctt caacccaacg ctccatcatg gatgatttca aacgcctaag agatgacctc   300
gtcagcagag gtgtcttcaa gccaagcgtc atgcatgttg tataccgctg cttggaagtc   360
gttgctctct atctcattgg cttctatttg gctctgtgca ccagtaatgt gtacgttggg   420
tgtgctgtac ttggtgtagc tcaaggtcgt gctggttggt tgatgcatga aggaggtcat   480
cactctctga ctggtaactg aaagttgac cagttcctcc aagaactatt tttcggcatt    540
ggttgtggta tgtcagctgc gtggtggcgc aatgcacaca acaagcatca cgctgctcct   600
cagcatttag ggaaagatgt tgatctcgag acattgcctc tggtcgcctt caataaggcc   660
gtacttcgag gccgtctacc gtctgtctgg atcagatcac aagctgtgtg ctttgcaccg   720
atatcaacac tactggtatc gttcttttgg caattctacc tacacccgag gcatattatt   780
aggacaggtc gacgaatgga gtctttctgg ctactcgtac gctacttagt tattgtgtac   840
ctcgggttca gctatggatt ggtatcggtc ttgttatgtt acatcgcaag tgtgcatgtt   900
ggtggtatgt acatctttgt acacttcgct ctatcacata cacatttacc tgtcattaac   960
cagcatggta gagctaactg gttggaatac gcatctaagc acacagttaa tgtgtcaact  1020
aacaattatt tcgtcacatg gctcatgagt tatttgaatt atcaaataga gcatcatctc  1080
ttcccgtcat gtccccagtt tagattccct ggttacgtca gtatgagggt tcgagaattt  1140
tttcataagc atggattgaa gtataacgag gtcggctatc tacatgcact caatctcaca  1200
ttttcaaatc tggctgctgt tgccatagtg gaatag                             1236
```

<210> SEQ ID NO 69
<211> LENGTH: 411
<212> TYPE: PRT
<213> ORGANISM: Perkinsus marinus

<400> SEQUENCE: 69

Met Ser Ser Leu Thr Leu Tyr Arg Gly Pro Phe Ser Arg Met Val Leu
1               5                   10                  15

Pro Arg Gln Glu Ile Cys Ile Asp Gly Arg Ile Tyr Asp Val Thr Glu
            20                  25                  30

Phe Ile Asn Arg His Pro Gly Gly Lys Ile Ile Leu Phe Gln Val Gly
        35                  40                  45

Ala Asp Ala Thr Asp Ala Phe Arg Glu Phe His Ala Gly Ser Glu Lys
    50                  55                  60

Ala Glu Lys Ile Leu Lys Thr Leu Pro Ser Arg Asp Asp Asp Gly Thr
65                  70                  75                  80

Phe Leu Pro Ser Thr Gln Arg Ser Ile Met Asp Asp Phe Lys Arg Leu
                85                  90                  95

Arg Asp Asp Leu Val Ser Arg Gly Val Phe Lys Pro Ser Val Met His
            100                 105                 110

Val Val Tyr Arg Cys Leu Glu Val Ala Leu Tyr Leu Ile Gly Phe
        115                 120                 125

Tyr Leu Ala Leu Cys Thr Ser Asn Val Tyr Val Gly Cys Ala Val Leu
    130                 135                 140

Gly Val Ala Gln Gly Arg Ala Gly Trp Leu Met His Glu Gly Gly His

```
                145                 150                 155                 160
His Ser Leu Thr Gly Asn Trp Lys Val Asp Gln Phe Leu Gln Glu Leu
                165                 170                 175

Phe Phe Gly Ile Gly Cys Gly Met Ser Ala Ala Trp Trp Arg Asn Ala
                180                 185                 190

His Asn Lys His His Ala Ala Pro Gln His Leu Gly Lys Asp Val Asp
                195                 200                 205

Leu Glu Thr Leu Pro Leu Val Ala Phe Asn Lys Ala Val Leu Arg Gly
210                 215                 220

Arg Leu Pro Ser Val Trp Ile Arg Ser Gln Ala Val Cys Phe Ala Pro
225                 230                 235                 240

Ile Ser Thr Leu Leu Val Ser Phe Phe Trp Gln Phe Tyr Leu His Pro
                245                 250                 255

Arg His Ile Ile Arg Thr Gly Arg Met Glu Ser Phe Trp Leu Leu
                260                 265                 270

Val Arg Tyr Leu Val Ile Val Tyr Leu Gly Phe Ser Tyr Gly Leu Val
                275                 280                 285

Ser Val Leu Leu Cys Tyr Ile Ala Ser Val His Val Gly Gly Met Tyr
290                 295                 300

Ile Phe Val His Phe Ala Leu Ser His Thr His Leu Pro Val Ile Asn
305                 310                 315                 320

Gln His Gly Arg Ala Asn Trp Leu Glu Tyr Ala Ser Lys His Thr Val
                325                 330                 335

Asn Val Ser Thr Asn Asn Tyr Phe Val Thr Trp Leu Met Ser Tyr Leu
                340                 345                 350

Asn Tyr Gln Ile Glu His His Leu Phe Pro Ser Cys Pro Gln Phe Arg
                355                 360                 365

Phe Pro Gly Tyr Val Ser Met Arg Val Arg Glu Phe Phe His Lys His
                370                 375                 380

Gly Leu Lys Tyr Asn Glu Val Gly Tyr Leu His Ala Leu Asn Leu Thr
385                 390                 395                 400

Phe Ser Asn Leu Ala Ala Val Ala Ile Val Glu
                405                 410

<210> SEQ ID NO 70
<211> LENGTH: 1128
<212> TYPE: DNA
<213> ORGANISM: Helobdella robusta

<400> SEQUENCE: 70
atgaattgtg ttaccgaggt gaacagcatc attgctagcc ttatcaaggc tgctttcctc       60
tactctaacc ctcagaccaa gatcagaggt atcaaccttg ataccagct tcctaagaac      120 ctcccttctg tgatcgagat caagagggtt atcccttctc attgcttcgt tccttctacc     180
tgccgttctc ttctttacgc tctcaaggac gttgttcaga tccttttcgc ttgggttctc    240
ctttggtact tgcttcctct cactaactgg atcgctctca aggttctcat gatcttcgtg    300
tactggggaa tccagggaac tttcttcatg ggactcttcg ttatgggaca tgattgtgga    360
cacggaagct tctctaagta ccgtcttttg aacgatgttg tgggaactat ctctcacgct    420
ttcctcttcg tgccttacta ccagtggaag cttactcatc agaaccacca caagttcacc    480
ggaaacatgg ataaggacga ggttttctac cctgctagag cttctcaaaa gcctagcatc    540
aactctgttc tccctggatt cggatacgga atcggatggt tcacttacct cttcatcgga    600
tacttcccta agagtgtc tcacttcaac ctcttcgacg agatgttcag aggacatgaa    660
```

```
gttgcttgca ccctttctct tctcacctac ggaatgaacg gaactctttg ctactggttc     720
tacctcagct acggattcaa gatcctcttc gtgttctacc ttgctcctct cttcatctac     780
ggaagctaca tggttatcgt gactttcctt caccactctg aggttaacat cccttggtac     840
gctgatcaaa actggaacta cgtgaaggga cagctttcta ccatcgacag aaactacgga     900
cttgttcacc atgctatcca ctgtatcgga actcatcaga tgcatacat gttcaccaag      960 atccctcatt accaccttga ggaagctact agacacttcc gttctgcttt ccctgagctt    1020
gttaagtctt gcgacgagcc tatcctctct tctttcgtcc gtatgttcaa gaagtacaac    1080
cagcaacagg ttgtggctga taacgctctc gaggtgtact acaagtga                 1128
```

<210> SEQ ID NO 71
<211> LENGTH: 375
<212> TYPE: PRT
<213> ORGANISM: Helobdella robusta

<400> SEQUENCE: 71

```
Met Asn Cys Val Thr Glu Val Asn Ser Ile Ile Ala Ser Leu Ile Lys
1               5                   10                  15

Ala Ala Phe Leu Tyr Ser Asn Pro Gln Thr Lys Ile Arg Gly Ile Asn
            20                  25                  30

Leu Asp Thr Gln Leu Pro Lys Asn Leu Pro Ser Val Ile Glu Ile Lys
        35                  40                  45

Arg Val Ile Pro Ser His Cys Phe Val Pro Ser Thr Cys Arg Ser Leu
    50                  55                  60

Leu Tyr Ala Leu Lys Asp Val Val Gln Ile Leu Phe Ala Trp Val Leu
65                  70                  75                  80

Leu Trp Tyr Leu Pro Leu Thr Asn Trp Ile Ala Leu Lys Val Leu
                85                  90                  95

Met Ile Phe Val Tyr Trp Gly Ile Gln Gly Thr Phe Met Gly Leu
                100                 105                 110

Phe Val Met Gly His Asp Cys Gly His Gly Ser Phe Ser Lys Tyr Arg
            115                 120                 125

Leu Leu Asn Asp Val Val Gly Thr Ile Ser His Ala Phe Leu Phe Val
        130                 135                 140

Pro Tyr Tyr Gln Trp Lys Leu Thr His Gln Asn His His Lys Phe Thr
145                 150                 155                 160

Gly Asn Met Asp Lys Asp Glu Val Phe Tyr Pro Ala Arg Ala Ser Gln
                165                 170                 175

Lys Pro Ser Ile Asn Ser Val Leu Pro Gly Phe Gly Tyr Gly Ile Gly
            180                 185                 190

Trp Phe Thr Tyr Leu Phe Ile Gly Tyr Phe Pro Arg Arg Val Ser His
        195                 200                 205

Phe Asn Leu Phe Asp Glu Met Phe Arg Gly His Glu Val Ala Cys Thr
    210                 215                 220

Leu Ser Leu Leu Thr Tyr Gly Met Asn Gly Thr Leu Cys Tyr Trp Phe
225                 230                 235                 240

Tyr Leu Ser Tyr Gly Phe Lys Ile Leu Phe Val Phe Tyr Leu Ala Pro
                245                 250                 255

Leu Phe Ile Tyr Gly Ser Tyr Met Val Ile Val Thr Phe Leu His His
            260                 265                 270

Ser Glu Val Asn Ile Pro Trp Tyr Ala Asp Gln Asn Trp Asn Tyr Val
        275                 280                 285
```

```
Lys Gly Gln Leu Ser Thr Ile Asp Arg Asn Tyr Gly Leu Val His His
    290                 295                 300

Ala Ile His Cys Ile Gly Thr His Gln Met His His Met Phe Thr Lys
305                 310                 315                 320

Ile Pro His Tyr His Leu Glu Glu Ala Thr Arg His Phe Arg Ser Ala
                325                 330                 335

Phe Pro Glu Leu Val Lys Ser Cys Asp Glu Pro Ile Leu Ser Ser Phe
            340                 345                 350

Val Arg Met Phe Lys Lys Tyr Asn Gln Gln Val Val Ala Asp Asn
        355                 360                 365

Ala Leu Glu Val Tyr Tyr Lys
    370                 375

<210> SEQ ID NO 72
<211> LENGTH: 1086
<212> TYPE: DNA
<213> ORGANISM: Phytophthora infestans

<400> SEQUENCE: 72
atggcgacga aggaggcgta tgtgttcccc actctgacgg agatcaagcg gtcgctacct      60
aaagactgtt tcgaggcttc ggtgcctctg tcgctctact acaccgtgcg ttgtctggtg     120
atcgcggtgg ctctaacctt cggtctcaac tacgctcgcg ctctgcccga ggtcgagagc     180
ttctgggctc tggacgccgc actctgcacg ggctacatct tgctgcaggg catcgtgttc     240
tggggcttct tcacggtggg ccacgatgcc ggccacggcg ccttctcgcg ctaccacctg     300
cttaacttcg tggtgggcac tttcatgcac tcgctcatcc tcacgccctt cgagtcgtgg     360
aagctcacgc accgtcacca ccacaagaac acgggcaaca ttgaccgtga cgaggtcttc     420
tacccgcaac gcaaggccga cgaccaccgc ctgtctcgca acctgattct ggcgctcggg     480
gcagcgtggc tcgcctattt ggtcgagggc ttccctcctc gtaaggtcaa ccacttcaac     540
ccgttcgagc tctgttcgt gcgtcaggtg tcagctgtgg taatctctct tctcgcccac     600
ttcttcgtgg ccggactctc catctatctg agcctccagc tgggccttaa gacgatggca     660
atctactact atggacctgt ttttgtgttc ggcagcatgc tggtcattac caccttccta     720
caccacaatg atgaggagac cccatggtac gccgactcgg agtggacgta cgtcaagggc     780
aacctctcgt ccgtggaccg atcgtacggc gcgctcattg acaacctgag ccacaacatc     840
ggcacgcacc agatccacca ccttttccct atcattccgc actacaaact caagaaagcc     900
actgcggcct ccaccaggc tttccctgag ctcgtgcgca agagcgacga gccaattatc     960
aaggctttct tccgggttgg acgtctctac gcaaactacg gcgttgtgga ccaggaggcg    1020
aagctcttca cgctaaagga agccaaggcg gcgaccgagg cggcggccaa gaccaagtcc    1080
acgtaa                                                               1086

<210> SEQ ID NO 73
<211> LENGTH: 361
<212> TYPE: PRT
<213> ORGANISM: Phytophthora infestans

<400> SEQUENCE: 73

Met Ala Thr Lys Glu Ala Tyr Val Phe Pro Thr Leu Thr Glu Ile Lys
1               5                   10                  15

Arg Ser Leu Pro Lys Asp Cys Phe Glu Ala Ser Val Pro Leu Ser Leu
            20                  25                  30

Tyr Tyr Thr Val Arg Cys Leu Val Ile Ala Val Ala Leu Thr Phe Gly
```

```
                35                  40                  45
Leu Asn Tyr Ala Arg Ala Leu Pro Glu Val Glu Ser Phe Trp Ala Leu
 50                  55                  60
Asp Ala Ala Leu Cys Thr Gly Tyr Ile Leu Gln Gly Ile Val Phe
 65                  70                  75                  80
Trp Gly Phe Phe Thr Val Gly His Asp Ala Gly His Gly Ala Phe Ser
                 85                  90                  95
Arg Tyr His Leu Leu Asn Phe Val Val Gly Thr Phe Met His Ser Leu
            100                 105                 110
Ile Leu Thr Pro Phe Glu Ser Trp Lys Leu Thr His Arg His His His
        115                 120                 125
Lys Asn Thr Gly Asn Ile Asp Arg Asp Glu Val Phe Tyr Pro Gln Arg
130                 135                 140
Lys Ala Asp Asp His Pro Leu Ser Arg Asn Leu Ile Leu Ala Leu Gly
145                 150                 155                 160
Ala Ala Trp Leu Ala Tyr Leu Val Glu Gly Phe Pro Pro Arg Lys Val
                165                 170                 175
Asn His Phe Asn Pro Phe Glu Pro Leu Phe Val Arg Gln Val Ser Ala
            180                 185                 190
Val Val Ile Ser Leu Leu Ala His Phe Val Ala Gly Leu Ser Ile
        195                 200                 205
Tyr Leu Ser Leu Gln Leu Gly Leu Lys Thr Met Ala Ile Tyr Tyr Tyr
210                 215                 220
Gly Pro Val Phe Val Phe Gly Ser Met Leu Val Ile Thr Thr Phe Leu
225                 230                 235                 240
His His Asn Asp Glu Glu Thr Pro Trp Tyr Ala Asp Ser Glu Trp Thr
                245                 250                 255
Tyr Val Lys Gly Asn Leu Ser Ser Val Asp Arg Ser Tyr Gly Ala Leu
            260                 265                 270
Ile Asp Asn Leu Ser His Asn Ile Gly Thr His Gln Ile His His Leu
        275                 280                 285
Phe Pro Ile Ile Pro His Tyr Lys Leu Lys Lys Ala Thr Ala Ala Phe
290                 295                 300
His Gln Ala Phe Pro Glu Leu Val Arg Lys Ser Asp Glu Pro Ile Ile
305                 310                 315                 320
Lys Ala Phe Phe Arg Val Gly Arg Leu Tyr Ala Asn Tyr Gly Val Val
                325                 330                 335
Asp Gln Glu Ala Lys Leu Phe Thr Leu Lys Glu Ala Lys Ala Ala Thr
            340                 345                 350
Glu Ala Ala Ala Lys Thr Lys Ser Thr
        355                 360
```

<210> SEQ ID NO 74
<211> LENGTH: 903
<212> TYPE: DNA
<213> ORGANISM: Ostreococcus tauri

<400> SEQUENCE: 74

```
atgagcgcct ccggtgcgct gctgcccgcg atcgcgttcg ccgcgtacgc gtacgcgacg    60
tacgcctacg cctttgagtg gtcgcacgcg aatggcatcg acaacgtcga cgcgcgcgag   120
tggatcggtg cgctgtcgtt gaggctcccg gcgatcgcga cgacgatgta cctgttgttc   180
tgcctggtcg gaccgaggtt gatggcgaag cgcgaggcgt cgacccgaa ggggttcatg    240 ctggcgtaca atgcgtatca gacggcgttc aacgtcgtcg tgctcgggat gttcgcgcga   300
```

-continued

```
gagatctcgg ggctggggca gcccgtgtgg gggtcaacca tgccgtggag cgatagaaaa      360
tcgtttaaga tcctcctcgg ggtgtggttg cactacaaca accaatattt ggagctattg      420
gacactgtgt tcatggttgc gcgcaagaag acgaagcagt tgagcttctt gcacgtttat      480
catcacgccc tgttgatctg gcgtggtgg ttggtgtgtc acttgatggc acgaacgat       540
tgtatcgatg cctacttcgg cgcggcgtgc aactcgttca ttcacatcgt gatgtactcg      600
tattatctca tgtcggcgct cggcattcga tgcccgtgga agcgatacat cacccaggct      660
caaatgctcc aattcgtcat tgtcttcgcg cacgccgtgt tcgtgctgcg tcagaagcac      720
tgcccggtca cccttccttg ggcgcaaatg ttcgtcatga cgaacatgct cgtgctcttc      780
gggaacttct acctcaaggc gtactcgaac aagtcgcgcg gcgacggcgc gagttccgtg      840
aaaccagccg agaccacgcg cgcgcccagc gtgcgacgca cgcgatctcg aaaaattgac      900
taa                                                                   903
```

<210> SEQ ID NO 75
<211> LENGTH: 300
<212> TYPE: PRT
<213> ORGANISM: Ostreococcus tauri

<400> SEQUENCE: 75

```
Met Ser Ala Ser Gly Ala Leu Leu Pro Ala Ile Ala Phe Ala Ala Tyr
1               5                   10                  15

Ala Tyr Ala Thr Tyr Ala Tyr Ala Phe Glu Trp Ser His Ala Asn Gly
            20                  25                  30

Ile Asp Asn Val Asp Ala Arg Glu Trp Ile Gly Ala Leu Ser Leu Arg
        35                  40                  45

Leu Pro Ala Ile Ala Thr Thr Met Tyr Leu Leu Phe Cys Leu Val Gly
    50                  55                  60

Pro Arg Leu Met Ala Lys Arg Glu Ala Phe Asp Pro Lys Gly Phe Met
65                  70                  75                  80

Leu Ala Tyr Asn Ala Tyr Gln Thr Ala Phe Asn Val Val Leu Gly
                85                  90                  95

Met Phe Ala Arg Glu Ile Ser Gly Leu Gly Gln Pro Val Trp Gly Ser
            100                 105                 110

Thr Met Pro Trp Ser Asp Arg Lys Ser Phe Lys Ile Leu Leu Gly Val
            115                 120                 125

Trp Leu His Tyr Asn Asn Gln Tyr Leu Glu Leu Leu Asp Thr Val Phe
130                 135                 140

Met Val Ala Arg Lys Lys Thr Lys Gln Leu Ser Phe Leu His Val Tyr
145                 150                 155                 160

His His Ala Leu Leu Ile Trp Ala Trp Trp Leu Val Cys His Leu Met
                165                 170                 175

Ala Thr Asn Asp Cys Ile Asp Ala Tyr Phe Gly Ala Ala Cys Asn Ser
            180                 185                 190

Phe Ile His Ile Val Met Tyr Ser Tyr Tyr Leu Met Ser Ala Leu Gly
        195                 200                 205

Ile Arg Cys Pro Trp Lys Arg Tyr Ile Thr Gln Ala Gln Met Leu Gln
    210                 215                 220

Phe Val Ile Val Phe Ala His Ala Val Phe Val Leu Arg Gln Lys His
225                 230                 235                 240

Cys Pro Val Thr Leu Pro Trp Ala Gln Met Phe Val Met Thr Asn Met
                245                 250                 255
```

```
Leu Val Leu Phe Gly Asn Phe Tyr Leu Lys Ala Tyr Ser Asn Lys Ser
                260                 265                 270

Arg Gly Asp Gly Ala Ser Ser Val Lys Pro Ala Glu Thr Thr Arg Ala
            275                 280                 285

Pro Ser Val Arg Arg Thr Arg Ser Arg Lys Ile Asp
        290                 295                 300

<210> SEQ ID NO 76
<211> LENGTH: 1560
<212> TYPE: DNA
<213> ORGANISM: Thraustochytrium sp.

<400> SEQUENCE: 76
atgactgttg atacgacga ggagatccca ttcgagcaag ttagggctca taacaagcca      60
gacgacgctt ggtgtgctat tcacggacac gtgtacgacg ttaccaagtt cgcttcagtt    120
cacccaggag gagatattat cttgctcgct gctggaaagg aagctactgt cctctacgag    180
acctaccatg ttagaggagt gtctgacgct gtgctcagaa agtacagaat aggaaagttg    240
ccagacggac aaggaggagc taacgagaag gagaagagaa ccttgtctgg attgtcctct    300
gcttcttact acacctggaa ctccgatttc tacagagtga tgaggagag agttgtggct    360 agattgaagg agagaggaaa ggctagaaga ggaggatacg aactctggat caaggctttc    420
ttgctccttg ttggattctg gtcctctctt tactggatgt gcaccctcga tccatctttc    480
ggagctatct tggctgctat gtctttggga gtgttcgctg cttttgttgg aacctgcatc    540
caacacgatg gaaaccacgg agctttcgct caatctagat gggttaacaa ggtggcagga    600
tggactttgg atatgatcgg agcttctgga atgacttggg agttccaaca cgtgttggga    660
caccacccat acactaactt gatcgaggag gagaacggat gcaaaaggt gtccggaaag    720 aagatggata ccaagttggc tgatcaagag tctgatccag atgtgttctc cacctaccca    780
atgatgagat gcaccccttg gcaccagaag aggtggtatc acaggttcca gcacatctac    840 ggaccttca tcttcggatt catgaccatc aacaaggtgg tgactcaaga tgttggagtg    900
gtgttgagaa agagactctt ccaaatcgat gctgagtgca gatatgcttc cccaatgtac    960
gttgctaggt tctggattat gaaggctttg accgtgttgt atatggttgc tttgccttgt  1020
tatatgcaag gaccttggca cggattgaaa ctcttcgcta tcgctcactt cacttgcgga  1080
gaggttttgg ctaccatgtt catcgtgaac cacattatcg agggagtgtc ttacgcttct  1140
aaggatgctg ttaagggaac tatggctcca ccaaagacta tgcacggagt gacccccaatg  1200 aacaacacta gaaggaggt tgaggctgag gcttctaagt ctggagctgt ggttaagtct  1260
gtgccattgg atgattggc tgctgttcag tgccaaacct ctgtgaactg gtctgttgga  1320
tcttggtttt ggaaccactt ctctggagga ctcaaccacc aaatcgagca ccacctcttc  1380
ccaggattgt ctcacgagac ctactaccac atccaagacg tggttcaatc tacctgtgct  1440
gagtacggag ttccatacca acacgagcca tctttgtgga ctgcttactg gaagatgctc  1500
gaacacctta gacaattggg aaacgaggag actcacgagt catggcagag agctgcttga  1560

<210> SEQ ID NO 77
<211> LENGTH: 309
<212> TYPE: PRT
<213> ORGANISM: Thraustochytrium sp.

<400> SEQUENCE: 77

Met Thr Trp Glu Phe Gln His Val Leu Gly His His Pro Tyr Thr Asn
1               5                   10                  15
```

Leu Ile Glu Glu Glu Asn Gly Leu Gln Lys Val Ser Gly Lys Lys Met
            20                  25                  30

Asp Thr Lys Leu Ala Asp Gln Glu Ser Asp Pro Asp Val Phe Ser Thr
        35                  40                  45

Tyr Pro Met Met Arg Leu His Pro Trp His Lys Arg Trp Tyr His
    50                  55                  60

Arg Phe Gln His Ile Tyr Gly Pro Phe Ile Phe Gly Phe Met Thr Ile
65                  70                  75                  80

Asn Lys Val Val Thr Gln Asp Val Gly Val Val Leu Arg Lys Arg Leu
                85                  90                  95

Phe Gln Ile Asp Ala Glu Cys Arg Tyr Ala Ser Pro Met Tyr Val Ala
            100                 105                 110

Arg Phe Trp Ile Met Lys Ala Leu Thr Val Leu Tyr Met Val Ala Leu
        115                 120                 125

Pro Cys Tyr Met Gln Gly Pro Trp His Gly Leu Lys Leu Phe Ala Ile
    130                 135                 140

Ala His Phe Thr Cys Gly Glu Val Leu Ala Thr Met Phe Ile Val Asn
145                 150                 155                 160

His Ile Ile Glu Gly Val Ser Tyr Ala Ser Lys Asp Ala Val Lys Gly
                165                 170                 175

Thr Met Ala Pro Pro Lys Thr Met His Gly Val Thr Pro Met Asn Asn
            180                 185                 190

Thr Arg Lys Glu Val Glu Ala Glu Ser Lys Ser Gly Ala Val Val
        195                 200                 205

Lys Ser Val Pro Leu Asp Asp Trp Ala Ala Val Gln Cys Gln Thr Ser
    210                 215                 220

Val Asn Trp Ser Val Gly Ser Trp Phe Trp Asn His Phe Ser Gly Gly
225                 230                 235                 240

Leu Asn His Gln Ile Glu His His Leu Phe Pro Gly Leu Ser His Glu
                245                 250                 255

Thr Tyr Tyr His Ile Gln Asp Val Val Gln Ser Thr Cys Ala Glu Tyr
            260                 265                 270

Gly Val Pro Tyr Gln His Glu Pro Ser Leu Trp Thr Ala Tyr Trp Lys
        275                 280                 285

Met Leu Glu His Leu Arg Gln Leu Gly Asn Glu Glu Thr His Glu Ser
290                 295                 300

Trp Gln Arg Ala Ala
305

<210> SEQ ID NO 78
<211> LENGTH: 942
<212> TYPE: DNA
<213> ORGANISM: Sphaeroforma arctica

<400> SEQUENCE: 78
atgaccgaga ctgtgctgtg ggtgctgggc atcgtgtggg tcgtgtcgtt cgcgtcgtac    60
ctcgtgccgc agctcctgct caagctgcgc agtgtgcaga tctgaagga caagtatggc    120 gcaaagtggg ctctggtcac cggcgggtct agcgggattg ccgtgcgat cgttgagacg    180 ctcgctggcc aaggcctcaa catcgtcgtc gttgccatgc aggacaaggt cctcgacact    240
tctgtggagg agtacaagaa ggcgttccca agtgtcgaat tcgcaaggt gggggtcgac    300 ctgtcctccg cggaccgaat gcagcccatg cgtgaggcga ccaaagatat cgatgtgcag    360
gtcatcgtga caacgccgg ctatatcaag accggtttct ttgcggagac ccctttcggc    420

-continued

```
gcgcagctgg cgaaccacaa cgtgaacgca accgccgcca tggaggttgc ccaccactac      480
atcagcgcga tgcgggctaa gggtctcaaa gggtgcgtca ccttcacctc gtccccggct      540
ggattcatgc cgtgcccttt cagcgtcatg tacggcgcga ccaaggcgta tttgactact      600
tttgcgcaga gcctggcgcc ggagcttcgg tgtgacggga tcgacgtttg cgttgtgcac      660
ccctcgcccg tcgcctcgag cttttacgac aatacccacg ctcttgacgc cctgctgttc      720
ttcaaaagca ccgcgacggg gccgcagact atcgccaaca tcttgctcgc caacgtcggc      780
cgagcagtca ccatcgacca gggctactac ccaatctgcg tcaagctgct tcttaaagtg      840
ctcgacgtca actttctcgc cgagaccatc gcctccgtag cacactttat gcccgacttt      900
aaggccatga agtccacctc gtcgccgaag aaggtcgctt ga                        942

<210> SEQ ID NO 79
<211> LENGTH: 445
<212> TYPE: PRT
<213> ORGANISM: Sphaeroforma arctica

<400> SEQUENCE: 79

Met Pro Pro His Ser Arg Thr Lys Val Val Ser Asp Ser Asp Pro Glu
1               5                   10                  15

Leu Ser Asp Leu Lys Met Lys His Phe Thr Arg Glu Glu Ile Leu Asn
                20                  25                  30

His Thr Asn Asp Lys Tyr Cys Ile Leu Glu Asp Gly Val Tyr Asp Leu
            35                  40                  45

Thr Asn Phe Arg Asp Lys His Pro Gly Gly Asp Val Leu Asp Phe Phe
        50                  55                  60

Pro Gly Gln Asp Ala Thr Pro His Phe Tyr Met Leu His Gln Tyr Glu
65                  70                  75                  80

Ser Leu Pro Ser Val Leu Ala Glu Tyr Lys Val Gly Ser Val Ala Arg
                85                  90                  95

Asp Asp Ser Tyr Val Tyr His Thr Pro Leu Met Lys Gln Ile Lys Ser
            100                 105                 110

Ala Val Arg Lys Val Met Pro Met Gln Glu Trp Trp Ala Pro Pro Ser
        115                 120                 125

Trp Tyr Ile Lys Ala Cys Ala Ile Leu Ala Ala Thr Leu Tyr Thr Asp
    130                 135                 140

Tyr Leu Trp Ile Ala Ser Gly Pro Thr Ile Pro Leu Ala Ile Val Ser
145                 150                 155                 160

Gly Leu Leu Tyr Ala Ala Ile Gly Leu Asn Ile Gln His Asp Ala Asn
                165                 170                 175

His Gly Ser Val Ser Arg Asn Pro Met Val Asn Arg Leu Phe Gly Tyr
            180                 185                 190

Ser Gln Asp Trp Ile Gly Gly Ser Arg Met Leu Trp Ile Arg Gln His
        195                 200                 205

Val Val Gly His His Thr His Cys Asn Arg His Gln His Asp Pro Asp
    210                 215                 220

Val Lys Gly Gly Ser Val Ile Thr Leu Ser Arg Tyr Ser Leu Pro Lys
225                 230                 235                 240

Glu Phe His His Ile Gln Gln Tyr Tyr Phe Leu Pro Leu Ile Gln Leu
                245                 250                 255

Leu Gly Phe Gln Trp Val Phe Leu Gly Leu His Asp Leu Ile Glu Met
            260                 265                 270

Lys Tyr Lys Gly Glu Lys Leu Pro Glu Ser Tyr Arg Lys Glu Arg Asn
```

```
                275                 280                 285
Ile Ala Ile Gly Leu Arg Val Phe Phe Phe Ile Arg Lys Phe Val Val
            290                 295                 300

Pro Phe Ala Leu His Phe Ser Trp Tyr Thr Leu Leu Cys Thr Tyr Leu
305                 310                 315                 320

Trp Met Ala Ile Ala Ala Leu Tyr Leu Gly Phe Phe Ile Leu Ser
                325                 330                 335

His Ile Phe Val Gly Ala Lys Ser Leu Pro Glu Asp Ala Lys Asn Ile
            340                 345                 350

Asp Trp Ala Arg His Gln Ile Glu Ser Ser Asn Val Cys Gly Glu
                355                 360                 365

Lys Leu Gly Ile Ser Asn Gly Gly Leu Asn Tyr Gln Ile Glu His His
            370                 375                 380

Leu Phe Pro Arg Met Ser His Ala His Tyr Ser Lys Ile Gln Pro Val
385                 390                 395                 400

Val Gln Lys Val Cys Glu Glu Asn Gly Val Asn Tyr Lys Lys Phe Gly
                405                 410                 415

Thr Ile Leu Ser Asn Leu Asp Ser Thr Phe Arg Gln Val Lys Ala Leu
            420                 425                 430

Gly Ser Val Ala Val Tyr Asn Glu Phe Met Glu Gly Leu
                435                 440                 445
```

```
<210> SEQ ID NO 80
<211> LENGTH: 1453
<212> TYPE: DNA
<213> ORGANISM: Sphaeroforma arctica

<400> SEQUENCE: 80
taccaagaac cggaaaaact agcagctgta atacgactca ctatagggaa tattaagctc    60
gccctttgac gacatgcctc ctcacagtag aaccaaggtg gtcagtgact cagatcccga   120
gcttagtgat ctgaagatga agcacttcac gcgagaagag atcctcaacc acaccaatga   180
caagtactgc atcttggagg atggtgtgta tgatctcacg aacttcaggg ataagcatcc   240
tggtggcgat gttctggact tctttcccgg acaggatgcc acacctcact tctacatgct   300
gcaccaatac gaatcgctac cgtctgttct ggccgagtac aaggtgggca gtgtagccag   360
agatgacagc tatgtgtacc acacaccgct gatgaagcag atcaagtctg cagtgcgcaa   420
ggtcatgccc atgcaagaat ggtgggcgcc ccgtcgtgg tacatcaaag cctgtgctat   480
tctagcagca accctctaca cggactactt gtggattgcg tctgggccca ccattccgtt   540
ggcgatcgtt tccggtctgc tgtacgccgc aattggctta acattcagc acgatgccaa   600
ccacgggtcc gtgagcagga atcccatggt taatcgatta ttcggttact ctcaggattg   660
gatcggggga tcgcgtatgc tgtggatccg ccagcatgtt gttggtcacc atacacactg   720
caataggcat cagcatgacc agatgtaaa gggcggctca gtcatcactc tgtcgcggta   780
ttctctgccc aaggaattcc accacatcca gcagtactac ttcctgccgt tgatccaact   840
gctcggattc caatgggtgt tcctggggtt gcacgacctg attgagatga agtacaaggg   900
agaaaagctg ccggagagct accgaaagga gcgaaacatc gctatcggcc ttcgtgtttt   960
ttttttcatc cgtaaattcg ttgtaccgtt tgccctgcat ttctcgtggt acacgctcct  1020
ctgcacctac ctgtggatgg ccattgctgc tctgtacctg gcttcttct tcattctgtc  1080
gcacatcttc gtgggggcta agtcgttgcc ggaggatgcc aagaacattg attgggctag  1140
gcatcaaatc gagtcgtcct cgaacgtctg cggagagaag cttggcatct ccaacggcgg  1200
```

```
cctgaactat cagattgagc atcacttgtt ccccaggatg agtcatgcgc actacagcaa    1260
gatacagccg gtggtgcaga aggtgtgtga ggagaacggg gtgaactaca agaagttcgg    1320
taccatcctc agcaatctgg actcgaccttt ccgacaggtg aaggcgttgg gatcggttgc    1380
ggtgtacaac gagtttatgg aaggcttgtg agctgtgagt aaagggcgag ctcgagtcac    1440
tcatgaaagc cca                                                       1453

<210> SEQ ID NO 81
<211> LENGTH: 104
<212> TYPE: DNA
<213> ORGANISM: Artificial
<220> FEATURE:
<223> OTHER INFORMATION: Primer

<400> SEQUENCE: 81
ataaaagtat caacaaaaaa ttgttaatat acctctatac tttaacgtca aggagaaaaa     60
accccggatc ggcgcgccac catgaccgag actgtgctgt gggt                    104

<210> SEQ ID NO 82
<211> LENGTH: 101
<212> TYPE: DNA
<213> ORGANISM: Artificial
<220> FEATURE:
<223> OTHER INFORMATION: Primer

<400> SEQUENCE: 82
aactataaaa aaataaatag ggacctagac ttcaggttgt ctaactcctt ccttttcggt     60
tagagcggat ttaattaatc aagcgaccttt cttcggcgac g                      101

<210> SEQ ID NO 83
<211> LENGTH: 2055
<212> TYPE: DNA
<213> ORGANISM: Sphaeroforma arctica
<220> FEATURE:
<223> OTHER INFORMATION: fatty acyl CoA synthetase

<400> SEQUENCE: 83
atgggaaact ttctatcatc agaagcccct gccggcgagg cgtccggata cctataccgc     60
gacccaagcg acccgaaatt gaaggcgcag agtgtgatag caccgggtgg taactggggt    120
gcagatgctc accgctgtcc caaatatgtt gatggcaaag ccgaatggac tgaccttatc    180
acatccggca cacccggtcg cgagacctgc tacgcgaact tccaagcgac ggccaaagaa    240 caggggaca agccatggct gggcactcgt aaggtgcttt ctgacggaaa gcccggacct    300
tacgagttca tcacatacgg cgaaggcgct aagctggccg agcagatcgg aagtggtcta    360
atgaagttgg gtgttgcgcc taagagccct tttggagtat attccaagaa tcgtaccgag    420
tggctacttg ctgaacaagg agctaactgc tacagcatcc ccaccgtagc catctacgac    480
accctgggcg cagattcagt gcactacgta atggagcact ctgagatggt tggcgctttc    540
ttcgagagca agcaactgtc agttgtattg ggagccatca agaagggctt gccaaacttc    600
aaggttgcaa ttagtttcga tgaggtcacc gaagaggata aggaagacta caaggatgtc    660
ggcgttgatc tctacccgat caccgagtta tatgccttgg gcaaggataa atcgttcct    720 caccagcctc ccggcccgga tgatttgcac attcttatgt acacatccgg taccacaggc    780
gctcctaagg gtgtcatgat cactcaccgc agtatagtgt cactgcttgt ggggcttgct    840
aacgttatgg ctttgactag taatgatgtc cacttctcct tcttgccgct ggcccatatt    900
```

```
ttcgagcgtt tgactcagac atactgtgtg cgatgggcct gctcagtcgg attcttccgt    960
ggtgtcatcc ccgagcttat ggcggacgtg caggctctgc gacccaccta ctttgttgcc   1020
gtacctcgtg tgctaacacg catctatgac aagatcatcc agggtgttaa ggccgctgga   1080
ggagtcaagg agattctctt caacaaggca tttgctgcca gagatgccgc tctaaagaac   1140
ggagaagaca cacctatcta caatgcgctt atctttaaca agctgaagat ggcgctcgga   1200
ggtcgtgttc gtttcattct taccggatct gcacccctgg accccacagt gcacaacttt   1260
ttgcgcgtgt gcgtgtgtcc cgtcattttg caagggtatg gactaacaga gacctgtgct   1320
ggtgctgcca tctccttgac aacagatgtt gagctcggcc atgtaggtcc ccctctgaat   1380
gtgttcgaga cgaagctcgt gagtatcccc gatatgaact atctcactac tgacgagcag   1440
cctcgtggtg aggtgtgcat ccgtggagca ggtatcttcc agggctactt caagatgccc   1500
gagaagacca aggaagacat tgacgaggag ggttggttcc acaccggtga tgttggtcgc   1560
tggaacgatt ctggaagtct gtcaatcatc gaccgtaaga agtccatttt caagctggca   1620
caaggtgagt atctggctgc cgagtatctc gagcagcagt acggcaagtg tgagcacgcc   1680
ggacaggtgt ttgtgtatgg cgatcccttc cgtacctacc ctctggcagt gattgttcct   1740
gaggaggagg tggttatgct atgggcgaag gcaaacaagg tcagtggaag cttcaaggag   1800
atttgtaaaa cgccagagct aaaggctcta ctgaaggcgg aggttgtcga tgtgcacaag   1860
acatacaagc tcaagggata cgaactggtc aaggacttca tcgtcgagtc cgaggttttt   1920
actgtggata acgagttgct tactcccacg ttcaaattga agcgtcctaa cgctaccaag   1980
aaataccaag cggcactcac tgagatgtac gacaaggtcg atgccgaact tgccgcccgc   2040
caagccaaga aatga                                                    2055
```

<210> SEQ ID NO 84
<211> LENGTH: 684
<212> TYPE: PRT
<213> ORGANISM: Sphaeroforma arctica
<220> FEATURE:
<223> OTHER INFORMATION: fatty acyl CoA synthetase

<400> SEQUENCE: 84

Met Gly Asn Phe Leu Ser Ser Glu Ala Pro Ala Gly Glu Ala Ser Gly
1               5                   10                  15

Tyr Leu Tyr Pro Asp Pro Ser Asp Pro Lys Leu Lys Ala Gln Ser Val
            20                  25                  30

Ile Ala Pro Gly Gly Asn Trp Gly Ala Asp Ala His Arg Cys Pro Lys
        35                  40                  45

Tyr Val Asp Gly Lys Ala Glu Trp Thr Asp Leu Ile Thr Ser Gly Thr
    50                  55                  60

Pro Gly Arg Glu Thr Cys Tyr Ala Asn Phe Gln Ala Thr Ala Lys Glu
65                  70                  75                  80

Gln Gly Asp Lys Pro Trp Leu Gly Thr Arg Lys Val Leu Ser Asp Gly
                85                  90                  95

Lys Pro Gly Pro Tyr Glu Phe Ile Thr Tyr Gly Glu Gly Ala Lys Leu
            100                 105                 110

Ala Glu Gln Ile Gly Ser Gly Leu Met Lys Leu Gly Val Ala Pro Lys
        115                 120                 125

Ser Pro Phe Gly Val Tyr Ser Lys Asn Arg Thr Glu Trp Leu Leu Ala
    130                 135                 140

Glu Gln Gly Ala Asn Cys Tyr Ser Ile Pro Thr Val Ala Ile Tyr Asp
145                 150                 155                 160

```
Thr Leu Gly Ala Asp Ser Val His Tyr Val Met Glu His Ser Glu Met
                165                 170                 175

Val Gly Ala Phe Phe Glu Ser Lys Gln Leu Ser Val Val Leu Gly Ala
            180                 185                 190

Ile Lys Lys Gly Leu Pro Asn Phe Lys Val Ala Ile Ser Phe Asp Glu
                195                 200                 205

Val Thr Glu Glu Asp Lys Glu Asp Tyr Lys Asp Val Gly Val Asp Leu
            210                 215                 220

Tyr Pro Ile Thr Glu Leu Tyr Ala Leu Gly Lys Asp Asn Ile Val Pro
225                 230                 235                 240

His Gln Pro Pro Gly Pro Asp Asp Leu His Ile Leu Met Tyr Thr Ser
                245                 250                 255

Gly Thr Thr Gly Ala Pro Lys Gly Val Met Ile Thr His Arg Ser Ile
                260                 265                 270

Val Ser Leu Leu Val Gly Leu Ala Asn Val Met Ala Leu Thr Ser Asn
            275                 280                 285

Asp Val His Phe Ser Phe Leu Pro Leu Ala His Ile Phe Glu Arg Leu
            290                 295                 300

Thr Gln Thr Tyr Cys Val Arg Trp Ala Cys Ser Val Gly Phe Phe Arg
305                 310                 315                 320

Gly Val Ile Pro Glu Leu Met Ala Asp Val Gln Ala Leu Arg Pro Thr
                325                 330                 335

Tyr Phe Val Ala Val Pro Arg Val Leu Thr Arg Ile Tyr Asp Lys Ile
                340                 345                 350

Ile Gln Gly Val Lys Ala Ala Gly Gly Val Lys Glu Ile Leu Phe Asn
            355                 360                 365

Lys Ala Phe Ala Ala Arg Asp Ala Ala Leu Lys Asn Gly Glu Asp Thr
            370                 375                 380

Pro Ile Tyr Asn Ala Leu Ile Phe Asn Lys Leu Lys Met Ala Leu Gly
385                 390                 395                 400

Gly Arg Val Arg Phe Ile Leu Thr Gly Ser Ala Pro Leu Asp Pro Thr
                405                 410                 415

Val His Asn Phe Leu Arg Val Cys Val Cys Pro Val Ile Leu Gln Gly
            420                 425                 430

Tyr Gly Leu Thr Glu Thr Cys Ala Gly Ala Ala Ile Ser Leu Thr Thr
            435                 440                 445

Asp Val Glu Leu Gly His Val Gly Pro Pro Leu Asn Val Phe Glu Thr
            450                 455                 460

Lys Leu Val Ser Ile Pro Asp Met Asn Tyr Leu Thr Thr Asp Glu Gln
465                 470                 475                 480

Pro Arg Gly Glu Val Cys Ile Arg Gly Ala Gly Ile Phe Gln Gly Tyr
                485                 490                 495

Phe Lys Met Pro Glu Lys Thr Lys Glu Asp Ile Asp Glu Glu Gly Trp
                500                 505                 510

Phe His Thr Gly Asp Val Gly Arg Trp Asn Asp Ser Gly Ser Leu Ser
            515                 520                 525

Ile Ile Asp Arg Lys Lys Ser Ile Phe Lys Leu Ala Gln Gly Glu Tyr
            530                 535                 540

Leu Ala Ala Glu Tyr Leu Glu Gln Gln Tyr Gly Lys Cys Glu His Ala
545                 550                 555                 560

Gly Gln Val Phe Val Tyr Gly Asp Pro Phe Arg Thr Tyr Pro Leu Ala
                565                 570                 575
```

-continued

```
Val Ile Val Pro Glu Glu Val Val Met Leu Trp Ala Lys Ala Asn
                580                 585                 590

Lys Val Ser Gly Ser Phe Lys Glu Ile Cys Lys Thr Pro Glu Leu Lys
            595                 600                 605

Ala Leu Leu Lys Ala Glu Val Val Asp Val His Lys Thr Tyr Lys Leu
        610                 615                 620

Lys Gly Tyr Glu Leu Val Lys Asp Phe Ile Val Glu Ser Glu Val Phe
625                 630                 635                 640

Thr Val Asp Asn Glu Leu Leu Thr Pro Thr Phe Lys Leu Lys Arg Pro
                645                 650                 655

Asn Ala Thr Lys Lys Tyr Gln Ala Ala Leu Thr Glu Met Tyr Asp Lys
            660                 665                 670

Val Asp Ala Glu Leu Ala Ala Arg Gln Ala Lys Lys
        675                 680

<210> SEQ ID NO 85
<211> LENGTH: 485
<212> TYPE: PRT
<213> ORGANISM: Artificial
<220> FEATURE:
<223> OTHER INFORMATION: delta-4 desaturase long preferred consensus
      sequence

<400> SEQUENCE: 85

Met Pro Pro His Ala Ala Thr Lys Val Gly Gly Asp Ser Asp Pro Glu
1               5                   10                  15

Leu Arg Asp Leu Lys Met Glu His Phe Ser Tyr Glu Arg Ile Leu Asn
            20                  25                  30

Asp Glu Arg Asp Asp Leu Cys Ile Val Gly Asp Gly Val Tyr Asp Ala
        35                  40                  45

Thr Ala Phe Arg Asp Lys His Pro Gly Gly Ala Asp Phe Val Asp Leu
    50                  55                  60

Phe Gly Gly Arg Asp Ala Thr Pro His Phe Phe Glu Tyr His Arg Arg
65                  70                  75                  80

Glu Trp Pro Pro Ala Val Leu Ala Lys Tyr Lys Val Gly Ser Leu Asp
                85                  90                  95

Arg Asp Asp Ser Tyr Val Gln His Asp Ser Gly Tyr Leu Arg Leu Cys
            100                 105                 110

Ala Glu Val Asn Gly Ile Leu Pro Lys Gly Ser Gly Gly Trp Ala Pro
        115                 120                 125

Pro Ser Trp Trp Ile Lys Ala Cys Ala Leu Leu Val Ala Ala Leu Tyr
    130                 135                 140

Leu Asp Tyr Tyr Met Leu Ala Arg Gly Pro Thr Ile Leu Leu Ala Ile
145                 150                 155                 160

Ile Leu Gly Leu Leu Phe Ala Trp Ile Gly Leu Asn Ile Gln His Asp
                165                 170                 175

Ala Asn His Gly Ala Leu Ser Arg Asn Pro Val Val Asn Tyr Leu Phe
            180                 185                 190

Gly Tyr Ala Gln Asp Trp Ile Gly Gly Ser Met Met Leu Trp Leu Gln
        195                 200                 205

Gln His Val Val Gly His His Leu His Thr Asn Asp Ile Asp His Asp
    210                 215                 220

Pro Asp Val Lys Gly Gly Gly Ala Leu Arg Leu Lys Pro Thr Asp Gly
225                 230                 235                 240

Trp Leu Pro Trp His His Leu Gln Gln Leu Tyr Phe Leu Pro Leu Glu
                245                 250                 255
```

Ala Leu Tyr Gly Phe Lys Trp Val Phe Leu Asp Leu His Glu Leu Leu
                260                 265                 270

Glu Trp Lys Trp Glu Gly Glu Pro Ile Pro Pro Leu Ala Arg Pro Glu
        275                 280                 285

Phe Ala Pro Ala Val Gly Cys Lys Leu Gly Phe Trp Ala Arg Phe Val
290                 295                 300

Ala Leu Pro Leu Trp Leu His Pro Ser Trp His Thr Leu Leu Cys Val
305                 310                 315                 320

Cys Ala Trp Val Cys Thr Gly Ser Phe Tyr Leu Ala Phe Phe Phe Ile
                325                 330                 335

Leu Ser His Ile Phe Ile Gly Val Lys Ser Ile Gly Pro Asp Gly Lys
                340                 345                 350

Ser Leu Pro Arg Asn Ile Asp Trp Ala Arg Arg Gln Ile Glu Thr Ser
        355                 360                 365

Ser Asn Val Gly Gly Glu Trp Leu Gly His Leu Asn Gly Gly Leu Asn
370                 375                 380

Phe Gln Ile Glu His His Leu Phe Pro Arg Leu His His Ala His Tyr
385                 390                 395                 400

Ala Lys Ile Gln Pro Val Val Gln Lys Val Cys Glu Glu Asn Gly Val
                405                 410                 415

Asn Tyr Lys His Phe Pro Thr Ile Gly Ser Asn Leu Gly Ser Met Leu
                420                 425                 430

Ser His Leu Gly Ala Leu Gly Ala Arg Pro Thr Trp Asn Ala Glu Phe
        435                 440                 445

Met Ala Gly Leu Glu Glu Lys Ser Ser Val Glu Cys Arg Leu Arg Leu
450                 455                 460

Gly Ala Ala Cys Ala Arg Gly Cys Trp Cys Ser Asp Ala Ala Ser Leu
465                 470                 475                 480

Ile Ser Trp Leu Gly
                485

<210> SEQ ID NO 86
<211> LENGTH: 437
<212> TYPE: PRT
<213> ORGANISM: Artificial
<220> FEATURE:
<223> OTHER INFORMATION: delta-4 desaturase short preferred consensus
      sequence

<400> SEQUENCE: 86

Met Pro Pro His Ala Ala Thr Lys Gly Gly Asp Pro Glu Leu Arg Asp
1               5                   10                  15

Met Glu His Phe Ser Tyr Glu Arg Ile Leu Asn Asp Glu Arg Asp Asp
                20                  25                  30

Leu Cys Ile Val Gly Asp Gly Val Tyr Asp Ala Thr Ala Phe Arg Asp
            35                  40                  45

Lys His Pro Gly Gly Asp Phe Val Asp Leu Phe Gly Arg Asp Ala
        50                  55                  60

Thr Pro His Phe Phe Glu Tyr His Arg Arg Glu Trp Pro Pro Ala Val
65                  70                  75                  80

Leu Ala Lys Tyr Lys Val Gly Ser Leu Asp Arg Asp Asp Ser Tyr Val
                85                  90                  95

Gln His Asp Ser Gly Tyr Leu Arg Leu Cys Ala Glu Val Asn Gly Ile
            100                 105                 110

Leu Pro Lys Gly Ser Gly Trp Ala Pro Pro Ser Trp Trp Ile Lys Ala

```
                115                 120                 125
        Cys Ala Leu Leu Val Ala Ala Leu Tyr Leu Asp Tyr Tyr Met Leu Ala
            130                 135                 140

Arg Gly Pro Thr Ile Leu Leu Ala Ile Ile Leu Gly Leu Leu Phe Ala
        145                 150                 155                 160

Trp Ile Gly Leu Asn Ile Gln His Asp Ala Asn His Gly Ala Leu Ser
                        165                 170                 175

Arg Asn Pro Val Val Asn Tyr Leu Phe Gly Tyr Ala Gln Asp Trp Ile
                    180                 185                 190

Gly Gly Ser Met Met Leu Trp Leu Gln Gln His Val Gly His His
                195                 200                 205

Leu His Thr Asn Asp Ile Asp His Asp Pro Asp Val Lys Gly Gly Gly
            210                 215                 220

Ala Leu Arg Leu Lys Pro Thr Asp Gly Trp Leu Pro Trp His His Leu
        225                 230                 235                 240

Gln Gln Leu Tyr Phe Leu Pro Leu Glu Ala Leu Tyr Gly Phe Lys Trp
                        245                 250                 255

Val Phe Leu Asp Leu His Glu Leu Leu Glu Trp Lys Trp Glu Gly Glu
                    260                 265                 270

Pro Ile Pro Pro Leu Ala Arg Pro Glu Phe Ala Pro Ala Val Gly Cys
                275                 280                 285

Lys Leu Gly Phe Trp Ala Arg Phe Val Ala Leu Pro Leu Trp Leu His
            290                 295                 300

Pro Ser Trp His Thr Leu Leu Cys Val Cys Ala Trp Val Cys Thr Gly
        305                 310                 315                 320

Ser Phe Tyr Leu Ala Phe Phe Phe Ile Leu Ser His Ile Phe Ile Gly
                        325                 330                 335

Val Lys Ser Ile Gly Pro Asp Gly Asn Ile Asp Trp Ala Arg Arg Gln
                    340                 345                 350

Ile Glu Thr Ser Ser Asn Val Gly Gly Glu Trp Leu Gly His Leu Asn
                355                 360                 365

Gly Gly Leu Asn Phe Gln Ile Glu His His Leu Phe Pro Arg Leu His
            370                 375                 380

His Ala His Tyr Ala Lys Ile Gln Pro Val Val Gln Lys Val Cys Glu
        385                 390                 395                 400

Glu Asn Gly Val Asn Tyr Lys His Phe Pro Thr Ile Gly Ser Asn Leu
                        405                 410                 415

Gly Ser Met Leu Ser His Leu Gly Ala Leu Gly Ala Arg Pro Thr Glu
                    420                 425                 430

Phe Met Ala Gly Leu
                435

<210> SEQ ID NO 87
<211> LENGTH: 439
<212> TYPE: PRT
<213> ORGANISM: Artificial
<220> FEATURE:
<223> OTHER INFORMATION: delta-4 desaturase 92.6% sequence identity to
      SEQ ID NO 79

<400> SEQUENCE: 87

Met Pro Pro His Ser Arg Thr Lys Val Gly Asp Pro Glu Leu Ser Asp
1               5                   10                  15

Leu Met Lys His Phe Thr Arg Glu Glu Ile Leu Asn His Thr Asn Asp
            20                  25                  30
```

```
Asp Tyr Cys Ile Leu Glu Asp Gly Val Tyr Asp Leu Val Asn Phe Arg
         35                  40                  45

Asp Lys His Pro Gly Gly Asp Val Val Asp Phe Phe Pro Gly Gln Asp
 50                  55                  60

Ala Thr Pro His Phe Tyr Met Tyr His Gln Tyr Glu Ser Pro Pro Ser
 65                  70                  75                  80

Val Leu Ala Glu Tyr Lys Val Gly Ser Ile Ala Arg Asp Asp Ser Tyr
                 85                  90                  95

Val Tyr His Thr Pro Leu Met Lys Gln Ile Cys Ser Glu Val Arg Lys
            100                 105                 110

Val Met Pro Met Gln Glu Gly Trp Ala Pro Ser Trp Tyr Ile Lys
            115                 120                 125

Ala Cys Ala Ile Leu Ala Ala Thr Leu Tyr Thr Asp Tyr Leu Trp Ile
130                 135                 140

Ala Ser Gly Pro Thr Ile Pro Leu Ala Ile Val Ser Gly Leu Leu Tyr
145                 150                 155                 160

Ala Ala Ile Gly Leu Asn Ile Gln His Asp Ala Asn His Gly Ser Val
                165                 170                 175

Ser Arg Asn Pro Met Val Asn Arg Leu Phe Gly Tyr Ser Gln Asp Trp
            180                 185                 190

Ile Gly Gly Ser Arg Met Leu Trp Ile Gln Gln His Val Val Gly His
        195                 200                 205

His Thr His Cys Asn Arg Ile Gln His Asp Pro Asp Val Lys Gly Gly
    210                 215                 220

Ser Val Ile Arg Leu Ser Arg Tyr Ser Leu Pro Lys Pro Phe His His
225                 230                 235                 240

Ile Gln Gln Tyr Tyr Phe Leu Pro Leu Glu Gln Leu Leu Gly Phe Gln
                245                 250                 255

Trp Val Phe Leu Gly Ala His Asp Leu Ile Glu Met Arg Tyr Lys Gly
            260                 265                 270

Glu Lys Leu Pro Glu Ser Tyr Arg Lys Glu Arg Asn Ile Ala Ile Gly
        275                 280                 285

Leu Arg Val Phe Phe Phe Val Arg Lys Phe Ala Val Pro Leu Ala Leu
    290                 295                 300

His Phe Ser Trp Tyr Thr Leu Leu Cys Thr Tyr Leu Trp Met Cys Ile
305                 310                 315                 320

Ala Ala Leu Tyr Leu Gly Phe Phe Ile Leu Ser His Ile Phe Val
                325                 330                 335

Gly Ala Lys Ser Leu Pro Glu Asp Ala Asn Ile Asp Trp Ala Arg His
            340                 345                 350

Gln Ile Glu Ser Ser Ser Asn Val Cys Gly Glu Lys Leu Gly Ile Ser
        355                 360                 365

Asn Gly Gly Leu Asn Phe Gln Ile Glu His His Leu Phe Pro Arg Met
    370                 375                 380

Ser His Ala His Tyr Ser Lys Ile Gln Pro Val Val Gln Lys Val Cys
385                 390                 395                 400

Glu Glu Asn Gly Val Asn Tyr Lys Lys Phe Gly Thr Ile Gly Ser Asn
                405                 410                 415

Leu Gly Ser Leu Phe Arg Gln Leu Lys Ala Leu Gly Ser Val Ala Ile
            420                 425                 430

Tyr Glu Phe Met Glu Gly Leu
            435
```

```
<210> SEQ ID NO 88
<211> LENGTH: 438
<212> TYPE: PRT
<213> ORGANISM: Artificial
<220> FEATURE:
<223> OTHER INFORMATION: delta-4 desaturase 91.9% sequence identity to
      SEQ ID NO 79

<400> SEQUENCE: 88

Met Pro Pro His Ser Arg Thr Lys Gly Ser Asp Pro Glu Leu Ser Asp
1               5                   10                  15

Met Lys His Phe Thr Arg Glu Glu Ile Leu Asn His Thr Arg Asp Lys
                20                  25                  30

Tyr Cys Ile Leu Glu Asp Gly Val Tyr Asp Leu Thr Asn Phe Arg Asp
            35                  40                  45

Lys His Pro Gly Gly Asp Phe Leu Asp Leu Phe Pro Gly Gln Asp Ala
        50                  55                  60

Thr Pro His Phe Tyr Met Leu His Gln Lys Glu Ser Pro Pro Ser Val
65                  70                  75                  80

Leu Ala Glu Tyr Lys Val Gly Ser Leu Ala Arg Asp Asp Ser Tyr Thr
                85                  90                  95

His His Thr Ala Leu Met Lys Gln Ile Lys Ser Ala Val Arg Lys Val
            100                 105                 110

Met Pro Met Gln Glu Trp Trp Ala Pro Pro Ser Trp Tyr Ile Lys Ala
        115                 120                 125

Cys Ala Ile Leu Ala Ala Thr Leu Tyr Thr Asp Tyr Leu Trp Ile Ala
130                 135                 140

Ser Gly Pro Thr Ile Phe Leu Ala Ile Val Ser Gly Leu Leu Tyr Ala
145                 150                 155                 160

Ala Ile Gly Leu Asn Ile Gln His Asp Ala Asn His Gly Ser Val Ser
                165                 170                 175

Arg Asn Pro Val Val Asn Arg Leu Phe Gly Tyr Ser Gln Asp Trp Ile
            180                 185                 190

Gly Gly Ser Arg Met Leu Trp Ile Arg Gln His Val Val Gly His His
        195                 200                 205

Thr His Cys Asn Arg His Gln His Asp Pro Asp Val Lys Gly Gly Ser
        210                 215                 220

Val Ile Thr Leu Ser Arg Tyr Ser Leu Pro Lys Pro Trp His His Ile
225                 230                 235                 240

Gln Gln Tyr Tyr Phe Leu Pro Leu Ile Gln Leu Gly Phe Gln Trp
                245                 250                 255

Val Phe Leu Gly Leu His Asp Leu Ile Glu Met Lys Tyr Lys Gly Glu
            260                 265                 270

Lys Ile Pro Glu Ser Tyr Arg Lys Glu Arg Asn Ile Ala Ile Gly Cys
        275                 280                 285

Arg Val Phe Phe Phe Val Arg Lys Phe Ala Val Pro Phe Ala Leu His
    290                 295                 300

Pro Ser Trp Tyr Thr Leu Leu Cys Thr Tyr Leu Trp Met Ala Ile Gly
305                 310                 315                 320

Ala Phe Tyr Leu Gly Phe Phe Ile Leu Ser His Asn Phe Val Gly
                325                 330                 335

Ile Lys Ser Leu Pro Glu Asp Ala Asn Ile Glu Trp Ala Arg His Gln
            340                 345                 350

Ile Glu Ser Ser Ser Asn Val Cys Gly Glu Lys Leu Gly Ile Ser Asn
        355                 360                 365
```

```
Gly Gly Leu Asn Tyr Gln Ile Glu His His Leu Phe Pro Arg Met Ser
        370                 375                 380

His Ala His Tyr Ser Lys Ile Gln Pro Val Val Gln Lys Val Cys Glu
385                 390                 395                 400

Glu Asn Gly Val Asn Tyr Lys His Phe Gly Thr Ile Leu Ser Asn Leu
                405                 410                 415

Asp Ser Thr Phe Arg Gln Val Gly Ala Leu Gly Ala Val Ala Ile Tyr
            420                 425                 430

Glu Phe Met Ala Gly Leu
        435

<210> SEQ ID NO 89
<211> LENGTH: 437
<212> TYPE: PRT
<213> ORGANISM: Artificial
<220> FEATURE:
<223> OTHER INFORMATION: delta-4 desaturase 91.7% sequence identity to
      SEQ ID NO 79

<400> SEQUENCE: 89

Met Pro Pro His Ser Arg Thr Lys Val Ser Asp Pro Glu Leu Ser Asp
1               5                   10                  15

Met Lys His Phe Thr Arg Glu Glu Ile Leu Asp His Thr Asn Asp Lys
                20                  25                  30

Tyr Cys Ile Leu Glu Asp Gly Val Tyr Asp Leu Thr Asn Phe Arg Asp
            35                  40                  45

Lys His Pro Gly Gly Asp Val Leu Asp Phe Phe Pro Gly Gln Asp Ala
        50                  55                  60

Thr Pro His Phe Tyr Glu Leu His Arg Tyr Glu Ser Leu Pro Ser Val
65                  70                  75                  80

Leu Ala Glu Tyr Lys Val Gly Ser Val Ala Arg Asp Asp Ser Tyr Val
                85                  90                  95

Tyr Ala Thr Pro Leu Met Lys Gln Ile Lys Ser Ala Val Arg Lys Val
            100                 105                 110

Ile Pro Met Gln Glu Trp Trp Ala Pro Pro Ser Trp Trp Ile Lys Ala
        115                 120                 125

Cys Ala Leu Leu Ala Ala Ala Leu Tyr Thr Asp Tyr Leu Trp Ile Ala
    130                 135                 140

Ser Gly Pro Thr Ile Pro Leu Ala Ile Val Ile Gly Leu Leu Tyr Ala
145                 150                 155                 160

Ala Ile Gly Leu Asn Ile Gln His Asp Ala Asn His Gly Ser Ile Ser
                165                 170                 175

Arg Asn Pro Met Val Asn Arg Leu Phe Gly Tyr Ser Gln Asp Trp Ile
            180                 185                 190

Gly Gly Ser Arg Met Leu Trp Ile Arg Gln His Val Val Gly His His
        195                 200                 205

Thr His Cys Asn Arg His Asp His Asp Pro Asp Val Lys Gly Gly Ser
    210                 215                 220

Val Ile Thr Leu Ser Pro Tyr Ser Leu Pro Lys Glu Phe His His Ile
225                 230                 235                 240

Gln Gln Leu Tyr Phe Leu Pro Leu Glu Gln Leu Leu Gly Phe Gln Trp
                245                 250                 255

Val Phe Leu Gly Leu His Asp Leu Ile Glu Trp Lys Tyr Lys Gly Glu
            260                 265                 270

Lys Leu Pro Glu Leu Tyr Arg Lys Glu Arg Asn Ile Ala Ile Gly Cys
        275                 280                 285
```

```
Arg Ile Phe Phe Phe Ala Arg Lys Phe Val Ile Pro Phe Ala Leu His
            290                 295                 300
Phe Ser Trp Tyr Thr Leu Leu Cys Val Tyr Leu Trp Met Ala Thr Ala
305                 310                 315                 320
Ser Leu Tyr Leu Gly Phe Phe Ile Leu Ser His Ile Phe Ile Gly
                325                 330                 335
Ala Lys Ser Leu Pro Glu Asp Ala Asn Ile Asp Trp Ala Arg His Gln
            340                 345                 350
Ile Glu Ser Ser Ser Asn Val Gly Gly Glu Lys Leu Gly Ile Leu Asn
            355                 360                 365
Gly Gly Leu Asn Tyr Gln Ile Glu His His Leu Phe Pro Arg Met Ser
            370                 375                 380
His Ala His Tyr Ser Lys Ile Gln Pro Val Val Gln Lys Val Cys Glu
385                 390                 395                 400
Glu Asn Gly Val Asn Tyr Lys Lys Phe Gly Thr Ile Leu Ser Asn Leu
                405                 410                 415
Asp Ser Met Phe Arg His Val Lys Ala Leu Gly Ser Val Ala Val Glu
            420                 425                 430
Phe Met Ala Gly Leu
            435

<210> SEQ ID NO 90
<211> LENGTH: 439
<212> TYPE: PRT
<213> ORGANISM: Artificial
<220> FEATURE:
<223> OTHER INFORMATION: delta-4 desaturase 91.7% sequence identity to
      SEQ ID NO 79

<400> SEQUENCE: 90

Met Pro Pro His Ser Arg Thr Lys Val Ser Asp Ala Glu Leu Ser Asp
1               5                   10                  15
Met Lys His Phe Thr Arg Glu Arg Ile Leu Asn His Thr Asn Asp Lys
            20                  25                  30
Ile Cys Ile Leu Gly Asp Gly Val Tyr Asp Leu Ser Asn Phe Arg Asp
            35                  40                  45
Lys His Pro Gly Gly Asp Val Leu Asp Phe Phe Pro Gly Gln Asp Ala
        50                  55                  60
Thr Pro His Phe Tyr Met Phe His Lys Tyr Ala Ser Leu Pro Ser Val
65                  70                  75                  80
Leu Ala Glu Tyr Lys Val Gly Ser Leu Ala Arg Asp Asp Ser Tyr Val
                85                  90                  95
Gln His Thr Glu Leu Met Lys Gln Ile Lys Ser Ala Val Arg Ala Val
            100                 105                 110
Met Pro Met Gln Glu Trp Trp Ala Pro Pro Ser Trp Tyr Ile Lys Ala
            115                 120                 125
Cys Ala Ile Leu Ala Ala Thr Leu Tyr Leu Asp Tyr Leu Trp Ile Ala
        130                 135                 140
Arg Gly Pro Thr Ile Phe Leu Gly Ile Val Ser Gly Leu Leu Tyr Ala
145                 150                 155                 160
Ala Ile Gly Leu Asn Ile Gln His Asp Ala Asn His Gly Ser Val Ser
                165                 170                 175
Arg Asn Pro Met Val Asn Arg Leu Phe Gly Tyr Ser Gln Asp Trp Ile
            180                 185                 190
Gly Gly Ser Arg Met Leu Trp Ile Arg Gln His Val Val Gly His His
```

```
                195                 200                 205
Thr His Thr Asn Asp His Gln His Asp Pro Asp Val Lys Gly Gly Gly
    210                 215                 220

Val Ile Lys Leu Ser Pro Val Ser Leu Pro Leu Glu Phe His His Ile
225                 230                 235                 240

Gln Gln Tyr Tyr Phe Leu Pro Leu Asp Gln Leu Leu Gly Phe Gln Trp
                245                 250                 255

Val Phe Leu Gly Leu His Asp Leu Ile Glu Met Lys Trp Lys Gly Glu
            260                 265                 270

Lys Leu Pro Glu Leu Tyr Arg Lys Glu Tyr Asn Ile Ala Ile Gly Leu
        275                 280                 285

Arg Val Phe Phe Ile Arg Lys Phe Val Val Pro Phe Ala Leu His
    290                 295                 300

Phe Ser Trp Tyr Thr Leu Ile Cys Thr Tyr Leu Trp Met Ala Thr Ala
305                 310                 315                 320

Ala Leu Tyr Leu Ala Phe Phe Ile Leu Ser His Ile Phe Val Gly
                325                 330                 335

Ala Lys Ser Leu Pro Glu Asp Ala Lys Asn Ile Asp Trp Ala Arg His
            340                 345                 350

Gln Ile Glu Ser Ser Asn Val Cys Gly Glu Lys Leu Gly Ile Ser
        355                 360                 365

Asn Gly Gly Leu Asn Tyr Gln Ile Glu His His Leu Phe Pro Arg Met
    370                 375                 380

Ser His Ala His Tyr Ser Lys Ile Gln Pro Val Val Gln Lys Val Cys
385                 390                 395                 400

Glu Glu Asn Gly Val Asn Tyr Lys Lys Phe Gly Thr Ile Leu Ser Asn
                405                 410                 415

Leu Asp Ser Thr Phe Arg Gln Val Lys Ala Leu Gly Ser Val Pro Val
            420                 425                 430

Tyr Glu Phe Met Glu Gly Leu
        435

<210> SEQ ID NO 91
<211> LENGTH: 438
<212> TYPE: PRT
<213> ORGANISM: Artificial
<220> FEATURE:
<223> OTHER INFORMATION: delta-4 desaturase 91.7% sequence identity to
      SEQ ID NO 79

<400> SEQUENCE: 91

Met Pro Pro Ser Ser Arg Ser Lys Val Ser Asp Pro Glu Leu Ser Asp
1               5                   10                  15

Met Lys His Phe Thr Arg Glu Arg Ile Leu Asn His Thr Asn Asp Lys
            20                  25                  30

Tyr Cys Ile Val Glu Asp Gly Val Tyr Asp Leu Pro Asn Phe Arg Asp
        35                  40                  45

Lys His Pro Gly Gly Asp Val Leu Asp Phe Phe Gly Gly Gln Asp Ala
    50                  55                  60

Thr Pro His Phe Phe Met Phe His Gln Tyr Glu Ser Leu Pro Ser Val
65                  70                  75                  80

Leu Ala Glu Tyr Lys Val Gly Ser Leu Ala Arg Asp Asp Ser Tyr Val
                85                  90                  95

Tyr His Thr Glu Leu Met Lys Gln Ile Lys Ser Ala Val Arg Lys Val
            100                 105                 110
```

Ile Pro Met Gln Glu Trp Trp Ala Pro Pro Ser Trp Tyr Ile Lys Ala
            115                 120                 125

Cys Ala Ile Leu Ala Ala Thr Leu Tyr Thr Asp Tyr Leu Trp Ile Ala
            130                 135                 140

Lys Gly Pro Thr Ile Pro Leu Ala Ile Val Leu Gly Leu Leu Tyr Ala
145                 150                 155                 160

Ala Ile Gly Leu Asn Ile Gln His Asp Ala Asn His Gly Ser Val Ser
                165                 170                 175

Arg Asn Pro Met Val Asn Arg Leu Phe Gly Tyr Ser Gln Asp Trp Ile
            180                 185                 190

Gly Gly Ser Arg Val Leu Trp Ile Arg Gln His Val Val Gly His His
            195                 200                 205

Thr His Cys Asn Arg Ile Gln His Asp Pro Asp Val Lys Gly Gly Ser
            210                 215                 220

Val Ile Thr Leu Ser Arg Tyr Ser Leu Pro Met Glu Phe His His Ile
225                 230                 235                 240

Gln Gln Tyr Tyr Phe Leu Pro Leu Asp Gln Leu Leu Gly Phe Gln Trp
                245                 250                 255

Val Phe Leu Gly Leu His Glu Leu Ile Glu Met Lys Trp Lys Gly Glu
            260                 265                 270

Lys Leu Pro Glu Ser Tyr Arg Lys Glu Arg Asn Ile Ala Val Gly Cys
            275                 280                 285

Arg Val Phe Phe Phe Ala Arg Lys Phe Val Val Pro Phe Ala Leu Glu
            290                 295                 300

Phe Ser Trp Tyr Thr Leu Leu Cys Thr Tyr Leu Trp Met Ala Ile Ala
305                 310                 315                 320

Ala Phe Tyr Leu Gly Phe Phe Ile Leu Ser His Ile Phe Val Gly
                325                 330                 335

Ala Lys Ser Leu Gly Glu Asp Ala Lys Asn Ile Asp Trp Ala Arg His
            340                 345                 350

Gln Ile Glu Ser Ser Asn Val Cys Gly Glu Trp Leu Gly Ile Leu
            355                 360                 365

Asn Gly Gly Leu Asn Tyr Gln Ile Glu His His Leu Phe Pro Arg Met
370                 375                 380

Asn His Ala His Tyr Ser Lys Ile Glu Pro Val Val Gln Lys Val Cys
385                 390                 395                 400

Glu Glu Asn Gly Val Asn Tyr Lys Lys Phe Gly Thr Ile Leu Ser Asn
                405                 410                 415

Leu Asp Ser Met Phe Arg Gln Val Lys Ala Leu Gly Ser Val Ala Val
            420                 425                 430

Glu Phe Met Glu Gly Leu
        435

<210> SEQ ID NO 92
<211> LENGTH: 439
<212> TYPE: PRT
<213> ORGANISM: Artificial
<220> FEATURE:
<223> OTHER INFORMATION: delta-4 desaturase 91.7% sequence identity to
      SEQ ID NO 79

<400> SEQUENCE: 92

Met Pro Pro Tyr Ser Arg Thr Glu Val Val Ser Asp Pro Glu Leu Lys
1               5                   10                  15

Asp Met Glu His Phe Ser Arg Glu Glu Ile Leu Asn His Thr Asn Asp
            20                  25                  30

-continued

Lys Tyr Cys Ile Leu Gly Asp Gly Val Tyr Asp Leu Thr Asn Phe Arg
            35              40              45

Asp Lys His Pro Gly Gly Glu Phe Leu Ser Phe Phe Pro Gly Gln Asp
 50              55              60

Ala Thr Pro His Phe Trp Met Leu His Gln Arg Glu Ser Leu Pro Gly
 65              70              75              80

Val Leu Ala Glu Tyr Lys Val Gly Ser Val Ala Arg Asp Asp Ser Tyr
                85              90              95

Val Tyr His Asp Pro Leu Met Lys Arg Ile Cys Ser Ala Val Arg Gly
                100             105             110

Val Met Pro Met Gln Glu Trp Trp Ala Pro Pro Ser Trp Tyr Ile Lys
                115             120             125

Ala Cys Ala Ile Leu Ala Ala Thr Leu Tyr Thr Asp Tyr Leu Trp Ile
        130             135             140

Ala Ser Gly Pro Thr Ile Pro Leu Ala Ile Val Ser Gly Leu Leu Tyr
145             150             155             160

Ala Ala Ile Gly Leu Asn Ile Gln His Asp Ala Asn His Gly Ser Leu
                165             170             175

Ser Arg Asn Pro Met Val Asn Arg Leu Phe Gly Tyr Ser Gln Asp Trp
                180             185             190

Ile Gly Gly Ser Arg Met Leu Trp Leu Arg Gln His Val Val Gly His
        195             200             205

His Thr His Cys Asn Arg His Gln His Asp Pro Asp Val Lys Gly Gly
        210             215             220

Ser Val Ile Thr Leu Ser Pro Tyr Ser Leu Pro Lys Glu Phe His His
225             230             235             240

Ile Gln Gln Leu Tyr Phe Leu Pro Leu Ile Gln Leu Leu Gly Phe Gln
                245             250             255

Trp Val Phe Leu Gly Leu His Asp Leu Ile Glu Met Lys Tyr Lys Gly
                260             265             270

Glu Lys Leu Pro Glu Ile Tyr Arg Lys Glu Arg Asn Pro Ala Ile Gly
        275             280             285

Leu Arg Leu Phe Phe Phe Ile Arg Lys Phe Val Val Pro Leu Ala Leu
        290             295             300

His Phe Ser Trp Tyr Thr Leu Leu Cys Thr Tyr Leu Trp Met Ala Ile
305             310             315             320

Ala Ala Leu Tyr Leu Gly Phe Phe Ile Leu Ser His Ile Phe Val
                325             330             335

Gly Ile Lys Ser Leu Pro Glu Asp Ala Asn Ile Asp Trp Ala Arg His
                340             345             350

Gln Ile Glu Ser Ser Asn Val Cys Gly Glu Lys Leu Gly Ile Met
        355             360             365

Asn Gly Gly Leu Asn Tyr Gln Ile Glu His His Leu Phe Pro Arg Met
        370             375             380

Ser His Ala His Tyr Ser Lys Ile Gln Pro Val Gln Lys Val Cys
385             390             395             400

Glu Glu Asn Gly Val Asn Tyr Lys His Phe Gly Thr Ile Leu Ser Asn
                405             410             415

Leu Asp Ser Thr Phe Arg Gln Val Lys Ala Leu Gly Ser Val Pro Thr
                420             425             430

Tyr Glu Phe Leu Gly Gly Leu
            435

```
<210> SEQ ID NO 93
<211> LENGTH: 441
<212> TYPE: PRT
<213> ORGANISM: Artificial
<220> FEATURE:
<223> OTHER INFORMATION: delta-4 desaturase 91.7% sequence identity to
      SEQ ID NO 79

<400> SEQUENCE: 93

Met Pro Pro His Ser Arg Thr Lys Val Ser Asp Asp Pro Glu Leu Ser
1               5                   10                  15

Asp Leu Met Lys His Phe Ala Arg Glu Glu Ile Leu Asn Asp Asn Asn
            20                  25                  30

Asp Asp Tyr Cys Ile Leu Glu Asp Gly Val Tyr Asp Leu Thr Asn Phe
        35                  40                  45

Arg Asp Lys His Pro Gly Gly Asp Val Leu Asp Phe Phe Pro Gly Gln
    50                  55                  60

Asp Ala Thr Pro His Phe Tyr Met Phe His Gln Tyr Glu Ser Leu Pro
65                  70                  75                  80

Ser Val Leu Ala Lys Tyr Lys Val Gly Ser Val Ala Arg Asp Asp Ser
                85                  90                  95

Tyr Val Tyr His Thr Pro Leu Met Leu Gln Ile Lys Ser Glu Val Arg
            100                 105                 110

Ala Val Leu Pro Met Gln Glu Trp Trp Ala Pro Pro Ser Trp Tyr Ile
        115                 120                 125

Lys Ala Cys Ala Ile Leu Ala Ala Thr Leu Tyr Thr Asp Tyr Leu Trp
    130                 135                 140

Ile Ala Ser Gly Pro Thr Ile Phe Leu Ala Ile Val Ser Gly Leu Leu
145                 150                 155                 160

Tyr Ala Ala Ile Gly Leu Asn Ile Gln His Asp Ala Asn His Gly Ser
                165                 170                 175

Val Ser Arg Asn Pro Met Val Asn Arg Leu Phe Gly Tyr Ser Gln Asp
            180                 185                 190

Trp Ile Gly Gly Ser Arg Met Leu Trp Ile Arg Gln His Val Val Gly
        195                 200                 205

His His Thr His Cys Asn Asp His Gln His Asp Pro Asp Val Lys Gly
    210                 215                 220

Gly Ser Ala Ile Thr Leu Ser Pro Thr Ser Leu Pro Lys Glu Phe His
225                 230                 235                 240

His Ile Gln Gln Tyr Tyr Phe Leu Pro Leu Asp Gln Leu Tyr Gly Phe
                245                 250                 255

Gln Trp Val Phe Leu Gly Leu His Asp Leu Ile Glu Met Lys Tyr Glu
            260                 265                 270

Gly Glu Lys Leu Pro Glu Ile Tyr Arg Lys Glu Arg Asn Ile Ala Ile
        275                 280                 285

Gly Leu Arg Val Phe Phe Phe Val Arg Lys Phe Ala Ile Pro Phe Ala
    290                 295                 300

Leu His Phe Ser Trp Tyr Thr Leu Leu Cys Thr Tyr Leu Trp Met Ala
305                 310                 315                 320

Ile Ala Ala Leu Tyr Leu Gly Phe Phe Ile Leu Ser His Ile Phe
                325                 330                 335

Val Gly Val Lys Ser Leu Gly Glu Asp Gly Lys Asn Ile Asp Trp Ala
            340                 345                 350

Arg His Gln Ile Glu Ser Ser Ser Asn Val Cys Gly Glu Lys Leu Gly
        355                 360                 365
```

```
Ile Ser Asn Gly Gly Leu Asn Tyr Gln Ile Glu His His Leu Phe Pro
    370                 375                 380

Arg Met Asn His Ala His Tyr Ser Thr Ile Gln Pro Ile Val Gln Arg
385                 390                 395                 400

Val Cys Glu Glu Asn Gly Val Asn Tyr Lys Lys Phe Gly Thr Ile Leu
                405                 410                 415

Ser Asn Leu Asp Ser Thr Phe Ser Gln Ile Lys Ala Leu Gly Ser Val
                420                 425                 430

Ala Val Tyr Glu Phe Met Glu Lys Ile
                435                 440

<210> SEQ ID NO 94
<211> LENGTH: 437
<212> TYPE: PRT
<213> ORGANISM: Artificial
<220> FEATURE:
<223> OTHER INFORMATION: delta-4 desaturase 91.5% sequence identity to
      SEQ ID NO 79

<400> SEQUENCE: 94

Met Pro Pro His Ser Arg Thr Lys Val Ser Asp Pro Glu Leu Ser Asp
1               5                   10                  15

Met Lys His Phe Ala Arg Glu Arg Ile Ala Asn His Thr Asn Asp Lys
                20                  25                  30

Tyr Cys Ile Leu Glu Asp Gly Val Tyr Asp Leu Thr Asn Phe Arg Asp
            35                  40                  45

Lys His Pro Gly Gly Asp Val Leu Asp Ile Phe Pro Gly Gln Asp Ala
        50                  55                  60

Thr Pro His Phe Tyr Met Tyr His Gln Lys Glu Trp Pro Pro Ser Val
65                  70                  75                  80

Leu Ala Glu Tyr Lys Val Gly Ser Val Ala Arg Asp Asp Ser Tyr Val
                85                  90                  95

Tyr His Thr Pro Leu Gln Lys Gln Leu Lys Ser Ala Val Arg Lys Val
            100                 105                 110

Met Pro Lys Gly Ser Trp Trp Ala Pro Pro Ser Trp Tyr Ile Lys Ala
        115                 120                 125

Cys Ala Ile Leu Ala Ala Thr Leu Tyr Leu Asp Tyr Leu Trp Ile Leu
    130                 135                 140

Ser Gly Pro Thr Ile Pro Leu Ala Ile Val Ile Gly Leu Leu Tyr Ala
145                 150                 155                 160

Ala Ile Gly Leu Asn Ile Gln His Asp Ala Asn His Gly Ser Val Ser
                165                 170                 175

Arg Asn Pro Met Val Asn Arg Leu Phe Gly Tyr Gly Gln Asp Trp Ile
            180                 185                 190

Gly Gly Ser Arg Met Leu Trp Ile Arg Gln His Val Val Gly His His
        195                 200                 205

Thr His Cys Asn Arg Val Gln His Asp Pro Asp Ile Lys Gly Gly Ser
    210                 215                 220

Val Ile Thr Leu Ser Arg Tyr Ser Leu Pro Leu Glu Phe His His Ile
225                 230                 235                 240

Gln Gln Tyr Tyr Phe Leu Pro Leu Glu Gln Leu Gly Phe Gln Trp
                245                 250                 255

Val Phe Leu Gly Ala His Asp Leu Ile Glu Met Lys Tyr Lys Gly Glu
            260                 265                 270

Lys Leu Pro Glu Ser Tyr Arg Lys Glu Tyr Asn Ile Ala Ile Gly Leu
```

```
                275                 280                 285
Arg Val Phe Phe Trp Ile Arg Lys Phe Val Pro Phe Ala Leu His
    290                 295                 300

Phe Ser Trp Tyr Thr Leu Leu Cys Thr Tyr Leu Trp Met Ala Thr Ala
305                 310                 315                 320

Ala Leu Tyr Leu Gly Phe Phe Ile Leu Ser His Ile Phe Ile Gly
                325                 330                 335

Ala Lys Ser Leu Pro Glu Asp Ala Asn Ile Asp Trp Ala Arg His Gln
                340                 345                 350

Ile Glu Ser Ser Ser Asn Val Cys Gly Asp Lys Leu Gly Ile Ser Asn
                355                 360                 365

Gly Gly Leu Asn Tyr Gln Ile Glu His His Leu Phe Pro Arg Met Ser
    370                 375                 380

His Ala His Tyr Ser Lys Ile Gln Pro Val Val Gln Lys Val Cys Glu
385                 390                 395                 400

Glu Met Gly Val Asn Tyr Lys Lys Phe Gly Thr Ile Gly Ser Asn Leu
                405                 410                 415

Asp Ser Thr Phe Arg Tyr Val Lys Ala Leu Gly Ser Val Ala Val Glu
                420                 425                 430

Phe Met Glu Gly Leu
        435

<210> SEQ ID NO 95
<211> LENGTH: 438
<212> TYPE: PRT
<213> ORGANISM: Artificial
<220> FEATURE:
<223> OTHER INFORMATION: delta-4 desaturase 91.5% sequence identity to
      SEQ ID NO 79

<400> SEQUENCE: 95

Met Pro Pro His Ser Arg Thr Lys Val Ser Asp Pro Glu Leu Ser Asp
1               5                   10                  15

Met Lys His Phe Thr Arg Glu Lys Ile Leu Asn His Thr Asn Asp Lys
                20                  25                  30

Tyr Cys Ile Leu Gly Asp Gly Val Tyr Asp Cys Thr Asn Phe Arg Asp
            35                  40                  45

Lys His Pro Gly Gly Asp Phe Leu Asp Phe Phe Gly Gly Gln Asp Ala
        50                  55                  60

Thr Pro His Phe Tyr Gln Leu His Gln Tyr Glu Ser Leu Pro Ser Val
65                  70                  75                  80

Leu Ala Lys Tyr Lys Val Gly Ser Val Ala Arg Asp Asp Ser Tyr Val
                85                  90                  95

His His Thr Glu Leu Met Lys Gln Ile Lys Ser Ala Val Arg Ala Val
            100                 105                 110

Met Pro Met Gly Glu Trp Trp Ala Pro Pro Ser Trp Tyr Ile Lys Ala
        115                 120                 125

Cys Ala Ile Leu Ala Ala Thr Leu Tyr Thr Asp Tyr Leu Trp Ile Ala
    130                 135                 140

Ser Gly Pro Thr Ile Pro Leu Ala Ile Val Ile Gly Leu Leu Tyr Ala
145                 150                 155                 160

Ala Ile Gly Leu Asn Ile Gln His Asp Ala Asn His Gly Ala Val Ser
                165                 170                 175

Arg Asn Pro Met Val Asn Arg Leu Phe Gly Tyr Ser Gln Asp Trp Ile
            180                 185                 190
```

Gly Gly Ser Arg Met Leu Trp Ile Arg Gln His Val Gly His His
            195                 200                 205

Leu His Cys Asn Arg Ile Gln His Asp Pro Asp Val Lys Gly Gly Ser
    210                 215                 220

Val Ile Thr Leu Ser Arg Tyr Ser Leu Pro Met Glu Phe His His Ile
225                 230                 235                 240

Gln Gln Tyr Tyr Phe Leu Pro Leu Ile Gln Leu Tyr Gly Phe Gln Trp
            245                 250                 255

Val Phe Leu Gly Leu Asn Asp Leu Ile Glu Met Lys Tyr Lys Gly Glu
        260                 265                 270

Lys Leu Pro Glu Ser Tyr Arg Lys Glu Arg Asn Ile Ala Ile Gly Cys
        275                 280                 285

Arg Val Phe Phe Phe Ile Arg Lys Phe Ala Val Pro Phe Ala Leu His
        290                 295                 300

Phe Ser Trp Tyr Thr Leu Leu Cys Thr Cys Leu Trp Met Ala Ile Ala
305                 310                 315                 320

Ala Leu Tyr Leu Gly Phe Phe Ile Leu Ser His Ile Phe Val Gly
            325                 330                 335

Ala Lys Ser Leu Pro Glu Asp Ala Asn Ile Asp Trp Ala Arg His Gln
        340                 345                 350

Ile Glu Ser Ser Ser Asn Val Gly Gly Glu Trp Leu Gly Ile Ser Asn
    355                 360                 365

Gly Gly Leu Asn Tyr Gln Ile Glu His His Leu Phe Pro Arg Met Ser
        370                 375                 380

His Ala His Tyr Ser Lys Ile Gln Pro Ile Val Gln Lys Val Cys Glu
385                 390                 395                 400

Glu Asn Gly Val Asn Tyr Lys His Phe Pro Thr Ile Leu Ser Asn Leu
            405                 410                 415

Gly Ser Thr Phe Arg Tyr Ile Gly Ala Leu Gly Ser Val Pro Val Tyr
        420                 425                 430

Glu Phe Met Glu Gly Leu
        435

<210> SEQ ID NO 96
<211> LENGTH: 437
<212> TYPE: PRT
<213> ORGANISM: Artificial
<220> FEATURE:
<223> OTHER INFORMATION: delta-4 desaturase 91.5% sequence identity to
      SEQ ID NO 79

<400> SEQUENCE: 96

Met Pro Pro His Ser Arg Thr Lys Val Ser Asp Pro Glu Leu Ser Asp
1               5                   10                  15

Met Lys His Phe Thr Tyr Glu Glu Ile Leu Asn His Thr Asn Asp Lys
            20                  25                  30

Tyr Cys Ile Leu Glu Asp Gly Val Tyr Asp Leu Thr Asn Phe Arg Asp
        35                  40                  45

Lys His Pro Gly Gly Asp Val Leu Asp Phe Phe Pro Gly Gln Asp Ala
    50                  55                  60

Thr Pro His Phe Tyr Gln Leu His Gln Arg Glu Trp Pro Pro Ser Ile
65                  70                  75                  80

Met Ala Glu Tyr Lys Val Gly Ser Val Asp Arg Asp Asp Ser Tyr Val
            85                  90                  95

Tyr His Thr Ser Leu Met Lys Gln Ile Cys Cys Ala Val Arg Lys Val
        100                 105                 110

```
Met Pro Arg Gln Ser Trp Trp Ala Pro Pro Ser Trp Tyr Ile Lys Ala
        115                 120                 125

Cys Ala Leu Leu Ala Ala Thr Leu Tyr Leu Asp Tyr Leu Trp Ile Ala
    130                 135                 140

Ser Gly Pro Thr Ile Leu Leu Ala Ile Val Ser Gly Leu Leu Tyr Ala
145                 150                 155                 160

Ala Ile Gly Leu Asn Ile Gln His Asp Ala Asn His Gly Ser Leu Ser
                165                 170                 175

Arg Asn Pro Met Val Asn Arg Leu Phe Gly Tyr Ser Gln Asp Trp Ile
            180                 185                 190

Gly Gly Ser Arg Met Leu Trp Ile Arg Gln His Val Val Gly His His
        195                 200                 205

Thr His Cys Asn Arg His Gln His Asp Pro Asp Val Lys Gly Gly Ser
    210                 215                 220

Ala Ile Thr Leu Ser Pro Tyr Ser Leu Pro Lys Glu Phe His His Ile
225                 230                 235                 240

Gln Gln Tyr Tyr Phe Leu Pro Leu Ile Gln Leu Tyr Gly Phe Gln Trp
                245                 250                 255

Val Phe Leu Gly Leu His Asp Leu Ile Glu Met Lys Tyr Lys Gly Glu
            260                 265                 270

Pro Leu Ser Glu Ile Tyr Arg Lys Glu Arg Asn Pro Ala Ile Gly Leu
        275                 280                 285

Arg Ile Phe Phe Phe Ile Arg Lys Phe Val Val Pro Phe Ala Leu His
    290                 295                 300

Phe Ser Trp Tyr Thr Leu Leu Cys Thr Tyr Leu Trp Met Ala Ile Ala
305                 310                 315                 320

Ala Leu Tyr Leu Gly Phe Phe Phe Ile Leu Ser His Ile Phe Val Gly
                325                 330                 335

Ala Lys Ser Leu Pro Glu Asp Ala Asn Ile Asp Trp Ala Arg His Gln
            340                 345                 350

Ile Glu Ser Ser Ser Asn Val Cys Gly Glu Lys Leu Gly Ile Met Asn
        355                 360                 365

Gly Gly Leu Asn Tyr Gln Ile Glu His His Leu Phe Pro Arg Met Ser
    370                 375                 380

His Ala His Tyr Ser Lys Ile Gln Pro Val Val Gln Lys Ile Cys Glu
385                 390                 395                 400

Asp Asn Gly Val Asn Tyr Lys Lys Phe Gly Thr Ile Leu Ser Asn Leu
                405                 410                 415

Asp Ser Thr Phe Arg Tyr Val Lys Ala Leu Gly Ser Val Ala Val Glu
            420                 425                 430

Phe Met Glu Lys Leu
        435

<210> SEQ ID NO 97
<211> LENGTH: 437
<212> TYPE: PRT
<213> ORGANISM: Artificial
<220> FEATURE:
<223> OTHER INFORMATION: delta-4 desaturase 91.2% sequence identity to
      SEQ ID NO 79

<400> SEQUENCE: 97

Met Pro Pro His Ser Arg Thr Lys Gly Ser Asp Pro Glu Leu Ser Asp
1               5                   10                  15

Met Lys His Phe Thr Arg Glu Glu Lys Leu Asn His Thr Arg Asp Lys
```

-continued

```
                20                  25                  30
Ile Cys Ile Leu Gly Asp Gly Val Tyr Asp Leu Val Cys Phe Arg Asp
                35                  40                  45
Glu His Pro Gly Gly Asp Val Val Asp Phe Phe Pro Gly Gln Asp Ala
            50                  55                  60
Thr Pro His Phe Tyr Met Leu His Gln Tyr Glu Trp Leu Pro Ser Val
 65                  70                  75                  80
Leu Ala Glu Tyr Lys Val Gly Ser Val Ala Arg Asp Asp Ser Tyr Val
                85                  90                  95
Tyr His Thr Pro Leu Met Lys Gln Ile Lys Ser Ala Val Arg Ala Val
                100                 105                 110
Met Pro Met Gln Glu Gly Trp Ala Pro Pro Ser Trp Tyr Ile Lys Ala
            115                 120                 125
Cys Ala Leu Leu Val Ala Thr Leu Tyr Thr Asp Tyr Leu Trp Ile Ala
            130                 135                 140
Ser Gly Pro Thr Ile Pro Leu Ala Ile Val Ser Gly Leu Leu Tyr Ala
145                 150                 155                 160
Ala Ile Gly Leu Asn Ile Gln His Asp Ala Asn His Gly Ser Val Ser
                165                 170                 175
Arg Asn Pro Val Val Asn Arg Leu Phe Gly Tyr Ser Gln Asp Trp Ile
                180                 185                 190
Gly Gly Ser Arg Met Leu Trp Ile Arg Gln His Val Val Gly His His
                195                 200                 205
Thr His Cys Asn Asp His Gln His Asp Pro Asp Ile Lys Gly Gly Ser
            210                 215                 220
Val Ile Thr Leu Lys Arg Tyr Asp Leu Trp Leu Pro Phe His His
225                 230                 235                 240
Gln Gln Tyr Tyr Phe Leu Pro Gly Ile Gln Leu Leu Gly Phe Gln Trp
                245                 250                 255
Val Phe Leu Gly Leu His Asp Leu Ile Glu Met Lys Tyr Lys Gly Glu
                260                 265                 270
Lys Leu Pro Pro Ser Tyr Arg Lys Leu Arg Asn Ile Ala Ile Gly Leu
                275                 280                 285
Arg Val Phe Phe Ile Arg Lys Phe Val Val Pro Phe Ala Leu His
            290                 295                 300
Phe Ser Trp Tyr Thr Leu Leu Cys Ile Tyr Leu Trp Met Ala Ile Ala
305                 310                 315                 320
Ala Leu Tyr Leu Ala Phe Phe Ile Leu Ser His Ile Phe Val Gly
                325                 330                 335
Val Lys Ser Leu Pro Glu Asp Ala Asn Ile Asp Trp Ala Arg His Gln
            340                 345                 350
Ile Glu Ser Ser Asn Val Cys Gly Glu Lys Leu Gly Ile Ser Asn
            355                 360                 365
Gly Gly Leu Asn Tyr Gln Ile Glu His His Leu Phe Pro Arg Met Ser
            370                 375                 380
His Ala His Tyr Ser Lys Ile Gln Pro Val Val Gln Lys Val Cys Glu
385                 390                 395                 400
Glu Asn Gly Ile Asn Tyr Lys Lys Phe Gly Thr Ile Ala Ser Asn Leu
                405                 410                 415
Asp Ser Thr Phe Arg Gln Val Lys Ala Leu Gly Ser Val Pro Val Glu
            420                 425                 430
Phe Met Glu Gly Leu
            435
```

```
<210> SEQ ID NO 98
<211> LENGTH: 437
<212> TYPE: PRT
<213> ORGANISM: Artificial
<220> FEATURE:
<223> OTHER INFORMATION: delta-4 desaturase 91.2% sequence identity to
      SEQ ID NO 79

<400> SEQUENCE: 98

Met Pro Pro His Ala Arg Thr Lys Val Ser Asp Pro Glu Leu Ser Asp
1               5                   10                  15

Met Lys His Phe Thr Arg Glu Glu Ile Leu Asn His Thr Asn Asp Asp
            20                  25                  30

Tyr Cys Ile Leu Gly Asp Gly Val Tyr Asp Ser Thr Asn Phe Arg Asp
        35                  40                  45

Lys His Pro Gly Gly Asp Val Leu Asp Phe Phe Pro Gly Gln Asp Ala
    50                  55                  60

Thr Pro His Phe Tyr Met Leu His Gln Tyr Glu Ser Leu Pro Ser Val
65                  70                  75                  80

Leu Ala Arg Tyr Lys Val Gly Ser Val Ala Arg Asp Asp Ser Phe Thr
                85                  90                  95

Tyr His Thr Pro Leu Met Lys Gln Ile Lys Ser Glu Val Arg Lys Ile
            100                 105                 110

Leu Pro Met Gly Glu Trp Trp Ala Pro Ser Trp Tyr Ile Lys Ala
            115                 120                 125

Cys Ala Leu Leu Ala Ala Thr Leu Tyr Leu Asp Tyr Leu Trp Leu Ala
130                 135                 140

Ser Gly Pro Thr Ile Pro Leu Ala Ile Val Ser Gly Leu Leu Tyr Ala
145                 150                 155                 160

Ala Ile Gly Leu Asn Ile Gln His Asp Ala Asn His Gly Ser Leu Ser
                165                 170                 175

Arg Asn Pro Val Val Asn Arg Leu Phe Gly Tyr Ser Gln Asp Trp Ile
            180                 185                 190

Gly Gly Ser Arg Val Leu Trp Ile Gln Gln His Val Val Gly His His
            195                 200                 205

Thr His Cys Asn Arg His Gln His Asp Pro Asp Val Lys Gly Gly Ser
    210                 215                 220

Val Ile Thr Leu Ser Arg Tyr Ser Leu Pro Lys Glu Phe His His Ile
225                 230                 235                 240

Gln Gln Tyr Tyr Phe Leu Pro Leu Glu Gln Leu Leu Gly Phe Gln Trp
                245                 250                 255

Val Phe Leu Gly Leu Asn Asp Leu Ile Glu Trp Lys Tyr Lys Gly Glu
            260                 265                 270

Lys Leu Pro Glu Ser Tyr Arg Lys Asp Arg Ala Ile Ala Ile Gly Leu
        275                 280                 285

Arg Val Phe Phe Phe Ile Arg Lys Phe Val Ile Pro Phe Ala Leu His
    290                 295                 300

Phe Ser Trp Tyr Thr Leu Leu Cys Val Tyr Leu Trp Met Ala Ile Ala
305                 310                 315                 320

Ala Leu Tyr Leu Cys Phe Phe Ile Leu Ser His Ile Phe Val Gly
                325                 330                 335

Ala Gly Ser Leu Pro Glu Asp Ala Asn Ile Asp Trp Ala Arg His Gln
            340                 345                 350

Ile Glu Ser Ser Ser Asn Val Cys Gly Glu Lys Leu Gly Ile Leu Asn
```

```
                355                 360                 365
Gly Gly Leu Asn Tyr Gln Ile Glu His His Leu Phe Pro Arg Met Ser
        370                 375                 380

His Ala His Tyr Ser Lys Ile Ala Pro Val Val Gln Lys Val Cys Glu
385                 390                 395                 400

Glu Asn Gly Val Asn Tyr Lys Lys Phe Gly Thr Ile Leu Ser Asn Leu
                405                 410                 415

Asp Ala Thr Phe Arg Gln Val Lys Ala Leu Gly Ser Val Ala Val Glu
            420                 425                 430

Phe Met Glu Lys Leu
        435

<210> SEQ ID NO 99
<211> LENGTH: 439
<212> TYPE: PRT
<213> ORGANISM: Artificial
<220> FEATURE:
<223> OTHER INFORMATION: delta-4 desaturase 91% sequence identity to
      SEQ ID NO 79

<400> SEQUENCE: 99

Met Pro Pro His Ser Ala Thr Lys Gly Ser Asp Val Pro Glu Leu Ser
1               5                   10                  15

Asp Ala Lys His Phe Ala Arg Glu Ile Leu Asn His Thr Arg Asp
            20                  25                  30

Lys Tyr Cys Ile Leu Gly Asp Gly Val Tyr Asp Ser Thr Ala Phe Arg
            35                  40                  45

Asp Lys His Pro Gly Gly Asp Tyr Leu Asp Phe Phe Pro Gly Gln Asp
        50                  55                  60

Ala Thr Pro His Phe Tyr Gln Phe His Gln Tyr Ala Ser Leu Pro Ser
65                  70                  75                  80

Val Leu Ala Glu Tyr Lys Val Gly Ser Val Ala Arg Asp Asp Ser Tyr
                85                  90                  95

Val Gln His Thr Glu Leu Met Lys Gln Ile Cys Ser Ala Val Arg Lys
            100                 105                 110

Val Met Pro Met Gln Glu Trp Trp Ala Pro Ser Trp Tyr Ile Lys
            115                 120                 125

Ala Cys Ala Leu Leu Ala Ala Thr Leu Tyr Thr Asp Tyr Leu Trp Ile
        130                 135                 140

Ala Ser Gly Pro Thr Ile Pro Leu Ala Ile Val Ser Gly Leu Leu Tyr
145                 150                 155                 160

Ala Trp Ile Gly Leu Asn Ile Gln His Asp Ala Asn His Gly Ser Val
                165                 170                 175

Ser Arg Asn Pro Met Val Asn Arg Leu Phe Gly Tyr Ser Gln Asp Trp
            180                 185                 190

Ile Gly Gly Ser Arg Met Leu Trp Ile Arg Lys His Val Val Gly His
        195                 200                 205

His Thr His Cys Asn Arg Val Gln His Asp Pro Asp Val Lys Gly Gly
    210                 215                 220

Ser Val Ile Thr Leu Ser Arg Tyr Ser Leu Pro Leu Glu Trp His His
225                 230                 235                 240

Ile Gln Gln Ile Tyr Phe Leu Pro Leu Ile Gln Leu Tyr Gly Phe Gln
                245                 250                 255

Trp Val Phe Leu Gly Leu His Asp Leu Leu Glu Met Lys Tyr Lys Gly
            260                 265                 270
```

```
Glu Lys Leu Pro Pro Ile Tyr Arg Lys Glu Arg Asn Ile Ala Ile Gly
            275                 280                 285

Cys Arg Val Phe Phe Phe Ile Arg Lys Phe Val Val Pro Phe Ala Leu
    290                 295                 300

His Phe Thr Trp Tyr Thr Leu Leu Cys Thr Tyr Leu Trp Met Ala Ile
305                 310                 315                 320

Ala Ala Leu Tyr Leu Gly Phe Phe Phe Ile Leu Ser His Ile Phe Val
                325                 330                 335

Gly Ala Lys Ser Leu Pro Pro Asp Ala Asn Ile Asp Trp Ala Arg His
            340                 345                 350

Gln Ile Glu Ser Ser Asn Val Cys Gly Glu Lys Leu Gly Ile Ile
            355                 360                 365

Asn Gly Gly Leu Asn Tyr Gln Ile Glu His His Leu Phe Pro Arg Met
370                 375                 380

Ser His Ser His Tyr Ser Lys Ile Gln Pro Val Val Gln Lys Val Cys
385                 390                 395                 400

Glu Glu Asn Gly Val Asn Tyr Lys Lys Phe Gly Thr Ile Leu Ser Asn
                405                 410                 415

Leu Asp Ser Thr Phe Lys Gln Val Lys Ala Leu Gly Ser Val Ala Val
            420                 425                 430

Tyr Glu Phe Met Glu Gly Leu
            435

<210> SEQ ID NO 100
<211> LENGTH: 439
<212> TYPE: PRT
<213> ORGANISM: Artificial
<220> FEATURE:
<223> OTHER INFORMATION: delta-4 desaturase 91% sequence identity to
      SEQ ID NO 79

<400> SEQUENCE: 100

Met Pro Pro His Ser Arg Thr Glu Val Ser Asp Pro Glu Leu Ser Asp
1               5                   10                  15

Leu Met Lys His Phe Thr Arg Glu Glu Ile Leu Asn His Asn Asn Asp
                20                  25                  30

Lys Tyr Cys Ile Leu Glu Asp Gly Val Tyr Asp Leu Thr Cys Phe Arg
            35                  40                  45

Asp Lys His Pro Gly Gly Asp Val Leu Asp Phe Phe Pro Gly Gln Asp
    50                  55                  60

Ala Thr Pro Gly Phe Tyr Met Leu His Gln Tyr Ala Ser Pro Pro Ser
65                  70                  75                  80

Val Leu Ala Glu Tyr Lys Val Gly Ser Val Glu Arg Asp Asp Ser Tyr
                85                  90                  95

Val Gln His Thr Ser Gly Met Lys Gln Ile Lys Ser Ala Val Arg Ala
            100                 105                 110

Val Met Pro Met Gln Glu Trp Trp Ala Pro Pro Ser Trp Trp Ile Lys
        115                 120                 125

Ala Cys Ala Ile Leu Ala Ala Thr Leu Tyr Thr Asp Tyr Leu Trp Ile
130                 135                 140

Ala Ser Gly Pro Thr Ile Pro Leu Ala Ile Val Ile Gly Leu Leu Tyr
145                 150                 155                 160

Ala Ala Ile Gly Leu Asn Ile Gln His Asp Ala Asn His Gly Ser Ile
                165                 170                 175

Ser Arg Asn Pro Met Val Asn Arg Leu Phe Gly Tyr Ser Gln Asp Trp
            180                 185                 190
```

-continued

```
Ile Gly Gly Ser Arg Met Leu Trp Ile Arg Gln His Val Val Gly His
        195                 200                 205

His Thr His Cys Asn Arg His Gln His Asp Pro Asp Ile Lys Gly Gly
210                 215                 220

Ser Val Ile Thr Leu Ser Pro Tyr Ser Leu Pro Lys Glu Phe His His
225                 230                 235                 240

Ile Gln Gln Tyr Tyr Phe Leu Pro Leu Asp Gln Leu Tyr Gly Phe Gln
        245                 250                 255

Trp Val Phe Leu Gly Leu His Asp Leu Ile Asp Trp Lys Tyr Lys Gly
        260                 265                 270

Glu Lys Leu Pro Glu Ser Tyr Arg Pro Asp Phe Asn Ile Ala Ile Gly
        275                 280                 285

Leu Arg Val Phe Phe Phe Ala Arg Phe Ala Val Pro Phe Ala Leu
        290                 295                 300

His Phe Ser Trp Tyr Thr Leu Leu Cys Thr Tyr Leu Trp Val Ala Ile
305                 310                 315                 320

Ala Ala Leu Tyr Leu Gly Phe Phe Ile Leu Ser His Ile Phe Ile
                325                 330                 335

Gly Ile Lys Ser Leu Pro Glu Asp Ala Lys Asn Ile Asp Trp Ala Arg
                340                 345                 350

His Gln Ile Glu Ser Ser Asn Val Cys Gly Glu Lys Leu Gly His
        355                 360                 365

Ser Asn Gly Gly Leu Asn Tyr Gln Ile Glu His His Leu Phe Pro Arg
        370                 375                 380

Met Ser His Ala His Tyr Ser Lys Ile Gln Pro Val Val Gln Lys Val
385                 390                 395                 400

Cys Glu Glu Asn Gly Val Asn Tyr Lys Lys Phe Pro Thr Ile Leu Ser
                405                 410                 415

Asn Leu Asp Ser Leu Phe Arg Gln Val Lys Gly Leu Gly Ser Val Ala
                420                 425                 430

Thr Glu Phe Met Glu Gly Leu
        435

<210> SEQ ID NO 101
<211> LENGTH: 439
<212> TYPE: PRT
<213> ORGANISM: Artificial
<220> FEATURE:
<223> OTHER INFORMATION: delta-4 desaturase 91% sequence identity to
      SEQ ID NO 79

<400> SEQUENCE: 101

Met Pro Pro His Ser Arg Thr Lys Gly Ser Asp Pro Glu Leu Ser Asp
1               5                   10                  15

Leu Met Lys His Phe Thr Arg Glu Glu Ile Leu Gly His Thr Asn Pro
                20                  25                  30

Asp Tyr Cys Ile Leu Gly Asp Gly Val Tyr Asp Leu Thr Asn Phe Arg
            35                  40                  45

Asp Glu His Pro Gly Gly Asp Val Leu Asp Phe Phe Pro Gly Gln Asp
        50                  55                  60

Ala Thr Pro His Phe Phe Gln Phe His Gln Arg Glu Trp Leu Pro Ser
65                  70                  75                  80

Val Leu Ala Glu Tyr Phe Val Gly Ser Val Ala Arg Asp Asp Ser Tyr
                85                  90                  95

Val Gln His Thr Ser Leu Met Lys Gln Ile Lys Ser Ala Val Arg Lys
```

```
                100             105             110
Val Met Pro Met Gly Glu Trp Trp Ala Pro Ser Trp Tyr Ile Lys
        115             120             125

Ala Cys Ala Ile Leu Val Ala Thr Leu Tyr Thr Asp Tyr Leu Met Ile
    130             135             140

Ala Ser Gly Pro Thr Ile Pro Leu Ala Ile Val Ile Gly Leu Leu Tyr
145             150             155             160

Ala Ala Ile Gly Leu Asn Ile Gln His Asp Ala Asn His Gly Ser Val
                165             170             175

Ser Arg Asn Pro Met Val Asn Arg Leu Phe Gly Tyr Ser Gln Asp Trp
            180             185             190

Ile Gly Gly Ser Arg Met Leu Trp Ile Arg Gln His Val Val Gly His
        195             200             205

His Thr His Cys Asn Arg Ile Gln His Asp Pro Asp Val Lys Gly Gly
    210             215             220

Ser Val Leu Thr Leu Ser Arg Tyr Ser Leu Pro Lys Glu Phe His His
225             230             235             240

Ile Gln Gln Tyr Tyr Phe Leu Pro Leu Ile Gln Leu Leu Gly Phe Gln
                245             250             255

Trp Val Phe Leu Gly Leu His Asp Leu Ile Glu Met Lys Tyr Lys Gly
            260             265             270

Glu Lys Leu Pro Glu Ser Tyr Arg Lys Glu Tyr Asn Ile Ala Ile Gly
        275             280             285

Leu Arg Val Phe Phe Phe Ala Arg Lys Val Val Pro Phe Ala Leu
    290             295             300

His Phe Ser Trp Tyr Thr Leu Leu Cys Ile Tyr Ala Trp Met Ala Ser
305             310             315             320

Ala Ser Leu Tyr Leu Gly Phe Phe Phe Ile Leu Ser His Leu Phe Val
                325             330             335

Gly Ala Lys Ser Leu Pro Glu Asp Ala Asn Ile Asp Trp Ala Arg His
            340             345             350

Gln Ile Glu Ser Ser Ser Asn Val Gly Gly Glu Lys Leu Gly His Ser
        355             360             365

Asn Gly Gly Leu Asn Tyr Gln Ile Glu His His Leu Phe Pro Arg Met
    370             375             380

Ser His Ala His Tyr Ser Lys Ile Gln Pro Val Val Gln Lys Ile Cys
385             390             395             400

Glu Glu Asn Gly Val Asn Tyr Lys His Phe Gly Thr Ile Leu Ser Asn
                405             410             415

Leu Asp Ser Thr Phe Arg Gln Val Lys Ala Leu Gly Ser Val Ala Val
            420             425             430

Tyr Glu Phe Met Glu Lys Pro
        435

<210> SEQ ID NO 102
<211> LENGTH: 438
<212> TYPE: PRT
<213> ORGANISM: Artificial
<220> FEATURE:
<223> OTHER INFORMATION: delta-4 desaturase 91% sequence identity to
      SEQ ID NO 79

<400> SEQUENCE: 102

Met Pro Pro His Ser Arg Arg Lys Val Ser Asp Pro Glu Leu Ser Asp
1               5               10              15
```

-continued

Leu Met Lys His Phe Thr Arg Glu Arg Ile Leu Asn His Thr Arg Asp
           20                  25                  30

Lys Tyr Cys Ile Leu Glu Asp Gly Val Tyr Asp Leu Thr Asn Phe Arg
           35                  40                  45

Asp Lys His Pro Gly Gly Asp Val Leu Asp Phe Phe Pro Gly Gln Asp
           50                  55                  60

Ala Thr Pro His Phe Tyr Gln Tyr His Gln His Glu Ser Leu Pro Ser
65                  70                  75                  80

Val Leu Ala Arg Tyr Lys Val Gly Ser Val Glu Arg Asp Asp Ser Tyr
               85                  90                  95

Val Tyr His Asp Pro Leu Met Leu Gln Ile Lys Ser Ala Val Arg Lys
               100                 105                 110

Val Ile Pro Met Gln Glu Trp Trp Ala Pro Pro Ser Trp Tyr Ile Lys
               115                 120                 125

Ala Cys Ala Ile Leu Ile Ala Thr Leu Phe Thr Asp Tyr Leu Trp Ile
           130                 135                 140

Ala Ser Gly Pro Thr Ile Pro Leu Ala Ile Val Ser Gly Leu Leu Tyr
145                 150                 155                 160

Ala Trp Ile Gly Leu Asn Ile Gln His Asp Ala Asn His Gly Ser Val
               165                 170                 175

Ser Arg Asn Pro Met Val Asn Arg Leu Phe Gly Tyr Ser Gln Asp Trp
               180                 185                 190

Ile Gly Gly Asn Arg Met Leu Trp Ile Arg Gln His Val Gly His
               195                 200                 205

His Thr His Cys Asn Arg Val Gln His Asp Pro Asp Val Lys Gly Gly
           210                 215                 220

Ser Val Ile Thr Leu Ser Pro Tyr Ser Leu Trp Lys Glu Phe His His
225                 230                 235                 240

Leu Gln Gln Tyr Tyr Phe Leu Pro Leu Glu Gln Leu Gly Phe Gln
               245                 250                 255

Trp Ile Phe Leu Gly Leu His Asp Leu Ile Glu Met Lys Trp Lys Gly
           260                 265                 270

Glu Lys Leu Pro Glu Ser Tyr Arg Lys Glu Arg Asn Ile Ala Ile Gly
           275                 280                 285

Leu Arg Val Phe Phe Phe Ile Arg Lys Phe Val Val Pro Phe Ala Leu
           290                 295                 300

Gln Phe Ser Trp Tyr Thr Leu Leu Cys Thr Tyr Leu Trp Met Ala Thr
305                 310                 315                 320

Ala Ala Leu Tyr Leu Gly Phe Phe Phe Ile Leu Ser His Leu Phe Ile
               325                 330                 335

Gly Val Lys Ser Ile Pro Glu Asp Ala Asn Ile Asp Trp Ala Arg His
               340                 345                 350

Gln Ile Glu Ser Ser Ser Asn Val Cys Gly Glu Lys Leu Gly Ile Met
           355                 360                 365

Asn Gly Gly Leu Asn Tyr Gln Ile Glu His His Leu Phe Pro Arg Met
370                 375                 380

Ser His Ala His Tyr Ser Lys Ile Gln Pro Val Val Gln Lys Val Cys
385                 390                 395                 400

Glu Glu Asp Gly Val Asn Tyr Lys Lys Phe Gly Thr Ile Leu Ser Asn
               405                 410                 415

Leu Gly Ser Thr Phe Lys Gln Val Gly Ala Leu Gly Ser Val Ala Val
           420                 425                 430

Glu Phe Met Glu Gly Leu

<210> SEQ ID NO 103
<211> LENGTH: 438
<212> TYPE: PRT
<213> ORGANISM: Artificial
<220> FEATURE:
<223> OTHER INFORMATION: delta-4 desaturase 91% sequence identity to SEQ ID NO 79

<400> SEQUENCE: 103

```
Met Pro Pro His Ser Arg Thr Lys Val Ser Asp Pro Glu Leu Ser Ala
1               5                   10                  15

Met Lys His Phe Thr Arg Glu Glu Ile Leu Asn His Thr Asn Asp Lys
            20                  25                  30

Tyr Cys Ile Leu Glu Asp Gly Val Tyr Asp Leu Thr Asn Phe Arg Asp
        35                  40                  45

Lys His Pro Gly Gly Asp Val Leu Asp Phe Phe Pro Gly Gln Asp Ala
    50                  55                  60

Thr Pro His Phe Tyr Met Leu His Gln Lys Glu Ser Leu Pro Ala Val
65                  70                  75                  80

Leu Ala Glu Tyr Lys Val Gly Ser Val Ala Arg Asp Asp Ser Tyr Val
                85                  90                  95

Tyr His Asp Ala Leu His Lys Gln Ile Lys Ser Ala Val Arg Lys Val
            100                 105                 110

Met Pro Met Gln Glu Trp Trp Ala Pro Pro Ser Trp Tyr Ile Lys Ala
        115                 120                 125

Cys Ala Ile Ile Val Ala Thr Leu Tyr Thr Asp Tyr Leu Met Ile Ala
    130                 135                 140

Ser Gly Pro Thr Ile Leu Leu Ala Ile Val Ser Gly Leu Leu Phe Ala
145                 150                 155                 160

Trp Ile Gly Leu Asn Ile Gln His Asp Ala Asn His Gly Ser Val Ser
                165                 170                 175

Arg Asn Pro Met Val Asn Arg Leu Phe Gly Tyr Ser Gln Asp Trp Ile
            180                 185                 190

Gly Gly Ser Arg Met Leu Trp Ile Arg Gln His Val Val Gly His His
        195                 200                 205

Thr His Cys Asn Arg His Gln His Asp Pro Asp Val Lys Gly Gly Ser
    210                 215                 220

Val Ile Thr Leu Ser Arg Tyr Ser Leu Pro Lys Glu Phe His His Leu
225                 230                 235                 240

Gln Gln Leu Tyr Phe Leu Pro Leu Glu Gln Leu Gly Phe Gln Trp
                245                 250                 255

Val Phe Leu Gly Leu His Asp Leu Ile Glu Trp Lys Tyr Lys Gly Glu
            260                 265                 270

Lys Leu Ser Glu Ser Tyr Arg Lys Glu Arg Gly Ile Ala Ile Gly Leu
        275                 280                 285

Lys Val Gly Phe Trp Ile Arg Phe Val Val Pro Phe Ala Leu His
    290                 295                 300

Phe Thr Trp Tyr Thr Leu Leu Cys Thr Tyr Leu Trp Val Cys Ile Ala
305                 310                 315                 320

Ala Leu Tyr Leu Gly Phe Phe Ile Leu Ser His Ile Phe Val Gly
                325                 330                 335

Val Lys Ser Leu Gly Glu Asp Ala Asn Ile Asp Trp Ala Arg His Gln
            340                 345                 350
```

```
Ile Glu Ser Ser Ser Asn Val Cys Gly Glu Lys Leu Gly Ile Ile Asn
            355                 360                 365

Gly Gly Leu Asn Tyr Gln Ile Glu His His Leu Phe Pro Arg Met Ser
        370                 375                 380

His Ala His Tyr Ser Lys Ile Gln Pro Val Val Gln Lys Val Cys Glu
385                 390                 395                 400

Glu Asn Gly Val Asn Tyr Lys His Phe Gly Thr Ile Leu Ser Asn Leu
                405                 410                 415

Asp Ser Thr Phe Lys Gln Val Gly Leu Gly Ser Val Pro Val Tyr
            420                 425                 430

Glu Phe Met Glu Gly Leu
        435

<210> SEQ ID NO 104
<211> LENGTH: 440
<212> TYPE: PRT
<213> ORGANISM: Artificial
<220> FEATURE:
<223> OTHER INFORMATION: delta-4 desaturase 91% sequence identity to
      SEQ ID NO 79

<400> SEQUENCE: 104

Met Pro Pro His Ser Arg Thr Lys Val Ser Asp Asp Pro Glu Leu Ser
1               5                   10                  15

Asp Leu Met Lys His Phe Thr Tyr Glu Glu Ile Leu Asn Asp Thr Arg
            20                  25                  30

Asp Lys Tyr Cys Ile Leu Gly Asp Gly Val Tyr Asp Ser Thr Asn Phe
        35                  40                  45

Arg Asp Lys His Pro Gly Gly Asp Val Leu Asp Phe Phe Pro Gly Gln
50                  55                  60

Asp Ala Thr Pro His Phe Tyr Met Tyr His Gln Arg Glu Trp Leu Pro
65                  70                  75                  80

Ser Val Leu Ser Glu Phe Lys Val Gly Ser Leu Ala Arg Asp Asp Ser
            85                  90                  95

Tyr Val Tyr His Thr Pro Leu Met Lys Gln Ile Lys Ser Ala Val Arg
        100                 105                 110

Lys Val Met Pro Met Gln Glu Trp Trp Ala Pro Pro Ser Trp Tyr Ile
    115                 120                 125

Lys Ala Cys Ala Ile Leu Val Ala Thr Leu Tyr Thr Asp Tyr Leu Trp
    130                 135                 140

Ile Ala Arg Gly Pro Thr Ile Pro Leu Ala Ile Val Ser Gly Leu Leu
145                 150                 155                 160

Tyr Ala Ala Ile Gly Leu Asn Ile Gln His Asp Ala Asn His Gly Gly
                165                 170                 175

Val Ser Arg Asn Pro Val Val Asn Arg Leu Phe Gly Tyr Ser Gln Asp
            180                 185                 190

Trp Ile Gly Gly Ser Arg Met Leu Trp Ile Arg Gln His Val Val Gly
        195                 200                 205

His His Thr His Thr Asn Arg His Gln His Asp Pro Asp Val Lys Gly
    210                 215                 220

Gly Ser Val Ile Thr Leu Ser Pro Thr Ser Leu Pro Met Glu Phe His
225                 230                 235                 240

His Ile Gln Gln Ile Tyr Phe Leu Pro Leu Glu Ala Leu Leu Gly Phe
                245                 250                 255

Gln Trp Val Phe Leu Asp Leu His Asp Leu Leu Glu Met Lys Tyr Lys
            260                 265                 270
```

```
Gly Glu Lys Leu Pro Glu Ser Tyr Arg Lys Glu Arg Asn Ile Ala Ile
            275                 280                 285

Gly Leu Arg Val Phe Phe Ile Arg Lys Val Val Leu Pro Phe Ala
        290                 295                 300

Leu His Phe Ser Trp Tyr Thr Leu Leu Cys Thr Cys Leu Trp Met Ala
305                 310                 315                 320

Ile Ala Ala Phe Tyr Leu Gly Phe Phe Ile Leu Ser His Asn Phe
            325                 330                 335

Val Gly Ala Lys Ser Leu Pro Glu Asp Ala Asn Val Asp Trp Ala Arg
            340                 345                 350

His Gln Ile Glu Ser Ser Asn Val Gly Gly Glu Lys Leu Gly Ile
            355                 360                 365

Ser Asn Gly Gly Leu Asn Tyr Gln Ile Glu His His Leu Phe Pro Arg
            370                 375                 380

Met Ser His Ala His Tyr Ser Lys Ile Gln Pro Val Val Gln Lys Val
385                 390                 395                 400

Cys Glu Glu Asn Gly Val Lys Tyr Lys Lys Phe Gly Thr Ile Leu Ser
                405                 410                 415

Asn Leu Asp Ser Thr Phe Arg His Val Gly Ala Leu Gly Ser Val Ala
            420                 425                 430

Val Tyr Glu Phe Met Glu Lys Leu
        435                 440

<210> SEQ ID NO 105
<211> LENGTH: 439
<212> TYPE: PRT
<213> ORGANISM: Artificial
<220> FEATURE:
<223> OTHER INFORMATION: delta-4 desaturase 91% sequence identity to
      SEQ ID NO 79

<400> SEQUENCE: 105

Met Pro Pro His Ala Arg Arg Lys Val Ser Asp Pro Glu Leu Ser Ala
1               5                   10                  15

Ala Lys His Phe Thr Arg Glu Arg Ile Leu Asn His Thr Arg Asp Lys
            20                  25                  30

Tyr Cys Ile Leu Glu Asp Gly Val Tyr Asp Leu Thr Asn Phe Arg Asp
        35                  40                  45

Glu His Pro Gly Gly Asp Val Leu Asp Ile Phe Pro Gly Gln Asp Ala
    50                  55                  60

Thr Pro His Phe Tyr Met Leu His Arg Tyr Glu Ser Pro Pro Ser Val
65                  70                  75                  80

Leu Ala Glu Tyr Lys Val Gly Ser Val Ala Arg Asp Asp Ser Phe Thr
                85                  90                  95

Tyr His Thr Pro Leu Met Lys Arg Ile Lys Ser Ala Val Arg Ala Val
            100                 105                 110

Met Pro Met Gln Glu Trp Trp Ala Pro Pro Ser Trp Tyr Ile Lys Ala
        115                 120                 125

Cys Ala Ile Leu Val Ala Thr Leu Tyr Leu Asp Tyr Leu Trp Ile Ala
    130                 135                 140

Lys Gly Pro Thr Ile Pro Leu Ala Ile Val Ile Gly Leu Leu Phe Ala
145                 150                 155                 160

Ala Ile Gly Leu Asn Ile Gln His Asp Ala Asn His Gly Ser Val Ser
                165                 170                 175

Arg Asn Pro Met Val Asn Arg Leu Phe Gly Tyr Ser Gln Asp Trp Ile
```

```
                180                 185                 190
Gly Gly Ser Met Met Leu Trp Ile Gln Gln His Val Gly His His
            195                 200                 205

Thr His Cys Asn Arg His Gln His Asp Pro Asp Val Lys Gly Gly Ser
210                 215                 220

Val Ile Thr Leu Ser Arg Tyr Ser Gly Pro Lys Glu Phe His His Ile
225                 230                 235                 240

Gln Gln Ile Tyr Phe Leu Pro Leu Ile Gln Leu Leu Gly Phe Gln Trp
            245                 250                 255

Val Phe Leu Gly Leu His Asp Leu Ile Glu Met Lys Tyr Lys Gly Glu
            260                 265                 270

Lys Leu Pro Pro Ser Tyr Arg Lys Glu Arg Asn Ile Ala Ile Gly Cys
            275                 280                 285

Arg Val Phe Phe Phe Ile Arg Lys Phe Val Pro Phe Ala Leu His
            290                 295                 300

Phe Ser Trp Tyr Thr Leu Leu Cys Thr Cys Leu Trp Met Ala Ile Ala
305                 310                 315                 320

Ala Leu Tyr Leu Ala Phe Phe Phe Ile Leu Ser His Ile Phe Val Gly
                325                 330                 335

Ala Lys Ser Leu Pro Glu Asp Ala Lys Asn Ile Glu Trp Ala Arg His
            340                 345                 350

Gln Ile Glu Ser Ser Ser Asn Val Cys Gly Lys Leu Gly His Ser
            355                 360                 365

Asn Gly Gly Leu Asn Tyr Gln Ile Glu His His Leu Phe Pro Arg Leu
370                 375                 380

Ser His Ser His Tyr Ser Lys Ile Gln Pro Val Val Gln Lys Val Cys
385                 390                 395                 400

Glu Glu Asn Gly Val Asn Tyr Lys Lys Phe Pro Thr Ile Gly Ser Asn
                405                 410                 415

Leu Asp Ser Thr Phe Arg His Val Lys Ala Leu Gly Ser Val Ala Val
                420                 425                 430

Tyr Glu Phe Met Glu Gly Leu
            435

<210> SEQ ID NO 106
<211> LENGTH: 438
<212> TYPE: PRT
<213> ORGANISM: Artificial
<220> FEATURE:
<223> OTHER INFORMATION: delta-4 desaturase 90.8% sequence identity to
      SEQ ID NO 79

<400> SEQUENCE: 106

Met Pro Pro His Ser Arg Thr Lys Val Ser Ala Pro Glu Leu Ser Asp
1               5                   10                  15

Met Lys His Phe Thr Arg Glu Glu Ile Ala Asn His Thr Asn Asp Lys
            20                  25                  30

Leu Cys Ile Leu Glu Asp Gly Val Tyr Asp Leu Thr Asn Phe Arg Asp
        35                  40                  45

Lys His Pro Gly Gly Asp Phe Leu Asp Phe Phe Pro Gly Gln Asp Ala
    50                  55                  60

Thr Pro His Phe Tyr Met Leu His Gln Arg Glu Trp Leu Pro Ser Val
65                  70                  75                  80

Leu Ala Glu Tyr Lys Val Gly Ser Val Ala Arg Asp Asp Ser Tyr Val
                85                  90                  95
```

```
Gln His Asp Pro Leu Met Lys Arg Ile Lys Ser Ala Val Arg Lys Val
            100                 105                 110

Ile Pro Met Gln Glu Trp Trp Ala Pro Pro Ser Trp Tyr Ile Lys Ala
        115                 120                 125

Cys Ala Ile Leu Ile Ala Thr Leu Tyr Thr Asp Tyr Leu Trp Ile Ala
    130                 135                 140

Ser Gly Pro Thr Ile Pro Leu Ala Ile Val Ser Gly Leu Leu Phe Ala
145                 150                 155                 160

Ala Ile Gly Leu Asn Ile Gln His Asp Ala Asn His Gly Ser Val Ser
                165                 170                 175

Arg Asn Pro Met Val Asn Tyr Leu Phe Gly Tyr Gly Gln Asp Trp Ile
            180                 185                 190

Gly Gly Ser Arg Met Leu Trp Ile Arg Gln His Val Val Gly His His
        195                 200                 205

Thr His Cys Asn Arg Val Gln His Asp Pro Asp Val Lys Gly Gly Ser
    210                 215                 220

Val Ile Arg Leu Ser Arg Tyr Ser Leu Pro Met Glu Phe His His Ile
225                 230                 235                 240

Gln Gln Tyr Tyr Phe Leu Pro Leu Glu Gln Leu Leu Gly Phe Gln Trp
                245                 250                 255

Val Phe Leu Gly Leu His Asp Leu Ile Glu Met Lys Tyr Lys Gly Glu
            260                 265                 270

Lys Leu Pro Glu Ser Tyr Arg Lys Glu Phe Asn Ile Ala Ile Gly Leu
        275                 280                 285

Arg Val Gly Phe Phe Ala Arg Lys Phe Val Pro Phe Ala Leu His Pro
    290                 295                 300

Pro Ser Trp Tyr Thr Leu Leu Cys Thr Cys Leu Trp Met Ala Ile Ala
305                 310                 315                 320

Ala Phe Tyr Leu Ala Phe Phe Phe Ile Leu Ser His Ile Phe Val Gly
                325                 330                 335

Ala Lys Ser Leu Pro Pro Asp Ala Asn Ile Asp Trp Ala Arg His Gln
            340                 345                 350

Ile Glu Thr Ser Ser Asn Val Cys Gly Asp Trp Leu Gly His Ser Asn
        355                 360                 365

Gly Gly Leu Asn Tyr Gln Ile Glu His His Leu Phe Pro Arg Met Ser
    370                 375                 380

His Ala His Tyr Ser Lys Ile Gln Pro Ile Val Gln Lys Val Cys Glu
385                 390                 395                 400

Glu Asn Gly Val Asn Tyr Lys His Phe Gly Thr Ile Leu Ser Asn Leu
                405                 410                 415

Asp Ser Ile Phe Arg Gln Val Lys Ala Leu Gly Ser Val Ala Thr Tyr
            420                 425                 430

Glu Phe Met Glu Gly Leu
        435

<210> SEQ ID NO 107
<211> LENGTH: 438
<212> TYPE: PRT
<213> ORGANISM: Artificial
<220> FEATURE:
<223> OTHER INFORMATION: delta-4 desaturase 90.8% sequence identity to
      SEQ ID NO 79

<400> SEQUENCE: 107

Met Pro Pro His Ser Arg Thr Lys Val Ser Asp Pro Glu Leu Ser Ala
1               5                   10                  15
```

-continued

```
Leu Met Lys His Phe Thr Arg Glu Glu Ile Leu Gly Asp Asn Asn Asp
            20                  25                  30

Lys Tyr Cys Ile Leu Glu Asp Gly Val Tyr Asp Leu Thr Asn Phe Arg
        35                  40                  45

Asp Lys His Pro Gly Gly Glu Val Leu Asp Phe Phe Pro Gly Gln Asp
    50                  55                  60

Ala Thr Pro Gly Phe Tyr Met Leu His Gln Tyr Ala Ser Leu Pro Ala
65                  70                  75                  80

Val Leu Ala Glu Tyr Gly Val Gly Ser Val Ala Arg Asp Asp Ser Tyr
                85                  90                  95

Val His His Thr Pro Leu Met Lys Gln Ile Cys Ser Asp Val Arg Lys
            100                 105                 110

Val Met Pro Met Gly Glu Gly Trp Ala Pro Pro Ser Trp Tyr Ile Lys
        115                 120                 125

Ala Cys Ala Ile Leu Ala Ala Thr Leu Tyr Thr Asp Tyr Leu Trp Ile
    130                 135                 140

Ala Arg Gly Pro Thr Ile Pro Leu Ala Ile Val Ile Gly Leu Leu Phe
145                 150                 155                 160

Ala Ala Ile Gly Leu Asn Ile Gln His Asp Ala Asn His Gly Ser Val
                165                 170                 175

Ser Arg Asn Pro Met Val Asn Arg Leu Phe Gly Tyr Ser Gln Asp Trp
            180                 185                 190

Ile Gly Gly Ser Arg Met Leu Trp Ile Arg Gln His Val Val Gly His
        195                 200                 205

His Leu His Cys Asn Arg His Gln His Asp Pro Asp Val Lys Gly Gly
    210                 215                 220

Ser Val Ile Thr Leu Ser Arg Tyr Ser Leu Trp Leu Glu Phe His His
225                 230                 235                 240

Ile Gln Gln Tyr Tyr Phe Leu Pro Leu Ile Gln Leu Leu Gly Phe Gln
                245                 250                 255

Trp Val Phe Leu Gly Leu His Asp Leu Ile Glu Trp Lys Tyr Lys Gly
            260                 265                 270

Glu Lys Leu Pro Glu Ser Ala Arg Pro Glu Arg Asn Ile Ala Ile Gly
        275                 280                 285

Leu Arg Val Phe Phe Phe Ala Arg Lys Ile Ile Val Pro Phe Ala Leu
    290                 295                 300

His Phe Ser Trp Tyr Thr Leu Leu Cys Thr Cys Leu Trp Met Ala Thr
305                 310                 315                 320

Ala Ala Leu Tyr Leu Gly Phe Phe Phe Ile Leu Ser His Ile Phe Val
                325                 330                 335

Gly Ala Lys Ser Leu Pro Glu Asp Ala Asn Ile Asp Trp Ala Arg His
            340                 345                 350

Gln Ile Glu Ser Ser Ser Asn Val Gly Gly Glu Lys Leu Gly Ile Leu
        355                 360                 365

Asn Gly Gly Leu Asn Tyr Gln Ile Glu His His Leu Phe Pro Arg Met
    370                 375                 380

Ser His Ala His Tyr Ser Lys Ile Gln Pro Val Val Gln Lys Val Cys
385                 390                 395                 400

Glu Glu Asn Gly Val Asn Tyr Lys His Phe Gly Thr Ile Ala Ser Asn
                405                 410                 415

Leu Asp Ser Thr Phe Ser Gln Val Gly Ala Leu Gly Ser Val Ala Val
            420                 425                 430
```

Glu Phe Met Glu Gly Leu
        435

<210> SEQ ID NO 108
<211> LENGTH: 438
<212> TYPE: PRT
<213> ORGANISM: Artificial
<220> FEATURE:
<223> OTHER INFORMATION: delta-4 desaturase 90.8% sequence identity to
      SEQ ID NO 79

<400> SEQUENCE: 108

Met Pro Pro His Ser Arg Ser Lys Val Ser Asp Pro Glu Leu Lys Asp
1               5                   10                  15

Leu Met Lys His Phe Thr Arg Glu Glu Lys Leu Asn His Thr Asn Asp
            20                  25                  30

Lys Tyr Cys Ile Leu Glu Asp Gly Val Tyr Asp Leu Thr Asn Phe Arg
        35                  40                  45

Asp Lys His Pro Gly Gly Asp Val Leu Asp Leu Phe Pro Gly Gln Asp
    50                  55                  60

Ala Thr Pro Gly Phe Tyr Met Leu His Arg Tyr Glu Trp Leu Pro Ser
65                  70                  75                  80

Val Leu Ala Glu Tyr Lys Val Gly Ser Val Ala Arg Asp Asp Ser Tyr
                85                  90                  95

Val Tyr His Thr Pro Gly Tyr Lys Gln Ile Lys Ser Ala Val Asn Lys
            100                 105                 110

Val Met Pro Met Gln Glu Trp Trp Ala Pro Pro Ser Trp Tyr Ile Lys
        115                 120                 125

Ala Cys Ala Ile Leu Ala Ala Thr Leu Tyr Thr Asp Tyr Leu Trp Ile
    130                 135                 140

Ala Arg Gly Pro Thr Ile Pro Leu Ala Ile Val Leu Gly Leu Leu Tyr
145                 150                 155                 160

Ala Ala Ile Gly Leu Asn Ile Gln His Asp Ala Asn His Gly Ser Val
                165                 170                 175

Ser Arg Asn Pro Met Val Asn Arg Leu Phe Gly Tyr Ser Gln Asp Trp
            180                 185                 190

Ile Gly Gly Ser Arg Met Leu Trp Leu Arg Gln His Val Val Gly His
        195                 200                 205

His Thr His Cys Asn Asp Ile Gln His Asp Pro Asp Val Lys Gly Gly
    210                 215                 220

Gly Ala Ile Thr Leu Ser Arg Val Ser Ile Pro Lys Glu Phe His His
225                 230                 235                 240

Ile Gln Gln Tyr Tyr Phe Leu Pro Leu Asp Gln Leu Leu Gly Phe Gln
                245                 250                 255

Trp Val Phe Leu Gly Leu His Asp Leu Ile Glu Trp Lys Trp Lys Gly
            260                 265                 270

Glu Lys Leu Pro Pro Ser Tyr Arg Lys Glu Arg Asn Pro Ala Ile Gly
        275                 280                 285

Cys Arg Val Phe Phe Phe Ile Arg Lys Phe Val Val Pro Leu Ala Leu
    290                 295                 300

His Phe Ser Trp Tyr Thr Leu Leu Cys Thr Tyr Leu Trp Val Ala Thr
305                 310                 315                 320

Gly Ala Leu Tyr Leu Gly Phe Phe Ile Leu Ser His Ile Phe Val
                325                 330                 335

Gly Ala Gly Ser Leu Pro Glu Asp Ala Asn Ile Asp Trp Gly Arg His
            340                 345                 350

```
Gln Ile Glu Ser Ser Asn Val Cys Gly Glu Lys Leu Gly Ile Ser
        355                 360                 365

Asn Gly Gly Leu Asn Tyr Gln Ile Glu His His Leu Phe Pro Arg Met
370                 375                 380

Ser His Ala His Tyr Ser Lys Ile Gln Pro Val Val Gln Lys Ile Cys
385                 390                 395                 400

Glu Glu Asn Gly Val Asn Tyr Lys Lys Phe Gly Thr Ile Leu Ser Asn
                405                 410                 415

Leu Asp Ser Thr Phe Ser Gln Val Lys Ala Leu Gly Ser Val Pro Val
            420                 425                 430

Glu Phe Met Glu Gly Leu
        435
```

<210> SEQ ID NO 109
<211> LENGTH: 438
<212> TYPE: PRT
<213> ORGANISM: Artificial
<220> FEATURE:
<223> OTHER INFORMATION: delta-4 desaturase 90.8% sequence identity to
      SEQ ID NO 79

<400> SEQUENCE: 109

```
Met Pro Pro His Ser Arg Thr Lys Val Ser Val Pro Glu Leu Ser Asp
1               5                   10                  15

Leu Ala Lys His Phe Thr Arg Glu Glu Ile Leu Asn His Thr Asn Asp
            20                  25                  30

Lys Tyr Cys Ile Leu Glu Asp Gly Val Tyr Asp Leu Thr Asn Phe Arg
        35                  40                  45

Asp Lys His Pro Gly Gly Asp Val Leu Asp Phe Phe Pro Gly Gln Asp
    50                  55                  60

Ala Thr Pro His Phe Tyr Met Leu His Arg Tyr Glu Trp Pro Pro Ser
65              70                  75                  80

Val Leu Ala Glu Tyr Lys Val Gly Ser Val Ala Arg Asp Asp Ser Tyr
            85                  90                  95

Val Tyr His Thr Pro Leu Met Lys Gln Ile Lys Ser Ala Val Arg Lys
        100                 105                 110

Val Ile Pro Met Gly Glu Gly Trp Ala Pro Pro Ser Trp Tyr Ile Lys
    115                 120                 125

Ala Cys Ala Ile Leu Ala Ala Thr Leu Tyr Thr Asp Tyr Tyr Trp Ile
130                 135                 140

Ala Lys Gly Pro Thr Ile Pro Leu Ala Ile Val Ser Gly Leu Leu Tyr
145                 150                 155                 160

Ala Ala Ile Gly Leu Asn Ile Gln His Asp Ala Asn His Gly Ser Ile
            165                 170                 175

Ser Arg Asn Pro Met Val Asn Tyr Leu Phe Gly Tyr Ser Gln Asp Trp
        180                 185                 190

Ile Gly Gly Ser Arg Met Leu Trp Ile Gln Gln His Val Val Gly His
    195                 200                 205

His Thr His Cys Asn Glu Ile Asp His Asp Pro Asp Val Lys Gly Gly
210                 215                 220

Ser Val Ile Thr Leu Lys Arg Ser Ser Leu Pro Lys Glu Trp His His
225                 230                 235                 240

Ile Gln Gln Tyr Tyr Phe Leu Pro Leu Glu Gln Leu Leu Gly Phe Gln
            245                 250                 255

Trp Val Phe Leu Gly Leu His Asp Leu Ile Glu Trp Lys Tyr Lys Gly
```

-continued

```
                260                 265                 270
Glu Lys Leu Pro Glu Ile Tyr Arg Lys Glu Arg Asn Ile Ala Ile Gly
            275                 280                 285

Cys Arg Val Phe Phe Ala Arg Lys Phe Ala Val Pro Phe Ala Leu
        290                 295                 300

His Phe Ser Trp Tyr Thr Leu Leu Cys Thr Tyr Leu Trp Met Ala Ile
305                 310                 315                 320

Gly Ala Leu Tyr Leu Gly Phe Phe Ile Leu Ser His Ile Phe Val
            325                 330                 335

Gly Ala Lys Ser Leu Gly Pro Glu Ala Asn Ile Glu Trp Ala Arg His
            340                 345                 350

Gln Ile Glu Ser Ser Asn Val Cys Gly Glu Lys Leu Gly Ile Leu
            355                 360                 365

Asn Gly Gly Leu Asn Tyr Gln Ile Glu His His Leu Phe Pro Arg Met
            370                 375                 380

Ser His Ala His Tyr Ser Lys Ile Ala Pro Val Val Gln Arg Val Cys
385                 390                 395                 400

Glu Glu Asn Gly Val Asn Tyr Lys Lys Phe Gly Thr Ile Leu Ser Asn
                405                 410                 415

Leu Asp Ser Thr Phe Arg Gln Val Lys Ala Ile Gly Ser Val Ala Val
                420                 425                 430

Glu Phe Met Glu Gly Leu
            435

<210> SEQ ID NO 110
<211> LENGTH: 440
<212> TYPE: PRT
<213> ORGANISM: Artificial
<220> FEATURE:
<223> OTHER INFORMATION: delta-4 desaturase 90.8% sequence identity to
      SEQ ID NO 79

<400> SEQUENCE: 110

Met Pro Pro His Ser Arg Thr Lys Val Ser Asp Pro Glu Leu Ser Asp
1               5                   10                  15

Leu Met Lys His Phe Thr Arg Glu Lys Ile Leu Asn His Thr Asn Asp
                20                  25                  30

Lys Tyr Cys Ile Leu Glu Asp Gly Val Tyr Asp Leu Thr Asn Phe Arg
            35                  40                  45

Asp Lys His Pro Gly Gly Asp Phe Leu Asp Phe Phe Pro Gly Gln Asp
        50                  55                  60

Ala Thr Pro His Phe Tyr Met Leu His Gln Tyr Glu Trp Leu Pro Ser
65                  70                  75                  80

Val Leu Ala Glu Tyr Lys Val Gly Ser Val Ala Arg Asp Asp Ser Tyr
                85                  90                  95

Val Tyr His Asp Pro Leu His Leu Gln Ile Cys Cys Ala Val Arg Lys
            100                 105                 110

Val Met Pro Met Gln Glu Trp Trp Ala Pro Ser Trp Trp Ile Lys
        115                 120                 125

Ala Cys Ala Ile Leu Ile Ala Thr Leu Tyr Thr Asp Tyr Leu Trp Ile
130                 135                 140

Ala Ser Gly Pro Thr Ile Pro Leu Ala Ile Ile Ser Gly Leu Leu Tyr
145                 150                 155                 160

Ala Ala Ile Gly Leu Asn Ile Gln His Asp Ala Asn His Gly Ser Val
                165                 170                 175
```

```
Ser Arg Asn Pro Met Val Asn Tyr Leu Phe Gly Tyr Ser Gln Asp Trp
            180                 185                 190

Ile Gly Gly Ser Arg Met Leu Trp Ile Arg Gln His Val Val Gly His
        195                 200                 205

His Thr His Ser Asn Arg His Gln His Asp Pro Asp Val Lys Gly Gly
    210                 215                 220

Ser Val Ile Thr Leu Ser Arg Tyr Ser Leu Pro Met Glu Phe His His
225                 230                 235                 240

Ile Gln Gln Tyr Tyr Phe Leu Pro Leu Asp Ala Leu Tyr Gly Phe Gln
            245                 250                 255

Trp Val Phe Leu Gly Leu His Asp Leu Ile Glu Met Lys Trp Lys Gly
        260                 265                 270

Glu Pro Leu Pro Glu Leu Tyr Arg Lys Glu Arg Asn Ile Ala Ile Gly
    275                 280                 285

Leu Lys Val Phe Phe Phe Ile Arg Lys Phe Val Val Pro Phe Ala Leu
290                 295                 300

His Phe Ser Trp Tyr Thr Leu Leu Cys Thr Cys Ala Trp Met Ala Ile
            305                 310                 315             320

Ala Ala Leu Tyr Leu Ala Phe Phe Ile Leu Ser His Asn Phe Val
        325                 330                 335

Gly Ile Lys Ser Leu Pro Glu Asp Ala Ser Ile Asp Trp Ala Arg His
    340                 345                 350

Gln Ile Glu Ser Ser Ser Asn Val Gly Gly Glu Lys Leu Gly Ile Leu
        355                 360                 365

Asn Gly Gly Leu Asn Tyr Gln Ile Glu His His Leu Phe Pro Arg Met
    370                 375                 380

Ser His Ala His Tyr Ser Lys Ile Glu Pro Val Val Gln Lys Val Cys
385                 390                 395                 400

Glu Glu Asn Gly Val Asn Tyr Lys Lys Phe Gly Thr Ile Gly Ser Asn
            405                 410                 415

Leu Gly Ala Thr Phe Arg Tyr Val Lys Ala Leu Gly Ser Val Pro Thr
        420                 425                 430

Tyr Asn Glu Phe Met Glu Gly Leu
    435                 440

<210> SEQ ID NO 111
<211> LENGTH: 440
<212> TYPE: PRT
<213> ORGANISM: Artificial
<220> FEATURE:
<223> OTHER INFORMATION: delta-4 desaturase 90.8% sequence identity to
      SEQ ID NO 79

<400> SEQUENCE: 111

Met Pro Pro His Ser Arg Thr Lys Gly Ser Asp Asp Pro Glu Leu Ser
1               5                   10                  15

Asp Met Lys His Phe Thr Tyr Glu Glu Ile Leu Asn His Thr Asn Pro
            20                  25                  30

Lys Tyr Cys Ile Leu Glu Asp Gly Val Tyr Asp Leu Asn Asn Phe Arg
        35                  40                  45

Asp Lys His Pro Gly Gly Asp Phe Leu Asp Phe Pro Gly Gln Asp
    50                  55                  60

Ala Thr Pro His Phe Tyr Met Phe His Gln His Val Ser Leu Pro Ser
65                  70                  75                  80

Val Leu Ala Glu Tyr Lys Val Gly Ser Ile Ala Arg Asp Asp Ser Tyr
            85                  90                  95
```

Val Tyr His Asp Pro Leu Met Lys Gln Ile Lys Ser Ala Val Arg Gly
            100                 105                 110

Val Met Pro Met Gln Glu Trp Trp Ala Pro Pro Ser Trp Tyr Ile Lys
            115                 120                 125

Ala Cys Ala Ile Leu Ala Ala Thr Leu Tyr Thr Asp Tyr Tyr Trp Leu
130                 135                 140

Ala Ser Gly Pro Thr Ile Pro Leu Gly Ile Val Ser Gly Leu Leu Tyr
145                 150                 155                 160

Ala Ala Ile Gly Leu Asn Ile Gln His Asp Ala Asn His Gly Ser Leu
            165                 170                 175

Ser Arg Asn Pro Met Val Asn Arg Leu Phe Gly Tyr Ser Gln Asp Trp
            180                 185                 190

Ile Gly Gly Asn Arg Met Leu Trp Ile Arg Gln His Val Val Gly His
            195                 200                 205

His Thr His Cys Asn Arg Ile Asp His Asp Pro Asp Val Lys Gly Gly
            210                 215                 220

Gly Val Ile Thr Leu Ser Arg Ser Ser Leu Pro Lys Glu Phe His His
225                 230                 235                 240

Ile Gln Gln Tyr Tyr Phe Leu Pro Leu Glu Gln Leu Tyr Gly Phe Gln
            245                 250                 255

Trp Val Phe Leu Gly Leu His Asp Leu Leu Glu Met Lys Tyr Lys Gly
            260                 265                 270

Glu Lys Leu Pro Glu Ser Ala Arg Lys Glu Arg Asn Ile Ala Ile Gly
            275                 280                 285

Leu Arg Val Phe Phe Phe Ile Arg Lys Phe Val Pro Phe Trp Leu
            290                 295                 300

His Phe Ser Trp Tyr Thr Leu Leu Cys Thr Tyr Leu Trp Met Ala Thr
305                 310                 315                 320

Ala Ala Phe Tyr Leu Cys Phe Phe Ile Leu Ser His Ile Phe Val
            325                 330                 335

Gly Val Lys Ser Leu Pro Glu Asp Ala Lys Asn Ile Asp Trp Ala Arg
            340                 345                 350

His Gln Ile Glu Ser Ser Ser Asn Val Cys Gly Glu Lys Leu Gly Ile
            355                 360                 365

Ser Asn Gly Gly Leu Asn Tyr Gln Ile Glu His His Leu Phe Pro Arg
370                 375                 380

Met His His Ala His Tyr Ser Lys Ile Ala Pro Val Val Gln Lys Val
385                 390                 395                 400

Cys Glu Glu Met Gly Val Asn Tyr Lys Lys Phe Gly Thr Ile Leu Ser
            405                 410                 415

Asn Leu Asp Ser Thr Phe Arg Gln Ile Lys Ala Leu Gly Ser Val Ala
            420                 425                 430

Val Tyr Glu Tyr Met Glu Gly Leu
        435                 440

<210> SEQ ID NO 112
<211> LENGTH: 440
<212> TYPE: PRT
<213> ORGANISM: Artificial
<220> FEATURE:
<223> OTHER INFORMATION: delta-4 desaturase 90.8% sequence identity to
      SEQ ID NO 79

<400> SEQUENCE: 112

Met Pro Pro His Ser Arg Thr Lys Val Ser Asp Asp Pro Glu Leu Ser

-continued

```
1               5                   10                  15
Asp Met Lys His Phe Ser Arg Glu Glu Ile Leu Asp His Thr Arg Asp
                20                  25                  30
Lys Tyr Cys Ile Leu Glu Asp Gly Val Tyr Asp Leu Asn Asn Phe Arg
                35                  40                  45
Asp Lys His Pro Gly Gly Asp Val Leu Asp Phe Pro Gly Gln Asp
            50                  55                  60
Ala Thr Pro Gly Phe Tyr Met Leu His Gln Arg Glu Ser Leu Pro Gly
65                  70                  75                  80
Val Leu Ala Glu Tyr Phe Val Gly Ser Ile Ala Arg Asp Asp Ser Phe
                85                  90                  95
Val His His Glu Pro Leu Met Lys Gln Ile Cys Ser Ala Val Arg Gly
                100                 105                 110
Val Leu Pro Met Gln Glu Trp Trp Ala Pro Pro Ser Trp Tyr Ile Lys
                115                 120                 125
Ala Cys Ala Ile Leu Ala Ala Thr Leu Tyr Thr Asp Tyr Leu Trp Ile
                130                 135                 140
Ala Ser Gly Pro Thr Ile Pro Leu Ser Ile Val Ile Gly Leu Leu Tyr
145                 150                 155                 160
Ala Ala Ile Gly Leu Asn Ile Gln His Asp Ala Asn His Gly Ser Val
                165                 170                 175
Ser Arg Asn Pro Met Val Asn Arg Leu Phe Gly Tyr Ser Gln Asp Trp
                180                 185                 190
Ile Gly Gly Ser Arg Val Leu Trp Ile Gln Lys His Val Val Gly His
                195                 200                 205
His Thr His Cys Asn Arg Val Asp His Asp Pro Asp Val Lys Gly Gly
                210                 215                 220
Ser Val Ile Thr Leu Ser Pro Ser Ser Leu Pro Lys Glu Phe His His
225                 230                 235                 240
Ile Gln Gln Tyr Tyr Phe Leu Pro Leu Asp Gln Leu Leu Gly Phe Gln
                245                 250                 255
Trp Val Phe Leu Gly Leu His Asp Leu Ile Glu Met Arg Tyr Lys Gly
                260                 265                 270
Glu Lys Leu Pro Glu Ser Tyr Arg Lys Glu Phe Asn Ile Ala Ile Gly
                275                 280                 285
Leu Arg Val Phe Phe Phe Ile Arg Lys Phe Val Val Pro Phe Ala Leu
                290                 295                 300
His Phe Ser Trp Tyr Thr Leu Leu Cys Thr Tyr Leu Trp Met Ala Ile
305                 310                 315                 320
Ala Ala Leu Tyr Leu Gly Phe Phe Ile Leu Ser His Ile Phe Val
                325                 330                 335
Gly Val Lys Ser Leu Pro Glu Asp Ala Lys Asn Ile Asp Trp Ala Arg
                340                 345                 350
His Gln Ile Glu Ser Ser Asn Val Cys Gly Glu Trp Leu Gly His
                355                 360                 365
Ser Asn Gly Gly Leu Asn Tyr Gln Ile Glu His His Leu Phe Pro Arg
                370                 375                 380
Met Asn His Ala His Tyr Ser Lys Ile Gln Pro Val Val Gln Lys Val
385                 390                 395                 400
Cys Glu Glu Asn Gly Val Asn Tyr Lys Lys Phe Pro Thr Ile Gly Ser
                405                 410                 415
Asn Leu Asp Ser Ile Phe Arg Gln Val Lys Ala Leu Gly Ala Val Ala
                420                 425                 430
```

Val Tyr Glu Phe Met Glu Gly Pro
         435                 440

<210> SEQ ID NO 113
<211> LENGTH: 442
<212> TYPE: PRT
<213> ORGANISM: Artificial
<220> FEATURE:
<223> OTHER INFORMATION: delta-4 desaturase 90.8% sequence identity to
      SEQ ID NO 79

<400> SEQUENCE: 113

Met Pro Pro His Ser Arg Arg Lys Val Ser Asp Ser Asp Pro Glu Leu
1               5                   10                  15

Arg Asp Leu Met Lys His Phe Thr Arg Glu Glu Ile Leu Asn His Thr
            20                  25                  30

Asn Asp Lys Tyr Cys Ile Leu Glu Asp Gly Val Tyr Asp Leu Thr Asn
        35                  40                  45

Phe Arg Asp Lys His Pro Gly Gly Asp Tyr Leu Asp Phe Phe Pro Gly
    50                  55                  60

Gln Asp Ala Thr Pro His Phe Tyr Met Tyr His Gln Tyr Val Ser Leu
65                  70                  75                  80

Pro Ser Leu Leu Ala Glu Tyr Lys Val Gly Ser Val Ala Arg Asp Asp
                85                  90                  95

Ser Tyr Val Tyr His Thr Pro Leu Met Lys Gln Ile Lys Ala Asp Val
            100                 105                 110

Arg Lys Val Met Pro Met Gly Glu Trp Trp Ala Pro Pro Ser Trp Tyr
        115                 120                 125

Ile Lys Ala Cys Ala Leu Ile Val Ala Thr Leu His Thr Asp Tyr Leu
    130                 135                 140

Trp Ile Ala Ser Gly Pro Thr Ile Pro Leu Ala Ile Val Leu Gly Leu
145                 150                 155                 160

Leu Tyr Ala Ala Ile Gly Leu Asn Ile Gln His Asp Ala Asn His Gly
                165                 170                 175

Ser Val Ser Arg Asn Pro Met Val Asn Arg Leu Phe Gly Tyr Ser Gln
            180                 185                 190

Asp Trp Ile Gly Gly Ser Arg Met Leu Trp Ile Arg Gln His Val Val
        195                 200                 205

Gly His His Thr His Cys Asn Arg His Gln His Asp Pro Asp Val Lys
    210                 215                 220

Gly Gly Ser Val Ile Gln Leu Ser Pro Thr Ser Leu Pro Leu Glu Phe
225                 230                 235                 240

His Ala Ile Gln Gln Tyr Tyr Phe Leu Pro Gly Ile Gln Leu Leu Gly
                245                 250                 255

Phe Lys Trp Val Phe Leu Gly Leu His Asp Leu Ile Glu Met Lys Tyr
            260                 265                 270

Lys Gly Glu Lys Leu Ser Glu Ser Tyr Arg Lys Asp Arg Asn Ile Ala
        275                 280                 285

Ile Gly Leu Arg Val Phe Phe Trp Val Arg Phe Val Val Pro Phe
    290                 295                 300

Ala Leu His Phe Ser Trp Tyr Thr Ile Leu Cys Ile Tyr Leu Trp Met
305                 310                 315                 320

Ala Ile Gly Ala Leu Tyr Leu Gly Phe Phe Phe Ile Leu Ser His Ile
                325                 330                 335

Phe Val Gly Ala Lys Ser Leu Pro Pro Asp Ala Lys Asn Ile Asp Trp

```
                    340                 345                 350
Ala Arg His Gln Ile Glu Ser Ser Asn Val Cys Gly Asp Lys Leu
                355                 360                 365

Gly Ile Ser Asn Gly Gly Leu Asn Tyr Gln Ile Glu His His Leu Phe
            370                 375                 380

Pro Arg Leu Ser His Ala His Tyr Ala Pro Ile Gln Pro Val Val Arg
385                 390                 395                 400

Lys Val Cys Glu Glu Asn Gly Val Asn Tyr Lys Lys Phe Gly Thr Ile
                405                 410                 415

Gly Ser Asn Leu Asp Ser Thr Phe Gln Tyr Val Lys Ala Leu Gly Ser
                420                 425                 430

Val Ala Val Tyr Glu Phe Met Glu Gly Leu
                435                 440

<210> SEQ ID NO 114
<211> LENGTH: 437
<212> TYPE: PRT
<213> ORGANISM: Artificial
<220> FEATURE:
<223> OTHER INFORMATION: delta-4 desaturase 90.6% sequence identity to
      SEQ ID NO 79

<400> SEQUENCE: 114

Met Pro Pro His Ser Arg Thr Lys Val Ser Asp Pro Glu Leu Ser Asp
1               5                   10                  15

Met Glu His Phe Ala Arg Glu Arg Ile Leu Asn His Thr Asn Asp Lys
            20                  25                  30

Tyr Cys Ile Leu Glu Asp Gly Val Tyr Asp Leu Thr Asn Phe Arg Asp
        35                  40                  45

Lys His Pro Gly Gly Asp Tyr Leu Asp Ile Phe Pro Gly Gln Asp Ala
    50                  55                  60

Thr Pro His Phe Tyr Met Leu His Gln Tyr Glu Trp Pro Pro Ser Val
65                  70                  75                  80

Leu Ala Arg Tyr Lys Val Gly Ser Leu Ala Arg Asp Asp Ser Tyr Val
                85                  90                  95

Gln His Thr Pro Leu Met Lys Gln Ile Cys Ser Ala Val Arg Lys Val
            100                 105                 110

Met Pro Met Gln Glu Trp Trp Ala Pro Pro Ser Trp Tyr Ile Lys Ala
        115                 120                 125

Cys Ala Ile Leu Ala Ala Thr Leu Tyr Thr Asp Tyr Tyr Trp Ile Ala
    130                 135                 140

Ser Gly Pro Thr Ile Pro Leu Gly Ile Val Ser Gly Leu Leu Tyr Ala
145                 150                 155                 160

Ala Ile Gly Leu Asn Ile Gln His Asp Ala Asn His Gly Ser Val Ser
                165                 170                 175

Arg Asn Pro Met Val Asn Arg Leu Phe Gly Tyr Ser Gln Asp Trp Ile
            180                 185                 190

Gly Gly Ser Arg Leu Leu Trp Ile Arg Gln His Val Val Gly His His
        195                 200                 205

Thr His Cys Asn Asp His Gln His Asp Pro Asp Val Lys Gly Gly Ser
    210                 215                 220

Val Leu Thr Leu Ser Arg Val Ser Leu Pro Lys Glu Phe His His Ile
225                 230                 235                 240

Gln Gln Tyr Tyr Phe Leu Pro Leu Ile Val Leu Tyr Gly Phe Gln Trp
                245                 250                 255
```

-continued

```
Val Phe Leu Asp Leu His Asp Leu Ile Glu Met Arg Tyr Lys Gly Glu
            260                 265                 270

Lys Leu Pro Glu Ser Tyr Arg Pro Glu Arg Asn Ile Ala Ile Gly Cys
        275                 280                 285

Arg Ile Phe Phe Phe Ala Arg Lys Phe Ala Val Pro Phe Ala Leu His
    290                 295                 300

Phe Ser Trp Tyr Thr Leu Leu Cys Thr Tyr Leu Trp Val Ala Ile Ala
305                 310                 315                 320

Ser Leu Tyr Leu Gly Phe Phe Phe Ile Leu Ser His Asn Phe Val Gly
                325                 330                 335

Ala Lys Ser Leu Pro Glu Asp Ala Asn Ile Asp Trp Ala Arg His Gln
            340                 345                 350

Ile Glu Asn Ser Ser Asn Val Cys Gly Glu Lys Leu Gly Ile Leu Asn
        355                 360                 365

Gly Gly Leu Asn Tyr Gln Ile Glu His His Leu Phe Pro Arg Met His
    370                 375                 380

His Ala His Tyr Ser Lys Ile Gln Pro Val Val Gln Lys Val Cys Glu
385                 390                 395                 400

Glu Asn Gly Val Asn Tyr Lys His Phe Gly Thr Ile Leu Ser Asn Leu
                405                 410                 415

Asp Ser Ile Phe Arg Gln Val Lys Ala Leu Gly Ser Val Ala Val Glu
            420                 425                 430

Phe Met Glu Gly Leu
            435

<210> SEQ ID NO 115
<211> LENGTH: 438
<212> TYPE: PRT
<213> ORGANISM: Artificial
<220> FEATURE:
<223> OTHER INFORMATION: delta-4 desaturase 90.6% sequence identity to
      SEQ ID NO 79

<400> SEQUENCE: 115

Met Pro Pro His Ser Arg Thr Lys Val Gly Asp Pro Glu Leu Lys Asp
1               5                   10                  15

Met Lys His Phe Thr Tyr Glu Arg Ile Leu Asn His Thr Arg Asp Lys
            20                  25                  30

Tyr Cys Ile Leu Glu Asp Gly Val Tyr Asp Ser Thr Asn Phe Arg Asp
        35                  40                  45

Lys His Pro Gly Gly Asp Val Leu Asp Phe Phe Pro Gly Gln Asp Ala
    50                  55                  60

Thr Pro His Phe Tyr Met Leu His Lys Tyr Glu Trp Pro Pro Ser Ile
65                  70                  75                  80

Leu Ala Glu Tyr Lys Val Gly Ser Val Ala Arg Asp Asp Ser Tyr Val
                85                  90                  95

Gln Ala Thr Pro Leu Met Leu Gln Ile Lys Ser Ala Val Arg Lys Val
            100                 105                 110

Met Pro Met Gln Glu Trp Trp Ala Pro Pro Ser Trp Tyr Ile Lys Ala
        115                 120                 125

Cys Ala Ile Leu Ala Ala Thr Leu Tyr Thr Asp Tyr Leu Trp Ile Ala
    130                 135                 140

Arg Gly Pro Thr Ile Leu Leu Ala Ile Val Ser Gly Leu Leu Tyr Ala
145                 150                 155                 160

Trp Ile Gly Leu Asn Ile Gln His Asp Ala Asn His Gly Ala Val Ser
                165                 170                 175
```

```
Arg Asn Pro Met Val Asn Arg Leu Phe Gly Tyr Ser Gln Asp Trp Ile
            180                 185                 190

Gly Gly Ser Arg Met Leu Trp Ile Arg Gln His Val Gly His His
        195                 200                 205

Thr His Thr Asn Arg His Gln His Asp Pro Asp Val Lys Gly Gly Ser
210                 215                 220

Val Ile Thr Leu Ser Arg Tyr Asp Leu Pro Lys Glu Phe His His Ile
225                 230                 235                 240

Gln Gln Tyr Tyr Phe Leu Pro Gly Glu Gln Leu Leu Gly Phe Gln Trp
                245                 250                 255

Val Phe Leu Gly Leu His Glu Leu Ile Glu Met Lys Trp Lys Gly Glu
            260                 265                 270

Lys Leu Pro Glu Ser Tyr Arg Pro Glu Arg Asn Pro Ala Ile Gly Leu
        275                 280                 285

Lys Val Gly Phe Trp Ile Arg Lys Val Val Ile Pro Phe Ala Leu His
    290                 295                 300

Phe Ser Trp Tyr Thr Leu Leu Cys Thr Tyr Leu Trp Met Ala Ile Ala
305                 310                 315                 320

Ala Leu Tyr Leu Gly Phe Phe Phe Ile Leu Ser His Ile Phe Val Gly
                325                 330                 335

Val Lys Ser Leu Pro Glu Asp Ala Asn Ile Asp Trp Ala Arg His Gln
            340                 345                 350

Ile Glu Ser Ser Ser Asn Val Cys Gly Glu Lys Leu Gly Ile Met Asn
        355                 360                 365

Gly Gly Leu Asn Tyr Gln Ile Glu His His Leu Phe Pro Arg Met Ser
    370                 375                 380

His Ala His Tyr Ser Lys Ile Gln Pro Val Val Gln Lys Val Cys Glu
385                 390                 395                 400

Glu Asn Gly Val Asn Tyr Lys Lys Phe Gly Thr Ile Leu Ser Asn Leu
                405                 410                 415

Asp Ala Thr Phe Arg Gln Ile Lys Ala Leu Gly Ser Val Ala Val Tyr
            420                 425                 430

Glu Tyr Met Glu Gly Leu
        435

<210> SEQ ID NO 116
<211> LENGTH: 440
<212> TYPE: PRT
<213> ORGANISM: Artificial
<220> FEATURE:
<223> OTHER INFORMATION: delta-4 desaturase 90.6% sequence identity to
      SEQ ID NO 79

<400> SEQUENCE: 116

Met Pro Pro His Ser Arg Lys Lys Val Val Ser Asp Pro Glu Leu Ser
1               5                   10                  15

Asp Leu Met Lys His Phe Ser Tyr Glu Arg Ile Leu Asn His Thr Asn
            20                  25                  30

Asp Asp Tyr Cys Ile Leu Gly Asp Gly Val Tyr Asp Leu Thr Asn Phe
        35                  40                  45

Arg Asp Lys His Pro Gly Gly Asp Tyr Leu Asp Phe Phe Pro Gly Gln
    50                  55                  60

Asp Ala Thr Pro His Phe Trp Met Leu His Gln Lys Glu Ser Pro Pro
65                  70                  75                  80

Ser Val Leu Ala Glu Tyr Lys Val Gly Ser Val Ala Arg Asp Asp Ser
```

```
                    85                  90                  95
Tyr Val Tyr Tyr Asp Pro Leu Met Lys Gln Ile Lys Ser Ala Val Arg
                100                 105                 110

Lys Val Met Pro Met Gln Glu Gly Trp Ala Pro Pro Ser Trp Tyr Ile
            115                 120                 125

Lys Ala Cys Ala Ile Leu Ala Ala Thr Leu Tyr Thr Asp Tyr Leu Trp
        130                 135                 140

Leu Ala Ser Gly Pro Thr Ile Pro Leu Ser Ile Ser Gly Leu Leu
145                 150                 155                 160

Tyr Ala Trp Ile Gly Leu Asn Ile Gln His Asp Ala Asn His Gly Ser
                165                 170                 175

Leu Ser Arg Asn Pro Met Val Asn Arg Leu Phe Gly Tyr Gly Gln Asp
            180                 185                 190

Trp Ile Gly Gly Ser Arg Met Leu Trp Ile Arg Gln His Val Val Gly
        195                 200                 205

His His Thr His Ser Asn Arg His Gln His Asp Pro Asp Leu Lys Gly
210                 215                 220

Gly Ser Val Ile Arg Leu Ser Arg Thr Ser Leu Pro Leu Glu Phe His
225                 230                 235                 240

His Ile Gln Gln Tyr Tyr Phe Leu Pro Leu Asp Gln Leu Leu Gly Phe
                245                 250                 255

Gln Trp Val Phe Leu Gly Leu Asn Asp Leu Ile Glu Met Arg Tyr Lys
            260                 265                 270

Gly Glu Pro Leu Pro Glu Ser Tyr Arg Lys Glu Arg Asn Ile Ala Ile
        275                 280                 285

Gly Leu Lys Ile Phe Phe Val Arg Lys Phe Val Val Pro Phe Ala
290                 295                 300

Leu His Phe Ser Trp Tyr Thr Leu Leu Cys Thr Cys Ala Trp Met Ala
305                 310                 315                 320

Ile Ala Ala Leu Tyr Leu Gly Phe Phe Ile Leu Ser His Ile Phe
                325                 330                 335

Val Gly Ala Lys Ser Leu Pro Glu Asp Ala Asn Ile Asp Trp Ala Arg
            340                 345                 350

His Gln Ile Glu Ser Ser Asn Val Cys Gly Glu Lys Leu Gly His
        355                 360                 365

Ser Asn Gly Gly Leu Asn Tyr Gln Ile Glu His Leu Phe Pro Arg
370                 375                 380

Met Ser His Ala His Tyr Ser Lys Ile Gln Pro Val Val Gln Arg Val
385                 390                 395                 400

Cys Glu Glu Asn Gly Val Asn Tyr Lys Lys Phe Gly Thr Ile Leu Ser
                405                 410                 415

Asn Leu Asp Ser Thr Phe Ser Gln Val Lys Ala Leu Gly Ala Val Ala
            420                 425                 430

Val Tyr Glu Phe Met Gly Gly Leu
        435                 440

<210> SEQ ID NO 117
<211> LENGTH: 438
<212> TYPE: PRT
<213> ORGANISM: Artificial
<220> FEATURE:
<223> OTHER INFORMATION: delta-4 desaturase 90.6% sequence identity to
      SEQ ID NO 79

<400> SEQUENCE: 117
```

```
Met Pro Pro His Ser Arg Thr Lys Val Ser Asp Asp Pro Glu Leu Ser
1               5                   10                  15

Asp Ala Lys His Phe Thr Arg Glu Glu Ile Leu Gly His Thr Asn Asp
            20                  25                  30

Lys Tyr Cys Ile Leu Glu Asp Gly Val Tyr Asp Cys Thr Asn Phe Arg
                35                  40                  45

Asp Lys His Pro Gly Gly Asp Val Leu Asp Ile Phe Gly Gly Gln Asp
        50                  55                  60

Ala Thr Pro His Phe Tyr Met Leu His Gln Tyr Glu Ser Pro Pro Ser
65                  70                  75                  80

Val Leu Ala Lys Tyr Lys Val Gly Ser Val Glu Arg Asp Asp Ser Tyr
                85                  90                  95

Val Tyr His Glu Pro Leu Met Lys Gln Ile Lys Ser Ala Val Arg Lys
                100                 105                 110

Val Ile Pro Met Gln Glu Gly Trp Ala Pro Pro Ser Trp Trp Ile Lys
            115                 120                 125

Ala Cys Ala Leu Leu Ala Ala Thr Leu Tyr Thr Asp Tyr Leu Trp Ile
        130                 135                 140

Ala Arg Gly Pro Thr Ile Pro Leu Ala Ile Val Ser Gly Leu Leu Tyr
145                 150                 155                 160

Ala Ala Ile Gly Leu Asn Ile Gln His Asp Ala Asn His Gly Ser Val
                165                 170                 175

Ser Arg Asn Pro Met Val Asn Arg Leu Phe Gly Tyr Ser Gln Asp Trp
            180                 185                 190

Ile Gly Gly Ser Met Met Leu Trp Ile Arg Gln His Val Val Asn His
        195                 200                 205

His Thr His Cys Asn Arg Ile Asp His Asp Pro Asp Val Lys Gly Gly
210                 215                 220

Ser Val Ile Thr Leu Ser Arg Tyr Ser Leu Pro Lys Glu Phe His Ala
225                 230                 235                 240

Ile Gln Gln Tyr Tyr Phe Leu Pro Leu Glu Gln Leu Leu Gly Phe Lys
                245                 250                 255

Trp Ile Phe Leu Gly Ala His Asp Leu Ile Glu Met Lys Tyr Lys Gly
            260                 265                 270

Glu Lys Ile Pro Glu Ser Tyr Arg Lys Glu Arg Asn Ile Ala Ile Gly
        275                 280                 285

Leu Arg Val Phe Phe Phe Ile Arg Lys Ile Val Val Pro Phe Ala Leu
        290                 295                 300

His Pro Ser Trp Tyr Thr Leu Leu Cys Thr Tyr Leu Trp Met Cys Ile
305                 310                 315                 320

Ala Ala Leu Tyr Leu Ala Phe Phe Ile Leu Ser His Ile Phe Val
                325                 330                 335

Gly Ala Lys Ser Leu Pro Pro Asp Ala Asn Ile Asp Trp Ala Arg His
            340                 345                 350

Gln Ile Glu Asn Ser Ser Asn Val Cys Gly Glu Trp Leu Gly Tyr Leu
                355                 360                 365

Asn Gly Gly Leu Asn Tyr Gln Ile Glu His His Leu Phe Pro Arg Met
            370                 375                 380

Ser His Ala His Tyr Ser Lys Ile Gln Pro Val Val Gln Lys Val Cys
385                 390                 395                 400

Glu Glu Asn Gly Val Asn Tyr Lys Lys Phe Gly Thr Ile Leu Ser Asn
                405                 410                 415

Leu Asp Ser Thr Phe Arg Gln Val Lys Ala Leu Gly Ala Val Pro Val
```

Glu Phe Met Glu Gly Leu
                435

<210> SEQ ID NO 118
<211> LENGTH: 441
<212> TYPE: PRT
<213> ORGANISM: Artificial
<220> FEATURE:
<223> OTHER INFORMATION: delta-4 desaturase 90.6% sequence identity to
      SEQ ID NO 79

<400> SEQUENCE: 118

Met Pro Pro His Ser Arg Arg Lys Val Ser Asp Pro Glu Leu Arg Asp
1               5                   10                  15

Leu Lys Ala Lys His Phe Thr Tyr Thr Glu Ile Leu Asn His Thr Asn
            20                  25                  30

Asp Asp Leu Cys Ile Leu Glu Asp Gly Val Tyr Asp Leu Thr Asn Phe
        35                  40                  45

Arg Asp Lys His Pro Gly Gly Asp Val Ile Asp Ile Phe Pro Gly Gln
    50                  55                  60

Asp Ala Thr Pro Gly Phe Tyr Met Leu His Lys Tyr Glu Ser Leu Pro
65                  70                  75                  80

Ser Val Leu Ala Glu Phe Lys Val Gly Ser Val Ala Arg Asp Asp Ser
                85                  90                  95

Tyr Val Tyr His Thr Pro Leu Met Leu Gln Ile Lys Ser Ala Val Arg
            100                 105                 110

Lys Val Leu Pro Met Gly Glu Trp Trp Ala Pro Ser Trp Tyr Ile
        115                 120                 125

Lys Ala Cys Ala Ile Leu Ala Ala Thr Leu Tyr Leu Asp Tyr Tyr Trp
130                 135                 140

Ile Ala Arg Gly Pro Thr Ile Leu Leu Ala Ile Val Leu Gly Leu Leu
145                 150                 155                 160

Tyr Ala Ala Ile Gly Leu Asn Ile Gln His Asp Ala Asn His Gly Ser
                165                 170                 175

Val Ser Arg Asn Pro Met Val Asn Arg Leu Phe Gly Tyr Ala Gln Asp
            180                 185                 190

Trp Ile Gly Gly Ser Arg Met Leu Trp Ile Gln Gln His Val Val Gly
        195                 200                 205

His His Thr His Cys Asn Asp His Gln His Asp Pro Asp Val Lys Gly
    210                 215                 220

Gly Ser Val Ile Thr Leu Ser Arg Tyr Ser Leu Pro Leu Glu Phe His
225                 230                 235                 240

His Ile Gln Gln Tyr Tyr Phe Leu Pro Leu Glu Gln Leu Leu Gly Phe
                245                 250                 255

Gln Trp Val Phe Leu Gly Ala His Asp Leu Ile Glu Met Lys Tyr Glu
            260                 265                 270

Gly Glu Lys Leu Pro Glu Ser Tyr Arg Lys Glu Arg Asn Ile Ala Ile
        275                 280                 285

Gly Cys Arg Val Phe Phe Ile Arg Lys Phe Val Val Pro Phe Ala
    290                 295                 300

Leu His Phe Ser Trp Tyr Thr Leu Leu Cys Thr Tyr Ala Trp Val Ala
305                 310                 315                 320

Ile Ala Ala Phe Tyr Leu Gly Phe Phe Ile Leu Ser His Ile Phe
                325                 330                 335

Ile Gly Ala Lys Ser Leu Pro Glu Asp Ala Lys Asn Ile Asp Trp Val
              340                 345                 350

Arg His Gln Ile Glu Ser Ser Asn Val Cys Gly Glu Lys Leu Gly
              355                 360                 365

His Ser Asn Gly Gly Leu Asn Tyr Gln Ile Glu His His Leu Phe Pro
          370                 375                 380

Arg Met Ser His Ala His Tyr Ser Lys Ile Gln Pro Val Val Gln Lys
385                 390                 395                 400

Val Cys Glu Glu Met Gly Ile Asn Tyr Lys Lys Phe Gly Thr Ile Gly
              405                 410                 415

Ser Asn Leu Asp Ser Thr Leu Arg Gln Val Lys Ala Leu Gly Ser Val
              420                 425                 430

Ala Val Tyr Glu Phe Met Glu Gly Leu
              435                 440

<210> SEQ ID NO 119
<211> LENGTH: 438
<212> TYPE: PRT
<213> ORGANISM: Artificial
<220> FEATURE:
<223> OTHER INFORMATION: delta-4 desaturase 90.3% sequence identity to
      SEQ ID NO 79

<400> SEQUENCE: 119

Met Pro Pro His Ser Arg Thr Glu Val Ser Asp Pro Glu Leu Lys Ala
1               5                   10                  15

Met Lys His Phe Thr Arg Glu Glu Ile Leu Asn His Thr Asn Asp Asp
              20                  25                  30

Ile Cys Ile Leu Glu Asp Gly Val Tyr Asp Leu Thr Asn Phe Arg Asp
          35                  40                  45

Lys His Pro Gly Gly Asp Tyr Leu Asp Phe Phe Pro Gly Arg Asp Ala
      50                  55                  60

Thr Pro His Phe Tyr Met Leu His Gln Tyr Glu Ser Leu Pro Ser Val
65                  70                  75                  80

Leu Ala Glu Tyr Lys Val Gly Ser Ile Ala Arg Asp Asp Ser Tyr Val
              85                  90                  95

Tyr His Thr Pro Gly Met Lys Gln Ile Cys Ala Glu Val Arg Lys Val
          100                 105                 110

Met Pro Met Gly Glu Trp Trp Ala Pro Pro Ser Trp Tyr Ile Lys Ala
      115                 120                 125

Cys Ala Ile Ile Ala Ala Thr Leu Tyr Thr Asp Tyr Leu Trp Ile Ala
130                 135                 140

Ser Gly Pro Thr Ile Pro Leu Ala Ile Val Ser Gly Leu Leu Tyr Ala
145                 150                 155                 160

Ala Ile Gly Leu Asn Ile Gln His Asp Ala Asn His Gly Ser Val Ser
              165                 170                 175

Arg Asn Pro Met Val Asn Arg Leu Phe Gly Tyr Ser Gln Asp Trp Ile
          180                 185                 190

Gly Gly Ser Arg Met Leu Trp Ile Arg Gln His Val Val Gly His His
      195                 200                 205

Thr His Thr Asn Arg His Gln His Asp Pro Asp Val Lys Gly Gly Ser
      210                 215                 220

Val Ile Thr Leu Ser Arg Tyr Ser Leu Trp Lys Glu Phe His His Ile
225                 230                 235                 240

Gln Gln Tyr Tyr Phe Leu Pro Leu Asp Gln Leu Leu Gly Phe Gln Trp
              245                 250                 255

Val Phe Leu Gly Leu His Asp Leu Ile Glu Met Lys Tyr Lys Gly Glu
              260                 265                 270

Lys Ile Pro Glu Ser Ala Arg Pro Glu Tyr Asn Pro Ala Ile Gly Leu
              275                 280                 285

Arg Val Phe Phe Phe Ile Arg Lys Phe Val Pro Phe Trp Leu His
              290                 295                 300

Phe Ser Trp Tyr Thr Leu Ile Cys Thr Tyr Ala Trp Met Ala Ile Ala
305                 310                 315                 320

Ala Phe Tyr Leu Gly Phe Phe Ile Leu Ser His Asn Phe Val Gly
                  325                 330                 335

Ala Lys Ser Leu Pro Pro Asp Ala Asn Ile Asp Trp Ala Arg His Gln
              340                 345                 350

Ile Glu Thr Ser Ser Asn Val Cys Gly Glu Lys Leu Gly Ile Ser Asn
              355                 360                 365

Gly Gly Leu Asn Tyr Gln Ile Glu His His Leu Phe Pro Arg Met His
              370                 375                 380

His Ala His Tyr Ser Lys Ile Gln Pro Val Val Gln Lys Ile Cys Glu
385                 390                 395                 400

Glu Asn Gly Val Asn Tyr Lys His Phe Gly Thr Ile Gly Ser Asn Leu
              405                 410                 415

Asp Ser Thr Leu Gln Gln Val Lys Ala Leu Gly Ser Val Pro Val Tyr
              420                 425                 430

Glu Phe Met Glu Gly Leu
              435

<210> SEQ ID NO 120
<211> LENGTH: 438
<212> TYPE: PRT
<213> ORGANISM: Artificial
<220> FEATURE:
<223> OTHER INFORMATION: delta-4 desaturase 90.3% sequence identity to
      SEQ ID NO 79

<400> SEQUENCE: 120

Met Pro Pro His Ser Arg Thr Lys Val Ser Asp Asp Pro Glu Leu Arg
1               5                   10                  15

Asp Met Lys His Phe Thr Arg Glu Glu Ile Leu Asn His Thr Asn Asp
              20                  25                  30

Asp Tyr Cys Ile Leu Gly Asp Gly Val Tyr Asp Leu Thr Asn Phe Arg
              35                  40                  45

Asp Lys His Pro Gly Gly Asp Val Leu Ser Phe Phe Pro Gly Gln Asp
              50                  55                  60

Ala Thr Pro His Phe Tyr Met Leu His Gln Tyr Glu Ser Leu Pro Ser
65                  70                  75                  80

Val Leu Ala Glu Tyr Lys Val Gly Ser Ile Ala Arg Asp Asp Ser Tyr
              85                  90                  95

Val Tyr Ala Glu Pro Leu Gln Lys Gln Ile Lys Ser Ala Val Arg Lys
              100                 105                 110

Val Leu Pro Met Gly Glu Trp Trp Ala Pro Pro Ser Trp Tyr Ile Lys
              115                 120                 125

Ala Cys Ala Ile Leu Ala Ala Thr Leu Phe Leu Asp Tyr Leu Trp Ile
              130                 135                 140

Ala Ser Gly Pro Thr Ile Pro Leu Ala Ile Val Ser Gly Leu Leu Tyr
145                 150                 155                 160

Ala Ala Ile Gly Leu Asn Ile Gln His Asp Ala Asn His Gly Ser Val

```
                165                 170                 175
Ser Arg Asn Pro Met Val Asn Arg Leu Phe Gly Tyr Ser Gln Asp Trp
            180                 185                 190

Ile Gly Gly Ser Arg Met Leu Trp Ile Arg Gln His Val Val Gly His
        195                 200                 205

His Thr His Cys Asn Glu His Asp His Asp Pro Asp Val Lys Gly Gly
    210                 215                 220

Ser Val Ile Gln Leu Ser Pro Tyr Asp Leu Trp Met Pro Phe His His
225                 230                 235                 240

Ile Gln Gln Ile Tyr Phe Leu Pro Leu Ile Val Leu Leu Gly Phe Gln
                245                 250                 255

Trp Val Phe Leu Gly Leu His Asp Leu Ile Glu Met Lys Tyr Lys Gly
            260                 265                 270

Glu Lys Leu Pro Pro Ser Tyr Arg Lys Glu Tyr Asn Pro Ala Ile Gly
        275                 280                 285

Leu Arg Val Phe Phe Trp Ile Arg Lys Phe Val Pro Phe Trp Leu
    290                 295                 300

His Phe Ser Trp Tyr Thr Leu Leu Cys Thr Cys Leu Trp Met Ala Ile
305                 310                 315                 320

Ala Ala Phe Tyr Leu Gly Phe Phe Ile Leu Ser His Ile Phe Val
                325                 330                 335

Gly Ala Lys Ser Leu Pro Glu Asp Ala Ser Ile Asp Trp Ala Arg His
            340                 345                 350

Gln Ile Glu Ser Ser Ser Asn Val Gly Gly Glu Lys Leu Gly His Ser
        355                 360                 365

Asn Gly Gly Leu Asn Tyr Gln Ile Glu His His Leu Phe Pro Arg Met
    370                 375                 380

Ser His Ala His Tyr Ser Lys Ile Gln Pro Val Val Gln Lys Val Cys
385                 390                 395                 400

Glu Glu Asn Gly Val Asn Tyr Lys Lys Phe Pro Thr Ile Gly Ser Asn
                405                 410                 415

Leu Asp Ser Ile Phe Arg Gln Val Lys Ala Leu Ala Ser Val Ala Val
            420                 425                 430

Glu Phe Met Glu Gly Leu
        435

<210> SEQ ID NO 121
<211> LENGTH: 437
<212> TYPE: PRT
<213> ORGANISM: Artificial
<220> FEATURE:
<223> OTHER INFORMATION: delta-4 desaturase 90.3% sequence identity to
      SEQ ID NO 79

<400> SEQUENCE: 121

Met Pro Pro His Ser Arg Thr Lys Val Ser Asp Pro Glu Leu Lys Asp
1               5                   10                  15

Met Lys His Phe Thr Arg Glu Glu Ile Leu Asn His Thr Asn Asp Lys
                20                  25                  30

Tyr Cys Ile Leu Gly Asp Gly Val Tyr Asp Leu Thr Asn Phe Arg Asp
            35                  40                  45

Glu His Pro Gly Gly Asp Val Leu Asp Phe Phe Pro Gly Gln Asp Ala
        50                  55                  60

Thr Pro His Phe Tyr Gln Leu His Arg Tyr Glu Trp Pro Pro Ser Val
65                  70                  75                  80
```

Leu Ser Glu Tyr Lys Val Gly Ser Val Ala Arg Asp Asp Ser Tyr Val
                85                  90                  95

His His Thr Pro Leu His Lys Gln Leu Lys Ser Ala Val Arg Lys Val
            100                 105                 110

Leu Pro Met Gly Glu Trp Trp Ala Pro Pro Ser Trp Tyr Ile Lys Ala
        115                 120                 125

Cys Ala Ile Leu Ile Ala Thr Leu Tyr Thr Asp Tyr Leu Trp Ile Ala
    130                 135                 140

Ser Gly Pro Thr Ile Phe Leu Ala Ile Val Ser Gly Leu Leu Phe Ala
145                 150                 155                 160

Trp Ile Gly Leu Asn Ile Gln His Asp Ala Asn His Gly Ser Val Ser
                165                 170                 175

Arg Asn Pro Met Val Asn Arg Leu Phe Gly Tyr Ser Gln Asp Trp Ile
            180                 185                 190

Gly Gly Ser Arg Met Leu Trp Leu Arg Gln His Val Gly His His
        195                 200                 205

Thr His Cys Asn Arg His Asp His Asp Pro Val Lys Gly Gly
    210                 215                 220

Val Ile Arg Leu Ser Arg Tyr Ser Leu Pro Met Pro Phe His His Ile
225                 230                 235                 240

Gln Gln Ile Tyr Phe Leu Pro Leu Ile Gln Leu Tyr Gly Phe Gln Trp
                245                 250                 255

Val Phe Leu Gly Leu His Asp Leu Ile Glu Met Lys Tyr Lys Gly Glu
            260                 265                 270

Lys Ile Pro Glu Ser Tyr Arg Lys Leu Tyr Asn Ile Ala Val Gly Leu
        275                 280                 285

Lys Val Phe Phe Phe Ile Arg Lys Phe Val Val Pro Phe Ala Leu His
290                 295                 300

Phe Ser Trp Tyr Thr Leu Leu Cys Thr Tyr Leu Trp Met Ala Ile Ala
305                 310                 315                 320

Ala Leu Tyr Leu Gly Phe Phe Ile Leu Ser His Leu Phe Val Gly
                325                 330                 335

Ala Lys Ser Leu Pro Glu Asp Ala Asn Ile Glu Trp Ala Arg His Gln
            340                 345                 350

Ile Glu Ser Ser Ser Asn Val Cys Gly Glu Trp Leu Gly Ile Ser Asn
        355                 360                 365

Gly Gly Leu Asn Tyr Gln Ile Glu His His Leu Phe Pro Arg Met Ser
370                 375                 380

His Ala His Tyr Ser Lys Ile Gln Pro Val Val Gln Lys Val Cys Glu
385                 390                 395                 400

Glu Asn Gly Val Asn Tyr Lys Lys Phe Gly Thr Ile Leu Ser Asn Leu
                405                 410                 415

Gly Ser Thr Phe Arg Gln Val Lys Ala Leu Gly Ser Val Ala Val Glu
            420                 425                 430

Phe Met Glu Gly Ile
        435

<210> SEQ ID NO 122
<211> LENGTH: 440
<212> TYPE: PRT
<213> ORGANISM: Artificial
<220> FEATURE:
<223> OTHER INFORMATION: delta-4 desaturase 90.3% sequence identity to
      SEQ ID NO 79

<400> SEQUENCE: 122

-continued

```
Met Pro Pro His Ser Arg Thr Lys Val Ser Asp Pro Glu Leu Ser Asp
1               5                   10                  15

Leu Met Lys His Phe Ser Arg Thr Arg Ile Leu Asn His Thr Asn Asp
            20                  25                  30

Lys Tyr Cys Ile Leu Glu Asp Gly Val Tyr Asp Leu Thr Asn Phe Arg
        35                  40                  45

Asp Lys His Pro Gly Gly Asp Val Leu Asp Leu Phe Pro Gly Gln Asp
    50                  55                  60

Ala Thr Pro His Phe Tyr Glu Leu His Gln Tyr Glu Trp Leu Pro Ala
65                  70                  75                  80

Val Leu Ala Glu Tyr Gly Val Gly Ser Ile Ala Arg Asp Asp Ser Tyr
                85                  90                  95

Val Tyr His Asp Pro Leu Met Leu Arg Leu Lys Cys Glu Val Asn Gly
            100                 105                 110

Val Met Pro Arg Gly Glu Gly Trp Ala Pro Ser Trp Tyr Ile Lys
            115                 120                 125

Ala Cys Ala Ile Leu Ala Ala Thr Leu Tyr Thr Asp Tyr Leu Trp Ile
        130                 135                 140

Ala Ser Gly Pro Thr Ile Pro Leu Ala Ile Val Ser Gly Leu Leu Tyr
145                 150                 155                 160

Ala Ala Ile Gly Leu Asn Ile Gln His Asp Ala Asn His Gly Ser Val
                165                 170                 175

Ser Arg Asn Pro Met Val Asn Arg Leu Phe Gly Tyr Ser Gln Asp Trp
            180                 185                 190

Ile Gly Gly Ser Arg Met Leu Trp Ile Arg Gln His Val Val Gly His
            195                 200                 205

His Ile His Ser Asn Arg His Asp His Asp Pro Asp Val Lys Gly Gly
    210                 215                 220

Gly Val Ile Arg Leu Ser Arg Tyr Ser Leu Pro Lys Glu Phe His His
225                 230                 235                 240

Ile Gln Gln Ile Tyr Phe Leu Pro Leu Ile Gln Leu Tyr Gly Phe Gln
            245                 250                 255

Trp Val Phe Leu Gly Leu His Asp Leu Ile Glu Met Lys Tyr Lys Gly
            260                 265                 270

Glu Lys Leu Pro Glu Ser Tyr Arg Lys Glu Arg Asn Ile Ala Ile Gly
            275                 280                 285

Leu Arg Val Phe Phe Phe Ile Arg Lys Phe Ile Leu Pro Phe Ala Leu
    290                 295                 300

His Phe Ser Trp Tyr Thr Leu Leu Cys Thr Cys Leu Trp Val Ala Ile
305                 310                 315                 320

Ala Ala Leu Tyr Leu Gly Phe Phe Ile Leu Ser His Ile Phe Val
                325                 330                 335

Gly Ala Lys Ser Leu Pro Glu Asp Ala Lys Asn Ile Asp Trp Ala Arg
            340                 345                 350

His Gln Ile Glu Ser Ser Ser Asn Val Cys Gly Glu Lys Leu Gly Ile
            355                 360                 365

Ser Asn Gly Gly Leu Asn Tyr Gln Ile Glu His His Leu Phe Pro Arg
    370                 375                 380

Met His His Ala His Tyr Ala Lys Ile Gln Pro Val Val Gln Lys Val
385                 390                 395                 400

Cys Glu Glu Asn Gly Ile Asn Tyr Lys Lys Phe Gly Thr Ile Leu Ser
            405                 410                 415
```

-continued

Asn Leu Gly Ser Thr Phe Gln Gln Val Lys Ala Ile Gly Ser Val Ala
              420                 425                 430

Val Tyr Glu Phe Met Glu Gly Pro
            435                 440

<210> SEQ ID NO 123
<211> LENGTH: 438
<212> TYPE: PRT
<213> ORGANISM: Artificial
<220> FEATURE:
<223> OTHER INFORMATION: delta-4 desaturase 90.1% sequence identity to
      SEQ ID NO 79

<400> SEQUENCE: 123

Met Pro Pro His Ser Arg Thr Lys Val Ser Ala Pro Glu Leu Ser Asp
1               5                   10                  15

Leu Met Lys His Phe Thr Arg Glu Lys Ile Leu Asn His Thr Asn Asp
            20                  25                  30

Lys Ile Cys Ile Leu Glu Asp Gly Val Tyr Asp Ala Thr Asn Phe Arg
        35                  40                  45

Asp Lys His Pro Gly Gly Asp Tyr Leu Asp Phe Phe Pro Gly Gln Asp
    50                  55                  60

Ala Thr Pro His Phe Tyr Met Tyr His Gln Tyr Glu Ser Pro Pro Ser
65                  70                  75                  80

Val Leu Ala Glu Phe Lys Val Gly Ser Val Ala Arg Asp Asp Ser Tyr
                85                  90                  95

Thr Tyr His Asp Pro Leu Tyr Lys Arg Ile Lys Ser Asp Val Arg Lys
            100                 105                 110

Val Leu Pro Met Gln Glu Trp Trp Ala Pro Ser Trp Tyr Ile Lys
        115                 120                 125

Ala Cys Ala Ile Leu Ala Ala Ala Leu Tyr Leu Asp Tyr Leu Met Ile
    130                 135                 140

Ala Ser Gly Pro Thr Ile Pro Leu Ala Ile Val Ser Gly Leu Leu Tyr
145                 150                 155                 160

Ala Ala Ile Gly Leu Asn Ile Gln His Asp Ala Asn His Gly Ser Val
                165                 170                 175

Ser Arg Asn Pro Met Val Asn Arg Leu Phe Gly Tyr Ser Gln Asp Trp
            180                 185                 190

Ile Gly Gly Ser Arg Leu Leu Trp Ile Arg Gln His Val Val Gly His
        195                 200                 205

His Thr His Cys Asn Arg Val Gln His Asp Pro Asp Val Lys Gly Gly
    210                 215                 220

Ser Val Ile Thr Leu Ser Arg Tyr Ser Leu Trp Lys Glu Phe His His
225                 230                 235                 240

Ile Gln Gln Tyr Tyr Phe Leu Pro Leu Ile Gln Leu Tyr Gly Phe Gln
                245                 250                 255

Trp Val Phe Leu Gly Leu His Asp Leu Ile Asp Trp Lys Tyr Lys Gly
            260                 265                 270

Glu Lys Leu Pro Glu Ser Cys Arg Lys Glu Arg Ala Ile Ala Ile Gly
        275                 280                 285

Leu Arg Val Gly Phe Phe Ala Lys Phe Val Leu Pro Leu Trp Leu
    290                 295                 300

His Phe Ser Trp Tyr Thr Leu Leu Cys Thr Cys Leu Trp Met Ala Val
305                 310                 315                 320

Ala Ala Leu Tyr Leu Gly Phe Phe Ile Leu Ser His Ile Phe Val
                325                 330                 335

Gly Ala Lys Ser Leu Pro Glu Asp Ala Asn Ile Asp Trp Ala Arg His
            340                 345                 350

Gln Ile Glu Ser Ser Asn Val Gly Glu Lys Leu Gly Ile Ser
            355                 360                 365

Asn Gly Gly Leu Asn Tyr Gln Ile Glu His His Leu Phe Pro Arg Met
            370                 375                 380

Ser His Ser His Tyr Ser Pro Ile Ala Pro Val Val Gln Lys Val Cys
385                 390                 395                 400

Glu Glu Asn Gly Val Asn Tyr Lys Lys Phe Gly Thr Ile Leu Ser Asn
                405                 410                 415

Leu Asp Ser Thr Phe Arg Gln Ile Lys Ala Leu Gly Ser Val Ala Val
                420                 425                 430

Glu Phe Met Glu Gly Leu
            435

<210> SEQ ID NO 124
<211> LENGTH: 439
<212> TYPE: PRT
<213> ORGANISM: Artificial
<220> FEATURE:
<223> OTHER INFORMATION: delta-4 desaturase 90.1% sequence identity to
      SEQ ID NO 79

<400> SEQUENCE: 124

Met Pro Pro His Ser Ala Thr Lys Val Ser Val Pro Glu Leu Ser Asp
1               5                   10                  15

Leu Ala Lys His Phe Thr Arg Glu Glu Ile Leu Asn His Thr Asn Asp
                20                  25                  30

Lys Tyr Cys Ile Leu Glu Asp Gly Val Tyr Asp Leu Thr Asn Phe Arg
            35                  40                  45

Asp Lys His Pro Gly Gly Asp Val Ile Asp Phe Phe Pro Gly Gln Asp
        50                  55                  60

Ala Thr Pro His Phe Trp Met Phe His Gln Lys Glu Ser Pro Pro Ser
65                  70                  75                  80

Val Leu Ser Glu Tyr Lys Val Gly Ser Val Ala Arg Asp Asp Ser Tyr
                85                  90                  95

Thr His His Asp Pro Leu Met Lys Gln Ile Lys Ser Ala Val Arg Lys
            100                 105                 110

Val Ile Pro Arg Gln Glu Trp Trp Ala Pro Ser Trp Trp Ile Lys
        115                 120                 125

Ala Cys Ala Ile Leu Ala Ala Thr Leu His Thr Asp Tyr Leu Trp Ile
130                 135                 140

Ala Ser Gly Pro Thr Ile Pro Leu Ala Ile Val Ser Gly Leu Leu Tyr
145                 150                 155                 160

Ala Trp Ile Gly Leu Asn Ile Gln His Asp Ala Asn His Gly Ser Val
                165                 170                 175

Ser Arg Asn Pro Met Val Asn Arg Leu Phe Gly Tyr Ser Gln Asp Trp
            180                 185                 190

Ile Gly Gly Ser Arg Met Leu Trp Ile Arg Gln His Val Val Gly His
        195                 200                 205

His Thr His Cys Asn Asp His Gln His Asp Pro Asp Val Lys Gly Gly
    210                 215                 220

Ser Val Ile Thr Leu Ser Pro Tyr Ser Leu Pro Lys Glu Phe His Ala
225                 230                 235                 240

Ile Gln Gln Tyr Tyr Phe Leu Pro Leu Asp Gln Leu Tyr Gly Phe Gln

```
                    245                 250                 255
Trp Val Phe Leu Gly Ala His Asp Leu Ile Glu Met Lys Tyr Lys Gly
            260                 265                 270

Glu Pro Leu Pro Glu Ser Tyr Arg Lys Glu Tyr Asn Ile Ala Ile Gly
            275                 280                 285

Leu Arg Val Phe Phe Ile Arg Lys Phe Val Leu Pro Phe Ala Leu
            290                 295                 300

His Pro Thr Trp Tyr Thr Leu Leu Cys Ile Tyr Leu Trp Met Ala Ile
305                 310                 315                 320

Ala Ala Phe Tyr Leu Gly Phe Phe Ile Leu Ser His Ile Phe Val
            325                 330                 335

Gly Ala Lys Ser Leu Pro Pro Asp Ala Lys Asn Ile Asp Trp Ala Arg
            340                 345                 350

His Gln Ile Glu Ser Ser Asn Val Cys Gly Glu Trp Leu Gly Ile
            355                 360                 365

Ser Asn Gly Gly Leu Asn Tyr Gln Ile Glu His His Leu Phe Pro Arg
370                 375                 380

Met Asn His Ala His Tyr Ser Lys Ile Glu Pro Val Val Gln Lys Val
385                 390                 395                 400

Cys Glu Glu Asn Gly Val Asn Tyr Lys His Phe Gly Thr Ile Gly Ser
                405                 410                 415

Asn Leu Asp Ser Thr Phe Arg Gln Val Lys Ala Leu Gly Ala Val Pro
            420                 425                 430

Val Glu Phe Met Glu Gly Leu
            435

<210> SEQ ID NO 125
<211> LENGTH: 438
<212> TYPE: PRT
<213> ORGANISM: Artificial
<220> FEATURE:
<223> OTHER INFORMATION: delta-4 desaturase 90.1% sequence identity to
      SEQ ID NO 79

<400> SEQUENCE: 125

Met Pro Pro His Ser Arg Thr Glu Val Ser Asp Asp Pro Glu Leu Ser
1               5                   10                  15

Asp Met Lys His Phe Thr Arg Glu Glu Ile Leu Asn His Thr Asn Asp
            20                  25                  30

Lys Leu Cys Ile Leu Glu Asp Gly Val Tyr Asp Ala Thr Asn Phe Arg
        35                  40                  45

Asp Lys His Pro Gly Gly Asp Phe Leu Asp Phe Phe Pro Gly Gln Asp
    50                  55                  60

Ala Thr Pro His Phe Tyr Met Tyr His Gln Tyr Glu Ser Pro Pro Ser
65                  70                  75                  80

Val Leu Ala Lys Tyr Lys Val Gly Ser Val Asp Arg Asp Asp Ser Tyr
                85                  90                  95

Val Tyr His Thr Pro Leu Met Lys Gln Ile Lys Ser Ala Val Arg Lys
            100                 105                 110

Ile Met Pro Arg Gln Glu Trp Trp Ala Pro Pro Ser Trp Trp Ile Lys
        115                 120                 125

Ala Cys Ala Ile Leu Val Ala Thr Leu Tyr Thr Asp Tyr Leu Trp Ile
    130                 135                 140

Ala Ser Gly Pro Thr Ile Leu Leu Gly Ile Val Ser Gly Leu Leu Tyr
145                 150                 155                 160
```

```
Ala Ala Ile Gly Leu Asn Ile Gln His Asp Ala Asn His Gly Ser Val
            165                 170                 175

Ser Arg Asn Pro Val Val Asn Arg Leu Phe Gly Tyr Ser Gln Asp Trp
        180                 185                 190

Ile Gly Gly Ser Arg Met Leu Trp Ile Arg Gln His Val Val Gly His
        195                 200                 205

His Thr His Thr Asn Asp Ile Gln His Asp Pro Asp Val Lys Gly Gly
        210                 215                 220

Ser Val Ile Arg Leu Ser Arg Tyr Ser Ile Trp Lys Pro Phe His His
225                 230                 235                 240

Ile Gln Gln Tyr Tyr Phe Leu Pro Leu Asp Gln Leu Tyr Gly Phe Gln
                245                 250                 255

Trp Val Phe Leu Gly Leu His Asp Leu Ile Glu Met Lys Tyr Lys Gly
                260                 265                 270

Glu Lys Leu Pro Glu Ser Tyr Arg Pro Leu Arg Asn Ile Ala Ile Gly
            275                 280                 285

Leu Arg Val Phe Phe Val Arg Lys Phe Val Leu Pro Phe Ala Leu
            290                 295                 300

His Phe Ser Trp Tyr Thr Leu Leu Cys Ile Tyr Leu Trp Met Ala Ile
305                 310                 315                 320

Ala Ala Leu Tyr Leu Gly Phe Phe Phe Ile Leu Ser His Ile Phe Val
                325                 330                 335

Gly Ala Lys Ser Leu Pro Glu Asp Gly Asn Ile Asp Trp Val Arg His
                340                 345                 350

Gln Ile Glu Ser Ser Asn Val Gly Gly Lys Leu Gly Ile Ser
            355                 360                 365

Asn Gly Gly Leu Asn Tyr Gln Ile Glu His His Leu Phe Pro Arg Met
370                 375                 380

Ser His Ala His Tyr Ser Lys Ile Gln Pro Val Val Gln Lys Val Cys
385                 390                 395                 400

Glu Glu Asp Gly Val Lys Tyr Lys Lys Phe Gly Thr Ile Ala Ser Asn
                405                 410                 415

Leu Asp Ser Thr Leu Ser Gln Val Lys Ala Leu Gly Ser Val Ala Val
                420                 425                 430

Glu Phe Met Glu Gly Leu
            435

<210> SEQ ID NO 126
<211> LENGTH: 438
<212> TYPE: PRT
<213> ORGANISM: Artificial
<220> FEATURE:
<223> OTHER INFORMATION: delta-4 desaturase 90.1% sequence identity to
      SEQ ID NO 79

<400> SEQUENCE: 126

Met Pro Pro His Ser Arg Thr Lys Gly Gly Asp Pro Glu Leu Ser Asp
1               5                   10                  15

Met Lys His Phe Thr Arg Glu Lys Ile Leu Asn His Thr Asn Asp Lys
                20                  25                  30

Tyr Cys Ile Val Glu Asp Gly Val Tyr Asp Leu Thr Asn Phe Arg Asp
            35                  40                  45

Lys His Pro Gly Gly Asp Val Leu Asp Phe Phe Gly Gly Gln Asp Ala
        50                  55                  60

Thr Pro His Phe Phe Met Leu His Gln Arg Glu Ser Pro Pro Ser Leu
65                  70                  75                  80
```

```
Leu Ala Glu Tyr Lys Val Gly Ser Val Ala Arg Asp Asp Ser Tyr Val
                85                  90                  95

Tyr His Thr Pro Leu Met Lys Gln Ile Cys Ser Ala Val Asn Gly Val
            100                 105                 110

Met Pro Met Gly Glu Gly Trp Ala Pro Ser Trp Tyr Ile Lys Ala
        115                 120                 125

Cys Ala Ile Leu Ala Ala Thr Leu Tyr Leu Asp Trp Leu Trp Ile Ala
    130                 135                 140

Ser Gly Pro Thr Ile Pro Leu Ala Ile Val Ser Gly Leu Leu Tyr Ala
145                 150                 155                 160

Ala Ile Gly Leu Asn Ile Gln His Asp Ala Asn His Gly Ala Val Ser
                165                 170                 175

Arg Asn Pro Ala Val Asn Arg Leu Phe Gly Tyr Ser Gln Asp Trp Ile
            180                 185                 190

Gly Gly Ser Arg Met Leu Trp Ile Arg Gln His Val Gly His His
        195                 200                 205

Thr His Cys Asn Asp His Gln His Asp Pro Asp Val Lys Gly Gly Ser
    210                 215                 220

Ala Ile Thr Leu Ser Arg Thr Asp Leu Pro Lys Glu Phe His His Ile
225                 230                 235                 240

Gln Gln Tyr Tyr Phe Leu Pro Leu Gln Leu Leu Gly Phe Gln Trp
                245                 250                 255

Val Phe Leu Gly Leu His Asp Leu Ile Glu Met Lys Tyr Lys Gly Glu
            260                 265                 270

Pro Leu Pro Glu Ser Tyr Arg Lys Leu Arg Asn Ile Ala Val Gly Cys
        275                 280                 285

Arg Ile Phe Phe Phe Ala Arg Lys Phe Ala Val Pro Phe Ala Leu His
    290                 295                 300

Phe Ser Trp Tyr Thr Leu Leu Cys Thr Cys Leu Trp Met Ala Ile Ala
305                 310                 315                 320

Ala Leu Tyr Leu Gly Phe Phe Ile Leu Ser His Ile Phe Val Gly
                325                 330                 335

Ala Lys Ser Leu Pro Pro Asp Ala Asn Ile Asp Trp Ala Arg His Gln
        340                 345                 350

Ile Glu Ser Ser Ser Asn Val Cys Gly Glu Lys Leu Gly Ile Ser Asn
    355                 360                 365

Gly Gly Leu Asn Tyr Gln Ile Glu His His Leu Phe Pro Arg Met Ser
370                 375                 380

His Ala His Tyr Ser Lys Ile Gln Pro Val Val Arg Lys Val Cys Glu
385                 390                 395                 400

Glu Asn Gly Ile Asn Tyr Lys Lys Phe Gly Thr Ile Leu Ser Asn Leu
                405                 410                 415

Asp Ser Thr Phe Arg Gln Leu Lys Ala Ile Gly Ser Val Pro Val Tyr
            420                 425                 430

Glu Phe Met Glu Gly Leu
        435

<210> SEQ ID NO 127
<211> LENGTH: 439
<212> TYPE: PRT
<213> ORGANISM: Artificial
<220> FEATURE:
<223> OTHER INFORMATION: delta-4 desaturase 90.1% sequence identity to
      SEQ ID NO 79
```

<400> SEQUENCE: 127

```
Met Pro Pro His Ser Ala Lys Lys Gly Ser Asp Val Pro Glu Leu Arg
1               5                   10                  15

Asp Leu Met Lys His Phe Thr Arg Thr Glu Ile Leu Asn His Thr Asn
            20                  25                  30

Asp Lys Leu Cys Ile Leu Gly Asp Gly Val Tyr Asp Leu Thr Asn Phe
        35                  40                  45

Arg Asp Lys His Pro Gly Gly Asp Val Leu Asp Phe Phe Pro Gly Gln
    50                  55                  60

Asp Ala Thr Pro His Phe Tyr Met Leu His Gln Tyr Glu Ser Leu Pro
65                  70                  75                  80

Ser Val Leu Ala Glu Tyr Gly Val Gly Ser Val Asp Arg Asp Asp Ser
                85                  90                  95

Tyr Val Tyr His Thr Pro Leu His Lys Gln Ile Lys Ser Ala Val Arg
            100                 105                 110

Lys Val Met Pro Met Gln Glu Trp Trp Ala Pro Pro Ser Trp Tyr Ile
        115                 120                 125

Lys Ala Cys Ala Ile Leu Ala Ala Thr Leu Tyr Leu Asp Tyr Leu Trp
    130                 135                 140

Ile Ala Ser Gly Pro Thr Ile Pro Leu Ala Ile Val Ser Gly Leu Leu
145                 150                 155                 160

Tyr Ala Ala Ile Gly Leu Asn Ile Gln His Asp Ala Asn His Gly Gly
                165                 170                 175

Val Ser Arg Asn Pro Met Val Asn Tyr Leu Phe Gly Tyr Ser Gln Asp
            180                 185                 190

Trp Ile Gly Gly Ser Arg Met Leu Trp Ile Arg Gln His Val Val Gly
        195                 200                 205

His His Thr His Cys Asn Arg His Gln His Asp Pro Asp Val Lys Gly
    210                 215                 220

Gly Gly Val Ile Thr Leu Ser Pro Tyr Ser Leu Pro Lys Glu Phe His
225                 230                 235                 240

His Ile Gln Gln Tyr Tyr Phe Leu Pro Leu Glu Gln Leu Leu Gly Phe
                245                 250                 255

Lys Trp Val Phe Leu Gly Leu His Asp Leu Ile Glu Met Lys Tyr Lys
            260                 265                 270

Gly Glu Lys Leu Pro Glu Ser Tyr Arg Lys Glu Arg Asn Ile Ala Val
        275                 280                 285

Gly Leu Arg Val Phe Phe Phe Ile Arg Lys Phe Val Ile Pro Phe Ala
    290                 295                 300

Leu His Phe Ser Trp His Thr Leu Leu Cys Ile Tyr Leu Trp Met Ala
305                 310                 315                 320

Ile Gly Ala Leu Tyr Leu Gly Phe Phe Val Leu Ser His Ile Phe
                325                 330                 335

Val Gly Val Gly Ser Leu Gly Glu Asp Ala Asn Val Asp Trp Ala Arg
            340                 345                 350

His Gln Ile Glu Thr Ser Ser Asn Val Cys Gly Glu Lys Leu Gly Ile
        355                 360                 365

Met Asn Gly Gly Leu Asn Tyr Gln Ile Glu His Leu Phe Pro Arg
    370                 375                 380

Met Ser His Ala His Tyr Ser Pro Ile Gln Pro Val Val Gln Lys Val
385                 390                 395                 400

Cys Glu Glu Asn Gly Val Lys Tyr Lys Lys Phe Gly Thr Ile Leu Ser
                405                 410                 415
```

```
Asn Leu Asp Ser Thr Phe Ser Gln Val Lys Ala Leu Gly Ser Val Ala
                420                 425                 430

Thr Glu Phe Met Gly Lys Ile
        435

<210> SEQ ID NO 128
<211> LENGTH: 437
<212> TYPE: PRT
<213> ORGANISM: Artificial
<220> FEATURE:
<223> OTHER INFORMATION: delta-4 desaturase 89.9% sequence identity to
      SEQ ID NO 79

<400> SEQUENCE: 128

Met Pro Pro His Ser Arg Thr Lys Val Gly Asp Pro Glu Leu Ser Asp
1               5                   10                  15

Met Lys His Phe Thr Arg Glu Glu Ile Leu Asp His Thr Asn Asp Lys
                20                  25                  30

Leu Cys Ile Leu Glu Asp Gly Val Tyr Asp Ala Thr Ala Phe Arg Asp
            35                  40                  45

Lys His Pro Gly Gly Asp Val Leu Asp Phe Phe Pro Gly Gln Asp Ala
        50                  55                  60

Thr Pro His Phe Tyr Met Tyr His Gln His Glu Ser Pro Pro Ser Val
65                  70                  75                  80

Leu Ala Glu Tyr Lys Val Gly Ser Leu Ala Arg Asp Asp Ser Tyr Val
                85                  90                  95

Tyr His Thr Ala Gly Met Lys Gln Ile Lys Ser Ala Val Arg Gly Ile
            100                 105                 110

Ile Pro Met Gln Glu Trp Trp Ala Pro Pro Ser Trp Tyr Ile Lys Ala
        115                 120                 125

Cys Ala Ile Leu Ala Ala Thr Leu Tyr Thr Asp Tyr Leu Trp Ile Ala
130                 135                 140

Ser Gly Pro Thr Ile Pro Leu Ala Ile Val Ser Gly Leu Leu Tyr Ala
145                 150                 155                 160

Ala Ile Gly Leu Asn Ile Gln His Asp Ala Asn His Gly Ser Val Ser
                165                 170                 175

Arg Asn Pro Ala Val Asn Arg Leu Phe Gly Tyr Ser Gln Asp Trp Ile
            180                 185                 190

Gly Gly Ser Met Met Leu Trp Ile Arg Gln His Val Val Gly His His
        195                 200                 205

Thr His Thr Asn Arg Ile Asp His Asp Pro Asp Val Lys Gly Gly Ser
    210                 215                 220

Val Ile Gln Leu Ser Pro Ser Ser Leu Pro Lys Pro Trp His His Ile
225                 230                 235                 240

Gln Gln Tyr Tyr Phe Leu Pro Leu Ile Gln Leu Leu Gly Phe Gln Trp
                245                 250                 255

Val Phe Leu Gly Leu His Asp Leu Ile Glu Trp Lys Tyr Lys Gly Glu
            260                 265                 270

Lys Leu Pro Glu Ser Cys Arg Lys Glu Arg Asn Ile Ala Ile Gly Cys
        275                 280                 285

Arg Ile Phe Phe Phe Ala Arg Lys Phe Ala Val Pro Phe Trp Leu His
    290                 295                 300

Phe Ser Trp Tyr Thr Leu Leu Cys Thr Tyr Leu Trp Met Ala Ile Ala
305                 310                 315                 320

Ala Leu Tyr Leu Gly Phe Phe Ile Leu Ser His Ile Phe Ile Gly
```

```
                    325                 330                 335
Ala Gly Ser Leu Pro Glu Asp Ala Asn Ile Asp Trp Ala Arg His Gln
                340                 345                 350

Ile Glu Ser Ser Ser Asn Val Cys Gly Glu Lys Leu Gly Ile Ile Asn
                355                 360                 365

Gly Gly Leu Asn Tyr Gln Ile Glu His His Leu Phe Pro Arg Met Ser
            370                 375                 380

His Ala His Tyr Ser Lys Ile Gln Pro Val Val Gln Lys Val Cys Glu
385                 390                 395                 400

Glu Asn Gly Val Asn Tyr Lys His Phe Gly Thr Ile Leu Ser Asn Leu
                405                 410                 415

Asp Ser Thr Phe Arg Gln Val Lys Ala Leu Gly Ser Val Pro Val Glu
                420                 425                 430

Phe Met Glu Gly Pro
            435

<210> SEQ ID NO 129
<211> LENGTH: 439
<212> TYPE: PRT
<213> ORGANISM: Artificial
<220> FEATURE:
<223> OTHER INFORMATION: delta-4 desaturase 89.9% sequence identity to
      SEQ ID NO 79

<400> SEQUENCE: 129

Met Pro Pro His Ser Arg Thr Lys Val Ser Asp Val Pro Glu Leu Ser
1               5                   10                  15

Asp Leu Met Lys His Phe Thr Arg Glu Glu Ile Leu Asn His Asn Asn
                20                  25                  30

Asp Lys Ile Cys Ile Leu Gly Asp Gly Val Tyr Asp Leu Thr Asn Phe
            35                  40                  45

Arg Asp Lys His Pro Gly Gly Asp Val Leu Asp Phe Phe Pro Gly Gln
        50                  55                  60

Asp Ala Thr Pro His Phe Tyr Met Tyr His Gln Tyr Glu Ser Pro Pro
65              70                  75                  80

Ser Val Leu Ala Glu Tyr Lys Val Gly Ser Val Ala Arg Asp Asp Lys
                85                  90                  95

Tyr Val Gln His Thr Pro Leu Met Lys Gln Ile Lys Ala Asp Val Arg
                100                 105                 110

Lys Val Met Pro Met Gly Glu Trp Trp Ala Pro Pro Ser Trp Tyr Ile
            115                 120                 125

Lys Ala Cys Ala Ile Leu Ile Ala Thr Leu Tyr Thr Asp Tyr Leu Trp
        130                 135                 140

Ile Ala Arg Gly Pro Thr Ile Pro Leu Ala Ile Val Ser Gly Leu Leu
145                 150                 155                 160

Tyr Ala Ala Ile Gly Leu Asn Ile Gln His Asp Ala Asn His Gly Ser
                165                 170                 175

Leu Ser Arg Asn Pro Met Val Asn Arg Leu Phe Gly Tyr Ala Gln Asp
            180                 185                 190

Trp Ile Gly Gly Ser Arg Met Leu Trp Ile Arg Gln His Val Val Gly
        195                 200                 205

His His Leu His Cys Asn Arg Ile Asp His Asp Pro Asp Val Lys Gly
        210                 215                 220

Gly Ser Val Ile Lys Leu Ser Pro Tyr Asp Gly Pro Lys Glu Trp His
225                 230                 235                 240
```

His Ile Gln Gln Ile Tyr Phe Leu Pro Leu Ile Gln Leu Tyr Gly Phe
                245                 250                 255

Gln Trp Val Phe Leu Gly Leu His Asp Leu Ile Glu Trp Arg Tyr Lys
            260                 265                 270

Gly Glu Lys Leu Pro Glu Ser Tyr Arg Lys Glu Phe Asn Ile Ala Ile
        275                 280                 285

Gly Leu Arg Val Phe Phe Ile Arg Phe Val Leu Pro Phe Ala
    290                 295                 300

Leu His Phe Ser Trp His Thr Leu Leu Cys Thr Tyr Leu Trp Met Ala
305                 310                 315                 320

Ile Gly Ala Leu Tyr Leu Ala Phe Phe Phe Ile Leu Ser His Ile Phe
                325                 330                 335

Val Gly Ala Lys Ser Leu Pro Pro Asp Ala Asn Ile Asp Trp Ala Arg
            340                 345                 350

His Gln Ile Glu Ser Ser Ser Asn Val Cys Gly Glu Trp Leu Gly Ile
        355                 360                 365

Ser Asn Gly Gly Leu Asn Tyr Gln Ile Glu His Leu Phe Pro Arg
    370                 375                 380

Met His His Ala His Tyr Ser Pro Ile Gln Pro Val Val Gln Arg Val
385                 390                 395                 400

Cys Glu Glu Asn Gly Val Asn Tyr Lys Lys Phe Gly Thr Ile Ala Ser
                405                 410                 415

Asn Leu Asp Ser Thr Phe Arg Gln Val Lys Ala Leu Gly Ser Val Ala
            420                 425                 430

Val Glu Phe Met Glu Gly Leu
            435

<210> SEQ ID NO 130
<211> LENGTH: 438
<212> TYPE: PRT
<213> ORGANISM: Artificial
<220> FEATURE:
<223> OTHER INFORMATION: delta-4 desaturase 89.7% sequence identity to
      SEQ ID NO 79

<400> SEQUENCE: 130

Met Pro Pro His Ser Arg Thr Lys Val Ser Asp Asp Ala Glu Leu Ser
1               5                   10                  15

Asp Met Lys His Phe Thr Arg Glu Glu Ile Leu Asp His Thr Asn Asp
            20                  25                  30

Lys Tyr Cys Ile Leu Glu Asp Gly Val Tyr Asp Cys Thr Asn Phe Arg
        35                  40                  45

Asp Lys His Pro Gly Gly Asp Val Ile Asp Phe Phe Pro Gly Gln Asp
    50                  55                  60

Ala Thr Pro His Phe Tyr Met Leu His Gln Lys Ala Trp Pro Pro Ser
65                  70                  75                  80

Val Leu Ala Glu Tyr Phe Val Gly Ser Val Ala Arg Asp Asp Ser Tyr
                85                  90                  95

Val Gln His Glu Pro Leu His Lys Gln Ile Cys Ser Ala Val Arg Lys
            100                 105                 110

Val Met Pro Met Gln Glu Trp Trp Ala Pro Ser Tyr Ile Lys
        115                 120                 125

Ala Cys Ala Ile Leu Ala Ala Thr Leu Tyr Thr Asp Tyr Leu Trp Ile
    130                 135                 140

Ala Ser Gly Pro Thr Ile Pro Leu Ser Ile Val Ser Gly Leu Leu Tyr
145                 150                 155                 160

```
Ala Ala Ile Gly Leu Asn Ile Gln His Asp Ala Asn His Gly Ser Val
            165                 170                 175

Ser Arg Asn Pro Met Val Asn Tyr Leu Phe Gly Tyr Gly Gln Asp Trp
            180                 185                 190

Ile Gly Gly Ser Arg Val Leu Trp Ile Arg Gln His Val Val Gly His
            195                 200                 205

His Thr His Thr Asn Asp His Asp His Asp Pro Asp Val Lys Gly Gly
            210                 215                 220

Ser Val Ile Thr Leu Ser Arg Ser Ser Gly Pro Lys Glu Trp His His
225                 230                 235                 240

Ile Gln Gln Tyr Tyr Phe Leu Pro Gly Ile Gln Leu Tyr Gly Phe Lys
            245                 250                 255

Trp Val Phe Leu Gly Leu His Asp Leu Ile Glu Trp Lys Tyr Lys Gly
            260                 265                 270

Glu Lys Leu Pro Glu Ile Tyr Arg Lys Glu Arg Asn Ile Ala Ile Gly
            275                 280                 285

Leu Arg Val Phe Phe Phe Ile Arg Lys Phe Val Pro Phe Ala Leu
            290                 295                 300

His Phe Ser Trp Tyr Thr Leu Leu Cys Thr Tyr Ala Trp Met Ala Thr
305                 310                 315                 320

Gly Ala Phe Tyr Leu Gly Phe Phe Ile Leu Ser His Ile Phe Ile
            325                 330                 335

Gly Ala Lys Ser Leu Pro Glu Asp Ala Asn Ile Asp Trp Ala Arg His
            340                 345                 350

Gln Ile Glu Ser Ser Asn Val Cys Gly Glu Lys Leu Gly Tyr Ser
            355                 360                 365

Asn Gly Gly Leu Asn Tyr Gln Ile Glu His His Leu Phe Pro Arg Met
            370                 375                 380

Ser His Ala His Tyr Ser Lys Ile Gln Pro Val Val Arg Lys Val Cys
385                 390                 395                 400

Glu Asp Asn Gly Val Asn Tyr Lys His Phe Gly Thr Ile Leu Ser Asn
            405                 410                 415

Leu Gly Ser Thr Phe Arg Gln Val Lys Ala Leu Gly Ser Val Ala Val
            420                 425                 430

Glu Phe Met Glu Gly Pro
            435

<210> SEQ ID NO 131
<211> LENGTH: 438
<212> TYPE: PRT
<213> ORGANISM: Artificial
<220> FEATURE:
<223> OTHER INFORMATION: delta-4 desaturase 89.7% sequence identity to
      SEQ ID NO 79

<400> SEQUENCE: 131

Met Pro Pro His Ala Arg Thr Lys Gly Ser Asp Pro Glu Leu Lys Asp
1               5                   10                  15

Met Lys His Phe Thr Arg Glu Glu Ile Leu Asn His Asn Asn Asp Lys
            20                  25                  30

Tyr Cys Ile Leu Gly Asp Gly Val Tyr Asp Leu Thr Asn Phe Arg Asp
            35                  40                  45

Lys His Pro Gly Gly Asp Tyr Leu Asp Phe Phe Gly Gly Gln Asp Ala
            50                  55                  60

Thr Pro His Phe Tyr Glu Tyr His Gln His Glu Ser Pro Pro Ser Val
```

```
                65                  70                  75                  80
Leu Ala Glu Tyr Lys Val Gly Ser Val Ala Arg Asp Asp Ser Tyr Val
                    85                  90                  95
Gln His Thr Glu Leu Met Lys Gln Ile Lys Ser Ala Val Arg Gly Val
                100                 105                 110
Leu Pro Met Gln Glu Trp Trp Ala Pro Ser Trp Tyr Ile Lys Ala
                115                 120                 125
Cys Ala Leu Ile Val Ala Thr Leu Tyr Leu Asp Tyr Leu Trp Ile Ala
                130                 135                 140
Ser Gly Pro Thr Ile Phe Leu Ala Ile Val Ser Gly Leu Leu Tyr Ala
145                 150                 155                 160
Ala Ile Gly Leu Asn Ile Gln His Asp Ala Asn His Gly Ser Val Ser
                    165                 170                 175
Arg Asn Pro Val Val Asn Arg Leu Phe Gly Tyr Ser Gln Asp Trp Ile
                180                 185                 190
Gly Gly Ser Arg Met Leu Trp Ile Gln Lys His Val Val Gly His His
                195                 200                 205
Leu His Cys Asn Arg His Gln His Asp Pro Asp Val Lys Gly Gly Ser
210                 215                 220
Val Ile Thr Leu Ser Pro Tyr Ser Gly Trp Lys Glu Phe His His Leu
225                 230                 235                 240
Gln Gln Ile Tyr Phe Leu Pro Leu Ile Gln Leu Leu Gly Phe Gln Trp
                    245                 250                 255
Val Phe Leu Gly Leu His Asp Leu Ile Glu Met Lys Tyr Lys Gly Glu
                260                 265                 270
Lys Leu Pro Glu Ile Tyr Arg Lys Leu Arg Asn Ile Ala Ile Gly Cys
                275                 280                 285
Arg Val Phe Phe Phe Ile Arg Lys Phe Val Pro Phe Trp Leu His
                290                 295                 300
Phe Ser Trp Tyr Thr Leu Leu Cys Thr Tyr Leu Trp Met Ala Ser Ala
305                 310                 315                 320
Ala Leu Tyr Leu Gly Phe Phe Ile Leu Ser His Ile Phe Val Gly
                    325                 330                 335
Ala Lys Ser Leu Pro Glu Asp Ala Asn Ile Asp Trp Ala Arg Arg Gln
                340                 345                 350
Ile Glu Ser Ser Asn Val Cys Gly Glu Lys Leu Gly His Ser Asn
                355                 360                 365
Gly Gly Leu Asn Tyr Gln Ile Glu His His Leu Phe Pro Arg Met Ser
        370                 375                 380
His Ala His Tyr Ala Lys Ile Gln Pro Val Val Gln Lys Val Cys Glu
385                 390                 395                 400
Glu Asn Gly Val Asn Tyr Lys His Phe Gly Thr Ile Leu Ser Asn Leu
                    405                 410                 415
Asp Ser Thr Phe Arg Gln Val Lys Ala Leu Gly Ser Val Ala Val Tyr
                420                 425                 430
Glu Phe Leu Glu Gly Leu
            435

<210> SEQ ID NO 132
<211> LENGTH: 438
<212> TYPE: PRT
<213> ORGANISM: Artificial
<220> FEATURE:
<223> OTHER INFORMATION: delta-4 desaturase 89.7% sequence identity to
      SEQ ID NO 79
```

<400> SEQUENCE: 132

```
Met Pro Pro His Gly Arg Thr Glu Gly Ser Asp Pro Glu Leu Arg Asp
1               5                   10                  15

Met Lys His Phe Thr Arg Glu Arg Ile Leu Asp His Thr Asn Asp Lys
            20                  25                  30

Leu Cys Ile Leu Glu Asp Gly Val Tyr Asp Leu Asn Asn Phe Arg Asp
        35                  40                  45

Lys His Pro Gly Gly Asp Phe Leu Asp Phe Phe Pro Gly Gln Asp Ala
    50                  55                  60

Thr Pro His Phe Phe Gln Leu His Gln Tyr Glu Ser Leu Pro Ser Val
65                  70                  75                  80

Leu Ala Glu Tyr Lys Val Gly Ser Val Ala Arg Asp Asp Ser Tyr Val
                85                  90                  95

Tyr His Asp Pro Leu Met Lys Gln Leu Lys Ser Ala Val Arg Ala Val
            100                 105                 110

Met Pro Lys Gln Glu Gly Trp Ala Pro Pro Ser Trp Tyr Ile Lys Ala
        115                 120                 125

Cys Ala Ile Leu Ala Ala Thr Leu Tyr Leu Asp Tyr Leu Trp Ile Ala
    130                 135                 140

Ser Gly Pro Thr Ile Pro Leu Ala Ile Val Ser Gly Leu Leu Tyr Ala
145                 150                 155                 160

Ala Ile Gly Leu Asn Ile Gln His Asp Ala Asn His Gly Ser Ile Ser
                165                 170                 175

Arg Asn Pro Met Val Asn Tyr Leu Phe Gly Tyr Ser Gln Asp Trp Ile
            180                 185                 190

Gly Gly Ser Arg Met Leu Trp Ile Arg Gln His Val Val Gly His His
        195                 200                 205

Thr His Cys Asn Arg His Gln His Asp Pro Asp Val Lys Gly Gly Ser
    210                 215                 220

Val Ile Thr Leu Ser Pro Tyr Ser Leu Pro Lys Glu Trp His His Ile
225                 230                 235                 240

Gln Gln Tyr Tyr Phe Leu Pro Leu Asp Gln Leu Leu Gly Phe Gln Trp
                245                 250                 255

Val Phe Leu Gly Leu His Asp Leu Ile Asp Met Arg Tyr Lys Gly Glu
            260                 265                 270

Lys Leu Pro Pro Ile Tyr Arg Lys Glu Arg Ala Pro Ala Ile Gly Leu
        275                 280                 285

Arg Val Phe Phe Phe Ile Arg Phe Phe Val Pro Phe Trp Leu His Pro
    290                 295                 300

Pro Ser Trp Tyr Thr Leu Leu Cys Thr Cys Ala Trp Val Ala Ile Ala
305                 310                 315                 320

Ala Phe Tyr Leu Gly Phe Phe Ile Leu Ser His Ile Phe Val Gly
                325                 330                 335

Ile Lys Ser Leu Pro Glu Asp Ala Lys Asn Ile Asp Trp Ala Arg His
            340                 345                 350

Gln Ile Glu Ser Ser Ser Asn Val Cys Gly Asp Lys Leu Gly Tyr Ser
        355                 360                 365

Asn Gly Gly Leu Asn Tyr Gln Ile Glu His His Leu Phe Pro Arg Met
    370                 375                 380

Ser His Ala His Tyr Ser Lys Ile Gln Pro Val Val Gln Lys Val Cys
385                 390                 395                 400

Glu Glu Asn Gly Val Asn Tyr Lys Lys Phe Gly Thr Ile Leu Ser Asn
```

```
                405                 410                 415
Leu Asp Ser Thr Phe Arg Gln Val Lys Ala Leu Gly Ser Val Pro Val
        420                 425                 430

Glu Phe Met Glu Gly Leu
        435

<210> SEQ ID NO 133
<211> LENGTH: 440
<212> TYPE: PRT
<213> ORGANISM: Artificial
<220> FEATURE:
<223> OTHER INFORMATION: delta-4 desaturase 89.7% sequence identity to
      SEQ ID NO 79

<400> SEQUENCE: 133

Met Pro Pro His Ser Arg Thr Lys Val Ser Asp Pro Glu Leu Arg Asp
1               5                   10                  15

Leu Met Lys His Phe Thr Arg Glu Glu Ile Leu Asn His Thr Asn Asp
            20                  25                  30

Asp Tyr Cys Ile Leu Gly Asp Gly Val Tyr Asp Leu Thr Asn Phe Arg
        35                  40                  45

Asp Glu His Pro Gly Gly Asp Phe Leu Asp Phe Phe Pro Gly Gln Asp
    50                  55                  60

Ala Thr Pro His Phe Tyr Met Leu His Gln Arg Glu Ser Leu Pro Ser
65                  70                  75                  80

Val Leu Ala Glu Tyr Lys Val Gly Ser Val Asp Arg Asp Asp Ser Tyr
                85                  90                  95

Val Gln His Glu Pro Leu Met Lys Gln Ile Lys Ser Ala Val Arg Lys
            100                 105                 110

Ile Met Pro Lys Gln Glu Trp Trp Ala Pro Pro Ser Trp Trp Ile Lys
        115                 120                 125

Ala Cys Ala Ile Leu Ala Ala Ala Leu Tyr Thr Asp Tyr Leu Trp Ile
    130                 135                 140

Leu Ser Gly Pro Thr Ile Pro Leu Ala Ile Val Ser Gly Leu Leu Tyr
145                 150                 155                 160

Ala Trp Ile Gly Leu Asn Ile Gln His Asp Ala Asn His Gly Ser Ile
                165                 170                 175

Ser Arg Asn Pro Met Val Asn Arg Leu Phe Gly Tyr Ser Gln Asp Trp
            180                 185                 190

Ile Gly Gly Ser Arg Met Leu Trp Ile Arg Gln His Val Val Gly His
        195                 200                 205

His Ile His Cys Asn Arg His Asp His Asp Pro Asp Leu Lys Gly Gly
    210                 215                 220

Ser Ala Ile Gln Leu Ser Arg Val Ser Leu Pro Lys Glu Phe His His
225                 230                 235                 240

Ile Gln Gln Tyr Tyr Phe Leu Pro Leu Glu Gln Leu Tyr Gly Phe Gln
                245                 250                 255

Trp Val Phe Leu Gly Leu His Asp Leu Ile Asp Met Lys Trp Lys Gly
            260                 265                 270

Glu Lys Leu Pro Glu Ser Tyr Arg Pro Glu Tyr Asn Ile Ala Ile Gly
        275                 280                 285

Leu Arg Val Gly Phe Phe Ile Arg Lys Phe Val Pro Leu Ala Leu
    290                 295                 300

His Phe Ser Trp Tyr Thr Leu Leu Cys Thr Tyr Leu Trp Met Ala Ile
305                 310                 315                 320
```

Ala Ala Leu Tyr Leu Cys Phe Phe Ile Leu Ser His Ile Phe Val
                325                 330                 335

Gly Ile Lys Ser Leu Pro Glu Asp Ala Lys Asn Ile Asp Trp Ala Arg
            340                 345                 350

His Gln Ile Glu Ser Ser Asn Val Gly Gly Glu Lys Leu Gly His
        355                 360                 365

Ile Asn Gly Gly Leu Asn Tyr Gln Ile Glu His His Leu Phe Pro Arg
    370                 375                 380

Met Ser His Ala His Tyr Ala Lys Ile Gln Pro Val Val Gln Lys Val
385                 390                 395                 400

Cys Glu Glu Asn Gly Val Asn Tyr Lys His Phe Gly Thr Ile Ala Ser
                405                 410                 415

Asn Leu Asp Ala Leu Phe Arg Gln Val Lys Ala Leu Gly Ser Val Pro
            420                 425                 430

Val Tyr Glu Phe Met Glu Gly Leu
        435                 440

<210> SEQ ID NO 134
<211> LENGTH: 437
<212> TYPE: PRT
<213> ORGANISM: Artificial
<220> FEATURE:
<223> OTHER INFORMATION: delta-4 desaturase 89.7% sequence identity to
      SEQ ID NO 79

<400> SEQUENCE: 134

Met Pro Pro His Ser Arg Thr Lys Val Gly Asp Pro Glu Leu Arg Ala
1               5                   10                  15

Met Glu His Phe Thr Arg Glu Arg Ile Leu Asn His Thr Asn Asp Lys
            20                  25                  30

Tyr Cys Ile Leu Glu Asp Gly Val Tyr Asp Leu Thr Asn Phe Arg Asp
        35                  40                  45

Lys His Pro Gly Gly Asp Val Ile Asp Phe Phe Pro Gly Arg Asp Ala
    50                  55                  60

Thr Pro His Phe Tyr Met Leu His Gln Arg Glu Ser Leu Pro Ser Val
65              70                  75                  80

Leu Ala Glu Tyr Phe Val Gly Ser Val Ala Arg Asp Asp Ser Tyr Val
                85                  90                  95

Tyr Tyr Thr Pro Leu His Lys Gln Ile Lys Ser Ala Val Arg Gly Val
            100                 105                 110

Met Pro Met Gln Ser Trp Trp Ala Pro Pro Ser Trp Tyr Ile Lys Ala
        115                 120                 125

Cys Ala Ile Leu Ala Ala Thr Leu His Thr Asp Tyr Leu Trp Ile Ala
    130                 135                 140

Ser Gly Pro Thr Ile Pro Leu Ala Ile Val Leu Gly Leu Leu Tyr Ala
145                 150                 155                 160

Ala Ile Gly Leu Asn Ile Gln His Asp Ala Asn His Gly Ser Val Ser
                165                 170                 175

Arg Asn Pro Met Val Asn Arg Leu Phe Gly Tyr Ser Gln Asp Trp Ile
            180                 185                 190

Gly Gly Ser Arg Met Leu Trp Ile Arg Gln His Val Val Gly His His
        195                 200                 205

Ile His Thr Asn Arg His Gln His Asp Pro Asp Val Lys Gly Gly Ser
    210                 215                 220

Val Ile Arg Leu Ser Arg Tyr Ser Leu Trp Lys Glu Phe His His Ile
225                 230                 235                 240

```
Gln Gln Tyr Tyr Phe Leu Pro Leu Glu Gln Leu Tyr Gly Phe Gln Trp
            245                 250                 255

Ile Phe Leu Gly Leu His Asp Leu Ile Glu Met Lys Tyr Lys Gly Glu
        260                 265                 270

Lys Leu Pro Glu Leu Tyr Arg Lys Glu Phe Asn Ile Ala Ile Gly Leu
    275                 280                 285

Arg Val Phe Phe Phe Ala Arg Lys Phe Val Val Pro Phe Ala Leu His
290                 295                 300

Phe Ser Trp Tyr Thr Leu Leu Cys Thr Tyr Leu Trp Met Ala Ile Gly
305                 310                 315                 320

Ala Phe Tyr Leu Cys Phe Phe Ile Leu Ser His Ile Phe Val Gly
            325                 330                 335

Val Lys Ser Ile Pro Glu Asp Ala Asn Ile Asp Trp Ala Arg His Gln
        340                 345                 350

Ile Glu Ser Ser Ser Asn Val Cys Gly Glu Trp Leu Gly Ile Ser Asn
    355                 360                 365

Gly Gly Leu Asn Tyr Gln Ile Glu His His Leu Phe Pro Arg Met Ser
370                 375                 380

His Ala His Tyr Ser Lys Ile Glu Pro Val Val Gln Lys Val Cys Glu
385                 390                 395                 400

Glu Asn Gly Val Lys Tyr Lys Lys Phe Pro Thr Ile Leu Ser Asn Leu
            405                 410                 415

Asp Ser Thr Phe Arg Gln Ile Gly Ala Leu Gly Ser Val Ala Val Glu
        420                 425                 430

Tyr Met Glu Lys Leu
            435

<210> SEQ ID NO 135
<211> LENGTH: 438
<212> TYPE: PRT
<213> ORGANISM: Artificial
<220> FEATURE:
<223> OTHER INFORMATION: delta-4 desaturase 89.7% sequence identity to
      SEQ ID NO 79

<400> SEQUENCE: 135

Met Pro Pro His Gly Arg Thr Lys Val Ser Asp Asp Pro Glu Leu Ser
1               5                   10                  15

Asp Met Lys His Phe Thr Arg Glu Glu Ile Leu Asn His Thr Asn Asp
            20                  25                  30

Lys Tyr Cys Ile Leu Glu Asp Gly Val Tyr Asp Leu Thr Asn Phe Arg
        35                  40                  45

Asp Glu His Pro Gly Gly Asp Val Leu Asp Phe Phe Pro Gly Gln Asp
    50                  55                  60

Ala Thr Pro His Phe Trp Met Tyr His Arg Tyr Ala Ser Pro Pro Ser
65                  70                  75                  80

Val Leu Ala Glu Tyr Lys Val Gly Ser Val Asp Arg Asp Asp Ser Tyr
            85                  90                  95

Val Tyr His Glu Pro Leu Met Lys Gln Leu Lys Ala Asp Val Arg Lys
        100                 105                 110

Val Met Pro Met Gln Glu Gly Trp Ala Pro Pro Ser Trp Ile Lys
    115                 120                 125

Ala Cys Ala Ile Leu Ala Ala Thr Leu His Leu Asp Tyr Leu Met Ile
    130                 135                 140

Ala Lys Gly Pro Thr Ile Pro Leu Ala Ile Val Ser Gly Leu Leu Tyr
```

```
            145                 150                 155                 160
        Ala Ala Ile Gly Leu Asn Ile Gln His Asp Ala Asn His Gly Ser Val
                        165                 170                 175

Ser Arg Asn Pro Met Val Asn Arg Leu Phe Gly Tyr Ser Gln Asp Trp
                        180                 185                 190

Ile Gly Gly Ser Arg Met Leu Trp Ile Arg Glu His Val Val Gly His
                        195                 200                 205

His Thr His Cys Asn Arg His Gln His Asp Pro Asp Val Lys Gly Gly
                210                 215                 220

Ser Val Ile Thr Leu Ser Pro Tyr Ser Leu Pro Leu Pro Phe His His
        225                 230                 235                 240

Ile Gln Gln Tyr Tyr Phe Leu Pro Leu Glu Gln Leu Tyr Gly Phe Gln
                        245                 250                 255

Trp Val Phe Leu Gly Leu His Asp Leu Ile Glu Met Lys Tyr Lys Gly
                        260                 265                 270

Glu Pro Leu Pro Glu Ser Tyr Arg Lys Glu Arg Asn Ile Ala Ile Gly
                        275                 280                 285

Leu Arg Val Phe Phe Phe Val Arg Lys Ile Val Val Pro Phe Ala Leu
                        290                 295                 300

His Phe Ser Trp Tyr Thr Leu Leu Cys Thr Tyr Leu Trp Met Ala Ser
        305                 310                 315                 320

Ala Ala Phe Tyr Leu Ala Phe Phe Ile Leu Ser His Ile Phe Val
                        325                 330                 335

Gly Val Lys Ser Leu Gly Glu Asp Ala Asn Ile Asp Trp Ala Arg Arg
                        340                 345                 350

Gln Ile Glu Ser Ser Asn Val Cys Gly Glu Lys Leu Gly Ile Ser
                        355                 360                 365

Asn Gly Gly Leu Asn Tyr Gln Ile Glu His His Leu Phe Pro Arg Met
                        370                 375                 380

Ser His Ala His Tyr Ser Lys Ile Gln Pro Val Val Gln Lys Val Cys
        385                 390                 395                 400

Glu Glu Asp Gly Val Asn Tyr Lys Lys Phe Pro Thr Ile Leu Ser Asn
                        405                 410                 415

Leu Asp Ala Thr Phe Arg His Val Gly Ala Leu Gly Ser Val Ala Val
                        420                 425                 430

Glu Phe Met Glu Lys Leu
                        435

<210> SEQ ID NO 136
<211> LENGTH: 438
<212> TYPE: PRT
<213> ORGANISM: Artificial
<220> FEATURE:
<223> OTHER INFORMATION: delta-4 desaturase 89.7% sequence identity to
      SEQ ID NO 79

<400> SEQUENCE: 136

Met Pro Pro His Ser Arg Arg Lys Val Ser Asp Pro Glu Leu Ser Asp
1               5                   10                  15

Ala Lys His Phe Thr Tyr Thr Glu Lys Leu Asn His Thr Asn Pro Lys
                20                  25                  30

Tyr Cys Ile Leu Glu Asp Gly Val Tyr Asp Leu Ser Asn Phe Arg Asp
            35                  40                  45

Lys His Pro Gly Gly Asp Val Leu Asp Phe Phe Pro Gly Gln Asp Ala
        50                  55                  60
```

Thr Pro His Phe Tyr Met Tyr His Gln Tyr Glu Ser Pro Ser Val
65                  70                  75                  80

Met Ala Glu Tyr Lys Val Gly Ser Val Ala Arg Asp Asp Ser Tyr Val
            85                  90                  95

Tyr Ala Thr Glu Leu Met Leu Gln Ile Lys Ser Ala Val Arg Lys Val
        100                 105                 110

Met Pro Met Gln Glu Trp Trp Ala Pro Pro Ser Trp Tyr Ile Lys Ala
    115                 120                 125

Cys Ala Ile Ile Ala Ala Thr Leu Tyr Thr Asp Tyr Leu Trp Ile Ala
130                 135                 140

Ser Gly Pro Thr Ile Pro Leu Ala Ile Val Leu Gly Leu Leu Tyr Ala
145                 150                 155                 160

Trp Ile Gly Leu Asn Ile Gln His Asp Ala Asn His Gly Ser Val Ser
                165                 170                 175

Arg Asn Pro Met Val Asn Arg Leu Phe Gly Tyr Ser Gln Asp Trp Ile
            180                 185                 190

Gly Gly Ser Arg Met Leu Trp Ile Arg Gln His Val Val Gly His His
        195                 200                 205

Thr His Cys Asn Arg Ile Gln His Asp Pro Asp Val Lys Gly Gly Gly
    210                 215                 220

Val Ile Thr Leu Ser Arg Thr Ser Leu Pro Lys Glu Phe His His Ile
225                 230                 235                 240

Gln Gln Leu Tyr Phe Leu Pro Leu Ile Gln Leu Tyr Gly Phe Gln Trp
                245                 250                 255

Val Phe Leu Asp Leu His Asp Leu Ile Glu Met Lys Tyr Lys Gly Glu
            260                 265                 270

Pro Leu Pro Pro Leu Tyr Arg Lys Glu Phe Ala Ile Ala Ile Gly Leu
        275                 280                 285

Arg Val Gly Phe Trp Ile Arg Lys Phe Val Val Pro Phe Ala Leu His
    290                 295                 300

Phe Ser Trp Tyr Thr Leu Leu Cys Ile Tyr Leu Trp Met Ala Ser Ala
305                 310                 315                 320

Ala Phe Tyr Leu Gly Phe Phe Phe Ile Leu Ser His Ile Phe Val Gly
                325                 330                 335

Ala Lys Ser Leu Pro Glu Asp Ala Lys Asn Ile Asp Trp Ala Arg His
            340                 345                 350

Gln Ile Glu Ser Ser Ser Asn Val Cys Gly Glu Lys Leu Gly His Ser
        355                 360                 365

Asn Gly Gly Leu Asn Tyr Gln Ile Glu His His Leu Phe Pro Arg Met
    370                 375                 380

Ser His Ala His Tyr Ala Pro Ile Gln Pro Val Val Gln Lys Ile Cys
385                 390                 395                 400

Glu Glu Asn Gly Ile Asn Tyr Lys Lys Phe Gly Thr Ile Leu Ser Asn
                405                 410                 415

Leu Asp Ser Thr Phe Arg Gln Val Lys Ala Leu Gly Ser Arg Ala Thr
            420                 425                 430

Glu Phe Met Glu Gly Leu
        435

<210> SEQ ID NO 137
<211> LENGTH: 439
<212> TYPE: PRT
<213> ORGANISM: Artificial
<220> FEATURE:
<223> OTHER INFORMATION: delta-4 desaturase 89.7% sequence identity to

SEQ ID NO 79

<400> SEQUENCE: 137

Met Pro Pro His Ala Arg Ser Glu Val Ser Asp Pro Glu Leu Ser Asp
1               5                   10                  15

Leu Met Lys His Phe Thr Arg Glu Arg Ile Leu Asn His Asn Asn Asp
            20                  25                  30

Lys Tyr Cys Ile Leu Gly Asp Gly Val Tyr Asp Cys Val Asn Phe Arg
        35                  40                  45

Asp Lys His Pro Gly Gly Asp Phe Val Asp Phe Phe Pro Gly Gln Asp
    50                  55                  60

Ala Thr Pro His Phe Phe Met Leu His Arg His Glu Ser Leu Pro Ser
65                  70                  75                  80

Val Leu Ala Glu Tyr Lys Val Gly Ser Val Ala Arg Asp Asp Ser Tyr
            85                  90                  95

Val Tyr His Asp Pro Leu Met Lys Gln Ile Cys Ser Ala Val Arg Lys
        100                 105                 110

Val Met Pro Met Gln Ser Trp Trp Ala Pro Pro Ser Trp Trp Ile Lys
    115                 120                 125

Ala Cys Ala Ile Leu Ala Ala Thr Leu Tyr Thr Asp Tyr Leu Trp Ile
130                 135                 140

Ala Ser Gly Pro Thr Ile Pro Leu Ala Ile Val Leu Gly Leu Leu Tyr
145                 150                 155                 160

Ala Ala Ile Gly Leu Asn Ile Gln His Asp Ala Asn His Gly Ser Val
            165                 170                 175

Ser Arg Asn Pro Met Val Asn Tyr Leu Phe Gly Tyr Ser Gln Asp Trp
        180                 185                 190

Ile Gly Gly Ser Arg Met Leu Trp Ile Arg Gln His Val Val Gly His
    195                 200                 205

His Thr His Thr Asn Asp His Asp His Asp Pro Asp Val Lys Gly Gly
210                 215                 220

Ser Val Ile Thr Leu Ser Arg Tyr Ser Leu Pro Lys Glu Phe His His
225                 230                 235                 240

Ile Gln Gln Ile Tyr Phe Leu Pro Leu Ile Gln Leu Tyr Gly Phe Gln
            245                 250                 255

Trp Val Phe Leu Asp Ala His Asp Leu Ile Glu Met Lys Tyr Lys Gly
        260                 265                 270

Glu Lys Ile Pro Glu Ser Tyr Arg Lys Glu Arg Ala Ile Ala Ile Gly
    275                 280                 285

Cys Arg Val Phe Phe Phe Ile Arg Lys Phe Val Leu Pro Phe Ala Leu
290                 295                 300

His Phe Ser Trp Tyr Thr Leu Leu Cys Thr Cys Leu Trp Met Ala Ile
305                 310                 315                 320

Ala Ala Leu Tyr Leu Gly Phe Phe Phe Ile Leu Ser His Ile Phe Val
            325                 330                 335

Gly Ala Lys Ser Ile Gly Glu Asp Ala Asn Ile Asp Trp Gly Arg Arg
        340                 345                 350

Gln Ile Glu Ser Ser Ser Asn Val Cys Gly Glu Lys Leu Gly Ile Ile
    355                 360                 365

Asn Gly Gly Leu Asn Tyr Gln Ile Glu His His Leu Phe Pro Arg Met
370                 375                 380

Ser His Ala His Tyr Ser Lys Ile Gln Pro Val Val Gln Lys Val Cys
385                 390                 395                 400

```
Glu Glu Asn Gly Val Asn Tyr Lys Lys Phe Gly Thr Ile Gly Ser Asn
                405                 410                 415

Leu Asp Ser Thr Phe Arg His Leu Lys Ala Leu Gly Ser Val Ala Val
            420                 425                 430

Tyr Glu Phe Met Glu Gly Pro
        435

<210> SEQ ID NO 138
<211> LENGTH: 439
<212> TYPE: PRT
<213> ORGANISM: Artificial
<220> FEATURE:
<223> OTHER INFORMATION: delta-4 desaturase 89.7% sequence identity to
      SEQ ID NO 79

<400> SEQUENCE: 138

Met Pro Pro His Ala Arg Thr Lys Val Gly Asp Pro Glu Leu Ser Asp
1               5                   10                  15

Leu Met Glu His Phe Thr Arg Glu Glu Ile Leu Gly His Glu Asn Asp
            20                  25                  30

Lys Tyr Cys Ile Leu Glu Asp Gly Val Tyr Asp Leu Asn Asn Phe Arg
        35                  40                  45

Asp Lys His Pro Gly Gly Asp Val Leu Asp Ile Phe Pro Gly Gln Asp
    50                  55                  60

Ala Thr Pro His Phe Trp Met Leu His Gln Arg Val Ser Pro Pro Ser
65                  70                  75                  80

Val Leu Ala Glu Tyr Lys Val Gly Ser Val Ala Arg Asp Asp Ser Tyr
                85                  90                  95

Val Tyr His Thr Pro Leu Tyr Lys Gln Ile Lys Ser Ala Val Arg Lys
            100                 105                 110

Val Ile Pro Met Gly Glu Trp Trp Ala Pro Pro Ser Trp Trp Ile Lys
        115                 120                 125

Ala Cys Ala Ile Leu Ala Ala Thr Leu Tyr Thr Asp Tyr Tyr Trp Ile
    130                 135                 140

Ala Ser Gly Pro Thr Ile Pro Leu Ala Ile Val Ile Gly Leu Leu Tyr
145                 150                 155                 160

Ala Ala Ile Gly Leu Asn Ile Gln His Asp Ala Asn His Gly Ser Val
                165                 170                 175

Ser Arg Asn Pro Met Val Asn Arg Leu Phe Gly Tyr Ser Gln Asp Trp
            180                 185                 190

Ile Gly Gly Ser Arg Met Leu Trp Ile Arg Gln His Val Val Gly His
        195                 200                 205

His Thr His Cys Asn Arg His Gln His Asp Pro Asp Val Lys Gly Gly
    210                 215                 220

Ser Val Ile Thr Leu Ser Arg Thr Ser Leu Trp Met Pro Phe His His
225                 230                 235                 240

Ile Gln Gln Ile Tyr Phe Leu Pro Gly Glu Gln Leu Leu Gly Phe Gln
                245                 250                 255

Trp Val Phe Leu Gly Leu His Asp Leu Ile Glu Met Lys Tyr Lys Gly
            260                 265                 270

Glu Lys Leu Pro Glu Ser Ala Arg Lys Glu Arg Asn Ile Ala Ile Gly
        275                 280                 285

Leu Arg Ile Phe Phe Phe Ile Arg Lys Phe Val Val Pro Phe Ala Leu
    290                 295                 300

His Phe Ser Trp His Thr Leu Leu Cys Thr Tyr Leu Trp Met Ala Ser
305                 310                 315                 320
```

Ala Ala Leu Tyr Leu Gly Phe Phe Ile Leu Ser His Ile Phe Val
            325                 330                 335

Gly Ala Gly Ser Leu Pro Pro Glu Ala Lys Asn Ile Asp Trp Gly Arg
            340                 345                 350

His Gln Ile Glu Ser Ser Ser Asn Val Gly Gly Glu Lys Leu Gly Ile
            355                 360                 365

Leu Asn Gly Gly Leu Asn Phe Gln Ile Glu His His Leu Phe Pro Arg
            370                 375                 380

Met Ser His Ala His Tyr Ser Lys Ile Gln Pro Val Val Gln Lys Val
385                 390                 395                 400

Cys Glu Glu Asn Gly Val Asn Tyr Lys Lys Phe Pro Thr Ile Leu Ser
            405                 410                 415

Asn Leu Asp Ser Thr Phe Lys Gln Ile Gly Ala Leu Gly Ser Val Ala
            420                 425                 430

Val Glu Phe Leu Glu Gly Leu
            435

<210> SEQ ID NO 139
<211> LENGTH: 438
<212> TYPE: PRT
<213> ORGANISM: Artificial
<220> FEATURE:
<223> OTHER INFORMATION: delta-4 desaturase 89.7% sequence identity to
      SEQ ID NO 79

<400> SEQUENCE: 139

Met Pro Pro His Ser Arg Thr Lys Val Ser Asp Pro Glu Leu Ser Ala
1               5                   10                  15

Leu Met Lys His Phe Thr Arg Glu Lys Lys Leu Asn His Thr Asn Asp
            20                  25                  30

Asp Tyr Cys Ile Leu Gly Asp Gly Val Tyr Asp Leu Thr Ala Phe Arg
            35                  40                  45

Asp Lys His Pro Gly Gly Asp Val Leu Asp Phe Phe Pro Gly Gln Asp
            50                  55                  60

Ala Thr Pro His Phe Phe Met Leu His Gln Tyr Glu Ser Leu Pro Ala
65                  70                  75                  80

Val Leu Ala Glu Tyr Lys Val Gly Ser Ile Ala Arg Asp Asp Ser Tyr
            85                  90                  95

Val Tyr Tyr Thr Ala Leu Met Lys Gln Ile Lys Ser Ala Val Arg Ala
            100                 105                 110

Val Met Pro Met Gly Glu Trp Trp Ala Pro Pro Ser Trp Tyr Ile Lys
            115                 120                 125

Ala Cys Ala Ile Leu Ala Ala Thr Leu Tyr Thr Asp Tyr Leu Trp Ile
            130                 135                 140

Ala Ser Gly Pro Thr Ile Leu Leu Ala Ile Val Ser Gly Leu Leu Phe
145                 150                 155                 160

Ala Ala Ile Gly Leu Asn Ile Gln His Asp Ala Asn His Gly Ser Val
            165                 170                 175

Ser Arg Asn Pro Met Val Asn Arg Leu Phe Gly Tyr Ser Gln Asp Trp
            180                 185                 190

Ile Gly Gly Ser Arg Met Leu Trp Ile Arg Glu His Val Val Asn His
            195                 200                 205

His Leu His Thr Asn Arg His Gln His Asp Pro Asp Leu Lys Gly Gly
            210                 215                 220

Ser Val Ile Thr Leu Ser Arg Thr Asp Leu Pro Lys Pro Phe His His

```
                225                 230                 235                 240
Ile Gln Gln Tyr Tyr Phe Leu Pro Leu Glu Gln Leu Tyr Gly Phe Gln
                    245                 250                 255

Trp Val Phe Leu Gly Leu His Asp Leu Ile Glu Trp Lys Tyr Lys Gly
                260                 265                 270

Glu Pro Leu Pro Glu Ser Tyr Arg Lys Glu Arg Asn Ile Ala Val Gly
            275                 280                 285

Leu Arg Val Phe Phe Phe Ile Arg Phe Phe Ile Ile Pro Phe Trp Leu
        290                 295                 300

Glu Phe Ser Trp Tyr Thr Leu Leu Cys Thr Tyr Leu Trp Met Ala Ile
305                 310                 315                 320

Ala Ala Leu Tyr Leu Gly Phe Phe Phe Ile Leu Ser His Ile Phe Val
                325                 330                 335

Gly Ala Lys Ser Leu Pro Glu Asp Ala Asn Ile Asp Trp Ala Arg Arg
            340                 345                 350

Gln Ile Glu Ser Ser Asn Val Cys Gly Glu Lys Leu Gly His Ser
        355                 360                 365

Asn Gly Gly Leu Asn Phe Gln Ile Glu His His Leu Phe Pro Arg Met
    370                 375                 380

Ser His Ala His Tyr Ser Lys Ile Gln Pro Val Val Gln Lys Val Cys
385                 390                 395                 400

Glu Glu Asn Gly Val Asn Tyr Lys Lys Phe Gly Thr Ile Gly Ser Asn
                405                 410                 415

Leu Asp Ser Thr Phe Arg His Val Lys Ala Leu Gly Ser Val Ala Val
            420                 425                 430

Glu Phe Met Glu Gly Pro
        435

<210> SEQ ID NO 140
<211> LENGTH: 438
<212> TYPE: PRT
<213> ORGANISM: Artificial
<220> FEATURE:
<223> OTHER INFORMATION: delta-4 desaturase 89.4% sequence identity to
      SEQ ID NO 79

<400> SEQUENCE: 140

Met Pro Pro His Ser Arg Thr Lys Val Ser Asp Pro Glu Leu Ser Asp
1               5                   10                  15

Met Lys His Phe Thr Arg Glu Glu Ile Leu Asn His Thr Arg Asp Lys
                20                  25                  30

Tyr Cys Ile Leu Glu Asp Gly Val Tyr Asp Ala Thr Ala Phe Arg Asp
            35                  40                  45

Lys His Pro Gly Gly Asp Tyr Ile Asp Phe Phe Pro Gly Gln Asp Ala
        50                  55                  60

Thr Pro His Phe Tyr Met Leu His Arg Tyr Glu Ser Leu Pro Ser Val
65                  70                  75                  80

Leu Ala Glu Tyr Lys Val Gly Ser Val Ala Arg Asp Asp Ser Tyr Val
                85                  90                  95

Gln His Asp Glu Leu Met Leu Gln Leu Lys Ala Ala Val Arg Ala Val
            100                 105                 110

Met Pro Met Gln Glu Trp Trp Ala Pro Pro Ser Trp Tyr Ile Lys Ala
        115                 120                 125

Cys Ala Ile Leu Ala Ala Thr Leu Tyr Leu Asp Tyr Leu Trp Ile Ala
    130                 135                 140
```

-continued

```
Ser Gly Pro Thr Ile Pro Leu Gly Ile Val Leu Gly Leu Leu Tyr Ala
145                 150                 155                 160

Ala Ile Gly Leu Asn Ile Gln His Asp Ala Asn His Gly Ser Val Ser
            165                 170                 175

Arg Asn Pro Val Val Asn Arg Leu Phe Gly Tyr Ser Gln Asp Trp Ile
        180                 185                 190

Gly Gly Ser Arg Met Leu Trp Leu Arg Gln His Val Gly His His
    195                 200                 205

Leu His Ser Asn Glu His Gln His Asp Pro Asp Ile Lys Gly Gly Ser
    210                 215                 220

Ala Ile Arg Leu Ser Pro Tyr Ser Leu Pro Lys Glu Trp His His Ile
225                 230                 235                 240

Gln Gln Leu Tyr Phe Leu Pro Gly Ile Gln Leu Gly Phe Gln Trp
                245                 250                 255

Val Phe Leu Gly Leu His Asp Leu Ile Glu Met Lys Tyr Lys Gly Glu
                260                 265                 270

Lys Leu Pro Pro Ser Tyr Arg Lys Glu Arg Asn Ile Ala Ile Gly Cys
            275                 280                 285

Arg Val Phe Phe Trp Ile Arg Lys Phe Val Pro Phe Ala Leu His
    290                 295                 300

Phe Ser Trp Tyr Thr Leu Leu Cys Thr Tyr Leu Trp Met Ala Ile Gly
305                 310                 315                 320

Ala Leu Tyr Leu Gly Phe Phe Val Leu Ser His Ile Phe Val Gly
                325                 330                 335

Ala Lys Ser Leu Pro Glu Asp Ala Lys Asn Val Asp Trp Ala Arg His
            340                 345                 350

Gln Ile Glu Ser Ser Ser Asn Val Cys Gly Glu Lys Leu Gly Ile Ser
        355                 360                 365

Asn Gly Gly Leu Asn Tyr Gln Ile Glu His His Leu Phe Pro Arg Met
    370                 375                 380

Ser His Ala His Tyr Ser Lys Ile Gln Pro Val Val Arg Lys Val Cys
385                 390                 395                 400

Glu Glu Asn Gly Ile Asn Tyr Lys His Phe Pro Thr Ile Leu Ser Asn
                405                 410                 415

Leu Asp Ser Thr Phe Arg Gln Val Lys Ala Leu Gly Ser Val Pro Thr
            420                 425                 430

Glu Phe Met Glu Gly Leu
        435

<210> SEQ ID NO 141
<211> LENGTH: 438
<212> TYPE: PRT
<213> ORGANISM: Artificial
<220> FEATURE:
<223> OTHER INFORMATION: delta-4 desaturase 89.4% sequence identity to
      SEQ ID NO 79

<400> SEQUENCE: 141

Met Pro Pro His Ser Arg Thr Lys Val Ser Asp Ala Glu Leu Ser Asp
1               5                   10                  15

Leu Met Lys His Phe Thr Arg Glu Glu Ile Leu Asn Asp Thr Asn Asp
            20                  25                  30

Lys Tyr Cys Ile Leu Glu Asp Gly Val Tyr Asp Leu Thr Asn Phe Arg
        35                  40                  45

Asp Lys His Pro Gly Gly Asp Val Leu Asp Phe Phe Pro Gly Gln Asp
    50                  55                  60
```

```
Ala Thr Pro Gly Phe Trp Met Phe His Gln Tyr Ala Trp Leu Pro Ser
 65                  70                  75                  80

Val Leu Ala Glu Tyr Lys Val Gly Ser Ile Ala Arg Asp Asp Ser Tyr
                 85                  90                  95

Val Gln Tyr Thr Pro Leu Met Leu Gln Ile Lys Cys Ala Val Arg Lys
            100                 105                 110

Val Leu Pro Met Gln Ser Trp Trp Ala Pro Pro Ser Trp Tyr Ile Lys
        115                 120                 125

Ala Cys Ala Ile Leu Ile Ala Thr Leu Tyr Thr Asp Tyr Leu Trp Ile
    130                 135                 140

Ala Ser Gly Pro Thr Ile Pro Leu Ala Ile Val Ile Gly Leu Leu Tyr
145                 150                 155                 160

Ala Ala Ile Gly Leu Asn Ile Gln His Asp Ala Asn His Gly Ser Val
                165                 170                 175

Ser Arg Asn Pro Met Val Asn Arg Leu Phe Gly Tyr Ser Gln Asp Trp
            180                 185                 190

Ile Gly Gly Ser Arg Met Leu Trp Ile Arg Glu His Val Val Gly His
        195                 200                 205

His Thr His Cys Asn Arg Ile Gln His Asp Pro Asp Ile Lys Gly Gly
    210                 215                 220

Ser Val Ile Thr Leu Ser Pro Ser Ser Leu Trp Leu Glu Trp His His
225                 230                 235                 240

Ile Gln Gln Tyr Tyr Phe Leu Pro Leu Glu Gln Leu Leu Gly Phe Gln
                245                 250                 255

Trp Ile Phe Leu Gly Leu His Asp Leu Ile Glu Trp Lys Tyr Glu Gly
            260                 265                 270

Glu Lys Ile Pro Glu Ser Tyr Arg Lys Leu Arg Asn Ile Ala Ile Gly
        275                 280                 285

Cys Arg Val Phe Phe Phe Ile Arg Lys Phe Ala Ile Pro Phe Ala Leu
    290                 295                 300

His Phe Ser Trp Tyr Thr Leu Leu Cys Thr Tyr Leu Trp Met Ala Thr
305                 310                 315                 320

Ala Ala Leu Tyr Leu Gly Phe Phe Ile Leu Ser His Ile Phe Val
                325                 330                 335

Gly Ala Lys Ser Leu Pro Glu Asp Ala Asn Ile Asp Trp Ala Arg Arg
            340                 345                 350

Gln Ile Glu Ser Ser Ser Asn Val Cys Gly Glu Trp Leu Gly Ile Ser
        355                 360                 365

Asn Gly Gly Leu Asn Tyr Gln Ile Glu His His Leu Phe Pro Arg Met
    370                 375                 380

Ser His Ala His Tyr Ser Lys Ile Gln Pro Val Val Gln Lys Val Cys
385                 390                 395                 400

Glu Glu Asn Gly Val Asn Tyr Lys Lys Phe Pro Thr Ile Leu Ser Asn
                405                 410                 415

Leu Gly Ser Thr Phe Gln His Val Lys Ala Leu Gly Ser Val Ala Val
            420                 425                 430

Glu Phe Met Glu Gly Leu
        435

<210> SEQ ID NO 142
<211> LENGTH: 439
<212> TYPE: PRT
<213> ORGANISM: Artificial
<220> FEATURE:
```

<223> OTHER INFORMATION: delta-4 desaturase 89.4% sequence identity to SEQ ID NO 79

<400> SEQUENCE: 142

| | | | | | | | | | | | | | | |
|---|---|---|---|---|---|---|---|---|---|---|---|---|---|---|
| Met | Pro | Pro | His | Ser | Arg | Thr | Lys | Val | Gly | Ser | Asp | Pro | Glu | Leu | Arg |
| 1 | | | | 5 | | | | | 10 | | | | | 15 | |
| Asp | Leu | Met | Lys | His | Phe | Thr | Arg | Glu | Glu | Ile | Leu | Asn | His | Thr | Arg |
| | | | 20 | | | | | 25 | | | | | 30 | | |
| Asp | Lys | Tyr | Cys | Ile | Leu | Glu | Asp | Gly | Val | Tyr | Asp | Leu | Thr | Asn | Phe |
| | | | 35 | | | | | 40 | | | | | 45 | | |
| Arg | Asp | Lys | His | Pro | Gly | Gly | Asp | Val | Val | Asp | Phe | Phe | Pro | Gly | Gln |
| | 50 | | | | | 55 | | | | | 60 | | | | |
| Asp | Ala | Thr | Pro | Gly | Phe | Tyr | Met | Leu | His | Gln | Tyr | Glu | Ser | Leu | Pro |
| 65 | | | | | 70 | | | | | 75 | | | | | 80 |
| Ser | Val | Leu | Ala | Lys | Tyr | Phe | Val | Gly | Ser | Val | Ala | Arg | Asp | Asp | Ser |
| | | | | 85 | | | | | 90 | | | | | 95 | |
| Tyr | Val | Tyr | His | Asp | Pro | Leu | Gln | Lys | Gln | Ile | Lys | Ser | Ala | Val | Arg |
| | | | 100 | | | | | 105 | | | | | 110 | | |
| Lys | Ile | Met | Pro | Arg | Gln | Glu | Trp | Trp | Ala | Pro | Pro | Ser | Trp | Trp | Ile |
| | | | 115 | | | | | 120 | | | | | 125 | | |
| Lys | Ala | Cys | Ala | Ile | Leu | Ala | Ala | Thr | Leu | Tyr | Leu | Asp | Tyr | Leu | Trp |
| | 130 | | | | | 135 | | | | | 140 | | | | |
| Ile | Ala | Lys | Gly | Pro | Thr | Ile | Phe | Leu | Ala | Ile | Ser | Gly | Leu | Leu |
| 145 | | | | | 150 | | | | | 155 | | | | | 160 |
| Tyr | Ala | Ala | Ile | Gly | Leu | Asn | Ile | Gln | His | Asp | Ala | Asn | His | Gly | Ser |
| | | | | 165 | | | | | 170 | | | | | 175 | |
| Val | Ser | Arg | Asn | Pro | Met | Val | Asn | Arg | Leu | Phe | Gly | Tyr | Ser | Gln | Asp |
| | | | 180 | | | | | 185 | | | | | 190 | | |
| Trp | Ile | Gly | Gly | Ser | Arg | Met | Leu | Trp | Leu | Arg | Gln | His | Val | Val | Gly |
| | | | 195 | | | | | 200 | | | | | 205 | | |
| His | His | Thr | His | Cys | Asn | Arg | His | Gln | His | Asp | Pro | Asp | Val | Lys | Gly |
| | 210 | | | | | 215 | | | | | 220 | | | | |
| Gly | Ser | Val | Ile | Lys | Leu | Lys | Pro | Thr | Ser | Leu | Trp | Leu | Glu | Phe | His |
| 225 | | | | | 230 | | | | | 235 | | | | | 240 |
| His | Ile | Gln | Gln | Tyr | Tyr | Phe | Leu | Pro | Leu | Asp | Gln | Leu | Leu | Gly | Phe |
| | | | | 245 | | | | | 250 | | | | | 255 | |
| Gln | Trp | Ile | Phe | Leu | Gly | Leu | His | Asp | Leu | Ile | Glu | Met | Arg | Tyr | Lys |
| | | | 260 | | | | | 265 | | | | | 270 | | |
| Gly | Glu | Lys | Leu | Pro | Pro | Ser | Tyr | Arg | Lys | Glu | Arg | Asn | Pro | Ala | Ile |
| | | | 275 | | | | | 280 | | | | | 285 | | |
| Gly | Cys | Arg | Val | Phe | Phe | Ile | Arg | Lys | Phe | Val | Val | Pro | Phe | Ala |
| | 290 | | | | | 295 | | | | | 300 | | | | |
| Leu | His | Phe | Ser | Trp | Tyr | Thr | Leu | Leu | Cys | Thr | Tyr | Leu | Trp | Val | Ala |
| 305 | | | | | 310 | | | | | 315 | | | | | 320 |
| Ile | Gly | Ala | Leu | Tyr | Leu | Gly | Phe | Phe | Phe | Ile | Leu | Ser | His | Ile | Phe |
| | | | | 325 | | | | | 330 | | | | | 335 | |
| Val | Gly | Ala | Lys | Ser | Leu | Pro | Glu | Asp | Ala | Asn | Ile | Asp | Trp | Ala | Arg |
| | | | 340 | | | | | 345 | | | | | 350 | | |
| His | Gln | Ile | Glu | Ser | Ser | Asn | Val | Gly | Gly | Asp | Lys | Leu | Gly | Tyr |
| | | | 355 | | | | | 360 | | | | | 365 | | |
| Ser | Asn | Gly | Gly | Leu | Asn | Tyr | Gln | Ile | Glu | His | His | Leu | Phe | Pro | Arg |
| | 370 | | | | | 375 | | | | | 380 | | | | |
| Met | Ser | His | Ala | His | Tyr | Ser | Lys | Ile | Gln | Pro | Val | Val | Gln | Arg | Val |
| 385 | | | | | 390 | | | | | 395 | | | | | 400 |

Cys Glu Glu Asn Gly Ile Asn Tyr Lys Lys Phe Gly Thr Ile Leu Ser
            405                 410                 415

Asn Leu Asp Ser Ile Phe Gln Gln Val Lys Ala Leu Ala Ser Val Pro
            420                 425                 430

Val Glu Tyr Met Glu Gly Leu
            435

<210> SEQ ID NO 143
<211> LENGTH: 440
<212> TYPE: PRT
<213> ORGANISM: Artificial
<220> FEATURE:
<223> OTHER INFORMATION: delta-4 desaturase 89.4% sequence identity to
      SEQ ID NO 79

<400> SEQUENCE: 143

Met Pro Pro His Ala Arg Thr Lys Val Ser Asp Pro Glu Leu Ser Asp
1               5                   10                  15

Ala Lys His Phe Thr Arg Glu Glu Ile Leu Asn His Thr Asn Asp Lys
            20                  25                  30

Leu Cys Ile Leu Glu Asp Gly Val Tyr Asp Ala Pro Asn Phe Arg Asp
        35                  40                  45

Lys His Pro Gly Gly Asp Val Leu Asp Phe Phe Pro Gly Gln Asp Ala
    50                  55                  60

Thr Pro His Phe Tyr Met Leu His Gln Tyr Glu Trp Pro Pro Ser Val
65                  70                  75                  80

Leu Ala Glu Tyr Lys Val Gly Ser Val Ala Arg Asp Asp Ser Tyr Thr
                85                  90                  95

Gln Ala Thr Pro Leu Met Lys Gln Ile Lys Ser Ala Val Arg Lys Val
            100                 105                 110

Met Pro Met Gly Glu Trp Trp Ala Pro Pro Ser Trp Tyr Ile Lys Ala
        115                 120                 125

Cys Ala Leu Leu Ala Ala Thr Leu His Thr Asp Tyr Leu Trp Ile Ala
    130                 135                 140

Ser Gly Pro Thr Ile Pro Leu Ala Ile Val Ser Gly Leu Leu Tyr Ala
145                 150                 155                 160

Ala Ile Gly Leu Asn Ile Gln His Asp Ala Asn His Gly Ser Val Ser
                165                 170                 175

Arg Asn Pro Met Val Asn Arg Leu Phe Gly Tyr Ser Gln Asp Trp Ile
            180                 185                 190

Gly Gly Ser Met Met Leu Trp Ile Arg Gln His Val Val Gly His His
        195                 200                 205

Thr His Ser Asn Arg His Gln His Asp Pro Asp Val Lys Gly Gly Ser
    210                 215                 220

Val Ile Lys Leu Ser Arg Tyr Ser Leu Pro Leu Glu Phe His His Ile
225                 230                 235                 240

Gln Gln Ile Tyr Phe Leu Pro Gly Asp Gln Leu Tyr Gly Phe Gln Trp
                245                 250                 255

Val Phe Leu Gly Leu His Asp Leu Ile Glu Met Lys Tyr Lys Gly Glu
            260                 265                 270

Lys Ile Ser Glu Ser Tyr Arg Lys Glu Arg Asn Pro Ala Ile Gly Cys
        275                 280                 285

Lys Val Phe Phe Phe Ile Arg Lys Phe Val Pro Phe Trp Leu His
    290                 295                 300

Phe Ser Trp Tyr Thr Leu Leu Cys Val Cys Leu Trp Met Ala Thr Ala

```
                305                 310                 315                 320
Ala Phe Tyr Leu Gly Phe Phe Ile Leu Ser His Asn Phe Val Gly
                    325                 330                 335

Val Lys Ser Leu Gly Pro Asp Ala Lys Asn Val Asp Trp Ala Arg His
            340                 345                 350

Gln Ile Glu Ser Ser Asn Val Cys Gly Glu Trp Leu Gly Ile Ser
            355                 360                 365

Asn Gly Gly Leu Asn Tyr Gln Ile Glu His His Leu Phe Pro Arg Met
    370                 375                 380

Asn His Ala His Tyr Ser Lys Ile Gln Pro Val Val Gln Lys Val Cys
385                 390                 395                 400

Glu Glu Asn Gly Val Asn Tyr Lys Lys Phe Pro Thr Ile Leu Ser Asn
                405                 410                 415

Leu Gly Ser Thr Phe Arg Gln Val Lys Ala Leu Gly Ser Val Ala Val
                420                 425                 430

Tyr Asn Glu Phe Leu Ala Gly Leu
                435                 440

<210> SEQ ID NO 144
<211> LENGTH: 438
<212> TYPE: PRT
<213> ORGANISM: Artificial
<220> FEATURE:
<223> OTHER INFORMATION: delta-4 desaturase 89.4% sequence identity to
      SEQ ID NO 79

<400> SEQUENCE: 144

Met Pro Pro His Ser Ala Thr Lys Val Ser Asp Pro Glu Leu Ser Asp
1               5                   10                  15

Met Lys His Phe Thr Arg Glu Lys Ile Leu Asp His Thr Asn Asp Lys
            20                  25                  30

Tyr Cys Ile Leu Glu Asp Gly Val Tyr Asp Cys Pro Asn Phe Arg Asp
        35                  40                  45

Lys His Pro Gly Gly Asp Val Leu Asp Phe Phe Pro Gly Gln Asp Ala
    50                  55                  60

Thr Pro His Phe Phe Glu Tyr His Gln His Glu Trp Leu Pro Ser Val
65                  70                  75                  80

Leu Ala Glu Tyr Phe Val Gly Ser Val Asp Arg Asp Asp Ser Tyr Val
                85                  90                  95

Tyr His Thr Ser Leu Met Lys Gln Ile Lys Ala Ala Val Arg Gly Ile
            100                 105                 110

Met Pro Arg Gln Glu Trp Trp Ala Pro Pro Ser Trp Tyr Ile Lys Ala
        115                 120                 125

Cys Ala Ile Leu Ala Ala Thr Leu Tyr Thr Asp Tyr Leu Trp Ile Ala
    130                 135                 140

Ser Gly Pro Thr Ile Pro Leu Ala Ile Val Ser Gly Leu Leu Tyr Ala
145                 150                 155                 160

Ala Ile Gly Leu Asn Ile Gln His Asp Ala Asn His Gly Ser Ile Ser
                165                 170                 175

Arg Asn Pro Met Val Asn Arg Leu Phe Gly Tyr Ser Gln Asp Trp Ile
            180                 185                 190

Gly Gly Ser Arg Met Leu Trp Ile Arg Gln His Val Val Gly His His
        195                 200                 205

Thr His Cys Asn Arg His Asp His Asp Pro Asp Leu Lys Gly Gly Ser
    210                 215                 220
```

```
Val Ile Lys Leu Ser Arg Tyr Asp Leu Pro Lys Glu Phe His His Ile
225                 230                 235                 240

Gln Gln Tyr Tyr Phe Leu Pro Leu Ile Gln Leu Leu Gly Phe Gln Trp
                245                 250                 255

Val Phe Leu Asp Leu His Asp Leu Ile Glu Trp Lys Tyr Lys Gly Glu
            260                 265                 270

Lys Leu Pro Glu Ser Cys Arg Pro Leu Arg Asn Ile Ala Ile Gly Leu
        275                 280                 285

Arg Ile Phe Phe Trp Ile Arg Lys Phe Val Val Pro Phe Ala Leu His
    290                 295                 300

Phe Ser Trp Tyr Thr Leu Leu Cys Thr Cys Leu Trp Met Ala Thr Ala
305                 310                 315                 320

Ala Leu Tyr Leu Cys Phe Phe Phe Ile Leu Ser His Ile Phe Val Gly
                325                 330                 335

Ile Lys Ser Leu Pro Glu Asp Ala Lys Asn Ile Asp Trp Ala Arg His
            340                 345                 350

Gln Ile Glu Asn Ser Ser Asn Val Cys Gly Lys Leu Gly Ile Ser
        355                 360                 365

Asn Gly Gly Leu Asn Tyr Gln Ile Glu His His Leu Phe Pro Arg Met
    370                 375                 380

Ser His Ala His Tyr Ser Lys Ile Gln Pro Val Val Gln Lys Val Cys
385                 390                 395                 400

Glu Glu Asn Gly Val Asn Tyr Lys Lys Phe Gly Thr Ile Leu Ser Asn
                405                 410                 415

Leu Asp Ser Thr Phe Lys Gln Leu Gly Ala Leu Gly Ser Arg Ala Thr
            420                 425                 430

Glu Phe Met Ala Gly Leu
        435

<210> SEQ ID NO 145
<211> LENGTH: 439
<212> TYPE: PRT
<213> ORGANISM: Artificial
<220> FEATURE:
<223> OTHER INFORMATION: delta-4 desaturase 89.4% sequence identity to
      SEQ ID NO 79

<400> SEQUENCE: 145

Met Pro Pro His Ser Arg Thr Lys Val Ser Asp Pro Glu Leu Lys
1               5                   10                  15

Asp Leu Met Lys His Phe Ser Tyr Glu Glu Ile Leu Asn Asp Thr Asn
            20                  25                  30

Asp Lys Tyr Cys Ile Leu Gly Asp Gly Val Tyr Asp Ala Thr Asn Phe
        35                  40                  45

Arg Asp Lys His Pro Gly Gly Asp Val Leu Asp Ile Phe Gly Gly Arg
    50                  55                  60

Asp Ala Thr Pro His Phe Tyr Glu Leu His Gln Tyr Glu Ser Leu Pro
65                  70                  75                  80

Ser Val Leu Ala Glu Tyr Lys Val Gly Ser Val Asp Arg Asp Ser
                85                  90                  95

Tyr Val Tyr His Asp Pro Leu Met Leu Gln Ile Lys Ser Ala Val Arg
            100                 105                 110

Lys Val Met Pro Met Gln Glu Trp Trp Ala Pro Pro Ser Trp Tyr Ile
        115                 120                 125

Lys Ala Cys Ala Ile Leu Val Ala Thr Leu Tyr Thr Asp Tyr Leu Met
    130                 135                 140
```

Ile Ala Ser Gly Pro Thr Ile Pro Leu Ala Ile Val Leu Gly Leu Leu
145                 150                 155                 160

Tyr Ala Ala Ile Gly Leu Asn Ile Gln His Asp Ala Asn His Gly Ser
                165                 170                 175

Ile Ser Arg Asn Pro Met Val Asn Arg Leu Phe Gly Tyr Ser Gln Asp
            180                 185                 190

Trp Ile Gly Gly Ser Arg Met Leu Trp Ile Arg Glu His Val Val Gly
        195                 200                 205

His His Thr His Cys Asn Asp His Gln His Asp Pro Asp Ile Lys Gly
    210                 215                 220

Gly Ser Ala Ile Thr Leu Ser Arg Tyr Ser Leu Pro Lys Glu Trp His
225                 230                 235                 240

His Ile Gln Gln Tyr Tyr Phe Leu Pro Leu Ile Ala Leu Leu Gly Phe
                245                 250                 255

Gln Trp Val Phe Leu Gly Leu His Asp Leu Ile Glu Trp Lys Tyr Lys
            260                 265                 270

Gly Glu Lys Ile Pro Glu Ser Tyr Arg Pro Glu Arg Asn Ile Ala Ile
        275                 280                 285

Gly Leu Arg Val Phe Phe Phe Ile Arg Lys Phe Ala Leu Pro Phe Ala
    290                 295                 300

Leu His Phe Ser Trp His Thr Leu Ile Cys Thr Tyr Leu Trp Met Ala
305                 310                 315                 320

Ile Gly Ala Phe Tyr Leu Gly Phe Phe Phe Ile Leu Ser His Ile Phe
                325                 330                 335

Val Gly Ile Lys Ser Leu Pro Glu Asp Ala Asn Val Asp Trp Ala Arg
            340                 345                 350

His Gln Ile Glu Ser Ser Ser Asn Val Cys Gly Glu Lys Leu Gly His
        355                 360                 365

Ser Asn Gly Gly Leu Asn Tyr Gln Ile Glu His His Leu Phe Pro Arg
    370                 375                 380

Met Ser His Ala His Tyr Ser Lys Ile Gln Pro Val Val Arg Lys Val
385                 390                 395                 400

Cys Glu Asp Asn Gly Val Asn Tyr Lys Lys Phe Pro Thr Ile Leu Ser
                405                 410                 415

Asn Leu Asp Ser Met Phe Arg Gln Val Lys Ala Leu Gly Ser Arg Ala
            420                 425                 430

Thr Glu Phe Met Glu Gly Leu
        435

<210> SEQ ID NO 146
<211> LENGTH: 439
<212> TYPE: PRT
<213> ORGANISM: Artificial
<220> FEATURE:
<223> OTHER INFORMATION: delta-4 desaturase 89.4% sequence identity to
      SEQ ID NO 79

<400> SEQUENCE: 146

Met Pro Pro His Ser Gly Thr Lys Val Ser Asp Asp Pro Glu Leu Ser
1               5                   10                  15

Asp Leu Met Lys His Phe Thr Tyr Glu Glu Ile Ala Asn His Thr Asn
                20                  25                  30

Asp Asp Tyr Cys Ile Leu Glu Asp Gly Val Tyr Asp Leu Val Asn Phe
            35                  40                  45

Arg Asp Glu His Pro Gly Gly Asp Val Leu Asp Phe Phe Pro Gly Gln

```
            50                  55                  60
Asp Ala Thr Pro Gly Phe Tyr Met Leu His Arg Tyr Glu Ser Leu Pro
 65                  70                  75                  80

Ala Val Leu Ala Glu Tyr Lys Val Gly Ser Val Glu Arg Asp Asp Ser
                 85                  90                  95

Tyr Val His His Asp Pro Leu Met Lys Gln Ile Cys Ser Glu Val Arg
            100                 105                 110

Lys Ile Met Pro Met Gln Glu Trp Trp Ala Pro Pro Ser Trp Trp Ile
        115                 120                 125

Lys Ala Cys Ala Ile Leu Ala Ala Thr Leu Tyr Thr Asp Tyr Leu Trp
130                 135                 140

Ile Ala Ser Gly Pro Thr Ile Pro Leu Ala Ile Val Ser Gly Leu Leu
145                 150                 155                 160

Phe Ala Ala Ile Gly Leu Asn Ile Gln His Asp Ala Asn His Gly Ser
                165                 170                 175

Val Ser Arg Asn Pro Met Val Asn Arg Leu Phe Gly Tyr Ser Gln Asp
            180                 185                 190

Trp Ile Gly Gly Ser Arg Val Leu Trp Ile Arg Gln His Val Val Gly
        195                 200                 205

His His Thr His Cys Asn Glu Val Gln His Asp Pro Asp Val Lys Gly
210                 215                 220

Gly Gly Val Ile Thr Leu Ser Arg Thr Ser Leu Pro Lys Glu Phe His
225                 230                 235                 240

His Ile Gln Gln Tyr Tyr Phe Leu Pro Leu Asp Gln Leu Leu Gly Phe
                245                 250                 255

Gln Trp Val Phe Leu Asp Leu His Asp Leu Leu Glu Met Lys Trp Lys
            260                 265                 270

Gly Glu Lys Leu Pro Glu Ser Ala Arg Pro Glu Arg Asn Ile Ala Ile
        275                 280                 285

Gly Leu Lys Val Phe Phe Ile Arg Lys Val Val Pro Phe Trp
290                 295                 300

Leu Gln Phe Ser Trp His Thr Leu Leu Cys Thr Tyr Leu Trp Met Ala
305                 310                 315                 320

Thr Ala Ala Leu Tyr Leu Ala Phe Phe Ile Leu Ser His Ile Phe
                325                 330                 335

Val Gly Ala Lys Ser Ile Pro Pro Asp Ala Asn Ile Asp Trp Ala Arg
            340                 345                 350

His Gln Ile Glu Ser Ser Ser Asn Val Cys Gly Glu Lys Leu Gly Ile
        355                 360                 365

Ser Asn Gly Gly Leu Asn Tyr Gln Ile Glu His His Leu Phe Pro Arg
370                 375                 380

Met Ser His Ala His Tyr Ser Pro Ile Gln Pro Val Val Gln Lys Val
385                 390                 395                 400

Cys Glu Glu Asn Gly Val Asn Tyr Lys Lys Phe Pro Thr Ile Leu Ser
                405                 410                 415

Asn Leu Asp Ser Thr Phe Arg Gln Ile Lys Ala Leu Gly Ser Val Ala
            420                 425                 430

Thr Glu Phe Met Glu Gly Leu
        435

<210> SEQ ID NO 147
<211> LENGTH: 437
<212> TYPE: PRT
<213> ORGANISM: Artificial
```

<220> FEATURE:
<223> OTHER INFORMATION: delta-4 desaturase 89.2% sequence identity to
     SEQ ID NO 79

<400> SEQUENCE: 147

```
Met Pro Pro His Ser Arg Thr Lys Gly Ser Ala Pro Glu Leu Ser Asp
1               5                   10                  15

Met Lys His Phe Ser Arg Glu Arg Ile Leu Asn His Thr Asn Asp Asp
            20                  25                  30

Tyr Cys Ile Leu Glu Asp Gly Val Tyr Asp Leu Thr Asn Phe Arg Asp
        35                  40                  45

Lys His Pro Gly Gly Asp Phe Leu Asp Phe Phe Pro Gly Gln Asp Ala
    50                  55                  60

Thr Pro His Phe Tyr Met Phe His Gln Tyr Glu Trp Leu Pro Ser Val
65                  70                  75                  80

Leu Ala Glu Tyr Gly Val Gly Ser Val Ala Arg Asp Asp Ser Tyr Val
                85                  90                  95

Gln His Thr Pro Leu Met Lys Gln Leu Lys Ser Ala Val Arg Lys Val
            100                 105                 110

Met Pro Met Gln Glu Trp Trp Ala Pro Pro Ser Trp Tyr Ile Lys Ala
        115                 120                 125

Cys Ala Ile Leu Ala Ala Thr Leu Tyr Thr Asp Tyr Leu Trp Ile Ala
    130                 135                 140

Lys Gly Pro Thr Ile Pro Leu Ala Ile Val Ser Gly Leu Leu Phe Ala
145                 150                 155                 160

Ala Ile Gly Leu Asn Ile Gln His Asp Ala Asn His Gly Ser Ile Ser
                165                 170                 175

Arg Asn Pro Met Val Asn Arg Leu Phe Gly Tyr Ser Gln Asp Trp Ile
            180                 185                 190

Gly Gly Gly Arg Met Leu Trp Ile Arg Glu His Val Gly His His
        195                 200                 205

Thr His Cys Asn Glu Ile Gln His Asp Pro Asp Val Lys Gly Gly Ser
    210                 215                 220

Val Ile Thr Leu Ser Pro Tyr Asp Leu Trp Lys Glu Phe His His Ile
225                 230                 235                 240

Gln Gln Tyr Tyr Phe Leu Pro Leu Ile Gln Leu Tyr Gly Phe Lys Trp
                245                 250                 255

Val Phe Leu Gly Leu His Asp Leu Ile Glu Met Lys Tyr Lys Gly Glu
            260                 265                 270

Lys Leu Pro Glu Ser Ala Arg Lys Glu Arg Asn Ile Ala Val Gly Leu
        275                 280                 285

Arg Val Phe Phe Phe Ile Arg Lys Val Val Pro Phe Ala Leu His
    290                 295                 300

Phe Thr Trp Tyr Thr Ile Leu Cys Thr Tyr Leu Trp Met Ala Ile Ala
305                 310                 315                 320

Ala Leu Tyr Leu Gly Phe Phe Phe Ile Leu Ser His Ile Phe Val Gly
                325                 330                 335

Ala Lys Ser Leu Gly Pro Asp Ala Asn Val Asp Trp Ala Arg His Gln
            340                 345                 350

Ile Glu Ser Ser Ser Asn Val Gly Gly Glu Lys Leu His Ser Asn
        355                 360                 365

Gly Gly Leu Asn Phe Gln Ile Glu His His Leu Phe Pro Arg Met His
    370                 375                 380

His Ala His Tyr Ala Lys Ile Gln Pro Val Val Gln Lys Ile Cys Glu
```

```
                385                 390                 395                 400
Glu Asn Gly Val Asn Tyr Lys Lys Phe Gly Thr Ile Leu Ser Asn Leu
                    405                 410                 415

Asp Ser Met Phe Ser Gln Val Lys Ala Leu Gly Ala Val Ala Val Glu
                420                 425                 430

Phe Met Glu Gly Leu
        435

<210> SEQ ID NO 148
<211> LENGTH: 437
<212> TYPE: PRT
<213> ORGANISM: Artificial
<220> FEATURE:
<223> OTHER INFORMATION: delta-4 desaturase 89.2% sequence identity to
      SEQ ID NO 79

<400> SEQUENCE: 148

Met Pro Pro Tyr Ser Arg Thr Lys Val Ser Val Pro Glu Leu Ser Asp
1               5                   10                  15

Met Lys His Phe Thr Arg Glu Glu Ile Leu Asn His Thr Asn Asp Lys
                20                  25                  30

Leu Cys Ile Val Glu Asp Gly Val Tyr Asp Cys Thr Asn Phe Arg Asp
            35                  40                  45

Lys His Pro Gly Gly Asp Val Leu Asp Leu Phe Pro Gly Gln Asp Ala
        50                  55                  60

Thr Pro His Phe Tyr Met Phe His Gln Tyr Glu Trp Leu Pro Ser Val
65                  70                  75                  80

Leu Ala Arg Tyr Lys Val Gly Ser Val Ala Arg Asp Asp Ser Tyr Val
                85                  90                  95

Tyr His Thr Pro Leu Met Lys Gln Ile Lys Ser Asp Val Arg Lys Ile
                100                 105                 110

Leu Pro Met Gln Glu Trp Trp Ala Pro Pro Ser Trp Tyr Ile Lys Ala
            115                 120                 125

Cys Ala Ile Leu Val Ala Ala Leu Tyr Leu Asp Tyr Leu Trp Ile Ala
        130                 135                 140

Ser Gly Pro Thr Ile Phe Leu Ala Ile Val Ser Gly Leu Leu Tyr Ala
145                 150                 155                 160

Ala Ile Gly Leu Asn Ile Gln His Asp Ala Asn His Gly Ser Val Ser
                165                 170                 175

Arg Asn Pro Met Val Asn Arg Leu Phe Gly Tyr Ser Gln Asp Trp Ile
            180                 185                 190

Gly Gly Gly Met Met Leu Trp Ile Arg Gln His Val Val Gly His His
        195                 200                 205

Thr His Cys Asn Asp Ile Gln His Asp Pro Asp Val Lys Gly Gly Ser
    210                 215                 220

Val Ile Lys Leu Ser Arg Thr Ser Ile Pro Leu Glu Trp His His Leu
225                 230                 235                 240

Gln Gln Tyr Tyr Phe Leu Pro Leu Ile Gln Leu Leu Gly Phe Gln Trp
                245                 250                 255

Val Phe Leu Asp Leu His Asp Leu Ile Glu Met Lys Tyr Lys Gly Glu
            260                 265                 270

Lys Leu Pro Glu Ser Tyr Arg Lys Glu Arg Asn Ile Ala Ile Gly Leu
        275                 280                 285

Arg Val Phe Phe Phe Ile Arg Lys Phe Val Val Pro Phe Ala Leu His
    290                 295                 300
```

```
Phe Ser Trp Tyr Thr Leu Leu Cys Thr Tyr Leu Trp Met Ala Ile Ala
305                 310                 315                 320

Ala Leu Tyr Leu Gly Phe Phe Ile Leu Ser His Leu Phe Val Gly
            325                 330                 335

Ala Lys Ser Leu Pro Pro Asp Gly Ser Ile Asp Trp Ala Arg His Gln
            340                 345                 350

Ile Glu Ser Ser Ser Asn Val Gly Gly Glu Lys Leu Gly Ile Ser Asn
            355                 360                 365

Gly Gly Leu Asn Tyr Gln Ile Glu His His Leu Phe Pro Arg Leu Ser
        370                 375                 380

His Ala His Tyr Ala Lys Ile Gln Pro Val Val Gln Lys Val Cys Glu
385                 390                 395                 400

Glu Asn Gly Val Asn Tyr Lys Lys Phe Pro Thr Ile Leu Ser Asn Leu
                405                 410                 415

Gly Ser Met Phe Arg Gln Val Lys Ala Leu Gly Ser Val Pro Val Glu
            420                 425                 430

Phe Met Ala Lys Leu
            435

<210> SEQ ID NO 149
<211> LENGTH: 437
<212> TYPE: PRT
<213> ORGANISM: Artificial
<220> FEATURE:
<223> OTHER INFORMATION: delta-4 desaturase 89.2% sequence identity to
      SEQ ID NO 79

<400> SEQUENCE: 149

Met Pro Pro His Ser Arg Thr Glu Val Gly Asp Pro Glu Leu Ser Asp
1               5                   10                  15

Met Lys His Phe Thr Arg Glu Glu Ile Ala Asn His Thr Asn Asp Asp
            20                  25                  30

Tyr Cys Ile Leu Glu Asp Gly Val Tyr Asp Leu Thr Cys Phe Arg Asp
        35                  40                  45

Lys His Pro Gly Gly Asp Val Leu Asp Phe Phe Pro Gly Gln Asp Ala
    50                  55                  60

Thr Pro His Phe Phe Met Phe His Gln Tyr Glu Ser Leu Pro Ser Val
65                  70                  75                  80

Leu Ala Glu Tyr Gly Val Gly Ser Val Ala Arg Asp Asp Ser Tyr Val
                85                  90                  95

Gln His Asp Pro Leu Met Lys Gln Ile Lys Ser Ala Val Arg Lys Ile
            100                 105                 110

Met Pro Met Gly Ser Trp Trp Ala Pro Pro Ser Trp Ile Lys Ala
        115                 120                 125

Cys Ala Ile Leu Ala Ala Thr Leu Tyr Thr Asp Tyr Leu Trp Ile Ala
    130                 135                 140

Arg Gly Pro Thr Ile Pro Leu Ala Ile Leu Gly Leu Leu Tyr Ala
145                 150                 155                 160

Ala Ile Gly Leu Asn Ile Gln His Asp Ala Asn His Gly Ser Val Ser
                165                 170                 175

Arg Asn Pro Met Val Asn Arg Leu Phe Gly Tyr Ser Gln Asp Trp Ile
            180                 185                 190

Gly Gly Asn Arg Met Leu Trp Ile Arg Gln His Val Val Gly His His
        195                 200                 205

Thr His Cys Asn Arg His Asp His Asp Pro Asp Val Lys Gly Gly Ser
    210                 215                 220
```

Val Ile Arg Leu Ser Arg Tyr Ser Leu Pro Lys Pro Trp His His Ile
225                 230                 235                 240

Gln Gln Ile Tyr Phe Leu Pro Leu Ile Gln Leu Leu Gly Phe Gln Trp
            245                 250                 255

Val Phe Leu Gly Leu His Asp Leu Ile Glu Met Arg Tyr Glu Gly Glu
            260                 265                 270

Lys Leu Pro Glu Ser Tyr Arg Lys Glu Arg Gly Ile Ala Val Gly Leu
            275                 280                 285

Arg Val Gly Phe Phe Ile Arg Lys Phe Val Val Pro Phe Trp Leu His
            290                 295                 300

Phe Ser Trp Tyr Thr Leu Leu Cys Thr Cys Leu Trp Met Ala Ile Gly
305                 310                 315                 320

Ala Phe Tyr Leu Gly Phe Phe Ile Leu Ser His Ile Phe Val Gly
            325                 330                 335

Ala Lys Ser Leu Pro Glu Asp Gly Asn Ile Asp Trp Ala Arg His Gln
            340                 345                 350

Ile Glu Ser Ser Ser Asn Val Gly Glu Lys Leu Gly Tyr Ser Asn
            355                 360                 365

Gly Gly Leu Asn Phe Gln Ile Glu His His Leu Phe Pro Arg Met Ser
370                 375                 380

His Ala His Tyr Ala Lys Ile Glu Pro Val Val Gln Lys Val Cys Glu
385                 390                 395                 400

Glu Asn Gly Val Asn Tyr Lys Lys Phe Pro Thr Ile Leu Ser Asn Leu
            405                 410                 415

Asp Ser Thr Phe Arg Gln Val Lys Ala Leu Gly Ser Val Pro Val Glu
            420                 425                 430

Phe Met Glu Gly Leu
            435

<210> SEQ ID NO 150
<211> LENGTH: 438
<212> TYPE: PRT
<213> ORGANISM: Artificial
<220> FEATURE:
<223> OTHER INFORMATION: delta-4 desaturase 89.2% sequence identity to
      SEQ ID NO 79

<400> SEQUENCE: 150

Met Pro Pro His Ser Gly Thr Lys Val Ser Asp Pro Glu Leu Ser Ala
1               5                   10                  15

Met Lys His Phe Ala Arg Glu Glu Ile Leu Asn His Thr Asn Asp Lys
            20                  25                  30

Ile Cys Ile Leu Glu Asp Gly Val Tyr Asp Leu Val Asn Phe Arg Asp
            35                  40                  45

Lys His Pro Gly Gly Asp Tyr Leu Asp Phe Phe Pro Gly Gln Asp Ala
    50                  55                  60

Thr Pro His Phe Tyr Met Leu His Arg Tyr Glu Ser Pro Pro Ser Val
65                  70                  75                  80

Leu Ala Glu Tyr Lys Val Gly Ser Val Ala Arg Asp Asp Ser Tyr Val
            85                  90                  95

Tyr His Thr Pro Leu Met Lys Gln Ile Lys Ser Ala Val Arg Lys Val
            100                 105                 110

Met Pro Met Gln Glu Trp Trp Ala Pro Pro Ser Trp Tyr Ile Lys Ala
            115                 120                 125

Cys Ala Ile Leu Ala Ala Thr Leu His Thr Asp Tyr Leu Met Ile Ala

```
                130             135             140
Ser Gly Pro Thr Ile Pro Leu Ala Ile Val Ser Gly Leu Leu Phe Ala
145                 150                 155                 160

Ala Ile Gly Leu Asn Ile Gln His Asp Ala Asn His Gly Ser Val Ser
                165                 170                 175

Arg Asn Pro Met Val Asn Arg Leu Phe Gly Tyr Ala Gln Asp Trp Ile
            180                 185                 190

Gly Gly Ser Arg Met Leu Trp Ile Gln Gln His Val Gly His His
        195                 200                 205

Thr His Cys Asn Arg Ile Asp His Asp Pro Asp Val Lys Gly Gly Ser
    210                 215                 220

Val Ile Thr Leu Ser Arg Thr Ser Leu Pro Leu Glu Phe His His Ile
225                 230                 235                 240

Gln Gln Leu Tyr Phe Leu Pro Leu Ile Gln Leu Tyr Gly Phe Gln Trp
                245                 250                 255

Val Phe Leu Asp Leu His Asp Leu Ile Glu Met Lys Tyr Lys Gly Glu
            260                 265                 270

Lys Leu Pro Glu Leu Tyr Arg Pro Glu Tyr Gly Ile Ala Ile Gly Leu
        275                 280                 285

Arg Val Phe Phe Trp Ile Arg Lys Phe Ile Val Pro Phe Ala Leu His
    290                 295                 300

Phe Ser Trp Tyr Thr Leu Leu Cys Thr Tyr Leu Trp Met Ala Ile Gly
305                 310                 315                 320

Ala Phe Tyr Leu Gly Phe Phe Ile Leu Ser His Ile Phe Val Gly
                325                 330                 335

Ala Lys Ser Leu Gly Glu Asp Gly Asn Ile Asp Trp Ala Arg His Gln
            340                 345                 350

Ile Glu Ser Ser Ser Asn Val Cys Gly Glu Lys Leu Gly Tyr Met Asn
        355                 360                 365

Gly Gly Leu Asn Tyr Gln Ile Glu His His Leu Phe Pro Arg Leu Ser
    370                 375                 380

His Ala His Tyr Ser Lys Ile Gln Pro Val Val Arg Lys Val Cys Glu
385                 390                 395                 400

Glu Asn Gly Val Asn Tyr Lys Lys Phe Gly Thr Ile Ala Ser Asn Leu
                405                 410                 415

Asp Ser Leu Phe Arg Tyr Leu Gly Leu Gly Ser Val Pro Val Tyr
            420                 425                 430

Glu Phe Met Glu Gly Leu
        435

<210> SEQ ID NO 151
<211> LENGTH: 437
<212> TYPE: PRT
<213> ORGANISM: Artificial
<220> FEATURE:
<223> OTHER INFORMATION: delta-4 desaturase 89.2% sequence identity to
      SEQ ID NO 79

<400> SEQUENCE: 151

Met Pro Pro His Ser Arg Thr Lys Val Ser Asp Pro Glu Leu Ser Asp
1               5                   10                  15

Met Lys His Phe Thr Arg Glu Glu Lys Leu Asn Asp Thr Asn Asp Asp
                20                  25                  30

Tyr Cys Ile Leu Glu Asp Gly Val Tyr Asp Leu Ser Asn Phe Arg Asp
            35                  40                  45
```

Lys His Pro Gly Gly Asp Tyr Val Asp Phe Phe Gly Gln Asp Ala
 50                  55                  60

Thr Pro His Phe Tyr Met Leu His Gln Arg Glu Ser Pro Pro Ser Val
 65                  70                  75                  80

Met Ser Lys Phe Lys Val Gly Ser Val Ala Arg Asp Asp Ser Tyr Val
                 85                  90                  95

Tyr His Thr Pro Leu Met Lys Gln Ile Lys Ser Ala Val Arg Lys Val
                100                 105                 110

Met Pro Lys Gln Glu Trp Trp Ala Pro Ser Trp Tyr Ile Lys Ala
            115                 120                 125

Cys Ala Ile Leu Ile Ala Thr Leu Phe Thr Asp Tyr Leu Met Ile Ala
130                 135                 140

Ser Gly Pro Thr Ile Pro Leu Ala Ile Val Ser Gly Leu Leu Tyr Ala
145                 150                 155                 160

Trp Ile Gly Leu Asn Ile Gln His Asp Ala Asn His Gly Ser Val Ser
                165                 170                 175

Arg Asn Pro Met Val Asn Arg Leu Phe Gly Tyr Ser Gln Asp Trp Ile
            180                 185                 190

Gly Gly Ser Arg Met Leu Trp Ile Gln Gln His Val Val Gly His His
            195                 200                 205

Thr His Cys Asn Arg His Gln His Asp Pro Asp Val Lys Gly Gly Ser
210                 215                 220

Ala Ile Thr Leu Ser Pro Tyr Ser Leu Trp Lys Glu Trp His His Ile
225                 230                 235                 240

Gln Gln Tyr Tyr Phe Leu Pro Leu Ile Gln Leu Leu Gly Phe Gln Trp
                245                 250                 255

Val Phe Leu Gly Leu His Asp Leu Ile Glu Met Lys Tyr Lys Gly Glu
            260                 265                 270

Pro Leu Pro Pro Ser Tyr Arg Lys Glu Arg Asn Ile Ala Ile Gly Leu
            275                 280                 285

Arg Val Phe Phe Trp Ile Arg Lys Val Val Pro Phe Trp Leu Gln
            290                 295                 300

Phe Ser Trp Tyr Thr Leu Leu Cys Thr Tyr Leu Trp Met Ala Ile Gly
305                 310                 315                 320

Ala Leu Tyr Leu Gly Phe Phe Ile Leu Ser His Ile Phe Val Gly
                325                 330                 335

Ala Lys Ser Leu Pro Glu Asp Ala Asn Ile Asp Trp Ala Arg His Gln
            340                 345                 350

Ile Glu Ser Ser Asn Val Cys Gly Glu Lys Leu Gly Tyr Leu Asn
            355                 360                 365

Gly Gly Leu Asn Phe Gln Ile Glu His His Leu Phe Pro Arg Met Ser
370                 375                 380

His Ala His Tyr Ser Thr Ile Gln Pro Val Val Gln Lys Val Cys Glu
385                 390                 395                 400

Glu Asn Gly Val Asn Tyr Lys Lys Phe Gly Thr Ile Leu Ser Asn Leu
                405                 410                 415

Asp Ser Met Leu Arg Gln Val Gly Ala Leu Gly Ser Val Pro Thr Glu
            420                 425                 430

Phe Leu Glu Gly Leu
            435

<210> SEQ ID NO 152
<211> LENGTH: 439
<212> TYPE: PRT

<213> ORGANISM: Artificial
<220> FEATURE:
<223> OTHER INFORMATION: delta-4 desaturase 89.2% sequence identity to SEQ ID NO 79

<400> SEQUENCE: 152

```
Met Pro Pro Tyr Ser Arg Thr Lys Val Val Ser Asp Pro Glu Leu Ser
1               5                   10                  15

Asp Ala Lys His Phe Thr Arg Glu Glu Ile Leu Asn His Thr Arg Asp
            20                  25                  30

Lys Tyr Cys Ile Leu Glu Asp Gly Val Tyr Asp Cys Thr Asn Phe Arg
        35                  40                  45

Asp Lys His Pro Gly Gly Asp Val Leu Asp Phe Phe Pro Gly Gln Asp
    50                  55                  60

Ala Thr Pro His Phe Tyr Met Leu His Arg Tyr Val Trp Leu Pro Ser
65                  70                  75                  80

Leu Leu Ser Glu Phe Lys Val Gly Ser Val Ala Arg Asp Asp Ser Tyr
                85                  90                  95

Val Tyr His Thr Glu Leu His Lys Gln Ile Cys Ser Ala Val Arg Lys
            100                 105                 110

Val Ile Pro Met Gln Glu Trp Trp Ala Pro Pro Ser Tyr Tyr Ile Lys
        115                 120                 125

Ala Cys Ala Ile Leu Val Ala Thr Leu Tyr Thr Asp Tyr Leu Trp Ile
    130                 135                 140

Ala Ser Gly Pro Thr Ile Phe Leu Gly Ile Ile Ile Gly Leu Leu Tyr
145                 150                 155                 160

Ala Ala Ile Gly Leu Asn Ile Gln His Asp Ala Asn His Gly Ser Ile
                165                 170                 175

Ser Arg Asn Pro Met Val Asn Arg Leu Phe Gly Tyr Ser Gln Asp Trp
            180                 185                 190

Ile Gly Gly Ser Arg Met Leu Trp Ile Arg Gln His Val Val Gly His
        195                 200                 205

His Thr His Cys Asn Arg His Gln His Asp Pro Asp Ile Lys Gly Gly
    210                 215                 220

Ser Val Ile Thr Leu Ser Arg Val Asp Leu Pro Lys Glu Phe His His
225                 230                 235                 240

Ile Gln Gln Leu Tyr Phe Leu Pro Leu Ile Gln Leu Tyr Gly Phe Gln
                245                 250                 255

Trp Val Phe Leu Gly Leu His Asp Leu Ile Glu Met Lys Trp Lys Gly
            260                 265                 270

Glu Lys Leu Ser Glu Ser Ala Arg Lys Glu Tyr Ala Ile Ala Ile Gly
        275                 280                 285

Leu Arg Val Phe Phe Phe Ile Arg Lys Val Val Pro Phe Ala Leu
    290                 295                 300

His Phe Ser Trp Tyr Thr Leu Leu Cys Thr Tyr Leu Trp Val Ala Ile
305                 310                 315                 320

Gly Ala Leu Tyr Leu Gly Phe Phe Ile Leu Ser His Ile Phe Ile
                325                 330                 335

Gly Ala Lys Ser Leu Pro Glu Asp Ala Lys Asn Ile Asp Trp Ala Arg
            340                 345                 350

His Gln Ile Glu Thr Ser Ser Asn Val Cys Gly Glu Trp Leu Gly Ile
        355                 360                 365

Met Asn Gly Gly Leu Asn Tyr Gln Ile Glu His Leu Phe Pro Arg
    370                 375                 380
```

```
Met Ser His Ala His Tyr Ala Lys Ile Gln Pro Val Val Gln Lys Val
385                 390                 395                 400

Cys Glu Glu Asn Gly Val Asn Tyr Lys His Phe Gly Thr Ile Leu Ser
            405                 410                 415

Asn Leu Asp Ser Leu Phe Arg His Val Lys Ala Leu Gly Ser Val Ala
        420                 425                 430

Val Glu Phe Met Ala Gly Leu
        435

<210> SEQ ID NO 153
<211> LENGTH: 439
<212> TYPE: PRT
<213> ORGANISM: Artificial
<220> FEATURE:
<223> OTHER INFORMATION: delta-4 desaturase 89.2% sequence identity to
      SEQ ID NO 79

<400> SEQUENCE: 153

Met Pro Pro His Ser Ala Thr Lys Val Ser Val Pro Glu Leu Ser Asp
1               5                   10                  15

Met Lys His Phe Thr Arg Glu Glu Ile Leu Asn His Thr Asn Asp Asp
            20                  25                  30

Tyr Cys Ile Leu Glu Asp Gly Val Tyr Asp Leu Thr Asn Phe Arg Asp
        35                  40                  45

Lys His Pro Gly Gly Asp Phe Leu Asp Leu Phe Gly Gly Gln Asp Ala
    50                  55                  60

Thr Pro His Phe Tyr Met Leu His Gln Arg Ala Ser Pro Pro Ser Val
65                  70                  75                  80

Leu Ala Glu Tyr Lys Val Gly Ser Val Asp Arg Asp Asp Ser Tyr Val
                85                  90                  95

Gln His Thr Pro Leu Met Lys Gln Ile Lys Ser Ala Val Arg Lys Ile
            100                 105                 110

Ile Pro Lys Gln Glu Trp Trp Ala Pro Pro Ser Trp Tyr Ile Lys Ala
        115                 120                 125

Cys Ala Leu Leu Ile Ala Thr Leu Tyr Thr Asp Tyr Tyr Trp Ile Ala
    130                 135                 140

Ser Gly Pro Thr Ile Pro Leu Ala Ile Val Leu Gly Leu Leu Tyr Ala
145                 150                 155                 160

Ala Ile Gly Leu Asn Ile Gln His Asp Ala Asn His Gly Ala Val Ser
                165                 170                 175

Arg Asn Pro Val Val Asn Arg Leu Phe Gly Tyr Ser Gln Asp Trp Ile
            180                 185                 190

Gly Gly Ser Met Met Leu Trp Ile Arg Gln His Val Val Asn His His
        195                 200                 205

Thr His Cys Asn Arg His Gln His Asp Pro Asp Val Lys Gly Gly Ser
    210                 215                 220

Val Ile Thr Leu Ser Pro Tyr Ser Leu Pro Lys Glu Trp His His Ile
225                 230                 235                 240

Gln Gln Tyr Tyr Phe Leu Pro Gly Glu Gln Leu Gly Phe Gln Trp
                245                 250                 255

Val Phe Leu Gly Leu Asn Glu Leu Ile Glu Met Lys Tyr Lys Gly Glu
            260                 265                 270

Lys Leu Pro Glu Ile Tyr Arg Lys Glu Arg Ala Ile Ala Val Gly Leu
        275                 280                 285

Arg Val Phe Phe Phe Ala Arg Lys Phe Val Ile Pro Phe Ala Leu His
    290                 295                 300
```

```
Phe Ser Trp Tyr Thr Leu Leu Cys Thr Cys Leu Trp Met Ala Ser Ala
305                 310                 315                 320

Ala Leu Tyr Leu Gly Phe Phe Ile Leu Ser His Ile Phe Val Gly
            325                 330                 335

Ala Lys Ser Leu Gly Pro Asp Ala Lys Asn Ile Glu Trp Ala Arg His
            340                 345                 350

Gln Ile Glu Ser Ser Ser Asn Val Cys Gly Glu Lys Leu Gly Ile Ser
            355                 360                 365

Asn Gly Gly Leu Asn Tyr Gln Ile Glu His His Leu Phe Pro Arg Met
            370                 375                 380

Ser His Ala His Tyr Ser Pro Ile Gln Pro Val Val Gln Lys Val Cys
385                 390                 395                 400

Glu Lys Asn Gly Val Asn Tyr Lys Lys Phe Gly Thr Ile Gly Ser Asn
                405                 410                 415

Leu Asp Ser Thr Phe Arg Gln Val Lys Ala Leu Gly Ser Arg Ala Val
            420                 425                 430

Tyr Glu Phe Met Glu Gly Leu
            435

<210> SEQ ID NO 154
<211> LENGTH: 439
<212> TYPE: PRT
<213> ORGANISM: Artificial
<220> FEATURE:
<223> OTHER INFORMATION: delta-4 desaturase 89.2% sequence identity to
      SEQ ID NO 79

<400> SEQUENCE: 154

Met Pro Pro His Ser Arg Thr Lys Val Ser Ala Pro Glu Leu Ser Asp
1               5                   10                  15

Leu Met Lys His Phe Thr Arg Glu Glu Ile Leu Asn His Thr Arg Asp
            20                  25                  30

Lys Tyr Cys Ile Val Gly Asp Gly Val Tyr Asp Leu Thr Asn Phe Arg
        35                  40                  45

Asp Lys His Pro Gly Gly Glu Phe Leu Asp Phe Phe Gly Gly Gln Asp
    50                  55                  60

Ala Thr Pro His Phe Tyr Met Leu His Gln Tyr Glu Trp Pro Pro Ser
65                  70                  75                  80

Ile Leu Ala Glu Tyr Lys Val Gly Ser Leu Asp Arg Asp Asp Ser Tyr
                85                  90                  95

Val His His Glu Ser Leu Met Lys Gln Ile Lys Ser Asp Val Arg Lys
            100                 105                 110

Ile Met Pro Met Gln Glu Trp Trp Ala Pro Pro Ser Trp Tyr Ile Lys
        115                 120                 125

Ala Cys Ala Leu Ile Val Ala Thr Leu Tyr Thr Asp Tyr Tyr Trp Ile
130                 135                 140

Ala Ser Gly Pro Thr Ile Pro Leu Ala Ile Val Ser Gly Leu Leu Tyr
145                 150                 155                 160

Ala Ala Ile Gly Leu Asn Ile Gln His Asp Ala Asn His Gly Ala Val
                165                 170                 175

Ser Arg Asn Pro Met Val Asn Arg Leu Phe Gly Tyr Ser Gln Asp Trp
            180                 185                 190

Ile Gly Gly Ser Arg Leu Leu Trp Ile Arg Gln His Val Val Gly His
        195                 200                 205

His Thr His Cys Asn Asp His Gln His Asp Pro Asp Val Lys Gly Gly
```

```
            210                 215                 220
Ser Val Leu Thr Leu Ser Arg Tyr Ser Leu Trp Met Glu Phe His His
225                 230                 235                 240

Leu Gln Gln Tyr Tyr Phe Leu Pro Leu Glu Gln Leu Leu Gly Phe Gln
                245                 250                 255

Trp Ile Phe Leu Gly Leu His Asp Leu Ile Glu Met Arg Tyr Lys Gly
                260                 265                 270

Glu Pro Leu Pro Pro Ser Tyr Arg Lys Glu Arg Gly Ile Ala Ile Gly
                275                 280                 285

Cys Arg Val Phe Phe Phe Ile Arg Lys Phe Val Val Pro Phe Ala Leu
            290                 295                 300

His Phe Ser Trp Tyr Thr Leu Leu Cys Thr Tyr Leu Trp Met Ala Ile
305                 310                 315                 320

Ala Ala Leu Tyr Leu Gly Phe Phe Ile Leu Ser His Ile Phe Ile
                325                 330                 335

Gly Ala Lys Ser Leu Pro Pro Asp Ala Asn Ile Asp Trp Ala Arg His
                340                 345                 350

Gln Ile Glu Ser Ser Ser Asn Val Cys Gly Asp Trp Leu Gly Ile Ser
                355                 360                 365

Asn Gly Gly Leu Asn Tyr Gln Ile Glu His His Leu Phe Pro Arg Met
370                 375                 380

Asn His Ala His Tyr Ser Lys Ile Gln Pro Ile Val Gln Lys Val Cys
385                 390                 395                 400

Glu Glu Asn Gly Val Asn Tyr Lys Lys Phe Gly Thr Ile Leu Ser Asn
                405                 410                 415

Leu Asp Ser Met Phe Arg Gln Val Lys Ala Leu Gly Ser Val Ala Val
                420                 425                 430

Tyr Glu Phe Met Glu Gly Leu
                435

<210> SEQ ID NO 155
<211> LENGTH: 440
<212> TYPE: PRT
<213> ORGANISM: Artificial
<220> FEATURE:
<223> OTHER INFORMATION: delta-4 desaturase 89.2% sequence identity to
      SEQ ID NO 79

<400> SEQUENCE: 155

Met Pro Pro His Ala Arg Thr Lys Val Val Gly Asp Asp Pro Glu Leu
1               5                   10                  15

Ser Ala Leu Met Lys His Phe Thr Arg Glu Glu Ile Leu Asn His Thr
                20                  25                  30

Asn Asp Asp Tyr Cys Ile Leu Glu Asp Gly Val Tyr Asp Cys Ser Ala
            35                  40                  45

Phe Arg Asp Lys His Pro Gly Gly Asp Val Leu Ser Phe Phe Pro Gly
        50                  55                  60

Gln Asp Ala Thr Pro His Phe Tyr Met Phe His Gln Arg Glu Ser Pro
65                  70                  75                  80

Pro Ala Val Leu Ala Glu Tyr Lys Val Gly Ser Val Ala Arg Asp Asp
                85                  90                  95

Ser Tyr Val Tyr His Thr Pro Leu Met Leu Gln Ile Lys Ser Ala Val
                100                 105                 110

Arg Lys Val Met Pro Met Gly Glu Trp Trp Ala Pro Pro Ser Trp Trp
            115                 120                 125
```

```
Ile Lys Ala Cys Ala Ile Ile Ala Ala Thr Leu Tyr Leu Asp Tyr Leu
        130                 135                 140

Trp Ile Ala Arg Gly Pro Thr Ile Pro Leu Ala Ile Val Ser Gly Leu
145                 150                 155                 160

Leu Phe Ala Ala Ile Gly Leu Asn Ile Gln His Asp Ala Asn His Gly
                165                 170                 175

Ser Ile Ser Arg Asn Pro Met Val Asn Arg Leu Phe Gly Tyr Ser Gln
            180                 185                 190

Asp Trp Ile Gly Gly Ser Arg Met Leu Trp Ile Arg Gln His Val Val
        195                 200                 205

Asn His His Thr His Cys Asn Arg His Gln His Asp Pro Asp Val Lys
    210                 215                 220

Gly Gly Ser Val Ile Arg Leu Ser Pro Tyr Ser Leu Trp Lys Glu Phe
225                 230                 235                 240

His His Ile Gln Gln Tyr Tyr Phe Leu Pro Leu Asp Gln Leu Tyr Gly
                245                 250                 255

Phe Gln Trp Val Phe Leu Asp Leu His Asp Leu Ile Glu Met Lys Tyr
            260                 265                 270

Lys Gly Glu Lys Leu Ser Glu Leu Tyr Arg Lys Glu Arg Asn Pro Ala
        275                 280                 285

Ile Gly Leu Arg Val Phe Phe Trp Ala Arg Lys Val Val Pro Phe
    290                 295                 300

Ala Leu His Pro Thr Trp Tyr Thr Leu Leu Cys Thr Tyr Leu Trp Met
305                 310                 315                 320

Ala Ile Ala Ala Leu Tyr Leu Gly Phe Phe Phe Ile Leu Ser His Leu
                325                 330                 335

Phe Val Gly Val Lys Ser Leu Pro Glu Asp Ala Asn Ile Asp Trp Ala
            340                 345                 350

Arg His Gln Ile Glu Ser Ser Ser Asn Val Cys Gly Glu Lys Leu Gly
        355                 360                 365

Ile Ser Asn Gly Gly Leu Asn Tyr Gln Ile Glu His His Leu Phe Pro
    370                 375                 380

Arg Met Ser His Ser His Tyr Ser Pro Ile Gln Pro Val Val Gln Lys
385                 390                 395                 400

Val Cys Glu Glu Asn Gly Val Asn Tyr Lys Lys Phe Pro Thr Ile Leu
                405                 410                 415

Ser Asn Leu Asp Ser Thr Phe Arg Gln Val Lys Gly Leu Gly Ser Arg
            420                 425                 430

Ala Val Glu Phe Met Gly Gly Leu
        435                 440

<210> SEQ ID NO 156
<211> LENGTH: 439
<212> TYPE: PRT
<213> ORGANISM: Artificial
<220> FEATURE:
<223> OTHER INFORMATION: delta-4 desaturase 89.2% sequence identity to
      SEQ ID NO 79

<400> SEQUENCE: 156

Met Pro Pro His Ser Arg Thr Lys Val Ser Asp Pro Glu Leu Ser Asp
1               5                   10                  15

Met Lys His Phe Thr Arg Glu Lys Ile Leu Asn His Thr Arg Asp Asp
            20                  25                  30

Tyr Cys Ile Leu Glu Asp Gly Val Tyr Asp Leu Thr Cys Phe Arg Asp
        35                  40                  45
```

Lys His Pro Gly Gly Asp Val Leu Asp Phe Phe Pro Gly Gln Asp Ala
 50                  55                  60

Thr Pro His Phe Tyr Met Leu His Gln Arg Ala Ser Leu Pro Ser Val
 65                  70                  75                  80

Leu Ser Glu Tyr Lys Val Gly Ser Val Ala Arg Asp Asp Ser Tyr Val
                 85                  90                  95

His His Asp Ala Leu Met Lys Gln Ile Lys Ser Ala Val Arg Gly Ile
            100                 105                 110

Met Pro Met Gln Glu Trp Trp Ala Pro Pro Ser Trp Tyr Ile Lys Ala
            115                 120                 125

Cys Ala Ile Leu Ile Ala Thr Leu His Thr Asp Tyr Tyr Trp Ile Ala
            130                 135                 140

Ser Gly Pro Thr Ile Pro Leu Ala Ile Val Ser Gly Leu Leu Tyr Ala
145                 150                 155                 160

Ala Ile Gly Leu Asn Ile Gln His Asp Ala Asn His Gly Ser Val Ser
                165                 170                 175

Arg Asn Pro Met Val Asn Arg Leu Phe Gly Tyr Ser Gln Asp Trp Ile
            180                 185                 190

Gly Gly Ser Arg Val Leu Trp Ile Arg Gln His Val Val Gly His His
            195                 200                 205

Thr His Cys Asn Arg Val Gln His Asp Pro Asp Val Lys Gly Gly Ser
210                 215                 220

Val Ile Arg Leu Gly Arg Tyr Asp Leu Pro Lys Glu Phe His His Leu
225                 230                 235                 240

Gln Gln Ile Tyr Phe Leu Pro Gly Glu Gln Leu Leu Gly Phe Lys Trp
                245                 250                 255

Val Phe Leu Gly Leu His Asp Leu Ile Glu Met Lys Tyr Lys Gly Glu
            260                 265                 270

Lys Ile Pro Glu Ser Tyr Arg Lys Glu Arg Asn Ile Ala Ile Gly Leu
            275                 280                 285

Arg Val Gly Phe Phe Ile Arg Phe Ile Ala Leu Pro Phe Ala Leu His
            290                 295                 300

Phe Ser Trp Tyr Thr Leu Leu Cys Thr Cys Leu Trp Met Ala Ile Ala
305                 310                 315                 320

Thr Leu Tyr Leu Gly Phe Phe Ile Leu Ser His Ile Phe Val Gly
                325                 330                 335

Ala Lys Ser Leu Pro Glu Glu Gly Asn Ile Glu Trp Ala Arg His Gln
            340                 345                 350

Ile Glu Ser Ser Ser Asn Val Cys Gly Glu Trp Leu Gly Ile Ser Asn
            355                 360                 365

Gly Gly Leu Asn Tyr Gln Ile Glu His His Leu Phe Pro Arg Leu His
            370                 375                 380

His Ala His Tyr Ser Lys Ile Gln Pro Val Val Arg Lys Val Cys Glu
385                 390                 395                 400

Glu Asn Gly Val Asn Tyr Lys Lys Phe Gly Thr Ile Leu Ser Asn Leu
                405                 410                 415

Asp Ala Met Phe Arg Gln Val Lys Ala Leu Gly Ser Val Ala Val Tyr
            420                 425                 430

Asn Glu Phe Met Glu Gly Leu
            435

<210> SEQ ID NO 157
<211> LENGTH: 439

```
<212> TYPE: PRT
<213> ORGANISM: Artificial
<220> FEATURE:
<223> OTHER INFORMATION: delta-4 desaturase 89.2% sequence identity to
      SEQ ID NO 79

<400> SEQUENCE: 157
```

| | | | | | | | | | | | | | | | |
|---|---|---|---|---|---|---|---|---|---|---|---|---|---|---|---|
| Met | Pro | Pro | His | Ser | Gly | Thr | Lys | Val | Ser | Asp | Pro | Glu | Leu | Ser | Asp |
| 1 | | | | 5 | | | | | 10 | | | | | 15 | |
| Leu | Met | Lys | His | Phe | Thr | Arg | Glu | Glu | Ile | Leu | Asn | His | Thr | Asn | Asp |
| | | | 20 | | | | | 25 | | | | | 30 | | |
| Lys | Tyr | Cys | Ile | Leu | Glu | Asp | Gly | Val | Tyr | Asp | Ser | Thr | Cys | Phe | Arg |
| | | 35 | | | | | 40 | | | | | 45 | | | |
| Asp | Glu | His | Pro | Gly | Gly | Glu | Val | Leu | Asp | Phe | Phe | Pro | Gly | Gln | Asp |
| | 50 | | | | | 55 | | | | | 60 | | | | |
| Ala | Thr | Pro | Gly | Phe | Tyr | Glu | Leu | His | Gln | Tyr | Glu | Trp | Leu | Pro | Ser |
| 65 | | | | | 70 | | | | | 75 | | | | | 80 |
| Val | Leu | Ala | Glu | Tyr | Lys | Val | Gly | Ser | Val | Ala | Arg | Asp | Asp | Ser | Tyr |
| | | | | 85 | | | | | 90 | | | | | 95 | |
| Val | Tyr | His | Thr | Pro | Gly | Met | Lys | Gln | Ile | Lys | Ser | Ala | Val | Asn | Lys |
| | | | 100 | | | | | 105 | | | | | 110 | | |
| Val | Met | Pro | Lys | Gln | Glu | Trp | Trp | Ala | Pro | Pro | Ser | Trp | Tyr | Ile | Lys |
| | | | 115 | | | | | 120 | | | | | 125 | | |
| Ala | Cys | Ala | Ile | Ile | Ala | Ala | Ala | Leu | Tyr | Thr | Asp | Tyr | Leu | Trp | Ile |
| | 130 | | | | | 135 | | | | | 140 | | | | |
| Ala | Ser | Gly | Pro | Thr | Ile | Pro | Leu | Ala | Ile | Val | Ser | Gly | Leu | Leu | Phe |
| 145 | | | | | 150 | | | | | 155 | | | | | 160 |
| Ala | Ala | Ile | Gly | Leu | Asn | Ile | Gln | His | Asp | Ala | Asn | His | Gly | Ser | Val |
| | | | | 165 | | | | | 170 | | | | | 175 | |
| Ser | Arg | Asn | Pro | Met | Val | Asn | Arg | Leu | Phe | Gly | Tyr | Gly | Gln | Asp | Trp |
| | | | 180 | | | | | 185 | | | | | 190 | | |
| Ile | Gly | Gly | Gly | Arg | Met | Leu | Trp | Leu | Gln | Gln | His | Val | Val | Gly | His |
| | | | 195 | | | | | 200 | | | | | 205 | | |
| His | Thr | His | Cys | Asn | Arg | Val | Gln | His | Asp | Pro | Asp | Val | Lys | Gly | Gly |
| | 210 | | | | | 215 | | | | | 220 | | | | |
| Ser | Val | Leu | Gln | Leu | Ser | Arg | Tyr | Asp | Leu | Trp | Lys | Glu | Phe | His | His |
| 225 | | | | | 230 | | | | | 235 | | | | | 240 |
| Ile | Gln | Gln | Tyr | Tyr | Phe | Leu | Pro | Met | Asp | Ala | Leu | Leu | Gly | Phe | Gln |
| | | | | 245 | | | | | 250 | | | | | 255 | |
| Trp | Val | Phe | Leu | Gly | Leu | His | Asp | Leu | Ile | Glu | Met | Lys | Tyr | Lys | Gly |
| | | | 260 | | | | | 265 | | | | | 270 | | |
| Glu | Lys | Leu | Pro | Glu | Ile | Tyr | Arg | Lys | Asp | Arg | Asn | Ile | Ala | Ile | Gly |
| | | | 275 | | | | | 280 | | | | | 285 | | |
| Leu | Lys | Val | Phe | Phe | Ile | Arg | Lys | Phe | Ile | Ile | Pro | Phe | Ala | Leu | |
| | 290 | | | | | 295 | | | | | 300 | | | | |
| Gln | Phe | Ser | Trp | Tyr | Thr | Leu | Leu | Cys | Thr | Tyr | Leu | Trp | Val | Cys | Val |
| 305 | | | | | 310 | | | | | 315 | | | | | 320 |
| Ala | Ala | Phe | Tyr | Leu | Gly | Phe | Phe | Ile | Leu | Ser | His | Ile | Phe | Ile | |
| | | | | 325 | | | | | 330 | | | | | 335 | |
| Gly | Ala | Lys | Ser | Leu | Pro | Glu | Asp | Ala | Lys | Asn | Ile | Asp | Trp | Ala | Arg |
| | | | 340 | | | | | 345 | | | | | 350 | | |
| His | Gln | Ile | Glu | Ser | Ser | Ser | Asn | Val | Cys | Gly | Glu | Trp | Leu | Gly | Ile |
| | | | 355 | | | | | 360 | | | | | 365 | | |
| Ser | Asn | Gly | Gly | Leu | Asn | Tyr | Gln | Ile | Glu | His | His | Leu | Phe | Pro | Arg |
| | 370 | | | | | 375 | | | | | 380 | | | | |

```
Met Ser His Ala His Tyr Ser Lys Ile Ala Pro Val Gln Lys Val
385                 390                 395                 400

Cys Glu Glu Asn Gly Val Asn Tyr Lys Lys Phe Pro Thr Ile Ala Ser
                405                 410                 415

Asn Leu Asp Ser Leu Phe Arg Gln Val Lys Ala Leu Gly Ser Val Ala
            420                 425                 430

Val Glu Phe Met Glu Gly Leu
        435
```

<210> SEQ ID NO 158
<211> LENGTH: 439
<212> TYPE: PRT
<213> ORGANISM: Artificial
<220> FEATURE:
<223> OTHER INFORMATION: delta-4 desaturase 89% sequence identity to
      SEQ ID NO 79

<400> SEQUENCE: 158

```
Met Pro Pro His Ser Arg Thr Lys Gly Ser Asp Asp Pro Glu Leu Ser
1               5                   10                  15

Asp Leu Ala Lys His Phe Thr Arg Thr Lys Lys Leu Asn His Glu Asn
            20                  25                  30

Asp Lys Tyr Cys Ile Leu Gly Asp Gly Val Tyr Asp Ser Thr Cys Phe
        35                  40                  45

Arg Asp Lys His Pro Gly Gly Asp Val Leu Asp Phe Phe Pro Gly Gln
    50                  55                  60

Asp Ala Thr Pro His Phe Tyr Met Tyr His Gln Tyr Glu Ser Leu Pro
65              70                  75                  80

Ser Val Leu Ala Glu Tyr Lys Val Gly Ser Ile Asp Arg Asp Asp Ser
                85                  90                  95

Tyr Val Gln His Thr Pro Leu Met Lys Gln Ile Lys Ala Asp Val Arg
            100                 105                 110

Lys Val Met Pro Met Gln Glu Gly Trp Ala Pro Pro Ser Trp Tyr Ile
        115                 120                 125

Lys Ala Cys Ala Ile Leu Ala Ala Thr Leu His Leu Asp Tyr Leu Met
130                 135                 140

Ile Ala Arg Gly Pro Thr Ile Pro Leu Ala Ile Val Leu Gly Leu Leu
145                 150                 155                 160

Tyr Ala Ala Ile Gly Leu Asn Ile Gln His Asp Ala Asn His Gly Ser
                165                 170                 175

Val Ser Arg Asn Pro Met Val Asn Arg Leu Phe Gly Tyr Ser Gln Asp
            180                 185                 190

Trp Ile Gly Gly Ser Arg Leu Leu Trp Ile Arg Gln His Val Val Gly
        195                 200                 205

His His Leu His Cys Asn Arg His Gln His Asp Pro Asp Val Lys Gly
    210                 215                 220

Gly Gly Ala Ile Arg Leu Ser Arg Tyr Ser Leu Pro Lys Glu Phe His
225                 230                 235                 240

His Ile Gln Gln Tyr Tyr Phe Leu Pro Leu Glu Gln Leu Tyr Gly Phe
                245                 250                 255

Gln Trp Val Phe Leu Gly Leu Asn Asp Leu Leu Glu Met Lys Tyr Lys
            260                 265                 270

Gly Glu Lys Leu Pro Pro Ser Cys Arg Lys Glu Arg Asn Ile Ala Ile
        275                 280                 285

Gly Leu Arg Val Phe Phe Trp Ile Arg Lys Phe Val Val Pro Phe Ala
```

```
              290                 295                 300
Leu His Phe Ser Trp Tyr Thr Leu Leu Cys Ile Tyr Leu Trp Met Ala
305                 310                 315                 320

Thr Ala Ala Leu Tyr Leu Gly Phe Phe Ile Leu Ser His Ile Phe
                325                 330                 335

Val Gly Ala Lys Ser Leu Pro Pro Asp Ala Asn Ile Asp Trp Ala Arg
                340                 345                 350

Arg Gln Ile Glu Ser Ser Asn Val Cys Gly Glu Lys Leu Gly Ile
                355                 360                 365

Ser Asn Gly Gly Leu Asn Tyr Gln Ile Glu His His Leu Phe Pro Arg
                370                 375                 380

Met Ser His Ala His Tyr Ser Lys Ile Gln Pro Val Val Arg Lys Val
385                 390                 395                 400

Cys Glu Glu Asn Gly Val Asn Tyr Lys Lys Phe Pro Thr Ile Gly Ser
                405                 410                 415

Asn Leu Asp Ser Thr Phe Arg Gln Val Lys Ala Leu Gly Ser Val Pro
                420                 425                 430

Val Glu Phe Met Glu Gly Leu
                435

<210> SEQ ID NO 159
<211> LENGTH: 437
<212> TYPE: PRT
<213> ORGANISM: Artificial
<220> FEATURE:
<223> OTHER INFORMATION: delta-4 desaturase 89% sequence identity to
      SEQ ID NO 79

<400> SEQUENCE: 159

Met Pro Pro His Ala Gly Thr Glu Val Ser Asp Pro Glu Leu Ser Asp
1               5                   10                  15

Met Lys His Phe Thr Arg Glu Glu Ile Leu Asn His Thr Asn Asp Lys
                20                  25                  30

Ile Cys Ile Leu Glu Asp Gly Val Tyr Asp Cys Thr Ala Phe Arg Asp
                35                  40                  45

Lys His Pro Gly Gly Asp Val Leu Asp Phe Phe Pro Gly Gln Asp Ala
                50                  55                  60

Thr Pro His Phe Trp Met Phe His Gln Arg Glu Ser Pro Pro Ser Val
65                  70                  75                  80

Leu Ala Glu Tyr Lys Val Gly Ser Val Ala Arg Asp Asp Ser Tyr Val
                85                  90                  95

Tyr His Thr Glu Gly Met Leu Gln Ile Lys Ser Ala Val Arg Lys Val
                100                 105                 110

Met Pro Lys Gln Glu Trp Trp Ala Pro Pro Ser Trp Tyr Ile Lys Ala
                115                 120                 125

Cys Ala Ile Leu Ala Ala Thr Leu Tyr Thr Asp Tyr Leu Trp Ile Leu
                130                 135                 140

Ser Gly Pro Thr Ile Phe Leu Ala Ile Val Ser Gly Leu Leu Tyr Ala
145                 150                 155                 160

Ala Ile Gly Leu Asn Ile Gln His Asp Ala Asn His Gly Ser Val Ser
                165                 170                 175

Arg Asn Pro Met Val Asn Arg Leu Phe Gly Tyr Ser Gln Asp Trp Ile
                180                 185                 190

Gly Gly Asn Met Met Leu Trp Ile Arg Lys His Val Val Gly His His
                195                 200                 205
```

```
Thr His Cys Asn Asp His Gln His Asp Pro Asp Val Lys Gly Gly Ser
    210                 215                 220

Val Ile Thr Leu Ser Pro Tyr Ser Gly Trp Met Glu Phe His His Ile
225                 230                 235                 240

Gln Gln Tyr Tyr Phe Leu Pro Leu Asp Gln Leu Tyr Gly Phe Gln Trp
                245                 250                 255

Val Phe Leu Gly Leu His Glu Leu Ile Glu Trp Lys Tyr Lys Gly Glu
            260                 265                 270

Lys Leu Pro Glu Ile Cys Arg Lys Glu Arg Gly Ile Ala Ile Gly Leu
        275                 280                 285

Arg Val Phe Phe Trp Ile Arg Lys Phe Val Pro Phe Ala Leu His
    290                 295                 300

Phe Ser Trp Tyr Thr Leu Leu Cys Thr Tyr Leu Trp Met Ala Ile Ala
305                 310                 315                 320

Ala Leu Tyr Leu Ala Phe Phe Val Leu Ser His Ile Phe Val Gly
                325                 330                 335

Ala Lys Ser Leu Pro Pro Asp Ala Asn Ile Asp Trp Ala Arg His Gln
                340                 345                 350

Ile Glu Ser Ser Asn Val Cys Gly Glu Lys Leu Gly Ile Leu Asn
            355                 360                 365

Gly Gly Leu Asn Tyr Gln Ile Glu His His Leu Phe Pro Arg Met Ser
    370                 375                 380

His Ser His Tyr Ser Thr Ile Gln Pro Val Val Gln Lys Val Cys Glu
385                 390                 395                 400

Glu Asn Gly Val Asn Tyr Lys His Phe Gly Thr Ile Leu Ser Asn Leu
                405                 410                 415

Asp Ser Thr Phe Arg Gln Val Lys Ala Leu Gly Ser Val Pro Ile Glu
            420                 425                 430

Phe Met Glu Gly Leu
            435

<210> SEQ ID NO 160
<211> LENGTH: 437
<212> TYPE: PRT
<213> ORGANISM: Artificial
<220> FEATURE:
<223> OTHER INFORMATION: delta-4 desaturase 89% sequence identity to
      SEQ ID NO 79

<400> SEQUENCE: 160

Met Pro Pro His Ser Arg Thr Lys Val Gly Asp Pro Glu Leu Ser Asp
1               5                   10                  15

Met Lys His Phe Thr Arg Glu Glu Ile Leu Asn His Thr Asn Asp Asp
            20                  25                  30

Tyr Cys Ile Leu Glu Asp Gly Val Tyr Asp Cys Asn Asn Phe Arg Asp
        35                  40                  45

Lys His Pro Gly Gly Asp Phe Leu Asp Phe Phe Pro Gly Gln Asp Ala
    50                  55                  60

Thr Pro His Phe Tyr Met Leu His Gln Arg Glu Ser Leu Pro Ser Val
65                  70                  75                  80

Leu Ala Glu Phe Lys Val Gly Ser Val Ala Arg Asp Asp Ser Tyr Val
                85                  90                  95

Tyr His Asp Pro Gly His Lys Gln Ile Lys Cys Ala Val Arg Gly Val
            100                 105                 110

Met Pro Arg Gln Glu Trp Trp Ala Pro Pro Ser Trp Tyr Ile Lys Ala
        115                 120                 125
```

```
Cys Ala Ile Leu Ala Ala Thr Leu Tyr Thr Asp Tyr Leu Trp Ile Ala
        130                 135                 140

Ser Gly Pro Thr Ile Pro Leu Ala Ile Val Ile Gly Leu Leu Tyr Ala
145                 150                 155                 160

Ala Ile Gly Leu Asn Ile Gln His Asp Ala Asn His Gly Ala Val Ser
                165                 170                 175

Arg Asn Pro Met Val Asn Arg Leu Phe Gly Tyr Ser Gln Asp Trp Ile
            180                 185                 190

Gly Gly Ser Arg Val Leu Trp Ile Arg Gln His Val Val Gly His His
        195                 200                 205

Leu His Cys Asn Asp Val Gln His Asp Pro Asp Ile Lys Gly Gly Ser
    210                 215                 220

Val Ile Thr Leu Ser Pro Tyr Ser Gly Trp Lys Glu Phe His His Ile
225                 230                 235                 240

Gln Gln Leu Tyr Phe Leu Pro Leu Glu Gln Leu Tyr Gly Phe Gln Trp
                245                 250                 255

Val Phe Leu Gly Leu His Asp Leu Ile Glu Met Lys Tyr Lys Gly Glu
            260                 265                 270

Pro Leu Pro Glu Ser Tyr Arg Pro Glu Tyr Asn Ile Ala Ile Gly Leu
        275                 280                 285

Arg Ile Phe Phe Phe Ala Arg Lys Phe Val Val Pro Phe Ala Leu Glu
    290                 295                 300

Phe Ser Trp Tyr Thr Leu Leu Cys Thr Tyr Leu Trp Met Ala Ile Ala
305                 310                 315                 320

Ala Leu Tyr Leu Gly Phe Phe Ile Leu Ser His Ile Phe Val Gly
                325                 330                 335

Val Lys Ser Leu Pro Pro Asp Ala Asn Val Asp Trp Ala Arg His Gln
            340                 345                 350

Ile Glu Asn Ser Ser Asn Val Cys Gly Glu Lys Leu Gly Ile Ser Asn
        355                 360                 365

Gly Gly Leu Asn Tyr Gln Ile Glu His His Leu Phe Pro Arg Met Ser
    370                 375                 380

His Ala His Tyr Ser Lys Ile Gln Pro Val Val Gln Lys Val Cys Glu
385                 390                 395                 400

Glu Asn Gly Val Asn Tyr Lys Lys Phe Pro Thr Ile Leu Ser Asn Leu
                405                 410                 415

Asp Ser Leu Phe Lys Gln Ile Lys Ala Leu Gly Ala Val Ala Val Glu
            420                 425                 430

Phe Met Glu Gly Leu
        435

<210> SEQ ID NO 161
<211> LENGTH: 439
<212> TYPE: PRT
<213> ORGANISM: Artificial
<220> FEATURE:
<223> OTHER INFORMATION: delta-4 desaturase 89% sequence identity to
      SEQ ID NO 79

<400> SEQUENCE: 161

Met Pro Pro His Ser Arg Thr Lys Gly Ser Asp Pro Glu Leu Ser Asp
1               5                   10                  15

Ala Lys His Phe Thr Arg Glu Arg Ile Leu Asn Asp Thr Asn Asp Lys
            20                  25                  30

Leu Cys Ile Leu Gly Asp Gly Val Tyr Asp Leu Thr Ala Phe Arg Asp
```

```
                35                  40                  45
Lys His Pro Gly Gly Asp Phe Leu Asp Phe Pro Gly Gln Asp Ala
 50                  55                  60

Thr Pro His Phe Tyr Met Leu His Gln Tyr Glu Trp Leu Pro Ser Val
 65                  70                  75                  80

Leu Ala Lys Tyr Lys Val Gly Ser Ile Ala Arg Asp Ser Tyr Val
                 85                  90                  95

His His Asp Pro Leu Met Lys Gln Ile Lys Ser Ala Val Arg Ala Val
                100                 105                 110

Leu Pro Arg Gln Glu Trp Trp Ala Pro Ser Trp Tyr Ile Lys Ala
                115                 120                 125

Cys Ala Ile Leu Ala Ala Thr Leu Tyr Thr Asp Tyr Leu Trp Ile Ala
            130                 135                 140

Ser Gly Pro Thr Ile Pro Leu Ala Ile Ile Ser Gly Leu Leu Tyr Ala
145                 150                 155                 160

Ala Ile Gly Leu Asn Ile Gln His Asp Ala Asn His Gly Ser Val Ser
                165                 170                 175

Arg Asn Pro Met Val Asn Arg Leu Phe Gly Tyr Ser Gln Asp Trp Ile
                180                 185                 190

Gly Gly Ser Arg Met Leu Trp Ile Arg Gln His Val Gly His His
                195                 200                 205

Leu His Thr Asn Arg His Asp His Asp Pro Asp Val Lys Gly Gly Ser
210                 215                 220

Val Leu Thr Leu Ser Arg Tyr Ser Ile Trp Lys Glu Phe His His Ile
225                 230                 235                 240

Gln Gln Leu Tyr Phe Leu Pro Leu Asp Gln Leu Leu Gly Phe Gln Trp
                245                 250                 255

Val Phe Leu Gly Leu His Asp Leu Ile Glu Met Arg Tyr Lys Gly Glu
                260                 265                 270

Lys Leu Pro Pro Ser Tyr Arg Pro Leu Arg Asn Ile Ala Ile Gly Leu
                275                 280                 285

Arg Val Gly Phe Phe Ile Arg Phe Val Val Pro Phe Ala Leu His
290                 295                 300

Phe Ser Trp Tyr Thr Leu Leu Cys Thr Tyr Ala Trp Met Cys Ile Gly
305                 310                 315                 320

Ala Leu Tyr Leu Gly Phe Phe Ile Leu Ser His Ile Phe Val Gly
                325                 330                 335

Ala Gly Ser Leu Pro Glu Asp Ala Lys Asn Ile Asp Trp Ala Arg His
                340                 345                 350

Gln Ile Glu Thr Ser Ser Asn Val Cys Gly Glu Lys Leu Gly Ile Ser
                355                 360                 365

Asn Gly Gly Leu Asn Tyr Gln Ile Glu His His Leu Phe Pro Arg Met
                370                 375                 380

Ser His Ser His Tyr Ser Pro Ile Gln Pro Val Val Gln Lys Val Cys
385                 390                 395                 400

Glu Glu Asn Gly Val Asn Tyr Lys Lys Phe Gly Thr Ile Leu Ser Asn
                    405                 410                 415

Leu Asp Ser Leu Phe Ser Gln Ile Lys Ala Leu Gly Ser Val Pro Thr
                420                 425                 430

Tyr Glu Phe Met Glu Gly Leu
                435

<210> SEQ ID NO 162
```

<211> LENGTH: 439
<212> TYPE: PRT
<213> ORGANISM: Artificial
<220> FEATURE:
<223> OTHER INFORMATION: delta-4 desaturase 89% sequence identity to
      SEQ ID NO 79

<400> SEQUENCE: 162

```
Met Pro Pro His Gly Arg Thr Lys Val Ser Asp Pro Glu Leu Ser Asp
1               5                   10                  15

Met Glu His Phe Ser Arg Thr Glu Ile Leu Asn His Thr Asn Asp Lys
            20                  25                  30

Leu Cys Ile Leu Glu Asp Gly Val Tyr Asp Leu Thr Asn Phe Arg Asp
        35                  40                  45

Lys His Pro Gly Gly Asp Tyr Leu Asp Phe Phe Pro Gly Gln Asp Ala
    50                  55                  60

Thr Pro His Phe Tyr Glu Phe His Gln Tyr Glu Ser Pro Pro Ser Val
65                  70                  75                  80

Met Ala Glu Tyr Phe Val Gly Ser Val Ala Arg Asp Asp Ser Tyr Val
                85                  90                  95

Tyr His Thr Pro Leu Met Lys Gln Ile Lys Ser Ala Val Asn Lys Val
            100                 105                 110

Leu Pro Met Gly Ser Trp Trp Ala Pro Pro Ser Trp Tyr Ile Lys Ala
        115                 120                 125

Cys Ala Ile Leu Ala Ala Thr Leu Tyr Thr Asp Tyr Leu Met Ile Ala
    130                 135                 140

Ser Gly Pro Thr Ile Pro Leu Ala Ile Val Ser Gly Leu Leu Tyr Ala
145                 150                 155                 160

Ala Ile Gly Leu Asn Ile Gln His Asp Ala Asn His Gly Gly Val Ser
                165                 170                 175

Arg Asn Pro Met Val Asn Arg Leu Phe Gly Tyr Ser Gln Asp Trp Ile
            180                 185                 190

Gly Gly Ser Arg Met Leu Trp Ile Arg Gln His Val Val Gly His His
        195                 200                 205

Thr His Cys Asn Arg Val Gln His Asp Pro Asp Val Lys Gly Gly Gly
    210                 215                 220

Val Ile Thr Leu Ser Pro Tyr Ser Leu Trp Met Glu Phe His His Ile
225                 230                 235                 240

Gln Gln Tyr Tyr Phe Leu Pro Leu Glu Val Leu Tyr Gly Phe Gln Trp
                245                 250                 255

Val Phe Leu Gly Leu His Asp Leu Ile Glu Trp Lys Tyr Lys Gly Glu
            260                 265                 270

Lys Leu Ser Glu Ser Tyr Arg Lys Asp Arg Asn Pro Ala Ile Gly Leu
        275                 280                 285

Arg Val Phe Phe Phe Ala Arg Phe Val Leu Pro Phe Ala Leu Glu
    290                 295                 300

Phe Ser Trp Tyr Thr Leu Leu Cys Thr Tyr Leu Trp Met Ala Ile Gly
305                 310                 315                 320

Ala Phe Tyr Leu Gly Phe Phe Ile Leu Ser His Ile Phe Ile Gly
                325                 330                 335

Ala Lys Ser Ile Pro Glu Asp Ala Lys Asn Ile Asp Trp Val Arg His
            340                 345                 350

Gln Ile Glu Ser Ser Ser Asn Val Cys Gly Glu Lys Leu Gly Ile Ser
        355                 360                 365

Asn Gly Gly Leu Asn Tyr Gln Ile Glu His His Leu Phe Pro Arg Met
```

```
            370                 375                 380
Ser His Ala His Tyr Ser Lys Ile Gln Pro Val Val Gln Lys Val Cys
385                 390                 395                 400

Glu Glu Asn Gly Val Asn Tyr Lys Lys Phe Gly Thr Ile Gly Ser Asn
                405                 410                 415

Leu Asp Ser Ile Phe Lys Gln Val Lys Ala Leu Gly Ser Val Ala Thr
                420                 425                 430

Tyr Glu Phe Met Glu Gly Pro
            435

<210> SEQ ID NO 163
<211> LENGTH: 439
<212> TYPE: PRT
<213> ORGANISM: Artificial
<220> FEATURE:
<223> OTHER INFORMATION: delta-4 desaturase 89% sequence identity to
      SEQ ID NO 79

<400> SEQUENCE: 163

Met Pro Pro His Ser Ala Thr Lys Val Ser Asp Val Pro Glu Leu Ser
1               5                   10                  15

Asp Leu Met Lys His Phe Ser Arg Glu Glu Ile Leu Asn His Thr Asn
            20                  25                  30

Asp Lys Ile Cys Ile Leu Gly Asp Gly Val Tyr Asp Leu Thr Asn Phe
        35                  40                  45

Arg Asp Lys His Pro Gly Gly Asp Val Ile Asp Phe Phe Pro Gly Gln
    50                  55                  60

Asp Ala Thr Pro His Phe Tyr Met Leu His Gln Tyr Glu Ser Pro Pro
65                  70                  75                  80

Ser Val Leu Ala Glu Tyr Lys Val Gly Ser Val Ala Arg Asp Asp Ser
                85                  90                  95

Tyr Val Tyr His Asp Pro Leu Met Lys Arg Ile Cys Ser Ala Val Arg
            100                 105                 110

Lys Val Met Pro Met Gln Glu Trp Trp Ala Pro Pro Ser Trp Trp Ile
        115                 120                 125

Lys Ala Cys Ala Leu Leu Ala Ala Thr Leu Tyr Thr Asp Tyr Leu Trp
130                 135                 140

Leu Ala Ser Gly Pro Thr Ile Pro Leu Ala Ile Val Leu Gly Leu Leu
145                 150                 155                 160

Tyr Ala Ala Ile Gly Leu Asn Ile Gln His Asp Ala Asn His Gly Ser
                165                 170                 175

Val Ser Arg Asn Pro Met Val Asn Arg Leu Phe Gly Tyr Ser Gln Asp
            180                 185                 190

Trp Ile Gly Gly Ser Arg Met Leu Trp Ile Arg Gln His Val Val Gly
        195                 200                 205

His His Ile His Thr Asn Arg His Gln His Asp Pro Asp Val Lys Gly
    210                 215                 220

Gly Ser Ala Ile Arg Leu Ser Pro Thr Ser Leu Pro Lys Glu Phe His
225                 230                 235                 240

His Ile Gln Gln Tyr Tyr Phe Leu Pro Leu Ile Gln Leu Leu Gly Phe
                245                 250                 255

Gln Trp Val Phe Leu Gly Ala Asn Asp Leu Ile Glu Met Lys Tyr Glu
            260                 265                 270

Gly Glu Lys Leu Pro Glu Ser Tyr Arg Pro Glu Arg Asn Ile Ala Ile
        275                 280                 285
```

```
Gly Cys Arg Val Phe Phe Ile Arg Lys Phe Ile Val Pro Phe Ala
    290                 295                 300
Leu Glu Phe Thr Trp Tyr Thr Leu Leu Cys Thr Tyr Leu Trp Met Ala
305                 310                 315                 320
Thr Ala Ala Leu Tyr Leu Gly Phe Phe Phe Ile Leu Ser His Ile Phe
                325                 330                 335
Ile Gly Ala Lys Ser Leu Gly Pro Asp Gly Asn Ile Asp Trp Ala Arg
            340                 345                 350
His Gln Ile Glu Asn Ser Ser Asn Val Gly Gly Glu Lys Leu Gly Ile
        355                 360                 365
Ser Asn Gly Gly Leu Asn Tyr Gln Ile Glu His His Leu Phe Pro Arg
    370                 375                 380
Met His His Ala His Tyr Ser Thr Ile Gln Pro Val Val Gln Lys Val
385                 390                 395                 400
Cys Glu Glu Met Gly Val Asn Tyr Lys Lys Phe Gly Thr Ile Gly Ser
                405                 410                 415
Asn Leu Asp Ser Thr Leu Arg Gln Val Lys Gly Leu Gly Ser Val Pro
            420                 425                 430
Thr Glu Phe Met Glu Gly Leu
        435

<210> SEQ ID NO 164
<211> LENGTH: 438
<212> TYPE: PRT
<213> ORGANISM: Artificial
<220> FEATURE:
<223> OTHER INFORMATION: delta-4 desaturase 89% sequence identity to
      SEQ ID NO 79

<400> SEQUENCE: 164

Met Pro Pro His Ser Arg Arg Lys Val Gly Ser Asp Pro Glu Leu Arg
1               5                   10                  15
Asp Met Lys His Phe Thr Arg Glu Glu Ile Leu Asn His Asn Asn Asp
            20                  25                  30
Lys Tyr Cys Ile Leu Glu Asp Gly Val Tyr Asp Leu Thr Asn Phe Arg
        35                  40                  45
Asp Lys His Pro Gly Gly Asp Val Leu Asp Phe Phe Pro Gly Gln Asp
    50                  55                  60
Ala Thr Pro His Phe Tyr Met Leu His Gln Arg Glu Ser Leu Pro Ser
65                  70                  75                  80
Ile Leu Ala Glu Tyr Lys Val Gly Ser Val Ala Arg Asp Asp Ser Tyr
                85                  90                  95
Val Tyr Ala Thr Ser Leu Met Lys Arg Ile Lys Ser Glu Val Arg Gly
            100                 105                 110
Val Met Pro Met Gly Ser Trp Trp Ala Pro Pro Ser Tyr Ile Lys
        115                 120                 125
Ala Cys Ala Ile Leu Ala Ala Thr Leu Tyr Leu Asp Tyr Leu Trp Ile
    130                 135                 140
Ala Ser Gly Pro Thr Ile Pro Leu Ala Ile Val Ser Gly Leu Leu Phe
145                 150                 155                 160
Ala Ala Ile Gly Leu Asn Ile Gln His Asp Ala Asn His Gly Ser Val
                165                 170                 175
Ser Arg Asn Pro Ala Val Asn Arg Leu Phe Gly Tyr Ser Gln Asp Trp
            180                 185                 190
Ile Gly Gly Asn Arg Met Leu Trp Ile Arg Glu His Val Val Gly His
        195                 200                 205
```

His Leu His Thr Asn Arg His Gln His Asp Pro Asp Ile Lys Gly Gly
    210                 215                 220

Ser Val Leu Gln Leu Ser Arg Val Ser Ile Pro Lys Glu Phe His His
225                 230                 235                 240

Ile Gln Gln Tyr Tyr Phe Leu Pro Leu Ile Gln Leu Tyr Gly Phe Gln
                    245                 250                 255

Trp Val Phe Leu Gly Leu His Asp Leu Ile Glu Met Lys Tyr Lys Gly
                260                 265                 270

Glu Pro Leu Pro Pro Ser Tyr Arg Lys Glu Arg Asn Ile Ala Ile Gly
            275                 280                 285

Cys Arg Leu Phe Phe Ile Arg Lys Phe Val Val Pro Phe Ala Leu
        290                 295                 300

His Phe Ser Trp Tyr Thr Leu Leu Cys Val Cys Leu Trp Met Ala Ile
305                 310                 315                 320

Gly Ala Leu Tyr Leu Gly Phe Phe Val Leu Ser His Ile Phe Ile
                325                 330                 335

Gly Ala Lys Ser Leu Pro Glu Asp Gly Asn Ile Asp Trp Ala Arg His
                340                 345                 350

Gln Ile Glu Ser Ser Asn Val Cys Gly Lys Leu Gly Ile Met
            355                 360                 365

Asn Gly Gly Leu Asn Tyr Gln Ile Glu His His Leu Phe Pro Arg Met
370                 375                 380

Ser His Ala His Tyr Ala Lys Ile Ala Pro Val Val Gln Lys Val Cys
385                 390                 395                 400

Glu Glu Asn Gly Val Asn Tyr Lys Lys Phe Gly Thr Ile Gly Ser Asn
                405                 410                 415

Leu Asp Ser Thr Phe Arg Gln Ile Gly Ala Leu Gly Ser Val Ala Val
            420                 425                 430

Glu Phe Met Glu Gly Leu
        435

<210> SEQ ID NO 165
<211> LENGTH: 439
<212> TYPE: PRT
<213> ORGANISM: Artificial
<220> FEATURE:
<223> OTHER INFORMATION: delta-4 desaturase 88.8% sequence identity to
      SEQ ID NO 79

<400> SEQUENCE: 165

Met Pro Pro His Ser Arg Thr Lys Val Ser Asp Pro Glu Leu Ser Asp
1               5                   10                  15

Leu Met Lys His Phe Thr Arg Glu Glu Ile Leu Gly Asp Thr Asn Asp
                20                  25                  30

Asp Tyr Cys Ile Leu Gly Asp Gly Val Tyr Asp Leu Thr Asn Phe Arg
            35                  40                  45

Asp Lys His Pro Gly Gly Asp Tyr Leu Asp Phe Phe Pro Gly Gln Asp
        50                  55                  60

Ala Thr Pro His Phe Tyr Gln Leu His Gln Tyr Glu Trp Pro Pro Ser
65                  70                  75                  80

Val Leu Ala Glu Phe Gly Val Gly Ser Val Ala Arg Asp Asp Ser Tyr
                85                  90                  95

Val His His Thr Pro Leu Met Lys Arg Ile Lys Ser Ala Val Asn Lys
            100                 105                 110

Val Met Pro Arg Gln Glu Trp Trp Ala Pro Pro Ser Trp Trp Ile Lys

```
            115                 120                 125
Ala Cys Ala Ile Leu Ala Ala Thr Leu Tyr Thr Asp Tyr Leu Trp Ile
        130                 135                 140

Ala Ser Gly Pro Thr Ile Leu Ala Ile Val Ile Gly Leu Leu Tyr
145                 150                 155                 160

Ala Ala Ile Gly Leu Asn Ile Gln His Asp Ala Asn His Gly Ser Val
                165                 170                 175

Ser Arg Asn Pro Met Val Asn Arg Leu Phe Gly Tyr Ser Gln Asp Trp
            180                 185                 190

Ile Gly Gly Ser Met Met Leu Trp Leu Arg Gln His Val Val Gly His
        195                 200                 205

His Thr His Cys Asn Asp Gln His Asp Pro Asp Val Lys Gly Gly
    210                 215                 220

Ser Val Leu Thr Leu Ser Arg Tyr Ser Leu Pro Met Glu Phe His His
225                 230                 235                 240

Ile Gln Gln Ile Tyr Phe Leu Pro Leu Glu Gln Leu Leu Gly Phe Gln
                245                 250                 255

Trp Val Phe Leu Asp Leu His Asp Leu Ile Glu Met Lys Tyr Lys Gly
            260                 265                 270

Glu Lys Leu Pro Glu Ser Tyr Arg Lys Glu Arg Asn Ile Ala Ile Gly
        275                 280                 285

Cys Arg Ile Phe Phe Phe Val Arg Lys Phe Val Pro Phe Ala Leu
    290                 295                 300

His Pro Ser Trp Tyr Thr Leu Leu Cys Thr Tyr Leu Trp Met Ala Thr
305                 310                 315                 320

Ala Ala Leu Tyr Leu Gly Phe Phe Phe Ile Leu Ser His Ile Phe Val
                325                 330                 335

Gly Ile Lys Ser Leu Pro Glu Asp Ala Asn Ile Asp Trp Ala Arg His
            340                 345                 350

Gln Ile Glu Ser Ser Ser Asn Val Cys Gly Asp Lys Leu Gly Tyr Ile
        355                 360                 365

Asn Gly Gly Leu Asn Tyr Gln Ile Glu His His Leu Phe Pro Arg Leu
370                 375                 380

Ser His Ala His Tyr Ser Lys Ile Gln Pro Val Val Gln Lys Val Cys
385                 390                 395                 400

Glu Lys Asn Gly Val Asn Tyr Lys His Phe Pro Thr Ile Ala Ser Asn
                405                 410                 415

Leu Gly Ser Thr Phe Arg Gln Leu Gly Ala Leu Gly Ala Val Ala Val
            420                 425                 430

Tyr Glu Phe Met Gly Gly Leu
        435

<210> SEQ ID NO 166
<211> LENGTH: 437
<212> TYPE: PRT
<213> ORGANISM: Artificial
<220> FEATURE:
<223> OTHER INFORMATION: delta-4 desaturase 88.8% sequence identity to
      SEQ ID NO 79

<400> SEQUENCE: 166

Met Pro Pro His Ser Arg Thr Lys Val Ser Asp Pro Glu Leu Ser Asp
1               5                   10                  15

Met Glu His Phe Thr Arg Glu Glu Ile Leu Asn His Thr Asn Asp Lys
            20                  25                  30
```

```
Leu Cys Ile Leu Glu Asp Gly Val Tyr Asp Leu Thr Asn Phe Arg Asp
         35                  40                  45
Lys His Pro Gly Gly Asp Val Leu Asp Phe Phe Pro Gly Gln Asp Ala
 50                  55                  60
Thr Pro His Phe Tyr Met Phe His Arg Tyr Glu Ser Leu Pro Ser Val
 65                  70                  75                  80
Leu Ala Glu Tyr Lys Val Gly Ser Ile Ala Arg Asp Asp Ser Tyr Val
                 85                  90                  95
Tyr Ala Thr Glu Leu Met Lys Gln Ile Lys Ser Ala Val Arg Lys Val
             100                 105                 110
Ile Pro Met Gln Glu Gly Trp Ala Pro Pro Ser Trp Tyr Ile Lys Ala
             115                 120                 125
Cys Ala Ile Leu Ile Ala Thr Leu Tyr Leu Asp Tyr Leu Trp Leu Leu
             130                 135                 140
Ser Gly Pro Thr Ile Pro Leu Ala Ile Val Ser Gly Leu Leu Tyr Ala
145                 150                 155                 160
Ala Ile Gly Leu Asn Ile Gln His Asp Ala Asn His Gly Ser Val Ser
                 165                 170                 175
Arg Asn Pro Met Val Asn Arg Leu Phe Gly Tyr Gly Gln Asp Trp Ile
             180                 185                 190
Gly Gly Ser Arg Leu Leu Trp Ile Arg Gln His Val Val Gly His His
             195                 200                 205
Thr His Cys Asn Arg His Gln His Asp Pro Asp Val Lys Gly Gly Ser
             210                 215                 220
Val Ile Gln Leu Ser Arg Tyr Asp Gly Trp Met Glu Phe His Ala Ile
225                 230                 235                 240
Gln Gln Tyr Tyr Phe Leu Pro Leu Glu Gln Leu Tyr Gly Phe Lys Trp
                 245                 250                 255
Val Phe Leu Gly Ala His Asp Leu Ile Glu Met Lys Trp Glu Gly Glu
             260                 265                 270
Lys Leu Pro Glu Leu Tyr Arg Lys Glu Arg Asn Ile Ala Ile Gly Leu
             275                 280                 285
Arg Val Phe Phe Phe Ala Arg Lys Phe Val Ile Pro Phe Ala Leu His
             290                 295                 300
Phe Ser Trp Tyr Thr Leu Leu Cys Val Tyr Leu Trp Val Ala Ile Ala
305                 310                 315                 320
Ala Leu Tyr Leu Gly Phe Phe Ile Leu Ser His Ile Phe Val Gly
                 325                 330                 335
Ala Lys Ser Leu Pro Glu Asp Gly Ser Val Glu Trp Ala Arg His Gln
             340                 345                 350
Ile Glu Ser Ser Ser Asn Val Cys Gly Glu Lys Leu Gly Ile Ser Asn
             355                 360                 365
Gly Gly Leu Asn Tyr Gln Ile Glu His His Leu Phe Pro Arg Met Ser
             370                 375                 380
His Ala His Tyr Ser Lys Ile Gln Pro Val Val Gln Lys Val Cys Glu
385                 390                 395                 400
Glu Met Gly Val Asn Tyr Lys Lys Phe Gly Thr Ile Gly Ser Asn Leu
                 405                 410                 415
Gly Ser Thr Phe Gln Gln Val Gly Ala Leu Gly Ala Val Ala Val Glu
             420                 425                 430
Phe Met Glu Gly Leu
             435
```

```
<210> SEQ ID NO 167
<211> LENGTH: 438
<212> TYPE: PRT
<213> ORGANISM: Artificial
<220> FEATURE:
<223> OTHER INFORMATION: delta-4 desaturase 88.8% sequence identity to
      SEQ ID NO 79

<400> SEQUENCE: 167
```

Met Pro Pro His Ser Ala Thr Lys Val Val Ser Ala Pro Glu Leu Ser
1               5                   10                  15

Asp Met Lys His Phe Ser Arg Glu Lys Ile Leu Asn His Glu Asn Asp
            20                  25                  30

Lys Ile Cys Ile Leu Glu Asp Gly Val Tyr Asp Leu Thr Asn Phe Arg
        35                  40                  45

Asp Lys His Pro Gly Gly Asp Val Leu Asp Leu Phe Pro Gly Gln Asp
    50                  55                  60

Ala Thr Pro His Phe Tyr Met Leu His Gln Tyr Glu Ser Leu Pro Ser
65                  70                  75                  80

Val Met Ala Glu Tyr Lys Val Gly Ser Val Ala Arg Asp Asp Lys Tyr
                85                  90                  95

Val His His Thr Pro Leu Met Lys Gln Ile Lys Ser Glu Val Arg Lys
            100                 105                 110

Val Met Pro Met Gln Glu Trp Trp Ala Pro Pro Ser Trp Tyr Ile Lys
        115                 120                 125

Ala Cys Ala Ile Leu Ala Ala Thr Leu Tyr Thr Asp Tyr Leu Trp Ile
    130                 135                 140

Ala Ser Gly Pro Thr Ile Pro Leu Ala Ile Val Ser Gly Leu Leu Phe
145                 150                 155                 160

Ala Ala Ile Gly Leu Asn Ile Gln His Asp Ala Asn His Gly Ser Val
                165                 170                 175

Ser Arg Asn Pro Met Val Asn Arg Leu Phe Gly Tyr Ser Gln Asp Trp
            180                 185                 190

Ile Gly Gly Asn Arg Met Leu Trp Ile Arg Gln His Val Val Gly His
        195                 200                 205

His Leu His Ser Asn Arg His Asp His Asp Pro Asp Leu Lys Gly Gly
    210                 215                 220

Ser Val Ile Gln Leu Ser Arg Tyr Ser Leu Pro Lys Glu Phe His His
225                 230                 235                 240

Leu Gln Gln Tyr Tyr Phe Leu Pro Leu Ile Gln Leu Tyr Gly Phe Gln
                245                 250                 255

Trp Val Phe Leu Gly Ala His Asp Leu Ile Glu Trp Arg Trp Lys Gly
            260                 265                 270

Glu Lys Leu Pro Pro Ser Tyr Arg Pro Glu Phe Asn Ile Ala Ile Gly
        275                 280                 285

Cys Arg Ile Phe Phe Phe Ile Arg Lys Phe Val Val Pro Phe Ala Leu
    290                 295                 300

His Pro Ser Trp Tyr Thr Leu Leu Cys Thr Tyr Leu Trp Met Ala Thr
305                 310                 315                 320

Ala Ala Leu Tyr Leu Gly Phe Phe Ile Leu Ser His Leu Phe Val
                325                 330                 335

Gly Val Lys Ser Leu Pro Glu Asp Ala Asn Ile Glu Trp Ala Arg Arg
            340                 345                 350

Gln Ile Glu Ser Ser Asn Val Gly Gly Glu Lys Leu Gly Ile Leu
        355                 360                 365

```
Asn Gly Gly Leu Asn Tyr Gln Ile Glu His His Leu Phe Pro Arg Met
    370                 375                 380

Ser His Ala His Tyr Ser Pro Ile Gln Pro Val Val Gln Lys Val Cys
385                 390                 395                 400

Glu Glu Asn Gly Val Asn Tyr Lys Lys Phe Gly Thr Ile Gly Ser Asn
                405                 410                 415

Leu Gly Ser Thr Phe Arg Gln Val Lys Ala Leu Gly Ser Arg Ala Thr
                420                 425                 430

Glu Phe Leu Glu Gly Leu
                435

<210> SEQ ID NO 168
<211> LENGTH: 438
<212> TYPE: PRT
<213> ORGANISM: Artificial
<220> FEATURE:
<223> OTHER INFORMATION: delta-4 desaturase 88.8% sequence identity to
      SEQ ID NO 79

<400> SEQUENCE: 168

Met Pro Pro His Ser Arg Arg Lys Val Ser Asp Ala Pro Glu Leu Arg
1               5                   10                  15

Asp Met Lys His Phe Ser Arg Glu Glu Ile Leu Asp His Asn Asn Asp
                20                  25                  30

Lys Tyr Cys Ile Leu Glu Asp Gly Val Tyr Asp Leu Thr Ala Phe Arg
            35                  40                  45

Asp Lys His Pro Gly Gly Glu Val Leu Asp Phe Phe Pro Gly Gln Asp
        50                  55                  60

Ala Thr Pro His Phe Tyr Met Tyr His Gln Tyr Glu Ser Pro Pro Ser
65                  70                  75                  80

Val Leu Ala Glu Tyr Lys Val Ser Val Ala Arg Asp Asp Ser Phe
                85                  90                  95

Val Tyr His Thr Glu Leu Met Lys Gln Ile Cys Ala Ala Val Asn Lys
                100                 105                 110

Val Met Pro Met Gln Ser Trp Trp Ala Pro Pro Ser Trp Tyr Ile Lys
            115                 120                 125

Ala Cys Ala Leu Leu Ala Ala Thr Leu Tyr Leu Asp Tyr Leu Trp Ile
        130                 135                 140

Ala Ser Gly Pro Thr Ile Leu Leu Ala Ile Val Ser Gly Leu Leu Tyr
145                 150                 155                 160

Ala Ala Ile Gly Leu Asn Ile Gln His Asp Ala Asn His Gly Ala Leu
                165                 170                 175

Ser Arg Asn Pro Met Val Asn Arg Leu Phe Gly Tyr Ser Gln Asp Trp
                180                 185                 190

Ile Gly Gly Ser Arg Met Leu Trp Ile Arg Gln His Val Val Asn His
            195                 200                 205

His Thr His Cys Asn Arg His Asp His Asp Pro Asp Val Lys Gly Gly
        210                 215                 220

Ser Val Ile Gln Leu Lys Arg Tyr Ser Leu Pro Leu Pro Phe His His
225                 230                 235                 240

Ile Gln Gln Tyr Tyr Phe Leu Pro Leu Ile Gln Leu Leu Gly Phe Gln
                245                 250                 255

Trp Val Phe Leu Gly Leu His Glu Leu Ile Glu Met Lys Tyr Lys Gly
            260                 265                 270

Glu Lys Leu Pro Glu Leu Tyr Arg Pro Glu Arg Asn Ile Ala Ile Gly
        275                 280                 285
```

```
Cys Arg Val Phe Phe Phe Ile Arg Lys Phe Ala Val Pro Phe Ala Leu
290                 295                 300

His Phe Ser Trp His Thr Leu Leu Cys Thr Tyr Leu Trp Met Ala Ile
305                 310                 315                 320

Ala Ala Phe Tyr Leu Cys Phe Phe Ile Leu Ser His Ile Phe Val
            325                 330                 335

Gly Ala Gly Ser Leu Gly Glu Glu Ala Asn Ile Asp Trp Ala Arg His
            340                 345                 350

Gln Ile Glu Ser Ser Ser Asn Val Cys Gly Glu Lys Leu Gly Ile Ser
        355                 360                 365

Asn Gly Gly Leu Asn Tyr Gln Ile Glu His His Leu Phe Pro Arg Met
370                 375                 380

Ser His Ala His Tyr Ser Lys Ile Gln Pro Val Val Gln Lys Val Cys
385                 390                 395                 400

Glu Glu Met Gly Val Asn Tyr Lys Lys Phe Gly Thr Ile Leu Ser Asn
            405                 410                 415

Leu Asp Ser Thr Leu Arg Gln Val Lys Ala Leu Gly Ser Val Pro Val
            420                 425                 430

Glu Tyr Met Ala Gly Leu
        435
```

<210> SEQ ID NO 169
<211> LENGTH: 439
<212> TYPE: PRT
<213> ORGANISM: Artificial
<220> FEATURE:
<223> OTHER INFORMATION: delta-4 desaturase 88.5% sequence identity to SEQ ID NO 79

<400> SEQUENCE: 169

```
Met Pro Pro His Ser Arg Ser Glu Val Ser Asp Asp Pro Glu Leu Ser
1               5                   10                  15

Asp Leu Met Lys His Phe Thr Arg Glu Glu Ile Leu Asn His Thr Asn
            20                  25                  30

Asp Asp Leu Cys Ile Leu Gly Asp Gly Val Tyr Asp Leu Thr Asn Phe
        35                  40                  45

Arg Asp Lys His Pro Gly Gly Glu Val Leu Asp Phe Phe Pro Gly Arg
50                  55                  60

Asp Ala Thr Pro His Phe Phe Met Leu His Gln Arg Glu Trp Leu Pro
65                  70                  75                  80

Ser Val Leu Ala Glu Tyr Lys Val Gly Ser Val Ala Arg Asp Asp Ser
            85                  90                  95

Tyr Val Tyr His Glu Pro Gly Met Lys Gln Ile Lys Ser Ala Val Arg
            100                 105                 110

Lys Val Met Pro Met Gln Glu Gly Trp Ala Pro Pro Ser Trp Tyr Ile
        115                 120                 125

Lys Ala Cys Ala Ile Leu Val Ala Thr Leu Tyr Thr Asp Tyr Leu Trp
130                 135                 140

Ile Ala Ser Gly Pro Thr Ile Phe Leu Ala Ile Val Ser Gly Leu Leu
145                 150                 155                 160

Tyr Ala Ala Ile Gly Leu Asn Ile Gln His Asp Ala Asn His Gly Ser
            165                 170                 175

Val Ser Arg Asn Pro Met Val Asn Arg Leu Phe Gly Tyr Ser Gln Asp
            180                 185                 190

Trp Ile Gly Gly Ser Arg Met Leu Trp Ile Arg Gln His Val Val Gly
```

```
            195                 200                 205
His His Thr His Cys Asn Arg Ile Gln His Asp Pro Asp Val Lys Gly
    210                 215                 220

Gly Ser Ala Ile Gln Leu Ser Arg Tyr Ser Leu Trp Met Glu Trp His
225                 230                 235                 240

His Ile Gln Gln Ile Tyr Phe Leu Pro Leu Asp Gln Leu Leu Gly Phe
                245                 250                 255

Gln Trp Ile Phe Leu Gly Leu His Asp Leu Ile Glu Trp Lys Tyr Glu
            260                 265                 270

Gly Glu Pro Leu Pro Glu Ser Tyr Arg Lys Glu Arg Asn Pro Ala Ile
        275                 280                 285

Gly Leu Arg Val Phe Phe Ile Arg Lys Phe Val Ile Pro Phe Ala
    290                 295                 300

Leu His Pro Ser Trp Tyr Thr Leu Leu Cys Thr Cys Leu Trp Met Ala
305                 310                 315                 320

Thr Ala Ser Leu Tyr Leu Gly Phe Phe Phe Ile Leu Ser His Ile Phe
                325                 330                 335

Val Gly Ala Lys Ser Leu Pro Glu Asp Ala Ser Val Glu Trp Ala Arg
            340                 345                 350

His Gln Ile Glu Thr Ser Ser Asn Val Gly Gly Glu Lys Leu Gly Ile
        355                 360                 365

Ser Asn Gly Gly Leu Asn Phe Gln Ile Glu His Leu Phe Pro Arg
    370                 375                 380

Met Ser His Ala His Tyr Ser Lys Ile Gln Pro Val Val Gln Lys Val
385                 390                 395                 400

Cys Glu Glu Asn Gly Ile Asn Tyr Lys His Phe Gly Thr Ile Leu Ser
                405                 410                 415

Asn Leu Gly Ser Thr Phe Arg Gln Val Lys Ala Leu Gly Ser Val Pro
            420                 425                 430

Val Glu Phe Met Ala Lys Leu
        435

<210> SEQ ID NO 170
<211> LENGTH: 437
<212> TYPE: PRT
<213> ORGANISM: Artificial
<220> FEATURE:
<223> OTHER INFORMATION: delta-4 desaturase 88.3% sequence identity to
      SEQ ID NO 79

<400> SEQUENCE: 170

Met Pro Pro His Gly Arg Thr Lys Val Gly Asp Pro Glu Leu Ser Asp
1               5                   10                  15

Met Lys His Phe Thr Arg Glu Glu Ile Leu Asn His Thr Asn Asp Lys
            20                  25                  30

Tyr Cys Ile Leu Glu Asp Gly Val Tyr Asp Ala Ser Ala Phe Arg Asp
        35                  40                  45

Lys His Pro Gly Gly Asp Phe Leu Asp Phe Phe Pro Gly Gln Asp Ala
    50                  55                  60

Thr Pro Gly Phe Tyr Met Phe His Gln His Glu Trp Pro Pro Ser Val
65                  70                  75                  80

Leu Ala Glu Tyr Lys Val Gly Ser Val Ala Arg Asp Asp Ser Tyr Val
                85                  90                  95

Tyr His Thr Pro Leu Met Lys Gln Ile Cys Ser Ala Val Arg Lys Val
            100                 105                 110
```

Met Pro Lys Gly Glu Trp Trp Ala Pro Ser Trp Tyr Ile Lys Ala
            115                 120                 125

Cys Ala Ile Leu Ala Ala Thr Leu Tyr Leu Asp Tyr Leu Trp Ile Ala
130                 135                 140

Ser Gly Pro Thr Ile Pro Leu Ala Ile Val Ile Gly Leu Leu Tyr Ala
145                 150                 155                 160

Ala Ile Gly Leu Asn Ile Gln His Asp Ala Asn His Gly Ala Val Ser
                165                 170                 175

Arg Asn Pro Met Val Asn Arg Leu Phe Gly Tyr Ser Gln Asp Trp Ile
            180                 185                 190

Gly Gly Ser Arg Leu Leu Trp Ile Arg Gln His Val Val Gly His His
        195                 200                 205

Thr His Cys Asn Asp Val Gln His Asp Pro Asp Leu Lys Gly Gly Ser
    210                 215                 220

Val Ile Thr Leu Ser Arg Thr Ser Leu Pro Lys Glu Phe His His Leu
225                 230                 235                 240

Gln Gln Tyr Tyr Phe Leu Pro Leu Glu Ala Leu Tyr Gly Phe Gln Trp
                245                 250                 255

Val Phe Leu Gly Leu His Asp Leu Ile Glu Met Lys Tyr Lys Gly Glu
            260                 265                 270

Lys Leu Ser Pro Ser Tyr Arg Lys Leu Arg Asn Ile Ala Ile Gly Leu
        275                 280                 285

Arg Ile Phe Phe Phe Ala Arg Lys Phe Val Ile Pro Phe Ala Leu His
    290                 295                 300

Phe Ser Trp Tyr Thr Leu Leu Cys Thr Cys Ala Trp Met Ala Thr Ala
305                 310                 315                 320

Thr Leu Tyr Leu Gly Phe Phe Phe Ile Leu Ser His Ile Phe Val Gly
                325                 330                 335

Ala Lys Ser Leu Pro Glu Asp Gly Asn Val Asp Trp Ala Arg His Gln
            340                 345                 350

Ile Glu Ser Ser Ser Asn Val Cys Gly Glu Lys Leu Gly His Leu Asn
        355                 360                 365

Gly Gly Leu Asn Tyr Gln Ile Glu His His Leu Phe Pro Arg Met Ser
    370                 375                 380

His Ala His Tyr Ser Thr Ile Glu Pro Val Val Gln Lys Val Cys Glu
385                 390                 395                 400

Glu Asn Gly Val Lys Tyr Lys Phe Gly Thr Ile Leu Ser Asn Leu
                405                 410                 415

Asp Ser Thr Phe Lys Gln Val Lys Ala Leu Gly Ser Val Ala Val Glu
            420                 425                 430

Phe Met Glu Gly Leu
        435

<210> SEQ ID NO 171
<211> LENGTH: 438
<212> TYPE: PRT
<213> ORGANISM: Artificial
<220> FEATURE:
<223> OTHER INFORMATION: delta-4 desaturase 88.3% sequence identity to
      SEQ ID NO 79

<400> SEQUENCE: 171

Met Pro Pro His Ser Arg Lys Lys Gly Ser Asp Pro Glu Leu Ser Asp
1               5                   10                  15

Leu Ala Lys His Phe Thr Arg Glu Arg Ile Leu Asn His Thr Arg Asp
            20                  25                  30

```
Lys Tyr Cys Ile Leu Glu Asp Gly Val Tyr Asp Leu Thr Asn Phe Arg
         35                  40                  45

Asp Lys His Pro Gly Gly Asp Val Leu Asp Phe Phe Pro Gly Gln Asp
         50                  55                  60

Ala Thr Pro His Phe Tyr Met Leu His Gln Tyr Glu Trp Pro Pro Ser
 65              70                  75                      80

Val Leu Ala Arg Tyr Gly Val Gly Ser Val Ala Arg Asp Asp Ser Tyr
                 85                  90                  95

Val Tyr Ala Asp Pro Leu Met Leu Gln Ile Cys Ser Ala Val Asn Lys
                100                 105                 110

Val Ile Pro Met Gln Glu Trp Trp Ala Pro Pro Ser Trp Ile Lys
            115                 120                 125

Ala Cys Ala Ile Leu Val Ala Thr Leu Phe Thr Asp Tyr Leu Trp Leu
            130                 135                 140

Ala Lys Gly Pro Thr Ile Pro Leu Ala Ile Val Ser Gly Leu Leu Phe
145                 150                 155                 160

Ala Ala Ile Gly Leu Asn Ile Gln His Asp Ala Asn His Gly Ser Val
                165                 170                 175

Ser Arg Asn Pro Met Val Asn Arg Leu Phe Gly Tyr Ser Gln Asp Trp
            180                 185                 190

Ile Gly Gly Ser Arg Met Leu Trp Leu Arg Gln His Val Val Gly His
        195                 200                 205

His Thr His Cys Asn Arg Ile Asp His Asp Pro Asp Val Lys Gly Gly
        210                 215                 220

Ser Val Ile Arg Leu Ser Arg Tyr Ser Leu Pro Lys Glu Phe His His
225                 230                 235                 240

Ile Gln Gln Ile Tyr Phe Leu Pro Leu Ile Gln Leu Gly Phe Gln
                245                 250                 255

Trp Val Phe Leu Gly Leu His Asp Leu Ile Glu Met Arg Tyr Lys Gly
            260                 265                 270

Glu Lys Leu Pro Glu Ser Tyr Arg Lys Glu Arg Asn Pro Ala Val Gly
        275                 280                 285

Leu Arg Ile Phe Phe Ala Arg Lys Phe Val Ile Pro Phe Ala Leu
        290                 295                 300

His Phe Ser Trp Tyr Thr Leu Leu Cys Thr Cys Ala Trp Met Ala Ile
305                 310                 315                 320

Ala Ala Leu Tyr Leu Gly Phe Phe Ile Leu Ser His Ile Phe Val
                325                 330                 335

Gly Ile Lys Ser Leu Gly Pro Asp Ala Asn Val Asp Trp Ala Arg His
            340                 345                 350

Gln Ile Glu Ser Ser Asn Val Cys Gly Glu Trp Leu Gly Ile Leu
        355                 360                 365

Asn Gly Gly Leu Asn Tyr Gln Ile Glu His His Leu Phe Pro Arg Met
    370                 375                 380

Asn His Ala His Tyr Ser Lys Ile Gln Pro Ile Val Gln Lys Val Cys
385                 390                 395                 400

Glu Glu Asn Gly Val Asn Tyr Lys His Phe Gly Thr Ile Leu Ser Asn
                405                 410                 415

Leu Asp Ser Thr Phe Arg Gln Ile Lys Ala Leu Gly Ser Arg Ala Val
            420                 425                 430

Glu Phe Met Glu Gly Leu
            435
```

```
<210> SEQ ID NO 172
<211> LENGTH: 440
<212> TYPE: PRT
<213> ORGANISM: Artificial
<220> FEATURE:
<223> OTHER INFORMATION: delta-4 desaturase 88.3% sequence identity to
      SEQ ID NO 79

<400> SEQUENCE: 172

Met Pro Pro His Ser Arg Thr Lys Gly Ser Asp Val Ala Glu Leu Ser
1               5                   10                  15

Asp Leu Met Lys His Phe Thr Arg Thr Glu Ile Ala Asn His Thr Arg
            20                  25                  30

Asp Lys Tyr Cys Ile Leu Glu Asp Gly Val Tyr Asp Ala Asn Asn Phe
        35                  40                  45

Arg Asp Lys His Pro Gly Gly Asp Val Ile Asp Ile Phe Pro Gly Gln
    50                  55                  60

Asp Ala Thr Pro His Phe Phe Glu Leu His Gln Tyr Ala Ser Pro Pro
65                  70                  75                  80

Ser Val Leu Ser Glu Tyr Lys Val Gly Ser Val Ala Arg Asp Asp Ser
                85                  90                  95

Tyr Val Tyr His Thr Pro Leu Met Lys Gln Ile Lys Ser Ala Val Arg
            100                 105                 110

Lys Val Met Pro Lys Gly Glu Gly Trp Ala Pro Pro Ser Trp Tyr Ile
        115                 120                 125

Lys Ala Cys Ala Ile Leu Ala Ala Thr Leu Tyr Leu Asp Tyr Tyr Trp
    130                 135                 140

Ile Ala Arg Gly Pro Thr Ile Pro Leu Ala Ile Val Ser Gly Leu Leu
145                 150                 155                 160

Tyr Ala Ala Ile Gly Leu Asn Ile Gln His Asp Ala Asn His Gly Ser
                165                 170                 175

Val Ser Arg Asn Pro Met Val Asn Arg Leu Phe Gly Tyr Ser Gln Asp
            180                 185                 190

Trp Ile Gly Gly Ser Arg Met Leu Trp Ile Arg Gln His Val Val Gly
        195                 200                 205

His His Thr His Cys Asn Arg His Asp His Asp Pro Asp Val Lys Gly
    210                 215                 220

Gly Ser Val Ile Thr Leu Ser Arg Tyr Ser Ile Pro Lys Glu Trp His
225                 230                 235                 240

His Ile Gln Gln Leu Tyr Phe Leu Pro Leu Ile Gln Leu Tyr Gly Phe
                245                 250                 255

Gln Trp Val Phe Leu Asp Leu His Asp Leu Ile Glu Met Lys Trp Glu
            260                 265                 270

Gly Glu Pro Leu Pro Glu Ser Tyr Arg Lys Glu Arg Asn Pro Ala Ile
        275                 280                 285

Gly Leu Arg Leu Phe Phe Phe Val Arg Lys Ile Val Pro Phe Ala
    290                 295                 300

Leu His Phe Ser Trp Tyr Thr Leu Leu Cys Thr Tyr Leu Trp Met Ala
305                 310                 315                 320

Ile Gly Ala Leu Tyr Leu Cys Phe Phe Ile Leu Ser His Asn Phe
                325                 330                 335

Val Gly Ile Lys Ser Ile Pro Glu Asp Ala Ser Ile Asp Trp Ala Arg
            340                 345                 350

His Gln Ile Glu Ser Ser Ser Asn Val Gly Gly Glu Trp Leu Gly Tyr
        355                 360                 365
```

```
Leu Asn Gly Gly Leu Asn Tyr Gln Ile Glu His His Leu Phe Pro Arg
        370                 375                 380

Met Ser His Ala His Tyr Ser Lys Ile Gln Pro Val Val Gln Lys Val
385                 390                 395                 400

Cys Glu Glu Asn Gly Val Asn Tyr Lys Lys Phe Gly Thr Ile Leu Ser
                405                 410                 415

Asn Leu Asp Ser Thr Phe Arg His Val Lys Ala Leu Gly Ala Val Ala
                420                 425                 430

Val Tyr Glu Phe Met Glu Gly Leu
            435                 440

<210> SEQ ID NO 173
<211> LENGTH: 440
<212> TYPE: PRT
<213> ORGANISM: Artificial
<220> FEATURE:
<223> OTHER INFORMATION: delta-4 desaturase 88.3% sequence identity to
      SEQ ID NO 79

<400> SEQUENCE: 173

Met Pro Pro His Gly Arg Thr Lys Val Ser Asp Val Pro Glu Leu Ser
1               5                   10                  15

Asp Leu Ala Lys His Phe Ser Arg Glu Glu Ile Leu Asn His Thr Asn
            20                  25                  30

Asp Lys Tyr Cys Ile Leu Glu Asp Gly Val Tyr Asp Ala Thr Asn Phe
        35                  40                  45

Arg Asp Lys His Pro Gly Gly Asp Val Ile Asp Phe Phe Pro Gly Arg
50                  55                  60

Asp Ala Thr Pro His Phe Trp Met Leu His Arg Tyr Glu Trp Pro Pro
65                  70                  75                  80

Ser Val Leu Ala Glu Tyr Gly Val Gly Ser Val Ala Arg Asp Asp Lys
                85                  90                  95

Phe Val His His Thr Ala Leu Met Lys Gln Ile Lys Ser Ala Val Arg
            100                 105                 110

Ala Val Leu Pro Met Gln Glu Trp Trp Ala Pro Pro Ser Trp Tyr Ile
        115                 120                 125

Lys Ala Cys Ala Ile Leu Ala Ala Thr Leu Phe Thr Asp Tyr Leu Trp
130                 135                 140

Ile Ala Ser Gly Pro Thr Ile Pro Leu Ala Ile Val Leu Gly Leu Leu
145                 150                 155                 160

Tyr Ala Trp Ile Gly Leu Asn Ile Gln His Asp Ala Asn His Gly Ser
                165                 170                 175

Val Ser Arg Asn Pro Val Val Asn Arg Leu Phe Gly Tyr Ser Gln Asp
            180                 185                 190

Trp Ile Gly Gly Gly Arg Met Leu Trp Ile Arg Gln His Val Val Gly
        195                 200                 205

His His Thr His Cys Asn Arg His Asp His Pro Asp Val Lys Gly
            210                 215                 220

Gly Ser Val Ile Thr Leu Lys Arg Val Ser Leu Pro Leu Glu Trp His
225                 230                 235                 240

His Ile Gln Gln Tyr Tyr Phe Leu Pro Leu Ile Gln Leu Leu Gly Phe
                245                 250                 255

Gln Trp Val Phe Leu Gly Leu Asn Asp Leu Ile Glu Trp Lys Tyr Lys
            260                 265                 270

Gly Glu Lys Leu Ser Glu Ile Cys Arg Lys Glu Arg Asn Ile Ala Ile
```

```
                275                 280                 285
Gly Leu Arg Val Phe Phe Val Arg Lys Phe Val Pro Phe Ala
    290                 295                 300

Leu His Phe Ser Trp His Thr Leu Leu Cys Thr Tyr Leu Trp Met Ala
305                 310                 315                 320

Ile Ala Ala Leu Tyr Leu Gly Phe Phe Ile Leu Ser His Ile Phe
                325                 330                 335

Val Gly Ala Lys Ser Leu Gly Glu Asp Ala Asn Ile Asp Trp Ala Arg
                340                 345                 350

His Gln Ile Glu Thr Ser Ser Asn Val Gly Gly Asp Lys Leu Gly Tyr
                355                 360                 365

Ser Asn Gly Gly Leu Asn Tyr Gln Ile Glu His His Leu Phe Pro Arg
    370                 375                 380

Met Asn His Ala His Tyr Ala Lys Ile Gln Pro Val Val Gln Lys Val
385                 390                 395                 400

Cys Glu Glu Asn Gly Val Lys Tyr Lys His Phe Gly Thr Ile Leu Ser
                405                 410                 415

Asn Leu Asp Ser Thr Phe Lys Gln Val Lys Ala Leu Gly Ser Val Ala
                420                 425                 430

Val Tyr Glu Phe Leu Ala Gly Leu
                435                 440

<210> SEQ ID NO 174
<211> LENGTH: 440
<212> TYPE: PRT
<213> ORGANISM: Artificial
<220> FEATURE:
<223> OTHER INFORMATION: delta-4 desaturase 88.3% sequence identity to
      SEQ ID NO 79

<400> SEQUENCE: 174

Met Pro Pro His Ala Gly Thr Lys Val Ser Asp Asp Pro Glu Leu Arg
1               5                   10                  15

Asp Leu Met Lys His Phe Thr Arg Glu Glu Ile Leu Asn His Thr Asn
                20                  25                  30

Pro Lys Tyr Cys Ile Leu Gly Asp Gly Val Tyr Asp Ala Thr Asn Phe
            35                  40                  45

Arg Asp Lys His Pro Gly Gly Asp Val Leu Asp Phe Phe Pro Gly Gln
50                  55                  60

Asp Ala Thr Pro Gly Phe Tyr Met Phe His Gln Tyr Glu Ser Leu Pro
65                  70                  75                  80

Gly Leu Leu Ala Arg Tyr Lys Val Gly Ser Val Ala Arg Asp Asp Ser
                85                  90                  95

Tyr Thr His His Asp Pro Leu Met Lys Gln Leu Cys Ser Ala Val Arg
                100                 105                 110

Lys Val Met Pro Met Gln Glu Trp Trp Ala Pro Pro Ser Trp Tyr Ile
            115                 120                 125

Lys Ala Cys Ala Ile Leu Ile Ala Thr Leu Tyr Leu Asp Tyr Leu Met
            130                 135                 140

Ile Ala Ser Gly Pro Thr Ile Pro Leu Ala Ile Val Leu Gly Leu Leu
145                 150                 155                 160

Phe Ala Ala Ile Gly Leu Asn Ile Gln His Asp Ala Asn His Gly Ser
                165                 170                 175

Val Ser Arg Asn Pro Met Val Asn Arg Leu Phe Gly Tyr Ala Gln Asp
                180                 185                 190
```

```
Trp Ile Gly Gly Ser Arg Met Leu Trp Ile Arg Gln His Val Val Gly
            195                 200                 205

His His Thr His Cys Asn Asp Val Gln His Asp Pro Asp Val Lys Gly
    210                 215                 220

Gly Ser Val Ile Gln Leu Ser Arg Tyr Ser Leu Pro Lys Pro Phe His
225                 230                 235                 240

His Leu Gln Gln Tyr Tyr Phe Leu Pro Leu Glu Gln Leu Tyr Gly Phe
                245                 250                 255

Gln Trp Val Phe Leu Gly Leu His Asp Leu Ile Glu Met Lys Tyr Lys
            260                 265                 270

Gly Glu Lys Leu Pro Glu Ser Tyr Arg Lys Glu Phe Asn Pro Ala Ile
        275                 280                 285

Gly Leu Arg Val Gly Phe Phe Ile Arg Phe Phe Val Val Pro Phe Ala
    290                 295                 300

Leu Gln Phe Ser Trp Tyr Thr Leu Leu Cys Thr Cys Leu Trp Met Ala
305                 310                 315                 320

Val Ala Ala Phe Tyr Leu Gly Phe Phe Ile Leu Ser His Ile Phe
                325                 330                 335

Val Gly Val Lys Ser Leu Pro Glu Asp Ala Asn Ile Asp Trp Ala Arg
            340                 345                 350

His Gln Ile Glu Ser Ser Asn Val Cys Gly Glu Lys Leu Gly Ile
        355                 360                 365

Ser Asn Gly Gly Leu Asn Tyr Gln Ile Glu His His Leu Phe Pro Arg
    370                 375                 380

Leu Ser His Ala His Tyr Ala Pro Ile Gln Pro Val Val Gln Lys Val
385                 390                 395                 400

Cys Glu Asp Asn Gly Ile Asn Tyr Lys Lys Phe Gly Thr Ile Leu Ser
                405                 410                 415

Asn Leu Asp Ser Thr Phe Arg Gln Val Lys Ala Leu Gly Ala Val Ala
            420                 425                 430

Thr Tyr Glu Phe Leu Ala Gly Leu
        435                 440

<210> SEQ ID NO 175
<211> LENGTH: 439
<212> TYPE: PRT
<213> ORGANISM: Artificial
<220> FEATURE:
<223> OTHER INFORMATION: delta-4 desaturase 88.3% sequence identity to
      SEQ ID NO 79

<400> SEQUENCE: 175

Met Pro Pro His Ser Arg Thr Lys Val Ser Asp Pro Glu Leu Ser Asp
1               5                   10                  15

Leu Met Lys His Phe Thr Arg Glu Glu Ile Leu Asn His Asn Asn Asp
            20                  25                  30

Lys Tyr Cys Ile Leu Glu Asp Gly Val Tyr Asp Leu Thr Asn Phe Arg
        35                  40                  45

Asp Lys His Pro Gly Gly Asp Val Leu Asp Leu Phe Pro Gly Gln Asp
    50                  55                  60

Ala Thr Pro Gly Phe Tyr Met Leu His Gln His Val Ser Leu Pro Ser
65                  70                  75                  80

Val Leu Ala Glu Tyr Lys Val Gly Ser Val Asp Arg Asp Asp Ser Tyr
                85                  90                  95

Val Tyr His Thr Pro Leu Gln Lys Gln Leu Cys Ser Ala Val Arg Lys
            100                 105                 110
```

Val Ile Pro Met Gln Glu Trp Trp Ala Pro Ser Trp Tyr Ile Lys
            115                 120                 125

Ala Cys Ala Ile Leu Ala Ala Thr Leu Tyr Thr Asp Tyr Leu Trp Ile
130                 135                 140

Ala Ser Gly Pro Thr Ile Pro Leu Ala Ile Val Ser Gly Leu Leu Tyr
145                 150                 155                 160

Ala Ala Ile Gly Leu Asn Ile Gln His Asp Ala Asn His Gly Val
            165                 170                 175

Ser Arg Asn Pro Ala Val Asn Tyr Leu Phe Gly Tyr Ala Gln Asp Trp
            180                 185                 190

Ile Gly Gly Gly Arg Met Leu Trp Ile Gln Lys His Val Val Asn His
            195                 200                 205

His Ile His Thr Asn Asp Val Gln His Asp Pro Asp Val Lys Gly Gly
            210                 215                 220

Ser Ala Ile Lys Leu Lys Arg Tyr Ser Leu Trp Lys Glu Phe His His
225                 230                 235                 240

Ile Gln Gln Tyr Tyr Phe Leu Pro Leu Ile Gln Leu Gly Phe Gln
            245                 250                 255

Trp Val Phe Leu Gly Leu His Asp Leu Ile Glu Met Lys Tyr Lys Gly
            260                 265                 270

Glu Pro Leu Pro Pro Ser Ala Arg Pro Glu Arg Gly Ile Ala Ile Gly
            275                 280                 285

Leu Arg Val Phe Phe Phe Ile Arg Lys Phe Val Leu Pro Phe Ala Leu
            290                 295                 300

His Phe Ser Trp Tyr Thr Leu Leu Cys Ile Tyr Leu Trp Met Ala Ile
305                 310                 315                 320

Ala Ala Leu Tyr Leu Gly Phe Phe Val Leu Ser His Ile Phe Val
            325                 330                 335

Gly Ala Lys Ser Leu Pro Pro Asp Ala Asn Ile Asp Trp Ala Arg His
            340                 345                 350

Gln Ile Glu Ser Ser Ser Asn Val Cys Gly Glu Lys Leu Gly Ile Ser
            355                 360                 365

Asn Gly Gly Leu Asn Tyr Gln Ile Glu His His Leu Phe Pro Arg Met
            370                 375                 380

Asn His Ala His Tyr Ser Lys Ile Gln Pro Ile Val Gln Arg Ile Cys
385                 390                 395                 400

Glu Asp Asn Gly Val Asn Tyr Lys Lys Phe Pro Thr Ile Gly Ser Asn
            405                 410                 415

Leu Asp Ser Leu Phe Ser Gln Val Lys Ala Leu Gly Ser Val Ala Ile
            420                 425                 430

Tyr Glu Phe Met Gly Gly Leu
            435

<210> SEQ ID NO 176
<211> LENGTH: 439
<212> TYPE: PRT
<213> ORGANISM: Artificial
<220> FEATURE:
<223> OTHER INFORMATION: delta-4 desaturase 88.1% sequence identity to
      SEQ ID NO 79

<400> SEQUENCE: 176

Met Pro Pro His Ser Arg Lys Lys Val Gly Ser Asp Pro Glu Leu Ser
1               5                   10                  15

Asp Met Lys His Phe Thr Arg Glu Glu Lys Leu Asn His Thr Asn Asp

```
                20                  25                  30
Lys Tyr Cys Ile Leu Gly Asp Gly Val Tyr Asp Leu Thr Asn Phe Arg
                35                  40                  45
Asp Lys His Pro Gly Gly Asp Val Leu Ser Phe Phe Pro Gly Gln Asp
                50                  55                  60
Ala Thr Pro His Phe Phe Met Leu His Arg Lys Glu Ser Pro Pro Ser
65                  70                  75                  80
Val Leu Ala Glu Tyr Lys Val Gly Ser Val Glu Arg Asp Asp Lys Tyr
                85                  90                  95
Thr Tyr His Thr Pro Leu Met Lys Gln Ile Lys Ala Ala Val Arg Lys
                100                 105                 110
Val Met Pro Arg Gly Glu Trp Trp Ala Pro Ser Trp Tyr Ile Lys
                115                 120                 125
Ala Cys Ala Ile Leu Ala Ala Thr Leu Tyr Thr Asp Trp Leu Trp Leu
                130                 135                 140
Ala Ser Gly Pro Thr Ile Pro Leu Ala Ile Val Ser Gly Leu Leu Tyr
145                 150                 155                 160
Ala Ala Ile Gly Leu Asn Ile Gln His Asp Ala Asn His Gly Ser Ile
                165                 170                 175
Ser Arg Asn Pro Val Val Asn Arg Leu Phe Gly Tyr Ser Gln Asp Trp
                180                 185                 190
Ile Gly Gly Ser Met Met Leu Trp Ile Arg Glu His Val Val Gly His
                195                 200                 205
His Thr His Cys Asn Arg His Gln His Asp Pro Asp Val Lys Gly Gly
                210                 215                 220
Ser Val Ile Thr Leu Ser Pro Thr Asp Leu Trp Leu Pro Phe His His
225                 230                 235                 240
Ile Gln Gln Tyr Tyr Phe Leu Pro Leu Asp Gln Leu Tyr Gly Phe Gln
                245                 250                 255
Trp Val Phe Leu Gly Leu His Glu Leu Ile Glu Met Lys Tyr Lys Gly
                260                 265                 270
Glu Pro Leu Pro Glu Ser Tyr Arg Lys Glu Arg Asn Pro Ala Ile Gly
                275                 280                 285
Cys Lys Val Phe Phe Phe Ile Arg Lys Phe Ala Val Pro Phe Trp Leu
                290                 295                 300
Gln Pro Ser Trp Tyr Thr Leu Leu Cys Val Tyr Leu Trp Met Ala Ile
305                 310                 315                 320
Ala Ala Phe Tyr Leu Gly Phe Phe Ile Leu Ser His Ile Phe Val
                325                 330                 335
Gly Ala Lys Ser Ile Pro Glu Asp Ala Lys Ser Ile Asp Trp Ala Arg
                340                 345                 350
His Gln Ile Glu Ser Ser Asn Val Cys Gly Glu Lys Leu Gly Ile
                355                 360                 365
Ser Asn Gly Gly Leu Asn Tyr Gln Ile Glu His His Leu Phe Pro Arg
                370                 375                 380
Met Ser His Ala His Tyr Ser Lys Ile Gln Pro Val Val Gln Arg Val
385                 390                 395                 400
Cys Glu Glu Asn Gly Ile Asn Tyr Lys Lys Phe Gly Thr Ile Gly Ser
                405                 410                 415
Asn Leu Asp Ser Leu Leu Arg Gln Val Lys Ala Leu Gly Ser Val Ala
                420                 425                 430
Val Glu Phe Met Glu Gly Leu
                435
```

<210> SEQ ID NO 177
<211> LENGTH: 439
<212> TYPE: PRT
<213> ORGANISM: Artificial
<220> FEATURE:
<223> OTHER INFORMATION: delta-4 desaturase 88.1% sequence identity to SEQ ID NO 79

<400> SEQUENCE: 177

```
Met Pro Pro His Ser Arg Thr Lys Val Ser Asp Pro Glu Leu Ser Asp
1               5                   10                  15

Leu Met Lys His Phe Thr Arg Glu Glu Ile Leu Asn His Thr Asn Asp
            20                  25                  30

Lys Ile Cys Ile Leu Glu Asp Gly Val Tyr Asp Ala Thr Asn Phe Arg
        35                  40                  45

Asp Lys His Pro Gly Gly Asp Val Leu Asp Ile Phe Pro Gly Gln Asp
    50                  55                  60

Ala Thr Pro His Phe Tyr Met Leu His Gln Arg Glu Ser Pro Pro Gly
65                  70                  75                  80

Leu Leu Ala Lys Tyr Lys Val Gly Ser Val Ala Arg Asp Asp Ser Tyr
                85                  90                  95

Val Tyr His Glu Pro Leu Met Lys Gln Ile Lys Cys Glu Val Asn Lys
            100                 105                 110

Val Leu Pro Lys Gln Glu Trp Trp Ala Pro Ser Trp Tyr Ile Lys
        115                 120                 125

Ala Cys Ala Ile Leu Val Ala Thr Leu Tyr Leu Asp Tyr Tyr Trp Ile
    130                 135                 140

Ala Arg Gly Pro Thr Ile Pro Leu Ala Ile Val Ser Gly Leu Leu Tyr
145                 150                 155                 160

Ala Ala Ile Gly Leu Asn Ile Gln His Asp Ala Asn His Gly Ser Val
                165                 170                 175

Ser Arg Asn Pro Ala Val Asn Arg Leu Phe Gly Tyr Ser Gln Asp Trp
            180                 185                 190

Ile Gly Gly Ser Arg Met Leu Trp Ile Arg Lys His Val Val Gly His
        195                 200                 205

His Leu His Cys Asn Arg His Gln His Asp Pro Asp Val Lys Gly Gly
    210                 215                 220

Ser Val Leu Thr Leu Ser Pro Tyr Ser Leu Pro Lys Glu Phe His His
225                 230                 235                 240

Ile Gln Gln Leu Tyr Phe Leu Pro Leu Ile Val Leu Tyr Gly Phe Lys
                245                 250                 255

Trp Val Phe Leu Gly Leu His Asp Leu Ile Glu Met Arg Tyr Lys Gly
            260                 265                 270

Glu Lys Leu Pro Glu Leu Tyr Arg Lys Glu Phe Asn Ile Ala Ile Gly
        275                 280                 285

Leu Arg Leu Phe Phe Ile Arg Lys Phe Val Pro Phe Ala Leu
    290                 295                 300

His Pro Ser Trp His Thr Leu Leu Cys Thr Cys Leu Trp Val Ala Ser
305                 310                 315                 320

Ala Ala Leu Tyr Leu Gly Phe Phe Ile Leu Ser His Ile Phe Val
                325                 330                 335

Gly Ala Gly Ser Leu Pro Glu Asp Ala Ser Ile Asp Trp Ala Arg His
            340                 345                 350

Gln Ile Glu Ser Ser Ser Asn Val Gly Gly Glu Lys Leu Gly Ile Ser
```

```
                355                 360                 365
Asn Gly Gly Leu Asn Tyr Gln Ile Glu His His Leu Phe Pro Arg Met
    370                 375                 380

Ser His Ala His Tyr Ser Lys Ile Gln Pro Val Val Gln Lys Val Cys
385                 390                 395                 400

Glu Glu Asn Gly Ile Asn Tyr Lys Lys Phe Gly Thr Ile Leu Ser Asn
                405                 410                 415

Leu Asp Ser Leu Phe Arg His Leu Gly Ala Ile Gly Ser Arg Ala Thr
                420                 425                 430

Tyr Glu Phe Met Glu Gly Leu
                435

<210> SEQ ID NO 178
<211> LENGTH: 439
<212> TYPE: PRT
<213> ORGANISM: Artificial
<220> FEATURE:
<223> OTHER INFORMATION: delta-4 desaturase 87.9% sequence identity to
      SEQ ID NO 79

<400> SEQUENCE: 178

Met Pro Pro His Gly Arg Thr Glu Gly Gly Asp Pro Glu Leu Ser Asp
1               5                   10                  15

Met Lys His Phe Thr Tyr Glu Glu Ile Leu Asn His Thr Arg Asp Lys
                20                  25                  30

Ile Cys Ile Val Glu Asp Gly Val Tyr Asp Leu Thr Asn Phe Arg Asp
                35                  40                  45

Lys His Pro Gly Gly Asp Val Val Asp Leu Phe Gly Gly Gln Asp Ala
        50                  55                  60

Thr Pro His Phe Tyr Met Leu His Gln Tyr Glu Ser Pro Pro Ser Ile
65              70                  75                  80

Leu Ala Glu Tyr Lys Val Gly Ser Ile Ala Arg Asp Asp Ser Tyr Val
                85                  90                  95

Tyr His Thr Pro Gly Met Lys Arg Ile Lys Ala Glu Val Arg Lys Val
                100                 105                 110

Met Pro Lys Gly Glu Trp Trp Ala Pro Pro Ser Trp Tyr Ile Lys Ala
            115                 120                 125

Cys Ala Ile Leu Ala Ala Ala Leu Tyr Thr Asp Tyr Leu Trp Ile Ala
        130                 135                 140

Ser Gly Pro Thr Ile Pro Leu Ala Ile Val Ser Gly Leu Leu Tyr Ala
145                 150                 155                 160

Trp Ile Gly Leu Asn Ile Gln His Asp Ala Asn His Gly Ser Val Ser
                165                 170                 175

Arg Asn Pro Met Val Asn Arg Leu Phe Gly Tyr Ser Gln Asp Trp Ile
                180                 185                 190

Gly Gly Ser Arg Met Leu Trp Ile Gln Gln His Val Val Gly His His
            195                 200                 205

Ile His Cys Asn Arg Val Gln His Asp Pro Asp Val Lys Gly Gly Ser
        210                 215                 220

Val Ile Lys Leu Ser Pro Tyr Ser Leu Pro Met Glu Phe His Ile
225                 230                 235                 240

Gln Gln Tyr Tyr Phe Leu Pro Leu Glu Gln Leu Tyr Gly Phe Gln Trp
                245                 250                 255

Val Phe Leu Gly Leu His Asp Leu Leu Glu Trp Lys Tyr Lys Gly Glu
                260                 265                 270
```

```
Lys Ile Pro Glu Ile Ala Arg Lys Glu Arg Gly Ile Ala Ile Gly Leu
            275                 280                 285

Arg Val Phe Phe Phe Val Arg Lys Phe Val Pro Leu Ala Leu Glu
        290                 295                 300

Phe Thr Trp His Thr Leu Leu Cys Thr Tyr Leu Trp Met Cys Val Ala
305                 310                 315                 320

Ala Phe Tyr Leu Gly Phe Phe Phe Ile Leu Ser His Ile Phe Val Gly
                325                 330                 335

Ile Gly Ser Leu Pro Glu Asp Ala Lys Asn Ile Asp Trp Ala Arg His
            340                 345                 350

Gln Ile Glu Ser Ser Ser Asn Val Cys Gly Glu Lys Leu Gly Tyr Ser
        355                 360                 365

Asn Gly Gly Leu Asn Tyr Gln Ile Glu His His Leu Phe Pro Arg Met
370                 375                 380

Ser His Ala His Tyr Ser Lys Ile Gln Pro Val Val Gln Lys Val Cys
385                 390                 395                 400

Glu Glu Asn Gly Val Asn Tyr Lys Lys Phe Gly Thr Ile Leu Ser Asn
                405                 410                 415

Leu Asp Ser Met Phe Arg Gln Val Lys Ala Leu Gly Ser Val Ala Val
            420                 425                 430

Tyr Glu Phe Met Glu Gly Leu
        435

<210> SEQ ID NO 179
<211> LENGTH: 437
<212> TYPE: PRT
<213> ORGANISM: Artificial
<220> FEATURE:
<223> OTHER INFORMATION: delta-4 desaturase 87.9% sequence identity to
      SEQ ID NO 79

<400> SEQUENCE: 179

Met Pro Pro His Ser Arg Thr Lys Val Ser Asp Pro Glu Leu Arg Asp
1               5                   10                  15

Met Lys His Phe Thr Arg Thr Glu Ile Leu Asn His Thr Arg Asp Lys
            20                  25                  30

Tyr Cys Ile Leu Gly Asp Gly Val Tyr Asp Leu Thr Cys Phe Arg Asp
        35                  40                  45

Lys His Pro Gly Gly Asp Val Leu Asp Phe Phe Pro Gly Gln Asp Ala
    50                  55                  60

Thr Pro His Phe Tyr Met Leu His Gln Tyr Glu Trp Pro Pro Ala Val
65                  70                  75                  80

Leu Ala Glu Tyr Lys Val Gly Ser Val Ala Arg Asp Asp Ser Tyr Val
                85                  90                  95

His His Thr Pro Leu Met Lys Gln Ile Lys Ser Glu Val Arg Lys Val
            100                 105                 110

Met Pro Met Gln Glu Trp Trp Ala Pro Pro Ser Trp Tyr Ile Lys Ala
        115                 120                 125

Cys Ala Leu Leu Val Ala Ala Leu Tyr Thr Asp Tyr Leu Met Ile Ala
130                 135                 140

Ser Gly Pro Thr Ile Pro Leu Ala Ile Val Ser Gly Leu Leu Tyr Ala
145                 150                 155                 160

Ala Ile Gly Leu Asn Ile Gln His Asp Ala Asn His Gly Ala Val Ser
                165                 170                 175

Arg Asn Pro Met Val Asn Arg Leu Phe Gly Tyr Ser Gln Asp Trp Ile
            180                 185                 190
```

```
Gly Gly Ser Arg Met Leu Trp Ile Arg Glu His Val Gly His His
            195                 200                 205

Leu His Cys Asn Arg Ile Gln His Asp Pro Asp Val Lys Gly Gly Ser
        210                 215                 220

Ala Ile Arg Leu Ser Arg Tyr Ser Leu Trp Lys Pro Trp His His Leu
225                 230                 235                 240

Gln Gln Ile Tyr Phe Leu Pro Leu Ile Gln Leu Leu Gly Phe Lys Trp
                245                 250                 255

Val Phe Leu Asp Leu His Asp Leu Ile Glu Met Lys Tyr Lys Gly Glu
            260                 265                 270

Lys Leu Pro Glu Leu Tyr Arg Pro Leu Arg Asn Ile Ala Ile Gly Cys
        275                 280                 285

Arg Ile Phe Phe Phe Ile Arg Lys Phe Ala Leu Pro Phe Trp Leu His
290                 295                 300

Phe Thr Trp Tyr Thr Leu Leu Cys Thr Cys Leu Trp Met Ala Ile Ala
305                 310                 315                 320

Ser Leu Tyr Leu Ala Phe Phe Ile Leu Ser His Ile Phe Val Gly
                325                 330                 335

Ile Lys Ser Leu Gly Glu Asp Ala Asn Ile Asp Trp Ala Arg His Gln
            340                 345                 350

Ile Glu Ser Ser Asn Val Gly Gly Asp Lys Leu Gly Tyr Ser Asn
        355                 360                 365

Gly Gly Leu Asn Tyr Gln Ile Glu His His Leu Phe Pro Arg Met Ser
        370                 375                 380

His Ala His Tyr Ser Lys Ile Glu Pro Val Val Gln Lys Val Cys Glu
385                 390                 395                 400

Glu Asn Gly Val Asn Tyr Lys Lys Phe Pro Thr Ile Leu Ser Asn Leu
                405                 410                 415

Asp Ser Thr Phe Arg Gln Val Lys Ala Leu Gly Ser Val Ala Val Glu
            420                 425                 430

Phe Met Glu Gly Leu
        435

<210> SEQ ID NO 180
<211> LENGTH: 437
<212> TYPE: PRT
<213> ORGANISM: Artificial
<220> FEATURE:
<223> OTHER INFORMATION: delta-4 desaturase 87.9% sequence identity to
      SEQ ID NO 79

<400> SEQUENCE: 180

Met Pro Pro His Ser Arg Thr Lys Val Ser Asp Pro Glu Leu Lys Asp
1               5                   10                  15

Met Lys His Phe Ala Arg Glu Glu Ile Leu Asn His Thr Asn Asp Lys
            20                  25                  30

Tyr Cys Ile Leu Glu Asp Gly Val Tyr Asp Leu Thr Asn Phe Arg Asp
        35                  40                  45

Lys His Pro Gly Gly Asp Val Leu Asp Phe Phe Pro Gly Gln Asp Ala
    50                  55                  60

Thr Pro His Phe Tyr Met Leu His Arg Tyr Ala Trp Pro Pro Ser Val
65                  70                  75                  80

Leu Ala Glu Tyr Lys Val Gly Ser Val Asp Arg Asp Asp Ser Tyr Val
                85                  90                  95

Tyr His Thr Ser Leu Tyr Leu Gln Ile Lys Ser Ala Val Arg Lys Val
```

```
                100             105             110
Ile Pro Met Gln Glu Trp Trp Ala Pro Pro Ser Trp Trp Ile Lys Ala
            115                 120             125

Cys Ala Leu Leu Ala Ala Thr Leu Tyr Thr Asp Tyr Leu Met Ile Ala
            130                 135             140

Ser Gly Pro Thr Ile Pro Leu Gly Ile Val Ser Gly Leu Leu Tyr Ala
145                 150                 155                 160

Ala Ile Gly Leu Asn Ile Gln His Asp Ala Asn His Gly Ser Val Ser
                165                 170                 175

Arg Asn Pro Met Val Asn Arg Leu Phe Gly Tyr Ser Gln Asp Trp Ile
            180                 185                 190

Gly Gly Ser Arg Met Leu Trp Ile Arg Glu His Val Gly His His
            195                 200                 205

Thr His Cys Asn Arg His Gln His Asp Pro Asp Val Lys Gly Gly Gly
            210                 215                 220

Val Leu Lys Leu Ser Arg Tyr Asp Ile Trp Met Glu Phe His His Ile
225                 230                 235                 240

Gln Gln Leu Tyr Phe Leu Pro Leu Glu Gln Leu Leu Gly Phe Gln Trp
                245                 250                 255

Val Phe Leu Gly Leu His Asp Leu Ile Asp Met Lys Trp Lys Gly Glu
            260                 265                 270

Lys Leu Ser Glu Ser Ala Arg Pro Glu Arg Gly Ile Ala Ile Gly Leu
            275                 280                 285

Arg Val Phe Phe Trp Ile Arg Lys Phe Val Val Pro Phe Ala Leu His
            290                 295                 300

Phe Ser Trp Tyr Thr Leu Leu Cys Thr Tyr Ala Trp Val Ala Ser Ala
305                 310                 315                 320

Ala Phe Tyr Leu Gly Phe Phe Ile Leu Ser His Ile Phe Val Gly
                325                 330                 335

Ala Lys Ser Leu Pro Pro Asp Ala Ser Val Asp Trp Ala Arg His Gln
            340                 345                 350

Ile Glu Thr Ser Ser Asn Val Gly Gly Glu Lys Leu Gly Ile Ser Asn
            355                 360                 365

Gly Gly Leu Asn Tyr Gln Ile Glu His His Leu Phe Pro Arg Met Ser
            370                 375                 380

His Ala His Tyr Ser Lys Ile Gln Pro Val Val Gln Lys Val Cys Glu
385                 390                 395                 400

Glu Asn Gly Val Asn Tyr Lys Lys Phe Pro Thr Ile Ala Ser Asn Leu
                405                 410                 415

Asp Ser Thr Phe Ser Gln Val Lys Ala Leu Gly Ser Val Ala Val Glu
            420                 425                 430

Phe Met Gly Gly Ile
            435

<210> SEQ ID NO 181
<211> LENGTH: 438
<212> TYPE: PRT
<213> ORGANISM: Artificial
<220> FEATURE:
<223> OTHER INFORMATION: delta-4 desaturase 87.4% sequence identity to
      SEQ ID NO 79

<400> SEQUENCE: 181

Met Pro Pro His Ala Arg Ser Lys Val Ser Asp Pro Glu Leu Ser Asp
1               5                   10                  15
```

```
Met Lys His Phe Thr Arg Glu Arg Ile Leu Asn Asp Glu Asn Asp Lys
              20                  25                  30
Ile Cys Ile Leu Glu Asp Gly Val Tyr Asp Leu Thr Asn Phe Arg Asp
             35                  40                  45
Lys His Pro Gly Gly Asp Tyr Val Asp Phe Phe Gly Gly Gln Asp Ala
 50                  55                  60
Thr Pro His Phe Tyr Met Phe His Gln Tyr Glu Ser Pro Pro Ser Val
 65                      70                  75                  80
Leu Ala Glu Tyr Lys Val Gly Ser Val Ala Arg Asp Asp Ser Phe Val
                 85                  90                  95
Tyr His Glu Pro Leu Met Lys Gln Ile Lys Ser Ala Val Arg Lys Val
             100                 105                 110
Met Pro Arg Gly Glu Trp Trp Ala Pro Pro Ser Trp Tyr Ile Lys Ala
             115                 120                 125
Cys Ala Ile Leu Ala Ala Thr Leu Tyr Thr Asp Tyr Leu Trp Ile Ala
 130                 135                 140
Arg Gly Pro Thr Ile Pro Leu Ala Ile Val Leu Gly Leu Leu Phe Ala
145                 150                 155                 160
Ala Ile Gly Leu Asn Ile Gln His Asp Ala Asn His Gly Ser Leu Ser
                 165                 170                 175
Arg Asn Pro Met Val Asn Arg Leu Phe Gly Tyr Ser Gln Asp Trp Ile
             180                 185                 190
Gly Gly Ser Arg Leu Leu Trp Leu Arg Glu His Val Gly His His
             195                 200                 205
Thr His Cys Asn Arg His Asp His Asp Pro Asp Val Lys Gly Gly Gly
210                 215                 220
Val Leu Lys Leu Ser Arg Ser Ser Leu Pro Met Glu Phe His His Ile
225                 230                 235                 240
Gln Gln Ile Tyr Phe Leu Pro Leu Glu Gln Leu Leu Gly Phe Gln Trp
                 245                 250                 255
Val Phe Leu Gly Leu His Asp Leu Ile Glu Met Lys Tyr Lys Gly Glu
             260                 265                 270
Pro Leu Pro Glu Leu Tyr Arg Lys Glu Arg Asn Ile Ala Val Gly Leu
             275                 280                 285
Arg Val Phe Phe Phe Ile Arg Lys Phe Val Val Pro Phe Ala Leu His
290                 295                 300
Pro Ser Trp His Thr Leu Leu Cys Ile Cys Leu Trp Met Ala Ile Gly
305                 310                 315                 320
Ala Leu Tyr Leu Gly Phe Phe Phe Ile Leu Ser His Ile Phe Val Gly
                 325                 330                 335
Ile Lys Ser Leu Pro Glu Asp Ala Lys Asn Ile Asp Trp Ala Arg His
             340                 345                 350
Gln Ile Glu Ser Ser Asn Val Cys Gly Glu Lys Leu Gly His Ser
             355                 360                 365
Asn Gly Gly Leu Asn Tyr Gln Ile Glu His His Leu Phe Pro Arg Met
370                 375                 380
Ser His Ser His Tyr Ser Lys Ile Glu Pro Val Val Gln Lys Val Cys
385                 390                 395                 400
Glu Asp Asn Gly Ile Asn Tyr Lys Lys Phe Gly Thr Ile Leu Ser Asn
                 405                 410                 415
Leu Asp Ser Thr Leu Arg Gln Leu Gly Ala Leu Gly Ser Arg Pro Val
             420                 425                 430
Glu Phe Met Glu Gly Leu
```

435

<210> SEQ ID NO 182
<211> LENGTH: 439
<212> TYPE: PRT
<213> ORGANISM: Artificial
<220> FEATURE:
<223> OTHER INFORMATION: delta-4 desaturase 87.4% sequence identity to
      SEQ ID NO 79

<400> SEQUENCE: 182

```
Met Pro Pro His Ser Arg Thr Lys Val Val Ser Asp Pro Glu Leu Ser
1               5                   10                  15

Asp Met Glu His Phe Thr Arg Thr Glu Ile Leu Asn His Glu Asn Asp
            20                  25                  30

Lys Tyr Cys Ile Leu Glu Asp Gly Val Tyr Asp Leu Ser Asn Phe Arg
        35                  40                  45

Asp Lys His Pro Gly Gly Glu Tyr Leu Asp Phe Phe Pro Gly Gln Asp
    50                  55                  60

Ala Thr Pro Gly Phe Phe Gln Leu His Gln Tyr Ala Ser Leu Pro Gly
65                  70                  75                  80

Val Leu Ala Arg Tyr Lys Val Gly Ser Ile Asp Arg Asp Asp Ser Tyr
                85                  90                  95

Val Gln His Thr Ser Leu Met Lys Gln Ile Cys Ser Ala Val Arg Lys
            100                 105                 110

Val Met Pro Arg Gly Glu Trp Trp Ala Pro Ser Trp Trp Ile Lys
        115                 120                 125

Ala Cys Ala Ile Ile Ile Ala Thr Leu Tyr Leu Asp Tyr Leu Trp Ile
130                 135                 140

Ala Ser Gly Pro Thr Ile Pro Leu Ala Ile Val Ser Gly Leu Leu Phe
145                 150                 155                 160

Ala Ala Ile Gly Leu Asn Ile Gln His Asp Ala Asn His Gly Ala Leu
                165                 170                 175

Ser Arg Asn Pro Met Val Asn Arg Leu Phe Gly Tyr Ala Gln Asp Trp
            180                 185                 190

Ile Gly Gly Ser Met Met Leu Trp Ile Gln Gln His Val Val Gly His
        195                 200                 205

His Thr His Cys Asn Arg Val Gln His Asp Pro Asp Val Lys Gly Gly
    210                 215                 220

Gly Val Ile Thr Leu Ser Pro Thr Ser Leu Pro Leu Glu Phe His His
225                 230                 235                 240

Ile Gln Gln Tyr Tyr Phe Leu Pro Leu Ile Gln Leu Leu Gly Phe Gln
                245                 250                 255

Trp Val Phe Leu Gly Leu His Asp Leu Ile Glu Met Lys Tyr Lys Gly
            260                 265                 270

Glu Lys Leu Pro Glu Ser Ala Arg Lys Glu Tyr Gly Ile Ala Ile Gly
        275                 280                 285

Leu Lys Val Phe Phe Trp Ile Arg Lys Val Val Pro Phe Trp Leu
    290                 295                 300

His Phe Ser Trp Tyr Thr Leu Leu Cys Ile Tyr Leu Trp Met Ala Ile
305                 310                 315                 320

Gly Ala Leu Tyr Leu Ala Phe Phe Ile Leu Ser His Ile Phe Val
                325                 330                 335

Gly Ala Lys Ser Leu Pro Glu Asp Gly Lys Asn Ile Asp Trp Ala Arg
            340                 345                 350
```

His Gln Ile Glu Ser Ser Asn Val Cys Gly Lys Leu Gly Ile
            355                 360                 365

Ser Asn Gly Gly Leu Asn Tyr Gln Ile Glu His His Leu Phe Pro Arg
    370                 375                 380

Met Ser His Ser His Tyr Ser Lys Ile Gln Pro Val Val Gln Lys Val
385                 390                 395                 400

Cys Glu Glu Asn Gly Ile Asn Tyr Lys Lys Phe Gly Thr Ile Leu Ser
                405                 410                 415

Asn Leu Asp Ser Ile Phe Arg Gln Val Gly Ala Leu Gly Ser Val Ala
            420                 425                 430

Val Glu Phe Leu Glu Gly Leu
            435

<210> SEQ ID NO 183
<211> LENGTH: 439
<212> TYPE: PRT
<213> ORGANISM: Artificial
<220> FEATURE:
<223> OTHER INFORMATION: delta-4 desaturase 87.2% sequence identity to
      SEQ ID NO 79

<400> SEQUENCE: 183

Met Pro Pro His Ser Arg Thr Lys Gly Ser Asp Asp Pro Glu Leu Ser
1               5                   10                  15

Asp Leu Met Lys His Phe Thr Arg Glu Lys Ile Leu Asn Asp Asn Asn
            20                  25                  30

Asp Lys Tyr Cys Ile Val Gly Asp Gly Val Tyr Asp Ala Thr Asn Phe
        35                  40                  45

Arg Asp Lys His Pro Gly Gly Glu Phe Leu Asp Phe Phe Pro Gly Gln
    50                  55                  60

Asp Ala Thr Pro His Phe Tyr Met Phe His Gln Tyr Glu Ser Leu Pro
65                  70                  75                  80

Ser Ile Leu Ala Glu Tyr Lys Val Gly Ser Leu Glu Arg Asp Asp Ser
                85                  90                  95

Tyr Thr Tyr His Asp Ser Leu Met Lys Gln Ile Lys Ser Ala Val Arg
            100                 105                 110

Lys Val Ile Pro Met Gln Glu Trp Trp Ala Pro Ser Trp Tyr Ile
        115                 120                 125

Lys Ala Cys Ala Ile Leu Ile Ala Thr Leu Tyr Leu Asp Tyr Leu Trp
    130                 135                 140

Ile Ala Ser Gly Pro Thr Ile Phe Leu Ala Ile Val Leu Gly Leu Leu
145                 150                 155                 160

Tyr Ala Trp Ile Gly Leu Asn Ile Gln His Asp Ala Asn His Gly Ser
                165                 170                 175

Val Ser Arg Asn Pro Met Val Asn Arg Leu Phe Gly Tyr Ser Gln Asp
            180                 185                 190

Trp Ile Gly Gly Ser Arg Val Leu Trp Ile Arg Gln His Val Val Gly
        195                 200                 205

His His Ile His Ser Asn Arg His Gln His Asp Pro Asp Val Lys Gly
    210                 215                 220

Gly Gly Val Ile Thr Leu Ser Arg Val Ser Leu Pro Lys Glu Phe His
225                 230                 235                 240

His Ile Gln Gln Tyr Tyr Phe Leu Pro Leu Glu Gln Leu Gly Phe
                245                 250                 255

Lys Trp Val Phe Leu Gly Leu His Asp Leu Ile Asp Met Lys Tyr Lys
            260                 265                 270

Gly Glu Lys Leu Pro Glu Ser Tyr Arg Lys Glu Arg Gly Ile Ala Ile
            275                 280                 285

Gly Cys Arg Val Gly Phe Phe Ala Arg Lys Ile Val Val Pro Phe Ala
        290                 295                 300

Leu Gln Phe Ser Trp His Thr Leu Leu Cys Val Tyr Leu Trp Val Ala
305                 310                 315                 320

Ile Ala Thr Leu Tyr Leu Ala Phe Phe Ile Leu Ser His Ile Phe
                325                 330                 335

Ile Gly Ala Lys Ser Leu Pro Pro Asp Ala Asn Ile Asp Trp Ala Arg
                340                 345                 350

His Gln Ile Glu Ser Ser Asn Val Cys Gly Glu Lys Leu Gly Ile
            355                 360                 365

Met Asn Gly Gly Leu Asn Tyr Gln Ile Glu His His Leu Phe Pro Arg
    370                 375                 380

Met Ser His Ala His Tyr Ser Thr Ile Gln Pro Val Val Gln Arg Val
385                 390                 395                 400

Cys Glu Glu Asn Gly Val Asn Tyr Lys His Phe Gly Thr Ile Gly Ser
                405                 410                 415

Asn Leu Asp Ser Thr Phe Arg Gln Val Lys Ala Leu Gly Ser Val Ala
                420                 425                 430

Val Glu Phe Leu Glu Gly Leu
        435

<210> SEQ ID NO 184
<211> LENGTH: 439
<212> TYPE: PRT
<213> ORGANISM: Artificial
<220> FEATURE:
<223> OTHER INFORMATION: delta-4 desaturase 87% sequence identity to
      SEQ ID NO 79

<400> SEQUENCE: 184

Met Pro Pro His Ala Ala Thr Glu Val Ser Val Pro Glu Leu Ser Asp
1               5                   10                  15

Leu Met Lys His Phe Ser Arg Thr Glu Ile Leu Asn Asp Thr Arg Asp
            20                  25                  30

Lys Tyr Cys Ile Leu Glu Asp Gly Val Tyr Asp Leu Pro Asn Phe Arg
        35                  40                  45

Asp Lys His Pro Gly Gly Asp Tyr Val Asp Phe Phe Pro Gly Gln Asp
    50                  55                  60

Ala Thr Pro His Phe Tyr Met Leu His Gln Tyr Glu Trp Pro Pro Ser
65                  70                  75                  80

Val Leu Ala Glu Tyr Gly Val Gly Ser Val Ala Arg Asp Asp Ser Phe
                85                  90                  95

Val His His Asp Pro Leu Met Leu Gln Leu Cys Ser Asp Val Arg Lys
            100                 105                 110

Val Met Pro Met Gly Glu Trp Trp Ala Pro Ser Trp Trp Ile Lys
            115                 120                 125

Ala Cys Ala Ile Leu Ala Ala Thr Leu Tyr Leu Asp Tyr Leu Trp Leu
    130                 135                 140

Ala Ser Gly Pro Thr Ile Pro Leu Ala Ile Ile Ser Gly Leu Leu Tyr
145                 150                 155                 160

Ala Ala Ile Gly Leu Asn Ile Gln His Asp Ala Asn His Gly Ser Val
                165                 170                 175

Ser Arg Asn Pro Met Val Asn Arg Leu Phe Gly Tyr Ser Gln Asp Trp

```
            180                 185                 190
Ile Gly Gly Ser Arg Met Leu Trp Ile Arg Gln His Val Gly His
            195                 200                 205
His Ile His Cys Asn Arg His Gln His Asp Pro Asp Val Lys Gly Gly
            210                 215                 220
Gly Val Ile Thr Leu Ser Arg Tyr Asp Leu Pro Met Glu Phe His His
225                 230                 235                 240
Leu Gln Gln Leu Tyr Phe Leu Pro Leu Ile Ala Leu Leu Gly Phe Gln
                    245                 250                 255
Trp Val Phe Leu Gly Leu His Asp Leu Ile Glu Trp Lys Tyr Lys Gly
                260                 265                 270
Glu Lys Leu Pro Glu Ile Tyr Arg Lys Glu Arg Gly Ile Ala Ile Gly
                275                 280                 285
Leu Arg Val Phe Phe Trp Ala Arg Phe Val Val Pro Phe Ala Leu
                290                 295                 300
Glu Phe Ser Trp Tyr Thr Leu Leu Cys Thr Tyr Leu Trp Met Ala Ile
305                 310                 315                 320
Ala Ala Leu Tyr Leu Gly Phe Phe Ile Leu Ser His Ile Phe Val
                    325                 330                 335
Gly Ala Lys Ser Leu Pro Glu Asp Ala Ser Ile Asp Trp Ala Arg Arg
                340                 345                 350
Gln Ile Glu Thr Ser Ser Asn Val Gly Gly Trp Leu Gly Ile Ile
                355                 360                 365
Asn Gly Gly Leu Asn Phe Gln Ile Glu His His Leu Phe Pro Arg Met
                370                 375                 380
Ser His Ala His Tyr Ser Thr Ile Gln Pro Val Val Gln Lys Val Cys
385                 390                 395                 400
Glu Glu Asn Gly Val Asn Tyr Lys Lys Phe Gly Thr Ile Gly Ser Asn
                    405                 410                 415
Leu Asp Ser Thr Phe Lys Gln Val Lys Ala Leu Gly Ser Val Pro Val
                420                 425                 430
Tyr Glu Phe Met Ala Gly Leu
        435

<210> SEQ ID NO 185
<211> LENGTH: 437
<212> TYPE: PRT
<213> ORGANISM: Artificial
<220> FEATURE:
<223> OTHER INFORMATION: delta-4 desaturase 87% sequence identity to
      SEQ ID NO 79

<400> SEQUENCE: 185

Met Pro Pro His Ser Arg Thr Lys Val Ser Val Pro Glu Leu Ser Asp
1               5                   10                  15

Met Lys His Phe Thr Arg Glu Glu Ile Leu Asn Asp Thr Asn Asp Asp
                20                  25                  30

Tyr Cys Ile Leu Glu Asp Gly Val Tyr Asp Leu Thr Asn Phe Arg Asp
            35                  40                  45

Lys His Pro Gly Gly Asp Phe Ile Asp Ile Phe Pro Gly Arg Asp Ala
        50                  55                  60

Thr Pro His Phe Tyr Met Tyr His Gln Arg Glu Ser Pro Pro Ser Val
65                  70                  75                  80

Leu Ser Glu Tyr Lys Val Gly Ser Leu Glu Arg Asp Asp Ser Phe Val
                85                  90                  95
```

```
His Tyr Thr Ala Leu Met Lys Gln Leu Lys Ser Glu Val Asn Lys Ile
            100                 105                 110

Met Pro Met Gly Glu Gly Trp Ala Pro Ser Trp Tyr Ile Lys Ala
        115                 120                 125

Cys Ala Leu Leu Val Ala Thr Leu Tyr Thr Asp Tyr Leu Met Ile Ala
    130                 135                 140

Lys Gly Pro Thr Ile Pro Leu Ser Ile Val Ile Gly Leu Leu Tyr Ala
145                 150                 155                 160

Trp Ile Gly Leu Asn Ile Gln His Asp Ala Asn His Gly Ser Val Ser
                165                 170                 175

Arg Asn Pro Met Val Asn Arg Leu Phe Gly Tyr Ser Gln Asp Trp Ile
            180                 185                 190

Gly Gly Ser Arg Met Leu Trp Ile Gln Gln His Val Val Gly His His
        195                 200                 205

Ile His Cys Asn Arg Ile Gln His Asp Pro Asp Val Lys Gly Gly Ser
    210                 215                 220

Val Ile Arg Leu Ser Arg Tyr Ser Leu Trp Lys Glu Phe His His Ile
225                 230                 235                 240

Gln Gln Tyr Tyr Phe Leu Pro Leu Glu Gln Leu Leu Gly Phe Gln Trp
                245                 250                 255

Val Phe Leu Gly Leu Asn Asp Leu Ile Asp Met Lys Trp Lys Gly Glu
            260                 265                 270

Lys Leu Pro Glu Ser Ala Arg Lys Glu Arg Asn Ile Ala Ile Gly Leu
        275                 280                 285

Lys Val Phe Phe Phe Ile Arg Lys Phe Val Pro Phe Ala Leu Gln
    290                 295                 300

Phe Ser Trp Tyr Thr Leu Leu Cys Thr Tyr Ala Trp Met Ala Ile Ala
305                 310                 315                 320

Ala Leu Tyr Leu Gly Phe Phe Phe Ile Leu Ser His Ile Phe Val Gly
                325                 330                 335

Ala Lys Ser Leu Pro Glu Glu Ala Asn Ile Asp Trp Ala Arg His Gln
            340                 345                 350

Ile Glu Ser Ser Ser Asn Val Cys Gly Glu Trp Leu Gly His Leu Asn
        355                 360                 365

Gly Gly Leu Asn Tyr Gln Ile Glu His His Leu Phe Pro Arg Met Ser
    370                 375                 380

His Ala His Tyr Ser Lys Ile Gln Pro Val Val Gln Lys Val Cys Glu
385                 390                 395                 400

Glu Asn Gly Val Lys Tyr Lys Lys Phe Gly Thr Ile Leu Ser Asn Leu
                405                 410                 415

Asp Ser Thr Phe Arg Gln Val Lys Ala Leu Gly Ser Val Pro Ile Glu
            420                 425                 430

Phe Met Glu Gly Leu
        435

<210> SEQ ID NO 186
<211> LENGTH: 439
<212> TYPE: PRT
<213> ORGANISM: Artificial
<220> FEATURE:
<223> OTHER INFORMATION: delta-4 desaturase 85.4% sequence identity to
      SEQ ID NO 79

<400> SEQUENCE: 186

Met Pro Pro His Ser Arg Thr Lys Val Ser Asp Asp Ala Glu Leu Lys
1               5                   10                  15
```

```
Asp Leu Met Lys His Phe Ala Arg Glu Glu Lys Leu Asn His Thr Asn
            20                  25                  30
Asp Lys Leu Cys Ile Leu Glu Asp Gly Val Tyr Asp Leu Pro Asn Phe
            35                  40                  45
Arg Asp Glu His Pro Gly Gly Asp Val Leu Ser Phe Phe Pro Gly Arg
 50                  55                  60
Asp Ala Thr Pro His Phe Tyr Gln Leu His Gln Lys Glu Ser Pro Pro
 65                  70                  75                  80
Ala Leu Leu Ala Glu Tyr Lys Val Gly Ser Val Ala Arg Asp Asp Ser
            85                  90                  95
Tyr Val Gln Tyr Thr Pro Leu His Leu Gln Ile Cys Ala Asp Val Asn
            100                 105                 110
Lys Val Met Pro Arg Gln Glu Trp Trp Ala Pro Pro Ser Trp Trp Ile
            115                 120                 125
Lys Ala Cys Ala Leu Leu Ala Ala Thr Leu Tyr Thr Asp Tyr Leu Trp
 130                 135                 140
Ile Ala Ser Gly Pro Thr Ile Pro Leu Ser Ile Val Leu Gly Leu Leu
145                 150                 155                 160
Phe Ala Trp Ile Gly Leu Asn Ile Gln His Asp Ala Asn His Gly Gly
            165                 170                 175
Val Ser Arg Asn Pro Met Val Asn Arg Leu Phe Gly Tyr Gly Gln Asp
            180                 185                 190
Trp Ile Gly Gly Ser Arg Met Leu Trp Ile Gln Gln His Val Val Gly
            195                 200                 205
His His Thr His His Cys Asn Arg His Gln His Asp Pro Asp Val Lys Gly
            210                 215                 220
Gly Ser Val Leu Lys Leu Ser Arg Tyr Asp Leu Trp Leu Glu Trp His
225                 230                 235                 240
His Ile Gln Gln Tyr Tyr Phe Leu Pro Gly Glu Gln Leu Tyr Gly Phe
            245                 250                 255
Gln Trp Val Phe Leu Gly Leu His Glu Leu Ile Glu Met Lys Tyr Lys
            260                 265                 270
Gly Glu Lys Leu Pro Glu Ser Cys Arg Lys Glu Arg Asn Pro Ala Ile
            275                 280                 285
Gly Leu Arg Val Gly Phe Trp Ile Arg Lys Ile Val Val Pro Phe Ala
            290                 295                 300
Leu His Phe Ser Trp Tyr Thr Leu Leu Cys Thr Cys Leu Trp Met Ala
305                 310                 315                 320
Ile Gly Ser Leu Tyr Leu Gly Phe Phe Phe Val Leu Ser His Ile Phe
            325                 330                 335
Val Gly Ala Lys Ser Leu Pro Asp Ala Ser Ile Asp Trp Ala Arg
            340                 345                 350
Arg Gln Ile Glu Ser Ser Ser Asn Val Cys Gly Asp Lys Leu Gly Ile
            355                 360                 365
Ser Asn Gly Gly Leu Asn Tyr Gln Ile Glu His Leu Phe Pro Arg
            370                 375                 380
Met Ser His Ala His Tyr Ser Lys Ile Gln Pro Val Val Gln Lys Val
385                 390                 395                 400
Cys Glu Asp Asp Gly Val Asn Tyr Lys Lys Phe Gly Thr Ile Leu Ser
            405                 410                 415
```

```
Asn Leu Asp Ser Thr Phe Arg Gln Leu Lys Ala Leu Gly Ser Val Pro
            420                 425                 430

Val Glu Phe Leu Glu Gly Leu
        435
```